(12) United States Patent
Beatty et al.

(10) Patent No.: US 12,103,907 B2
(45) Date of Patent: *Oct. 1, 2024

(54) TETRALIN AND TETRAHYDROQUINOLINE COMPOUNDS AS INHIBITORS OF HIF-2ALPHA

(71) Applicant: ARCUS BIOSCIENCES, INC., Hayward, CA (US)

(72) Inventors: Joel Worley Beatty, San Mateo, CA (US); Samuel Lawrie Drew, Millbrae, CA (US); Matthew Epplin, South San Francisco, CA (US); Jeremy Thomas Andre Fournier, Fremont, CA (US); Balint Gal, Hayward, CA (US); Tezcan Guney, Hayward, CA (US); Karl T. Haelsig, Berkeley, CA (US); Clayton Hardman, San Francisco, CA (US); Steven Donald Jacob, Oakland, CA (US); Jenna Leigh Jeffrey, Oakland, CA (US); Jaroslaw Kalisiak, Mountain View, CA (US); Kenneth Victor Lawson, San Francisco, CA (US); Manmohan Reddy Leleti, Dublin, CA (US); Erick Allen Lindsey, San Diego, CA (US); Artur Karenovich Mailyan, Hayward, CA (US); Debashis Mandal, Fremont, CA (US); Guillaume Mata, Berkeley, CA (US); Hyunyoung Moon, Foster City, CA (US); Jay Patrick Powers, Sisters, OR (US); Brandon Reid Rosen, San Mateo, CA (US); Yongli Su, Foster City, CA (US); Anh Thu Tran, Union City, CA (US); Zhang Wang, Petaluma, CA (US); Xuelei Yan, Foster City, CA (US); Kai Yu, Hayward, CA (US)

(73) Assignee: Arcus Biosciences, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/239,892

(22) Filed: Aug. 30, 2023

(65) Prior Publication Data
US 2024/0254079 A1 Aug. 1, 2024

Related U.S. Application Data

(60) Continuation of application No. 17/835,559, filed on Jun. 8, 2022, now Pat. No. 11,787,762, which is a
(Continued)

(51) Int. Cl.
C07C 317/32 (2006.01)
A61K 31/10 (2006.01)
(Continued)

(52) U.S. Cl.
CPC ............ *C07C 317/32* (2013.01); *A61K 31/10* (2013.01); *A61K 31/277* (2013.01); *A61K 31/343* (2013.01); *A61K 31/353* (2013.01); *A61K 31/365* (2013.01); *A61K 31/381* (2013.01); *A61K 31/404* (2013.01); *A61K 31/415* (2013.01); *A61K 31/416* (2013.01); *A61K 31/4174* (2013.01); *A61K 31/4192* (2013.01); *A61K 31/4196* (2013.01); *A61K 31/421* (2013.01); *A61K 31/423* (2013.01); *A61K 31/426* (2013.01); *A61K 31/428* (2013.01); *A61K 31/437* (2013.01); *A61K 31/44* (2013.01); *A61K 31/4412* (2013.01); *A61K 31/47* (2013.01); *A61K 31/4709* (2013.01); *A61K 31/472* (2013.01); *A61K 31/4965* (2013.01); *A61K 31/50* (2013.01); *A61K 31/5025* (2013.01); *A61K 31/505* (2013.01); *A61K 31/519* (2013.01); *A61K 31/538* (2013.01);
(Continued)

(58) Field of Classification Search
CPC .................................................. C07C 317/32
See application file for complete search history.

(56) References Cited

U.S. PATENT DOCUMENTS 9,796,697 B2    10/2017  Wehn et al.
11,407,712 B2 *  8/2022  Beatty .................. A61K 31/343
(Continued)

FOREIGN PATENT DOCUMENTS

CN    109776607 B    5/2019
CN    111303053 A    6/2020
(Continued)

OTHER PUBLICATIONS

Buchstaller et al., "Discovery of Cycloalkl(c)thiophenes as Novel Scaffolds for Hypoxia-Inducible Factor-2a Inhibitors", J. Med. Chem. 2023, 66, pp. 8666-8686.

Carroll et al., "Role of Hypoxia-Inducible Factor (HIF)-1 versus HIF-2 in the Regulation of HIF Target Genes in Response to Hypoxia, Insulin-Like Growth Factor-I, or Loss of von Hippel-Lindau Function: Implications for Targeting the HIF Pathway", Cancer Res 2006; 66: (12), Jun. 15, 2006, pp. 6264-6271.

(Continued)

*Primary Examiner* — Golam M Shameem
(74) *Attorney, Agent, or Firm* — Foley & Lardner LLP; Brittany J. Perla

(57) ABSTRACT

Compounds that inhibit HIF-2α, and compositions containing the compound(s) and methods for synthesizing the compounds, are described herein. Also described are the use of such compounds and compositions for the treatment of a diverse array of diseases, disorders, and conditions, including cancer- and immune-related disorders that are mediated, at least in part, by HIF-2α.

1 Claim, No Drawings

Related U.S. Application Data division of application No. 17/205,273, filed on Mar. 18, 2021, now Pat. No. 11,407,712.

(60) Provisional application No. 63/120,875, filed on Dec. 3, 2020, provisional application No. 62/991,952, filed on Mar. 19, 2020.

(51) Int. Cl.

| | | |
|---|---|---|
| *A61K 31/277* | (2006.01) |
| *A61K 31/343* | (2006.01) |
| *A61K 31/353* | (2006.01) |
| *A61K 31/365* | (2006.01) |
| *A61K 31/381* | (2006.01) |
| *A61K 31/404* | (2006.01) |
| *A61K 31/415* | (2006.01) |
| *A61K 31/416* | (2006.01) |
| *A61K 31/4174* | (2006.01) |
| *A61K 31/4192* | (2006.01) |
| *A61K 31/4196* | (2006.01) |
| *A61K 31/421* | (2006.01) |
| *A61K 31/423* | (2006.01) |
| *A61K 31/426* | (2006.01) |
| *A61K 31/428* | (2006.01) |
| *A61K 31/437* | (2006.01) |
| *A61K 31/44* | (2006.01) |
| *A61K 31/4412* | (2006.01) |
| *A61K 31/47* | (2006.01) |
| *A61K 31/4709* | (2006.01) |
| *A61K 31/472* | (2006.01) |
| *A61K 31/4965* | (2006.01) |
| *A61K 31/50* | (2006.01) |
| *A61K 31/5025* | (2006.01) |
| *A61K 31/505* | (2006.01) |
| *A61K 31/519* | (2006.01) |
| *A61K 31/538* | (2006.01) |
| *A61K 39/395* | (2006.01) |
| *A61K 45/06* | (2006.01) |
| *C07C 255/53* | (2006.01) |
| *C07C 317/22* | (2006.01) |
| *C07C 317/36* | (2006.01) |
| *C07D 209/34* | (2006.01) |
| *C07D 211/86* | (2006.01) |
| *C07D 213/57* | (2006.01) |
| *C07D 213/71* | (2006.01) |
| *C07D 213/73* | (2006.01) |
| *C07D 213/74* | (2006.01) |
| *C07D 213/84* | (2006.01) |
| *C07D 215/48* | (2006.01) |
| *C07D 217/04* | (2006.01) |
| *C07D 231/12* | (2006.01) |
| *C07D 231/56* | (2006.01) |
| *C07D 233/64* | (2006.01) |
| *C07D 237/20* | (2006.01) |
| *C07D 239/42* | (2006.01) |
| *C07D 241/12* | (2006.01) |
| *C07D 249/06* | (2006.01) |
| *C07D 249/08* | (2006.01) |
| *C07D 263/32* | (2006.01) |
| *C07D 263/57* | (2006.01) |
| *C07D 265/36* | (2006.01) |
| *C07D 277/30* | (2006.01) |
| *C07D 277/56* | (2006.01) |
| *C07D 277/64* | (2006.01) |
| *C07D 307/83* | (2006.01) |
| *C07D 311/22* | (2006.01) |
| *C07D 333/64* | (2006.01) |
| *C07D 401/04* | (2006.01) |
| *C07D 401/10* | (2006.01) |
| *C07D 409/10* | (2006.01) |
| *C07D 413/10* | (2006.01) |
| *C07D 471/04* | (2006.01) |
| *C07D 487/04* | (2006.01) |

(52) U.S. Cl.
CPC .......... *A61K 39/3955* (2013.01); *A61K 45/06* (2013.01); *C07C 255/53* (2013.01); *C07C 317/22* (2013.01); *C07C 317/36* (2013.01); *C07D 209/34* (2013.01); *C07D 211/86* (2013.01); *C07D 213/57* (2013.01); *C07D 213/71* (2013.01); *C07D 213/73* (2013.01); *C07D 213/74* (2013.01); *C07D 213/84* (2013.01); *C07D 215/48* (2013.01); *C07D 217/04* (2013.01); *C07D 231/12* (2013.01); *C07D 231/56* (2013.01); *C07D 233/64* (2013.01); *C07D 237/20* (2013.01); *C07D 239/42* (2013.01); *C07D 241/12* (2013.01); *C07D 249/06* (2013.01); *C07D 249/08* (2013.01); *C07D 263/32* (2013.01); *C07D 263/57* (2013.01); *C07D 265/36* (2013.01); *C07D 277/30* (2013.01); *C07D 277/56* (2013.01); *C07D 277/64* (2013.01); *C07D 307/83* (2013.01); *C07D 311/22* (2013.01); *C07D 333/64* (2013.01); *C07D 401/04* (2013.01); *C07D 401/10* (2013.01); *C07D 409/10* (2013.01); *C07D 413/10* (2013.01); *C07D 471/04* (2013.01); *C07D 487/04* (2013.01); *C07C 2602/08* (2017.05); *C07C 2602/10* (2017.05)

(56) References Cited

U.S. PATENT DOCUMENTS

| | | |
|---|---|---|
| 11,591,330 B2 | 2/2023 | Wei et al. |
| 11,787,762 B2 * | 10/2023 | Beatty .................. C07D 333/64 514/230.5 |
| 2009/0076037 A1 | 3/2009 | Connolly et al. |
| 2015/0148342 A1 | 5/2015 | Yue et al. |
| 2016/0362390 A1 | 12/2016 | Wehn et al. |
| 2019/0233440 A1 | 8/2019 | Planken et al. |
| 2023/0024438 A1 | 1/2023 | Beatty et al. |

FOREIGN PATENT DOCUMENTS

| | | |
|---|---|---|
| EP | 2 857 393 A1 | 4/2015 |
| EP | 2 857 393 B1 | 4/2015 |
| FR | 3071726 A1 | 4/2017 |
| WO | WO-2008/107455 A1 | 9/2008 |
| WO | WO-2014/078479 A2 | 5/2014 |
| WO | WO-2015/035223 A1 | 3/2015 |
| WO | WO-2015/095048 A1 | 6/2015 |
| WO | WO-2016/057242 A1 | 4/2016 |
| WO | WO-2016/144825 A1 | 9/2016 |
| WO | WO-2016/144826 A1 | 9/2016 |
| WO | WO-2016/145032 A1 | 9/2016 |
| WO | WO-2016/145045 A1 | 9/2016 |
| WO | WO-2016/145236 A1 | 9/2016 |
| WO | WO-2016/168510 A1 | 10/2016 |
| WO | WO-2017/053192 A1 | 3/2017 |
| WO | WO-2018/031680 A1 | 2/2018 |
| WO | WO-2019/191227 A1 | 10/2019 |
| WO | WO-2020/055883 A1 | 3/2020 |
| WO | WO-2020/081695 A1 | 4/2020 |
| WO | WO-2020/092100 A1 | 5/2020 |
| WO | WO-2020/214853 A1 | 10/2020 |
| WO | WO-2021/016280 A1 | 1/2021 |

(56) References Cited

FOREIGN PATENT DOCUMENTS

| | | |
|---|---|---|
| WO | WO-2021/105069 A1 | 6/2021 |
| WO | WO-2021/113436 A1 | 6/2021 |
| WO | WO-2021/188769 A1 | 9/2021 |

OTHER PUBLICATIONS

Chen et al., "Targeting Renal Cell Carcinoma with a HIF-2 antagonist", HHS Public Access, Author manuscript, Nature, Nov. 3, 2016; 539(7627): 112-117, doi: 10.1038/nature19796.

Cheng et al., "Marked and rapid effects of pharmacological HIF-2 antagonism on hypoxic ventilatory control", J Clin Invest. 2020 (Jan. 30, 2020); 130(5):2237-2251, https://doi.org/10.1172/JCI133194.

Cho et al., "On-Target Efficacy of a HIF2a Antagonist in Preclinical Kidney Cancer Models", HHS Public Access, Author manuscript, Nature. Nov. 3, 2016; 539(7627): 107-111, doi: 10.1038/nature19795.

Cho et al., "Targeting HIF2 in Clear Renal Cell Carcinoma", Cold Spring Harbor Symposia on Quantitative Biology, vol. LXXXI, pp. 113-121, doi: 10.1101/sqb.2016.81.030833.

Choueiri et al., "Targeting the HIF2-VEGF axis in renal cell carcinoma", Nature Medicine, Apr. 11, 2020, 26, pp. 1519-1530, https://doi.org/10.1038/s41591-020-1093-z.

Coliat et al., "Constitutive or Induced HIF-2 Addiction is Involved in Resistance to Anti-EGFR Treatment and Radiation Therapy in HNSCC", Cancers, 2019, 11, 1607, doi: 10.3390/cancers11101607.

Courtney et al., "Phase I Dose-Escalation Trial of PT2385, a First-in-Class Hypoxia-Inducible Factor-2 Antagonist in Patients With Previously Treated Advanced Clear Cell Renal Cell Carcinoma", Journal of Clinical Oncology, vol. 36, No. 9, Mar. 20, 2018, pp. 867-874.

Dai et al., "Therapeutic Targeting of Vascular Remodeling and Right Heart Failure in PAH with HIF-2 Inhibitor", American Journal of Respiratory and Critical Care Medicine, Jun. 2018, 198, 11, pp. 1423-1434, DOI:10.1164/rccm.201710-2079OC.

Ellinghaus et al., "BAY 87-2243, a highly potent and selective inhibitor of hypoxia-induced gene activation has antitumor activities by inhibition of mitochondrial complex I", Cancer Medicine, 2013; 2(5): 611-624, doi: 10.1002/cam4.112.

Fallah et al., "HIF Inhibitors: Status of Current Clinical Development", Current Oncology Reports, Jan. 22, 2019, 21;6, https://doi.org/10.1007/s11912-019-0752-z.

Fieser et al., "Synthesis of 6-Methylaceanthrene2", JACS (Jan. 1, 1952), 74(2), pp. 536-537.

Fuller et al., "Comparison of Desmethylsertraline With Sertraline as a Monoamine Uptake Inhibitor in Vivo", Prog. Neuoro-Psychopharmacol & Biol. Psychiat (Jan. 1, 1995) 19(1), pp. 135-149.

Gregg L. Semenza, "Hypoxia-inducible factors: mediators of cancer progression and targets for cancer therapy", Trends Pharmacol Sci., Apr. 2012, 33(4), pp. 207-214, doi: 10.1016/j.tips.2012.01.005.

Gupta et al., "Hypoxia-Inducible Factor Prolyl Hydroxylase Inhibitors: A Potential New Treatment for Anemia in Patients With CKD", Am J Kidney Dis., 2017, 69(6), pp. 815-826.

Gupta et al., "Targeting HIF-1a and HIF-2a to Overcome Treatment Resistance Mediated by Oncogenic KRAS in Colorectal Cancer", Journal of Cancer Therapy, 2013, 4, pp. 1132-1139, http://dx.doi.org/10.4236/jct.2013.46129.

Jarman et al., "HER2 regulates HIF-2a and drives an increased hypoxic response in breast cancer", Breast Cancer Research, (2019)21;10, https://doi.org/10.1186/s13058-019-1097-0.

Key et al., "Principles of Ligand Binding within a Completely Buried Cavity in HIF2a PAS-B", J. Am. Chem. Soc. 2009, 131, pp. 17647-17654.

Kizi et al., Azepine Product List, In: Chemical catalogue Azepine Ltd, Basingstoke, Hants, XP055811922 (Mar. 2, 2019), 1 page.

Lee et al., "(Aryloxyacetylamino)benzoic Acid Analogues: A New Class of Hypoxia-Inducible Factor-1 Inhibitors", J. Med. Chem., 2007. 50, pp. 1675-1684.

Li et al., "Advances in inhibition of protein-protein interactions targeting hypoxia-inducible factor-1 for cancer therapy", Bioorganic & Medicinal Chemistry, 27, (2019), pp. 1145-1158.

Li et al., "Small-Molecule Modulators of the Hypoxia-Inducible Factor Pathway: Development and Therapeutic Applications", J. Med. Chem., 2019, 62, pp. 5725-5749.

Lin et al., "Hypoxia-inducible factors: key regulators of myeloid cells during inflammation", The Journal of Clinical Investigation, vol. 126, No. 10, Oct. 2016, pp. 3661-3671.

Marceron et al., "Hypoxia-inducible factor 2a ins a negative regulator of osteoblastogenesis and bone mass accrual", Bone Research, (2019), 7:7.

Matelo et al., "HIF2a inhibitors for the treatment of VHL disease", Oncotarget, vol. 6, No. 27, pp. 22036-22037.

Miikkulainen et al., "Hypoxia-inducible factor (HIF)-prolyl hydroxylase 3 (PHD3) maintains high HIF2A mRNA levels in clear cell renal cell carcinoma", J. Biol. Chem., (2019), 294(10), pp. 3760-3771.

Murugesan et al., "Targeting HIF-2 as therapy for advanced cancers", Drug Discovery Today, vol. 23, No. 7, Jul. 2018, pp. 1444-1451.

Nabi et al., "Renal cell carcinoma: a review of biology and pathophysiology", F1000Research, 2018, 7(F1000 Faculty Rev):307.

Niechi et al., "Adenosine Depletion as a New Strategy to Decrease Glioblastoma Stem-Like Cells Aggressiveness", Cells, 2019, 8, 1353, doi: 10.3390/cells8111353.

Palazon et al., "HIF Transcription Factors, Inflammation, and Immunity", Immunity, Oct. 16, 2014, 41(4), pp. 518-527, doi: 10.1016/j.immuni.2014.09.008.

Pechulis et al., "4-Phenyl tetrahydroisoquinolines as dual norepinephrine and dopamine reuptake inhibitors", Bioorganic & Medical Chemistry Letters, 22, 2012, pp. 7219-7222.

Ricketts et al., "Targeting HIF2a in Clear-Cell Renal Cell Carcinoma", Cancer Cell 30, Oct. 10, 2016, pp. 515-517.

Rogers et al., "Development of Inhibitors of the PAS-B Domain of the HIF-2a Transcription Factor", J. Med. Chem., 2013, 56, pp. 1739-1747, dx.doi.org/10.1021/jm301847z.

Sano et al., "Design and synthesis of subtype-selective cyclooxygenase (COX) inhibitors derived from thalidomide", Bioorganic & Medical Chemistry, 13, 2005, pp. 3079-3091.

Scheuermann et al., "Allosteric Inhibition of Hypoxia Inducible Factor-2 with Small Molecules", Nat. Chem. Biol., Apr. 2013, 9(4), pp. 271-276, doi:10.1038/nchembio.1185.

Scheuermann et al., "Artificial ligand binding within the HIF2a PAS-B domain of the HIF2 transcription factor", PNAS, Jan. 13, 2009, vol. 106, No. 2, pp. 450-455.

Scheuermann et al., "Isoform-Selective and Stereoselective Inhibition of Hypoxia Inducible Factor-2", J. Med. Chem., 2015, 58, pp. 5930-5941, DOI; 10.1021/acs.jmedchem.5b00529.

Shimoda et al., "Revisiting the role of hypoxia-inducible factors in pulmonary hypertension", Current Opinion in Physiology, 2019, 7, pp. 33-40.

Thansandote et al., "Synthesis of Benzannulated N-Heterocycles by a Palladium-Catalyzed C—C/C—N Coupling of Bromoalkylamines", Organic Letters, Dec. 1, 2007, 9(25), pp. 5255-5258.

Wallace et al., "A Small-Molecule Antagonist of HIF2a Is Efficacious in Preclinical Models of Renal Cell Carcinoma", Cancer Res, 76(18), Sep. 15, 2016, pp. 5491-5500.

Wang et al., "HIF-2a mediated activation of the epidermal growth factor receptor potentiates head and neck cancer cell migration in response to hypoxia", Carcinogenesis, vol. 31, No. 7, Apr. 15, 2010, pp. 1202-1210, doi: 10.1093/carcin/bgq078.

Wehn et al., "Design and Activity of Specific Hypoxia-Inducible Factor-2a (HIF-2a) Inhibitors for the Treatment of Clear Cell Renal Cell Carcinoma: Discovery of Clinical Candidate (S)-3-((2,2-Difluoro-1-hydroxy-7-(methylsulfonyl)-2,3-dihydro-1H-inden-4-yl)oxy)-5-fluorobenzonitrile (PT2385)", J. Med. Chem., 2018, 61, pp. 9691-9721.

William G. Kaelin, Jr., MD, "The VHL Tumor Suppressor Gene: Insights Into Oxygen Sensing and Cancer", Transactions of the American Clinical and Climatological Association, vol. 128, 2017, pp. 298-307.

(56) References Cited

OTHER PUBLICATIONS

Wu et al., "Bidirectional Modulation of HIF-2 Activity through Chemical Ligands", Nat. Chem. Biol., Apr. 2019, 15(4), pp. 367-376, doi: 10.1038/s41589-019-0234-5.
Wu et al., "Structural integration in hypoxia-inducible factors", Nature, Aug. 20, 2015, vol. 524, pp. 303-308.
Xiang et al., "Hypoxia-inducible factors promote breast cancer stem cell specification and maintenance in response to hypoxia or cytotoxic chemotherapy", Advances in Cancer Research, vol. 141, 2019, 141, pp. 175-212, https://doi.org/10.1016/bs.acr.2018.11.001.
Yu et al., "Development of Inhibitors Targeting Hypoxia-Inducible Factor 1 and 2 for Cancer Therapy", Yonsei Medical Journal, May 2017, 58(3), pp. 489-496, https;//doi.org/10.3349/ymj.2017.58.3.489.
Zhen et al., "Endothelial PAS domain-containing protein 1 confers TKI-resistance by mediating EGFR and MET pathways in non-small cell lung cancer cells", Cancer Biology & Therapy, Apr. 2015, 16:4, pp. 549-557.
Fuller, et al., "Comparison of Desmethylsertraline with Sertraline as a Monoamine Uptake Inhibitor In Vivo", XP-002270139, Prog. Neuro-Psychopharmacol. & Biol. Psychiat., vol. 19, pp. 135-149, (1995).
Fieser, et al., "Synthesis of 6-Methylaceanthrene", Contribution from the Department of Chemistry, Harvard University, vol. 74, pp. 536-537.
Kizi, "Azepine Product List", In: "Chemical catalogue", Mar. 1, 2019 (Mar. 1, 2019), Azepine Ltd., Basingstoke, Hants, XP055811922, the whole document. Chemcats Copyright 2021 ACS on STN, 1 page, (2001).
Pechulis, et al., "4-Phenyl tetrahydroisoquinolines as dual norepinephrine and dopamine reuptake inhibitors", Bioorganic & Medicinal Chemistry Letters, Bioorganic & Medicinal Chemistry Letters 22, pp. 7219-7222, (2012).
Sano, et al., "Design and synthesis of subtype-selective cyclooxygenase (COX) inhibitors derived from thalidomide", Bioorganic & Medicinal Chemistry 13, pp. 3079-3091, (2005).
Thansandote, et al, "Synthesis of Benzannulated N-Heterocycles by a Palladium-Catalyzed C—C/C—N Coupling of Bromoalkylamines", Organic Letters, vol. 9, No. 25, pp. 5255-5258, (2007).
International Search Report received from the European Patent Office in related International Application No. PCT/US2021/022912 dated Jun. 9, 2021.

\* cited by examiner

TETRALIN AND TETRAHYDROQUINOLINE COMPOUNDS AS INHIBITORS OF HIF-2ALPHA

CROSS-REFERENCES TO RELATED APPLICATIONS

This application is a continuation of U.S. patent application Ser. No. 17/835,559 filed Jun. 8, 2022, which application is a divisional of U.S. patent application Ser. No. 17/205,273 filed Mar. 18, 2021 (now U.S. Pat. No. 11,407,712), which application claims the benefit of priority to U.S. Provisional Application Nos. 62/991,952, filed Mar. 19, 2020, and 63/120,875, filed Dec. 3, 2020, each of which is incorporated herein in its entirety for all purposes.

BACKGROUND

Hypoxia-inducible factor (HIF) transcription factors play an integral role in cellular response to low oxygen availability. [Immunity. 2014 Oct. 16; 41(4): 518-528.] HIFs are heterodimeric transcription factors consisting of a common constitutive subunit called the aryl hydrocarbon receptor nuclear translocator (ARNT, or HIF-β) and one of three HIF-α subunits. [J. Med. Chem. 2015, 58, 5930-5941.] Under normal conditions, the α-subunits are hydroxylated at conserved proline residues by prolyl-4-hydroxylases (PHDs), and subsequently targeted for degredation by the von Hippel-Lindau (pVHL) ubiquitin E3 ligase complex. [Cancer Res 2006; 66(12): 6264-70] However, under hypoxic conditions, HIF-α accumulate and enter the nucleus to activate the expression of genes that regulate metabolism, angiogenesis, cell proliferation and survival, immune evasion, and inflammatory response. [J. Med. Chem. 2018, 61, 9691-9721.]

Of the three different α-subunit isoforms, HIF-1α, HIF-2α and the less characterized HIF-3α, HIF-1α and HIF-2α overexpression have been associated with poor clinical outcomes in patients with various cancers. Specifically, HIF-2α has been found to be a marker of poor prognosis in glioblastoma, neuroblastoma, head and neck squamous carcinoma, and non-small cell lung cancer. Hypoxia is also prevalent in many acute and chronic inflammatory disorders, such as inflammatory bowel disease and rheumatoid arthritis. [J. Clin Invest. 2016; 126(10):3661-3671.]

In view of the significant role of HIF-2α in cancer, inflammation and other disorders, there is a need in the art for HIF-2α inhibitors. The present invention addresses this need and provides related advantages as well.

BRIEF SUMMARY

The present invention relates to compounds that inhibit the activity of hypoxia-inducible factor (HIF) family of transcription factors, particularly HIF-2α. The compounds are represented by Formula (I):

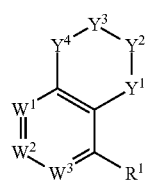

(I)

or a pharmaceutically acceptable salt, hydrate, or solvate thereof, wherein $W^1$, $W^2$, $W^3$, $Y^1$, $Y^2$, $Y^3$, $Y^4$, and $R^1$ have the meanings defined herein below.

In a related aspect, provided herein are methods for treating a disease or disorder mediated by HIF-2α in a subject (e.g., a human) comprising administering to the subject a therapeutically effective amount of at least one HIF-2α inhibitor described herein. Diseases and disorders mediated by HIF-2α include cancer, inflammation, autoimmune disorders and metabolic disorders, as described hereafter. Other diseases, disorders and conditions that can be treated or prevented, in whole or in part, by modulation of HIF-2α activity are candidate indications for the HIF-2α inhibitor compounds provided herein.

Also provided herein is the use of the described HIF-2α inhibitors in combination with one or more additional agents as hereinafter described.

DETAILED DESCRIPTION

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e. $C_{1-8}$ means one to eight carbons). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "hydroxyalkyl" refers to an alkyl group having the indicated number of carbon atoms (e.g., $C_{1-6}$ or $C_{1-8}$) and which is substituted with one or two hydroxy (OH) groups.

The term "hydroxyhaloalkyl" refers to an alkyl group having the indicated number of carbon atoms (e.g., $C_{1-6}$ or $C_{1-8}$) and which is substituted with one or two hydroxy (OH) groups and from one to six halogen atoms (e.g., F, Cl).

The term "alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups, in some embodiments, can be substituted or unsubstituted. When a group comprising an alkylene is optionally substituted, it is understood that the optional substitutions may be on the alkylene portion of the moiety.

The term "cycloalkyl," "carbocycle," or "carbocyclic ring" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. In some embodiments, the cycloalkyl compounds of the present disclosure are monocyclic $C_{3-6}$ cycloalkyl moieties.

The term "heterocycloalkyl," "heterocycle," or "heterocyclic ring" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The heterocycloalkyl may be a monocyclic, a bicyclic or a polycylic ring system, and may have one or two double bonds connecting ring vertices. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom. In some embodiments, the heterocycle is a 5- to 6-membered heterocycle.

As used herein, a wavy line, " ", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O)NH—" is meant to include a linkage in either orientation: —C(O)NH— or —NHC(O)—, and similarly, "—O—$CH_2CH_2$—" is meant to include both —O—$CH_2CH_2$— and —$CH_2CH_2$—O—.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl. The term is also meant to include fused cycloalkylphenyl and heterocycloalkylphenyl ring systems such as, for example, indane, tetrahydronaphthalene, chromane and isochromane rings. As a substituent group, the point of attachment to the remainder of the molecule, for a fused ring system can be through a carbon atom on the aromatic portion, a carbon atom on the cycloalkyl portion, or an atom on the heterocycloalkyl portion.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl," "aryl" and "heteroaryl"), in some embodiments, will be optionally substituted. Selected substituents for each type of radical are provided below.

Optional substituents for the alkyl radicals (including those groups often referred to as alkylene, alkenyl, and alkynyl) can be a variety of groups, for example, groups selected from: halogen, —OR', —NR'R", —SR', —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN (cyano), —NO$_2$, aryl, aryloxy, oxo (=O), cycloalkyl and heterocycloalkyl in a number ranging from zero to (2 m'+1), where m' is the total number of carbon atoms in such radical. R', R" and R"' each independently refer to hydrogen, unsubstituted $C_{1-8}$ alkyl, unsubstituted aryl, aryl substituted with 1-3 halogens, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Optional substituents for the cycloalkyl and heterocycloalkyl radicals can be a variety of groups, for example, groups selected from: alkyl optionally substituted with —C(O)OR', halogen, —OR', —NR'R", —SR', —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NH—C(NH$_2$)═NH, —NR'C(NH$_2$)═NH, —NH—C(NH$_2$)═NR', —S(O)R', —S(O)$_2$R', —S(O)$_2$NR'R", —NR'S(O)$_2$R", —CN (cyano), —NO$_2$, aryl, aryloxy, and oxo (═O), R', R" and R'" each independently refer to hydrogen, unsubstituted C$_{1-8}$ alkyl, unsubstituted aryl, aryl substituted with 1-3 halogens, C$_{1-8}$ alkoxy or C$_{1-8}$ thioalkoxy groups, or unsubstituted aryl-C$_{1-4}$ alkyl groups.

The optional substituents for the cycloalkyl and heterocycloalkyl radicals may also include olefins (═CR'R"), wherein R' and R" each independently refer to hydrogen, unsubstituted C$_{1-8}$ alkyl, unsubstituted aryl, aryl substituted with 1-3 halogens, C$_{1-8}$ alkoxy or C$_{1-8}$ thioalkoxy groups, or unsubstituted aryl-C$_{1-4}$ alkyl groups. For example, the olefin can be an unsubstituted olefin (═CH$_2$).

Similarly, optional substituents for the aryl and heteroaryl groups are varied and, for example, can be selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —NH—C(NH$_2$)═NH, —NR'C(NH$_2$)═NH, —NH—C(NH$_2$)═NR', —S(O)R', —S(O)$_2$R', —S(O)$_2$NR'R", —NR'S(O)$_2$R", —N$_3$, perfluoro(C$_{1-4}$)alkoxy, and perfluoro(C$_{1-4}$)alkyl, in a number ranging from zero to the total number of open valences on the aromatic ring system; and where R', R" and R'" are independently selected from hydrogen, C$_{1-8}$ alkyl, C$_{1-8}$ haloalkyl, C$_{3-6}$ cycloalkyl, C$_{2-8}$ alkenyl and C$_{2-8}$ alkynyl. Other suitable substituents include each of the above aryl substituents attached to a ring atom by an alkylene tether of from 1-6 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CR$^f$R$^g$)$_r$—B—, wherein A and B are independently —CH$_2$—, —O—, —NH—, —S—, —S(O)—, —S(O)$_2$—, —S(O)$_2$NR'— or a single bond, r is an integer of from 1 to 3, and R$^f$ and R$^g$ are each independently H or halogen. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al, "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention may be present, under particular conditions, as polymorphs. Polymorphism refers to the ability of a solid material to exist in more than one crystal structure form or phase, wherein the molecules in the crystal lattice have different arrangements or conformations. If such types of differences exist due to packing it is referred to as "packing polymorphism", and if they exist due to differences in conformation it is referred to as "conformational polymorphism". Different polymorphs of the same compound often display different physical properties, including packing properties, spectroscopic properties, thermodynamic properties, solubility, and melting point; kinetic properties such as rate of dissolution and stability; and mechanical properties such as hardness and tensile strength.

Polymorphs can be classified as one of two types according to their stability with respect to different ranges of temperature and pressure. In a monotropic system, only one polymorph (i.e., monotrope) is stable, and it exhibits lower free energy content and solubility at all temperatures and pressure below melting point. In an enantiotropic system, one polymorph is stable at a certain temperature and pressure, while the other polymorph(s) is stable at various temperatures and pressure.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application.

For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of HIF-2α, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of HIF-2α or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an HIF-2α inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an HIF-2α inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of HIF-2α, either directly or indirectly. A modulator may act alone, or it may use a cofactor, e.g., a protein, metal ion, or small molecule. Examples of modulators include small molecule compounds and other bioorganic molecules.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

Compounds that are selective may be particularly useful in the treatment of certain disorders or may offer a reduced likelihood of undesired side effects. In one embodiment, compounds of the present disclosure are selective over other HIF isoforms. In still another embodiment, the compounds of the present disclosure are selective over other kinases and targets in the HIF signaling pathway. Specific examples include HIF-1α and cytochrome P450 enzymes. Selectivity may be determined, for example, by comparing the inhibition of a compound as described herein against HIF-2α against the inhibition of a compound as described herein against another protein. In one embodiment, the selective inhibition of HIF-2α is at least 1000 times greater, 500 times greater, or 100 times greater, or 20 times greater than inhibition of another protein or isoform.

Compounds provided herein may have advantageous pharmacokinetic profiles including, for example, hepatocyte stability, clearance, and inhibition against CYP.

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

Compounds of the Disclosure

In one particular aspect, provided herein are compounds having Formula (I):

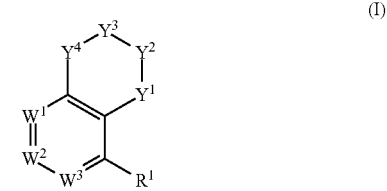

or a pharmaceutically acceptable salt, hydrate, or solvate thereof, wherein:

$Y^1$, $Y^2$, $Y^3$ and $Y^4$ are each independently selected from the group consisting of $CR^2R^3$, $NR^4$, $CR^6R^7$, $NR^7$, O, $SO_2$, and a bond; and one of $Y^1$, $Y^2$, $Y^3$ and $Y^4$ is $CR^6R^7$ or $NR^7$; and no more than one of $Y^1$, $Y^2$, $Y^3$ and $Y^4$ is a bond;

$W^1$, $W^2$ and $W^3$ are each independently selected from the group consisting of $CR^5$ and N;

$R^1$ is selected from the group consisting of H, halogen, hydroxy, CN, $NO_2$, —$NR^aR^b$, $C_{1-4}$ alkyl, $C_{1-4}$ haloalkyl, $C_{1-4}$ alkoxy, $C_{1-4}$ haloalkoxy, $C_{1-4}$ hydroxyalkyl, $C_{1-4}$ alkoxy$C_{1-4}$alkyl, $C_{3-8}$ cycloalkyl, —$S(O)_2R^a$, —$C(O)NR^aR^b$, —$S(O)(=NH)R^a$, and —$S(O)_2NR^aR^b$;

each $R^2$ and $R^3$ are each independently selected from the group consisting of H, halogen, CN, $NO_2$, OH, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-4}$ alkoxy$C_{1-4}$alkyl, $C_{3-8}$ cycloalkyl, —$S(O)_2R^a$, —$CO_2R^a$, —$C(O)R^a$, —$C(O)NR^aR^b$, —$S(O)_2NR^aR^b$, —$S(O)(=NH)R^a$, and —$NR^aR^b$;

each $R^4$ is independently selected from H, $C_{1-4}$ alkyl, $C_{3-8}$ cycloalkyl, and —$C(O)R^a$, each $R^5$ is independently selected from the group consisting of H, halogen, CN, $NO_2$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-4}$ alkoxyC$_{1-4}$alkyl, C$_{3-8}$ cycloalkyl, —S(O)$_2$R$^a$, —CO$_2$R$^a$, —C(O)R$^a$, —C(O)NR$^a$R$^b$, —S(O)$_2$NR$^a$R$^b$, —S(O)(=NH)R$^a$, and —NR$^a$R$^b$;

R$^6$ is selected from the group consisting of H, C$_{1-4}$ alkyl, OH, F and CN;

R$^7$ is a group having the formula:

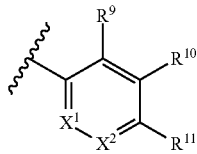

wherein:

X$^1$ is N or CR$^{8a}$,

X$^2$ is N or CR$^{8b}$;

R$^{8a}$ and R$^{8b}$ are independently selected from the group consisting of H, halogen, CN, NO$_2$, C$_{1-6}$ alkyl, C$_{1-6}$ haloalkyl, C$_{1-6}$ alkoxy, C$_{1-6}$ haloalkoxy, C$_{1-6}$ hydroxyalkyl, C$_{1-4}$ alkoxyC$_{1-4}$alkyl, C$_{3-6}$ cycloalkyl, —C(O)NR$^a$R$^b$, —S(O)$_2$NR$^a$R$^b$, and —S(O)$_2$R$^a$;

R$^9$ and R$^{10}$ are independently selected from the group consisting of H, halogen, CN, NO$_2$, C$_{1-6}$ alkyl, C$_{1-6}$ haloalkyl, C$_{1-6}$ alkoxy, C$_{1-6}$ haloalkoxy, C$_{1-6}$ hydroxyalkyl, C$_{1-6}$ hydroxyhaloalkyl, C$_{1-4}$ alkoxyC$_{1-4}$alkyl, C$_{3-8}$ cycloalkyl, —C(O)R$^a$, —C(O)OR$^a$, —C(O)NR$^a$R$^b$, —S(O)$_2$NR$^a$R$^b$, and —S(O)$_2$R$^a$;

R$^{11}$ is selected from the group consisting of H, halogen, CN, NO$_2$, C$_{1-6}$ alkyl, C$_{1-6}$ haloalkyl, C$_{1-6}$ alkoxy, C$_{1-6}$ haloalkoxy, C$_{1-6}$ hydroxyalkyl, C$_{1-6}$ hydroxyhaloalkyl, C$_{1-4}$ alkoxyC$_{1-4}$alkyl, C$_{3-8}$ cycloalkyl, —C(O)NR$^a$R$^b$, —S(O)$_2$NR$^a$R$^b$, —S(O)(=NH)R$^c$, —S(O)$_2$R$^c$ and a 5- or 6-membered heterocyclic or heteroaryl ring having from 1-3 heteroatoms as ring vertices selected from N, O, and S; wherein the heterocyclic or heteroaryl ring is optionally substituted with from one to three members independently selected from halogen, CN, NO$_2$, C$_{1-6}$ alkyl, C$_{1-6}$ haloalkyl, C$_{1-6}$ alkoxy, C$_{1-6}$ haloalkoxy, C$_{1-6}$ hydroxyalkyl, C$_{1-6}$ hydroxyhaloalkyl and C$_{1-4}$ alkoxyC$_{1-4}$ alkyl;

or R$^9$ and R$^{10}$ are combined to form a 5-membered carbocyclic or heterocyclic ring or a 6-membered carbocyclic, heterocyclic or heteroaryl ring, which is optionally substituted with one or more substituents, e.g., 1, 2, 3, or 4, independently selected from R$^{12}$, R$^{13}$, R$^{14}$, R$^{15}$, R$^{16}$, R$^{17}$, R$^{18}$ and R$^{19}$, the heterocyclic or heteroaryl ring each have from 1-4 heteroatoms as ring vertices selected from N, O and S;

or R$^{10}$ and R$^{11}$ are combined to form a 5- or 6-membered carbocyclic, heterocyclic or heteroaryl ring, which is optionally substituted with one or more substituents, e.g., 1, 2, 3, or 4, independently selected from R$^{12}$, R$^{13}$, R$^{14}$, R$^{15}$, R$^{16}$, R$^{17}$, R$^{18}$ and R$^{19}$, the heterocyclic or heteroaryl ring each have from 1-4 heteroatoms as ring vertices selected from N, O and S;

each of R$^{12}$, R$^{13}$, R$^{14}$, R$^{15}$, R$^{16}$, R$^{17}$, R$^{18}$ and R$^{19}$ is independently selected from the group consisting of H, halogen, CN, OH, C$_{1-4}$ alkyl, C$_{1-4}$ haloalkyl, C$_{1-4}$ alkoxy, C$_{1-4}$ haloalkoxy, C$_{1-4}$ hydroxyalkyl, C$_{1-4}$ alkoxyC$_{1-4}$alkyl and —NR$^a$R$^b$; or two R$^{12}$, R$^{13}$, R$^{14}$, R$^{15}$, R$^{16}$, R$^{17}$, R$^{18}$ and R$^{19}$ moieties on the same carbon atom combine to form an oxo group;

each R$^a$ and R$^b$ is independently selected from the group consisting of H, C$_{1-8}$ alkyl, C$_{1-8}$ haloalkyl, C$_{1-8}$ haloalkoxy, and C$_{1-8}$ hydroxyalkyl and R$^c$, when present, is selected from the group consisting of H, C$_{1-8}$ alkyl, C$_{1-8}$ alkoxy, C$_{1-8}$ haloalkyl, C$_{1-8}$ haloalkoxy, C$_{1-8}$ hydroxyalkyl, C$_{3-6}$ cycloalkyl, 3- to 6-membered heterocycloalkyl, and 5- or 6-membered heteroaryl, the heterocycloalkyl or heteroaryl ring each have from 1-4 heteroatoms as ring vertices selected from N, O and S, provided that when combined with the groups to which R$^a$, R$^b$, and Re are attached, N-oxide and peroxide linkages are not formed.

In some selected embodiments, the compound of Formula (I) or a pharmaceutically acceptable salt, hydrate, or solvate thereof, is a compound wherein each of Y$^2$, Y$^3$ and Y$^4$ is CR$^2$R$^3$.

In some selected embodiments, the compound of Formula (I) or a pharmaceutically acceptable salt, hydrate, or solvate thereof, is a compound wherein each of Y$^2$ and Y$^3$ is CR$^2$R$^3$, and Y$^4$ is a bond.

In some selected embodiments, the compound of Formula (I) is represented by Formula (II):

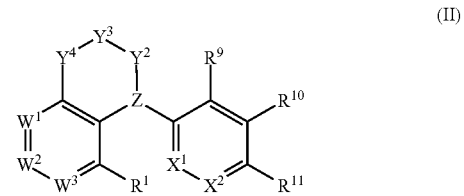

or a pharmaceutically acceptable salt, hydrate, or solvate thereof, wherein Z is N or CR$^6$, and the remaining groups have the meanings provided for Formula (I).

In some selected embodiments, the compound of Formula (I), or a pharmaceutically acceptable salt, hydrate, or solvate thereof has Formula (II):

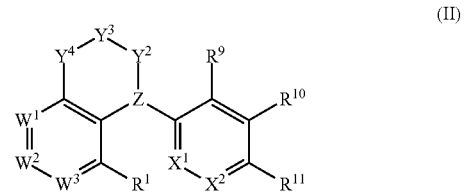

wherein

Z is N or CR$^6$;

Y$^2$, Y$^3$ and Y$^4$ are each independently selected from the group consisting of CR$^2$R$^3$, NR$^4$, O, SO$_2$, and a bond; and no more than one of Y$^2$, Y$^3$ and Y$^4$ is a bond;

W$^1$, W$^2$, and W$^3$ are each independently selected from the group consisting of CR$^5$ and N;

R$^1$ is selected from the group consisting of H, halogen, hydroxy, CN, NO$_2$, —NR$^a$R$^b$, C$_{1-4}$ alkyl, C$_{1-4}$ haloalkyl, C$_{1-4}$ alkoxy, C$_{1-4}$ haloalkoxy, C$_{1-4}$ hydroxyalkyl, C$_{1-4}$ alkoxyC$_{1-4}$alkyl, C$_{3-8}$ cycloalkyl, —S(O)$_2$R$^a$, —C(O)NR$^a$R$^b$, —S(O)(=NH)R$^a$, and —S(O)$_2$NR$^a$R$^b$;

each R$^2$ and R$^3$ are each independently selected from the group consisting of H, halogen, CN, NO$_2$, OH, C$_{1-6}$ alkyl, C$_{1-6}$ haloalkyl, C$_{1-6}$ alkoxy, C$_{1-6}$ haloalkoxy, C$_{1-6}$ hydroxyalkyl, C$_{1-4}$ alkoxyC$_{1-4}$alkyl, C$_{3-8}$ cycloalkyl, —S(O)$_2$R$^a$, —CO$_2$R$^a$, —C(O)R$^a$, —C(O)NR$^a$R$^b$, —S(O)$_2$NR$^a$R$^b$, —S(O)(=NH)R$^a$, and —NR$^a$R$^b$;

each R⁴ is independently selected from H, C₁₋₄ alkyl, C₃₋₈ cycloalkyl, and —C(O)Rᵃ, each R⁵ is independently selected from the group consisting of H, halogen, CN, NO₂, C₁₋₆ alkyl, C₁₋₆ haloalkyl, C₁₋₆ alkoxy, C₁₋₆ haloalkoxy, C₁₋₆ hydroxyalkyl, C₁₋₄ alkoxyC₁₋₄alkyl, C₃₋₈ cycloalkyl, —S(O)₂Rᵃ, —CO₂Rᵃ, —C(O)Rᵃ, —C(O)NRᵃRᵇ, —S(O)₂NRᵃRᵇ, —S(O)(=NH)Rᵃ, and —NRᵃRᵇ;

X¹ is N or CR⁸ᵃ,

X² is N or CR⁸ᵇ;

R⁸ᵃ and R⁸ᵇ are independently selected from the group consisting of H, halogen, CN, NH₂, NO₂, C₁₋₆ alkyl, C₁₋₆ haloalkyl, C₁₋₆ alkoxy, C₁₋₆ haloalkoxy, C₁₋₆ hydroxyalkyl, C₁₋₄ alkoxyC₁₋₄alkyl, C₃₋₆ cycloalkyl, —C(O)NRᵃRᵇ, —S(O)₂NRᵃRᵇ, and —S(O)₂Rᵃ;

R⁹ and R¹⁰ are independently selected from the group consisting of H, halogen, CN, NO₂, C₁₋₆ alkyl, C₁₋₆ haloalkyl, C₁₋₆ alkoxy, C₁₋₆ haloalkoxy, C₁₋₆ hydroxyalkyl, C₁₋₆ hydroxyhaloalkyl, C₁₋₄ alkoxyC₁₋₄alkyl, C₃₋₈ cycloalkyl, —C(O)Rᵃ, —C(O)ORᵃ, —C(O)NRᵃRᵇ, —S(O)₂NRᵃRᵇ, and —S(O)₂Rᵃ, R¹¹ is selected from the group consisting of H, halogen, CN, NO₂, C₁₋₆ alkyl, C₁₋₆ haloalkyl, C₁₋₆ alkoxy, C₁₋₆ haloalkoxy, C₁₋₆ hydroxyalkyl, C₁₋₆ hydroxyhaloalkyl, C₁₋₄ alkoxyC₁₋₄alkyl, C₃₋₈ cycloalkyl, —NRᵃRᵇ, —C(O)NRᵃRᵇ, —C(O)OH, —S(O)₂NRᵃRᵇ, —S(O)(=NH)Rᶜ, —S(O)₂Rᶜ, phenyl, 5- to 6-membered heterocyclic or 5- to 10-membered heteroaryl ring, wherein the heterocyclic and heteroaryl rings have from 1-3 heteroatoms as ring vertices selected from N, O, and S; wherein the phenyl is optionally fused to a 5- or 6-membered heterocycle having from 1-2 heteroatoms as ring vertices selected from N, O, and S; and wherein the phenyl, heterocyclic or heteroaryl rings are optionally substituted with from one to three members independently selected from halogen, CN, NO₂, NH₂, C(O)NH₂, S(O)₂CH₃, —CH₂NH₂, C₁₋₆ alkyl, C₁₋₆ haloalkyl, C₁₋₆ alkoxy, C₁₋₆ haloalkoxy, C₁₋₆ hydroxyalkyl, C₁₋₆ hydroxyhaloalkyl and C₁₋₄ alkoxyC₁₋₄alkyl; optionally wherein two members attached to the same carbon of the heterocyclic ring taken together form =CH₂ or oxo (=O) group;

or R⁹ and R¹⁰ are combined to form a 5-membered carbocyclic or heterocyclic ring or a 6-membered carbocyclic, heterocyclic or heteroaryl ring, which is optionally substituted with one or more substituents independently selected from R¹², R¹³, R¹⁴, R¹⁵, R¹⁶, R¹⁷, R¹⁸ and R¹⁹, the heterocyclic or heteroaryl ring each have from 1-4 heteroatoms as ring vertices selected from N, O and S;

or R¹⁰ and R¹¹ are combined to form a 5- or 6-membered carbocyclic, heterocyclic or heteroaryl ring, which is optionally substituted with one or more substituents independently selected from R¹², R¹³, R¹⁴, R¹⁵, R¹⁶, R¹⁷, R¹⁸ and R¹⁹, the heterocyclic or heteroaryl ring each have from 1-4 heteroatoms as ring vertices selected from N, O and S;

each of R¹², R¹³, R¹⁴, R¹⁵, R¹⁶, R¹⁷, R¹⁸ and R¹⁹ is independently selected from the group consisting of H, halogen, CN, OH, C₁₋₄ alkyl, C₁₋₄ haloalkyl, C₁₋₄ alkoxy, C₁₋₄ haloalkoxy, C₁₋₄ hydroxyalkyl, C₁₋₄ alkoxyC₁₋₄alkyl and —NRᵃRᵇ; or two R¹², R¹³, R¹⁴, R¹⁵, R¹⁶, R¹⁷, R¹⁸ and R¹⁹ moieties on the same carbon atom combine to form an oxo group;

each Rᵃ and Rᵇ is independently selected from the group consisting of H, C₁₋₈ alkyl, C₁₋₈ alkoxy, C₁₋₈ haloalkyl, C₁₋₈ haloalkoxy, and C₁₋₈ hydroxyalkyl and Rᶜ, when present, is selected from the group consisting of H, C₁₋₈ alkyl, C₁₋₈ alkoxy, C₁₋₈ haloalkyl, C₁₋₈ haloalkoxy, C₁₋₈ hydroxyalkyl, C₃₋₆ cycloalkyl, 3- to 6-membered heterocycloalkyl, and 5- or 6-membered heteroaryl, wherein the heterocycloalkyl or heteroaryl ring each have from 1-4 heteroatoms as ring vertices selected from N, O and S.

In some embodiments, the compound of Formula (II) is a compound or a pharmaceutically acceptable salt, hydrate, or solvate thereof wherein Y² is CR²R³, wherein each R² and R³ is H; and Y³ and Y⁴ are each CR²R³, wherein each R² and R³ are independently selected from H and F.

In some embodiments, the compound of Formula (II) is a compound or a pharmaceutically acceptable salt, hydrate, or solvate thereof wherein R¹¹ is SO₂Rᶜ. In some embodiments, Rᶜ is C₁₋₈ alkyl, or C₁₋₈ haloalkyl.

In some embodiments, the compound of Formula (II) is a compound or a pharmaceutically acceptable salt, hydrate, or solvate thereof wherein R¹¹ is selected from the group consisting of:

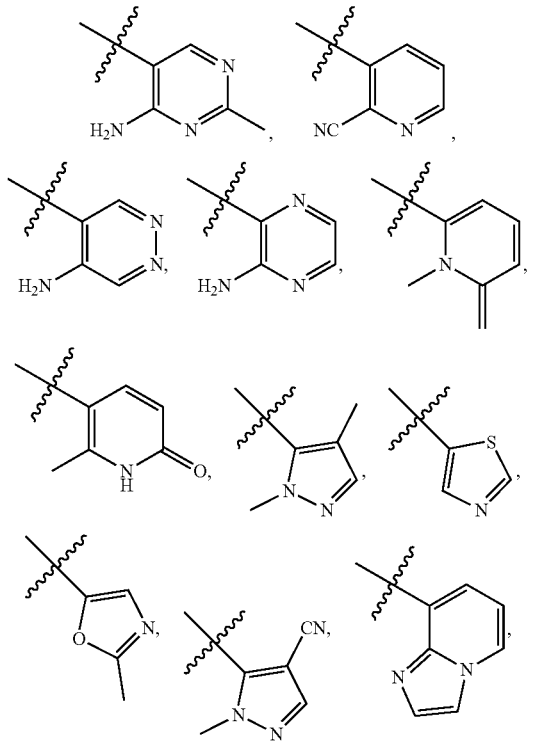

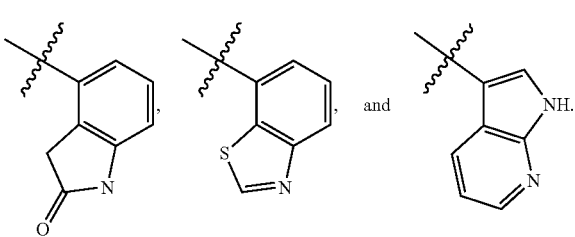

and

In some selected embodiments, the compound of Formula (I) is represented by Formula (III):

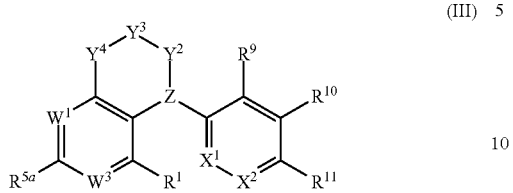

(III)

or a pharmaceutically acceptable salt, hydrate, or solvate thereof, $Y^2$, $Y^3$ and $Y^4$ are each independently selected from the group consisting of $CR^2R^3$, $NR^4$, $SO_2$, O and a bond; and no more than one of $Y^2$, $Y^3$ and $Y^4$ is a bond;

$W^1$ and $W^3$ are each independently selected from CH and N;

Z is N or $CR^6$;

$R^1$ is selected from the group consisting of halogen and CN;

each $R^2$ and $R^3$ are each independently selected from the group consisting of H, halogen, CN, $NO_2$, OH, $C_{1-3}$ alkyl, $C_{1-3}$ haloalkyl, $C_{1-3}$ alkoxy, $C_{1-3}$ haloalkoxy, $C_{1-3}$ hydroxyalkyl, $C_{1-4}$ alkoxy$C_{1-4}$alkyl, $C_{3-6}$ cycloalkyl, —S(O)$_2R^a$, —CO$_2R^a$, —C(O)$R^a$, —C(O)NR$^aR^b$, —S(O)$_2$NR$^aR^b$, —S(O)(=NH)$R^a$, and —NR$^aR^b$ each $R^4$ is independently selected from H, $C_{1-3}$ alkyl, $C_{3-6}$ cycloalkyl, and —C(O)$R^a$;

$R^{5a}$ is selected from the group consisting of hydrogen, halogen, and CN;

$R^6$ is H $X^1$ is N or $CR^{8a}$;

$X^2$ is N or CR 8b;

$R^{8a}$ and $R^{8b}$ are independently selected from the group consisting of H, halogen, CN, $NH_2$, $NO_2$, $C_{1-3}$ alkyl, $C_{1-3}$ haloalkyl, $C_{1-3}$ alkoxy, $C_{1-3}$ haloalkoxy, $C_{1-6}$ hydroxyalkyl, $C_{1-3}$ alkoxy$C_{1-4}$alkyl, $C_{3-6}$ cycloalkyl, —C(O)NR$^aR^b$, —S(O)$_2$NR$^aR^b$, and —S(O)$_2R^a$;

$R^9$ and $R^{10}$ are independently selected from the group consisting of H, halogen, CN, $NO_2$, $C_{1-3}$ alkyl, $C_{1-3}$ haloalkyl, $C_{1-3}$ alkoxy, $C_{1-3}$ haloalkoxy, $C_{1-3}$ hydroxyalkyl, $C_{1-3}$ hydroxyhaloalkyl, $C_{1-4}$ alkoxy$C_{1-4}$alkyl, $C_{3-8}$ cycloalkyl, —C(O)$R^a$, —C(O)OR$^a$, —C(O)NR$^aR^b$, —S(O)$_2$NR$^aR^b$, and —S(O)$_2R^a$;

$R^{11}$ is selected from the group consisting of H, halogen, CN, $NO_2$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ hydroxyhaloalkyl, $C_{1-4}$ alkoxy$C_{1-4}$alkyl, $C_{3-8}$ cycloalkyl, —C(O)NR$^aR^b$, —C(O)OH, —S(O)$_2$NR$^aR^b$, —S(O)(=NH)$R^c$, —S(O)$_2R^c$, phenyl, and a 5- or 6-membered heterocyclic or 5- to 10-membered heteroaryl ring, wherein the heterocyclic or heteroaryl ring has from 1-3 heteroatoms as ring vertices selected from N, O and S; wherein the phenyl is optionally fused to a 5- or 6-membered heterocycle having from 1-2 heteroatoms as ring vertices selected from N, O, and S; and wherein the phenyl, heterocyclic or heteroaryl ring is optionally substituted with from one to three members independently selected from halogen, CN, $NO_2$, $NH_2$, $C(O)NH_2$, $S(O)_2CH_3$, —$CH_2NH_2$, $C_{1-3}$ alkyl, $C_{1-3}$ haloalkyl, $C_{1-3}$ alkoxy, $C_{1-3}$ haloalkoxy, $C_{1-3}$ hydroxyalkyl, $C_{1-3}$ hydroxyhaloalkyl and $C_{1-3}$ alkoxy$C_{1-4}$alkyl; optionally wherein two members attached to the same carbon of the heterocyclic ring taken together form =$CH_2$ or oxo (=O) group;

or $R^9$ and $R^{10}$ are combined to form a 5-membered carbocyclic or heterocyclic ring or a 6-membered carbocyclic, heterocyclic or heteroaryl ring, which is optionally substituted with one or more substituents independently selected from $R^{12}$, $R^{13}$, $R^{14}$, $R^{15}$, $R^{16}$, $R^{17}$, $R^{18}$ and $R^{19}$, the heterocyclic or heteroaryl ring each have from 1-4 heteroatoms as ring vertices selected from N, O and S;

or $R^{10}$ and $R^{11}$ are combined to form a 5- or 6-membered carbocyclic, heterocyclic or heteroaryl ring, which is optionally substituted with one or more substituents independently selected from $R^{12}$, $R^{13}$, $R^{14}$, $R^{15}$, $R^{16}$, $R^{17}$, $R^{18}$ and $R^{19}$, the heterocyclic or heteroaryl ring each have from 1-4 heteroatoms as ring vertices selected from N, O and S;

each of $R^{12}$, $R^{13}$, $R^{14}$, $R^{15}$, $R^{16}$, $R^{17}$, $R^{18}$ and $R^{19}$ is independently selected from the group consisting of H, halogen, CN, OH, $C_{1-4}$ alkyl, $C_{1-4}$ haloalkyl, $C_{1-4}$ alkoxy, $C_{1-4}$ haloalkoxy, $C_{1-4}$ hydroxyalkyl, $C_{1-4}$ alkoxy$C_{1-4}$alkyl and —NR$^aR^b$, or two $R^{12}$, $R^{13}$, $R^{14}$, $R^{15}$, $R^{16}$, $R^{17}$, $R^{18}$ and $R^{19}$ moieties on the same carbon atom combine to form an oxo group;

each $R^a$ and $R^b$ is independently selected from the group consisting of H, $C_{1-3}$ alkyl, $C_{1-3}$ alkoxy, $C_{1-3}$ haloalkyl, $C_{1-3}$ haloalkoxy, and $C_{1-3}$ hydroxyalkyl; and $R^c$, when present, is selected from the group consisting of H, $C_{1-8}$ alkyl, $C_{1-8}$ alkoxy, $C_{1-8}$ haloalkyl, $C_{1-8}$ haloalkoxy, $C_{1-8}$ hydroxyalkyl, $C_{3-6}$ cycloalkyl, 3- to 6-membered heterocycloalkyl, and 5- or 6-membered heteroaryl, the heterocycloalkyl or heteroaryl ring each have from 1-4 heteroatoms as ring vertices selected from N, O and S.

In some selected embodiments, the compound of Formula (I) is represented by Formula (III):

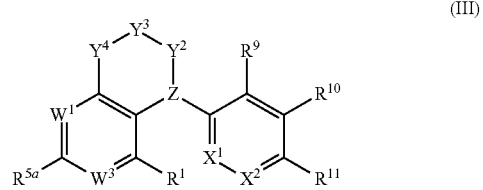

(III)

or a pharmaceutically acceptable salt, hydrate, or solvate thereof, $Y^2$, $Y^3$ and $Y^4$ are each independently selected from the group consisting of $CR^2R^3$, $NR^4$, $SO_2$, O and a bond; and no more than one of $Y^2$, $Y^3$ and $Y^4$ is a bond;

$W^1$ and $W^3$ are each independently selected from CH and N;

Z is N or $CR^6$;

$R^1$ is selected from the group consisting of halogen and CN;

each $R^2$ and $R^3$ are each independently selected from the group consisting of H, halogen, CN, $NO_2$, OH, $C_{1-3}$ alkyl, $C_{1-3}$ haloalkyl, $C_{1-3}$ alkoxy, $C_{1-3}$ haloalkoxy, $C_{1-3}$ hydroxyalkyl, $C_{1-4}$ alkoxy$C_{1-4}$alkyl, $C_{3-6}$ cycloalkyl, —S(O)$_2R^a$, —CO$_2R^a$, —C(O)$R^a$, —C(O)NR$^aR^b$, —S(O)$_2$NR$^aR^b$, —S(O)(=NH)$R^a$, and —NR$^aR^b$ each $R^4$ is independently selected from H, $C_{1-3}$ alkyl, $C_{3-6}$ cycloalkyl, and —C(O)$R^a$;

$R^{5a}$ is selected from the group consisting of hydrogen, halogen, and CN;

$R^6$ is H $X^1$ is N or $CR^{8a}$, $X^2$ is N or $CR^{8b}$, $R^{8a}$ and $R^{8b}$ are independently selected from the group consisting of H, halogen, CN, $NO_2$, $C_{1-3}$ alkyl, $C_{1-3}$ haloalkyl, $C_{1-3}$ alkoxy, $C_{1-3}$ haloalkoxy, $C_{1-6}$ hydroxyalkyl, $C_{1-3}$ alkoxy$C_{1-4}$alkyl, $C_{3-6}$ cycloalkyl, —C(O)$NR^aR^b$, —S(O)$_2NR^aR^b$, and —S(O)$_2R^a$;

$R^9$ and $R^{10}$ are independently selected from the group consisting of H, halogen, CN, $NO_2$, $C_{1-3}$ alkyl, $C_{1-3}$ haloalkyl, $C_{1-3}$ alkoxy, $C_{1-3}$ haloalkoxy, $C_{1-3}$ hydroxyalkyl, $C_{1-3}$ hydroxyhaloalkyl, $C_{1-4}$ alkoxy$C_{1-4}$alkyl, $C_{3-8}$ cycloalkyl, —C(O)$R^a$, —C(O)O$R^a$, —C(O)$NR^aR^b$, —S(O)$_2NR^aR^b$, and —S(O)$_2R^a$;

$R^{11}$ is selected from the group consisting of H, halogen, CN, $NO_2$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ hydroxyhaloalkyl, $C_{1-4}$ alkoxy$C_{1-4}$alkyl, $C_{3-8}$ cycloalkyl, —C(O)$NR^aR^b$, —S(O)$_2NR^aR^b$, —S(O)(=NH)$R^c$, —S(O)$_2R^c$ and a 5- or 6-membered heterocyclic or heteroaryl ring having from 1-3 heteroatoms as ring vertices selected from N, O and S; wherein the heterocyclic or heteroaryl ring is optionally substituted with from one to three members independently selected from halogen, CN, $NO_2$, $C_{1-3}$ alkyl, $C_{1-3}$ haloalkyl, $C_{1-3}$ alkoxy, $C_{1-3}$ haloalkoxy, $C_{1-3}$ hydroxyalkyl, $C_{1-3}$ hydroxyhaloalkyl and $C_{1-3}$ alkoxy$C_{1-4}$alkyl;

or $R^9$ and $R^{10}$ are combined to form a 5-membered carbocyclic or heterocyclic ring or a 6-membered carbocyclic, heterocyclic or heteroaryl ring, which is optionally substituted with $R^{12}$, $R^{13}$, $R^{14}$, $R^{15}$, $R^{16}$, $R^{17}$, $R^{18}$ and $R^{19}$, the heterocyclic or heteroaryl ring each have from 1-4 heteroatoms as ring vertices selected from N, O and S;

or $R^{10}$ and $R^{11}$ are combined to form a 5- or 6-membered carbocyclic, heterocyclic or heteroaryl ring, which is optionally substituted with $R^{12}$, $R^{13}$, $R^{14}$, $R^{15}$, $R^{16}$, $R^{17}$, $R^{18}$ and $R^{19}$, the heterocyclic or heteroaryl ring each have from 1-4 heteroatoms as ring vertices selected from N, O and S;

each of $R^{12}$, $R^{13}$, $R^{14}$, $R^{15}$, $R^{16}$, $R^{17}$, $R^{18}$ and $R^{19}$ is independently selected from the group consisting of H, halogen, CN, OH, $C_{1-4}$ alkyl, $C_{1-4}$ haloalkyl, $C_{1-4}$ alkoxy, $C_{1-4}$ haloalkoxy, $C_{1-4}$ hydroxyalkyl, $C_{1-4}$ alkoxy$C_{1-4}$alkyl and —$NR^aR^b$, or two $R^{12}$, $R^{13}$, $R^{14}$, $R^{15}$, $R^{16}$, $R^{17}$, $R^{18}$ and $R^{19}$ moieties on the same carbon atom combine to form an oxo group;

each $R^a$ and $R^b$ is independently selected from the group consisting of H, $C_{1-3}$ alkyl, $C_{1-3}$ alkoxy, $C_{1-3}$ haloalkyl, $C_{1-3}$ haloalkoxy, and $C_{1-3}$ hydroxyalkyl; and $R^c$, when present, is selected from the group consisting of H, $C_{1-8}$ alkyl, $C_{1-8}$ alkoxy, $C_{1-8}$ haloalkyl, $C_{1-8}$ haloalkoxy, $C_{1-8}$ hydroxyalkyl, $C_{3-6}$ cycloalkyl, 3- to 6-membered heterocycloalkyl, and 5- or 6-membered heteroaryl, the heterocycloalkyl or heteroaryl ring each have from 1-4 heteroatoms as ring vertices selected from N, O and S.

In some embodiments, the compound of Formula (III) is a compound or a pharmaceutically acceptable salt, hydrate, or solvate thereof wherein $Y^2$ is $CR^2R^3$, wherein each $R^2$ and $R^3$ is H; and $Y^3$ and $Y^4$ are each $CR^2R^3$, wherein each $R^2$ and $R^3$ are independently selected from H and F.

In some embodiments, the compound of Formula (III) is a compound or a pharmaceutically acceptable salt, hydrate, or solvate thereof wherein each $R^{5a}$ is halogen and $R^4$ is $CR^2R^3$ and $R^2$ and $R^3$ are chosen from H, F, and $OCH_3$.

In some embodiments, the compound of Formula (III) is a compound or a pharmaceutically acceptable salt, hydrate, or solvate thereof wherein $R^{11}$ is a phenyl, 5- or 6-membered heterocyclic, or 5- to 10-membered heteroaryl ring, wherein the heterocyclic or heteroaryl ring has from 1-3 heteroatoms as ring vertices selected from N, O, and S; wherein the phenyl is optionally fused to a 5- or 6-membered heterocycle having from 1-2 heteroatoms as ring vertices selected from N, O, and S; and wherein the phenyl, heterocyclic, or heteroaryl ring is optionally substituted with from one to three members independently selected from halogen, CN, $NO_2$, $NH_2$, C(O)$NH_2$, S(O)$_2CH_3$, —$CH_2NH_2$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ hydroxyhaloalkyl and $C_{1-4}$ alkoxy$C_{1-4}$alkyl; optionally wherein two members attached to the same carbon of the heterocyclic ring taken together form =$CH_2$ or oxo (=O) group.

In some selected embodiments, the compound of Formula (I) is represented by Formula (IV-a):

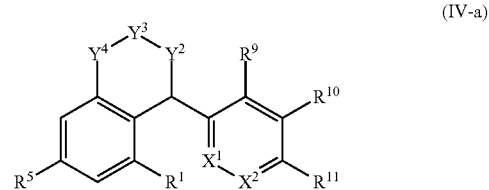

(IV-a)

or a pharmaceutically acceptable salt, hydrate, or solvate thereof, wherein $Y^2$, $Y^3$ and $Y^4$ are each independently selected from the group consisting of $CR^2R^3$, $NR^4$, $SO_2$, and a bond; and no more than one of $Y^2$, $Y^3$ and $Y^4$ is a bond;

$R^1$ is selected from the group consisting of halogen, CN, $C_{1-4}$ alkyl, $C_{1-4}$ haloalkyl, $C_{1-4}$ alkoxy, $C_{1-4}$ haloalkoxy, —S(O)$_2R^a$ and —C(O)$NR^aR^b$;

each $R^2$ and $R^3$ are each independently selected from the group consisting of H, halogen, CN, $NO_2$, OH, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-4}$ alkoxy$C_{1-4}$alkyl, $C_{3-8}$ cycloalkyl, —S(O)$_2R^a$ and —C(O)$NR^aR^b$;

each $R^4$ is independently selected from the group consisting of H, $C_{1-6}$ alkyl, $C_{3-8}$ cycloalkyl, and —C(O)$R^a$; and each $R^5$ is independently selected from the group consisting of H, halogen, CN, $NO_2$, $C_{1-6}$ alkyl, $C_{1-6}$ haloalkyl, $C_{1-6}$ alkoxy, $C_{1-6}$ haloalkoxy, $C_{3-8}$ cycloalkyl, —S(O)$_2R^a$, —C(O)$NR^aR^b$, and —S(O)$_2NR^aR^b$, and the reaming groups have the meanings provided for Formula (I). In some embodiments of the compound of Formula (IV-a), the remaining groups have the meanings provided for Formula (II).

In some embodiments, the compound of Formula (IV-a) is a compound or a pharmaceutically acceptable salt, hydrate, or solvate thereof wherein $X^1$ and $X^2$ are independently selected from the group consisting of CH and N.

In some selected embodiments, the compound of Formula (I) is represented by Formula (IV-b):

(IV-b)

or a pharmaceutically acceptable salt, hydrate, or solvate thereof, wherein
the subscript m is 1, 2, 3, 4, 5, 6, 7 or 8;
the subscript n is 1 or 2;
$R^z$ represents one or more of $R^{12}$, $R^{13}$, $R^{14}$, $R^{15}$, $R^{16}$, $R^{17}$, $R^{18}$ and $R^{19}$;
$Y^2$, $Y^3$ and $Y^4$ are each independently selected from the group consisting of $CR^2R^3$, $NR^4$, $SO_2$, and a bond; and no more than one of $Y^2$, $Y^3$ and $Y^4$ is a bond;
$R^1$ is selected from the group consisting of halogen, CN, $C_{1-4}$ alkyl, $C_{1-4}$ haloalkyl, $C_{1-4}$ alkoxy, $C_{1-4}$ haloalkoxy, $-S(O)_2R^a$ and $-C(O)NR^aR^b$;
each $R^2$ and $R^3$ are each independently selected from the group consisting of H, halogen, CN, $NO_2$, OH, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-4}$ alkoxy$C_{1-4}$alkyl, $C_{3-8}$ cycloalkyl, $-S(O)_2R^a$ and $-C(O)NR^aR^b$;
each $R^4$ is independently selected from H, $C_{1-6}$ alkyl, $C_{3-8}$ cycloalkyl, and $-C(O)R^a$;
$R^5$ is selected from the group consisting of H, halogen, CN, $NO_2$, $C_{1-6}$ alkyl, $C_{1-6}$ haloalkyl, $C_{1-6}$ alkoxy, $C_{1-6}$ haloalkoxy, $C_{3-8}$ cycloalkyl, $-S(O)_2R^a$, $-C(O)NR^aR^b$, and $-S(O)_2NR^aR^b$; and
each of $R^{12}$, $R^{13}$, $R^{14}$, $R^{15}$, $R^{16}$, $R^{17}$ and $R^{18}$ is independently selected from the group consisting of H, halogen, CN, OH, $C_{1-4}$ alkyl, $C_{1-4}$ haloalkyl, $C_{1-4}$ alkoxy, $C_{1-4}$ haloalkoxy, $C_{1-4}$ hydroxyalkyl, $C_{1-4}$ alkoxy$C_{1-4}$alkyl and $-NR^aR^b$, or two $R^{12}$, $R^{13}$, $R^{14}$, $R^{15}$, $R^{16}$, $R^{17}$, R 18 and $R^{19}$ moieties on the same carbon atom combine to form an oxo group, and the remaining groups have the meanings provided for Formula (I). In some embodiments of the compound of Formula (IV-b), the remaining groups have the meanings provided for Formula (II).

In some selected embodiments, the compound of Formula (IV-b) is a compound or a pharmaceutically acceptable salt, hydrate, or solvate thereof wherein $Y^4$ is a member selected from the group consisting of O and NH.

In some selected embodiments, the compound of Formula (I) is represented by Formula (IV-c):

(IV-c)

or a pharmaceutically acceptable salt, hydrate, or solvate thereof, wherein
$A^1$ is O or $CHR^{13}$;
$Y^2$, $Y^3$ and $Y^4$ are each independently selected from the group consisting of $CR^2R^3$, $NR^4$, $SO_2$, and a bond; and no more than one of $Y^2$, $Y^3$ and $Y^4$ is a bond;
$R^1$ is selected from the group consisting of halogen, CN, $C_{1-4}$ alkyl, $C_{1-4}$ haloalkyl, $C_{1-4}$ alkoxy, $C_{1-4}$ haloalkoxy, $-S(O)_2R^a$ and $-C(O)NR^aR^b$;
$R^5$ is selected from the group consisting of H, halogen, CN, $NO_2$, $C_{1-6}$ alkyl, $C_{1-6}$ haloalkyl, $C_{1-6}$ alkoxy, $C_{1-6}$ haloalkoxy, $C_{3-8}$ cycloalkyl, $-S(O)_2R^a$, $-C(O)NR^aR^b$, and $-S(O)_2NR^aR^b$;
$R^{11}$ is selected from the group consisting of H, halogen, CN, $NO_2$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ hydroxyhaloalkyl, $C_{1-4}$ alkoxy$C_{1-4}$alkyl, $C_{3-8}$ cycloalkyl, $-C(O)NR^aR^b$, $-S(O)_2NR^aR^b$, $-S(O)(=NH)R^c$, and $-S(O)_2R^c$;
each of $R^{13}$, $R^{14}$ and $R^{15}$ is independently selected from the group consisting of H, halogen, CN, OH, $C_{1-4}$ alkyl, $C_{1-4}$ haloalkyl, $C_{1-4}$ alkoxy, $C_{1-4}$ haloalkoxy, $C_{1-4}$ hydroxyalkyl, $C_{1-4}$ alkoxy$C_{1-4}$alkyl and $-NR^aR^b$, and
$R^{16}$ is selected from the group consisting of H, $C_{1-4}$ alkyl and $C_{1-4}$ fluoroalkyl,
and the remaining groups have the meanings provided for Formula (I). In some embodiments of the compound of Formula (IV-c), the remaining groups have the meanings provided for Formula (II).

In some selected embodiments, the compound of Formula (IV-c) is a compound or a pharmaceutically acceptable salt, hydrate, or solvate thereof wherein $R^{8b}$ is H.

In some embodiments, the compound of Formula (IV-c) is a compound or a pharmaceutically acceptable salt, hydrate, or solvate thereof wherein $Y^2$ is $CR^2R^3$, wherein each $R^2$ and $R^3$ is H; and $Y^3$ and $Y^4$ are each $CR^2R^3$, wherein each $R^2$ and $R^3$ are independently selected from H and F.

In some selected embodiments, the compound of Formula (I) is represented by Formula (IV-d):

(IV-d)

or a pharmaceutically acceptable salt, hydrate, or solvate thereof, wherein
$R^1$ is selected from the group consisting of halogen, CN, $C_{1-4}$ alkyl, $C_{1-4}$ fluoroalkyl, $C_{1-4}$ alkoxy, $-S(O)_2R^a$ and $-C(O)NR^aR^b$;
$R^2$ and $R^3$ are each independently selected from the group consisting of H, halogen, CN, $NO_2$, OH, $C_{1-6}$ alkyl, $C_{1-6}$ fluoroalkyl, $C_{1-6}$ alkoxy, $C_{1-6}$ fluoroalkoxy, $C_{1-6}$ hydroxyalkyl, $C_{1-4}$ alkoxy$C_{1-4}$alkyl and $-NR^aR^b$,
$R^5$ is selected from the group consisting of H, halogen, CN, $NO_2$, $C_{1-6}$ alkyl, $C_{1-6}$ fluoroalkyl, $C_{1-6}$ alkoxy, $C_{1-6}$ fluoroalkoxy, $C_{3-8}$ cycloalkyl, $-S(O)_2R^a$, $-C(O)NR^aR^b$, and $-S(O)_2NR^aR^b$;
$R^{11}$ is selected from the group consisting of H, halogen, CN, $NO_2$, $C_{1-6}$ alkyl, $C_{1-6}$ fluoroalkyl, $C_{1-6}$ alkoxy, $C_{1-6}$ fluoroalkoxy, $C_{1-6}$ hydroxyfluoralkyl, $C_{3-8}$ cycloalkyl, —C(O)NR$^a$R$^b$, —S(O)$_2$NR$^a$R$^b$, —S(O)(=NH)R$^c$, and —S(O)$_2$R$^c$;

each of R$^{12}$, R$^{13}$, R$^{14}$ and R$^{15}$ is independently selected from the group consisting of H, halogen, CN, OH, $C_{1-4}$ alkyl, $C_{1-4}$ alkoxy and —NR$^a$R$^b$, and the remaining groups have the meanings provided for Formula (I). In some embodiments of the compound of Formula (IV-d), the remaining groups have the meanings provided for Formula (II).

In some selected embodiments, the compound of Formula (I) is represented by Formula (IV-e):

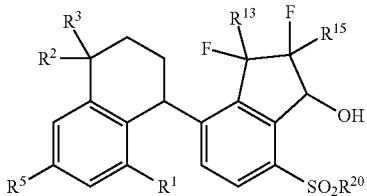

(IV-e)

or a pharmaceutically acceptable salt, hydrate, or solvate thereof, wherein

R$^1$ is selected from the group consisting of halogen, CN, $C_{1-4}$ alkyl, $C_{1-4}$ fluoroalkyl, $C_{1-4}$ alkoxy, —S(O)$_2$R$^a$ and —C(O)NR$^a$R$^b$;

R$^2$ and R$^3$ are each independently selected from the group consisting of H, halogen, CN, NO$_2$, OH, $C_{1-6}$ alkyl, $C_{1-6}$ fluoroalkyl, $C_{1-6}$ alkoxy, $C_{1-6}$ fluoroalkoxy, $C_{1-6}$ hydroxyalkyl, $C_{1-4}$ alkoxy$C_{1-4}$alkyl and —NR$^a$R$^b$, R$^5$ is selected from the group consisting of H, halogen, CN, NO$_2$, $C_{1-6}$ alkyl, $C_{1-6}$ fluoroalkyl, $C_{1-6}$ alkoxy, $C_{1-6}$ fluoroalkoxy, $C_{3-8}$ cycloalkyl, —S(O)$_2$R$^a$, —C(O)NR$^a$R$^b$, and —S(O)$_2$NR$^a$R$^b$;

each of R$^{13}$ and R$^{15}$ is independently selected from the group consisting of H, F and $C_{1-4}$ alkyl; and R$^{20}$ is selected from the group consisting of $C_{1-6}$ alkyl and $C_{1-6}$ fluoroalkyl, and the remaining groups have the for Formula (I).

In some embodiments, the compound of Formula (IV-e) is a compound or a pharmaceutically acceptable salt, hydrate, or solvate thereof wherein R$^{20}$ is selected from the group consisting of methyl, fluoromethyl, difluoromethyl and trifluoromethyl.

In some embodiments, the compound of Formula (II) is represented by Formula (IV-f):

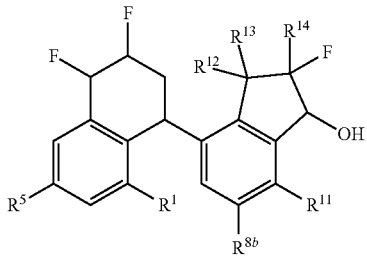

(IV-f)

or a pharmaceutically acceptable salt, hydrate, or solvate thereof, wherein the groups have the meanings provided for Formula (II). In some embodiments of the compound of Formula (IV-f), R$^{8b}$ is H.

In some selected embodiments, the compound of Formula (I) is represented by Formula (V-a):

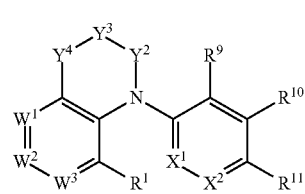

(V-a)

or a pharmaceutically acceptable salt, hydrate, or solvate thereof, wherein the groups have the meanings provided for Formula (I). In some embodiments of the compound of Formula (V-a), the groups have the meanings provided for Formula (II).

In some selected embodiments, the compound of Formula (I) is represented by Formula (V-b):

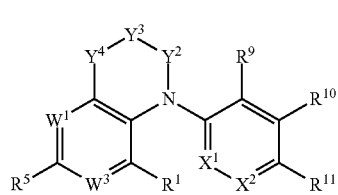

(V-b)

or a pharmaceutically acceptable salt, hydrate, or solvate thereof, wherein each R$^5$ is independently selected from the group consisting of H, halogen, CN, NO$_2$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-4}$ alkoxy$C_{1-4}$alkyl, $C_{3-8}$ cycloalkyl, —S(O)$_2$R$^a$, —CO$_2$R$^a$, —C(O)R$^a$, —C(O)NR$^a$R$^b$, —S(O)$_2$NR$^a$R$^b$, —S(O)(=NH)R$^a$, and —NR$^a$R$^b$; and the remaining groups have the meanings provided for Formula (I). In some embodiments of the compound of Formula (V-b), the remaining groups have the meanings provided for Formula (II).

In some embodiments, the compound of Formula (V-b) is a compound or a pharmaceutically acceptable salt, hydrate, or solvate thereof wherein R$^9$ and R$^{10}$ are each independently selected from the group consisting of H, halogen, CN, NO$_2$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ hydroxyhaloalkyl, $C_{1-4}$ alkoxy$C_{1-4}$alkyl, $C_{3-8}$ cycloalkyl, —C(O)R$^a$, —C(O)OR$^a$, —C(O)NR$^a$R$^b$, —S(O)$_2$NR$^a$R$^b$, and —S(O)$_2$R$^a$, and R$^{11}$ is selected from the group consisting of H, halogen, CN, NO$_2$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ hydroxyhaloalkyl, $C_{1-4}$ alkoxy$C_{1-4}$alkyl, $C_{3-8}$ cycloalkyl, —C(O)NR$^a$R$^b$, —S(O)$_2$NR$^a$R$^b$, and —S(O)$_2$R$^c$.

In some selected embodiments, the compound of Formula (I) is represented by Formula (V-c):

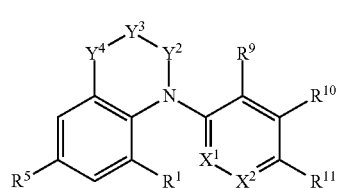

(V-c)

or a pharmaceutically acceptable salt, hydrate, or solvate thereof, wherein $Y^2$, $Y^3$ and $Y^4$ are each independently selected from the group consisting of $CR^2R^3$, $NR^4$, $SO_2$, and a bond; and no more than one of $Y^2$, $Y^3$ and $Y^4$ is a bond;

$R^1$ is selected from the group consisting of halogen, CN, $C_{1-4}$ alkyl, $C_{1-4}$ fluoroalkyl, $C_{1-4}$ alkoxy, —S(O)$_2$R$^a$ and —C(O)NR$^a$R$^b$;

$R^2$ and $R^3$ are each independently selected from the group consisting of H, halogen, CN, NO$_2$, OH, $C_{1-6}$ alkyl, $C_{1-6}$ fluoroalkyl, $C_{1-6}$ alkoxy, $C_{1-6}$ fluoroalkoxy, $C_{3-8}$ cycloalkyl, —S(O)$_2$R$^a$, —C(O)NR$^a$R$^b$, and —NR$^a$R$^b$;

$R^5$ is selected from the group consisting of H, halogen, CN, NO$_2$, $C_{1-6}$ alkyl, $C_{1-6}$ fluoroalkyl, $C_{1-6}$ alkoxy, $C_{1-6}$ fluoroalkoxy, $C_{3-8}$ cycloalkyl, —S(O)$_2$R$^a$, —C(O)NR$^a$R$^b$, and —S(O)$_2$NR$^a$R$^b$; and the remaining groups have the meanings provided for Formula (I). In some embodiments of the compound of Formula (V-c), the remaining groups have the meaning provided for Formula (II).

In some selected embodiments, the compound of Formula (I) is represented by Formula (V-d):

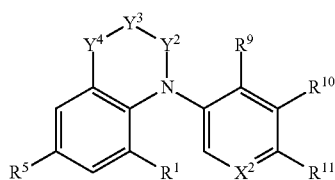

(V-d)

or a pharmaceutically acceptable salt, hydrate, or solvate thereof, wherein $Y^2$, $Y^3$ and $Y^4$ are each independently selected from the group consisting of $CR^2R^3$ and a bond; and no more than one of $Y^2$, $Y^3$ and $Y^4$ is a bond;

$R^1$ is selected from the group consisting of halogen, CN, $C_{1-4}$ alkyl, $C_{1-4}$ fluoroalkyl, $C_{1-4}$ alkoxy, —S(O)$_2$R$^a$ and —C(O)NR$^a$R$^b$;

$R^2$ and $R^3$ are each independently selected from the group consisting of H, halogen, CN, OH, $C_{1-6}$ alkyl, $C_{1-6}$ fluoroalkyl, $C_{1-6}$ hydroxyalkyl, $C_{1-6}$ alkoxy, $C_{1-6}$ fluoroalkoxy, $C_{1-4}$ alkoxyC$_{1-4}$alkyl, $C_{3-8}$ cycloalkyl, —S(O)$_2$R$^a$, —C(O)NR$^a$R$^b$, and —NR$^a$R$^b$, and $R^5$ is selected from the group consisting of H, halogen, CN, NO$_2$, $C_{1-6}$ alkyl, $C_{1-6}$ fluoroalkyl, $C_{1-6}$ alkoxy, $C_{1-6}$ fluoroalkoxy, $C_{3-8}$ cycloalkyl, —S(O)$_2$R$^a$, —C(O)NR$^a$R$^b$, and —S(O)$_2$NR$^a$R$^b$; and the remaining groups have the meanings provided for Formula (I). In some embodiments of the compound of Formula (V-d), the remaining groups have the meanings provided for Formula (II).

In some selected embodiments, the compound of Formula (I) is represented by Formula (V-e):

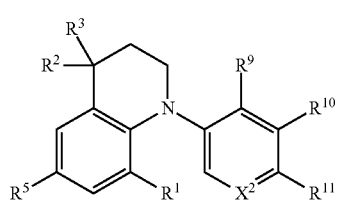

(V-e)

or a pharmaceutically acceptable salt, hydrate, or solvate thereof, wherein $R^1$ is selected from the group consisting of halogen, CN, $C_{1-4}$ alkyl, $C_{1-4}$ fluoroalkyl, $C_{1-4}$ alkoxy, —S(O)$_2$R$^a$ and —C(O)NR$^a$R$^b$;

$R^2$ and $R^3$ are each independently selected from the group consisting of H, halogen, CN, OH, $C_{1-6}$ alkyl, $C_{1-6}$ fluoroalkyl, $C_{1-6}$ hydroxyalkyl, $C_{1-6}$ alkoxy, $C_{1-6}$ fluoroalkoxy, $C_{1-4}$ alkoxyC$_{1-4}$ alkyl, $C_{3-8}$ cycloalkyl, —S(O)$_2$R$^a$, —C(O)NR$^a$R$^b$, and —NR$^a$R$^b$, and $R^5$ is selected from the group consisting of H, halogen, CN, NO$_2$, $C_{1-6}$ alkyl, $C_{1-6}$ fluoroalkyl, $C_{1-6}$ alkoxy, $C_{1-6}$ fluoroalkoxy, $C_{3-8}$ cycloalkyl, —S(O)$_2$R$^a$, —C(O)NR$^a$R$^b$, and —S(O)$_2$NR$^a$R$^b$; and the remaining groups have the meanings provided for Formula (I). In some embodiments of the compound of Formula (V-d), the remaining groups have the meanings provided for Formula (II).

In some embodiments, the compound of Formula (V-e) is a compound or a pharmaceutically acceptable salt, hydrate, or solvate thereof wherein $R^9$ and $R^{10}$ are combined to form a 5- or 6-membered carbocyclic or heterocyclic ring, which is optionally substituted with $R^{12}$, $R^{13}$, $R^{14}$, $R^{15}$, $R^{16}$, $R^{17}$, $R^{18}$ and $R^{19}$.

In some embodiments, the compound of Formula (V-e) is a compound or a pharmaceutically acceptable salt, hydrate, or solvate thereof wherein $R^9$ and $R^{10}$ are independently selected from the group consisting of H, halogen, CN, NO$_2$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ hydroxyhaloalkyl, $C_{1-4}$ alkoxyC$_{1-4}$alkyl, $C_{3-8}$ cycloalkyl, —C(O)R$^a$, —C(O)OR$^a$, —C(O)NR$^a$R$^b$, —S(O)$_2$NR$^a$R$^b$, and —S(O)$_2$R$^a$.

In some selected embodiments, the compound of Formula (I) is represented by Formula (V-f):

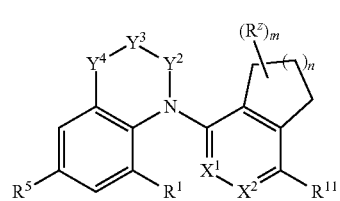

(V-f)

or a pharmaceutically acceptable salt, hydrate, or solvate thereof, wherein the subscript m is 1, 2, 3, 4, 5, 6, 7 or 8;

the subscript n is 1 or 2;

$R^z$ represents one or more of $R^{12}$, $R^{13}$, $R^{14}$, $R^{15}$, $R^{16}$, $R^{17}$, $R^{18}$ and $R^{19}$;

$Y^2$, $Y^3$ and $Y^4$ are each independently selected from the group consisting of $CR^2R^3$, $NR^4$, $SO_2$, and a bond; and no more than one of $Y^2$, $Y^3$ and $Y^4$ is a bond;

$R^1$ is selected from the group consisting of halogen, CN, $C_{1-4}$ alkyl, $C_{1-4}$ haloalkyl, $C_{1-4}$ alkoxy, $C_{1-4}$ haloalkoxy, —S(O)$_2$R$^a$ and —C(O)NR$^a$R$^b$;

each $R^2$ and $R^3$ are each independently selected from the group consisting of H, halogen, CN, NO$_2$, OH, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-4}$ alkoxyC$_{1-4}$alkyl, $C_{3-8}$ cycloalkyl, —S(O)$_2$R$^a$ and —C(O)NR$^a$R$^b$;

each $R^4$ is independently selected from H, $C_{1-6}$ alkyl, $C_{3-8}$ cycloalkyl, and —C(O)R$^a$;

$R^5$ is selected from the group consisting of H, halogen, CN, NO$_2$, $C_{1-6}$ alkyl, $C_{1-6}$ haloalkyl, $C_{1-6}$ alkoxy, $C_{1-6}$ haloalkoxy, $C_{3-8}$ cycloalkyl, $-S(O)_2R^a$, $-C(O)NR^aR^b$, and $-S(O)_2NR^aR^b$; and each of $R^{12}$, $R^{13}$, $R^{14}$, $R^{15}$, $R^{16}$, $R^{17}$, $R^{18}$ and $R^{19}$ is independently selected from the group consisting of H, halogen, CN, OH, $C_{1-4}$ alkyl, $C_{1-4}$ haloalkyl, $C_{1-4}$ alkoxy, $C_{1-4}$ haloalkoxy, $C_{1-4}$ hydroxyalkyl, $C_{1-4}$ alkoxy$C_{1-4}$alkyl and $-NR^aR^b$, or two $R^{12}$, $R^{13}$, $R^{14}$, $R^{15}$, $R^{16}$, $R^{17}$, $R^{18}$ and $R^{19}$ moieties on the same carbon atom combine to form an oxo group; and the remaining groups have the meanings provided for Formula (I). In some embodiments of the compound of Formula (V-f), the remaining groups have the meanings provided for Formula (II).

In some selected embodiments, the compound of Formula (I) is represented by Formula (V-g):

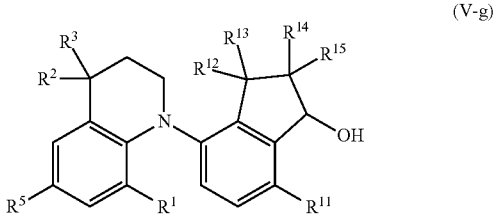

(V-g)

or a pharmaceutically acceptable salt, hydrate, or solvate thereof, wherein $R^1$ is selected from the group consisting of halogen, CN, $C_{1-4}$ alkyl, $C_{1-4}$ fluoroalkyl, $C_{1-4}$ alkoxy, $-S(O)_2R^a$ and $-C(O)NR^aR^b$;

$R^2$ and $R^3$ are each independently selected from the group consisting of H, halogen, CN, $NO_2$, OH, $C_{1-6}$ alkyl, $C_{1-6}$ fluoroalkyl, $C_{1-6}$ alkoxy, $C_{1-6}$ fluoroalkoxy, $C_{1-6}$ hydroxyalkyl, $C_{1-4}$ alkoxy$C_{1-4}$alkyl and $-NR^aR^b$;

$R^5$ is selected from the group consisting of H, halogen, CN, $NO_2$, $C_{1-6}$ alkyl, $C_{1-6}$ fluoroalkyl, $C_{1-6}$ alkoxy, $C_{1-6}$ fluoroalkoxy, $C_{3-8}$ cycloalkyl, $-S(O)_2R^a$, $-C(O)NR^aR^b$, and $-S(O)_2NR^aR^b$;

$R^{11}$ is selected from the group consisting of H, halogen, CN, $NO_2$, $C_{1-6}$ alkyl, $C_{1-6}$ fluoroalkyl, $C_{1-6}$ alkoxy, $C_{1-6}$ fluoroalkoxy, $C_{3-8}$ cycloalkyl, $-C(O)NR^aR^b$, $-S(O)_2NR^aR^b$, $-S(O)(=NH)R^c$, and $-S(O)_2R^c$;

each of $R^{12}$, $R^{13}$, $R^{14}$ and $R^{15}$ is independently selected from the group consisting of H, halogen, CN, OH, $C_{1-4}$ alkyl, $C_{1-4}$ alkoxy and $-NR^aR^b$, and the remaining groups have the meanings provided for Formula (I).

In some embodiments, the compound of Formula (V-g) is a compound or a pharmaceutically acceptable salt, hydrate, or solvate thereof wherein $R^{11}$ is a phenyl, 5- or 6-membered heterocyclic, or 5- to 10-membered heteroaryl ring, wherein the heterocyclic or heteroaryl ring has from 1-3 heteroatoms as ring vertices selected from N, O, and S; wherein the phenyl is optionally fused to a 5- or 6-membered heterocycle having from 1-2 heteroatoms as ring vertices selected from N, O, and S; and wherein the phenyl, heterocyclic, or heteroaryl ring is optionally substituted with from one to three members independently selected from halogen, CN, $NO_2$, $NH_2$, $C(O)NH_2$, $S(O)_2CH_3$, $-CH_2NH_2$, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ hydroxyhaloalkyl and $C_{1-4}$ alkoxy$C_{1-4}$alkyl; optionally wherein two members attached to the same carbon of the heterocyclic ring taken together form $=CH_2$ or oxo (=O) group.

In some selected embodiments, any one compound of Table 1, Table 2, or Table 3 is provided.

Identification of HIF-2α Inhibitors Possessing Desirable Characteristics

The present invention is drawn, in part, to the identification of inhibitors of HIF-2α with at least one property or characteristic that is of therapeutic relevance. Candidate inhibitors may be identified by using, for example, an art-accepted assay or model, examples of which are described herein.

After identification, candidate inhibitors can be further evaluated by using techniques that provide data regarding characteristics of the inhibitors (e.g., pharmacokinetic parameters, means of determining solubility or stability). Comparisons of the candidate inhibitors to a reference standard (which may the "best-of-class" of current inhibitors) are indicative of the potential viability of such candidates.

Methods of Synthesis

General Methods for the Preparation of Compounds of the Claims

For the most efficient preparation of any particular compound of the invention, one skilled in the art will recognize that the timing and the order of connection of the fragments and modification of the functionality present in any of the fragments may vary in the preparation of any given compound. A variety of methods have been used to prepare compounds of the invention, some of which are exemplified in the examples.

Prodrugs and Other Means of Drug Delivery and/or Half-Life Extension

In some aspects of the present invention, compounds described herein are administered in prodrug form.

In order to effect extension of therapeutic activity, drug molecules may be engineered to utilize carriers for delivery. Such carriers are either used in a non-covalent fashion, with the drug moiety physicochemically formulated into a solvent-carrier mixture, or by permanent covalent attachment of a carrier reagent to one of the drug moiety's functional groups (see generally WO 2015/0202317).

Several non-covalent approaches are favored. By way of example, but not limitation, in certain embodiments depot formulations comprising non-covalent drug encapsulation into polymeric carriers are employed. In such formulations, the drug molecule is combined with carrier material and processed such that the drug molecule becomes distributed inside the bulk carrier. Examples include microparticle polymer-drug aggregates (e.g., Degradex® Microspheres (Phosphorex, Inc.)), which are administered as an injectable suspension; polymer-drug molecule aggregates formulated as gels (e.g., Lupron Depot® (Abb Vie Inc.)), which are administered as a single bolus injection; and liposomal formulations (e.g., DepoCyt® (Pacira Pharmaceuticals)), where the carrier may be a polymeric or non-polymeric entity capable of solubilizing the drug. In these formulations, release of the drug molecule may occur when the carrier swells or physically deteriorates. In other instances, chemical degradation allows diffusion of the drug into the biological environment; such chemical degradation processes may be autohydrolytic or enzyme-catalyzed. Among other limitations, non-covalent drug encapsulation requires prevention of uncontrolled release of the drug, and dependence of the release mechanism of the drug upon biodegradation may cause interpatient variability.

In particular embodiments, drug molecules, including both small molecules and large molecules, are conjugated to a carrier through permanent covalent bonds. Certain small molecule therapeutics that exhibit low solubility in aqueous fluids may be solubilized by conjugation to hydrophilic polymers, examples of which are described elsewhere herein. Regarding large molecule proteins, half-life extension may be achieved by, for example, permanent covalent modification with a palmitoyl moiety, and by permanent covalent modification with another protein that itself has an extended half-life (e.g., Albuferon®). In general, drug molecules show decreased biological activity when a carrier is covalently conjugated to the drug.

In certain instances, limitations associated with either drug molecules comprising non-covalent polymer mixtures or permanent covalent attachment may be successfully addressed by employing a prodrug approach for chemical conjugation of the drug to the polymer carrier. In this context, therapeutic agents that are inactive or less active than the drug moiety itself are predictably transformed into active molecular entities. The reduced biological activity of the prodrug as compared to the released drug is advantageous if a slow or controlled release of the drug is desired. In such instances, release of the drug occurs over time, thereby reducing the necessity of repeated and frequent administration of the drug. A prodrug approach may also be advantageous when the drug moiety itself is not absorbed, or has less than optimal absorption, in the gastrointestinal tract; in these instances, the prodrug facilitates absorption of the drug moiety and is then cleaved off at some later time (e.g., via first-pass metabolism). The biologically active drug molecule is typically linked to the polymeric carrier moiety by a temporary bond formed between the carrier moiety and a hydroxy, amino or carboxy group of the drug molecule.

The approaches described above are associated with several limitations. Prodrug activation may occur by enzymatic or non-enzymatic cleavage of the temporary bond between the carrier and the drug molecule, or a sequential combination of both (e.g., an enzymatic step followed by a non-enzymatic modification). In an enzyme-free in vitro environment (e.g., an aqueous buffer solution), a temporary bond such as an ester or amide may undergo hydrolysis, but the corresponding rate of hydrolysis may be such that it is outside the therapeutically useful range. In contrast, in an in vivo environment, esterases or amidases are typically present, and the esterases and amidases may cause significant catalytic acceleration of the kinetics of hydrolysis from two-fold up to several orders of magnitude (see, e.g., Greenwald et al., (1999) J Med Chem 42(18):3857-67).

As described herein, prodrugs may be classified as i) bioprecursors and ii) carrier-linked prodrugs. Bioprecursors do not contain a carrier group and are activated by the metabolic creation of a functional group. In contrast, in carrier-linked prodrugs the active substance is conjugated to a carrier moiety via a temporary linkage at a functional group of the bioactive entity. Preferred functional groups are hydroxyl or amino groups. Both the attachment chemistry and hydrolysis conditions depend on the type of functional group employed. The carrier may be biologically inert (e.g., PEG) or may have targeting properties (e.g., an antibody). Cleavage of the carrier moiety of a carrier-linked prodrug results in the bioactive entity of interest, and the nature of the deprotected functional group of the bioactive entity often contributes to its bioactivity.

The patent and scientific literature describe many macromolecular prodrugs where the temporary linkage is a labile ester bond. In these cases, the functional group of the bioactive entity is either a hydroxyl group or a carboxylic acid (see, e.g. Cheng et al. (2003) Bioconjugate Chem 14:1007-17). In addition, it is often advantageous for biomacromolecules and certain small molecule drugs to link the carrier to an amino group(s) of the bioactive entity (e.g., the N-terminus or lysine amino groups of proteins). During preparation of the prodrug, the amino groups may be more chemoselectively addressed due to their greater nucleophilicity compared to hydroxylic or phenolic groups. This is especially relevant for proteins and peptides containing a great variety of different reactive functionalities, where non-selective conjugation reactions lead to undesired product mixtures requiring extensive characterization or purification, thus decreasing reaction yield and therapeutic efficiency of the active moiety.

In general, amide bonds are more stable against hydrolysis than ester bonds, and the rate of cleavage of the amide bond may be too slow for therapeutic utility in a carrier-linked prodrug. As a result, it may be advantageous to add structural chemical components in order to effect control over the cleavability of the prodrug amide bond. These additional cleavage-controlling chemical components that are provided neither by the carrier entity nor by the drug are generally referred to as "linkers". Prodrug linkers can have a major effect on the rate of hydrolysis of temporary bond, and variation of the chemical nature of the linkers often results in particular properties. Prodrug activation of amine-containing biologically active moieties by specific enzymes for targeted release requires that the structure of the linker display a structural motif recognized as a substrate by a corresponding endogenous enzyme. In these cases, the cleavage of the temporary bond occurs in a one-step process which is catalyzed by the enzyme. For example, the enzymatic release of cytarabine is effected by the protease plasmin, which concentration is relatively high in various kinds of tumor mass.

Interpatient variability is a major drawback of predominant enzymatic cleavage. Enzyme levels may differ significantly between subjects resulting in biological variation of prodrug activation by the enzymatic cleavage. Enzyme levels may also vary depending on the site of administration (e.g., for subcutaneous injection, certain areas of the body yield more predictable therapeutic effects than others). In addition, it is difficult to establish an in vivo—in vitro correlation of the pharmacokinetic properties for enzyme-dependent carrier-linked prodrugs.

Other carrier prodrugs employing temporary linkages to amino groups in the drug moiety are based on a cascade mechanism. Cascade cleavage is enabled by linker compounds that are composed of a structural combination of a masking group and an activating group. The masking group is attached to the activating group by means of a first temporary linkage such as an ester or a carbamate. The activating group is attached to an amino group of the drug molecule through a second temporary linkage (e.g., a carbamate). The stability or susceptibility to hydrolysis of the second temporary linkage is dependent on the presence or absence of the masking group. In the presence of the masking group, the second temporary linkage is highly stable and unlikely to release the drug molecule with therapeutically useful kinetics, whereas in the absence of the masking group this linkage becomes highly labile, resulting in rapid cleavage and release of the drug moiety.

The cleavage of the first temporary linkage is the rate-limiting step in the cascade mechanism. The first step may induce a molecular rearrangement of the activating group (e.g., a 1,6-elimination as described in Greenwald et al. (1999) J Med Chem 42:3657-67), and the rearrangement renders the second temporary linkage much more labile such that its cleavage is induced. Ideally, the cleavage rate of the first temporary linkage is identical to the desired release rate for the drug molecule in a given therapeutic scenario. In addition, it is desirable that the cleavage of the second temporary linkage be substantially instantaneous after its lability has been induced by cleavage of the first temporary bond.

Another embodiment comprises polymeric amino-containing prodrugs based on trimethyl lock lactonization (see, e.g., Greenwald et al. (2000) J Med Chem 43(3):457-87). In this prodrug system, substituted o-hydroxyphenyl-dimethylpropionic acid is linked to PEG by an ester, carbonate, or carbamate group as a first temporary linkage and to an amino group of a drug molecule by means of an amide bond as a second temporary linkage. The rate-determining step in drug release is the enzymatic cleavage of the first linkage, which is followed by fast amide cleavage by lactonization, releasing an aromatic lactone side product. The primary disadvantage of the prodrug systems described by Greenwald et al. is the release of highly reactive and potentially toxic aromatic small molecule side products like quinone methides or aromatic lactones after cleavage of the temporary linkage. The potentially toxic entities are released in a 1:1 stoichiometry with the drug and can assume high in vivo concentrations.

In certain embodiments of cascade prodrugs comprising aromatic activating groups based on 1,6-elimination, the masking group is structurally separate from the carrier. This may be effected by employing a stable bond between the polymer carrier and the activating group, wherein the stable bond does not participate in the cascade cleavage mechanism. If the carrier is not serving as a masking group and the activating group is coupled to the carrier by means of a stable bond, release of potentially toxic side products (such as the activating group) is avoided. The stable attachment of the activating group and the polymer also suppresses the release of drug-linker intermediates with undefined pharmacology.

A first example of the approach described in the preceding paragraph comprises a polymeric prodrug system based on a mandelic acid activating group (see, e.g., Shabat et al. (2004) Chem Eur J 10:2626-34). In this approach the masking group is linked to the activating group by a carbamate bond. The activating group is conjugated permanently to a polyacrylamide polymer via an amide bond. After enzymatic activation of the masking group by a catalytic antibody, the masking group is cleaved by cyclization and the drug is released; the activating group is still connected to the polyacrylamide polymer after drug release. A similar prodrug system is based on a mandelic acid activating group and an enzymatically cleavable ester-linked masking group (see, e.g., Lee et al. (2004) Angew Chem 116:1707-10).

When the aforementioned linkers are used, the 1,6-elimination step still generates a highly reactive aromatic intermediate. Even if the aromatic moiety remains permanently attached to the polymeric carrier, side reactions with potentially toxic by-products or immunogenic effects may result. Thus, it is advantageous to generate linker technologies for forming polymeric prodrugs of amine-containing active agents using aliphatic prodrug linkers that are not enzyme-dependent and do not generate reactive aromatic intermediates during cleavage. One such example uses PEG5000-maleic anhydride for the reversible modification of amino groups in tissue-type plasminogen activator and urokinase (see, e.g. (1987) Garman et al. FEBS Lett 223(2):361-65). Regeneration of functional enzyme from PEG-uPA conjugate upon incubation at pH 7.4 buffer by cleavage of the maleamic acid linkage follows first order kinetics with a half-life of roughly 6 hours. A disadvantage of the maleamic acid linkage is the lack of stability of the conjugate at lower pH values.

A further approach comprises a PEG cascade prodrug system based on N,N-bis-(2-hydroxyethyl)glycine amide (bicine) linker (see e.g. (2004) J Med Chem 47:726-34). In this system, two PEG carrier molecules are linked via temporary bonds to a bicine molecule coupled to an amino group of the drug molecule. The first steps in prodrug activation involves the enzymatic cleavage of the first temporary linkages connecting both PEG carrier molecules with the hydroxy groups of the bicine activating group. Different linkages between PEG and bicine result in different prodrug activation kinetics. The second step in prodrug activation involves the cleavage of the second temporary linkage connecting the bicine activating group to the amino group of the drug molecule. A disadvantage of this system is the slow hydrolysis rate of this second temporary bicine amide linkage, which results in the release of a bicine-modified prodrug intermediate that may show different pharmacokinetic, immunogenic, toxicity and pharmacodynamic properties as compared to the native parent drug molecule.

In particular embodiments, dipeptides are utilized for prodrug development for targeting or targeted transport as they are substrates for enzymes or biotransport systems. The non-enzymatic route for dipeptide prodrug formation, that is, the ability to undergo intramolecular cyclization to form the corresponding diketopiperazine (DKP) and release the active drug, is not well defined.

In some embodiments, dipeptides are attached to a drug moiety via ester bonds, as was described for dipeptide esters of the drug paracetamol (Gomes et al. (2005) Bio & Med Chem Lett). In this case, the cyclization reaction consists of a nucleophilic attack of the N-terminal amine of the peptide on the ester carbon atom to form a tetrahedral intermediate, which is followed by a proton transfer from the amine to the leaving group oxyanion with simultaneous formation of a peptide bond to give the cyclic DKP product and free drug. This method is applicable to hydroxyl-containing drugs in vitro but has been found to compete with enzymatic hydrolysis of the ester bond in vivo, as corresponding dipeptide esters released paracetamol at a much faster rate than in buffer (Gomes et al. (Molecules 12 (2007) 2484-2506). Susceptibility of dipeptide-based prodrugs to peptidases may be addressed by incorporating at least one non-natural amino acid in the dipeptide motif. However, endogenous enzymes capable of cleaving ester bonds are not limited to peptidases, and the enzyme-dependence of such prodrug cleavage still gives rise to unpredictable in vivo performance.

In some embodiments, enzyme-dependence is intentionally engineered into DKP prodrugs, such as where dipeptide ester prodrugs are formylated at the amino terminus of the dipeptide, and enzymatic deformylation is used to initiate diketopiperazine formation and subsequent cleavage of the ester-dipeptide bond, followed by release of the drug molecule (see, e.g., U.S. Pat. No. 7,163,923). By way of further example, an octapeptide is attached by an ester linkage to the 4-hydroxyl group of vinblastine and undergoes ester bond cleavage by DKP formation after specific enzymatic removal of the N-terminal hexapeptide (see Brady et al. (2002) J Med Chem 45:4706-15).

The scope of the DKP formation reaction has also been extended to amide prodrugs. By way of example, U.S. Pat. No. 5,952,294 describes prodrug activation using diketopiperazine formation for dipeptidyl amide prodrugs of cytarabine. In this case, the temporary linkage is formed between the carbonyl of a dipeptide and the aromatic amino group of cytarabine. However, it is unlikely that a slow-release effect can be achieved for such conjugates as there is no carrier or other half-life extending moiety or functionality present.

Dipeptide prodrugs comprising bioactive peptides such as GLP-1 capable of releasing the peptide through diketopiperazine formation of the dipeptidic extension have also been described (see, e.g., WO 2009/099763). The bioactive peptide moiety may include an additional PEG chain on one of its amino acid side chain residues to achieve extended circulation of the bioactive peptide. However, this approach is associated with several significant disadvantages. First, the PEG chain has to be linked to the peptide without compromising its bioactivity, which can be difficult to achieve for many peptide-based bioactive agents. Second, as the pegylated peptide itself is bioactive, the dipeptidic promoicty has an effect on the peptide's bioactivity and may negatively affect its receptor binding properties.

Specific exemplary technologies that may be used with the compounds of the present invention include those developed by ProLynx (San Francisco, CA) and Ascendis Pharma (Palo Alto, CA). The ProLynx technology platform utilizes sets of novel linkers that are pre-programmed to cleave at different rates to allow the controlled, predictable and sustained release of small molecules and peptides from circulating semi-solid macromolecular conjugates. The technology allows for maintenance of desired steady-state serum levels of therapeutic agents for weeks to months.

The Ascendis technology platform combines the benefits of prodrug and sustained release technologies to enhance the properties of small molecules and peptides. While in circulation, proprietary prodrugs release the unmodified active parent therapeutic agent at predetermined rates governed by physiological pH and temperature conditions. Because the therapeutic agent is released in its unmodified form, it retains its original mechanism of action.

Modifications to Enhance Inhibitor Characteristics

It is frequently beneficial, and sometimes imperative, to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity.

Modifications known in the art include pegylation, Fc-fusion and albumin fusion. Although generally associated with large molecule agents (e.g., polypeptides), such modifications have recently been evaluated with particular small molecules. By way of example, Chiang, M. et al. (J. Am. Chem. Soc., 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

Other known modifications include deuteration to improve pharmacokinetics, pharmacodynamics and toxicity profiles. Due to the greater atomic mass of deuterium, cleavage of the carbon-deuterium bond requires more energy than the carbon-hydrogen bond. Because these stronger bonds are more difficult to break, the rate of drug metabolism is slower as compared to non-deuterated forms, which allows for less frequent dosing and may further reduce toxicities. (Charles Schmidt, Nature Biotechnology, 2017, 35(6): 493-494; Harbeson, S. and Tung, R., Medchem News, 2014(2): 8-22).

Therapeutic and Prophylactic Uses

The present invention contemplates the use of the HIF-2α inhibitors described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

In some embodiments, the HIF-2α inhibitors described herein are administered in an amount effective to reverse, stop or slow the progression of HIF-2α-mediated dysregulation.

In one embodiment, a patient is selected for treatment as described herein based on the patient's level of HIF-2α expression. In some embodiments, a patient is selected for treatment as described herein based on the HIF-2α expression in a tumor of the patient. In still another embodiment, a patient is selected for treatment as described herein based on the presence or absence of a VHL mutation.

Oncology-related Disorders. The HIF-2α inhibitors described herein can be used to treat or prevent a proliferative condition or disorder, including a cancer, for example, cancer of the uterus, cervix, breast, prostate (such as metastatic castration resistant prostate cancer), testes, gastrointestinal tract (e.g., esophagus, oropharynx, stomach, small or large intestines, colon, or rectum), kidney, renal cell, bladder, bone, bone marrow, skin, head or neck, liver, gall bladder, bile ducts, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer may be metastatic or at risk of becoming metastatic, or may occur in a diffuse tissue, including cancers of the blood or bone marrow (e.g., leukemia).

In some embodiments, the present invention provides methods for treating a proliferative condition, cancer, tumor, or precancerous condition with a HIF-2α inhibitor and at least one additional therapeutic or diagnostic agent, examples of which are set forth elsewhere herein.

In some embodiments, the disease or disorder is VHL-associated, for example VHL-associated renal cell carcinoma.

Iron Overload Disorders. In one embodiment, the compounds described herein may be useful in treatment of iron overload disorders. The iron overload disorder may be primary or secondary. In one embodiment, the iron overload disorder may be hemochromatosis. In other embodiments, the compounds described herein may be useful in treating polycythemia such as, for example, polycythemia vera. In another embodiment, the compounds described herein may be useful in treating Pacak-Zhuang Syndrome. In still another embodiment, the compounds described herein may be useful for treating erythrocytosis.

Immune- and Inflammatory-related Disorders. A non-limiting list of immune- and inflammatory-related diseases, disorders and conditions which may be treated or prevented with the compounds and compositions of the present invention include arthritis (e.g., rheumatoid arthritis), kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), chronic obstructive pulmonary disease (COPD), atherosclerosis, allergic contact dermatitis and other eczemas, systemic sclerosis, transplantation and multiple sclerosis.

In particular embodiments of the present disclosure, the HIF-2α inhibitors are used to increase or enhance an immune response to an antigen by providing adjuvant activity. In a particular embodiment, at least one antigen or vaccine is administered to a subject in combination with at least one HIF-2α inhibitor of the present invention to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one HIF-2α inhibitor of the present invention.

In some embodiments, a HIF-2α inhibitor described herein can be combined with an immunosuppressive agent to reduce the number of immune effector cells.

Other Disorders. Embodiments of the present invention contemplate the administration of the HIF-2α inhibitors described herein to a subject for the treatment or prevention of any other disorder that may benefit from at least some level of HIF-2α inhibition. Such diseases, disorders and conditions include, for example, cardiovascular (e.g., cardiac ischemia or pulmonary arterial hypertension) and metabolic (e.g., diabetes, insulin resistance, obesity) disorders.

Pharmaceutical Compositions

The HIF-2α inhibitors of the present invention may be in the form of compositions suitable for administration to a subject. In general, such compositions are "pharmaceutical compositions" comprising an HIF-2α inhibitor(s) and one or more pharmaceutically acceptable or physiologically acceptable diluents, carriers or excipients. In certain embodiments, the HIF-2α inhibitors are present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., an inhibitor of HIF-2α function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a HIF-2α inhibitor contemplated by the present invention and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver a HIF-2α inhibitor, including implants (e.g., implantable pumps) and catheter systems, slow injection pumps and devices, all of which are well known to the skilled artisan.

Depot injections, which are generally administered subcutaneously or intramuscularly, may also be utilized to release the HIF-2α inhibitors disclosed herein over a defined period of time. Depot injections are usually either solid- or oil-based and generally comprise at least one of the formulation components set forth herein.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol.

Acceptable diluents, solvents and dispersion media that may be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the HIF-2α inhibitors in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The HIF-2α inhibitors contemplated by the present invention may be in the form of any other suitable pharmaceutical composition (e.g., sprays for nasal or inhalation use) currently known or developed in the future.

Routes of Administration

The present invention contemplates the administration of HIF-2α inhibitors, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the HIF-2α inhibitors disclosed herein over a defined period of time.

Particular embodiments of the present invention contemplate oral administration.

Combination Therapy

The present invention contemplates the use of HIF-2α inhibitors alone or in combination with one or more active therapeutic agents. The additional active therapeutic agents can be small chemical molecules; macromolecules such as proteins, antibodies, peptibodies, peptides, DNA, RNA or fragments of such macromolecules; or cellular or gene therapies. The combination therapy may target different, but complementary mechanisms of action and thereby have a synergistic therapeutic or prophylactic effect on the underlying disease, disorder, or condition.

In addition or alternatively, the combination therapy may allow for a dose reduction of one or more of the agents, thereby ameliorating, reducing or eliminating adverse effects associated with one or more of the agents.

The active therapeutic agents in such combination therapy can be formulated as a single composition or as separate compositions. If administered separately, each therapeutic agent in the combination can be given at or around the same time, or at different times. Furthermore, the therapeutic agents are administered "in combination" even if they have different forms of administration (e.g., oral capsule and intravenous), they are given at different dosing intervals, one therapeutic agent is given at a constant dosing regimen while another is titrated up, titrated down or discontinued, or each therapeutic agent in the combination is independently titrated up, titrated down, increased or decreased in dosage, or discontinued and/or resumed during a patient's course of therapy. If the combination is formulated as separate compositions, in some embodiments, the separate compositions are provided together in a kit.

In some embodiments, the additional therapeutic agent is an immunomodulatory agent. Suitable immunomodulatory agents that may be used in the present invention include CD40L, B7, and B7RP1; activating monoclonal antibodies (mAbs) to stimulatory receptors, such as, anti-CD40, anti-CD38, anti-ICOS, and 4-IBB ligand; dendritic cell antigen loading (in vitro or in vivo); anti-cancer vaccines such as dendritic cell cancer vaccines; cytokines/chemokines, such as, IL1, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); indoleamine 2,3-dioxygenase 1 (IDO1) inhibitors and immune-stimulatory oligonucleotides.

In certain embodiments, the present invention provides methods for tumor suppression of tumor growth comprising administration of a HIF-2α inhibitor described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC®); (ii) epidermal growth factor (EGF) receptor inhibitors, including kinase inhibitors and antibodies; (iii) her-2/neu receptor inhibitors (e.g., HERCEPTIN®); (iv) inhibitors of Akt family kinases or the Akt pathway (e.g., Trop2 inhibotors or rapamycin); (v) cell cycle kinase inhibitors (e.g., flavopiridol); and (vi) phosphatidyl inositol kinase inhibitors. Agents involved in immunomodulation can also be used in combination with the HIF-2α inhibitors described herein for the suppression of tumor growth in cancer patients.

In some embodiments, the additional therapeutic agent is a chemotherapeutic agent. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, pomalidomide, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU) with or without leucovorin; folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel nab-paclitaxel and docetaxel; chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; anthracyclines; arginase inhibitors (see PCT/

US2019/020507) and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as abiraterone, enzalutamide, flutamide, nilutamide, bicalutamide, leuprolide, and goserelin; and pharmaceutically acceptable salts, acids or derivatives of any of the above. In certain embodiments, combination therapy comprises a chemotherapy regimen that includes one or more chemotherapeutic agents. In certain embodiments, combination therapy comprises administration of a hormone or related hormonal agent.

Additional treatment modalities that may be used in combination with a HIF-2α inhibitor include radiotherapy, a monoclonal antibody against a tumor antigen, a complex of a monoclonal antibody and toxin, a T-cell adjuvant, bone marrow transplant, or antigen presenting cells (e.g., dendritic cell therapy), including TLR agonists which are used to stimulate such antigen presenting cells.

In certain embodiments, the present invention contemplates the use of the compounds described herein in combination with adoptive cell therapy, a new and promising form of personalized immunotherapy in which immune cells with anti-tumor activity are administered to cancer patients. Adoptive cell therapy is being explored using tumor-infiltrating lymphocytes (TIL) and T cells engineered to express, for example, chimeric antigen receptors (CAR) or T cell receptors (TCR). Adoptive cell therapy generally involves collecting T cells from an individual, genetically modifying them to target a specific antigen or to enhance their anti-tumor effects, amplifying them to a sufficient number, and infusion of the genetically modified T cells into a cancer patient. T cells can be collected from the patient to whom the expanded cells are later reinfused (e.g., autologous) or can be collected from donor patients (e.g., allogeneic).

In certain embodiments, the present invention contemplates the use of the compounds described herein in combination with RNA interference-based therapies to silence gene expression. RNAi begins with the cleavage of longer double-stranded RNAs into small interfering RNAs (siRNAs). One strand of the siRNA is incorporated into a ribonucleoprotein complex known as the RNA-induced silencing complex (RISC), which is then used to identify mRNA molecules that are at least partially complementary to the incorporated siRNA strand. RISC can bind to or cleave the mRNA, both of which inhibits translation.

In certain embodiments, the present invention contemplates the use of the compounds described herein in combination with agents that modulate the level of adenosine. Such therapeutic agents may act on the ectonucleotides that catalyze the conversion of ATP to adenosince, including ectonucleoside triphosphate diphosphohydrolase 1 (EN-TPD1, also known as CD39 or Cluster of Differentiation 39), which hydrolyzes ATP to ADP and ADP to AMP, and 5'-nucleotidase, ecto (NT5E or 5NT, also known as CD73 or Cluster of Differentiation 73), which converts AMP to adenosine. The enzymatic activities of CD39 and CD73 play strategic roles in calibrating the duration, magnitude, and chemical nature of purinergic signals delivered to various cells (e.g., immune cells). Alteration of these enzymatic activities can change the course or dictate the outcome of several pathophysiological events, including cancer, autoimmune diseases, infections, atherosclerosis, and ischemia-reperfusion injury, suggesting that these ecto-enzymes represent novel therapeutic targets for managing a variety of disorders. In one embodiment, the CD73 inhibitors are those described in WO2017/120508, WO2018/067424, WO2018/094148, and WO2020/046813. In another embodiment, the CD73 inhibitor is AB680.

Alternatively, such therapeutic agents can be adenosine 2 receptor (A$_2$R) antagonists. Adenosine can bind to and active four different G-protein coupled receptors: A$_1$R, A$_{2a}$R, A$_{2b}$R, and A$_3$R. The binding of adenosine to the A$_{2a}$R receptor, which is expressed on T cells, natural killer cells and myeloid cells such as dendritic cells, leads to increased intracellular levels of cyclic AMP and the impairment of maturation and/or activation of such cells. This process significantly impairs the activation of the immune system against cancer cells. In addition, A$_{2A}$R has been implicated in selectively enhancing anti-inflammatory cytokines, promoting the upregulation of PD-1 and CTLA-4, promoting the generation of LAG-3 and Foxp3+ regulatory T cells, and mediating the inhibition of regulatory T cells. PD-1, CTLA-4 and other immune checkpoints which are discussed further herein. Combining A2R antagonists in the combinations described herein may provide at least an aditive effect in view of their differing mechanisms of actions. In one embodiment, the present invention contemplates combination with the adenosine receptor antagonists described in WO2018/136700, WO2018/204661, WO2018/213377, or WO2020/023846. In another embodiment, the adenosine receptor antagonist is AB928.

In certain embodiments, the present invention contemplates the use of the compounds described herein in combination with inhibitors of phosphatidylinositol 3-kinases (PI3Ks), particularly the PI3Kγ isoform. PI3Kγ inhibitors can stimulate an anti-cancer immune response through the modulation of myeloid cells, such as by inhibiting suppressive myeloid cells, dampening immune-suppressive tumor-infiltrating macrophages or by stimulating macrophages and dendritic cells to make cytokines that contribute to effective T-cell responses leading to decreased cancer development and spread. PI3Kγ inhibitors include those described in PCT/US2020/035920.

In certain embodiments, the present invention contemplates the use of the compounds described herein in combination with inhibitors of arginase, which has been shown to be either responsible for or to participate in inflammation-triggered immune dysfunction, tumor immune escape, immunosuppression and immunopathology of infectious disease. Exemplary arginase compounds can be found, for example, in PCT/US2019/020507 and WO/2020/102646.

Immune Checkpoint Inhibitors. The present invention contemplates the use of the inhibitors of HIF-2α function described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T-cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms.

In the clinical setting, the blockade of immune checkpoints—which results in the amplification of antigen-specific T cell responses—has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not over-expressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor—ligand immune checkpoints can be modulated using agonist antibodies (for co-stimulatory pathways) or antagonist antibodies (for inhibitory pathways). Thus, in contrast to most antibodies currently approved for cancer therapy, antibodies that block immune checkpoints do not target tumor cells directly, but rather target lymphocyte receptors or their ligands in order to enhance endogenous antitumor activity. [See Pardoll, (April 2012) Nature Rev. Cancer 12:252-64].

Examples of immune checkpoints (ligands and receptors), some of which are selectively upregulated in various types of tumor cells, that are candidates for blockade include PD1 (programmed cell death protein 1); PD-L1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); TIGIT (T cell immunoreceptor with Ig and ITIM domains); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

The present invention contemplates the use of the inhibitors of HIF-2α function described herein in combination with inhibitors of the aforementioned immune-checkpoint receptors and ligands, as well as yet-to-be-described immune-checkpoint receptors and ligands. Certain modulators of immune checkpoints are currently approved, and many others are in development. When it was approved for the treatment of melanoma in 2011, the fully humanized CTLA4 monoclonal antibody ipilimumab (YERVOY®; Bristol-Myers Squibb) became the first immune checkpoint inhibitor to receive regulatory approval in the US. Fusion proteins comprising CTLA4 and an antibody (CTLA4-Ig; abatcept (ORENCIA®; Bristol-Myers Squibb)) have been used for the treatment of rheumatoid arthritis, and other fusion proteins have been shown to be effective in renal transplantation patients that are sensitized to Epstein Barr Virus. The next class of immune checkpoint inhibitors to receive regulatory approval were against PD-1 and its ligands PD-L1 and PD-L2. Approved anti-PD1 antibodies include nivolumab (OPDIVO®; Bristol-Myers Squibb) and pembrolizumab (KEYTRUDA®; Merck) for various cancers, including squamous cell carcinoma, classical Hodgkin lymphoma and urothelial carcinoma.

Approved anti-PD-L1 antibodies include avelumab (BAVENCIO®, EMD Serono & Pfizer), atezolizumab (TECENTRIQ®; Roche/Genentech), and durvalumab (IMFINZI®; AstraZeneca) for certain cancers, including urothelial carcinoma. While there are no approved therapeutics targeting TIGIT or its ligands CD155 and CD112, those in development include BMS-986207 (Bristol-Myers Squibb), MTIG7192A/RG6058 (Roche/Genentech), domvanalimab (AB154), and OMP-31M32 (OncoMed). In some combinations provided herein, the immune checkpoint inhibitor is selected from nivolumab, pembrolizumab, avelumab, atezolizumab, durvalumab, cemiplimab and zimberelimab. In another embodiment, the immune checkpoint inhibitor is selected from sintilmab, camrelizumab, tislelizumab, toripalimab, dostarlimab, retifanlimab, sasanlimab, budigalimab, BI-754091, cosibelimab, and spartalizumab.

In one aspect of the present invention, the claimed HIF-2α inhibitors are combined with an immuno-oncology agent that is (i) an agonist of a stimulatory (including a co-stimulatory) receptor or (ii) an antagonist of an inhibitory (including a co-inhibitory) signal on T cells, both of which result in amplifying antigen-specific T cell responses. Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), B7-H6, and B7-H7 (HHLA2). Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LT13R, LIGHT, DcR3, HVEM, VEGI/TLIA, TRAMP/DR3, EDAR, EDA1, XEDAR, EDA2, TNFR1, Lymphotoxin a/TNF13, TNFR2, TNFa, LT13R, Lymphotoxin a 1132, FAS, FASL, RELT, DR6, TROY, NGFR.

In another aspect, the immuno-oncology agent is a cytokine that inhibits T cell activation (e.g., IL-6, IL-10, TGF-B, VEGF, and other immunosuppressive cytokines) or a cytokine that stimulates T cell activation, for stimulating an immune response.

In one aspect, T cell responses can be stimulated by a combination of the disclosed HIF-2α inhibitors and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD2. Other agents that can be combined with the HIF-2α inhibitors of the present invention for the treatment of cancer include antagonists of inhibitory receptors on NK cells or agonists of activating receptors on NK cells. For example, compounds herein can be combined with antagonists of KIR, such as lirilumab. As another example, compounds described herein can be combined with lenvatinib or cabozantinib.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, the disclosed HIF-2α inhibitors can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO® (nivolumab), KEYTRUDA® (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224. In another embodiment, the agent is zimberelimab.

In another aspect, the immuno-oncology agent is a PD-L1 antagonist, such as an antagonistic PD-L1 antibody. Suitable PD-L1 antibodies include, for example, TECENTRIQ® (atezolizumab; MPDL3280A; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The present invention encompasses pharmaceutically acceptable salts, acids or derivatives of any of the above.

Examples of therapeutic agents useful in combination therapy for the treatment of cardiovascular and/or metabolic-related diseases, disorders and conditions include statins (e.g., CRESTOR®, LESCOL®, LIPITOR®, MEVACOR®, PRAVACOL®, and ZOCOR®), which inhibit the enzymatic synthesis of cholesterol; bile acid resins (e.g., COLESTID®, LO-CHOLEST®, PREVALITE®, QUESTRAN®, and WELCHOL®), which sequester cholesterol and prevent its absorption; ezetimibe (ZETIA®), which blocks cholesterol absorption; fibric acid (e.g., TRICOR®), which reduces triglycerides and may modestly increase HDL; niacin (e.g., NIACOR®), which modestly lowers LDL cholesterol and triglycerides; and/or a combination of the aforementioned (e.g., VYTORIN® (ezetimibe with simvastatin). Alternative cholesterol treatments that may be candidates for use in combination with the HIF-2α inhibitors described herein include various supplements and herbs (e.g., garlic, policosanol, and guggul).

The present invention encompasses pharmaceutically acceptable salts, acids or derivatives of any of the above.

Examples of therapeutic agents useful in combination therapy for immune- and inflammatory-related diseases, disorders or conditions include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous since one or more adverse effects of the steroid can be reduced or even eliminated by tapering the steroid dose required.

Additional examples of active agents that may be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-10, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, REMICADE®, HUMERA®, anti-TNF antibody fragments (e.g., CDP870), and soluble p55 or p75 TNF receptors, derivatives thereof, p75TNFRIgG (ENBREL®) or p55TNFR1gG (lenercept), soluble IL-13 receptor (sIL-13), and also TNFa-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the HIF-2α inhibitors described herein include interferon-131a (AVONEX®); interferon-131b (BETASERON®); copaxone; hyperbaric oxygen; intravenous immunoglobulin; clabribine; and antibodies to, or antagonists of, other human cytokines or growth factors (e.g., antibodies to CD40 ligand and CD80).

Dosing

The HIF-2α inhibitors of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the HIF-2α inhibitors of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the HIF-2α inhibitors contemplated by the present invention may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, more particularly 1 to 100 milligrams or 1, 2, 3, 4, 5, 6, 7, 8, 9, 10, 11, 12, 13, 14, 15, 16, 17, 18, 19, 20, 25, 30, 35 or 40 milligrams once daily.

In certain embodiments, the dosage of the desired HIF-2α inhibitor is contained in a "unit dosage form". The phrase "unit dosage form" refers to physically discrete units, each unit containing a predetermined amount of the HIF-2α inhibitor, either alone or in combination with one or more additional agents, sufficient to produce the desired effect. It will be appreciated that the parameters of a unit dosage form will depend on the particular agent and the effect to be achieved.

Kits

The present invention also contemplates kits comprising a compound described herein, and pharmaceutical compositions thereof. The kits are generally in the form of a physical structure housing various components, as described below, and may be utilized, for example, in practicing the methods described above.

A kit can include one or more of the compounds disclosed herein (provided in, e.g., a sterile container), which may be in the form of a pharmaceutical composition suitable for administration to a subject. The compounds described herein can be provided in a form that is ready for use (e.g., a tablet or capsule) or in a form requiring, for example, reconstitution or dilution (e.g., a powder) prior to administration. When the compounds described herein are in a form that needs to be reconstituted or diluted by a user, the kit may also include diluents (e.g., sterile water), buffers, pharmaceutically acceptable excipients, and the like, packaged with or separately from the compounds described herein. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (C), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; µg=microgram; mg=milligram; g=gram; kg=kilogram; dl or dL=deciliter; µl or µL=microliter; ml or mL=milliliter; 1 or L=liter; µM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbeco's Modification of Eagle's Medium; EDTA=ethylenediaminetetraacetic acid.

Materials and Methods

The following general materials and methods were used, where indicated, or may be used in the Examples below:

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N. Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Where the literature contains an assay or experimental procedure, such assay or procedure may serve as an alternative basis for evaluating the compounds described herein.

All reactions were performed using a Teflon-coated magnetic stir bar at the indicated temperature and were conducted under an inert atmosphere when stated. Reactions were monitored by TLC (silica gel 60 with fluorescence F254, visualized with a short wave/long wave UV lamp) and/or LCMS (Agilent 1100 series LCMS with UV detection at 254 nm using a binary solvent system [0.1% TFA in MeCN/0.1% TFA in $H_2O$] using either of the following column: Agilent Eclipse Plus C18 [3.5 µm, 4.6 mm i.d.×100 mm]). Flash chromatography was conducted on silica gel using an automated system (CombiFlash RF+ manufactured by Teledyne ISCO), with detection wavelengths of 254 and 280 nm. Reverse phase preparative HPLC was conducted on an Agilent 1260 Infinity series HPLC. Samples were eluted using a binary solvent system (0.1% TFA in MeCN/0.1% TFA in $H_2O$) with gradient elution on a Gemini C18 110 Å column (21.2 mm i.d.×250 mm) with detection at 254 nm. Final compounds obtained through preparative HPLC were concentrated. Reported yields are isolated yields unless otherwise stated. All assayed compounds were purified to >95% purity as determined by LCMS (Agilent 1100 series LCMS with UV detection at 254 nm using a binary solvent system [0.1% TFA in MeCN/0.1% TFA in $H_2O$] using the following column: Agilent Eclipse Plus C18 column [3.5 µm, 4.6 mm i.d.×100 mm]). $^1$H NMR spectra were recorded on a Varian 400 MHz NMR spectrometer equipped with an Oxford AS400 magnet. Chemical shifts (δ) are reported as parts per million (ppm) relative to residual undeuterated solvent as an internal reference.

Examples

Example 1: 2-chloro-3-(6,8-difluoro-1,2,3,4-tetrahydronaphthalen-1-yl)-6-methanesulfonylbenzonitrile

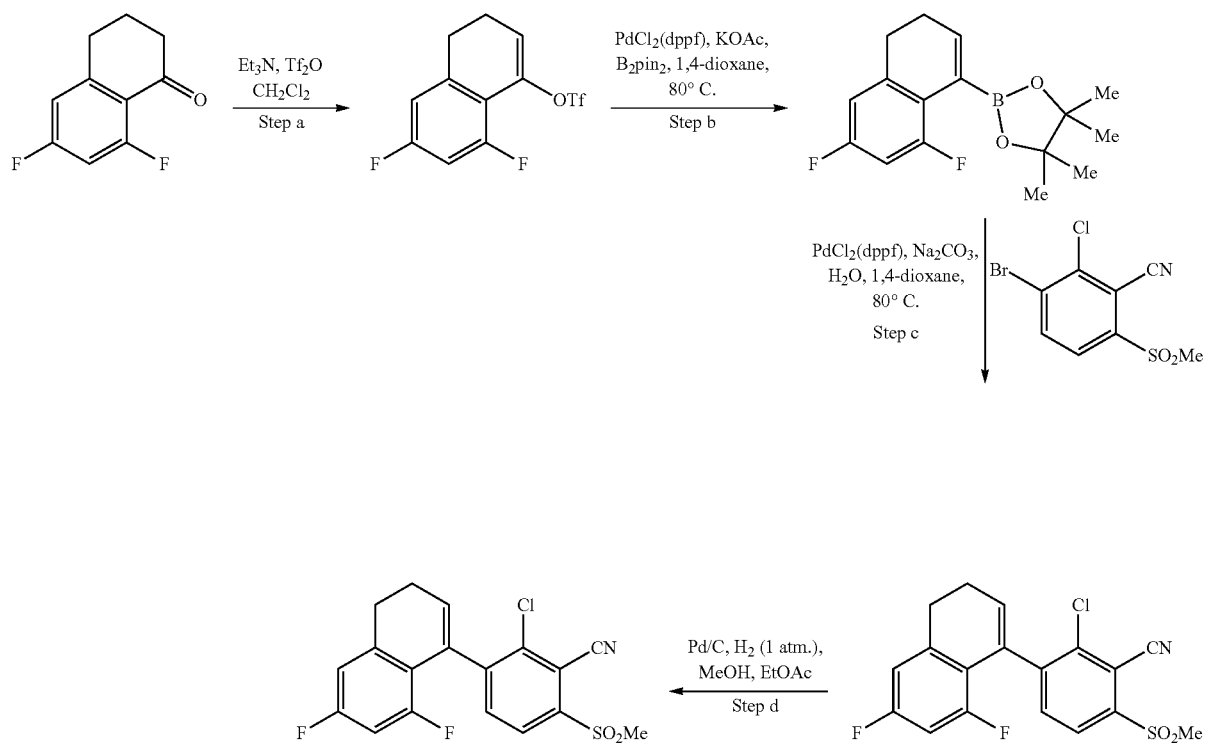

Step a: 6,8-difluoro-1,2,3,4-tetrahydronaphthalen-1-one (500 mg, 2.74 mmol) was dissolved in CH$_2$Cl$_2$ (11 ml, 0.25 M) and the resulting solution was sparged with nitrogen gas for 5 minutes. Triethylamine (574 µL, 1.5 equiv.) was added, and the solution was cooled to 0° C. before the addition of Tf$_2$O (691 µL, 1.5 equiv.). The reaction was allowed to warm to room temperature and was stirred overnight. The solution was quenched with water, extracted with CH$_2$Cl$_2$, and the resulting organics were dried over Na$_2$SO$_4$ and concentrated onto Celite. The crude material was flashed on silca gel (gradient, 0% to 20% ethyl acetate in hexanes) to yield the desired 5,7-difluoro-4-(trifluoromethylsulfonyloxy)-1,2-dihydronaphthalene (470 mg, 54% yield) as an oil.

Step b: A vial was charged with alkenyl triflate from step a (2.50 g, 7.96 mmol, 1.0 equiv.), PdCl$_2$(dppf) (872 mg, 1.19 mmol, 15 mol %), B$_2$pin$_2$ (2.82 g, 11.1 mmol, 1.4 equiv.), KOAc (1.72 g, 17.5 mmol, 2.2 equiv.) and 1,4-dioxane (20 ml). The vial was capped, and the reaction mixture was purged with N$_2$ for 2 minutes. The reaction was heated at 80° C. and stirred for 30 min. The reaction was cooled, filtered, and concentrated onto Celite. Purification by flash chromatography (SiO$_2$, hexane to 10% EtOAc) furnished the alkenyl pinacol boronic ester as a brown oil (1.16 g, 3.97 mmol, 50%).

Step c: To a vial containing the product from step b (100 mg, 0.342 mmol, 1.0 equiv.) was added 3-bromo-2-chloro-6-(methylsulfonyl)benzonitrile (100 mg, 0.342 mmol, 1.0 equiv.), PdCl$_2$(dppf) (25 mg, 0.034 mmol, 10 mol %), 1,4-dioxane (1 mL) and 1M aq. Na$_2$CO$_3$ solution (0.7 mL). The vial was capped and purged with N$_2$ for 2 minutes. The reaction was heated at 80° C. and stirred for 1.5 h. Once complete, the reaction was cooled, diluted with sat. aq. NH$_4$Cl solution (20 mL) and extracted with DCM (20 mL). The aqueous layer was separated and back extracted with additional DCM (2×20 mL). The organic layers were combined, washed with brine (40 mL), and dried over MgSO$_4$. Concentration under reduced pressure and purification by flash chromatography (SiO$_2$, hexane to 50% EtOAc gradient) furnished the cross-coupled product as a white solid that was taken onto the next step (58.6 mg, 0.154 mmol, 45%, ESI MS [M+H]$^+$ for C$_{18}$H$_{12}$ClF$_2$NO$_2$S, calcd 380.0, found 380.1).

Step d: To a vial containing the product from step c (58.6 mg, 0.154 mmol, 1.0 equiv.) was added Pd/C (10% Pd, 25 mg). The vial was evacuated and back-filled with N$_2$ (×3). MeOH (1 mL) and EtOAc (1 mL) were added, and the reaction mixture was purged with H$_2$ for 2 min, then stirred at room temperature under 1 atm H$_2$ for 16 h. The reaction vessel was flushed with N$_2$ and the mixture filtered through Celite, rinsing with EtOAc. Concentration under reduced pressure and purification by preparative reverse phase HPLC (20 to 100% gradient of acetonitrile and water with 0.1% TFA) furnished the product as a white solid. $^1$H NMR (400 MHZ, DMSO-d$_6$) δ 7.95 (d, J=8.2 Hz, 1H), 7.31 (d, J=8.2 Hz, 1H), 7.10-6.98 (m, 2H), 4.79-4.72 (m, 1H), 3.43 (s, 3H), 2.99-2.88 (m, 1H), 2.88-2.75 (m, 1H), 2.19-2.08 (m, 1H), 1.87-1.75 (m, 1H), 1.75-1.63 (m, 1H), 1.62-1.47 (m, 1H). ESI MS [M+H]$^+$ for C$_{18}$H$_{14}$ClF$_2$NO$_2$S, calcd 382.0, found 382.1.

Example 2a/b: (1S,2R)-4-[R-6,8-difluoro-1,2,3,4-tetrahydronaphth-1-yl]-2-fluoro-7-(trifluoromethylsulfonyl)-1-indanol

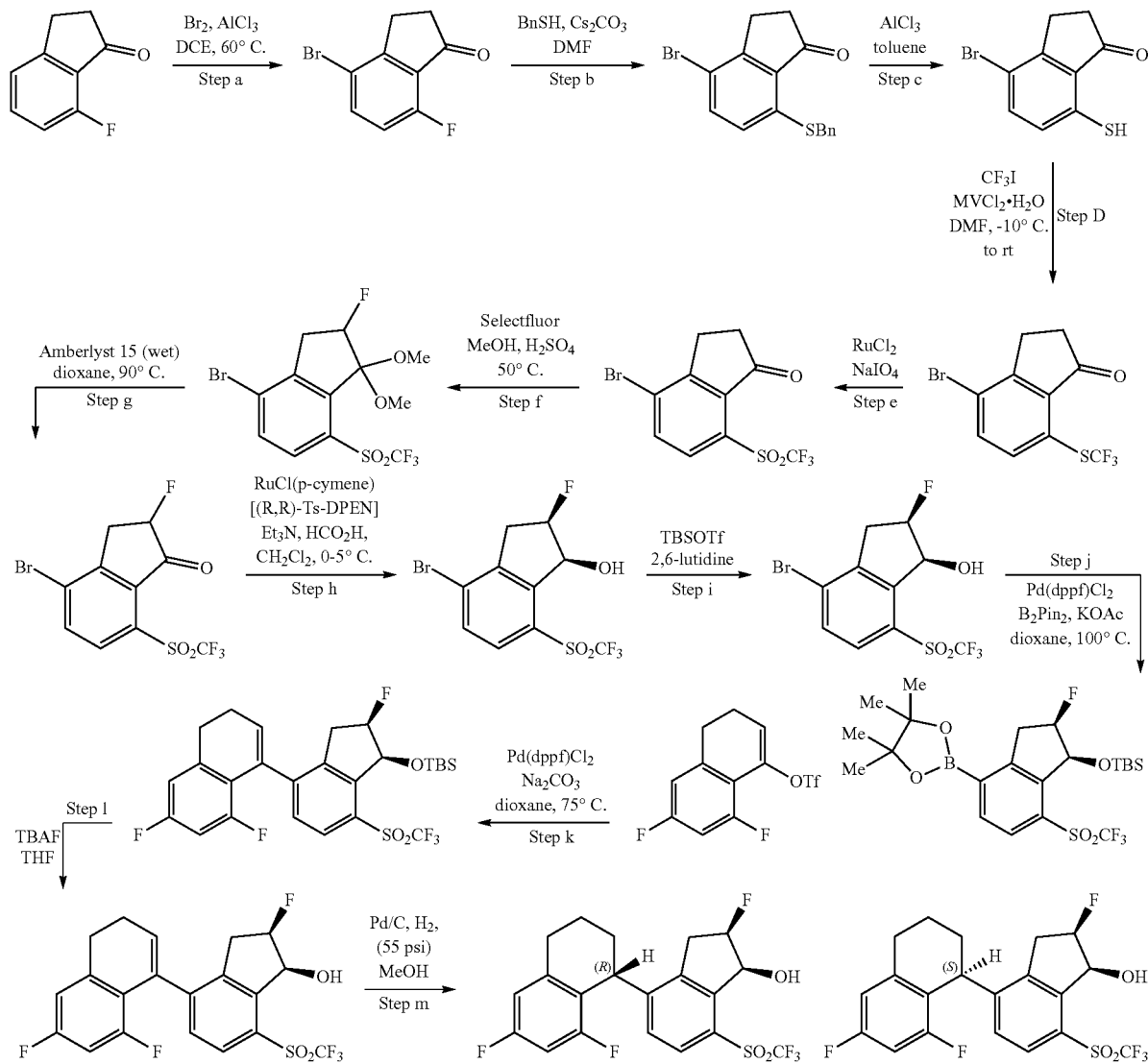

Step a: To a suspension of 7-fluoro-2,3-dihydro-1H-inden-1-one (10.0 g, 66.6 mmol) and aluminum trichloride (22.2 g, 166.5 mmol, 2.5 equiv.) in 1,2-dichloroethane (190 ml, 0.35M) was added bromine (3.58 ml, 70 mmol, 1.05 equiv.) dropwise. The resulting solution was heated to 60° C. for three hours, after which the reaction was cooled to room temperature and poured onto ice. The reaction was extracted with MTBE, dried over magnesium sulfate, and concentrated. The crude material was purified by flash chromatography (silica gel, 0% to 10% ethyl acetate in a 1:1 solution of $CH_2Cl_2$:hexanes) to yield 4-bromo-7-fluoro-2,3-dihydro-1H-inden-1-one.

Step b: To a suspension of 4-bromo-7-fluoro-2,3-dihydro-1H-inden-1-one (17.0 g, 74.3 mmol) and $Cs_2CO_3$ (26.6 g, 81.7 mmol, 1.1 equiv.) in DMF (372 ml, 0.2M) was added benzyl mercaptan (9.24 g, 8.71 ml, 1.0 equiv.). The reaction was stirred at room temperature for 90 minutes. The desired product was precipitated from solution through the addition of 1.5 L of water and was dried under high vacuum overnight. The resulting crude product (23.1 g, 93% yield) was taken on without further purification.

Step c: The crude thioether from the step b (23.1 g, 69.2 mmol) was suspended in toluene (692 ml, 0.1M). Aluminum trichloride (10.2 g, 1.1 equiv.) was added at room temperature. An additional portion of aluminum trichloride (3.6 g, 27 mmol, 0.4 equiv.) was added after three hours. After an additional three hours, the reaction was quenched with water, extracted with ethyl acetate, and concentrated. The crude material was purified by flash chromatography (silica gel, 0% to 20% ethyl acetate in a 1:3 solution of $CH_2Cl_2$ in hexanes) to yield the desired thiophenol as a yellow solid (13.4 g, 80% yield).

Step d: A solution of the thiophenol product from step c (6.7 g, 27.6 mmol) and methyl viologen dichloride hydrate (710 mg, 0.1 equiv.) in DMF (55 ml, 0.5M) was carefully degassed via three freeze-pump-thaw cycles under nitrogen. The resulting solution was cooled to −10 to −5° C. in a brine ice bath, and an excess of $CF_3I$ was sparged through the reaction mixture. The reaction was then stirred overnight under an atmosphere of CF$_3$I. The reaction was carefully quenched at room temperature with water (off-gassing of residual CF$_3$I occurs, use caution), extracted with ethyl acetate, and concentrated. The crude material was purified by flash chromatography (silica gel, 0% to 20% ethyl acetate in hexanes) to yield the desired thioether (5.21 g, 61% yield).

Step e: To a solution of the product from step d (10.45 g, 33.6 mmol) in MeCN (129 ml, 0.26 M with respect to starting material), CCl$_4$ (129 ml, 0.26 M with respect to starting material), and H$_2$O (258 ml, 0.13M with respect to starting material) was added ruthenium trichloride (697 mg, 3.36 mmol, 0.1 equiv.) followed by sodium periodate (29.6 g, 138.4 mmol, 4.12 equiv.). The reaction was stirred at room temperature for one hour, and upon completion was extracted with CH$_2$Cl$_2$ (×2). The combined organics were washed with saturated Na$_2$S$_2$O$_3$, washed with brine, and dried over sodium sulfate before concentrating. The crude material was purified by flash chromatography (silica gel, 0% to 10% ethyl acetate in a 1:3 solution of CH$_2$Cl$_2$ in hexanes) to yield the product sulfone as a white solid (10.53 g, 91% yield). ESI MS [M+H]$^+$ for C$_{10}$H$_6$BrF$_3$O$_3$S; calc 342.9, found 342.9.

Step f: A solution of the product sulfone from step e (3.5 g, 10.2 mmol) and Selectfluor (4.32 g, 12.2 mmol, 1.2 equiv.) in methanol (102 ml, 0.1M) was heated to 50° C. Sulfuric acid (27 µl, 5 mol %) was added, and the reaction was stirred at 50° C. for 48 hours. The solution was then diluted with diethyl ether, and the resulting white precipitate was filtered off and discarded. The organic solution was concentrated, and the crude material was purified by flash chromatography (silica gel, 0% to 10% ethyl acetate in a 1:3 solution of CH$_2$Cl$_2$ in hexanes) to yield the product dimethyl acetal as a white solid (3.57 g, 87% yield).

Step g: A solution of the product acetal from step f (3.18 g, 7.8 mmol) and wet Amberlyst 15 (4.77 g, 150 wt %) in dioxane (31 ml, 0.2 M) was heated to 90° C. overnight. Upon completion, the polymeric beads were removed by filtration, and the concentrated crude material was purified by flash chromatography (silica gel, 0% to 10% ethyl acetate in a 1:3 solution of CH$_2$Cl$_2$ in hexanes) to yield the desired fluorinated ketone (2.33 g, 83% yield).

Step h: A solution of the indanone product of step g (2.5 g, 6.93 mmol) in dichloromethane (28 ml, 0.25M) was sparged with nitrogen gas before the addition of formic acid (783 µL, 956 mg, 20.8 mmol, 3 equiv.) and triethylamine (1.94 ml, 1.41 g, 13.9 mmol, 2 equiv.) at 0° C. under nitrogen. RuCl(p-cymene)[(R,R)-Ts-DPEN] (44.5 mg, 0.07 mmol, 0.01 equiv.) was added, and the reaction was stirred for a minimum of 12 hours at 0 to 5° C. Upon full conversion, the reaction was quenched with saturated NaHCO$_3$ and extracted with CH$_2$Cl$_2$. The combined organics were concentrated, and the crude material was purified by flash chromatography (silica gel, 0% to 20% ethyl acetate in a 1:1 solution of CH$_2$Cl$_2$:hexanes) to yield the desired indanol (2.0 g, 80% yield) as a single diastereomer. The enantiomeric excess of this material was found to be 98% by chiral HPLC (Chiralpak AD-H, 20% iPrOH/hexanes, isocratic, 20 minutes) as compared to a racemic sample, which was obtained through reduction of the 2-fluoroindanone with sodium borohydride.

Step i: To a solution of the chiral indanol from step h (1.01 g, 2.75 mmol) in CH$_2$Cl$_2$ (11 ml, 0.25M) was added 2,6-lutidine (800 µL, 6.9 mmol, 2.5 equiv.) and TBSOTf (791 µL, 3.44 mmol, 1.25 equiv.) at 0° C. The reaction was allowed to warm to room temperature and was stirred overnight. Upon completion, the reaction was concentrated directly onto Celite and purified by flash chromatography (silica gel, 0% to 10% ethyl acetate in hexanes) to yield the TBS ether (1.35 g, 100% yield).

Step j: The TBS ether product of step i (674 mg, 1.41 mmol) was combined with B$_2$Pin$_2$ (457 mg, 1.8 mmol, 1.3 equiv.) Pd(dppf)Cl$_2$ (103 mg, 0.14 mmol, 0.1 equiv.) and potassium acetate (213 mg, 3 mmol, 2.2 equiv.) in dioxane (14 ml, 0.1M), and the resulting solution was heated to 100° C. for three hours. The reaction solution was concentrated, and the crude material was purified by flash chromatography (silica gel, 0% to 30% ethyl acetate in hexanes) to yield the desired boronic pinacol ester (638 mg, 86% yield) as a colorless oil.

Step k: The boronic ester product of step j (1.64 g, 3.13 mmol) was combined with 5,7-difluoro-4-(trifluoromethylsulfonyloxy)-1,2-dihydronaphthalene (1.18 g, 3.75 mmol, 1.2 equiv.), Pd(dppf)Cl$_2$ (227 mg, 0.31 mmol, 0.1 equiv.) and sodium carbonate (2M, aq., 3.13 ml, 2.0 equiv.) in dioxane (31 ml, 0.1M) and heated to 75° C. for three hours. Upon completion, the reaction was concentrated onto Celite and purified by flash chromatography (silica gel, 0% to 20% ethyl acetate in hexanes) to yield the desired alkene product (1.42 g, 86% yield) as a colorless resin.

Step l: TBAF (0.1M in THF, 0.3 mmol, 1.5 equiv.) was added to a cooled solution of the product of step k (113 mg, 0.2 mmol) at 0° C., and the reaction was allowed to warm to ambient temperature. After 2 hours the reaction was concentrated onto Celite and purified by flash chromatography (silica gel, 0% to 20% ethyl acetate in hexanes) to yield the free indanol (1S,2R)-4-(6,8-difluoro-3,4-dihydronaphth-1-yl)-2-fluoro-7-(trifluoromethylsulfonyl)-1-indanol (33.7 mg, 37% yield). $^1$H NMR (400 MHZ, CDCl$_3$): δ 7.92 (d, J=8.1 Hz, 1H), 7.49 (d, J=8.1 Hz, 1H), 6.81 (d, J=8.3 Hz, 1H), 6.56 (ddd, J=11.3, 8.7, 2.6 Hz, 1H), 6.15 (dd, J=4.9, 4.9 Hz, 1H), 5.58-5.51 (br m, 1H), 5.28-5.08 (m, 1H), 3.14-3.00 (m, 2H), 2.92-2.79 (m, 2H), 2.48-2.37 (m, 2H). ESI MS [M+Na]$^+$ for C$_{20}$H$_{14}$F$_6$O$_3$S; calcd 471.0, found 471.0.

Step m: The product indanol of step l was dissolved in methanol (700 µL, 0.1M) and added to palladium on carbon (3 mg, 10% Pd by weight) under an atmosphere of nitrogen. The reaction mixture was placed under an atmosphere of hydrogen at 55 psi and agitated in a Parr shaker overnight. The resulting diastereomers were separated by column chromatography (silica gel, 100% toluene) to yield (1S,2R)-4-[R-6,8-difluoro-1,2,3,4-tetrahydronaphth-1-yl]-2-fluoro-7-(trifluoromethylsulfonyl)-1-indanol (example 2a) as the less polar diastereomer. $^1$H NMR (400 MHz, CDCl$_3$): δ 7.76 (d, J=8.1 Hz, 1H), 6.98 (d, J=8.1 Hz, 1H), 6.75 (br d, J=10.0 Hz, 1H), 6.58 (dd, J=9.8 Hz, 1H), 5.59-5.55 (m, 1H), 5.41-5.23 (m, 1H), 4.41-4.36 (br m, 1H), 3.51-3.41 (m, 1H), 3.25-3.16 (m, 1H), 3.12 (d, J=4.1 Hz, 1H), 2.94-2.78 (m, 2H), 2.17-2.07 (m, 1H), 1.78-1.67 (m, 2H). ESI MS [M+Na]$^+$ for C$_{20}$H$_{16}$F$_6$O$_3$S; calcd 473.1, found 473.1. (1S,2R)-4-[S-6,8-difluoro-1,2,3,4-tetrahydronaphth-1-yl]-2-fluoro-7-(trifluoromethylsulfonyl)-1-indanol (example 2b) was isolated as the more polar diastereomer. $^1$H NMR (400 MHZ, CDCl$_3$): δ 7.75 (d, J=8.3 Hz, 1H), 6.92 (d, J=8.3 Hz, 1H), 6.79-6.72 (m, 1H), 6.62-6.54 (m, 1H), 5.60 (td, J=5.0, 3.7 Hz, 1H), 5.47-5.24 (m, 1H), 4.38-4.34 (m, 1H), 3.50-3.27 (m, 2H), 3.08 (d, 1H), 2.98-2.75 (m, 2H), 2.16-2.07 (m, 1H), 1.86-1.62 (m, 2H). ESI MS [M+Na]$^+$ for C$_{20}$H$_{16}$F$_6$O$_3$S; calcd 473.1, found 473.1.

Example 3: (1S,2R)-4-[(1S)-6,8-difluoro-1,2,3,4-tetrahydronaphthalen-1-yl]-2-fluoro-7-methanesulfonyl-2,3-dihydro-1H-inden-1-ol Example 4: (1S,2R)-4-[(1R)-6,8-difluoro-1,2,3,4-tetrahydronaphthalen-1-yl]-2-fluoro-7-methanesulfonyl-2,3-dihydro-1H-inden-1-ol

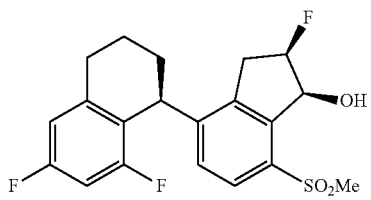

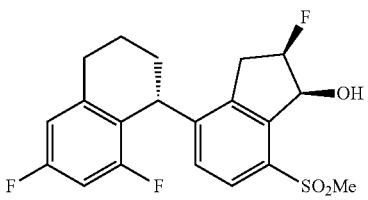 [SMILES: CS(=O)(=O)c1ccc([C@H]2CCCc3cc(F)cc(F)c32)c2c1[C@H](O)[C@H](F)C2]

The title compound was synthesized in a similar fashion to Example 2. $^1$H NMR (400 MHz, Chloroform-d) δ 7.70 (d, J=8.1 Hz, 1H), 6.84 (d, J=8.1 Hz, 1H), 6.73 (d, J=9.1 Hz, 1H), 6.56 (ddd, J=2.4, 9.1, 18.0 Hz, 1H), 5.65 (dt, J=4.8, 14.4 Hz, 1H), 5.49-5.31 (m, 1H), 4.36 (m, 1H), 3.66 (dd, J=5.1, 1.8 Hz, 1H), 3.40 (ddd, J=21.6, 16.9, 3.2 Hz, 1H), 3.25 (s, 3H), 3.16-2.99 (m, 1H), 2.95-2.74 (m, 2H), 2.13-2.00 (m, 1H), 1.76-1.62 (m, 3H). ESI MS [M–H$_2$O+H]$^+$ for C$_{20}$H$_{19}$F$_3$O$_3$S calcd 379.1, found 379.1.

The title compound was synthesized in a similar fashion to Example 2. $^1$H NMR (400 MHz, Chloroform-d) δ 7.71-7.67 (d, J=8.1 Hz, 1H), 6.81 (d, J=8.1 Hz, 1H), 6.73 (d, J=9.1, Hz, 1H), 6.55 (ddd, J=2.1, 9.2, 18.4 Hz, 1H), 5.67 (dt, J=4.7, 12.4 Hz, 1H), 5.51-5.33 (dq, J=4.7, 52.4 Hz, 1H), 4.32 (m, 1H), 3.59 (dd, J=4.4, 1.4 Hz, 1H), 3.31 (dd, J=21.2, 4.9 Hz, 2H), 3.23 (s, 3H), 2.94-2.76 (m, 2H), 2.14-2.05 (m, 1H), 1.83 (m, 1H), 1.75-1.65 (m, 2H). ESI MS [M–H$_2$O+H]$^+$ for C$_{20}$H$_{19}$F$_3$O$_3$S calcd 379.1, found 379.1.

Example 5: (8R)-3-fluoro-8-((1S,2R)-2-fluoro-1-hydroxy-7-((trifluoromethyl)sulfonyl)-2,3-dihydro-1H-inden-4-yl)-5,6,7,8-tetrahydronaphthalene-1-carbonitrile

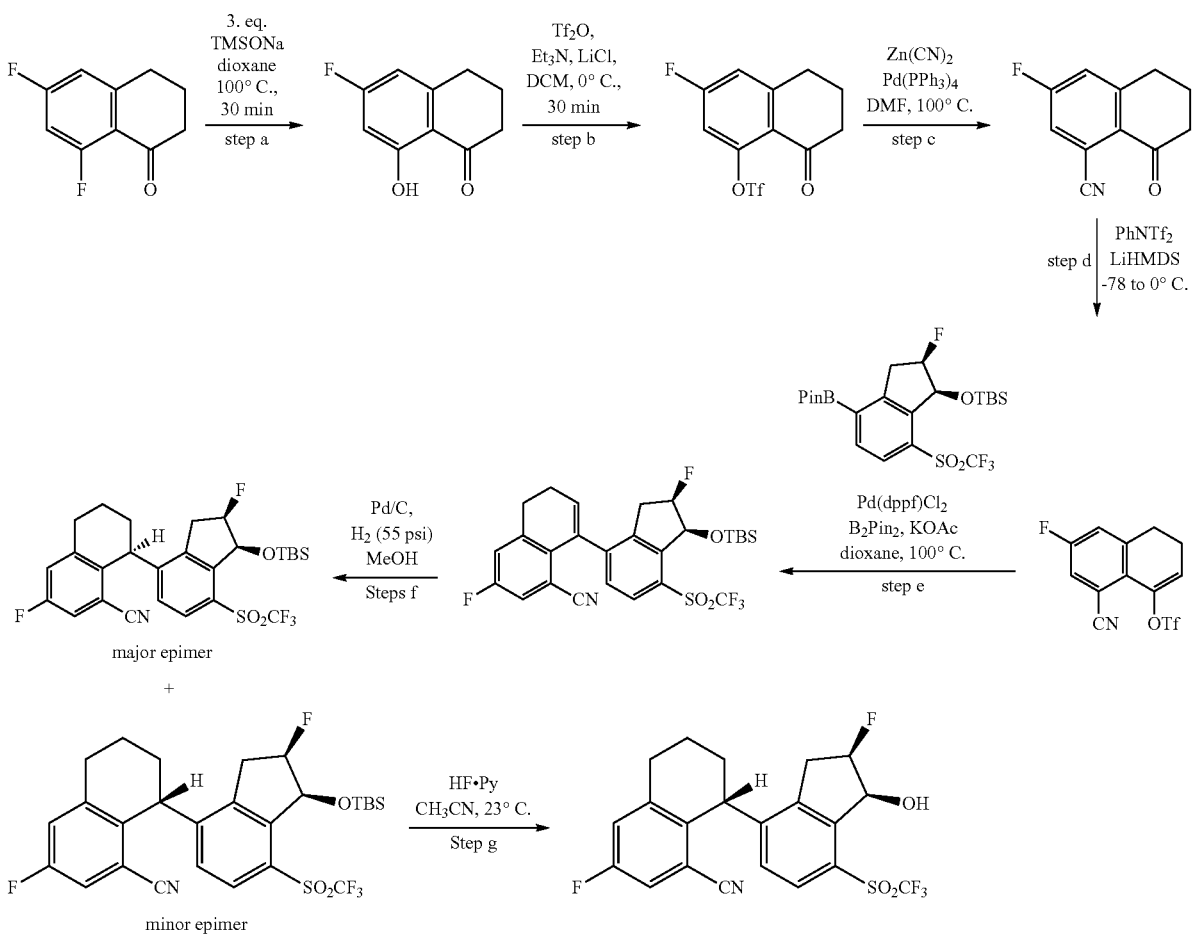

Step a: A solution of 6,8-difluoro-1,2,3,4-tetrahydronaphthalen-1-one (7 g, 38.4 mmol) and TMSONa (14.8 g, 115.3 mmol) in dioxane (128 mL) was refluxed for 20 min under nitrogen atmosphere. Upon disappearance of starting material (TLC analysis, 30% EtOAc in hexanes as an eluent, the desired product spot is the least polar) the mixture was cooled to room temperature and poured into saturated aqueous solution of $NH_4Cl$ (200 mL). The product was extracted with EtOAc (3×70 mL). Combined extracts were washed with brine (200 mL). The organic phase was separated and dried over $Na_2SO_4$. After all solvent was removed under reduced pressure, the crude product was purified by flash chromatography ($SiO_2$, hexanes/EtOAc gradient) to provide 8-hydroxy-6-fluoro-1,2,3,4-tetrahydronaphthalen-1-one as a yellow solid (4.7 g, 26.1 mmol, 68% yield). $^1$H NMR (400 MHZ, $CDCl_3$) δ 12.74 (d, J=1.5 Hz, 1H), 6.45 (dd, J=10.4, 2.5 Hz, 1H), 6.41 (ddd, J=9.1, 2.3, 1.2 Hz, 1H), 2.93-2.82 (m, 2H), 2.71-2.60 (m, 2H), 2.14-1.99 (m, 2H). $^1$H NMR (376 MHz, $CDCl_3$) δ −98.95 (t, J=9.7 Hz).

Step b: A mixture of 8-hydroxy-6-fluoro-1,2,3,4-tetrahydronaphthalen-1-one (5.3 g, 29.4 mmol) triethylamine (5.3 mL, 38.2 mmol) and LiCl (1.6 g, 38.2 mmol) in dichloromethane (150 mL) was cooled to 0° C. Trifluoromethanesulfonic anhydride (6.4 mL, 38.2 mmol) was added dropwise over 10 min. The mixture was stirred for additional 30 min before complete disappearance of starting material was observed by TLC analysis (30% EtOAc in hexanes as an eluent). Then the reaction was diluted with dichloromethane (50 mL) and sequentially washed with aqueous saturated solution of $NaHCO_3$ (150 mL), aqueous 1M HCl (100 mL) and brine (150 mL). The organic phase was separated and dried over $Na_2SO_4$. After all solvent was removed under reduced pressure, the crude product was purified by flash chromatography ($SiO_2$, hexanes/EtOAc gradient) to provide trifluoromethanesulfonic acid 8-oxo-6-fluoro-5,6,7,8-tetrahydro-naphthalen-1-yl ester as a yellow oil (8.1 g, 25.9 mmol, 88% yield). $^1$H NMR (400 MHz, $CDCl_3$) δ 7.03 (ddt, J=8.3, 2.5, 0.9 Hz, 1H), 6.86 (dd, J=8.3, 2.5 Hz, 1H), 3.10-2.87 (m, 2H), 2.84-2.58 (m, 2H), 2.30-2.07 (m, 2H). $^{19}$F NMR (376 MHz, $CDCl_3$) δ −73.66, −100.52 (t, J=8.5 Hz).

Step c: A mixture of trifluoromethanesulfonic acid 8-oxo-6-fluoro-5,6,7,8-tetrahydro-naphthalen-1-yl ester (8.1 g, 25.9 mmol), zinc cyanide (2.4 g, 20.7 mmol) and $Pd(PPh_3)^+$ (3.0 g, 0.26 mmol) in DMF (65 mL) was heated at 100° ° C. under nitrogen atmosphere for 3 hours. Once complete disappearance of starting material was observed by TLC analysis (30% EtOAc in hexanes as an eluent), the solution was cooled to ambient temperature and poured in a mixture of EtOAc (100 mL) and water (150 mL). The resulting suspension was filtered through a Celite plug. The organic phase was separated, and the aqueous solution was additionally extracted with EtOAc (2×50 mL). Combined organic phase was washed with water (2×150 mL) and brine (100 mL), dried over $Na_2SO_4$ and concentrated to dryness. The dry residue was fractionated by column chromatography ($SiO_2$, hexanes/EtOAc gradient) to provide 8-cyano-6-fluoro-1,2,3,4-tetrahydronaphthalen-1-one (4.0 g, 21.1 mmol, 82% yield) as a white crystalline solid. $^1$H NMR (400 MHZ, $CDCl_3$) δ 7.37 (ddt, J=8.0, 2.6, 0.6 Hz, 1H), 7.19 (ddt, J=8.3, 2.6, 0.9 Hz, 1H), 3.09-2.90 (m, 2H), 2.87-2.65 (m, 2H), 2.31-2.06 (m, 2H). $^{19}$F NMR (376 MHz, $CDCl_3$) δ −103.48 (t, J=8.2 Hz).

Step d: A solution of N-phenyl-bis(trifluoromethanesulfonimide) (11.3 g, 31.6 mmol) and 8-cyano-6-fluoro-1,2,3,4-tetrahydronaphthalen-1-one (4.0 g, 21.1 mmol) in THF (105 mL) was cooled to −78° C. under nitrogen atmosphere. Then 1 M solution of LiHMDS in THF (21.1 mmol, 21.1 mL) was added dropwise over 5 min period. The resulting brownish solution was stirred at −78° C. for additional 5 min and was transferred to an ice bath. After 30 min at 0° C. TLC analysis showed complete consumption of starting material. The reaction was quenched by addition of aqueous solution of $NH_4Cl$ (10 mL), then it was diluted with water (150 mL) and EtOAc (150 mL). Organic phase was separated, and the aqueous phase was additionally extracted with EtOAc 2×80 mL). Combined organic extracts were washed with brine (100 mL), dried over $Na_2SO_4$ and concentrated to dryness. The dry residue was fractionated by column chromatography ($SiO_2$, hexanes/EtOAc gradient) to provide 8-cyano-6-fluoro-3,4-dihydronaphthalen-1-yl trifluoromethanesulfonate (6.74 g, 21.0 mmol, 99% yield) as a white solid. $^1$H NMR (400 MHZ, $CDCl_3$) δ 7.28 (dd, J=8.0, 2.6 Hz, 1H), 7.17 (ddt, J=8.1, 2.6, 0.9 Hz, 1H), 6.30 (dd, J=5.4, 4.8 Hz, 1H), 2.94-2.80 (m, 2H), 2.61-2.40 (m, 2H). $^{19}$F NMR (376 MHz, $CDCl_3$) δ −72.31, −109.26 (t, J=8.0 Hz).

Step e: A solution of 2-[(1S,2R)-2-fluoro-1-(tertbutyldimethylsilyloxy)-7-(trifluoromethylsulfonyl)-4-indanyl]-4,4,5,5-tetramethyl-1,3,2-dioxaborolane (0.44 g, 0.84 mmol) and 8-cyano-6-fluoro-3,4-dihydronaphthalen-1-yl trifluoromethanesulfonate (0.27 g, 0.84 mmol) in dioxane (4.2 mL) was placed in 30 mL vial. Then $Pd(dppf)Cl_2$ (62 mg, 0.084 mmol) and aqueous sodium carbonate (2M solution, 0.84 ml, 1.68 mmol) were sequentially added. The mixture was degassed under vacuum, backfilled with nitrogen and heated at 90° C. for 1 hour. Upon completion, the reaction was concentrated onto Celite and fractionated by column chromatography ($SiO_2$, hexanes/EtOAc gradient) to yield the desired alkene product (0.401 g, 0.7 mmol, 84% yield) as a white foam. $^1$H NMR (400 MHz, $CDCl_3$, mixture of atropisomers) δ 7.98-7.86 (m, J=17.7, 8.2 Hz, 1H), 7.63-7.57 (m, 0.3H), 7.43-7.33 (m, 0.7H), 7.22 (dd, J=8.5, 2.6 Hz, 1H), 7.18-7.08 (m, 1H), 6.44-6.36 (m, 1H), 5.64-5.56 (m, 1H), 5.09-4.71 (m, 1H), 3.34-3.19 (m, 0.7H), 3.01-2.71 (m, 3H), 2.61-2.25 (m, 2.3H), 0.84 (s, 9H), 0.28-0.07 (m, 6H). $^{19}$F NMR (376 MHz, $CDCl_3$) δ−78.81, −111.26 (t, J=7.7 Hz), −111.52 (t, J=8.2 Hz), −195.20 (dd, J=51.0, 11.8 Hz), −195.85 (dd, J=50.9, 10.3 Hz).

Step f: The product of step e (0.25 g, 0.44 mmol) was dissolved in dry methanol (15 mL) and added to palladium on carbon (125 mg, 10% Pd by weight) under an atmosphere of nitrogen. The reaction mixture was placed under an atmosphere of hydrogen at 55 psi and agitated in a Parr shaker for 4 hours. The excess hydrogen was vented out and the mixture was degassed under vacuum and backfilled with nitrogen to remove residual hydrogen gas. The resulting suspension was filtered through a Celite pad, and the filtrate was concentrated to dryness under reduced pressure producing crude mixture of epimers (1:2 dr). The crude mixture from step f was subjected to column chromatography ($SiO_2$, hexanes/EtOAc gradient) to produce both epimers of the desired product. (R)-epimer (more polar product, 70 mg, 0.12 mmol, 28% yield): $^1$H NMR (400 MHz, $CDCl_3$) δ 7.70 (d, J=8.2 Hz, 1H), 7.20-7.11 (m, 2H), 6.72 (d, J=8.3 Hz, 1H), 5.62 (d, J=4.3 Hz, 1H), 5.01 (dddd, J=51.2, 8.8, 6.9, 4.3 Hz, 1H), 4.58 (dd, J=6.3, 3.0 Hz, 1H), 3.61 (dddd, J=14.8, 12.5, 8.8, 1.0 Hz, 1H), 3.18 (dd, J=14.8, 6.9 Hz, 1H), 3.03-2.93 (m, 1H), 2.93-2.81 (m, 1H), 2.26-2.07 (m, 1H), 1.95-1.65 (m, 2H), 1.63-1.45 (m, 1H), 0.83 (s, 9H), 0.17 (d, J=2.6 Hz, 3H), 0.13 (s, 3H). $^{19}$F NMR (376 MHz, $CDCl_3$) δ −78.71, −112.94 (t, J=8.2 Hz), −196.32 (dd, J=51.1, 12.8 Hz). (S)-epimer (less polar product, 120 mg, 0.21 mmol, 48% yield): $^1$H NMR (400 MHZ, $CDCl_3$) δ 7.70 (d, J=8.3 Hz, 1H), 7.21-7.07 (m, 2H), 6.69 (d, J=8.3 Hz, 1H), 5.63 (d, J=4.2 Hz, 1H), 5.03 (dddd, J=51.2, 8.3, 6.8, 4.3 Hz, 1H), 4.55 (dd, J=6.5, 3.3 Hz, 1H), 3.47 (ddd, J=14.9, 7.0, 1.5 Hz, 1H), 3.37-3.20 (m, 1H), 3.09-2.94 (m, 1H), 2.93-2.78 (m, 1H), 2.25-2.12 (m, 1H), 1.95-1.87 (m, 1H), 1.86-1.66 (m, 1H), 1.59-1.44 (m, 1H), 0.86 (s, 9H), 0.20 (d, J=2.3 Hz, 3H), 0.15 (s, 3H). $^{19}$F NMR (376 MHz, CDCl$_3$) δ −78.50, −112.92 (t, J=8.2 Hz), −194.99 (dd, J=51.1, 12.6 Hz).

Step h: A solution of the product from step f (8R-epimer, 70 mg, 0.122 mmol) in CH$_3$CN (2 mL) was placed in a 3 mL vial equipped with a magnetic stirrer, then HF·Py complex (hydrogen fluoride ~70%, pyridine ~30%, 0.2 mL) was added. The resulting colorless solution was stirred overnight at ambient temperature. After TLC analysis indicated complete consumption of the starting material the reaction was diluted with EtOAc (20 mL) and 1M aqueous HCl solution (20 mL). The product was extracted with EtOAc (2×10 mL), combined organic extracts were washed with aqueous NaHCO$_3$ (20 mL) and brine (20 mL), dried over Na$_2$SO$_4$ and concentrated to dryness. The residue was fractionated by column chromatography (SiO$_2$, hexanes/EtOAc gradient) to yield (8R)-3-fluoro-8-((1S,2R)-2-fluoro-1-hydroxy-7-((trifluoromethyl)sulfonyl)-2,3-dihydro-1H-inden-4-yl)-5,6,7,8-tetrahydronaphthalene-1-carbonitrile (52 mg, 0.114 mmol, 93% yield) as a white foam. $^1$H NMR (400 MHZ, CDCl$_3$) δ 7.75 (d, J=8.2 Hz, 1H), 7.21-7.13 (m, 2H), 6.77 (d, J=8.2 Hz, 1H), 5.56 (q, J=5.1 Hz, 1H), 5.32 (dtd, J=51.2, 6.4, 5.2 Hz, 1H), 4.59 (dd, J=6.3, 3.2 Hz, 1H), 3.62 (dddd, J=17.9, 16.1, 6.3, 1.0 Hz, 1H), 3.40-3.17 (m, 1H), 3.10-2.79 (m, 3H), 2.31-2.10 (m, 1H), 1.92-1.58 (m, 3H). $^{19}$F NMR (376 MHz, CDCl$_3$) δ −77.60, −112.71, −200.62 (dddd, J=51.2, 16.8, 10.9, 5.5 Hz). ESI MS [M+Na]$^+$ for C$_{21}$H$_{16}$F$_5$NO$_3$S; calcd 480.1, found 480.1

Example 6: (S)-3-fluoro-8-((1S,2R)-2-fluoro-1-hydroxy-7-((trifluoromethyl)sulfonyl)-2,3-dihydro-1H-inden-4-yl)-5,6,7,8-tetrahydronaphthalene-1-carbonitrile

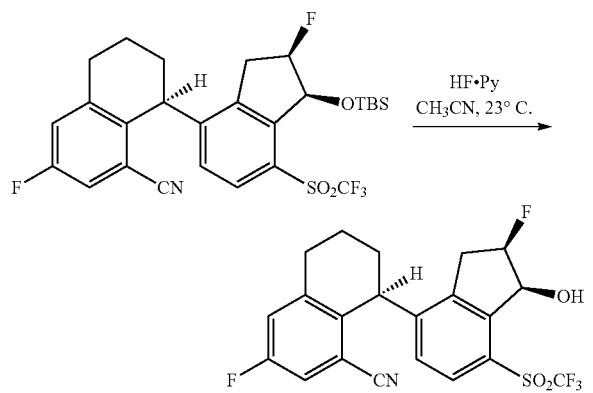

This compound was prepared according to protocol described in Example 5 from S-epimer of corresponding TBS-protected 1-indanol (150 mg, 0.262 mmol) and 0.4 mL of HF·Py complex. The title compound was isolated as a white foam (89 mg, 0.195 mmol, 74% yield). $^1$H NMR (400 MHZ, CDCl$_3$) δ 7.74 (d, J=8.2 Hz, 1H), 7.23-7.05 (m, 2H), 6.70 (d, J=8.2 Hz, 1H), 5.61 (ddd, J=6.1, 5.1, 3.9 Hz, 1H), 5.37 (dddd, J=51.4, 6.6, 6.0, 5.1 Hz, 1H), 4.56 (dd, J=6.4, 3.1 Hz, 1H), 3.65-3.49 (m, 1H), 3.47-3.27 (m, 1H), 3.17 (dd, J=3.9, 0.7 Hz, 1H), 3.08-2.69 (m, 2H), 2.30-2.09 (m, 1H), 1.98-1.86 (m, 1H), 1.83-1.64 (m, 2H). $^{19}$F NMR (376 MHz, CDCl$_3$) δ −77.73, −112.69, −200.05 (dddd, J=51.2, 18.3, 12.2, 6.2 Hz). ESI MS [M+Na]$^+$ for C$_{21}$H$_{16}$F$_5$NO$_3$S; calcd 480.1, found 480.1

Example 7: (8S)-3-fluoro-8-((1S,2R)-2-fluoro-1-hydroxy-7-(methylsulfonyl)-2,3-dihydro-1H-inden-4-yl)-5,6,7,8-tetrahydronaphthalene-1-carbonitrile

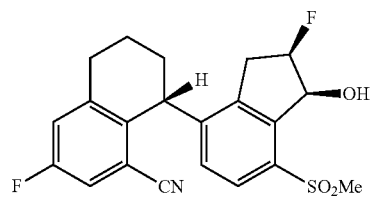 [SMILES: CS(=O)(=O)c1ccc([C@H]2CCCc3cc(F)cc(C#N)c32)c2c1[C@H](O)[C@H](F)C2]

The title compound was synthesized in a similar fashion to Example 5. $^1$H NMR (400 MHz, CDCl$_3$) δ 7.69 (dd, J=8.1, 0.8 Hz, 1H), 7.21-7.11 (m, 2H), 6.60 (d, J=8.1 Hz, 1H), 5.66 (dddd, J=13.0, 5.5, 4.9, 0.5 Hz, 1H), 5.40 (dddd, J=52.6, 5.7, 4.9, 3.6 Hz, 1H), 4.56 (dd, J=6.2, 2.9 Hz, 1H), 3.72-3.40 (m, 2H), 3.26 (s, 3H), 3.15 (ddd, J=23.3, 17.0, 5.8 Hz, 1H), 3.03-2.90 (m, 1H), 2.91-2.77 (m, 1H), 2.19-2.04 (m, 1H), 1.85-1.57 (m, 3H). $^{19}$F NMR (376 MHz, CDCl$_3$) δ −113.22, −199.17. ESI MS [M+Na]$^+$ for C$_{21}$H$_{19}$F$_2$NO$_3$S; calcd 426.1, found 426.1

Example 8: (1S,2R)-4-[(4R)-5,7-difluoro-3,4-dihydro-2H-1-benzopyran-4-yl]-2-fluoro-7-trifluoromethanesulfonyl-2,3-dihydro-1H-inden-1-ol

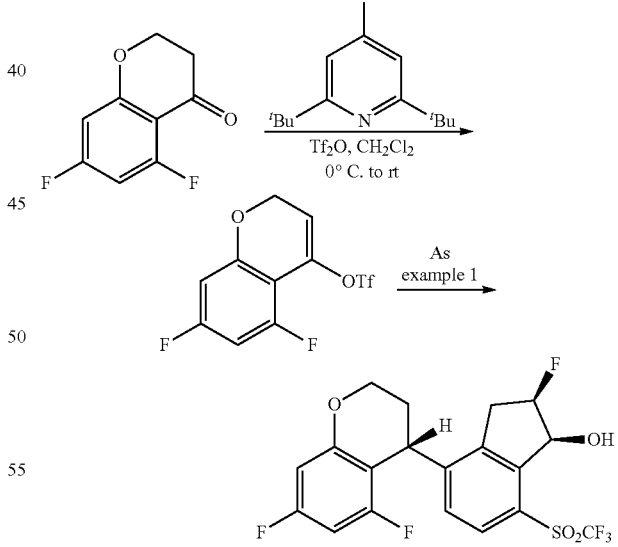

Step a: To a solution of 5,7-difluorochroman-4-one (500 mg, 2.71 mmol) in CH$_2$Cl$_2$ (12 mL, 0.2M) at 0° C. was added 2,6-di-tert-butylmethylpyridine (1.17 g, 5.69 mmol, 2.1 equiv.) followed by trifluoromethanesulfonic anhydride (860 µL, 5.14 mmol, 1.9 equiv.) dropwise. Reaction was stirred at 0° C. for 1 h and then warmed to rt for another 1 h. At this point, hexane (5 mL) was added to precipitate the pyridinium salt and the reaction mixture was filtered over a pad of Celite. Solvent was removed in vacuo and the crude residue was purified by flash chromatography (silica gel, 0% to 20% ethyl acetate in hexanes) to yield the desired vinyl triflate (754 mg, 88%) as a yellow oil. ESI MS [M+H]$^+$ for $C_{10}H_5F_5O_4S$ calcd 316.9, found 317.2.

Step b: The title compound was synthesized in a similar fashion to Example 1. $^1$H NMR (400 MHZ, CDCl$_3$) δ 7.85 (d, J=8.2 Hz, 1H), 7.17 (d, J=8.2 Hz, 1H), 6.59-6.45 (m, 1H), 6.45-6.35 (m, 1H), 5.60 (dd, J=6.6, 5.1 Hz, 1H), 5.51-5.22 (m, 1H), 4.45-4.34 (m, 1H), 4.29-4.14 (m, 1H), 4.08-3.98 (m, 1H), 3.61-3.42 (m, 1H), 3.28-3.16 (m, 1H), 2.43-2.33 (m, 1H), 1.96-1.80 (m, 1H). ESI MS [M+Na]$^+$ for $C_{19}H_{14}F_6O_4SNa$ calcd 475.0, found 475.0.

Example 9: 1-[2,2-difluoro-7-(methylsulfonyl)-4-indanyl]-6-fluoro-1,2,3,4-tetrahydronaphthalene

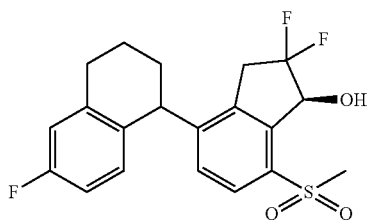 [SMILES: CS(=O)(=O)c1ccc(C2CCCc3cc(F)ccc32)c2c1[C@H](O)C(F)(F)C2]

The title compound was synthesized in a similar fashion to Example 1. $^1$H NMR (400 MHz, Methanol-d$_4$) δ 7.78 (dt, J=8.1, 1.7 Hz, 1H), 7.13 (dd, J=15.1, 8.1 Hz, 1H), 6.89 (ddd, J=9.8, 2.7, 1.1 Hz, 1H), 6.83-6.64 (m, 2H), 5.56-5.49 (m, 1H), 4.32-4.25 (m, 1H), 3.63-3.06 (m, 3H), 2.97-2.78 (m, 2H), 2.21-2.06 (m, 1H), 1.97-1.76 (m, 1H), 1.80-1.68 (m, 1H). ESI MS [M+H]$^+$ for $C_{20}H_{19}F_3O_3S$, calcd 380.4, found 380.1.

Example 10: 1-(2-chloro-3-cyano-4-trifluoromethanesulfonylphenyl)-6-fluoro-1,2,3,4-tetrahydroquinoline-8-carbonitrile

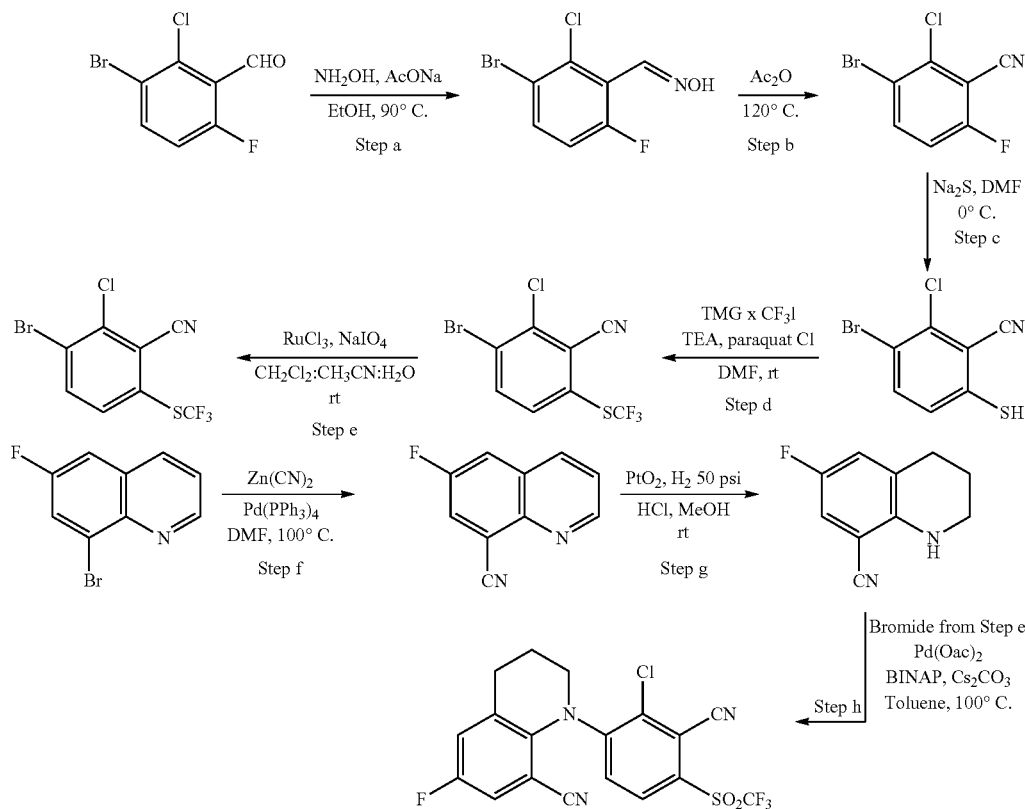

Step a: A suspension of the 3-bromo-2-chloro-6-fluorobenzaldehyde (25 g, 105.3 mmol), NH$_2$OH×HCl (8.8 g, 126.4 mmol, 1.2 equiv.) and NaOAc (10.4 g, 126.4 mmol, 1.2 equiv.) in anhydrous EtOH (100 mL) was stirred under reflux for overnight. Reaction was cooled to room temperature, evaporated and the residue was diluted with H$_2$O (300 mL). White solid was filtered off, washed with H$_2$O and dried under vacuum (24.3 g, 91%). Crude product was used in the next step without further purification. ESI MS [M+H]$^+$ for $C_7H_4BrClFNO$, calcd 251.9, found 251.9.

Step b: Oxime from step a was diluted with acetic anhydride (150 mL) and stirred at 120° C. for overnight, then cooled down and concentrated in vacuo to give brown solid (22.5 g, 99%). Crude product was used in the next step without further purification.

Step c: Product from step b (20 g, 85.3 mmol) was dissolved in anhydrous DMF (100 mL), cooled to 0° C. and anhydrous Na$_2$S (6.6 g, 85.3 mmol) was added in one portion. Reaction mixture was stirred for 2 h at 0° C., then quenched with H$_2$O (500 mL) and extracted with CH$_2$Cl$_2$ (3×200 mL). Organics were discarded and aqueous layer was neutralized with 10% KHSO$_4$ solution to pH~2 and extracted again with CH$_2$Cl$_2$ (3×150 mL). The combined organic layers were dried over MgSO₄, filtered and concentrated in vacuo to give yellow solid that was used in the next step without further purification (19.1 g, 90%). ESI MS [M–H]⁻ for C₇H₃BrClNS, calcd 245.9, found 245.9.

Step d: Product from step c (33.6 g, 135.2 mmol) was dissolved in anhydrous DMF (300 mL) and paraquat dichloride hydrate (3.5 g, 13.5 mmol, 10% mol.) was added. The mixture was cooled to 0° C. and trifluoroiodomethane×TMG reagent (33.6 mL, 162.2 mmol, 1.2 equiv.) was added followed by TEA (18.8 mL, 135.2 mmol). Reaction was stirred at 0° C. for 15 min. then warmed up to room temperature and stirred for overnight. Quenched with H₂O (1500 mL) and extracted with EtOAc (3×300 mL). Combined organics were washed with brine (2×100 mL), dried over MgSO₄, filtered and concentrated in vacuo. The residue was purified by column chromatography (silica gel, hex→30% EtOAc in hexanes) to afford the product as yellow solid (19.3 g, 45%).

Step e: The product from step d (18.5 g, 58.4 mmol) was dissolved in CH₂Cl₂:CH₃CN:H₂O (1:1:2; 300 mL) and NaIO₄ (50 g, 233.6 mmol, 4 equiv.) was added followed by RuCl₃×H₂O (394 mg, 1.75 mmol, 3% mol.). The reaction was stirred at room temperature for 1.5 h then diluted with H₂O (1000 mL) and 10% Na₂S₂O₃ solution (100 mL) and extracted with EtOAc (3×300 mL). Combined organics were dried over MgSO₄, filtered and concentrated in vacuo. The residue was purified by column chromatography (silica gel, hex→40% EtOAc in hexanes) to afford the product as white solid (19.4 g, 95%). ¹H NMR (400 MHZ, CDCl₃) δ 8.17 (d, J=8.6 Hz, 1H), 7.98 (d, J=8.6, 1H).

Step f: The mixture of 8-bromo-6-fluoroquinoline (15.7 g, 69.5 mmol), Zn(CN)₂ (4.9 g, 41.7 mmol, 0.8 equiv.) and Pd(PPh₃)₄ (8 g, 6.9 mmol, 10% mol) in anhydrous DMF (100 mL) was stirred at 100° ° C. for overnight. Then reaction was cooled to room temperature and diluted with H₂O (500 mL). Yellow solid was filtered off, washed with H₂O and dried under vacuum. Crude product was used in the next step without further purification.

Step g: The product from step f was placed in a Parr bottle and dissolved in MeOH (300 mL) and concentrated HCl (50 mL). The mixture was purged with N₂ and PtO₂ (1.56 g, 6.9 mmol, 10% mol) was added. The reaction was shaken under H₂ atmosphere (50 psi) for 5 h, then filtered through Celite, washed with MeOH and evaporated. Crude residue was purified by column chromatography (silica gel, hex→30% EtOAc in hexanes) to afford the product as a yellow solid (5.9 g, 48% over 2 steps). ¹H NMR (400 MHZ, CDCl₃) δ 6.90-6.81 (m, 2H), 4.63 (brs, 1H), 3.41-3.33 (m, 2H), 2.77-2.68 (m, 2H), 1.96-1.85 (m, 2H).

Step h: The mixture of bromide from step g (200 mg, 0.57 mmol), tetrahydroquinoline from step g (100 mg, 0.57 mmol), Pd(OAc)₂ (25 mg, 0.22 mmol, 20% mol.), rac-BINAP (87 mg, 0.14 mmol, 25% mol.) and Cs₂CO₃ (372 mg, 1.14 mmol, 2 equiv.) in anhydrous, degassed toluene (2 mL) was stirred at 100 C for 5 h. Whole reaction mixture was loaded on a silica gel cartridge and purified by column chromatography (silica gel, hex→30% EtOAc in hexanes) to afford the product as a yellow solid (44 mg, 17%). ¹H NMR (400 MHZ, CDCl₃) δ 8.02 (d, J=8.7 Hz, 1H), 7.34 (d, J=8.7 Hz, 1H), 7.19-7.13 (m, 1H), 7.11-7.07 (m, 1H), 3.90-3.57 (m, 2H), 3.06-2.82 (m, 2H), 2.20-1.78 (m, 2H). ESI MS [M+H]⁺ for C₁₈H₁₀ClF₄N₃O₂S, calcd 444.0, found 444.0.

Example 11: 1-(2-Chloro-3-cyano-4-methanesulfonylphenyl)-6-fluoro-1,2,3,4-tetrahydroquinoline-8-carbonitrile

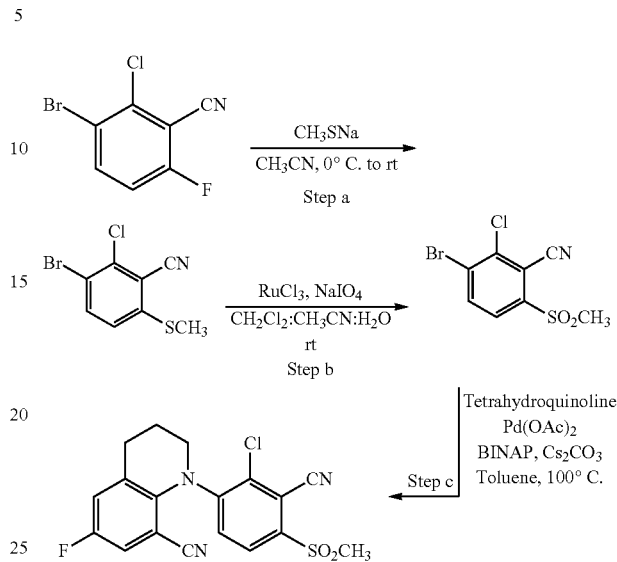

Step a: A solution of the 3-bromo-2-chloro-6-fluorobenzonitrile (5 g, 21.3 mmol) in anhydrous CH₃CN (100 mL) was cooled to 0° C. and then CH₃SNa (1.64 g, 23.4 mmol, 1.1 equiv.) was added in one portion. The mixture was stirred at 0° C. for 15 min. then the cooling batch was removed, and reaction was stirred at room temperature for overnight. Diluted with H₂O (300 mL) and the product was filtered off, (white solid, 4.6 g, 82%).

Step b was done in a similar fashion to Example 10. ¹H NMR (400 MHZ, CDCl₃) δ 8.07 (d, J=8.5 Hz, 1H), 7.95 (d, J=8.5 Hz, 1H), 3.30 (s, 3H).

Step c was done in a similar fashion to Example 10 (brown solid, 3.5 mg, 1%). ¹H NMR (400 MHZ, CDCl₃) δ 7.99 (d, J=8.5 Hz, 1H), 7.29 (d, J=8.5 Hz, 1H), 7.16-7.10 (m, 1H), 7.08-7.03 (m, 1H), 3.72-3.57 (m, 2H), 3.31 (s, 3H), 3.00-2.81 (m, 2H), 2.10-1.79 (m, 2H). ESI MS [M+H]⁺ for C₁₈H₁₃ClFN₃O₂S, calcd 390.0, found 390.0.

Example 12: 2-chloro-3-(8-chloro-6-fluoro-1,2,3,4-tetrahydroquinolin-1-yl)-6-trifluoromethanesulfonylbenzonitrile

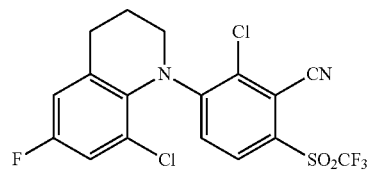

The title compound was synthesized in a similar fashion to Example 10. (yellow solid, 130 mg, 50%). ¹H NMR (400 MHZ, CDCl₃) δ 7.90 (d, J=8.8 Hz, 1H), 7.06 (d, J=8.8 Hz, 1H), 7.00-6.93 (m, 1H), 6.93-6.86 (m, 1H), 3.91-3.82 (m, 1H), 3.66-3.53 (m, 1H), 3.02-2.86 (m, 2H), 2.06-1.93 (m, 1H), 1.89-1.75 (m, 1H). ESI MS [M+H]⁺ for C₁₇H₁₀C₁₂F₄N₂O₂S, calcd 453.0, found 453.0.

Example 13: 2-chloro-3-(6,8-difluoro-1,2,3,4-tetrahydroquinolin-1-yl)-6-trifluoromethanesulfonylbenzonitrile

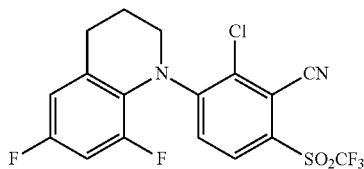

The title compound was synthesized in a similar fashion to Example 10. (yellow solid, 172 mg, 69%). ¹H NMR (400 MHZ, CDCl₃) δ 7.93 (d, J=8.8 Hz, 1H), 7.28 (d, J=8.8 Hz, 1H), 6.79-6.73 (m, 1H), 6.70-6.59 (m, 1H), 3.77-3.67 (m, 2H), 2.95-2.87 (m, 2H), 1.99-1.89 (m, 2H). ESI MS [M+H]⁺ for $C_{17}H_{10}ClF_5N_2O_2S$, calcd 437.0, found 437.0.

Example 14: 1-[5-cyano-6-(trifluoromethyl)pyridin-3-yl]-6-fluoro-1,2,3,4-tetrahydroquinoline-8-carbonitrile

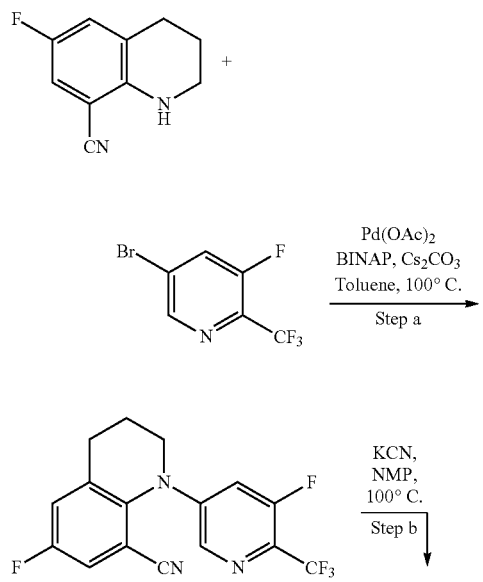

Step a: To a 40 mL vial was added 6-fluoro-1,2,3,4-tetrahydroquinoline-8-carbonitrile (61 mg, 0.344 mmol, 1.2 equiv.), 5-bromo-3-fluoro-2-(trifluoromethyl)-pyridine (70 mg, 0.287 mmol, 1.0 equiv.), Pd(OAc)₂ (13 mg, 0.057 mmol, 20 mol %), rac-BINAP (45 mg, 0.072 mmol, 25 mol %), Cs₂CO₃ (190 mg, 0.574 mmol, 2.0 equiv.) and toluene (1.5 mL). The reaction vessel was capped, and the mixture purged with N₂ for 2 min. The reaction was stirred at 100° C. for 2 h. The reaction mixture was cooled, concentrated onto Celite and purified by flash column chromatography (SiO₂, hexane→40% EtOAc in hexanes) to afford the product as a white solid (65 mg, 0.192 mmol, 55%, ESI MS [M+H]⁺ for $C_{16}H_{10}F_5N_3$, calcd 340.3, found 340.0).

Step b: A vial was charged with the product from step a (30 mg, 0.088 mmol, 1.0 equiv.), KCN (7.0 mg, 0.097 mmol, 1.1 equiv.), and NMP (0.3 mL). The reaction mixture was stirred at 100° ° C. for 4 h. The reaction was diluted with sat. aq. NaHCO₃ solution (10 mL) and extracted with EtOAc (10 mL). The aqueous layer was separated and back extracted with additional EtOAc (15 mL). The organic layers were combined, washed with H₂O (2×20 mL), brine (20 mL), and dried over MgSO₄. Concentration under reduced pressure and purification by flash chromatography furnished the product as a yellow solid (4.0 mg, 0.012 mmol, 13%). ¹H NMR (400 MHZ, DMSO-d₆) δ 8.70-8.63 (m, 1H), 8.31-8.25 (m, 1H), 7.70-7.64 (m, 1H), 7.61-7.54 (m, 1H), 3.86-3.80 (m, 2H), 2.80 (t, J=6.4 Hz, 2H), 1.95-1.87 (m, 2H). ESI MS [M+H]⁺ for $C_{17}H_{10}F_4N_4$, calcd 347.1, found 347.0.

Example 15: 1-[2-chloro-3-fluoro-4-(trifluoromethyl)phenyl]-6-fluoro-1,2,3,4-tetrahydroquinoline-8-carbonitrile

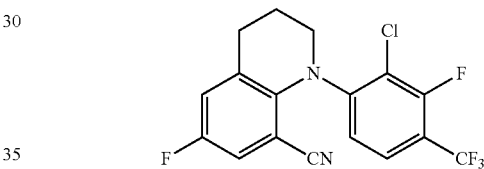

The title compound was synthesized in a similar fashion to Example 14 using 1-bromo-2-chloro-3-fluoro-4-(trifluoromethyl)-benzene. ¹H NMR (400 MHZ, DMSO-d₆) δ 7.74-7.67 (m, 1H), 7.53-7.43 (m, 2H), 7.13-7.04 (m, 1H), 3.74-3.48 (m, 2H), 3.07-2.77 (m, 2H), 2.06-1.64 (m, 2H). ESI MS [M+H]⁺ for $C_{17}H_{10}ClF_5N_2$, calcd 373.0, found 373.0.

Example 16: 6-fluoro-1-[8-(trifluoromethylsulfonyl)-5-isoquinolyl]-1,2,3,4-tetrahydroquinoline-8-carbonitrile

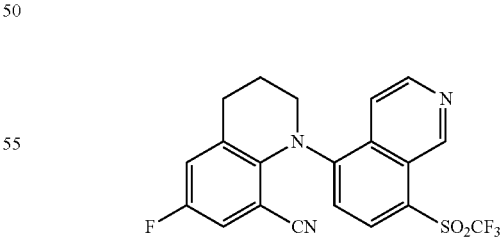

The title compound was synthesized in a similar fashion to Example 10. ¹H NMR (400 MHz, Chloroform-d) § 10.24 (s, 1H), 8.87 (d, J=6.1 Hz, 1H), 8.43 (d, J=8.2 Hz, 1H), 8.26 (dd, J=6.2, 0.9 Hz, 1H), 7.29 (d, J=8.2 Hz, 1H), 7.26-7.22 (m, 1H), 7.15-7.11 (m, 1H), 3.87-3.76 (m, 2H), 3.16-2.94 (m, 2H), 2.08-1.85 (m, 2H). ESI MS [M+H]⁺ for $C_{20}H_{13}F_6N_3O_2S$ calcd 436.1, found 436.1.

67

Example 17: (1S,2R)-4-[(S)-4-ethyl-6,8-difluoro-1,2,3,4-tetrahydroquinol-1-yl]-2-fluoro-7-(trifluoromethylsulfonyl)-1-indanol

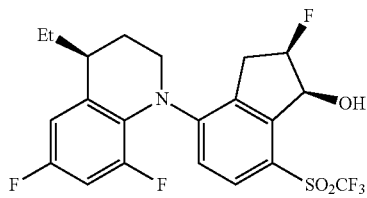

The title compound was synthesized in a similar fashion to Example 19. $^1$H NMR (400 MHz, Chloroform-d) δ 7.77 (d, J=8.4 Hz, 1H), 7.00 (s, OH), 6.83 (d, J=8.8 Hz, 1H), 6.70 (ddd, J=11.0, 8.3, 2.6 Hz, 1H), 5.51 (s, 1H), 5.18 (d, J=50.8 Hz, 1H), 3.69 (s, 2H), 3.00 (br m, 2H), 2.84 (p, J=6.4 Hz, 1H), 2.12-1.99 (m, 1H), 1.81 (br m, 2H), 1.60 (dq, J=14.5, 7.5 Hz, 1H), 0.98 (t, J=7.4 Hz, 3H). ESI MS [M+H]$^+$ for $C_{21}H_{19}F_6NO_3S$ calcd 480.1, found 480.1.

68

Example 18: 2-chloro-3-(6-fluoro-8-methoxy-3,4-dihydroquinolin-1(2H)-yl)-6-((trifluoromethyl)sulfonyl)benzonitrile

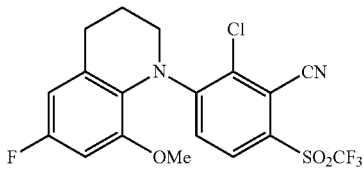

The title compound was synthesized in a similar fashion to Example 10. $^1$H NMR (400 MHz, CDCl$_3$) δ 7.84 (dd, J=8.8, 0.4 Hz, 1H), 7.13 (d, J=8.9 Hz, 1H), 6.54 (dd, J=8.6, 2.7 Hz, 1H), 6.43 (dd, J=10.2, 2.8 Hz, 1H), 3.74 (br. s, 2H), 3.51 (s, 3H), 2.95-2.79 (m, 2H), 1.91 (br. s, 2H). $^{19}$F NMR (376 MHZ, CDCl$_3$) δ−77.11, −115.53. ESI MS [M+H]$^+$ for $C_{18}H_{13}ClF_4N_2O_3S$; calcd 449.0, found 449.1

Example 19: 7-fluoro-4-((1S,2R)-2-fluoro-1-hydroxy-7-((trifluoromethyl)sulfonyl)-2,3-dihydro-1H-inden-4-yl)-3,4-dihydro-2H-benzo[b][1,4]oxazine-5-carbonitrile

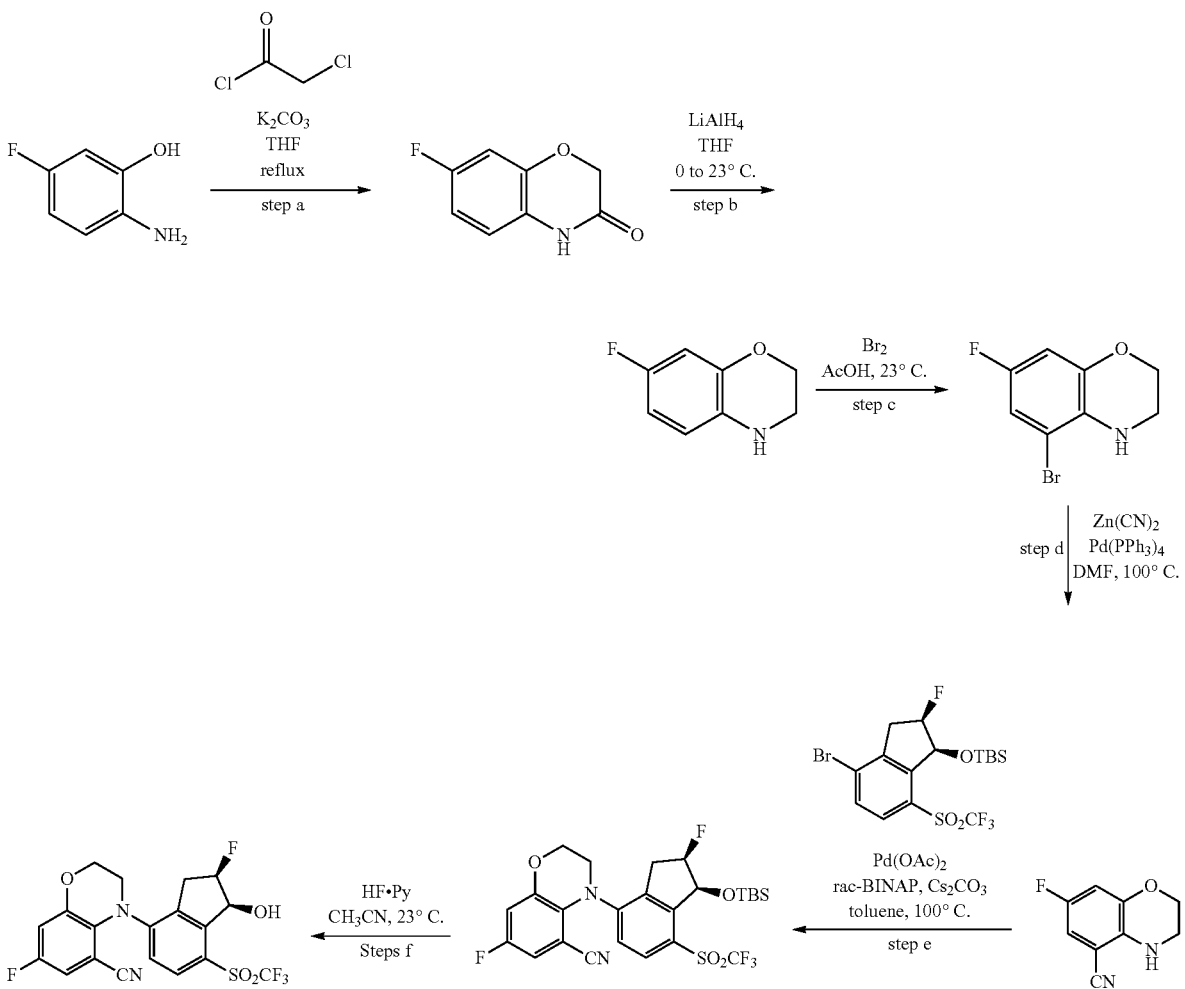

Step a: Chloroacetyl chloride (8.3 mL, 110 mmol) was added dropwise to a stirred suspension of 2-amino-5-fluorophenol (9.5 g, 75 mmol) and potassium carbonate (41.4 g, 300 mmol) in THF (120 mL) at 0° C. The reaction was stirred at ambient temperature for 30 min before it was maintained at 66° C. for 48 h. The mixture was cooled, filtered through Celite pad to remove inorganic solids and the filtrate was concentrated to dryness. The residue was fractionated by column chromatography (SiO$_2$, hexanes/EtOAc gradient) to yield 7-fluoro-2H-benzo[b][1,4]oxazin-3(4H)-one (5.5 g, 32.9 mmol, 44% yield) as a brown solid. $^1$H NMR (400 MHz, CDCl$_3$) δ 8.73 (s, 1H), 6.90-6.53 (m, 3H), 4.60 (s, 2H). $^{19}$F NMR (376 MHz, CDCl$_3$) δ −117.25.

Step b: Lithium aluminum hydride (1.2 g, 3.2 mmol) was carefully added in portions to a solution of 7-fluoro-2H-benzo[b][1,4]oxazin-3(4H)-one (3.5 g, 2.1 mmol) in THF (30 mL) at 0° C. Once the addition was complete, the cooling bath was removed, and the mixture was stirred at ambient temperature for 4 h. After TLC analysis indicated complete reaction, the mixture was quenched using Fieser protocol and the product was extracted diethyl ether. After all solvent was removed under reduced pressure, the crude product was purified by column chromatography (SiO$_2$, hexanes/EtOAc gradient) to produce 7-fluoro-3,4-dihydro-2H-benzo[b][1,4]oxazine (2.9 g, 18.9 mmol, 90% yield) as a brown solid. $^1$H NMR (400 MHZ, CDCl$_3$) δ 6.63-6.22 (m, 3H), 4.30-4.18 (m, 2H), 3.59 (s, 1H), 3.44-3.32 (m, 2H). $^{19}$F NMR (376 MHz, CDCl$_3$) δ −124.56.

Step c: Bromine (0.4 mL, 7.5 mmol) was added dropwise to a solution of 7-fluoro-3,4-dihydro-2H-benzo[b][1,4]oxazine (1 g, 6.5 mmol) in acetic acid (26 mL), that was placed in a water bath in order to maintain the reaction temperature below 25° C. Once the addition was complete, the reaction was stirred at ambient temperature for 10 min and poured in 5% aqueous NaHSO$_3$ (100 mL). The crude product was extracted with a mixture of EtOAc and hexanes (v/v 1:1, 3×35 mL), then combined extracts were washed with water (3×100 mL), aqueous NaHCO$_3$ (2×100 mL) and brine (50 mL). The solution was dried over Na$_2$SO$_4$ and the solvent was evaporated to dryness. The crude product was purified by column chromatography (SiO$_2$, hexanes/EtOAc gradient) to yield 5-bromo-7-fluoro-3,4-dihydro-2H-benzo[b][1,4]oxazine (1.05 g, 4.5 mmol, 70% yield) as a yellow oil. $^1$H NMR (400 MHZ, CDCl$_3$) δ 6.79 (dd, J=8.0, 2.8 Hz, 1H), 6.52 (dd, J=9.5, 2.8 Hz, 1H), 4.32-4.14 (m, 2H), 4.14-3.88 (br. s, 1H), 3.53-3.34 (m, 2H). $^{19}$F NMR (376 MHz, CDCl$_3$) δ −124.82 (d, J=8.3 Hz).

Step d: A mixture of 5-bromo-7-fluoro-3,4-dihydro-2H-benzo[b][1,4]oxazine (1.05 g, 4.5 mmol), zinc cyanide (0.43 g, 3.6 mmol) and Pd(PPh$_3$)$_4$ (0.52 g, 0.45 mmol) in DMF (11 mL) was heated at 100° C. under nitrogen atmosphere for 4 hours. Once complete disappearance of starting material was observed by TLC analysis (30% EtOAc in hexanes as an eluent), the solution was cooled to ambient temperature and poured in a mixture of EtOAc (50 mL) and water (50 mL). The resulting suspension was filtered through a Celite plug. The organic phase was separated, and the aqueous solution was additionally extracted with EtOAc (2×25 mL). Combined organic phase was washed with water (2×75 mL) and brine (75 mL), dried over Na$_2$SO$_4$ and concentrated to dryness. The dry residue was fractionated by column chromatography (SiO$_2$, hexanes/EtOAc gradient) to provide 7-fluoro-3,4-dihydro-2H-benzo[b][1,4]oxazine-5-carbonitrile (0.75 g, 4.2 mmol, 94% yield) as a white powder. $^1$H NMR (400 MHZ, CDCl$_3$) δ 6.78-6.54 (m, 2H), 4.51 (br. s, 1H), 4.33-4.17 (m, 2H), 3.60-3.40 (m, 2H). $^{19}$F NMR (376 MHz, CDCl$_3$) δ −124.17. ESI MS [M+Na]$^+$ for C$_9$H$_7$FN$_2$O; calcd 179.1, found 179.1.

Step e: The mixture of (1S,2R)-4-bromo-2-fluoro-1-(tert-butyl-dimethysilyl)-7-(trifluoromethylsulfonyl)indan (100 mg, 0.21 mmol), 7-fluoro-3,4-dihydro-2H-benzo[b][1,4]oxazine-5-carbonitrile (38 mg, 0.21 mmol), Pd(OAc)$_2$ (9.5 mg, 0.042 mmol), rac-BINAP (33 mg, 0.053 mmol) and Cs$_2$CO$_3$ (137 mg, 0.42 mmol) in anhydrous, degassed toluene (1 mL) was stirred at 100° ° C. for 6 h. Then the mixture was cooled to ambient temperature, diluted with EtOAc and filtered through a Celite pad to remove inorganic solids. The filtrate was concentrated on Celite and purified by column chromatography (SiO$_2$, hexanes/EtOAc gradient) to a mixture of product and unreacted benzomorpholine (55 mg). This mixture was submitted to step f without additional purification.

Step f: The mixture of TBS-protected indanol and unreacted benzomorpholine from previous step was dissolved in CH$_3$CN (1 mL) and placed in a 3 mL vial equipped with a magnetic stirrer, then HF·Py complex (hydrogen fluoride ~70%, pyridine ~30%, 0.1 mL) was added. The resulting solution was stirred overnight at ambient temperature. After TLC analysis indicated complete consumption of the starting material the reaction was diluted with EtOAc (20 mL) and 1M aqueous HCl solution (20 mL). The product was extracted with EtOAc (2×10 mL), combined organic extracts were washed with aqueous NaHCO$_3$ (20 mL) and brine (20 mL), dried over Na$_2$SO$_4$ and concentrated to dryness. The residue was fractionated by column chromatography (SiO$_2$, hexanes/EtOAc gradient) to yield 7-fluoro-4-((1S,2R)-2-fluoro-1-hydroxy-7-((trifluoromethyl)sulfonyl)-2,3-dihydro-1H-inden-4-yl)-3,4-dihydro-2H-benzo[b][1,4]oxazine-5-carbonitrile (25 mg, 0.054 mmol, 26% yield over two steps) as a yellowish oil. $^1$H NMR (400 MHZ, CDCl$_3$) δ 7.85 (d, J=8.6 Hz, 1H), 7.05-6.93 (m, 2H), 6.89 (dd, J=7.5, 2.8 Hz, 1H), 5.59 (br. s, 1H), 5.28 (br. d, J=49.6 Hz, 1H), 4.39 (d, J=11.5 Hz, 1H), 4.10 (br. s, 1H), 3.76-3.57 (m, 2H), 3.34 (br. s, 2H), 3.03 (s, 1H). $^{19}$F NMR (376 MHZ, CDCl$_3$) δ −78.08, −113.95, −199.41 (d, J=51.0 Hz). ESI MS [M+Na]$^+$ for C$_{19}$H$_{13}$F$_5$N$_2$O$_4$S; calcd 483.0, found 483.1

Example 20: 7-fluoro-4-((1S,2R)-2-fluoro-1-hydroxy-7-(methylsulfonyl)-2,3-dihydro-1H-inden-4-yl)-3,4-dihydro-2H-benzo[b][1,4]oxazine-5-carbonitrile

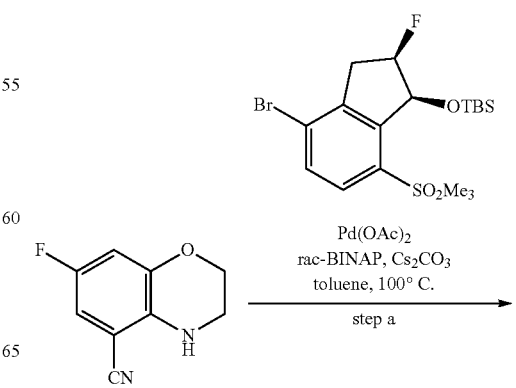

-continued

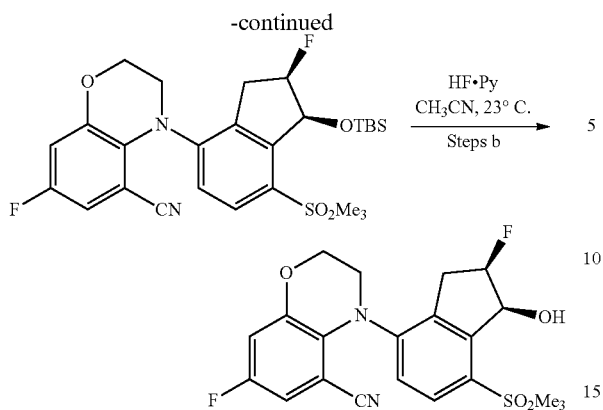

The title compound was synthesized in a similar fashion to Example 19. $^1$H NMR (400 MHz, CDCl$_3$) δ 7.80 (d, J=8.4 Hz, 1H), 6.99-6.79 (m, 3H), 5.68-5.61 (m, 1H), 5.37 (br. d, J=52.1, 1H), 4.38-4.23 (m, 1H), 4.18-4.02 (m, 1H), 3.72-3.48 (m, 3H), 3.43-2.93 (m, 5H). $^{19}$F NMR (376 MHZ, CDCl$_3$) δ −115.26, −199.17. ESI MS [M−OH]$^+$ for C$_{19}$H$_{16}$F$_2$N$_2$O$_4$S; calcd 389.1, found 389.1.

Example 21: 6,8-difluoro-8'-trifluoromethanesulfonyl-3,4-dihydro-2H-1,5'-biquinoline

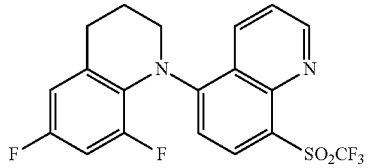

The title compound was synthesized in a similar fashion to Example 10. $^1$H NMR (400 MHz, CDCl$_3$) δ 9.15 (dd, J=4.3, 1.7 Hz, 1H), 8.61 (dd, J=8.6, 1.7 Hz, 1H), 8.44 (d, J=8.3 Hz, 1H), 7.60 (dd, J=8.6, 4.2 Hz, 1H), 7.08 (dd, J=8.3, 0.9 Hz, 1H), 6.85-6.76 (m, 1H), 6.71-6.61 (m, 1H), 3.86-3.69 (m, 2H), 3.04-2.96 (m, 2H), 1.99-1.82 (m, 2H). ESI MS [M+H]$^+$ for C$_{19}$H$_{13}$F$_5$N$_2$O$_2$S calcd 429.1, found 429.1.

Example 22: 4-(6,8-difluoro-1,2,3,4-tetrahydroquinolin-1-yl)-2,2-difluoro-7-methanesulfonyl-2,3-dihydro-1H-inden-1-ol

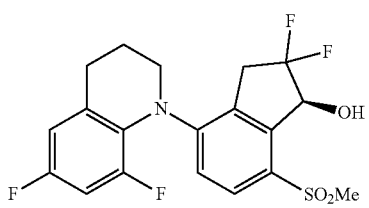 [SMILES: CS(=O)(=O)c1ccc(N2CCCc3cc(F)cc(F)c32)c2c1[C@H](O)C(F)(F)C2]

The title compound was synthesized in a similar fashion to Example 19. $^1$H NMR (400 MHz, Methanol-d$_4$) δ 7.76 (d, J=8.6 Hz, 1H), 7.03 (d, J=8.6 Hz, 1H), 6.85-6.80 (m, 1H), 6.77-6.69 (m, 1H), 5.50-5.44 (m, 1H), 3.66-3.57 (m, 3H), 3.22 (s, 3H), 3.18-3.03 (m, 1H), 2.93-2.84 (t, J=6.6 Hz, 2H), 1.96-1.84 (m, 2H). ESI MS [M+H]$^+$ for C$_{19}$H$_{17}$F$_4$NO$_3$S calcd 416.1, found 416.0.

Example 23: 6,8-difluoro-1-(2-nitro-4-trifluoromethanesulfonylphenyl)-1,2,3,4-tetrahydroquinoline

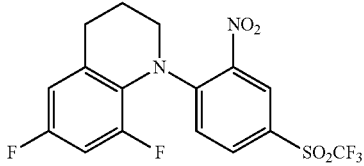

The title compound was synthesized in a similar fashion to Example 24. $^1$H NMR (400 MHz, CDCl$_3$) δ 8.46 (d, J=2.2 Hz, 1H), 7.94 (dd, J=8.9, 2.3 Hz, 1H), 7.33 (dd, J=8.9, 1.7 Hz, 1H), 6.82-6.76 (m, 1H), 6.76-6.63 (m, 1H), 3.77-3.50 (m, 2H), 2.92-2.81 (m, 2H), 2.15-1.99 (m, 2H). ESI MS [M+H]$^+$ for C$_{16}$H$_{11}$F$_5$N$_2$O$_4$S calcd 423.0, found 423.1.

Example 24: 6,8-difluoro-1-[2-nitro-4-(trifluoromethyl)phenyl]-1,2,3,4-tetrahydroquinoline

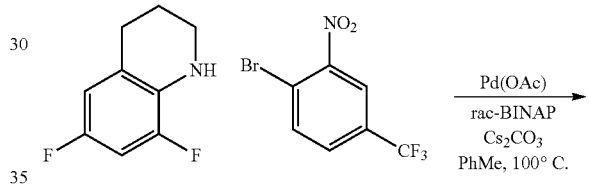

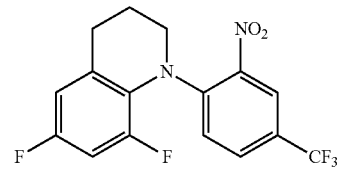

4-Bromo-3-nitrobenotrifluoride (270 mg, 1 mmol), 6,8-difluoro-1,2,3,4-tetrahydroquinoline (324 mg, 1.2 mmol), Pd(OAc)$_2$ (45 mg, 0.2 mmol), rac-BINAP (187 mg, 0.3 mmol), and Cs$_2$CO$_3$ (652 mg, 2 mmol), were suspended in PhMe (5 mL). The suspension was degassed with N$_2$ for 5 minutes at ambient temperature and heated to 100° C. for 1.5 hours. The mixture was cooled to room temperature, diluted with EtOAc, filtered, and concentrated onto Celite®. Purification by column chromatography (0-10% EtOAc/hexanes) afforded the title compound as an orange oil (125 mg, 35% yield). $^1$H NMR (400 MHZ, CDCl$_3$) δ 8.13 (dd, J=2.2, 0.9 Hz, 1H), 7.68-7.61 (m, 1H), 7.26-7.22 (m, 1H), 6.73 (dddt, J=8.4, 2.6, 1.7, 0.9 Hz, 1H), 6.63 (dddd, J=11.3, 8.4, 2.8, 0.7 Hz, 1H), 3.57 (s, 2H), 2.88 (tt, J=6.6, 0.8 Hz, 2H), 2.00 (q, J=6.2 Hz, 2H). $^{19}$F NMR (376 MHz, CDCl$_3$) δ −62.3 (3 F), −117.3 (1 F), −116.7 (1 F). ESI MS [M+H]$^+$ for C$_{16}$H$_{11}$F$_5$N$_2$O$_2$, calcd 359.1, found 359.1.

Example 25: 5-(6,8-Difluoro-1,2,3,4-tetrahydronaphth-1-yl)-8-(trifluoromethylsulfonyl)isoquinoline

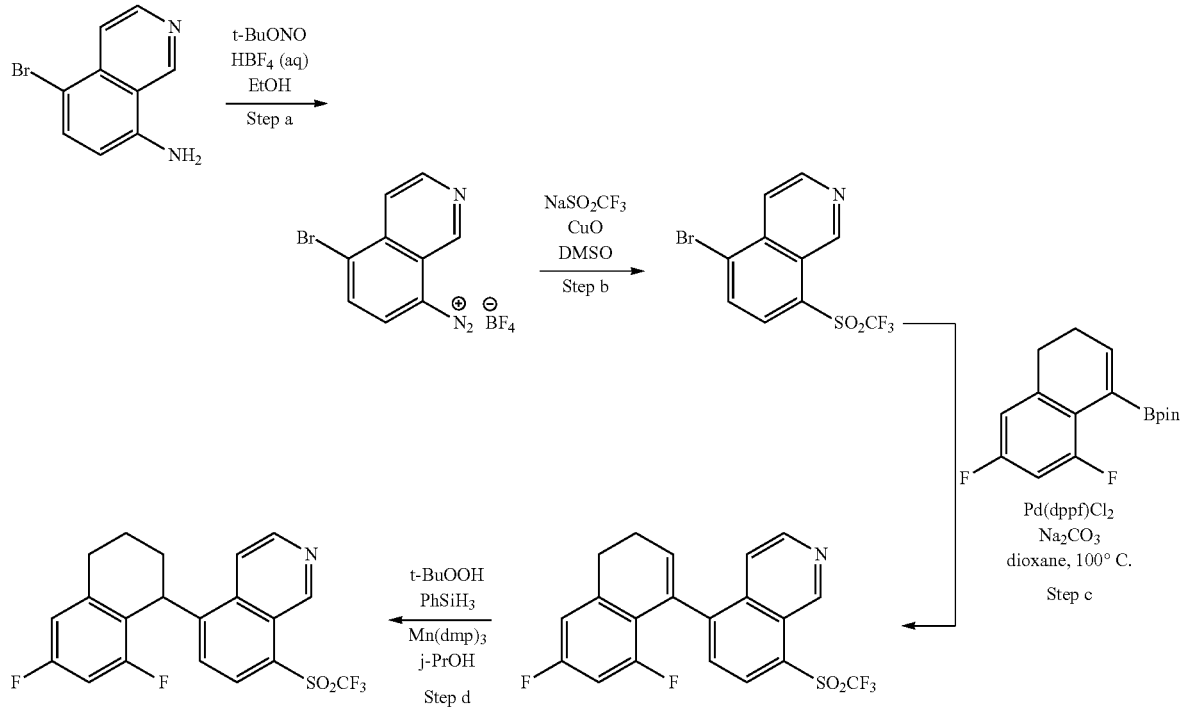

Step a: The 5-bromo-8-isoquinolylamine (2.23 g, 10 mmol, 1 eq.) was dissolved in a mixture of ethanol (3 mL) and aq. HBF$_4$ (48% wt, 2.62 mL, 20 mmol, 2 eq) and the solution was cooled to 0° C. t-BuONO (2.37 mL, 20 mmol, 2 eq.) was added dropwise, after which the reaction was left to stir for one hour. Et$_2$O (10 mL) was added to the reaction mixture, which was then filtered and washed with more Et$_2$O (2×10 mL). The filtrate was dried under vacuum for 30 minutes to yield the diazonium salt as an orange solid (3.06 g, 9.52 mmol, 95%). ESI MS [M]$^+$ for C$_9$H$_5$BrN$_3$ calcd. 234.0, found 234.0

Step b: To a vigorously stirred solution of NaSO$_2$CF$_3$ (4.68 g, 30 mmol, 3 eq.) and Cu$_2$O (143 mg, 1 mmol, 0.1 eq.) in DMSO (10 mL) was added a solution of the product of step a in DMSO (10 mL) using a dropping funnel. After the addition was complete, the reaction was left to stir for 2 hours, or until LCMS indicated complete conversion of the starting material. The reaction mixture was then diluted with EtOAc (100 mL) and water (100 mL). After separation of the layers, the aqueous was extracted with EtOAc (3×100 mL). The combined organics were washed with water (2×100 mL) and brine (100 mL), and finally dried over Na$_2$SO$_4$. The crude material was purified by flash column chromatography (SiO$_2$, 0 to 100% EtOAc/hexanes) yielding the product as a brown solid (716 mg, 2.94 mmol, 29%). ESI MS [M+H]$^+$ for C$_{10}$H$_5$BrF$_3$NO$_2$S calcd. 339.9, found 339.9.

Step c: A vial was charged with the product from step b (24 mg, 0.07 mmol, 1 eq), 2-(6,8-difluoro-3,4-dihydronaphth-1-yl)-4,4,5,5-tetramethyl-1,3,2-dioxaborolane (21 mg, 0.07 mmol, 1 eq.), Pd(dppf)Cl$_2$ (5 mg, 0.007 mmol, 0.1 eq.), an aqueous solution of Na$_2$CO$_3$ (1M, 0.21 mL, 3 eq.), and dioxane (1 mL). The vial was sparged with N$_2$ for 10 minutes and then heated to 100° C. for 16 hours. The reaction mixture was then cooled to room temperature, diluted with EtOAc, and washed with water. The organic phase was dried over Na$_2$SO$_4$ and concentrated. The crude material was purified by flash column chromatography (0 to 100% EtOAc/Hexanes) to afford the target product (7 mg, 0.016 mmol, 23%). ESI MS [M+H]$^+$ for C$_{20}$H$_{12}$F$_5$NO$_2$S calcd. 426.1, found 426.1.

Step d: The product from step c (7 mg, 0.016 mmol. 1 eq) was dissolved in i-PrOH (1 mL), and PhSiH$_3$ (4 µL, 0.032 mmol, 2 eq) and tert-butyl hyroperoxide (5.5 M in decane, 8 µL, 0.032 mmol, 2 eq) were added under nitrogen. This solution was sparged with nitrogen for 10 minutes before Mn(dmp)$_3$ (10 mg, 0.016 mmol, 1 eq) was added and the resulting mixture was sparged for another 30 seconds. The reaction was then left to stir for 16 hours under nitrogen.

After concentrating the reaction mixture, the crude material was purified by flash column chromatography (SiO$_2$, 0 to 100% EtOAc/hexanes) to afford the title compound (4 mg, 0.009 mmol, 57%). $^1$H NMR (400 MHZ, Chloroform-d) δ 10.23 (s, 1H), 8.85 (d, J=6.0 Hz, 1H), 8.31 (d, J=7.8 Hz, 1H), 8.14 (d, J=6.0 Hz, 1H), 7.16 (m, 1H), 6.84-6.79 (m, 1H), 6.67-6.59 (m, 1H), 5.12 (m, 1H), 3.02-2.78 (m, 2H), 2.33-2.19 (m, 1H), 2.05-1.97 (m, 1H), 1.84-1.70 (m, 1H), 1.57 (br m, J=17.9 Hz, 1H). ESI MS [M+H]$^+$ for C$_{20}$H$_{14}$F$_5$NO$_2$S calcd 428.1, found 428.1.

Examples 26-120: Compound Syntheses

The following Examples were prepared according to generic synthetic protocols described for other Examples as detailed in Table A below. Each of the Examples afforded characteristic physical data such as the mass spectral peaks indicated.

TABLE A

Syntheses of Examples 26-120

| Example | Structure | Synthesis According to Example | Mass Spec (Observed) |
|---------|-----------|-------------------------------|----------------------|
| 26 | 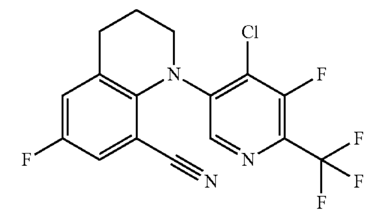 [SMILES: N#Cc1cc(F)cc2c1N(c1cnc(C(F)(F)F)c(F)c1Cl)CCC2] | 10 | 374.0 [M + H] |
| 27 | 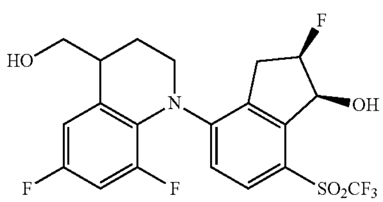 | 2, 19 | — |
| 28 | 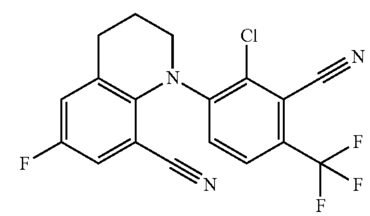 [SMILES: N#Cc1cc(F)cc2c1N(c1ccc(C(F)(F)F)c(C#N)c1Cl)CCC2] | 10 | 380.0 [M + H] |
| 29 | 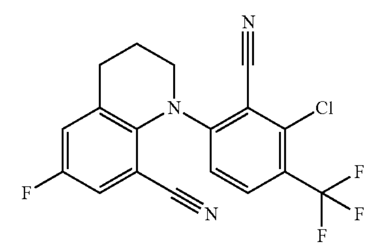 [SMILES: N#Cc1cc(F)cc2c1N(c1ccc(C(F)(F)F)c(Cl)c1C#N)CCC2] | 10 | 380.0 [M + H] |
| 30 | 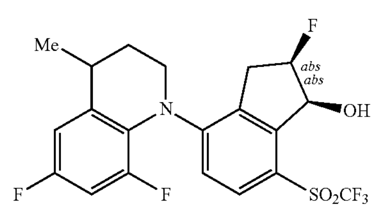 | 2, 19 | 466.1 [M + H] |
| 31 | 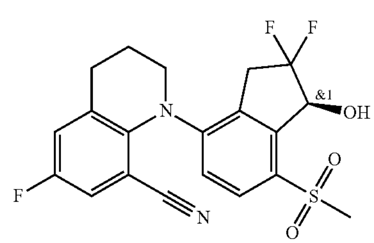 [SMILES: CS(=O)(=O)c1ccc(N2CCCc3cc(F)cc(C#N)c32)c2c1[C@H](O)C(F)(F)C2] | 5 | 423.1 [M + H] |

TABLE A-continued

Syntheses of Examples 26-120

| Example | Structure | Synthesis According to Example | Mass Spec (Observed) |
|---|---|---|---|
| 32 | 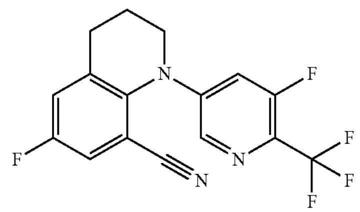 [SMILES: N#Cc1cc(F)cc2c1N(c1cnc(C(F)(F)F)c(F)c1)CCC2] | 10 | 340.0 [M + H] |
| 33 | 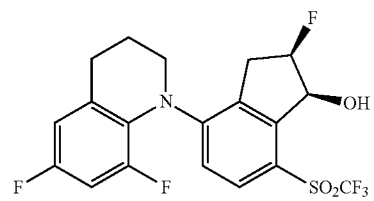 | 2, 19 | 452.1 [M + H] |
| 34 | 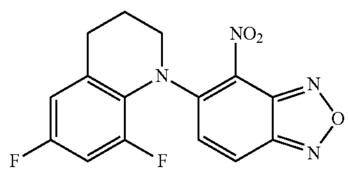 [SMILES: O=[N+]([O-])c1c(N2CCCc3cc(F)cc(F)c32)ccc2nonc12] | 10 | 333.1 [M + H] |
| 35 | 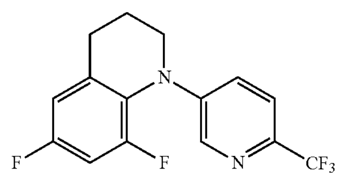 [SMILES: Fc1cc(F)c2c(c1)CCCN2c1ccc(C(F)(F)F)nc1] | 10 | 315.0 [M + H] |
| 36 | 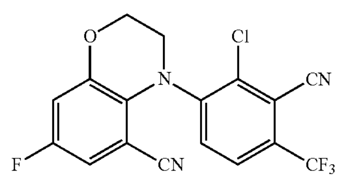 [SMILES: N#Cc1cc(F)cc2c1N(c1ccc(C(F)(F)F)c(C#N)c1Cl)CCO2] | 10, 19 | — |
| 37 | 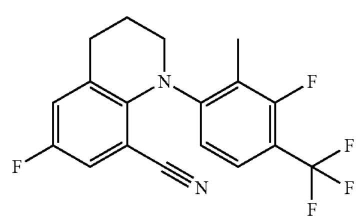 [SMILES: Cc1c(N2CCCc3cc(F)cc(C#N)c32)ccc(C(F)(F)F)c1F] | 10 | 353.1 [M + H] |
| 38 | 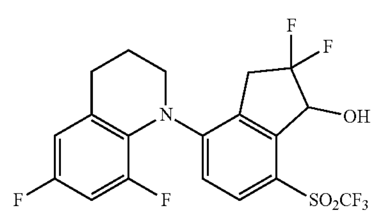 | 2, 19 | — |

TABLE A-continued
Syntheses of Examples 26-120
| Example | Structure | Synthesis According to Example | Mass Spec (Observed) |
|---|---|---|---|
| 39 | 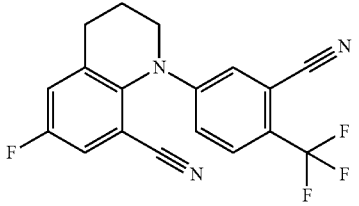 [SMILES: N#Cc1cc(N2CCCc3cc(F)cc(C#N)c32)ccc1C(F)(F)F] | 10 | 346.1 [M + H] |
| 40 | 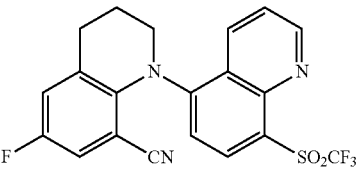 | 10 | — |
| 41 | 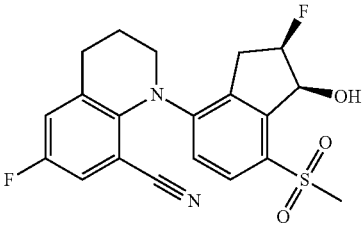 [SMILES: CS(=O)(=O)c1ccc(N2CCCc3cc(F)cc(C#N)c32)c2c1[C@H](O)[C@H](F)C2] | 5 | 427.1 [M + Na] |
| 42 | 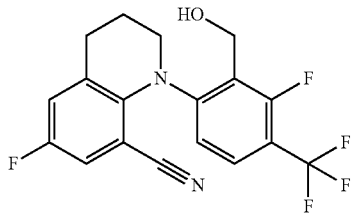 | 10 | 391.1 [M + Na] |
| 43 | 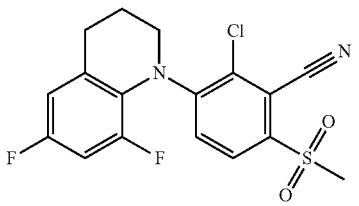 [SMILES: CS(=O)(=O)c1ccc(N2CCCc3cc(F)cc(F)c32)c(Cl)c1C#N] | 10 | 383.0 [M + H] |
| 44 | 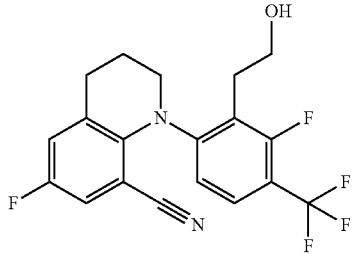 | 10 | 383.1 [M + H] |

TABLE A-continued

Syntheses of Examples 26-120

| Example | Structure | Synthesis According to Example | Mass Spec (Observed) |
|---|---|---|---|
| 45 | 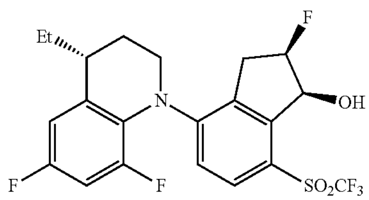 | 2, 19 | 480.1 [M + H] |
| 46 | 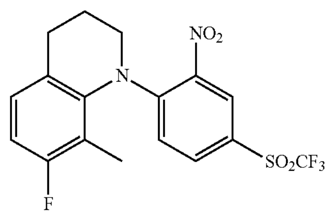 | 10 | 419.1 [M + H] |
| 47 | 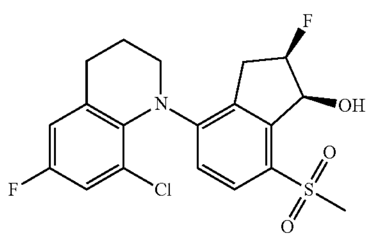 [SMILES: CS(=O)(=O)c1ccc(N2CCCc3cc(F)cc(Cl)c32)c2c1[C@H](O)[C@H](F)C2] | 5 | 414.0 [M + H] |
| 48 | 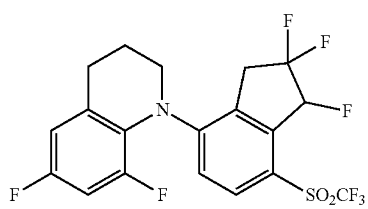 | 10, 19 | — |
| 49 | 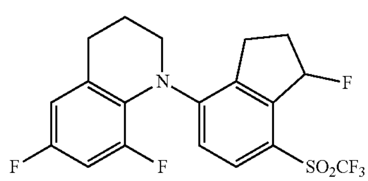 | 2, 10 | 436.1 [M + H] |
| 50 | 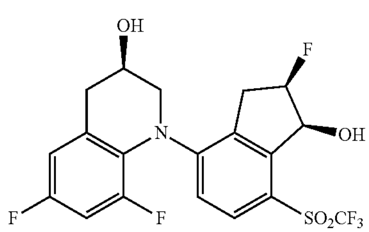 | 2, 10 | 468.1 [M + H] |
| 51 | 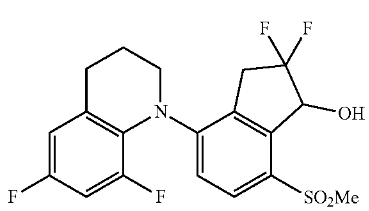 [SMILES: CS(=O)(=O)c1ccc(N2CCCc3cc(F)cc(F)c32)c2c1C(O)C(F)(F)C2] | 2, 10 | 416.0 [M + H] |

TABLE A-continued

Syntheses of Examples 26-120

| Example | Structure | Synthesis According to Example | Mass Spec (Observed) |
|---|---|---|---|
| 52 | 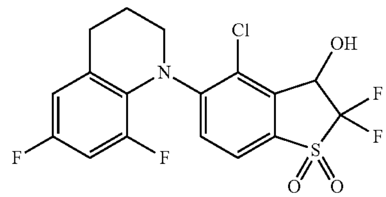 | 10 | 422.0 [M + H] |
| 53 | 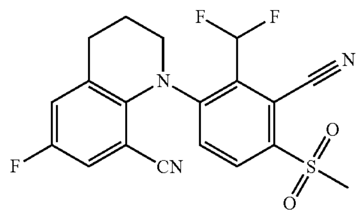 | 10 | 399.0 [M + H] |
| 54 | 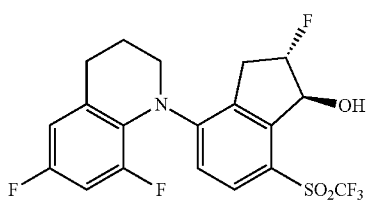 | 2, 19 | 452.1 [M + H] |
| 55 | 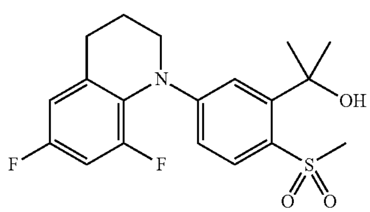 [SMILES: CC(C)(O)c1cc(N2CCCc3cc(F)cc(F)c32)ccc1S(C)(=O)=O] | 10 | 382.0 [M + H] |
| 56 | 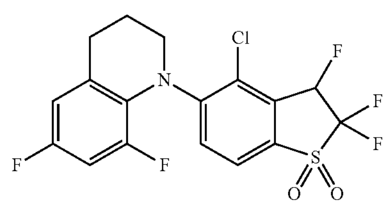 [SMILES: O=S1(=O)c2ccc(N3CCCc4cc(F)cc(F)c43)c(Cl)c2C(F)C1(F)F] | 10 | 424.0 [M + H] |
| 57 | 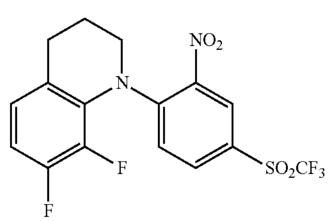 | 10 | 423.1 [M + H] |
| 58 | 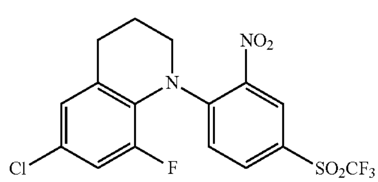 | 10 | 439.2 [M + H] |

TABLE A-continued

Syntheses of Examples 26-120

| Example | Structure | Synthesis According to Example | Mass Spec (Observed) |
|---------|-----------|-------------------------------|----------------------|
| 59 | 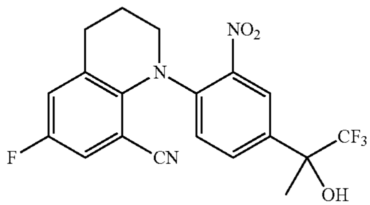 [SMILES: CC(O)(c1ccc(N2CCCc3cc(F)cc(C#N)c32)c([N+](=O)[O-])c1)C(F)(F)F] | 10 | 410.1 [M + H] |
| 60 | 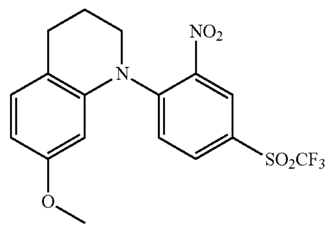 | 10 | 417.1 [M + H] |
| 61 | 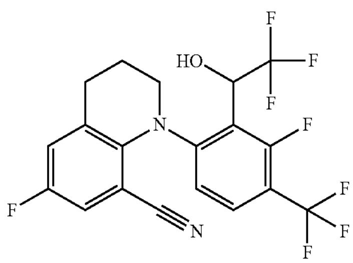 [SMILES: N#Cc1cc(F)cc2c1N(c1ccc(C(F)(F)F)c(F)c1C(O)C(F)(F)F)CCC2] | 10 | 437.1 [M + H] |
| 62 | 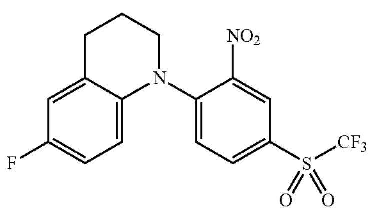 [SMILES: O=[N+]([O-])c1cc(S(=O)(=O)C(F)(F)F)ccc1N1CCCc2cc(F)ccc21] | 10 | 405.0 [M + H] |
| 63 | 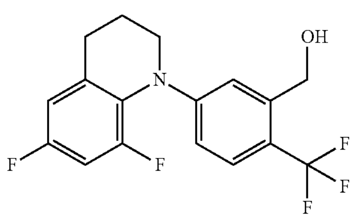 [SMILES: OCc1cc(N2CCCc3cc(F)cc(F)c32)ccc1C(F)(F)F] | 10 | 344.0 [M + H] |
| 64 | 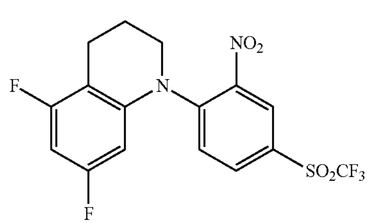 | 10 | 441.5 [M + H$_2$O + H] |

TABLE A-continued

Syntheses of Examples 26-120

| Example | Structure | Synthesis According to Example | Mass Spec (Observed) |
|---------|-----------|-------------------------------|----------------------|
| 65 | 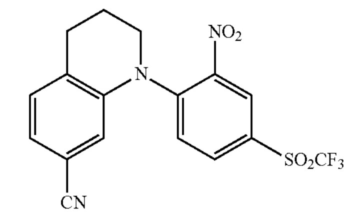 | 10 | 412.0 [M + H] |
| 66 | 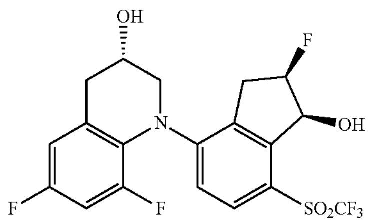 | 10, 19 | 468.1 [M + H] |
| 67 | 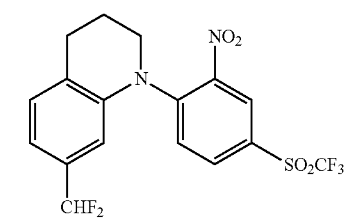 | 10 | 437.0 [M + H] |
| 68 | 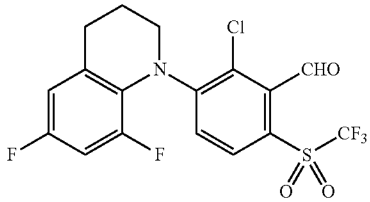 [SMILES: O=Cc1c(S(=O)(=O)C(F)(F)F)ccc(N2CCCc3cc(F)cc(F)c32)c1Cl] | 10 | — |
| 69 | 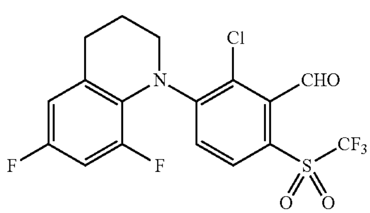 [SMILES: O=Cc1c(S(=O)(=O)C(F)(F)F)ccc(N2CCCc3cc(F)cc(F)c32)c1Cl] | 10 | — |
| 70 | 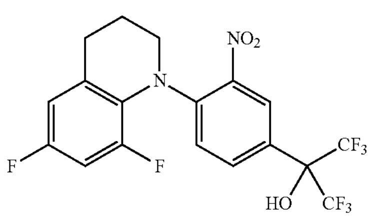 [SMILES: O=[N+]([O-])c1cc(C(O)(C(F)(F)F)C(F)(F)F)ccc1N1CCCc2cc(F)cc(F)c21] | 10 | 457.0 [M + H] |
| 71 | 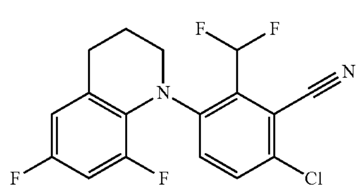 [SMILES: N#Cc1c(Cl)ccc(N2CCCc3cc(F)cc(F)c32)c1C(F)F] | 10 | 355.1 [M + H] |

TABLE A-continued

Syntheses of Examples 26-120

| Example | Structure | Synthesis According to Example | Mass Spec (Observed) |
|---------|-----------|-------------------------------|----------------------|
| 72 | 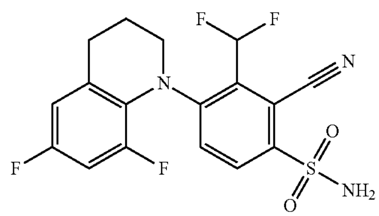 [SMILES: N#Cc1c(S(N)(=O)=O)ccc(N2CCCc3cc(F)cc(F)c32)c1C(F)F] | 10 | 422.0 [M + Na] |
| 73 | 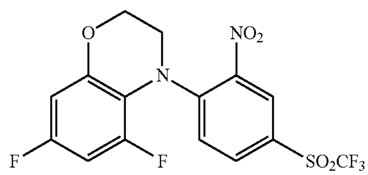 | 10 | 425.2 [M + H] |
| 74 | 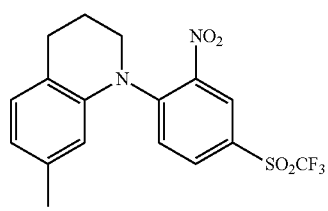 | 10 | 401.1 [M + H] |
| 75 | 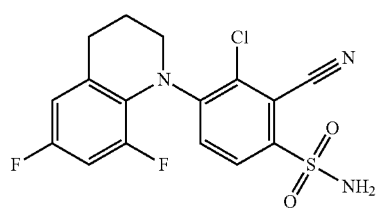 [SMILES: N#Cc1c(S(N)(=O)=O)ccc(N2CCCc3cc(F)cc(F)c32)c1Cl] | 10 | 384.0 [M + H] |
| 76 | 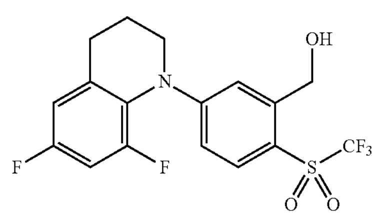 [SMILES: O=S(=O)(c1ccc(N2CCCc3cc(F)cc(F)c32)cc1CO)C(F)(F)F] | 10 | 408.0 [M + H] |
| 77 | 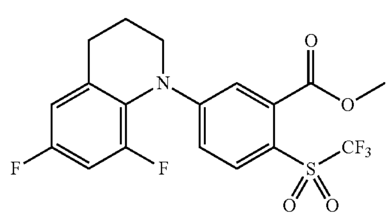 [SMILES: COC(=O)c1cc(N2CCCc3cc(F)cc(F)c32)ccc1S(=O)(=O)C(F)(F)F] | 10 | 436.0 [M + H] |
| 78 | 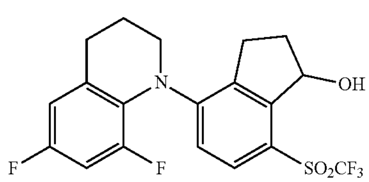 | 19 | — |

TABLE A-continued

Syntheses of Examples 26-120

| Example | Structure | Synthesis According to Example | Mass Spec (Observed) |
|---|---|---|---|
| 79 | 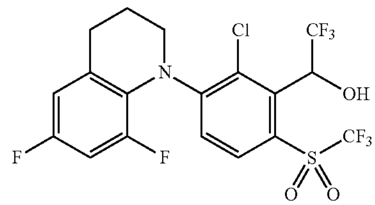 [SMILES: O=S(=O)(c1ccc(N2CCCc3cc(F)cc(F)c32)c(Cl)c1C(O)C(F)(F)F)C(F)(F)F] | 10 | 510.0 [M + H] |
| 80 | 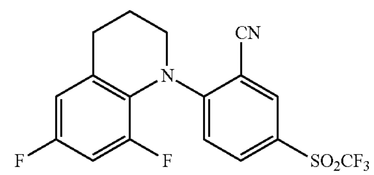 | 10 | 403.2 [M + H] |
| 81 | 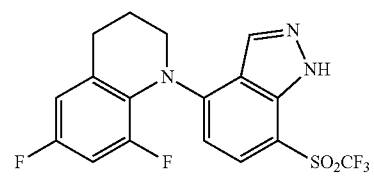 | 10 | 418.1 [M + H] |
| 82 | 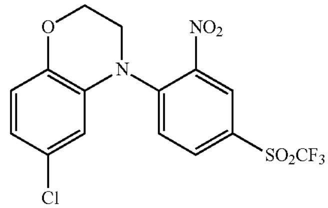 | 10 | 423.3 [M + H] |
| 83 | 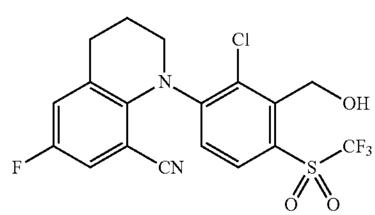 [SMILES: N#Cc1cc(F)cc2c1N(c1ccc(S(=O)(=O)C(F)(F)F)c(CO)c1Cl)CCC2] | 10 | 442.0 [M + H] |
| 84 | 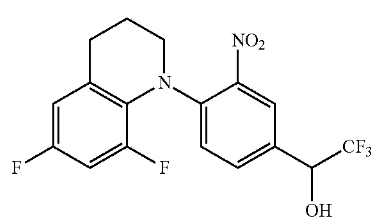 [SMILES: O=[N+]([O-])c1cc(C(O)C(F)(F)F)ccc1N1CCCc2cc(F)cc(F)c21] | 10 | 389.1 [M + H] |
| 85 | 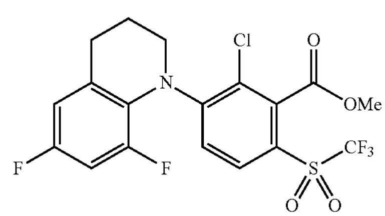 [SMILES: COC(=O)c1c(S(=O)(=O)C(F)(F)F)ccc(N2CCCc3cc(F)cc(F)c32)c1Cl] | 10 | 470.0 [M + H] |

TABLE A-continued

Syntheses of Examples 26-120

| Example | Structure | Synthesis According to Example | Mass Spec (Observed) |
|---|---|---|---|
| 86 | 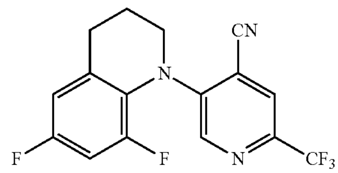 [SMILES: N#Cc1cc(C(F)(F)F)ncc1N1CCCc2cc(F)cc(F)c21] | 10 | 340.0 [M + H] |
| 87 | 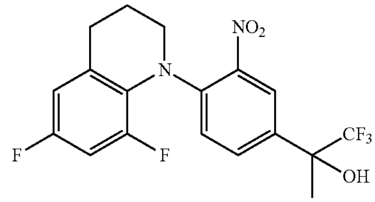 [SMILES: CC(O)(c1ccc(N2CCCc3cc(F)cc(F)c32)c([N+](=O)[O-])c1)C(F)(F)F] | 10 | 403.1 [M + H] |
| 88 | 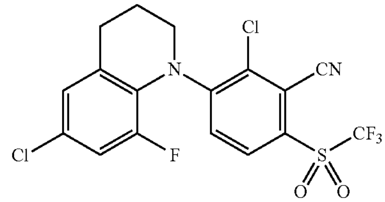 [SMILES: N#Cc1c(S(=O)(=O)C(F)(F)F)ccc(N2CCCc3cc(Cl)cc(F)c32)c1Cl] | 10 | 475.0 [M + Na] |
| 89 | 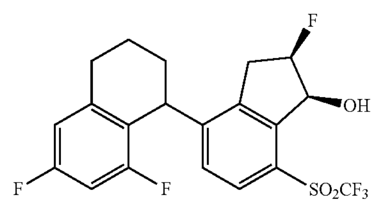 | 2 | — |
| 90 | 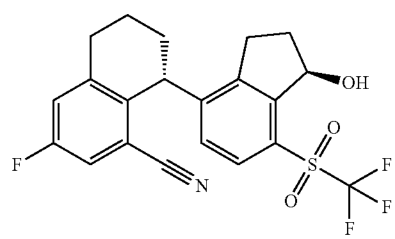 [SMILES: N#Cc1cc(F)cc2c1[C@@H](c1ccc(S(=O)(=O)C(F)(F)F)c3c1CC[C@H]3O)CCC2] | 2 | 462.0 [M + Na] |
| 91 | 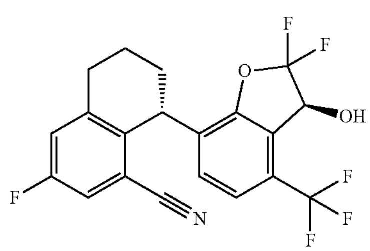 [SMILES: N#Cc1cc(F)cc2c1[C@@H](c1ccc(C(F)(F)F)c3c1OC(F)(F)[C@H]3O)CCC2] | 2 | 436.1 [M + Na] |
| 92 | 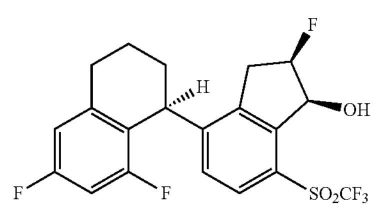 | 2 | — |

TABLE A-continued

Syntheses of Examples 26-120

| Example | Structure | Synthesis According to Example | Mass Spec (Observed) |
|---|---|---|---|
| 93 | 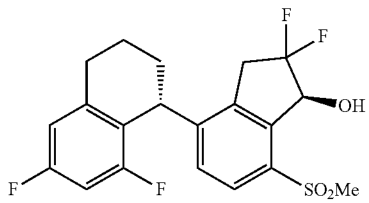 | 2 | 415.1 [M + H] |
| 94 | 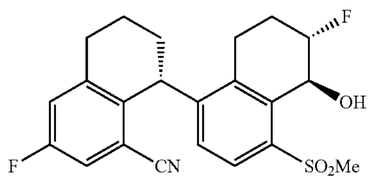 | 2 | 440.2 [M + Na] |
| 95 | 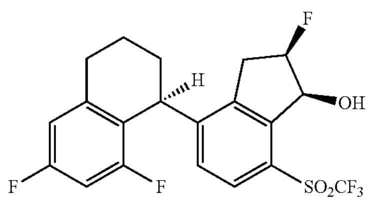 | 2 | — |
| 96 | 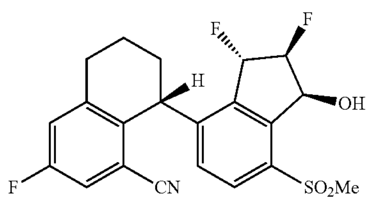 | 2, 5 | 422.0 [M + H] |
| 97 | 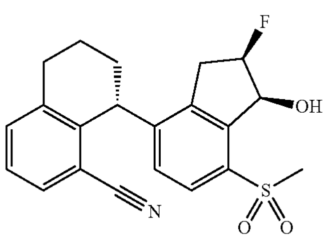 [SMILES: CS(=O)(=O)c1ccc([C@H]2CCCc3cccc(C#N)c32)c2c1[C@H](O)[C@H](F)C2] | 5 | 386.1 [M + H] |
| 98 | 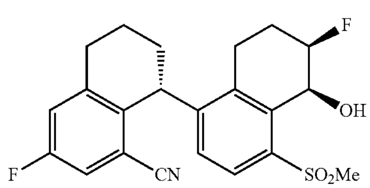 | 2 | 440.1 [M + Na] |
| 99 | 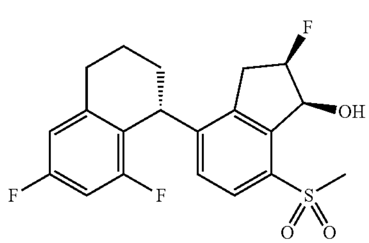 [SMILES: CS(=O)(=O)c1ccc([C@H]2CCCc3cc(F)cc(F)c32)c2c1[C@H](O)[C@H](F)C2] | 5 | 379.0 [M + H − H$_2$O] |

TABLE A-continued

Syntheses of Examples 26-120

| Example | Structure | Synthesis According to Example | Mass Spec (Observed) |
|---|---|---|---|
| 100 | 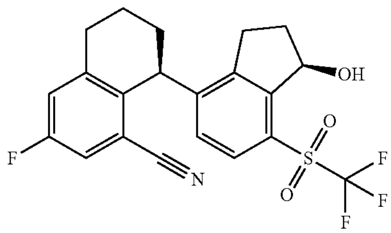 [SMILES: N#Cc1cc(F)cc2c1[C@H](c1ccc(S(=O)(=O)C(F)(F)F)c3c1CC[C@H]3O)CCC2] | 5 | 462.0 [M + Na] |
| 101 | 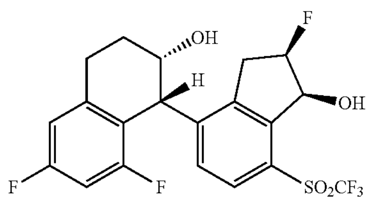 | 2 | 489.1 [M + Na] |
| 102 | 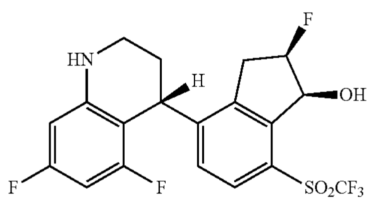 | 8 | 452.0 [M + H] |
| 103 | 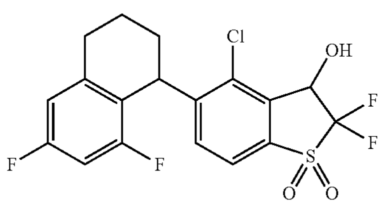 [SMILES: O=S1(=O)c2ccc(C3CCCc4cc(F)cc(F)c43)c(Cl)c2C(O)C1(F)F] | 2 | 421.1 [M + H] |
| 104 | 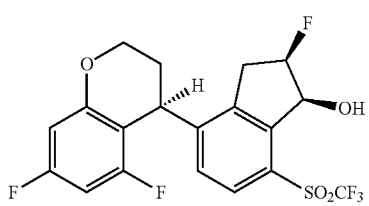 | 8 | 475.1 [M + Na] |
| 105 | 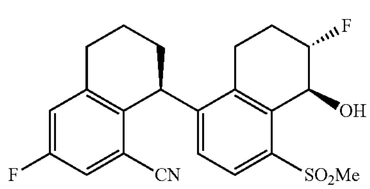 [SMILES: CS(=O)(=O)c1ccc([C@@H]2CCCc3cc(F)cc(C#N)c32)c2c1[C@H](O)[C@@H](F)CC2] | 2 | 440.1 [M + Na] |
| 106 | 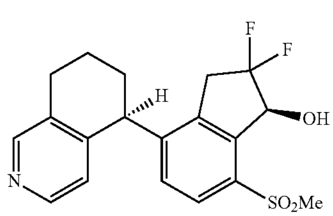 [SMILES: CS(=O)(=O)c1ccc([C@@H]2CCCc3cnccc32)c2c1[C@H](O)C(F)(F)C2] | 2 | 380.1 [M + H] |

TABLE A-continued

Syntheses of Examples 26-120

| Example | Structure | Synthesis According to Example | Mass Spec (Observed) |
|---|---|---|---|
| 107 | 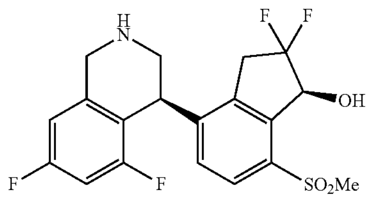 [SMILES: CS(=O)(=O)c1ccc([C@@H]2CNCc3cc(F)cc(F)c32)c2c1[C@H](O)C(F)(F)C2] | 8 | 416.1 [M + H] |
| 108 | 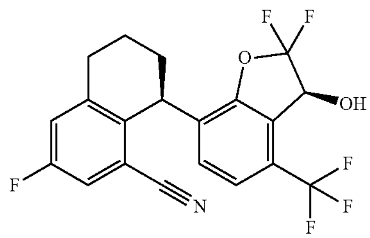 [SMILES: N#Cc1cc(F)cc2c1[C@H](c1ccc(C(F)(F)F)c3c1OC(F)(F)[C@H]3O)CCC2] | 2 | 436.0 [M + Na] |
| 109 | 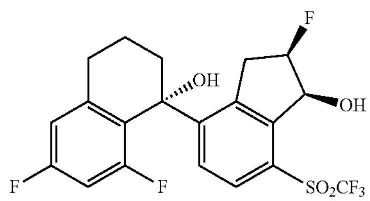 | 2 | 489.2 [M + Na] |
| 110 | 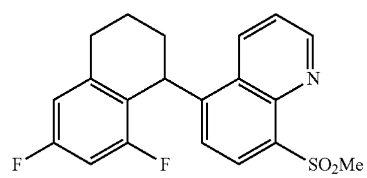 [SMILES: CS(=O)(=O)c1ccc(C2CCCc3cc(F)cc(F)c32)c2cccnc12] | 1 | 374.1 [M + H] |
| 111 | 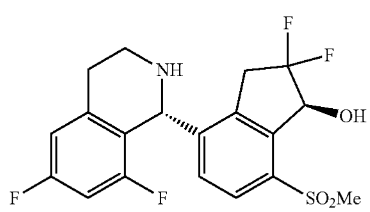 | 8 | 416.1 [M + H] |
| 112 | 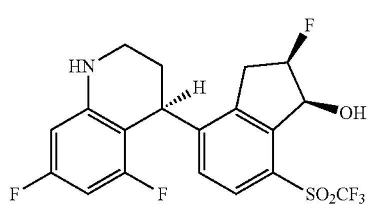 | 8 | 452.1 [M + H] |
| 113 | 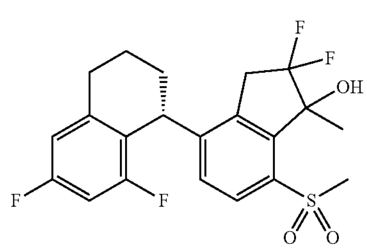 [SMILES: CC1(O)c2c(S(C)(=O)=O)ccc([C@H]3CCCc4cc(F)cc(F)c43)c2CC1(F)F] | 2 | 411.0 [M + H − H$_2$O] |

TABLE A-continued

Syntheses of Examples 26-120

| Example | Structure | Synthesis According to Example | Mass Spec (Observed) |
|---------|-----------|-------------------------------|----------------------|
| 114 | 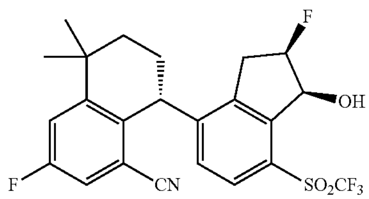 | 5 | — |
| 115 | 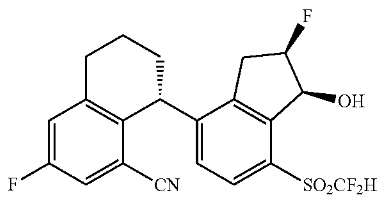 | 5 | 462.1 [M + Na] |
| 116 | 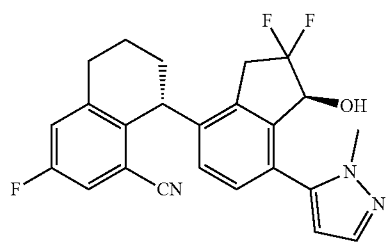 [SMILES: Cn1nccc1-c1ccc([C@H]2CCCc3cc(F)cc(C#N)c32)c2c1[C@H](O)C(F)(F)C2] | 2 | 424.2 [M + H] |
| 117 | 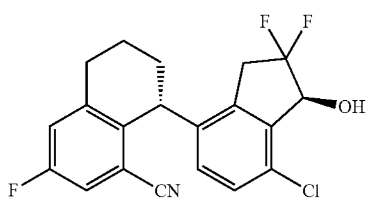 [SMILES: N#Cc1cc(F)cc2c1[C@@H](c1ccc(Cl)c3c1CC(F)(F)[C@H]3O)CCC2] | 2 | 400.1 [M + Na] |
| 118 | 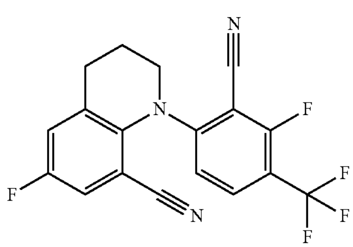 | 10 | 364.1 [M + H] |
| 119 | 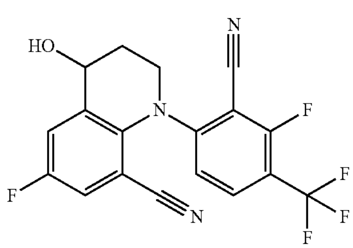 | 121 | 362.1 [M − H₂O] |

TABLE A-continued
Syntheses of Examples 26-120
| Example | Structure | Synthesis According to Example | Mass Spec (Observed) |
|---|---|---|---|
| 120 | 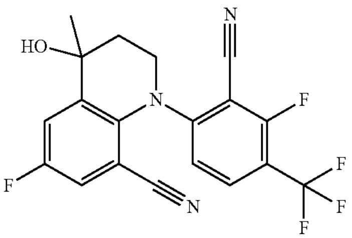 [SMILES: CC1(O)CCN(c2ccc(C(F)(F)F)c(F)c2C#N)c2c(C#N)cc(F)cc21] | 121 | 416.0 [M + Na] |
Example 121: (4S)-1-[2-Cyano-3-fluoro-4-(trifluoromethyl)phenyl]-4,6-difluoro-3,4-dihydro-2H-quinoline-8-carbonitrile
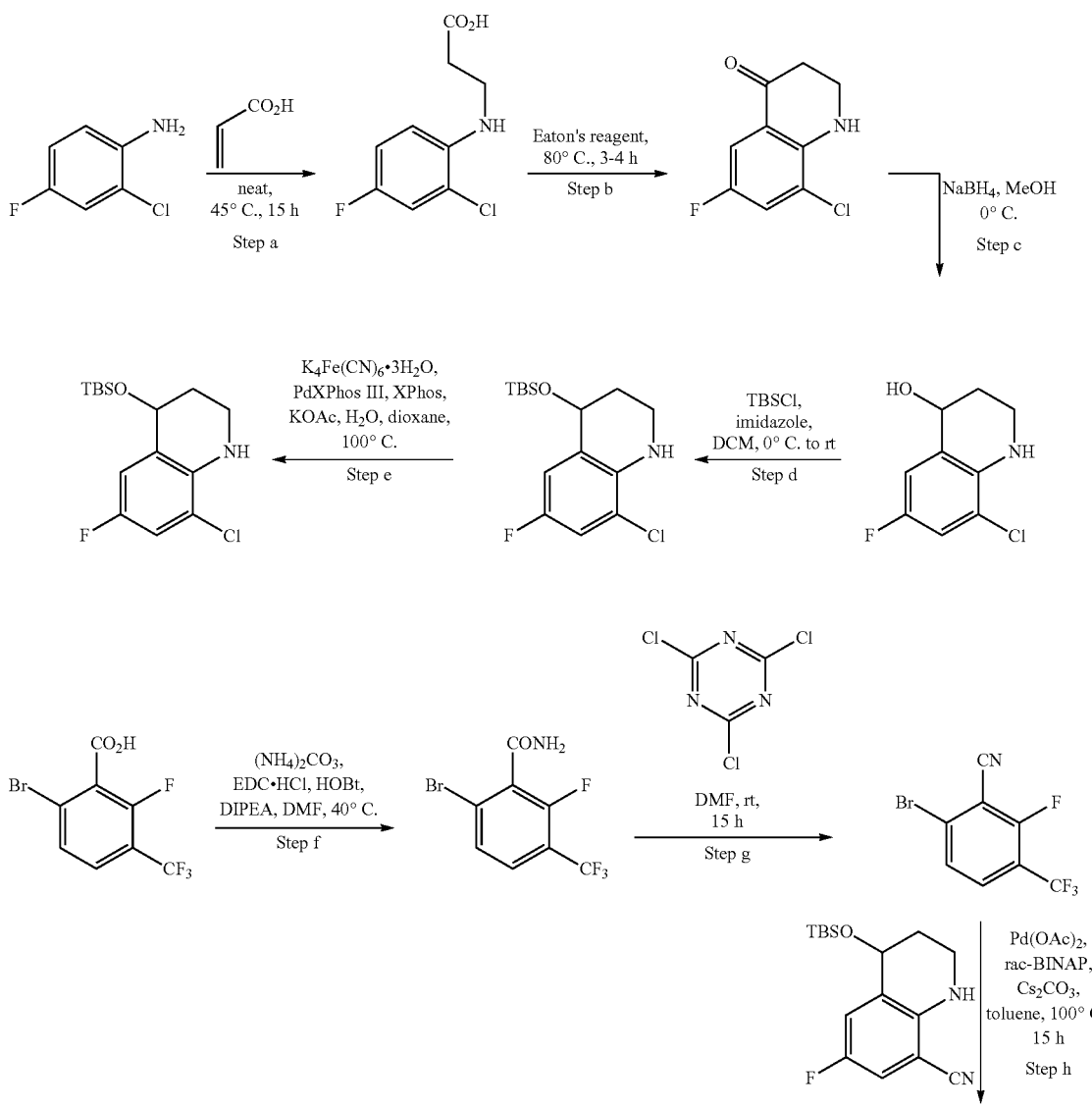

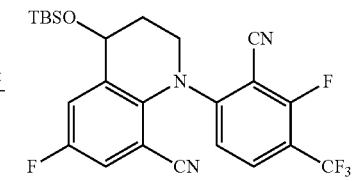
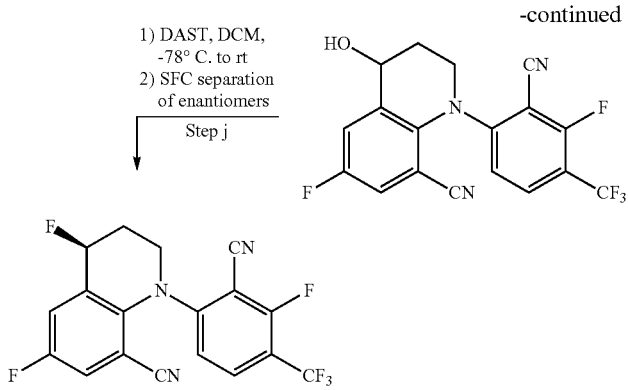

Step a: A flask was charged with 2-chloro-4-fluoroaniline (18.2 g, 15 mL, 1.0 mol. equiv.) and excess acrylic acid (46 g, 5.0 mol. equiv.) and the resulting mixture was stirred at 45° C. for 15 h. During this time, the product solidified from the reaction mixture and was collected by filtration, rinsing with hexanes, to afford the aniline product that was used crude in the next step (25.4 g, 93%).

Step b: The product from step a (25.4 g) was then added portion-wise to Eaton's reagent (100 mL) at 0° C. The resulting mixture was warmed to room temperature and then heated at 80° ° C. for 3 h. After this time, the reaction was cooled, and carefully poured onto ice, after which the product precipitated out of solution as a yellow solid (17.4 g, 75%).

Step c: A flask containing the product from the previous step (15 g, 75.3 mmol, 1.0 mol. equiv.) in MeOH (250 mL) was cooled to 0° C. under $N_2$. $NaBH_4$ (3.41 g, 90.4 mmol, 1.2 mol. equiv.) was added slowly in portions, after which the reaction was stirred at room temperature for 30 min. At this time, the reaction was placed in an ice bath, quenched with $H_2O$, and diluted with EtOAc. The aqueous layer was separated and back extracted with additional EtOAc. The organic layers were combined, washed with water, brine, and dried over $MgSO_4$. Concentration under reduced pressure furnished tetrahydroquinoline intermediate that was taken onto the next step without further purification.

Step d: To the crude intermediate from step c was added DCM (250 mL) and imidazole (7.70 g, ~1.5 mol. equiv.). The resulting mixture was cooled to 0° C. and TBSCl (17.0 g, ~1.5 equiv.) was added. The reaction was warmed to room temperature and stirred for 2 h. The reaction was filtered to remove imidazole hydrochloride and concentrated onto Celite. Purification by flash column chromatography ($SiO_2$, hexanes to 10% EtOAc/hexanes) furnished the TBS protected alcohol as a colorless oil (16.7 g, 70% over 2 steps).

Step e: A flask was charged with TBS alcohol from the previous step (6.0 g, 19 mmol, 1.0 mol. equiv.), $K_4Fe(CN)_6 \cdot 3H_2O$ (5.61 g, 13.3 mmol, 0.7 mol. equiv.), Pd XPhos gen III (0.803 g, 0.95 mmol, 5 mol %), XPhos (0.452 g, 0.95 mmol, 5 mol %), KOAc (0.242 g, 2.47 mmol, 0.13 mol. equiv.), $H_2O$ (40 mL) and 1,4-dioxane (40 mL). The resulting mixture was purged with $N_2$, heated at 100° C., and stirred vigorously under $N_2$. After 3 h, the reaction was cooled, and diluted with EtOAc and $H_2O$. The aqueous layer was separated and back extracted with additional EtOAc. Filtration through Celite to remove solids may improve the distinction of layers. The organic layers were combined and dried over $MgSO_4$. Purification by flash column chromatography ($SiO_2$, hexanes to 20% EtOAc) furnished the benzonitrile product as a yellow solid (5.68 g, 98%).

Step f: To a flask containing 6-bromo-2-fluoro-3-(trifluoromethyl)benzoic acid (10 g, 34.8 mmol, 1.0 mol. equiv.) was added DMF (70 mL), followed by EDC·HCl (9.98 g, 52.2 mmol, 1.5 mol. equiv.), HOBt·$H_2O$ (7.0 g, 52.2 mmol, 1.5 mol. equiv.), ammonium carbonate (16.7 g, 174 mmol, 5.0 mol. equiv.), and DIPEA (18 mL, 3.0 mol. equiv.). The resulting mixture was stirred overnight at 40° C. The reaction was partitioned between EtOAc and $H_2O$. The aqueous layer was separated and extracted with additional EtOAc. The organic layers were combined, washed with $H_2O$ to remove DMF, and dried over $MgSO_4$. Concentration under reduced pressure furnished crude amide that was taken onto the next step without purification.

Step g: To a flask containing crude amide from the previous step was added DMF (100 mL) and cyanuric trichloride (2.55 g, 13.9 mmol, ~0.6 mol. equiv.). The resulting mixture was stirred under $N_2$ at room temperature for 16 h. The reaction was partitioned between EtOAc and $H_2O$. The aqueous layer was separated and extracted with additional EtOAc. The organic layers were combined, washed with $H_2O$ to remove DMF, and dried over $MgSO_4$. Concentration under reduced pressure and purification by flash column chromatography ($SiO_2$, hexanes to 20% EtOAc) furnished the nitrile product as a white solid (2.68 g, 26% over 2 steps).

Step h: A vial was charged with benzonitrile from the previous step (1.0 g, 3.73 mmol, 1.0 mol. equiv.), 4-[tert-butyl(dimethyl)silyl]oxy-6-fluoro-1,2,3,4-tetrahydroquinoline-8-carbonitrile (1.10 g, 3.73 mmol, 1.0 mol. equiv.), $Pd(OAc)_2$ (0.167 g, 0.746 mmol, 20 mol %), rac-BINAP (0.580 g, 0.925 mmol, 25 mol %), $Cs_2CO_3$ (2.42 g, 7.46 mmol, 2.0 mol. equiv.) and toluene (15 mL). $N_2$ was bubbled through the reaction mixture for 3 min, the vial capped, and heated at 100° ° C. for 15 h. The reaction was monitored by TLC and NMR analysis. The reaction was cooled, filtered, and concentrated onto Celite. Purification by flash column chromatography ($SiO_2$, hexanes to 10 to 20% EtOAc) furnished the coupled product as a yellow solid (1.00 g, 54%). ESI MS $[M+H]^+$ for $C_{24}H_{24}FN_3OSi$, calcd 494.2, found 494.2.

Step i: A flask containing the product from the previous step (1.0 g, 2.02 mmol, 1.0 mol. equiv.) and THF (10 mL) was cooled to 0° C. and TBAF (1 M in THF, 3.0 mL, 1.5 mol. equiv.) was added. The reaction mixture was warmed to room temperature and stirred for 15 min. After this time, the reaction was quenched with sat. aq. $NH_4Cl$ solution and diluted with EtOAc. The aqueous layer was separated and back extracted with additional EtOAc. The organic layers were combined, washed with brine, and dried over MgSO$_4$. Concentration under reduced pressure and purification by flash column chromatography (SiO$_2$, hexanes to 20% to 50% to 80% EtOAc) furnished the alcohol product as a white solid (0.694 g, 91%).

Step j: A vial containing the alcohol product from the previous step (35 mg, 0.093 mmol, 1.0 mol. equiv.) in DCM (1 mL) was cooled to −78° C. DAST (20 μL, 0.149 mmol, 1.6 mol. equiv.) was added, and the reaction was allowed to warm to room temperature and stirred for 5 min. The reaction was quenched at 0° C. with sat. aq. NaHCO$_3$ solution and diluted with DCM. The aqueous layer was separated and back extracted with additional DCM. The organic layers were combined and dried over MgSO$_4$. Concentration under reduced pressure and purification by column chromatography (SiO$_2$, hexanes to 20% EtOAc) furnished racemic 1-[2-cyano-3-fluoro-4-(trifluoromethyl) phenyl]-4,6-difluoro-3,4-dihydro-2H-quinoline-8-carbonitrile as a white solid (13 mg, 37%). The enantiomers could be separated by preparative SFC chiral purification (2.0× 25.0 cm ChromegaChiral CC4 from ES Industries (West Berlin, NJ), CO$_2$ co-solvent Isopropanol/Hexane (1:9), 15% co-solvent at 100 mL/min) to furnish the title compound (4S)-1-[2-cyano-3-fluoro-4-(trifluoromethyl)phenyl]-4,6-difluoro-3,4-dihydro-2H-quinoline-8-carbonitrile as a white solid (98.8% ee, t$_R$=1.5 min). Absolute stereochemistry was confirmed by single crystal X-ray analysis. $^1$H NMR (400 MHZ, DMSO-d$_6$, appears as a 2:1 mixture of rotamers) δ 8.11 (t, J=8.6 Hz, 1H), 8.03 (t, J=8.6 Hz, 2H), 7.94-7.79 (m, 6H), 7.43 (d, J=8.8 Hz, 1H), 7.12 (d, J=8.7 Hz, 2H), 5.82 (dt, J=49.7, 2.9 Hz, 1H), 5.70 (dt, J=49.8, 2.9 Hz, 2H), 4.08-3.67 (m, 6H), 2.38-2.02 (m, 6H). ESI MS [(M−HF)+H]$^+$ for C$_{18}$H$_8$F$_5$N$_3$, calcd 362.0, found 362.0.

Example 122: 1-(3-chloro-2-cyano-4-methylsulfonylphenyl)-4,6-difluoro-3,4-dihydro-2H-quinoline-8-carbonitrile

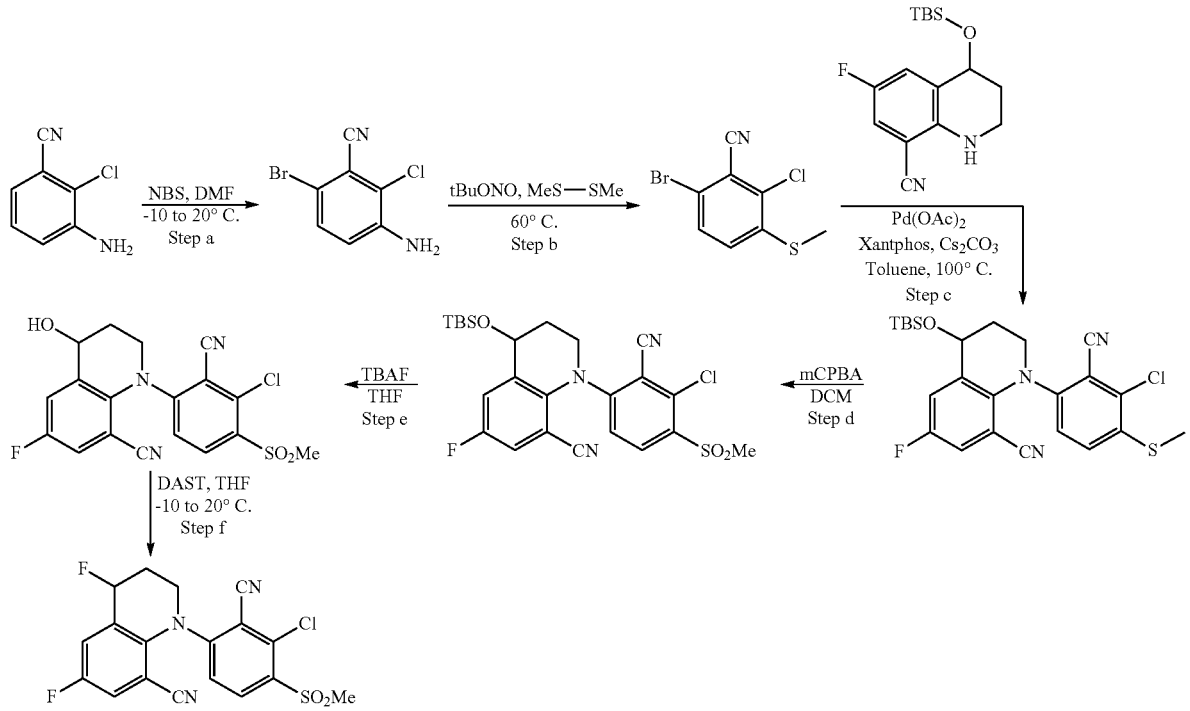

Step a: A solution of the 3-amino-2-chloro-benzonitrile (1 g, 6.58 mmol) in DMF (20 mL) was cooled to −10° C. and NBS (1.17 g, 6.58 mmol, 1.0 equiv.) in DMF (10 mL) was added dropwise over 10 min. The mixture was stirred at −10° C. for 10 min. then the cooling batch was removed, and reaction was stirred at room temperature for 1.5 h. Diluted with 10% Na$_2$S$_2$O$_3$ (100 mL) and extracted with EtOAc (3×100 mL). Combined organics were washed with brine (50 mL), dried over MgSO$_4$, filtered and concentrated in vacuo. The residue was purified by column chromatography (silica gel, hex→30% EtOAc in hexanes) to afford the product (0.92 g, 60%).

Step b: Product from step a (0.5 g, 2.16 mmol) was dissolved in MeCN (8.5 mL). tBuONO (0.39 mL, 3.25 mmol, 1.5 equiv.) and MeS-SMe (0.23 mL, 2.50 mmol, 1.2 equiv.) was added. The mixture was stirred at room temperature for 15 min. then heated at 60° C. for 1 h. The reaction mixture was cooled down and concentrated in vacuo. The residue was purified by column chromatography (silica gel, hex→30% EtOAc in hexanes) to afford the product as (0.36 g, 64%).

Step c: The mixture of bromide from step b (180 mg, 0.68 mmol, 1.5 equiv.), 4-[tert-butyl(dimethyl)silyl]oxy-6-fluoro-1,2,3,4-tetrahydroquinoline-8-carbonitrile (148 mg, 0.45 mmol), Pd(OAc)$_2$ (10 mg, 0.045 mmol, 10% mol.), Xantphos (52 mg, 0.09 mmol, 20% mol.) and Cs$_2$CO$_3$ (440 mg, 1.35 mmol, 3 equiv.) in anhydrous, degassed toluene (8 mL) was stirred at 100° C. for 15 h. Whole reaction mixture was loaded on a silica gel cartridge and purified by column chromatography (silica gel, hex→30% EtOAc in hexanes) to afford the product (88 mg, 40%).

Step d: Product from step c (88 mg, 0.18 mmol) was dissolved in DCM (4 mL). mCPBA (254 mg, 1.1 mmol, 6.0 equiv.) was added in one portion. Reaction mixture was stirred for 2 h at room temperature, then quenched 10% Na₂S₂O₃ (30 mL) and extracted with EtOAc (3×30 mL). Combined organics were washed with sat. NaHCO₃ (50 mL), dried over MgSO₄, filtered and concentrated in vacuo. The residue was purified by column chromatography (silica gel, hex→30% EtOAc in hexanes) to afford the product (quantitative yield).

Step e: Product from step d (0.18 mmol) was dissolved in THF (40 mL) and TBAF (1.0M in THF, 0.54 mL, 3.0 equiv.) was added. Reaction was stirred at room temperature for 15 min. Quenched with H₂O (10 mL) and extracted with EtOAc (2×20 mL). Combined organics were washed with brine (10 mL), dried over MgSO₄, filtered and concentrated in vacuo. The residue was purified by column chromatography (silica gel, hex→80% EtOAc in hexanes) to afford the product as yellow solid (58 mg, 80%).

Step f: The product from step e (25 mg, 0.05 mmol) in DCM (2 mL) was cooled to −10° C. and DAST (16 mg, 0.1 mmol, 2.0 equiv.) was added. The mixture was stirred at −10° C. for 10 min. then the cooling batch was removed, and reaction was stirred at room temperature for 0.5 h. Quenched with H₂O (10 mL) and extracted with EtOAc (2×20 mL). Combined organics were washed with brine (10 mL), dried over MgSO₄, filtered and concentrated in vacuo. The residue was purified by column chromatography (silica gel, hex→60% EtOAc in hexanes) to afford the product as yellow solid (23 mg, 95%). $^1$H NMR (400 MHZ, DMSO-d₆) δ 8.22 (d, J=8.8 Hz, 0.4H), 8.11 (d, J=8.8 Hz, 0.6H), 7.92-7.74 (m, 2H), 7.54 (d, J=8.8 Hz, 0.4H), 7.25 (d, J=8.8 Hz, 0.6H), 5.89-5.59 (m, 1H), 4.04-3.90 (m, 1H), 3.84-3.63 (m, 1H), 3.38 (m, 3H), 2.30-1.97 (m, 2H). ESI MS [M+H]⁺ for C₁₈H₁₂ClF₂N₃O₂S, calcd 408.0, found 408.0.

Example 123: 1-[3-Chloro-2-cyano-4-(trifluoromethyl)phenyl]-4,6-difluoro-3,4-dihydro-2H-quinoline-8-carbonitrile

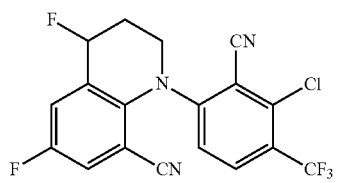 [SMILES: N#Cc1cc(F)cc2c1N(c1ccc(C(F)(F)F)c(Cl)c1C#N)CCC2F]

This compound was prepared in a similar fashion to Example 121 from 6-bromo-2-chloro-3-(trifluoromethyl) benzoic acid. $^1$H NMR (400 MHZ, DMSO-d₆, appears as a 2:1 mixture of rotamers) δ 8.15 (d, J=8.8 Hz, 1H), 8.05 (d, J=8.8 Hz, 2H), 7.93-7.86 (m, 4H), 7.86-7.77 (m, 2H), 7.57 (d, J=8.8 Hz, 1H), 7.26 (d, J=8.7 Hz, 2H), 5.82 (dt, J=49.7, 2.9 Hz, 1H), 5.70 (dt, J=49.8 Hz, 2.9 Hz, 2H), 4.05-3.91 (m, 3H), 3.88-3.66 (m, 3H), 2.32-2.00 (m, 6H). ESI MS [M+H]⁺ for C₁₈H₉ClF₅N₃, calcd 398.0, found 397.9.

Example 124: 1-[2-cyano-3-fluoro-4-(trifluoromethyl)phenyl]-6-fluoro-3,4-dihydro-2H-quinoline-4,8-dicarbonitrile

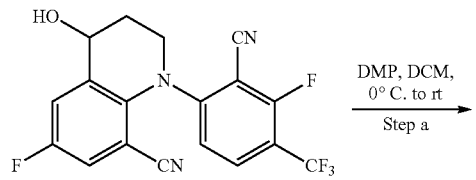

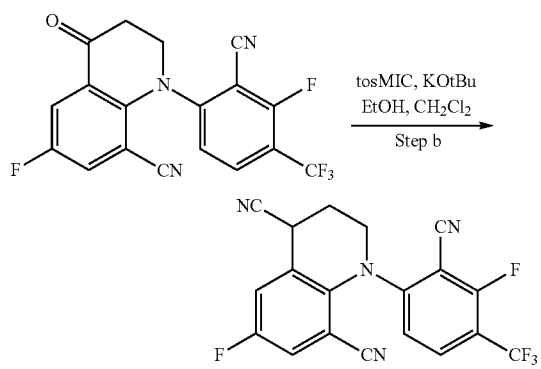

Step a: A vial containing 1-[2-cyano-3-fluoro-4-(trifluoromethyl)phenyl]-6-fluoro-4-hydroxy-3,4-dihydro-2H-quinoline-8-carbonitrile (110 mg, 0.290 mmol, 1.0 mol. equiv.) in DCM (1.5 mL) was cooled to 0° C. and DMP (150 mg, 0.348 mmol, 1.2 mol. equiv.) was added. The reaction mixture was warmed to room temperature and stirred for 20 min. The reaction was quenched with sat. aq. NaHCO₃ solution and sat. aq. Na₂S₂O₃ solution (1:1) and diluted with DCM. The mixture was stirred vigorously for 30 min. The organic layer was separated and washed with additional sat. aq. NaHCO₃/Na₂S₂O₃ solution. The organic layer was separated and dried over MgSO₄. Concentration under reduced pressure furnished ketone product as a yellow solid that was sufficiently purity to use in subsequent steps (110 mg, ~quant.). ESI MS [M+H]⁺ for C₁₈H₈F₅N₃O, calcd 378.1, found 378.1.

Step b: A solution of KOtBu (1M in THF, 520 μL, 2 equiv.) was added to a solution of 1-[2-cyano-3-fluoro-4-(trifluoromethyl)phenyl]-6-fluoro-4-oxo-2,3-dihydroquinoline-8-carbonitrile (100 mg, 0.265 mmol) and to sMIC (83 mg, 0.42 mmol, 1.6 equiv.) in dichloromethane (1.3 ml) at room temperature. Ethanol (18 mg, 0.4 mmol, 1.5 equiv) was added, and the reaction was stirred for 48 h at room temperature. Upon completion the reaction was quenched with 2N aq. HCl, extracted with dichloromethane, and purified by flash chromatography on silica gel to yield 1-[2-cyano-3-fluoro-4-(trifluoromethyl)phenyl]-6-fluoro-3,4-dihydro-2H-quinoline-4,8-dicarbonitrile. $^1$H NMR (400 MHZ, DMSO-d₆): δ 8.11-7.95 (m, 1H), 7.88-7.68 (m, overlap, 2H), 7.24 (dd, J=8.2, 8.2 Hz, 1H), 4.69-4.57 (m, 1H), 4.09-3.69 (m, 2H), 2.43-2.27 (m, 1H), 2.22-2.09 (m, 1H). ESI MS [M+H]⁺ for C₁₉H₉F₅N₄, calcd. 389.0, found 389.0.

Example 125: 1-[2-cyano-3-fluoro-4-(trifluoromethyl)phenyl]-4,4,6-trifluoro-2,3-dihydroquinoline-8-carbonitrile

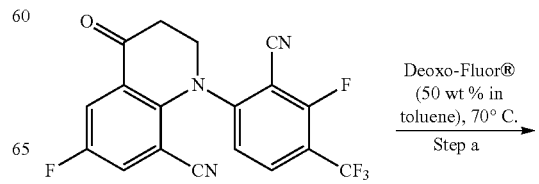

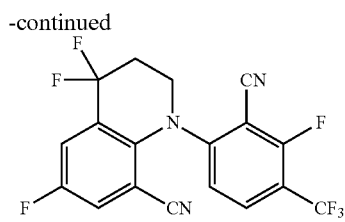

Step a: A solution of 1-[2-cyano-3-fluoro-4-(trifluoromethyl)phenyl]-6-fluoro-4-oxo-2,3-dihydroquinoline-8-carbonitrile (100 mg, 0.265 mmol) in 1 ml of a 50 wt % solution of Deoxo-Fluor® in toluene was heated to 70° C. overnight. Upon completion the reaction was cooled to 0° C. in an ice bath and quenched with water. The resulting solution was extracted with ethyl acetate and methylene chloride, and the crude concentrated material was purified by flash chromatography on silica gel (0% to 30% ethyl acetate in hexanes) to yield 1-[2-cyano-3-fluoro-4-(trifluoromethyl)phenyl]-4,4,6-trifluoro-2,3-dihydroquinoline-8-carbonitrile. $^1$H NMR (400 MHZ, CDCl$_3$): δ 7.75 (dd, J=8.2, 8.2 Hz, 1H), 7.68 (dd, J=7.8, 3.0 Hz, 1H), 7.27 (dd, J=7.2, 3.0 Hz, 1H), 6.92 (d, J=8.6 Hz, 1H), 4.16-4.09 (m, 1H), 3.99-3.92 (m, 1H), 2.53-2.39 (m, 2H). ESI MS [M+H]$^+$ for C$_{18}$H$_8$F$_7$N$_3$, calcd. 400.1, found 400.0.

Example 126: 1-[6-(1,1-Difluoroethyl)-5-fluoro-4-methylpyridin-3-yl]-4,4,6-trifluoro-2,3-dihydroquinoline-8-carbonitrile

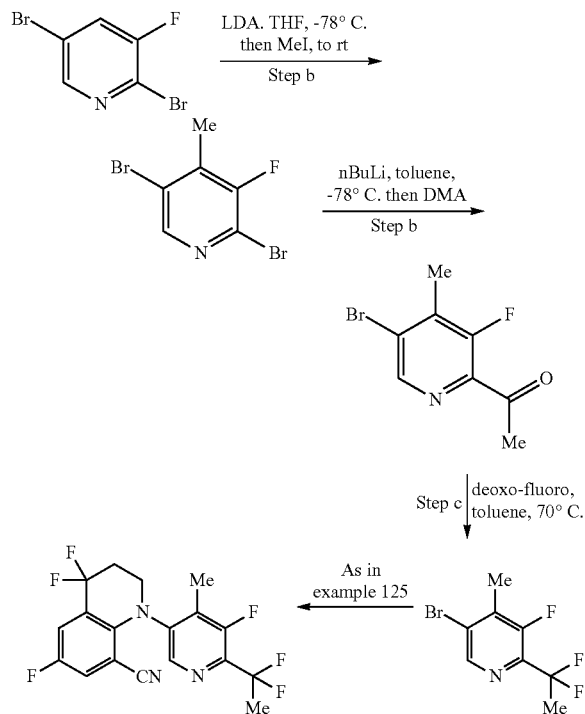

Step a: A flask containing 2,5-dibromo-3-fluoropyridine (6.00 g, 23.6 mmol, 1.0 mol. equiv.) in THF (100 mL) was cooled to −78° C. under N$_2$. A solution of LDA (2.0 M in heptane/THF/ethylbenzene, 17.7 mL, 1.5 mol. equiv.) was added slowly, and the resulting mixture stirred for 15 min. MeI (2.9 mL, 2.0 mol. equiv.) was added and the reaction mixture was allowed to warm to room temperature and stirred for 30 min. The reaction was cooled to 0° C. and quenched with sat. aq. NH$_4$Cl solution and diluted with EtOAc. The aqueous layer was separated and back extracted with additional EtOAc. The organic layers were combined and dried over MgSO$_4$. Concentration under reduced pressure and purification by flash column chromatography (SiO$_2$, hexanes to 15% EtOAc) furnished the methylated product as a yellow oil (3.64 g, 57%).

Step b: A flask containing the product from the previous step (3.00 g, 11.2 mmol, 1.0 mol. equiv.) in dry toluene (30 mL) was cooled to −78° C. under N$_2$. nBuLi (2.5 M in hexanes, 5.4 mL, 1.2 mol. equiv.) was added, and the reaction stirred for 30 min. After this time, the organolithium was trapped with anhydrous DMA (3.2 mL, 33.6 mmol, 2.0 mol. equiv.) and the reaction stirred for an additional 20 min. The reaction was quenched with sat. aq. NH$_4$Cl solution at −78° °C. After warming, the mixture was diluted with EtOAc. The aqueous layer was separated and back extracted with additional EtOAc. The organic layers were combined and dried over MgSO$_4$. Concentration under reduced pressure and purification by flash column chromatography (SiO$_2$, hexanes to 30% EtOAc) furnished the ketone product (906 mg, 35%).

Step c: To the ketone product from the previous step (400 mg, 1.72 mmol, 1.0 mol. equiv.) was added Deoxo-Fluor (2.7 M in toluene, 3.0 mL, 4.0 mol. equiv.) and the resulting mixture was stirred at 70° °C. for 9 h. The reaction mixture was poured onto ice, quenched with sat. aq. NaHCO$_3$ solution and diluted with EtOAc. The aqueous layer was separated and back extracted with additional EtOAc. The organic layers were combined and dried over MgSO$_4$. Concentration under reduced pressure and purification by flash column chromatography (SiO$_2$, hexanes to 20% EtOAc) furnished the difluorinated product as a yellow oil (342 mg, 78%). ESI MS [M+H]$^+$ for C$_8$H$_7$BrF$_3$N, calcd 253.9, found 253.8.

The title compound 1-[6-(1,1-difluoroethyl)-5-fluoro-4-methylpyridin-3-yl]-4,4,6-trifluoro-2,3-dihydroquinoline-8-carbonitrile was prepared in 4 additional steps from 5-bromo-2-(1,1-difluoroethyl)-3-fluoro-4-methylpyridine, in a similar fashion to Example 125. $^1$H NMR (400 MHZ, Chloroform-d) δ 7.96 (d, J=0.6 Hz, 1H), 7.67-7.62 (m, 1H), 7.31-7.27 (m, 1H), 3.90-3.79 (m, 1H), 3.55-3.46 (m, 1H), 2.59-2.40 (m, 2H), 2.38 (d, J=2.3 Hz, 3H), 2.05 (td, J=18.8, 0.7 Hz, 3H). ESI MS [M+H]$^+$ for C$_{18}$H$_{13}$F$_6$N$_3$, calcd 386.1, found 386.0.

Example 127: 1-[4-Chloro-5-fluoro-6-(trifluoromethyl)pyridin-3-yl]-4,4,6-trifluoro-2,3-dihydroquinoline-8-carbonitrile

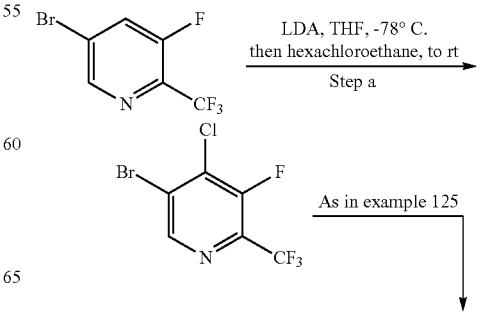

-continued

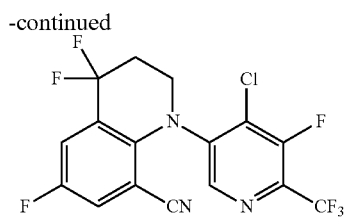

Step a: A flask containing 5-bromo-3-fluoro-2-(trifluoromethyl)pyridine (1.00 g, 4.09 mmol, 1.0 mol. equiv.) in THF (10 mL) was cooled to −78° C. under $N_2$. A solution of LDA (2.0 M in heptane/THF/ethylbenzene, 17.7 mL, 1.5 mol. equiv.) was added slowly, and the resulting mixture stirred for 15 min. A solution of hexachloroethane (1.93 g, 8.18 mmol, 2.0 mol. equiv.) in THF (3 mL) was added and the reaction mixture was warmed to room temperature and stirred for 15 min. The reaction was cooled to 0° C. and quenched with sat. aq. $NH_4Cl$ solution and diluted with EtOAc. The aqueous layer was separated and back extracted with additional EtOAc. The organic layers were combined and dried over $MgSO_4$. Concentration under reduced pressure and purification by flash column chromatography ($SiO_2$, hexanes to 15% EtOAc) furnished the chlorinated product as a yellow oil (824 mg, 72%).

The title compound 1-[4-chloro-5-fluoro-6-(trifluoromethyl)pyridin-3-yl]-4,4,6-trifluoro-2,3-dihydroquinoline-8-carbonitrile was prepared in 4 additional steps from 5-bromo-4-chloro-3-fluoro-2-(trifluoromethyl)pyridine, in a similar fashion to Example 125. $^1$H NMR (400 MHz, Chloroform-d) δ 8.18 (s, 1H), 7.69 (ddt, J=7.7, 3.0, 0.8 Hz, 1H), 7.34 (ddt, J=7.2, 3.1, 0.9 Hz, 1H), 4.07-3.90 (m, 1H), 3.83-3.70 (m, 1H), 2.63-2.41 (m, 2H). ESI MS [M+H]$^+$ for $C_{16}H_7F_7N_3$, calcd 410.0, found 409.9.

Example 128: 4,4,6-Trifluoro-1-[5-fluoro-4-methyl-6-(trifluoromethyl)pyridin-3-yl]-2,3-dihydroquinoline-8-carbonitrile equiv.) was added slowly, and the resulting mixture stirred for 15 min. MeI (0.55 mL, 2.0 mol. equiv.) was added and the reaction mixture was warmed to room temperature and stirred for 30 min. The reaction was cooled to 0° C. and quenched with sat. aq. $NH_4Cl$ solution and diluted with EtOAc. The aqueous layer was separated and back extracted with additional EtOAc. The organic layers were combined and dried over $MgSO_4$. Concentration under reduced pressure and purification by flash column chromatography ($SiO_2$, hexanes to 15% EtOAc) furnished the methylated product as a yellow oil (970 mg, 92%).

Step b: A vial was charged with the pyridine bromide from the previous step (350 mg, 1.36 mmol, 1.3 mol. equiv.), 4-[tert-butyl(dimethyl)silyl]oxy-6-fluoro-1,2,3,4-tetrahydroquinoline-8-carbonitrile (320 mg, 1.04 mmol, 1.0 mol. equiv.), $Pd(OAc)_2$ (46 mg, 0.20 mmol, 20 mol %), Xantphos (150 mg, 0.26 mmol, 25 mol %), $Cs_2CO_3$ (468 mg, 2.08 mmol, 2.0 mol. equiv.) and toluene (3.5 mL). $N_2$ was bubbled through the reaction mixture for 3 min, the vial capped, and heated at 100° ° C. for 24 h. The reaction was monitored by TLC and NMR analysis. The reaction was cooled, filtered, and concentrated onto Celite. Purification by flash column chromatography ($SiO_2$, hexanes to 20% EtOAc) furnished the coupled product as a yellow solid (240 mg, 47%).

Step c: A vial was charged with the product from step b (90 mg, 0.186 mmol, 1.0 mol. equiv.) and NMP (1.0 mL). KCN (18 mg, 0.28 mmol, 1.5 mol. equiv.) was added and the reaction was stirred at 110° C. An additional portion of KCN (18 mg, 0.28 mmol, 1.5 mol. equiv.) was added after 40 min and the reaction was continued for 15 h at 110° C. During this time the TBS group was also cleaved. The reaction was cooled and diluted with sat. aq. $NaHCO_3$ solution and EtOAc. The aqueous layer was separated and back extracted with additional EtOAc. The organic layers were combined and dried over $MgSO_4$. Concentration under reduced pressure and purification by flash column chromatography ($SiO_2$, hexanes to 60% EtOAc) furnished the benzonitrile

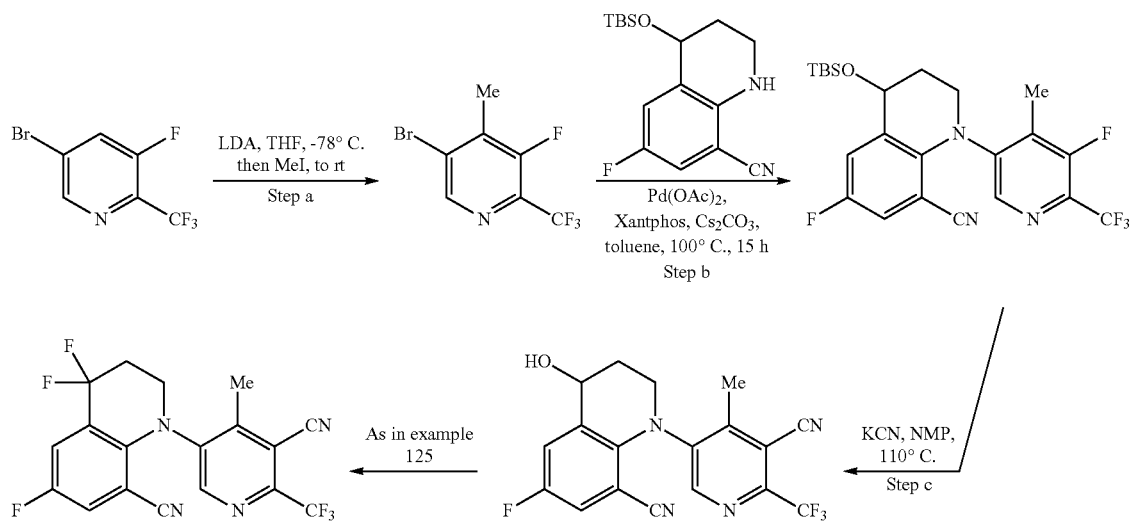

Step a: A flask containing 5-bromo-3-fluoro-2-(trifluoromethyl)pyridine (1.00 g, 4.10 mmol, 1.0 mol. equiv.) in THF (10 mL) was cooled to −78° C. under $N_2$. A solution of LDA (2.0 M in heptane/THF/ethylbenzene, 3.0 mL, 1.5 mol.

alcohol (18 mg, 0.048 mmol, 26%). ESI MS [M+H]$^+$ for $C_{18}H_{12}F_4NO$, calcd 377.1, found 377.0.

The title compound 1-[5-cyano-4-methyl-6-(trifluoromethyl)pyridin-3-yl]-4,4,6-trifluoro-2,3-dihydroquinoline-8- carbonitrile was prepared in 2 additional steps in a similar fashion to Examples 124 and 125. ¹H NMR (400 MHZ, Chloroform-d) δ 8.33 (s, 1H), 7.72-7.67 (m, 1H), 7.36-7.31 (m, 1H), 3.97-3.86 (m, 1H), 3.55-3.46 (m, 1H), 2.71 (s, 3H), 2.56-2.44 (m, 2H). ESI MS [M+H]⁺ for C₁₈H₁₀F₆N₄, calcd 397.1, found 397.0.

Example 129: 4,4,6-Trifluoro-1-[5-fluoro-4-methyl-6-(trifluoromethyl)pyridin-3-yl]-2,3-dihydroquinoline-8-carbonitrile

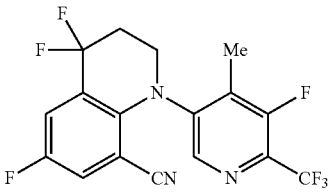 [SMILES: Cc1c(N2CCC(F)(F)c3cc(F)cc(C#N)c32)cnc(C(F)(F)F)c1F]

The title compound 4,4,6-trifluoro-1-[5-fluoro-4-methyl-6-(trifluoromethyl)pyridin-3-yl]-2,3-dihydroquinoline-8-carbonitrile was prepared in 3 additional steps in a similar fashion to Example 125. ¹H NMR (400 MHZ, DMSO-d₆) δ 8.40 (s, 1H), 7.96-7.90 (m, 1H), 7.87 (dd, J=8.0, 2.9 Hz, 1H), 3.95-3.80 (m, 1H), 3.78-3.65 (m, 1H), 2.70-2.52 (m, 2H), 2.33 (d, J=2.1 Hz, 3H). ESI MS [M+H]⁺ for C₁₇H₁₀F₇N₃, calcd 390.0, found 390.0.

Example 130: (3S,4R)-1-[2-Cyano-3-fluoro-4-(trifluoromethyl)phenyl]-3,4,6-trifluoro-1,2,3,4-tetrahydroquinoline-8-carbonitrile Amberlyst 15 (0.5 g, 150 wt %) was added. The reaction was stirred at 90° C. for 16 h. Upon completion, the polymeric beads were removed by filtration, and the concentrated crude material was purified by chromatography on silica gel (0 to 25% gradient EtOAc in Hexane) to give 1-[2-cyano-3-fluoro-4-(trifluoromethyl)phenyl]-3,6-difluoro-4-oxo-2,3-dihydroquinoline-8-carbonitrile as a yellow solid (1.28 g, 87% over two steps). ESI MS [M+H]⁺ for C₁₈H₈F₆N₃O₁, calcd 396.0, found 395.9.

Step b: The product from step a (250 mg, 0.63 mmol, 1.0 equiv.) was dissolved in CH₂Cl₂ (1.60 ml) and sparged with nitrogen gas before the addition of formic acid (70 μL, 1.90 mmol, 3.0 equiv.) and triethylamine (180 μl, 1.26 mmol, 2.0 equiv.) at 0° C. RuCl(p-cymene)[(S,S)-Ts-DPEN] (6 mg, 0.01 mmol, 1.5 mol %) was added, and the reaction was stirred for 16 hours at 5° C. Upon full conversion, the reaction was quenched with aqueous saturated NaHCO₃ solution and extracted with CH₂Cl₂. The combined organics were concentrated, and the crude material was purified by flash chromatography on silica gel (0 to 35% gradient EtOAc in Hexane) to give (3S,4R)-1-[2-cyano-3-fluoro-4-(trifluoromethyl)phenyl]-3,6-difluoro-4-hydroxy-3,4-dihydro-2H-quinoline-8-carbonitrile (160 mg, 64%) as a single diastereomer. ESI MS [M+H₂O]⁺ for C₁₈H₁₁F₆N₃O₂, calcd 415.0, found 415.0.

Step c: The product of step b (100 mg, 0.25 mmol, 1.0 equiv.) was dissolved in CH₂Cl₂ (2.5 mL) and the solution was cooled to −40° C. Diethylaminosulfur trifluoride (0.17 mL, 1.26 mmol, 5.0 equiv.) was added dropwise and the reaction mixture was slowly warmed to 0° C. over 2 h with stirring. The mixture was then diluted with CH₂Cl₂, poured into an aqueous saturated solution of NaHCO₃ and the layers were separated. The organic phase was washed with brine, dried over Na₂SO₄ and evaporated under reduced pressure.

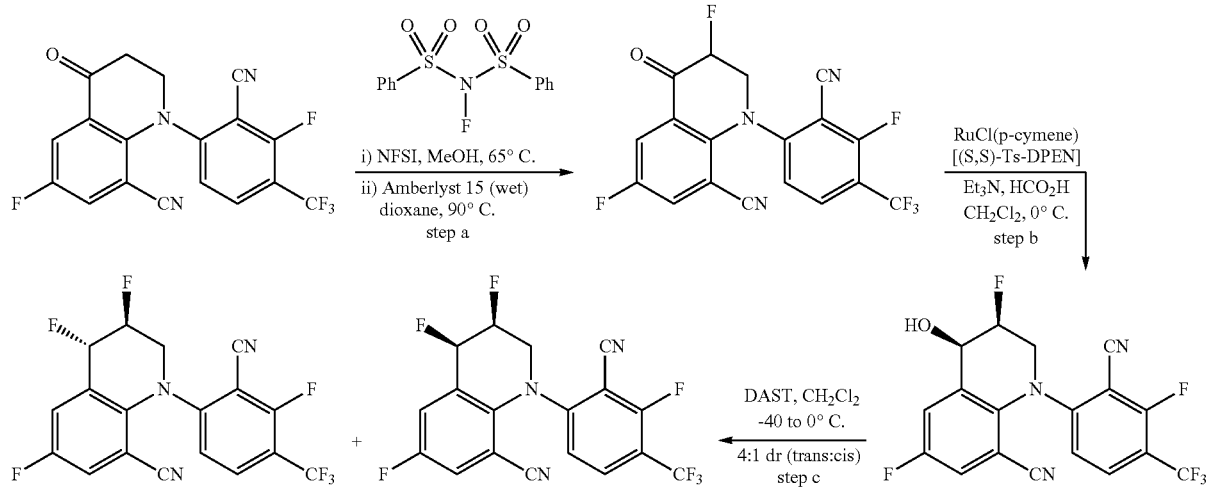

Step a: To a solution of 1-[2-cyano-3-fluoro-4-(trifluoromethyl)phenyl]-6-fluoro-4-oxo-2,3-dihydroquinoline-8-carbonitrile (1.20 g, 3.71 mmol, 1.0 equiv.) in MeOH (18 mL) was added N-fluorobenzenesulfonimide (1.29 g, 4.08 mmol, 1.1 equiv.). The reaction mixture was stirred at 65° C. for 16 h. The reaction was quenched with aqueous saturated NaHCO₃ solution and partitioned between EtOAc and water. The organic phase was washed with brine, dried over Na₂SO₄ and evaporated under reduced pressure. The resulting residue was dissolved in 1,4-dioxane (18 mL) and wet The resulting residue was purified by chromatography on silica gel (0 to 18% gradient EtOAc in Hexane) to give a mixture of diastereosiomer (4:1) with (3S,4S)-1-[2-cyano-3-fluoro-4-(trifluoromethyl)phenyl]-3,4,6-trifluoro-1,2,3,4-tetrahydroquinoline-8-carbonitrile (64 mg, 64%) and (3S,4R)-1-[2-cyano-3-fluoro-4-(trifluoromethyl)phenyl]-3,4,6-trifluoro-1,2,3,4-tetrahydroquinoline-8-carbonitrile (17 mg, 17%) as white solids (81% combined yields). Characterization reported for (3S,4R)-1-[2-cyano-3-fluoro-4-(trifluoromethyl)phenyl]-3,4,6-trifluoro-1,2,3,4-tetrahydroquinoline-8-carbonitrile. The enantiomeric excess of this material was 97% by chiral HPLC (Chiralpak AD-H, 15% iPrOH/hexanes, isocratic, 20 minutes), $R_T$ minor=7.18 min and $R_T$ major=7.70 min. $^1$H NMR (400 MHZ, DMSO-$d_6$) δ: 8.11-7.99 (m, 1H), 7.85 (dd, J=8.2, 3.0 Hz, 1H), 7.80-7.70 (m, 1H), 7.28 (d, J=9.0 Hz, 1H), 5.97 (dd, J=47.5, 3.0 Hz, 1H), 5.52 (d, J=51.5 Hz, 1H), 4.43-4.05 (m, 2H). $^{19}$F NMR (376 MHZ, DMSO-$d_6$) δ: −59.6 (3F), −108.7 (q, J=11.8, 11.2 Hz, 1F), −116.4 (t, J=8.6 Hz, 1F), −198.7 (m, 1F), −201.9 (m, 1F). ESI MS [M+H$_2$O]$^+$ for $C_{18}H_{10}F_7N_3O_1$, calcd 417.0, found 416.9.

Example 131: 1-[2-Cyano-3-fluoro-4-(trifluoromethyl)phenyl]-6-fluoro-4-methoxy-3,4-dihydro-2H-quinoline-8-carbonitrile

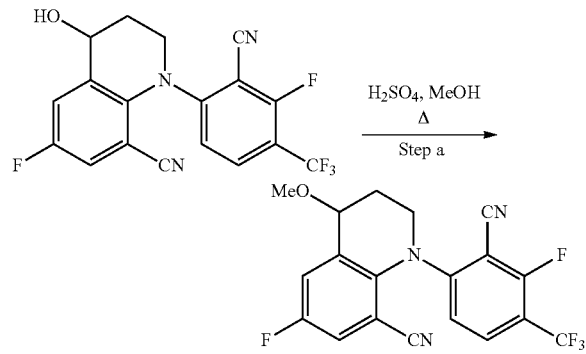

Step a: To a solution of 1-[2-cyano-3-fluoro-4-(trifluoromethyl)phenyl]-6-fluoro-4-hydroxy-3,4-dihydro-2H-quinoline-8-carbonitrile (80 mg, 0.21 mmol) in methanol (2.1 ml, 0.1M) was added concentrated sulfuric acid (120 μL) and the resulting solution was heated to reflux. Upon completion, the reaction solution was quenched with saturated NaHCO$_3$, extracted with ethyl acetate, and dried over Na$_2$SO$_4$. After concentration of the organics onto celite the resulting crude material was purified by flash chromatography (SiO$_2$) using a gradient of 0% to 100% dichloromethane in hexanes to yield 1-[2-cyano-3-fluoro-4-(trifluoromethyl)phenyl]-6-fluoro-4-methoxy-3,4-dihydro-2H-quinoline-8-carbonitrile. $^1$H NMR (400 MHZ, CDCl$_3$): δ 7.69 (dd, J=8.3, 8.3 Hz, 1H), 7.36 (d, J=8.0 Hz, 1H), 7.21 (dd, J=7.6, 3.0 Hz, 1H), 6.88 (d, J=8.8 Hz, 1H), 4.33 (s, 1H), 3.90 (br m, 2H), 4.36 (s, 3H), 2.18 (br m, 2H). ESI MS [M+H]$^+$ for $C_{19}H_{12}F_5N_3O$. calcd. 394.1, found 394.0.

Example 132: 1-[2-Cyano-4-(1,1-difluoroethyl)-3-fluorophenyl]-6-fluoro-4-methoxy-3,4-dihydro-2H-quinoline-8-carbonitrile

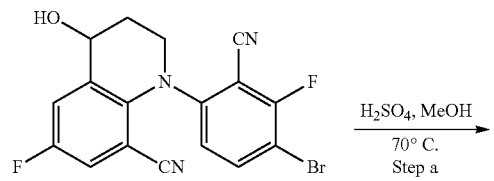

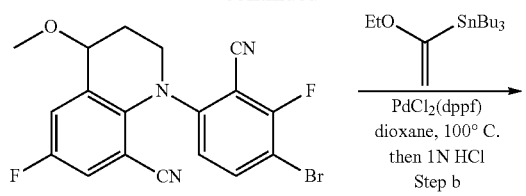

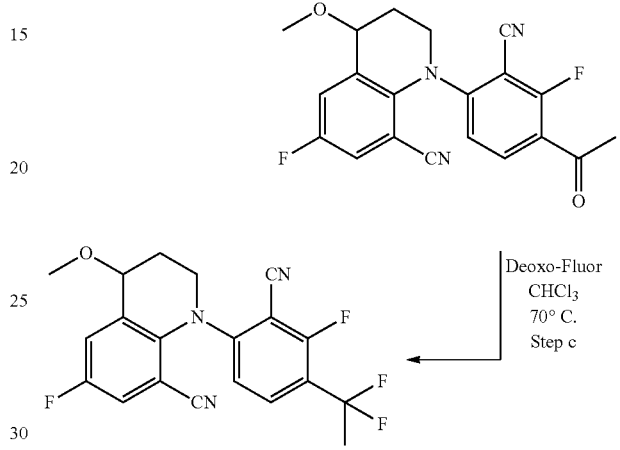

Step a: A solution of 1-(4-bromo-2-cyano-3-fluorophenyl)-6-fluoro-4-hydroxy-3,4-dihydro-2H-quinoline-8-carbonitrile (400 mg, 1.0 mmol) in MeOH (4 mL) and conc. H$_2$SO$_4$ (0.02 mL) was heated at 70° C. for 8 h. Then reaction was cooled to room temperature and quenched with sat. NaHCO$_3$ (20 mL), extracted with EtOAc (3×20 mL). Combined organics were washed with brine (20 mL), dried over MgSO$_4$, filtered and concentrated in vacuo. The residue was purified by column chromatography (silica gel, hex→40% EtOAc in hexanes) to afford the product (280 mg, 68%).

Step b: The mixture of the product from step a (280 mg, 0.69 mmol), Tributyl(1-ethoxyvinyl)tin (0.5 g, 1.39 mmol, 2.0 equiv.) and PdCl$_2$(dppf) (51 mg, 0.069 mmol, 10% mol) in 1,4-dioxane (7 mL) was stirred at 100° C. under N$_2$ for overnight. Then reaction was cooled to room temperature and diluted with 1N HCl (10 mL). Let it stir for 2 h. The mixture was quenched with water, extracted with EtOAc (3×20 mL). Combined organics were washed with brine (20 mL), dried over MgSO$_4$, filtered and concentrated in vacuo. The residue was purified by column chromatography (silica gel, hex→40% EtOAc in hexanes) to afford the product (0.26 g, quantitative yield).

Step c: A solution of the product from step b (130 mg, 0.35 mmol) and Deoxo-Fluor (50% wt in toluene) (1.25 g, 2.83 mmol, 8.0 equiv.) in CHCl$_3$ (1 mL) was heated at 70° C. for 12 h. Then reaction was cooled to room temperature and quenched with sat. NaHCO$_3$ (20 mL), extracted with EtOAc (3×20 mL). Combined organics were washed with brine (20 mL), dried over MgSO$_4$, filtered and concentrated in vacuo. The residue was purified by column chromatography (silica gel, hex→40% EtOAc in hexanes) to afford the product (28 mg, 20%).

$^1$H NMR (400 MHZ, DMSO-$d_6$) δ 7.77 (m, 1H), 7.73-7.57 (m, 2H), 7.06 (m, 1H), 4.42 (m, 1H), 3.85 (m, 1H), 3.70-3.56 (m, 1H), 3.35 (d, J=8.4 Hz, 3H), 2.20-1.79 (m, 5H). ESI MS [M+H]$^+$ for $C_{20}H_{15}F_4N_3O$, calcd 390.1, found 390.1.

Example 133: 1-[2-cyano-4-(1,1-difluoroethyl)-3-fluorophenyl]-4,4,6-trifluoro-1,2,3,4-tetrahydro-8-quinolinecarbonitrile

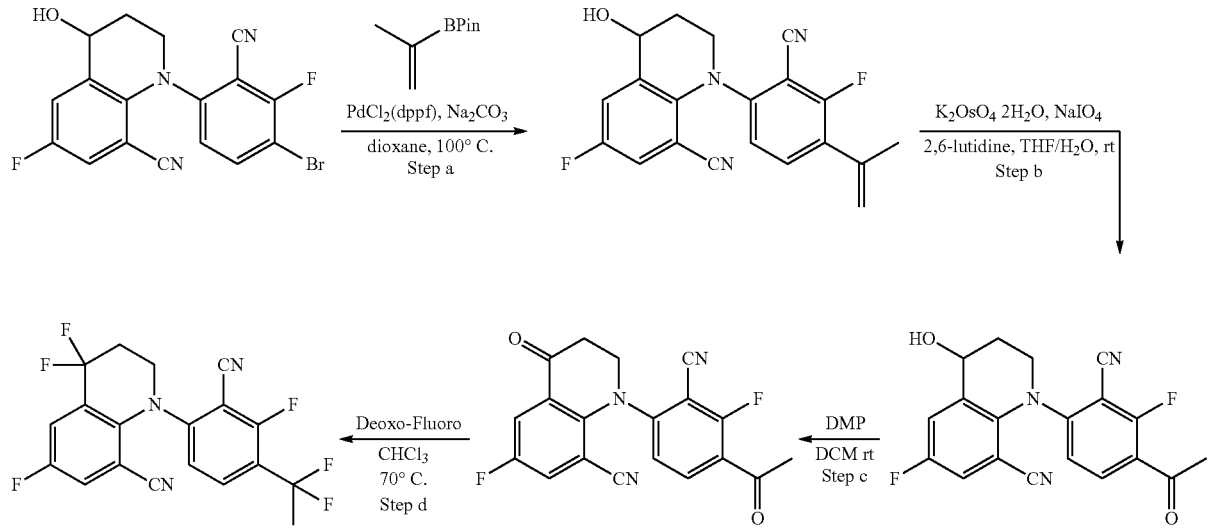

Step a: The mixture of 1-(4-bromo-2-cyano-3-fluorophenyl)-6-fluoro-4-hydroxy-3,4-dihydro-2H-quinoline-8-carbonitrile (500 mg, 1.28 mmol), isopropenylboronic acid pinacol ester (0.237 g, 1.41 mmol, 1.1 equiv.) and PdCl$_2$(dppf) (94 mg, 0.128 mmol, 10% mol) in 1,4-dioxane (6 mL) and 2.0M Na$_2$CO$_3$ (2 mL) was stirred at 90° C. under N$_2$ for overnight. Then reaction was quenched with water, extracted with EtOAc (3×50 mL). Combined organics were washed with brine (20 mL), dried over MgSO$_4$, filtered and concentrated in vacuo. The residue was purified by column chromatography (silica gel, hex→50% EtOAc in hexanes) to afford the product (0.50 g, quantitative yield).

Step b: The product from step a (0.5 g, 1.28 mmol) was dissolved in THF/H$_2$O (2:1; 6/3 mL). 2,6-lutidine (274 mg, 2.56 mmol, 2 equiv.) and NaIO$_4$ (1.64 g, 7.68 mmol, 6 equiv.) were added followed by K$_2$OsO$_4$ 2H$_2$O (24 mg, 0.06 mmol, 5% mol.). The reaction was stirred at room temperature for 15 h then diluted with 10% Na$_2$S$_2$O$_3$ solution (50 mL) and extracted with EtOAc (3×30 mL). Combined organics were dried over MgSO$_4$, filtered and concentrated in vacuo. The residue was purified by column chromatography (silica gel, hex→50% EtOAc in hexanes) to afford the product (390 mg, 87%).

Step c: The product from step b (0.39 g, 1.11 mmol) was dissolved in DCM (10 mL). Dess-Martin periodinane (705 mg, 1.65 mmol, 1.5 equiv.) was added. The reaction was stirred at room temperature for 0.5 h then diluted with 10% Na$_2$S$_2$O$_3$ solution (50 mL) and extracted with EtOAc (3×30 mL). Combined organics were dried over MgSO$_4$, filtered and concentrated in vacuo. The residue was purified by column chromatography (silica gel, hex→40% EtOAc in hexanes) to afford the product (240 mg, 62%).

Step d: A solution of the product from step c (120 mg, 0.34 mmol) and Deoxo-Fluor (50% wt in toluene) (2.42 g, 5.48 mmol, 16 equiv.) in CHCl$_3$ (1 mL) was heated at 70° C. for 12 h. Then reaction was cooled to room temperature and quenched with sat. NaHCO$_3$ (20 mL), extracted with EtOAc (3×20 mL). Combined organics were washed with brine (20 mL), dried over MgSO$_4$, filtered and concentrated in vacuo. The residue was purified by column chromatography (silica gel, hex→40% EtOAc in hexanes) to afford the product (25 mg, 20%). $^1$H NMR (400 MHZ, DMSO-d$_6$) δ 7.97 (d, J=8.2 Hz, 2H), 7.83 (t, J=8.7 Hz, 1H), 7.24 (d, J=8.6 Hz, 1H), 4.07-3.97 (m, 1H), 3.97-3.86 (m, 1H), 2.52 (m, 2H), 2.01 (t, J=19.2 Hz, 3H). ESI MS [M+H]$^+$ for C$_{19}$H$_{11}$F$_6$N$_3$, calcd 396.0, found 396.1.

Example 134: (5S,8R)-3,5-Difluoro-8-[(1S,2R)-2-fluoro-1-hydroxy-7-methylsulfonyl-2,3-dihydro-1H-inden-4-yl]-5,6,7,8-tetrahydronaphthalene-1-carbonitrile

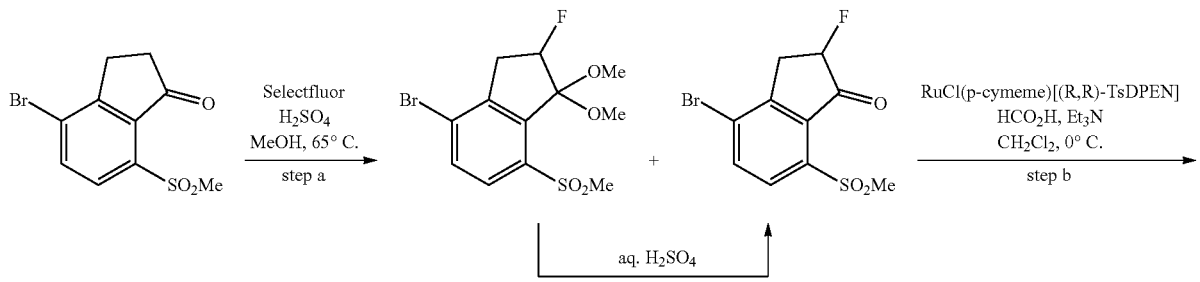

-continued

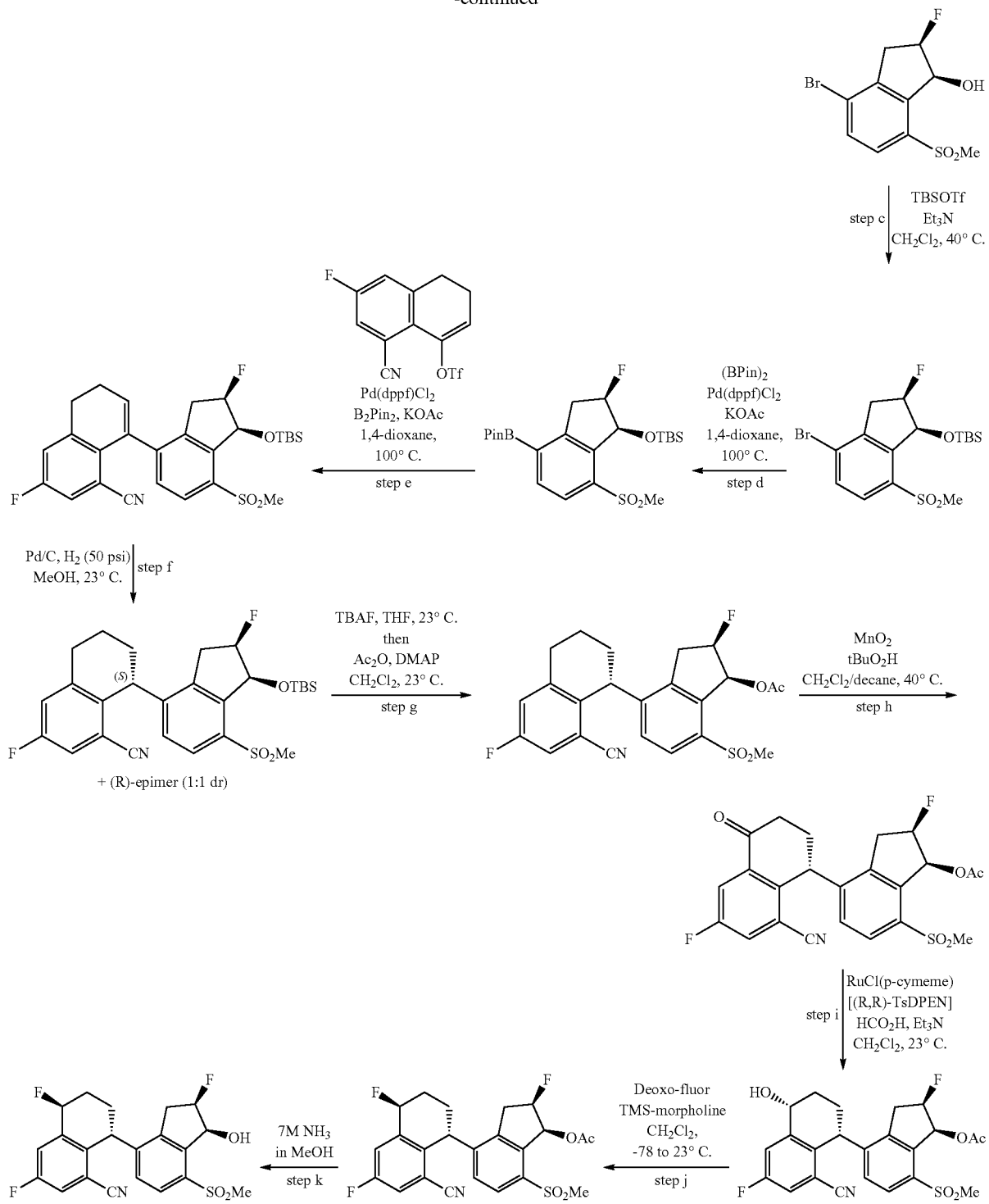

Step a: A solution of 4-bromo-7-methylsulfonyl-2,3-dihydroinden-1-one (25.0 g, 86.5 mmol) in 500 mL of dry methanol was loaded in 1 L single-neck round-bottom flask equipped with a stirring bar and a reflux condenser with a drying tube. SelectFluor (38.2 g, 104 mmol) and concentrated sulfuric acid (0.5 mL) were added sequentially, and the mixture was refluxed for 5 h. Once TLC analysis indicates complete disappearance of the starting material the reaction was cooled to ambient temperature. Aqueous sulfuric acid (0.3 M, 130 mL) was added, and the mixture was refluxed for 3 h to transform the corresponding dimethylacetal to the desired α-fluoroketone. The resulting clear solution was cooled to an ambient temperature and methanol was distilled off under reduced pressure. The residual mixture was diluted with dichloromethane (1 L) and water (500 mL). The organic phase was separated, and the aqueous solution was extracted with dichloromethane (2×100 mL). Combined organic extract was washed with brine (500 mL).

The organic phase was separated, dried over $Na_2SO_4$ and concentrated to dryness producing α-fluoroketone (25.9 g, 84.3 mmol, 97% yield) as a white solid.

Step b: The product from step a (25.9 g, 84.3 mmol) was placed in 1 L single-neck round-bottom flask equipped with a stirring bar. The flask was charged with dichloromethane (700 mL), formic acid (20.0 mL, 0.50 mol) and triethylamine (47.0 mL, 0.34 mol). The resulting solution was cooled to 0° ° C. and RuCl(p-cymene)[(R,R)-TsDPEN] (2.2 g, 3.4 mmol) was added. The resulting brownish solution was stirred at 0° C. for 16 h. Once TLC analysis shows complete conversion of the starting material the reaction was concentrated to about a half of its original volume under reduced pressure. The residual solution was sequentially washed with an aqueous 1M NaOH (400 mL) and brine (500 ml). The organic phase was separated, dried over $Na_2SO_4$ and concentrated to dryness to produce the crude product with sufficient purity for the next step.

Enantiopurity of this material (96% ee) was determined using HPLC-UV chromatography [Chiralpak® AD-H (4.6× 250 mm; 90% i-PrOH-hexanes; flow rate=1 mL/min; 10 μL injection of a 1 mg/mL solution; detection at 254 nm; $t_1$=4.89 min. (minor), $t_2$=5.26 min. (major)]

Step c: The crude material from the previous step was dissolved in dichloromethane (700 mL) and placed in 2 L three-neck round-bottom flask equipped with a thermometer, an addition funnel, a stirring bar and a reflux condenser with a drying tube. Triethylamine (105.0 mL, 0.81 mmol) was added to the mixture in one portion and the addition funnel was charged with TBSOTf (96.4 g, 0.37 mmol). Then TBSOTf was added dropwise causing an exothermic reaction with the rate required to maintain continuous reflux. Once the addition was complete the reaction mixture was reflux for additional 15 min upon which TLC analysis shows complete conversion of the starting material to the product. The solution was allowed to cool to ambient temperature, transferred into separatory funnel and sequentially washed with saturated aqueous $NH_4Cl$ (500 mL) and brine (500 mL). The organic phase was separated, dried over $Na_2SO_4$ and concentrated to dryness. The obtained crude product was purified by flash chromatography ($SiO_2$, hexanes/EtOAc gradient) to provide TBS ether as a white solid (26.5 g, 62.6 mmol, 74% yield over two steps).

Step d: The TBS ether product from the previous step (29.5 g, 70.0 mmol) was combined with $B_2Pin_2$ (23.0 g, 91.0 mmol, 1.3 equiv.), $Pd(dppf)Cl_2$ (5.1 g, 7.0 mmol, 0.1 equiv.) and potassium acetate (13.8 g, 0.14 mmol, 2.0 equiv.) in dioxane (230 ml) in 500 mL single-neck round-bottom flask equipped with a magnetic stirring bar and reflux condenser with nitrogen inlet adapter. The mixture was degassed under vacuum, backfilled with nitrogen and heated to 100° C. for 2 h. After $^1H$ NMR analysis of an aliquot indicated complete consumption of the starting material the reaction mixture was allowed to cool to ambient temperature and concentrated to dryness under reduced pressure. The residue was partitioned between EtOAc (500 mL) and water (300 mL). Organic layer was separated, and the aqueous phase was additionally extracted with EtOAc (2×100 mL). The combined organic extract was dried over $Na_2SO_4$ and the solvent was evaporated under reduced pressure to yield crude boronic pinacol ester that was used for the next step without further purification.

Step e: A solution of crude product from step d (70 mmol) and 8-cyano-6-fluoro-3,4-dihydronaphthalen-1-yl trifluoromethanesulfonate (22.5 g, 70.0 mmol) in dioxane (230 mL) was placed in 500 mL single-neck round-bottom flask equipped with a magnetic stirring bar and reflux condenser with nitrogen inlet. Then $Pd(dppf)Cl_2$ (5.1 g, 7.0 mmol) and aqueous sodium carbonate (2M solution, 70.0 ml, 40.0 mmol) were sequentially added. The mixture was degassed under vacuum, backfilled with nitrogen and heated to 100° C. for 1 h. Upon reaction completion, dioxane was removed under reduced pressure. The residue was partitioned between EtOAc (500 mL) and water (500 mL). Organic layer was separated, and the aqueous phase was additionally extracted with EtOAc (2×100 mL). The combined organic extract was washed with brine (500 mL), dried over $Na_2SO_4$ and concentrated to dryness. The crude product was purified by column chromatography ($SiO_2$, hexanes/EtOAc gradient) to yield the desired alkene (28.5 g, 55.3 mmol, 79% yield) as a white foam.

Step f: The alkene of step e (28.0 g, 54.0 mmol) was dissolved in dry methanol (540 mL) and added to palladium on carbon (5.0 g, 10% Pd by weight) under an atmosphere of nitrogen. The reaction mixture was placed under an atmosphere of hydrogen at 50 psi and agitated in a Parr shaker for 4 hours. The excess hydrogen was vented out and the mixture was sparged with nitrogen to remove residual hydrogen gas. The resulting suspension was filtered through a celite pad, and the filtrate was concentrated to dryness under reduced pressure producing crude mixture of epimers (1:1 dr). In order to isolate the more polar (S)-epimer the crude mixture was subjected to column chromatography ($SiO_2$, hexanes/EtOAc gradient) to produce the desired tetralin derivative (9.6 g, 18.5 mmol, 34% yield) as a white foam.

Step g: To a solution of the TBS ether from the step f in THF (93 mL) TBAF (37.2 mL, 37.2 mmol, 1 M solution in THF) was added dropwise at ambient temperature. The resulting brown solution was stirred for 20 min before TLC analysis indicated complete conversion of the starting material. The mixture was diluted with EtOAc (200 mL) and sequentially washed with water (200 mL) and brine (150 mL). The organic extract was dried over $Na_2SO_4$, concentrated to dryness and the crude product was submitted to acylation reaction without purification.

The dry material obtained in the previous transformation was dissolved in dichloromethane (50 mL), then DMAP (0.7 g, 5.8 mmol) and $Et_3N$ (8.0 mL, 77.0 mmol) were added. The reaction mixture was cooled to 0° ° C. and acetic anhydride (7.3 mL, 77.0 mmol) was added dropwise over 1 min period. The cooling bath was removed, and the reaction was stirred at room temperature for 30 min. Once TLC and LCMS analysis indicated complete transformation the solution was diluted with dichloromethane (150 mL) and sequentially washed with water (200 mL), saturated aqueous $NaHCO_3$ (100 mL) and brine (100 mL). The crude product was purified by column chromatography ($SiO_2$, hexanes/EtOAc gradient) to produce the desired acetate ester (8.3 g, 18.5 mmol, 100% yield) as a white powder.

Step h: The acetate ester (8.3 g, 18.6 mmol) from step g, $MnO_2$ (6.5 g, 75 mmol) and dichloromethane (93 mL) were loaded in 500 mL flask single-neck round-bottom flask equipped with a magnetic stirring bar and a reflux condenser. The mixture was cooled to 0° C. and $tBuO_2H$ (34 mL, 186 mmol, 5.5 M solution in decane) was added dropwise over 5 min. The reaction was stirred at 0° ° C. for 10 min, then it was allowed to warm to ambient temperature and stirred until gas formation ceased. The resulting black suspension was reflux for 24 h, then it was cooled to room temperature and additional amount of $MnO_2$ (6.5 g, 75 mmol) and $tBuO_2H$ (34 mL, 186 mmol, 5.5 M solution in decane) were added sequentially. The mixture was refluxed for additional 48 h, cooled to room temperature. Inorganic solids were removed by filtration. The filtrate was passed through a plug of celite, washed with water (100 mL), dried over Na$_2$SO$_4$ and concentrated to dryness. The crude product was purified by column chromatography (SiO$_2$, hexanes/EtOAc gradient) to produce the corresponding α-tetralone (6.2 g, 13.5 mmol, 72% yield) as a white powder.

Step i: A solution of α-tetralone (1.5 g, 3.3 mmol) from step h in dichloromethane (33 mL) was placed in 100 mL single-neck round bottom flask equipped with magnetic stirring bar and drying tube. The mixture was charged with formic acid (0.37 mL, 9.8 mmol), Et$_3$N (0.91 mL, 6.5 mmol) and RuCl(p-cymene)[(R,R)-Ts-DPEN] (62 mg, 0.1 mmol) at ambient temperature and stirred for 1 h. The resulting brown solution was diluted with dichloromethane (70 mL) and washed with aqueous saturated NaHCO$_3$. The organic extract was dried over Na$_2$SO$_4$ and concentrated to dryness under reduced pressure. The crude product was purified by column chromatography (SiO$_2$, dichloromethane/EtOAc gradient) to produce the corresponding 1,2,3,4-tetrahydro-1-naphthol (1.43 g, 3.1 mmol, 95% yield, single epimer) as white powder.

Step j: A solution of Deoxo-Fluor (3.4 ml, 9.1 mmol, 2.7 M in toluene) in dichloromethane (52 mL) was placed in 100 ml single-neck round bottom flask equipped with a magnetic stirring bar and nitrogen inlet and cooled to −78° C., then TMS-morpholine (1.65 mL, 9.2 mmol) was added dropwise. The reaction was stirred at −78° C. for 5 min, then the mixture was allowed to warm to room temperature and stirred for 2 h. The resulting transparent solution was cooled to −78° C. and solid 1,2,3,4-tetrahydro-1-naphthol (1.2 g, 2.6 mmol) from step i was added in one portion. The cooling bath was removed, and the reaction was stirred 30 min at room temperature. Once TLC analysis indicated complete consumption of the starting material the mixture was diluted with DCM (50 mL) and quenched with aqueous saturated NaHCO$_3$ (50 mL). The organic phase was separated, dried over Na$_2$SO$_4$ and concentrated to dryness. The dry residue was dissolved in 1,2-dimethoxyethane (60 mL) and AgClO$_4$·xH$_2$O (0.20 g) was added. The mixture was heated at 70° C. for 1 h, concentrated to dryness and the crude product was purified by column chromatography (SiO$_2$, dichloromethane/EtOAc gradient) followed by trituration with 30 mL of MTBE and filtration to yield the desired α-fluorotetralin (1.1 g, 2.4 mmol, 92% yield, single epimer) as a white solid.

Step k: α-Fluorotetralin from step j (1.1 g, 2.4 mmol) was suspended in 7M NH$_3$ solution in MeOH (90 mL) and the mixture was stirred at ambient temperature for 36 h. The resulting clear solution was concentrated to dryness under reduced pressure and the crude product was purified by column chromatography (SiO$_2$, dichloromethane/EtOAc gradient) followed by trituration with 30 mL of hexanes and filtration to yield the desired product (0.85 g, 2.0 mmol, 85% yield). $^1$H NMR (400 MHZ, CDCl$_3$) δ 7.69 (d, J=8.1 Hz, 1H), 7.51 (d, J=8.4, 1H), 7.39 (d, J=7.5 Hz, 1H), 6.43 (d, J=8.1 Hz, 1H), 5.69 (dt, J=13.5, 5.1 Hz, 1H), 5.65-5.33 (m, 2H), 4.67-4.60 (m, 1H), 3.58 (ddd, J=20.8, 16.8, 3.4 Hz, 1H), 3.44 (dd, J=5.7, 2.9 Hz, 1H), 3.28 (s, 3H), 3.28-3.10 (m, 1H), 2.56-2.38 (m, 1H), 2.24-2.04 (m, 1H), 2.02-1.79 (m, 1H), 1.76-1.65 (m, 1H). $^{19}$F NMR (376 MHz, CDCl$_3$) δ −110.92 (m), −157.06 (m), −199.18 (m). ESI MS [M+Na]$^+$ for C$_{21}$H$_{18}$F$_3$NO$_3$SNa, calcd 444.1, found 444.0).

Example 135: (8R)-3,5,5-Trifluoro-8-[(1S,2R)-2-fluoro-1-hydroxy-7-methylsulfonyl-2,3-dihydro-1H-inden-4-yl]-7,8-dihydro-6H-naphthalene-1-carbonitrile

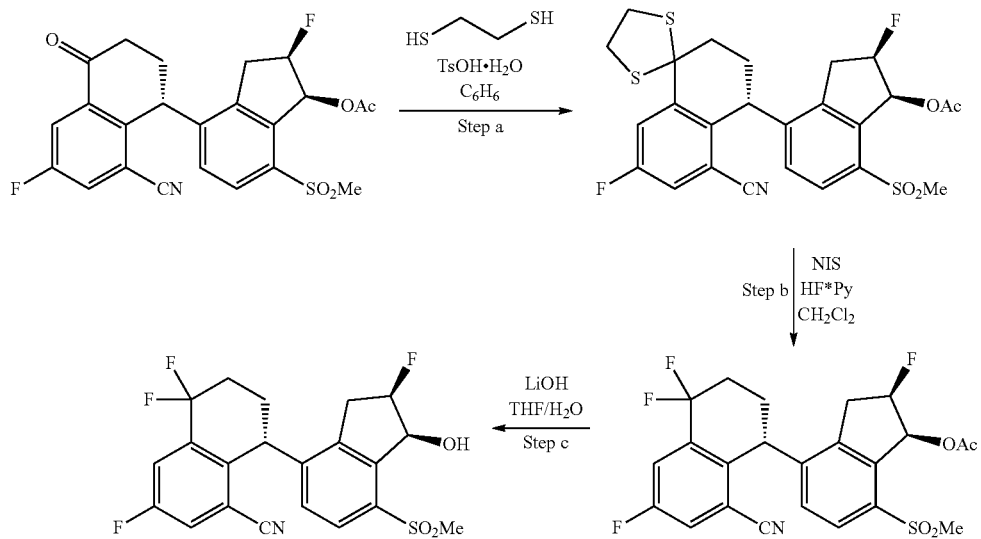

Step a: A mixture of [(1S,2R)-4-[(1R)-8-cyano-6-fluoro-4-oxo-2,3-dihydro-1H-naphthalen-1-yl]-2-fluoro-7-methylsulfonyl-2,3-dihydro-1H-inden-1-yl] acetate (145 mg, 0.31 mmol) prepared by the protocol from the Example 134, 1,2-ethanedithiol (0.38 mL, 4.6 mmol) and p-toluenesulfonic acid monohydrate (12.0 mg, 0.06 mmol) in benzene (25 mL) was placed in a single-neck round bottom flask equipped with Dean-Stark apparatus and a reflux condenser with nitrogen inlet adapter. The reaction was refluxed for 16 h, cooled to ambient temperature and washed with 1 M NaOH (25 mL). The organic phase was separated, dried over Na$_2$SO$_4$ and concentrated to dryness under reduced pressure. The crude product was purified by column chromatography (SiO$_2$, dichloromethane/EtOAc gradient) to produce the desired product (0.17 g, 0.31 mmol, 100% yield) as a colorless oil.

Step b: To a cooled to −78° C. suspension of N-iodosuccinimide (71.0 mg, 0.32 mmol) in dichloromethane (1 mL) HF·Py (0.19 mL, 0.80 mmol) was added. The resulting dark suspension was stirred for 5 min before a solution of 1,3-dithiolane from step a (85 mg, 0.16 mmol) in dichloromethane (1 mL) was added dropwise over 1 min. The reaction mixture was stirred at −78° C. for 20 min followed by additional 20 min at 0° C. Once TLC analysis indicated complete conversion of 1,3-dithiolane the reaction was diluted with dichloromethane (15 mL) and washed with a mixture of aqueous saturated $NaHCO_3$ and $Na_2S_2O_3$ (1:1, v/v). The organic phase was separated, dried over $Na_2SO_4$ and concentrated to dryness. The crude material was fractionated by column chromatography ($SiO_2$, dichloromethane/EtOAc gradient) to produce the desired product (33.0 mg, 0.07 mmol, 43% yield) as a white solid.

Step c: 1,1-Difluorotetraline from step b (33.0 mg, 0.07 mmol) was dissolved in THF (1 mL) and a solution of LiOH·$H_2O$ (8.5 mg, 0.2 mmol) in water (0.2 mL) was added at 0° C. The reaction was stirred at room temperature for 3 h and monitored by LCMS analysis. Once complete conversion was achieved the reaction was diluted with EtOAc (20 mL) and washed with 1M aqueous HCl (15 mL). The organic phase was separated, and the aqueous solution was additionally extracted with EtOAc (15 mL). The combined organic extract was washed with brine, dried over $Na_2SO_4$ and concentrated to dryness under reduced pressure. The crude product was purified by column chromatography ($SiO_2$, dichloromethane/EtOAc gradient) to produce the desired product (27.0 mg, 0.06 mmol, 90% yield) as a white solid. $^1H$ NMR (400 MHZ, $CDCl_3$) δ 7.84-7.65 (m, 2H), 7.51-7.38 (m, 1H), 6.56 (d, J=8.3 Hz, 1H), 5.68 (dt, J=13.5, 5.0 Hz, 1H), 5.51-5.32 (m, 1H), 4.64 (br. s, 1H), 3.68-3.42 (m, 2H), 3.27 (s, 3H), 3.23-3.03 (m, 1H), 2.62-2.38 (m, 1H), 2.38-2.08 (m, 2H), 1.95-1.85 (m, 1H). $^{19}F$ NMR (376 MHz, $CDCl_3$) δ −85.85 (d, J=5260.8 Hz), −109.12 (m), −199.20 (dtd, J=52.8, 22.4, 13.5 Hz). ESI MS [M+Na]$^+$ for $C_{21}H_{17}F_4NNaO_3S$, calcd 462.1, found 462.0).

Example 136: (5S,8R)-3,5-Difluoro-8-[(1S,2R)-2-fluoro-1-hydroxy-7-(trifluoromethylsulfonyl)-2,3-dihydro-1H-inden-4-yl]-5,6,7,8-tetrahydronaphthalene-1-carbonitrile

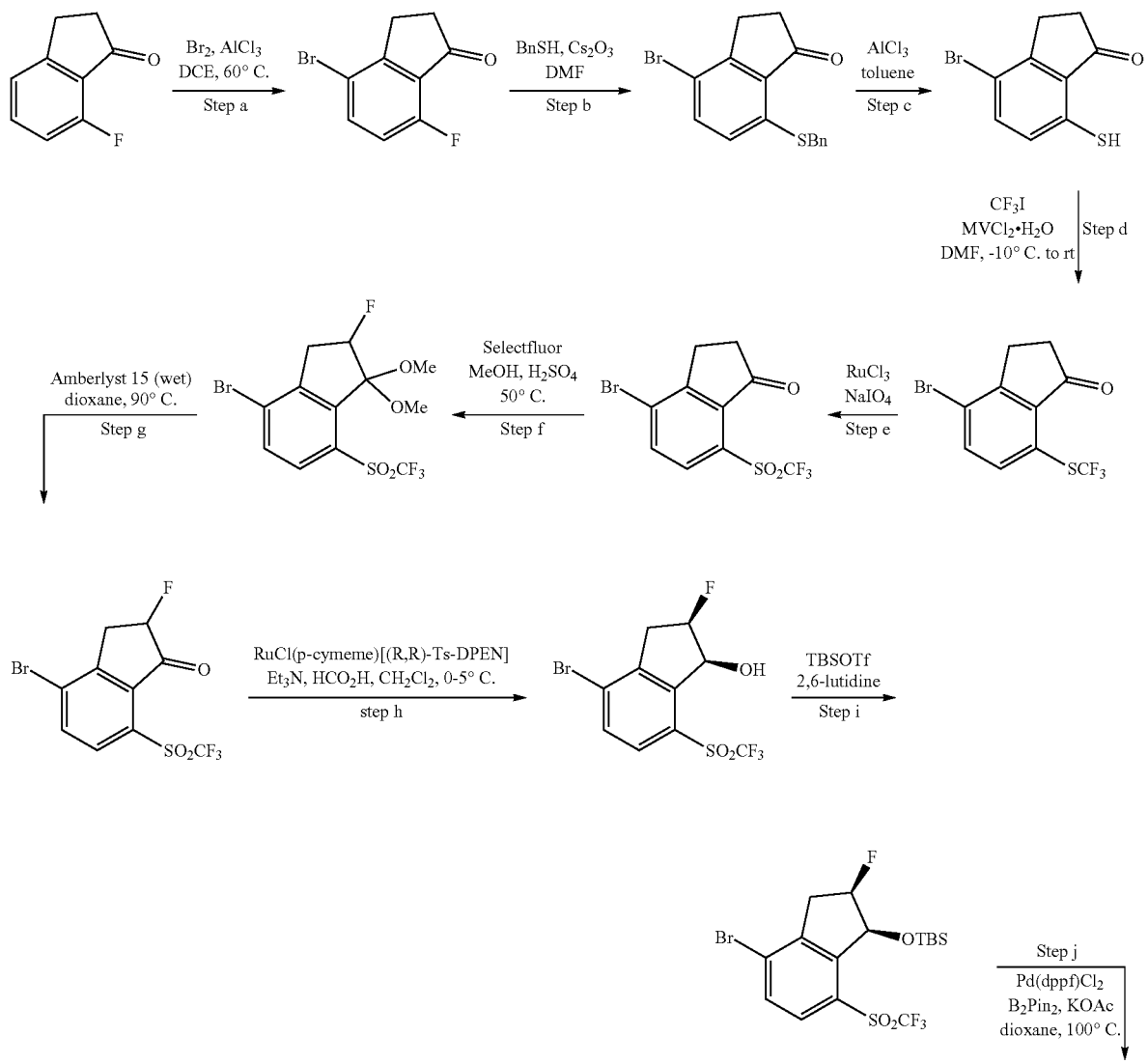

-continued

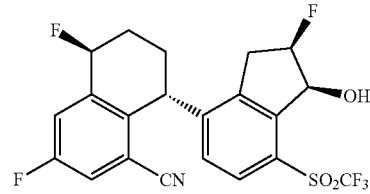 As in example 134 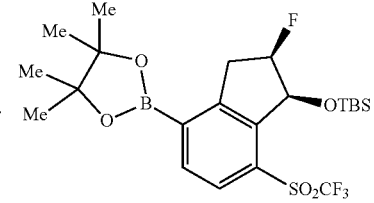

Step a: To a suspension of 7-fluoro-2,3-dihydro-1H-inden-1-one (10.0 g, 66.6 mmol) and aluminum trichloride (22.2 g, 166.5 mmol, 2.5 equiv.) in 1,2-dichloroethane (190 ml, 0.35M) was added bromine (3.58 ml, 70 mmol, 1.05 equiv.) dropwise. The resulting solution was heated to 60° C. for three hours, after which the reaction was cooled to room temperature and poured onto ice. The reaction was extracted with MTBE, dried over magnesium sulfate, and concentrated. The crude material was purified by flash chromatography (silica gel, 0% to 10% ethyl acetate in a 1:1 solution of $CH_2Cl_2$:hexanes) to yield 4-bromo-7-fluoro-2,3-dihydro-1H-inden-1-one.

Step b: To a suspension of 4-bromo-7-fluoro-2,3-dihydro-1H-inden-1-one (17.0 g, 74.3 mmol) and $Cs_2CO_3$ (26.6 g, 81.7 mmol, 1.1 equiv.) in DMF (372 ml, 0.2M) was added benzyl mercaptan (9.24 g, 8.71 ml, 1.0 equiv.). The reaction was stirred at room temperature for 90 minutes. The desired product was precipitated from solution through the addition of 1.5 L of water and was dried under high vacuum overnight. The resulting crude product (23.1 g, 93% yield) was taken on without further purification.

Step c: The crude thioether from the step b (23.1 g, 69.2 mmol) was suspended in toluene (692 ml, 0.1M). Aluminum trichloride (10.2 g, 1.1 equiv.) was added at room temperature. An additional portion of aluminum trichloride (3.6 g, 27 mmol, 0.4 equiv.) was added after three hours. Upon completion, the reaction was quenched with water, extracted with ethyl acetate, and concentrated. The crude material was purified by flash chromatography (silica gel, 0% to 20% ethyl acetate in a 1:3 solution of $CH_2Cl_2$ in hexanes) to yield the desired thiophenol as a yellow solid (13.4 g, 80% yield).

Step d: A solution of the thiophenol product from step c (6.7 g, 27.6 mmol) and methyl viologen dichloride hydrate (710 mg, 0.1 equiv.) in DMF (55 ml, 0.5M) was carefully degassed via three freeze-pump-thaw cycles under nitrogen. The resulting solution was cooled to −10 to −5° C. in a brine ice bath, and an excess of $CF_3I$ was sparged through the reaction mixture. The reaction was then stirred overnight under an atmosphere of $CF_3I$. The reaction was carefully quenched at room temperature with water (off-gassing of residual $CF_3I$ occurs, use caution), extracted with ethyl acetate, and concentrated. The crude material was purified by flash chromatography (silica gel, 0% to 20% ethyl acetate in hexanes) to yield the desired thioether (5.21 g, 61% yield).

Step e: To a solution of the product from step d (10.45 g, 33.6 mmol) in MeCN (129 ml, 0.26 M with respect to starting material), $CCl_4$ (129 ml, 0.26 M with respect to starting material), and $H_2O$ (258 ml, 0.13M with respect to starting material) was added ruthenium trichloride (697 mg, 3.36 mmol, 0.1 equiv.) followed by sodium periodate (29.6 g, 138.4 mmol, 4.12 equiv.). The reaction was stirred at room temperature for one hour, and upon completion was extracted with $CH_2Cl_2$ (×2). The combined organics were washed with saturated $Na_2S_2O_3$, washed with brine, and dried over sodium sulfate before concentrating. The crude material was purified by flash chromatography (silica gel, 0% to 10% ethyl acetate in a 1:3 solution of $CH_2Cl_2$ in hexanes) to yield the product sulfone as a white solid (10.53 g, 91% yield). ESI MS [M+H]$^+$ for $C_{10}H_6BrF_3O_3S$; calc 342.9, found 342.9.

Step f: A solution of the product sulfone from Step e (3.5 g, 10.2 mmol) and Selectfluor (4.32 g, 12.2 mmol, 1.2 equiv.) in methanol (102 ml, 0.1M) was heated to 50° C. Sulfuric acid (27 µl, 5 mol %) was added, and the reaction was stirred at 50° C. for 48 hours. The solution was then diluted with diethyl ether, and the resulting white precipitate was filtered off and discarded. The organic solution was concentrated, and the crude material was purified by flash chromatography (silica gel, 0% to 10% ethyl acetate in a 1:3 solution of $CH_2Cl_2$ in hexanes) to yield the product dimethyl acetal as a white solid (3.57 g, 87% yield).

Step g: A solution of the product acetal from Step f (3.18 g, 7.8 mmol) and wet Amberlyst 15 (4.77 g, 150 wt %) in dioxane (31 ml, 0.2 M) was heated to 90° C. overnight. Upon completion, the polymeric beads were removed by filtration, and the concentrated crude material was purified by flash chromatography (silica gel, 0% to 10% ethyl acetate in a 1:3 solution of $CH_2Cl_2$ in hexanes) to yield the desired fluorinated ketone (2.33 g, 83% yield).

Step h: A solution of the indanone product of Step g (2.5 g, 6.93 mmol) in dichloromethane (28 ml, 0.25M) was sparged with nitrogen gas before the addition of formic acid (783 µL, 956 mg, 20.8 mmol, 3 equiv.) and triethylamine (1.94 ml, 1.41 g, 13.9 mmol, 2 equiv.) at 0° C. under nitrogen. RuCl(p-cymene)[(R,R)-Ts-DPEN] (44.5 mg, 0.07 mmol, 0.01 equiv.) was added, and the reaction was stirred for a minimum of 12 hours at 0 to 5° C. Upon full conversion, the reaction was quenched with saturated $NaHCO_3$ and extracted with $CH_2Cl_2$. The combined organics were concentrated, and the crude material was purified by flash chromatography (silica gel, 0% to 20% ethyl acetate in a 1:1 solution of $CH_2Cl_2$:hexanes) to yield the desired indanol (2.0 g, 80% yield) as a single diastereomer. The enantiomeric excess of this material was found to be 98% by chiral HPLC (Chiralpak AD-H, 20% iPrOH/hexanes, isocratic, 20 minutes) as compared to a racemic sample, which was obtained through reduction of the 2-fluoroindanone with sodium borohydride.

Step i: To a solution of the chiral indanol from Step h (1.01 g, 2.75 mmol) in $CH_2Cl_2$ (11 ml, 0.25M) was added 2,6-lutidine (800 µL, 6.9 mmol, 2.5 equiv.) and TBSOTf (791 µL, 3.44 mmol, 1.25 equiv.) at 0° C. The reaction was allowed to warm to room temperature and was stirred overnight. Upon completion, the reaction was concentrated directly onto celite and purified by flash chromatography (silica gel, 0% to 10% ethyl acetate in hexanes) to yield the TBS ether (1.35 g, 100% yield).

Step j: The TBS ether product of Step i (674 mg, 1.41 mmol) was combined with $B_2Pin_2$ (457 mg, 1.8 mmol, 1.3 equiv.) Pd(dppf)Cl$_2$ (103 mg, 0.14 mmol, 0.1 equiv.) and potassium acetate (213 mg, 3 mmol, 2.2 equiv.) in dioxane (14 ml, 0.1M), and the resulting solution was heated to 100° ° C. for three hours. The reaction solution was concentrated, and the crude material was purified by flash chromatography (silica gel, 0% to 30% ethyl acetate in hexanes) to yield the desired boronic pinacol ester (638 mg, 86% yield) as a colorless oil.

The protocols for the following steps were identical to the Example 134. $^1$H NMR (400 MHz, CDCl$_3$) δ 7.75 (d, J=8.2 Hz, 1H), 7.52 (ddd, J=8.3, 2.8, 1.4 Hz, 1H), 7.40 (ddd, J=7.5, 2.7, 1.7 Hz, 1H), 6.60 (d, J=8.2 Hz, 1H), 5.73-5.50 (m, 2H), 5.46-5.23 (m, 1H), 4.74-4.60 (m, 1H), 3.79-3.51 (m, 1H), 3.36-3.20 (m, 1H), 3.02 (d, J=4.2 Hz, 1H), 2.61-2.43 (m, 1H), 2.22-2.09 (m, 1H), 1.97-1.86 (m, 1H), 1.81-1.73 (m, 1H). $^{19}$F NMR (376 MHz, CDCl$_3$) δ −77.43, −110.37 (d, J=1.6 Hz), −157.81 (d, J=45.0 Hz), −197.41--202.71 (m). ESI MS [M+Na]$^+$ for C$_{21}$H$_{15}$F$_6$NNaO$_3$S, calcd 498.1, found 498.0.

Example 137: (5S,8R)-8-[3-Chloro-2-cyano-4-(trifluoromethyl)phenyl]-3,5-difluoro-5,6,7,8-tetrahydronaphthalene-1-carbonitrile

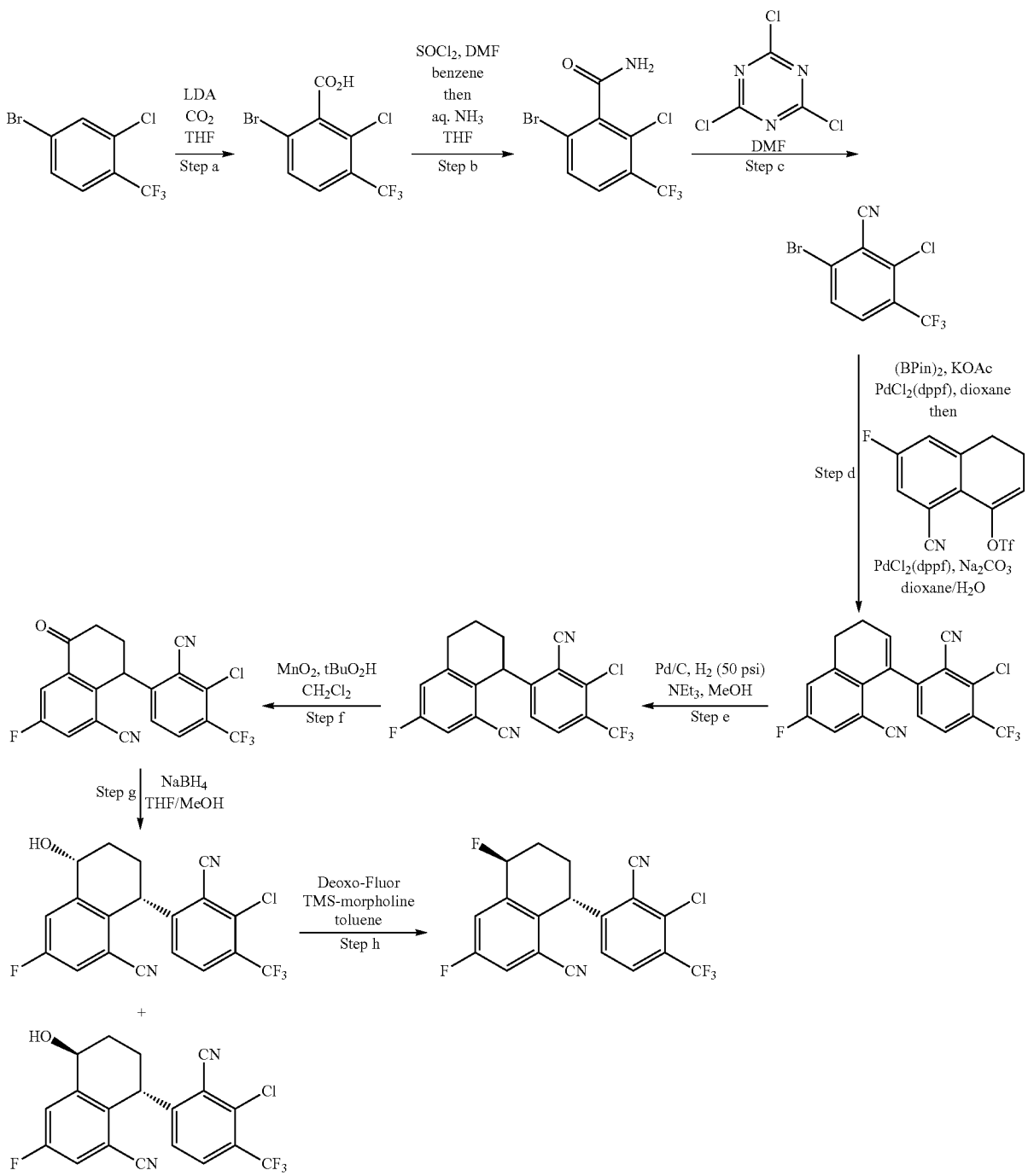

Step a: A solution of 4-bromo-2-chloro-1-(trifluoromethyl)benzene (15.0 g, 57.8 mmol) in tetrahydrofuran (600 mL) was placed in 1 L single-necked round bottom flask equipped with a nitrogen inlet adapter with rubber septum. The solution was cooled to −78° C. and LDA solution (43 ml, 87.0 mmol, 2 M solution in THF/heptane/ethylbenzene) was added via syringe dropwise over 10 min. The reaction mixture was stirred at −78° C. for 1 h before dry $CO_2$ gas was bubbled through the mixture for 30 min at −78° C. The cooling bath was replaced with ice/water mixture and $CO_2$ bubbling was continued for additional 30 min. The reaction mixture was carefully poured in aqueous 3 M HCl solution (700 mL) under vigorous stirring and the product was extracted with EtOAc (3×300 mL). Combined organic extract was washed with brine and dried over $Na_2SO_4$. The solvent was distilled off under reduced pressure, and the residue was partitioned between aqueous 3 M NaOH (400 mL) and MTBE (250 mL). The organic phase was separated, and the aqueous phase was additionally extracted with MTBE (200 mL). The separated aqueous solution was acidified with aqueous 3 M HCl to pH~3 and the product was extracted with dichloromethane (3×200 mL). The combined extract was dried over $Na_2SO_4$ and concentrated to dryness to yield the corresponding benzoic acid (17.5 g, 57.6 mmol, 99% yield) as an orange oil.

Step b: A mixture of the benzoic acid from step a (17.5 g, 57.6 mmol), thionyl chloride (12.6 mL, 173.0 mmol) and N,N-dimethylformamide (0.3 mL) in dry benzene (290 mL) was placed in 500 mL single-necked round bottom flask equipped with a reflux condenser with drying tube. The reaction was refluxed for 6 h, then cooled to ambient temperature, and the excess of thionyl chloride and benzene were distilled off under reduced pressure. The oil residue was dissolved in THF (150 mL) and added dropwise over 30 min to a cooled to 0° C. aqueous 30% ammonium hydroxide (150 mL). Once the addition was complete the reaction was vigorously stirred for 20 min. The product was extracted with dichloromethane (3×200 mL). The combined extract was dried over $Na_2SO_4$ and concentrated to dryness under reduced pressure. The oily residue was triturated with hexanes (200 mL) and the formed grey precipitate was collected by filtration to yield the corresponding benzamide (15.0 g, 49.7 mmol, 86% yield) as a grey solid.

Step c: A mixture of benzamide from step b (30.1 g, 99.5 mmol) and cyanuric chloride (25.6 g, 139.4 mmol) in N,N-dimethylformamide (170 mL) was heated at 70° C. for 2 h. Then the mixture was cooled to room temperature and poured into 500 mL of water. The product was extracted with EtOAc (3×200 mL). The combined organic extract was washed with water (2×300 mL) and brine (300 mL), dried over $Na_2SO_4$ and concentrated to dryness under reduced pressure. The resulting residue was fractionated by flash chromatography (silica gel, 0% to 25% ethyl acetate in hexanes) to yield the desired benzonitrile (15.1 g, 53.0 mmol, 53% yield) as a white crystalline solid.

Step d: The benzonitrile from step c (0.5 g, 1.8 mmol) was combined with $B_2Pin_2$ (0.58 g, 2.3 mmol, 1.3 equiv.), Pd(dppf)$Cl_2$ (0.13 g, 0.18 mmol, 0.1 equiv.) and potassium acetate (0.35 g, 3.5 mmol, 2.0 equiv.) in dioxane (9 ml, 0.2 M) in 40 mL vial with a magnetic stirring bar. The mixture was degassed under vacuum, backfilled with nitrogen and heated to 90° C. for 1 h. After TLC analysis indicated complete consumption of the starting material the reaction mixture was allowed to cool to ambient temperature and concentrated to dryness under reduced pressure. The residue was partitioned between EtOAc (30 mL) and water (20 mL). Organic layer was separated, and the aqueous phase was additionally extracted with EtOAc (2×15 mL). The combined organic extracts were dried over $Na_2SO_4$ and the solvent was evaporated under reduced pressure to yield the crude boronic pinacol ester that was used without further purification.

8-Cyano-6-fluoro-3,4-dihydronaphthalen-1-yl trifluoromethanesulfonate (0.57 g, 1.8 mmol) was added to the crude boronic pinacol ester along with dioxane (9 mL, 0.2 M) and the mixture was loaded into 40 ml vial. Then Pd(dppf)$Cl_2$ (0.13 g, 0.18 mmol) and aqueous 2 M sodium carbonate solution (1.8 ml, 3.6 mmol) were sequentially added. The mixture was degassed under vacuum, backfilled with nitrogen and heated to 100° C. for 1 h. Upon completion, dioxane was removed under reduced pressure. The residue was partitioned between EtOAc (30 mL) and water (20 mL). Organic layer was separated, and the aqueous phase was additionally extracted with EtOAc (2×15 mL). The combined organic extracts were washed with brine (30 mL), dried over $Na_2SO_4$ and concentrated to dryness. The crude product was purified by column chromatography ($SiO_2$, hexanes/EtOAc gradient) to yield the desired alkene (0.27 g, 0.7 mmol, 41% yield) as a brownish solid.

Step e: The alkene of step d (0.27 g, 0.7 mmol) was dissolved in dry methanol (10 mL) and triethylamine (0.5 mL, 3.6 mmol), then palladium on carbon (80.0 mg, 10% Pd by weight) was added under an atmosphere of nitrogen. The reaction mixture was placed under an atmosphere of hydrogen at 50 psi and agitated in a Parr shaker for 1 hour. The excess hydrogen was vented out and the mixture was sparged with nitrogen to remove residual hydrogen gas. The resulting suspension was filtered through a celite pad, and the filtrate was concentrated to dryness under reduced pressure producing crude mixture of the desired product and the corresponding dechlorinated compounds. In order to isolate the desired product, the crude mixture was subjected to column chromatography ($SiO_2$, hexanes/EtOAc gradient) to produce the tetralin derivative (0.1 g, 0.26 mmol, 37% yield) as a white solid.

Step f: The tetraline derivative from step e (0.3 g, 0.8 mmol), $MnO_2$ (0.28 g, 3.2 mmol) and dichloromethane (4 mL, 0.2 M) were loaded in 40 mL vial equipped with a magnetic stirring bar. The mixture was cooled to 0° C. and tBuO$_2$H (1.5 mL, 8 mmol, 5.5 M solution in decane) was added dropwise over 5 min. The reaction was stirred at 0° C. for 10 min, then it was allowed to warm to ambient temperature and stirred until gas formation ceased. The vial was sealed and the resulting black suspension was maintained at 40° C. for 24 h, then it was cooled to room temperature and additional amount of $MnO_2$ (0.28 g, 3.2 mmol) and tBuO$_2$H (1.5 mL, 8 mmol, 5.5 M solution in decane) were added sequentially. The mixture was refluxed for additional 48 h and cooled to room temperature. Inorganic solids were removed by filtration. The filtrate was diluted with dichloromethane (30 mL) passed through a plug of celite, washed with water (20 mL), dried over $Na_2SO_4$ and concentrated to dryness. The crude product was purified by column chromatography ($SiO_2$, hexanes/EtOAc gradient) to produce corresponding α-tetralone (0.14 g, 0.36 mmol, 45% yield) as a white solid.

Step g: To a cooled to 0° ° C. solution of α-tetralone from step f (70.0 mg, 0.18 mmol) in MeOH (2 mL) and THF (3 mL) mixture NaBH$_4$ (14.0 mg, 0.36 mmol) was added in one portion. The reaction was stirred for 10 min and poured in aqueous 1M HCl (10 mL). The crude product was extracted with EtOAc (3×30 mL). The combined organic extract was washed with brine, dried over $Na_2SO_4$ and concentrated to dryness to produce a mixture of racemic cis and trans diastereomers. In order to separate diastereomers the crude mixture was fractionated by column chromatography (SiO$_2$, hexanes/EtOAc gradient) to yield major cis diastereomer (52.0 mg, 0.13 mmol, 74% yield, less polar product) along with minor trans diastereomer (8.0 mg, 0.02 mmol, 11% yield, more polar product). Both compounds were obtained in a form of a white solid.

Step f: A solution of Deoxo-Fluor (0.17 ml, 0.45 mmol, 2.7 M in toluene) in toluene (2.6 mL) was cooled to 0° C. under nitrogen, then TMS-morpholine (81 μL, 0.46 mmol) was added. The reaction was stirred at 0° C. for 5 min, then it was allowed to warm to room temperature and stirred for 2 h. The resulting solution was cooled to 0° C. and solid 1,2,3,4-tetrahydro-1-naphthol (51.0 mg, 0.13 mmol) from step e was added in one portion. The cooling bath was removed, and the reaction was stirred 30 min at room temperature. Once TLC analysis indicated complete consumption of the starting material the mixture was diluted with EtOAc (20 mL) and quenched with aqueous saturated NaHCO$_3$ (10 mL). The organic phase was separated, dried over Na$_2$SO$_4$ and concentrated to dryness. The dry residue was purified by column chromatography (SiO$_2$, dichloromethane/EtOAc gradient) to yield the title compound (44.0 mg, 0.11 mmol, 86% yield, single epimer) as a white foam. $^1$H NMR (400 MHZ, CDCl$_3$) δ 7.70 (d, J=8.3 Hz, 1H), 7.54 (dd, J=8.5, 2.7 Hz, 1H), 7.41 (ddd, J=7.5, 2.7, 1.6 Hz, 1H), 6.54 (d, J=8.3 Hz, 1H), 5.58 (dt, J=49.9, 4.0 Hz, 1H), 4.95 (s, 1H), 2.75-2.50 (m, 1H), 2.26-2.10 (m, 1H), 2.07-1.78 (m, 2H). $^{19}$F NMR (376 MHz, CDCl$_3$) δ −63.06, −109.85, −159.45. ESI MS [M+Na]$^+$ for C$_{19}$H$_{10}$ClF$_5$N$_2$Na, calcd 419.0, found 419.2).

Example 138: (5R,8R)-8-[3-chloro-2-cyano-4-(trifluoromethyl)phenyl]-3,5-difluoro-5,6,7,8-tetrahydronaphthalene-1-carbonitrile

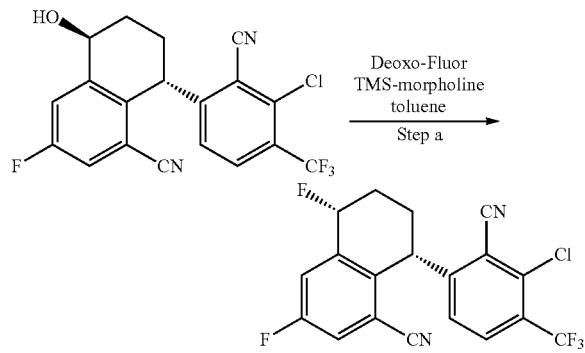

Step a: A solution of Deoxo-Fluor (26.0 μl, 0.07 mmol, 2.7 M in toluene) in toluene (0.25 mL) was cooled to 0° C. under nitrogen, then TMS-morpholine (13.0 μL, 0.072 mmol) was added. The reaction was stirred at 0° C. for 5 min, then it was allowed to warm to room temperature and stirred for 2 h. The resulting solution was cooled back to 0° C. and a suspension of 1,2,3,4-tetrahydro-1-naphthol (8.0 mg, 0.02 mmol, prepared by analogy to Example 134) in dry toluene (0.5 mL) was added. The cooling bath was removed, and the reaction was stirred 30 min at room temperature. Once TLC analysis indicated complete consumption of the starting material the mixture was diluted with EtOAc (10 mL) and quenched with aqueous saturated NaHCO$_3$ (3 mL). The organic phase was separated, dried over Na$_2$SO$_4$ and concentrated to dryness. The dry residue was purified by column chromatography (SiO$_2$, dichloromethane/EtOAc gradient) to yield the title compound (7.0 mg, 0.018 mmol, 87% yield, single epimer) as a white solid. $^1$H NMR (400 MHZ, CDCl$_3$) δ 7.74 (d, J=8.3 Hz, 1H), 7.58 (dd, J=8.5, 2.8 Hz, 1H), 7.37 (dd, J=7.6, 2.5 Hz, 1H), 6.68 (d, J=8.3 Hz, 1H), 5.62 (ddd, J=49.8, 8.4, 4.7 Hz, 1H), 4.89 (s, 1H), 2.51-2.31 (m, 1H), 2.34-2.07 (m, 2H), 2.03-1.86 (m, 1H). $^{19}$F NMR (376 MHz, CDCl$_3$) δ −63.03, −109.89, −169.86 (d, J=50.8 Hz). ESI MS [M+Na]$^+$ for C$_{19}$H$_{10}$ClF$_5$N$_2$Na, calcd 419.0, found 419.0).

Example 139: (5S,8S)-8-[6-(1,1-difluoroethyl)-5-fluoro-4-methylpyridin-3-yl]-3,5-difluoro-5,6,7,8-tetrahydronaphthalene-1-carbonitrile

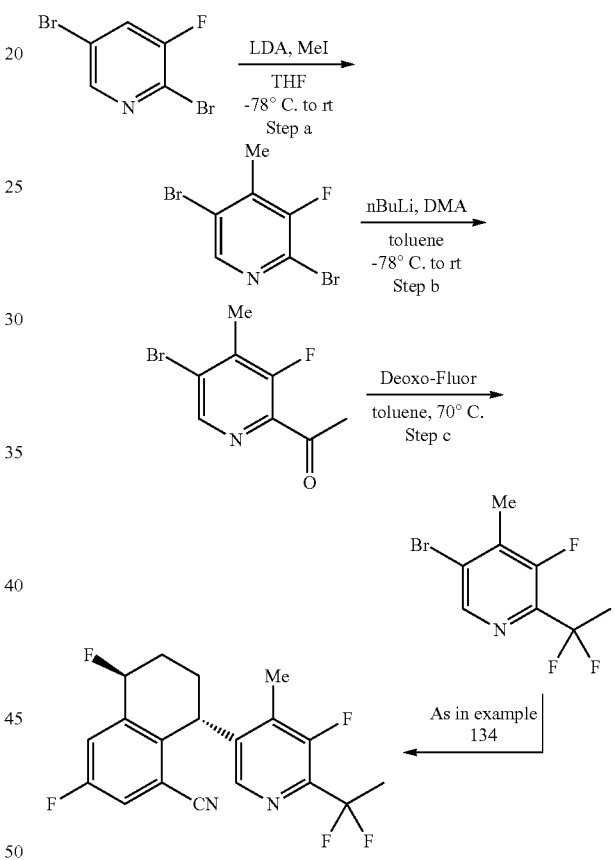

Step a: A mixture of LDA (30 mL, 59.3 ml, 2 M solution in THF/heptane/ethylbenzene) and dry THF (240 mL) was placed under an atmosphere of nitrogen in 500 mL single-neck round bottom flask equipped with a magnetic stirring bar and nitrogen inlet adapter with rubber septum. The solution was cooled to −78° C. under nitrogen and 2,5-dibromo-3-fluoropyridine (12.1 g, 47.4 mmol) solution in dry THF (40 mL) was added via syringe dropwise over 20 min. The resulting mixture was stirred for 30 min and MeI (5 mL, 81 mmol) was added dropwise over 5 min at −78° C. Then cooling bath was removed and the reaction was allowed to warm to ambient temperature and stirred for 1 h followed by quench with aqueous saturated NH$_4$Cl (200 mL). The mixture was transferred into separatory funnel, diluted with water (100 mL) and EtOAc (200 mL). The organic phase was separated, and the aqueous phase was additionally extracted with EtOAc (2×100 mL), Combined organic extracts were washed with brine, dried over Na$_2$SO$_4$, and the solvent was removed under reduced pressure. The crude material was purified by flash chromatography (silica gel, 0% to 30% ethyl acetate in hexanes) to yield 2,5-dibromo-3-fluoro-4-methyl-pyridine (12.0 g, 44.6 mmol, 94% yield) as a colorless crystallizing oil.

Step b: A solution of 2,5-dibromo-3-fluoro-4-methyl-pyridine (6.0 g, 22.3 mmol) in toluene (110 mL) was placed in 250 mL single-necked round bottom flask equipped with magnetic stirring bar and nitrogen inlet adapter with rubber septum. This solution was cooled to −78° ° C. and nBuLi (9.8 mL, 24.5 mmol) was added dropwise via syringe over 10 min. The resulting heterogenous solution was stirred at −78° C. for 20 min before N,N-dimethylacetamide (3.2 mL) was added dropwise over 1 min. The reaction mixture was stirred for 30 min and quenched with aqueous saturated NH$_4$Cl (50 mL) at −78° C. The resulting biphasic mixture was diluted with water (50 mL) and EtOAc (100 mL). The organic phase was separated, and the aqueous phase was additionally extracted with EtOAc (2×100 mL). The combined organic extract was washed with brine, dried over Na$_2$SO$_4$, and the solvent was removed under reduced pressure. The crude material was purified by flash chromatography (silica gel, 0% to 40% ethyl acetate in hexanes) to yield corresponding 2-acetylpyridine (2.8 g, 12.1 mmol, 54% yield) as a colorless crystallizing oil.

Step c: A mixture of 2-acetylpyridine from step b (2.8 g, 12.0 mmol) and deoxo-fluor (6.7 mL, 36 mmol) in toluene (60 mL) was placed in 250 mL single-neck round bottom flask equipped with stirring bar and reflux condenser with drying tube. The mixture was maintained at 70° C. for 24 h. Despite incomplete conversion the biphasic reaction was cooled to ambient temperature and poured in aqueous saturated NaHCO$_3$ (200 mL) under vigorous stirring. Then the mixture was diluted with EtOAc (200 mL) and filtered through a pad of celite. The organic phase was separated, and the aqueous phase was additionally extracted with EtOAc (2×70 mL). Combined organic extracts were washed with brine, dried over Na$_2$SO$_4$ and concentrated to dryness. The crude material was fractionated by flash chromatography (silica gel, 0% to 30% ethyl acetate in hexanes) to yield 5-bromo-2-(1,1-difluoroethyl)-3-fluoro-4-methylpyridine (1.9 g, 7.5 mmol, 63% yield) as a yellowish liquid.

The protocols for the following steps were identical to the Example 134. The title compounds characterization data: $^1$H NMR (400 MHZ, CDCl$_3$) δ 7.53-7.42 (m, 1H), 7.42-7.32 (m, 1H), 7.22 (s, 1H), 5.56 (dt, J=49.9, 3.3 Hz, 1H), 4.69 (br. s, 1H), 2.64-2.36 (m, 4H), 2.27-2.09 (m, 1H), 2.08-1.85 (m, 4H), 1.83-1.67 (m, 1H). $^{19}$F NMR (376 MHz, CDCl$_3$) δ −89.77 (m), −110.97 (m), −125.45, −156.81 (m). ESI MS [M+H]$^+$ for C$_{19}$H$_{16}$F$_5$N$_2$, calcd 367.1, found 367.2).

Example 140: (8R)-8-[(1S,2S,3R)-2,3-difluoro-1-hydroxy-7-methylsulfonyl-2,3-dihydro-1H-inden-4-yl]-3-fluoro-5,6,7,8-tetrahydronaphthalene-1-carbonitrile

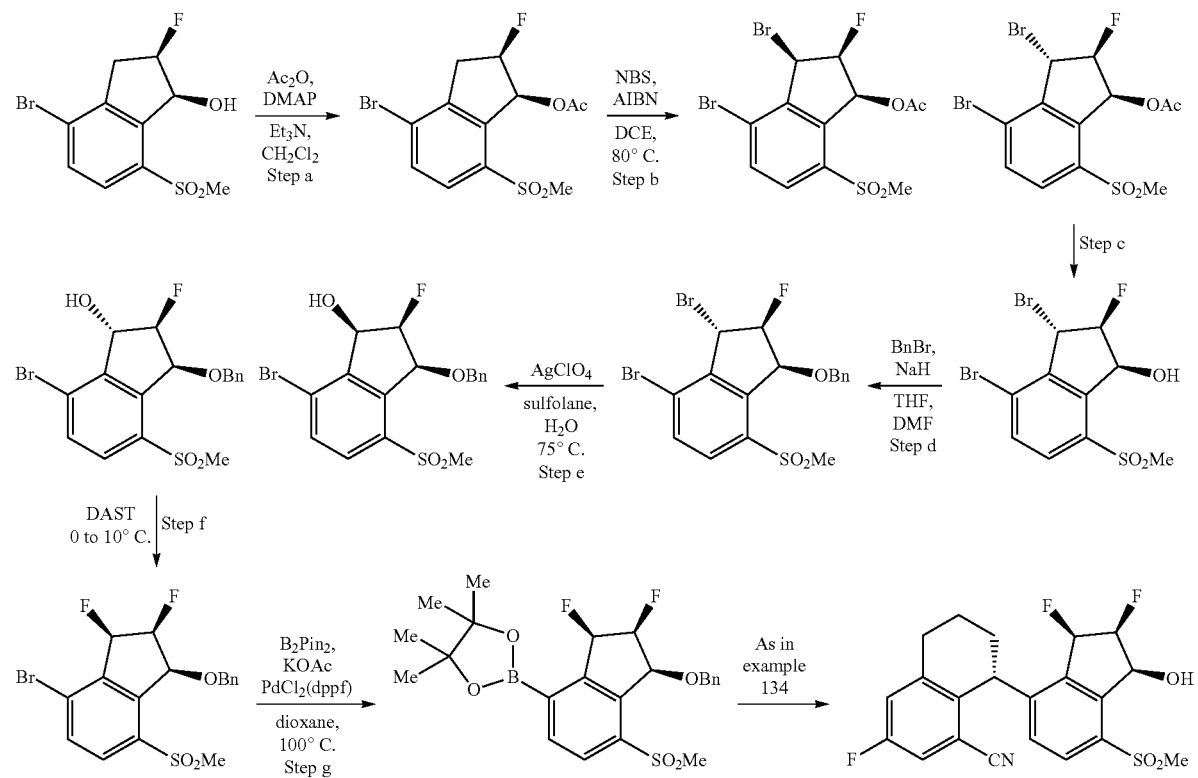

Step a: To an ice-cold solution of (1S,2R)-4-bromo-2-fluoro-7-methylsulfonyl-2,3-dihydro-1H-inden-1-ol (11.5 g, 37.3 mmol) in dichloromethane (190 ml, 0.2M) was added DMAP (1.4 g, 11.2 mmol) and triethylamine (10.4 ml, 75 mmol, 2 equiv.) followed by the dropwise addition of acetic anhydride (7.1 ml, 75 mmol, 2 equiv.). The solution was allowed to warm to room temperature and was stirred for one hour. Upon completion the reaction was quenched with saturated aq. NaHCO$_3$, the resulting solution was extracted with dichloromethane (2×), dried over Na$_2$SO$_4$, and concentrated onto celite. The crude material was purified by flash chromatography on silica gel (0-10% ethyl acetate in hexanes) to yield [(1S,2R)-4-bromo-2-fluoro-7-methylsulfonyl-2,3-dihydro-1H-inden-1-yl] acetate (13.1 g, 100% yield). ESI MS [M+H]+ for $C_{12}H_{12}BrFO_4S$, calcd. 351.0, found 351.0.

Step b: A solution of dichloroethane (0.2M, 190 ml) containing [(1S,2R)-4-bromo-2-fluoro-7-methylsulfonyl-2,3-dihydro-1H-inden-1-yl] acetate (13.5 g, 38.5 mmol), 2,2'-Azobis(2-methylpropionitrile) (40 mg, 1 mol %), and N-bromosuccinimide (7.54 g, 1.1 equiv) was heated to reflux for 90 minutes. Upon completion, the reaction was cooled and partitioned between ethyl acetate and saturated $NaHCO_3$. The organics were collected, washed with dilute $Na_2S_2O_3$, dried over $Na_2SO_4$, and concentrated onto celite. The crude material was purified by flash chromatography on silica gel (5% ethyl acetate in a 1:3 ratio of $CH_2Cl_2$:hexanes) to provide two brominated diastereomers, [(1S,2S,3R)-3,4-dibromo-2-fluoro-7-methylsulfonyl-2,3-dihydro-1H-inden-1-yl] acetate (6.83 g, 41% yield) and [(1S,2S,3S)-3,4-dibromo-2-fluoro-7-methylsulfonyl-2,3-dihydro-1H-inden-1-yl] acetate (2.5 g, 15% yield). The diastereomeric products elute in the order listed.

Step c: To a solution of [(1S,2S,3R)-3,4-dibromo-2-fluoro-7-methylsulfonyl-2,3-dihydro-1H-inden-1-yl] acetate (6.73 g, 15.6 mmol) in THF (0.08M, 195 ml) at 0° C. was added a 0.5 M aqueous solution of LiOH (5.93 ml, 1.5 equiv.) and the reaction was allowed to stir at 0° C. for three hours, at which time the reaction was quenched at 0° C. with 1N HCl. The resulting solution was extracted three times with methylene chloride, the organics were dried over $Na_2SO_4$, and flashed 0 to 20% ethyl acetate in [1:1 hexanes:dichloromethane] to yield (1S,2S,3S)-3,4-dibromo-2-fluoro-7-methylsulfonyl-2,3-dihydro-1H-inden-1-ol (3.68 g, 61% yield).

Step d: Sodium hydride (60% dispersion in mineral oil, 440 mg, 10.5 mmol, 1.1 equiv.) was added slowly at 0° C. to a solution of (1S,2S,3S)-3,4-dibromo-2-fluoro-7-methylsulfonyl-2,3-dihydro-1H-inden-1-ol (3.68 g, 9.5 mmol) and benzyl bromide (6.77 ml, 9.75 g, 57 mmol, 6 equiv.) in THF (38 ml, 0.25M with respect to indanol) and DMF (9.5 ml, 1M with respect to indanol). The reaction was allowed to warm to room temperature and was stirred overnight. The next day, 3 additional equivalents of BnBr and 0.55 equivalents of NaH were added, and the reaction went to completion within two hours. The solution was quenched with 1N HCl, extracted with ethyl acetate, dried over $Na_2SO_4$, and concentrated. The crude material was purified by flash chromatography on silica gel, 0 to 20% ethyl acetate in hexanes, to yield (1S,2S,3S)-1,7-dibromo-2-fluoro-4-methylsulfonyl-3-phenylmethoxy-2,3-dihydro-1H-indene as a white foam (2.46 g, 54% yield).

Step e: To a solution of (1S,2S,3S)-1,7-dibromo-2-fluoro-4-methylsulfonyl-3-phenylmethoxy-2,3-dihydro-1H-indene (2.46 g, 5.1 mmol) in sulfolane (28.4 ml) and water (5.6 ml) was added silver perchlorate hydrate (unknown hydrate stoichiometry) (2.13 g, ~10.3 mmol), and the reaction was heated to 75° C. overnight with the exclusion of light. After 23 hours, the starting material was almost fully consumed, and the reaction was quenched with $H_2O$. Upon dilution with MTBE silver salts can be filtered out of the biphasic mixture, and the organics were collected and dried over sodium sulfate. Purification by flash chromatography (0 to 5% to 50% ethyl acetate in dichloromethane) yielded the diastereomeric alcohol products (1R,2R,3S)-7-bromo-2-fluoro-4-methylsulfonyl-3-phenylmethoxy-2,3-dihydro-1H-inden-1-ol (750 mg, 35% yield) and (1S,2R,3S)-7-bromo-2-fluoro-4-methylsulfonyl-3-phenylmethoxy-2,3-dihydro-1H-inden-1-ol (470 mg, 22% yield). The diastereomeric products elute in the order listed, and the latter was taken on through further steps. ESI MS [M+Na]+ for $C_{17}H_{16}BrFO_4S$, calcd. 437.0, found 437.0.

Step f: To an ice-cold solution of (1S,2R,3S)-7-bromo-2-fluoro-4-methylsulfonyl-3-phenylmethoxy-2,3-dihydro-1H-inden-1-ol (386 mg, 0.93 mmol) in dichloromethane (0.1M, 9.3 ml) was added (diethylamino)sulfur trifluoride (492 µl, 600 mg, 3.7 mmol, 4 equiv.), and the resulting solution was stirred at temperatures between 0 and 10° C. for three hours, at which time it was quenched with saturated $NaHCO_3$. The organics were extracted with ethyl acetate, dried over $Na_2SO_4$, and purified by flash chromatography on silica gel (10% ethyl acetate in hexanes, isocratic) to yield two fluorinated products: (1S,2S,3S)-7-bromo-1,2-difluoro-4-methylsulfonyl-3-phenylmethoxy-2,3-dihydro-1H-indene (undesired, less polar, 158 mg, 40% yield) and (1R,2S,3S)-7-bromo-1,2-difluoro-4-methylsulfonyl-3-phenylmethoxy-2,3-dihydro-1H-indene (desired, more polar, 234 mg, 60% yield).

Step g: (1R,2S,3S)-7-bromo-1,2-difluoro-4-methylsulfonyl-3-phenylmethoxy-2,3-dihydro-1H-indene (234 mg, 0.56 mmol), $B_2Pin_2$ (185 mg, 0.73 mmol, 1.3 equiv.), KOAc (121 mg, 1.23 mmol, 2.2 equiv.) and $PdCl_2(dppf)$ (44 mg, 0.06 mmol, 10 mol %) were combined in dioxane (5.6 ml, 0.1M). The resulting solution was sparged with nitrogen and heated to 100° C. until all starting material was consumed (2.5 h). The crude reaction mixture was filtered over celite, concentrated, taken up in ethyl acetate, and washed with water to remove remaining KOAc. The resulting solid was taken on to the Suzuki cross-coupling step without further purification.

The title compound was completed in a similar fashion to Example 134. 1H NMR (400 MHz, $CDCl_3$): δ 7.96 (dd, J=8.1, 2.0 Hz, 1H), 7.23-7.17 (m, 2H), 6.86 (d, J=8.1 Hz, 1H), 5.91-5.75 (m, overlap, 2H), 5.20-5.02 (m, 1H), 4.95-4.91 (m, 1H), 3.02-2.84 (m, 3H), 2.28-2.19 (m, 1H), 1.93-1.85 (m, 1H), 1.79-1.58 (m, 2H).

Example 141: 8-[(1S)-7-cyano-2,2-difluoro-1-hydroxy-1,3-dihydroinden-4-yl]-3-fluoro-5,6,7,8-tetrahydronaphthalene-1-carbonitrile

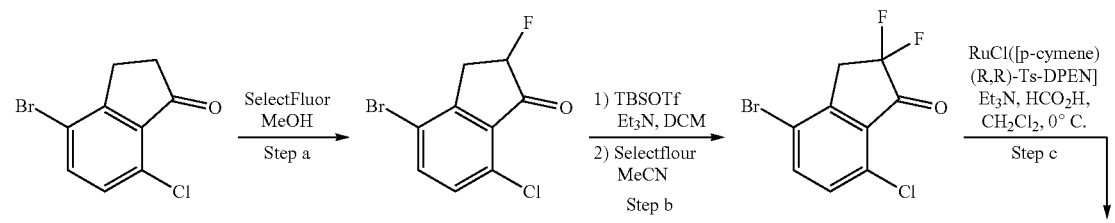

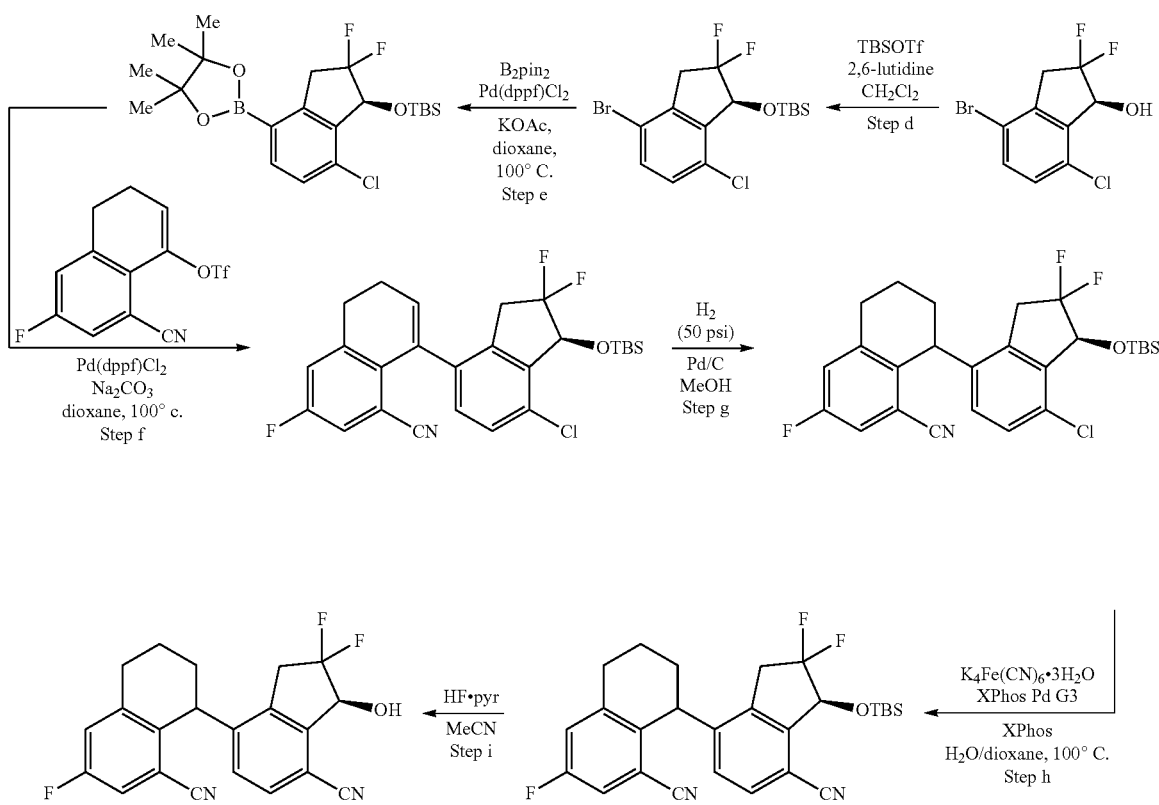

Step a: Performed in similar fashion to step a of Example 134.

Step b: To a solution of the product from step a (10 g, 38 mmol, 1 equiv.) in CH$_2$Cl$_2$ (190 mL, 0.2 M) at 0° ° C. was added Et$_3$N (32 mL, 228 mmol, 6 equiv.) followed by TBSOTf (17.5 mL, 76 mmol, 2 equiv). The reaction was left to warm to room temperature overnight. The reaction mixture was concentrated then dried under vacuum for 45 minutes. The crude silyl enol ether was dissolved in MeCN (190 mL, 0.2 M), then Selectfluor (20.2 g, 57 mmol, 1.5 equiv.) was added and the reaction was stirred at room temperature for 2 hours or until judged complete by TLC. The reaction mixture was diluted with EtOAc, washed with 0.2 M aqueous HCl, followed by brine. The organic layer was dried with MgSO$_4$ and concentrated. The crude product was purified by flash column chromatography (SiO$_2$, 0 to 50% EtOAc/hexanes) to yield the difluoroketone as a light-yellow solid (7.0 g, 24.9 mmol, 66%). $^1$H NMR (400 MHZ, Chloroform-d) δ 7.79 (d, J=8.4 Hz, 1H), 7.36 (dt, J=8.4, 0.9 Hz, 1H), 3.48 (td, J=12.6, 0.8 Hz, 2H).

Step c: Performed in similar fashion to step b of Example 134. $^1$H NMR (400 MHZ, Chloroform-d) δ 7.45 (d, J=8.5 Hz, 1H), 7.19 (d, J=8.5 Hz, 1H), 5.22 (d, J=12.4 Hz, 1H), 3.61-3.33 (m, 2H), 1.11 (t, J=7.1 Hz, 2H).

Step d: Performed in similar fashion to step c of Example 134. ESI MS [M+H]$^+$ for C$_{15}$H$_{20}$BrClF$_2$OSi calcd. 397.0, found 397.0.

Step e: Performed in similar fashion to step d of Example 134. The crude product was used in step f without column chromatographic purification.

Step f: Performed in similar fashion to step e of Example 134. ESI MS [M+H]$^+$ for C$_{26}$H$_{27}$ClF$_3$NOSi calcd. 490.2, found 490.2.

Step g: Performed in similar fashion to step f of Example 134 with 5 equivalents of Et$_3$N added to the reaction mixture. Diastereomers were not separated at this stage. ESI MS [M+H]$^+$ for C$_{26}$H$_{29}$ClF$_3$NOSi calcd. 492.2, found 492.2.

Step h: Aryl chloride (100 mg, 0.20 mmol, 1 equiv.), K$_4$Fe(CN)$_6$·3H$_2$O (59 mg, 0.14 mmol, 0.7 equiv.), XPhos Pd G3 (17 mg, 0.02 mmol, 0.1 equiv.), XPhos (10 mg, 0.02 mmol, 0.1 equiv.), and KOAc (4 mg, 0.04 mmol, 0.2 equiv.) were dissolved in 1:1 water/dioxane (2 mL, 0.1 M). The reaction mixture was sparged with nitrogen for 10 minutes and then heated to 100° C. After 2 hours, the reaction was judged complete by LCMS. The reaction mixture was let to cool to room temperature and then partitioned between EtOAc and water. The layers were separated and the aqueous was extracted three times with EtOAc. The combined organics were dried over Na$_2$SO$_4$ and concentrated. The crude product was purified by flash column chromatography (SiO$_2$, 0 to 50% EtOAc/hexanes) to afford the aryl nitrile product. ESI MS [M+H]$^+$ for C$_{27}$H$_{29}$F$_3$N$_2$OSi calcd. 483.2, found 483.2.

Step i: The product from step h was treated with an excess of HF-pyridine in acetonitrile. After stirring overnight the mixture was quenched with saturated NaHCO$_3$ and extracted with EtOAc. The product was purified by flash column chromatography. The final product was isolated as a 1:1 mixture of diastereomers (40 mg, 0.11 mmol. 54% over two steps). ESI MS [M]$^+$ for C$_{21}$H$_{15}$F$_3$N$_2$O calcd. 369.1, found 369.1. $^1$H NMR (400 MHZ, Chloroform-d) δ 7.47 (dd, J=8.0, 2.9 Hz, 1H), 7.18 (d, J=8.6 Hz, 2H), 6.60 (dd, J=14.3, 8.0 Hz, 1H), 5.33 (m, 1H), 4.45 (dt, J=9.0, 4.1 Hz, 1H), 3.88-3.27 (m, 2H), 3.10-2.80 (m, 3H), 2.23-2.08 (m, 1H), 1.89-1.70 (m, 2H).

Example 142: (5S,8R)-3,5-Difluoro-8-[3-oxo-7-(trifluoromethyl)-1,3-dihydro-2-benzofuran-4-yl]-5,6,7,8-tetrahydronaphthalene-1-carbonitrile

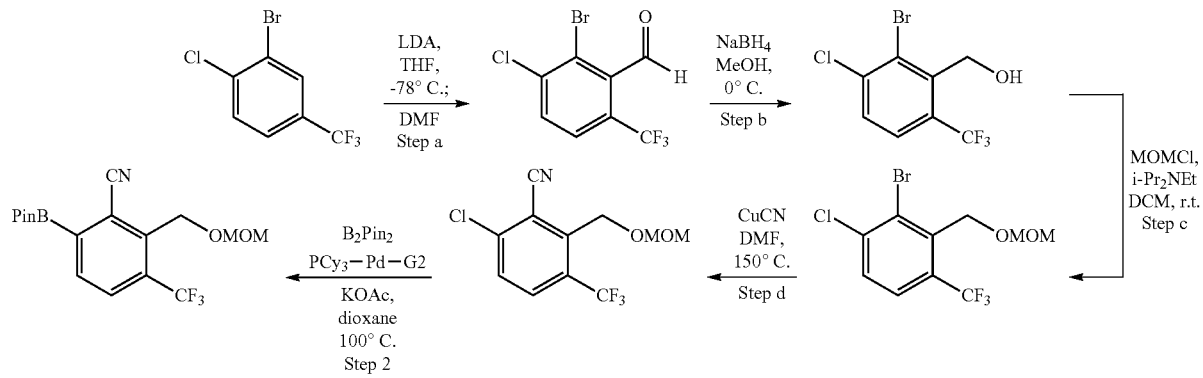

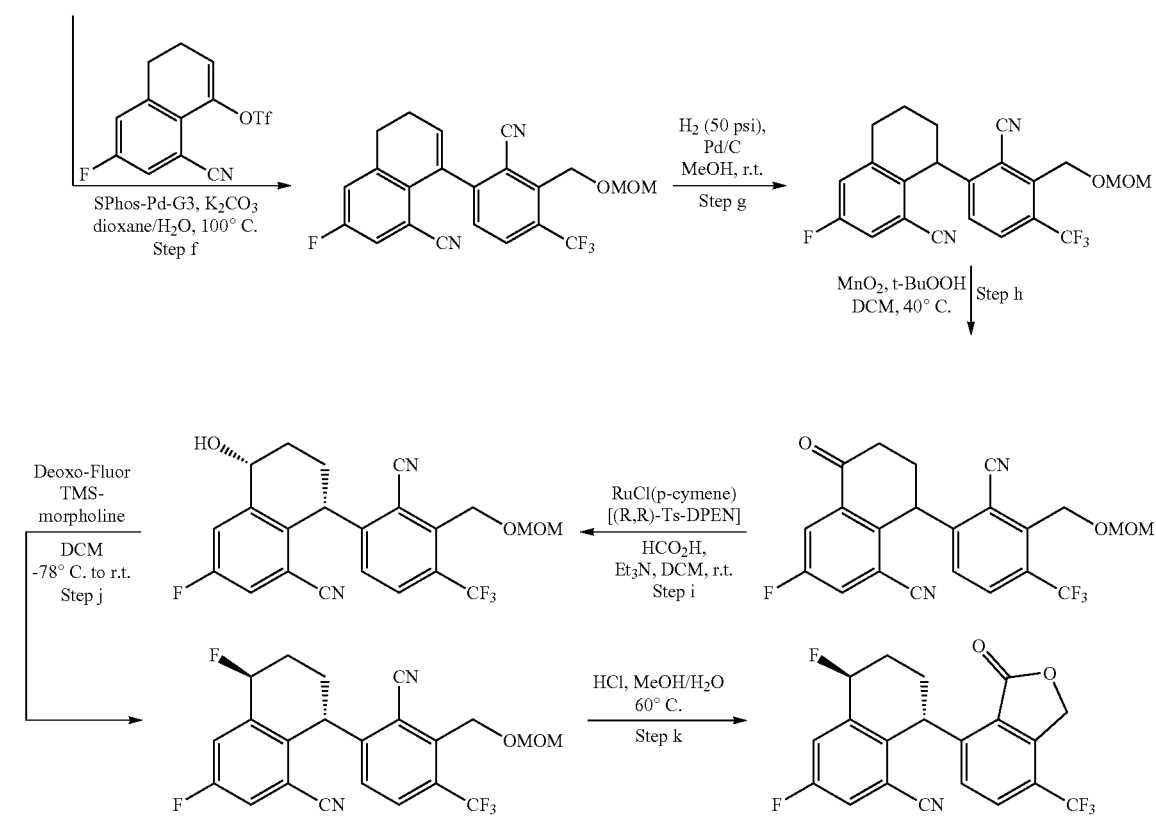

Step a: To a solution of 3-bromo-4-chlorobenzotrifluoride (3.5 mL, 23 mmol, 1.0 equiv.) in THF (75 mL) in a 250-mL round bottom flask was added LDA solution (2.0 M in THF/heptane/ethylbenzene, 17 mL, 1.5 equiv.) dropwise at −78° C. under $N_2$. After stirring at this temperature for 15 min, DMF (3.6 mL, 46 mmol, 2.0 equiv.) was added dropwise at −78° C. and the resulting mixture was kept stirring at this temperature for another 1.5 h when TLC showed the reaction was complete. The reaction mixture was then quenched with sat. aq. $NH_4Cl$ solution (60 mL), warmed to room temperature, and then extracted with EtOAc (100 mL×3). The organic layers were combined, washed with brine (60 mL), and dried over $Na_2SO_4$. Concentration under reduced pressure afforded the desired crude aldehyde product, and its isomer, which was taken directly onto the next step without purification (6.52 g).

Step b: The crude product from step a (with another batch, 8.45 g in total) in a 250-mL round bottom flask was dissolved in MeOH (100 mL) and cooled to 0° C. $NaBH_4$ (1.67 g, 1.5 equiv.) was added in portions and the resulting mixture was stirred at 0° C. for 30 min when TLC showed the reaction was completed. The reaction mixture was quenched with $H_2O$ and then concentrated under reduced pressure to remove most of the MeOH. The residue was extracted with EtOAc (100 mL×3). The organic layers were combined, washed with brine (60 mL), and dried over Na$_2$SO$_4$. Concentration under reduced pressure and purification by flash chromatography (SiO$_2$, 0 to 30% EtOAc/Hex) furnished the product as a white powder (2.75 g, 9.50 mmol, 41% yield over 2 steps). $^1$H NMR (400 MHZ, Chloroform-d) δ 7.60 (d, J=8.5 Hz, 1H), 7.50 (d, J=8.5 Hz, 1H), 5.09 (d, J=6.8 Hz, 2H), 2.20 (t, J=7.0 Hz, 1H).

Step c: To a solution of the product from step b (2.30 g, 8.0 mmol, 1.0 equiv.) and i-Pr$_2$NEt (2.8 mL, 16.0 mmol, 2.0 equiv.) in DCM (40 mL) was added chloromethyl methyl ether (1.2 mL, 16.0 mmol, 2.0 equiv.) dropwise at room temperature. The resulting mixture was stirred at this temperature for 22 h before being quenched with sat. aq. NaHCO$_3$ solution (20 mL). The aqueous phase was extracted with DCM (30 mL). The organic layers were combined, washed with brine (20 mL), and dried over Na$_2$SO$_4$. Concentration under reduced pressure afforded the crude product (1.84 g) which was subjected directly to the next step.

Step d: A 40-mL vial was charged with the crude product from step c (1.06 g) and DMF (20 mL). CuCN (1.43 g, 16 mmol, 2.0 equiv.) was added and the resulting mixture was heated at 150° C. for 2 h before being cooled to room temperature and diluted with EtOAc (50 mL). The organic phase was then washed with H$_2$O (20 mL×2) and brine (20 mL), and dried over Na$_2$SO$_4$. Concentration under reduced pressure and purification by flash chromatography (SiO$_2$, 10 to 40% EtOAc/Hex) furnished the product as a yellow solid (1.00 g, 3.6 mmol, 45% yield over 2 steps). $^1$H NMR (400 MHz, Chloroform-d) δ 7.77 (d, J=8.6 Hz, 1H), 7.71 (d, J=8.5 Hz, 1H), 4.94 (s, 2H), 4.81 (s, 2H), 3.45 (s, 3H).

Step e: A 40-mL vial was charged with the product from step d (1.00 g, 3.6 mmol, 1.0 equiv.), B$_2$Pin$_2$ (1.17 g, 4.6 mmol, 1.3 equiv.), PCy$_3$-Pd-G2 (0.213 g, 0.36 mmol, 10 mol %), KOAc (0.707 g 7.2 mmol, 2.0 equiv.) and 1,4-dioxane (10 mL). The reaction mixture was degassed with N$_2$ bubbling for 10 min before being heated. After 2 h stirring at 100° C., the reaction mixture was cooled, diluted with EtOAc (20 mL), washed with H$_2$O (10 mL), dried over Na$_2$SO$_4$, and concentrated to afford the crude product (1.84 g) which was used in the next step.

Step f: A 40-mL vial was charged with the crude product from step e (1.84 g), alkenyl triflate (1.16 g, 3.6 mmol, 1.0 equiv.), Pd(dppf)Cl$_2$ (0.263 g, 0.36 mmol, 10 mol %), Na$_2$CO$_3$ (0.763 g, 7.2 mmol, 2.0 equiv.), 1,4-dioxane (10 mL) and H$_2$O (2 mL). The reaction mixture was degassed with N$_2$ bubbling for 10 min before being heated. After 1 h stirring at 100° C., the reaction mixture was cooled, filtered, concentrated and purified by flash chromatography (SiO$_2$, 10 to 30% EtOAc/Hex) to furnish the product (0.743 g, 1.78 mmol, 50% yield over 2 steps). $^1$H NMR (400 MHZ, Chloroform-d) δ 7.79 (d, J=8. Hz, 1H), 7.61 (d, J=8.2 Hz, 1H), 7.23 (dd, J=8.2, 2.8 Hz, 1H), 7.14 (dd, J=8.0, 2.8 Hz, 1H), 6.35 (t, J=4.9 Hz, 1H), 4.61-4.52 (m, 3H), 4.50 (d, J=6.7 Hz, 1H), 3.29 (s, 3H), 2.92 (t, J=7.8 Hz, 2H), 2.57-2.39 (m, 2H).

Step g: A mixture of the product from step f (0.535 g, 1.3 mmol, 1.0 equiv.), Pd/C (10 wt % Pd, 0.600 g) in MeOH (10 mL) was shaken in parr hydrogenator under H$_2$ (50 psi) for 3 h when TLC showed the reaction was completed. The reaction mixture was then filtered through Celite and concentrated to afford the product which directly used in the next step.

Step h: To a vial containing the product from step g was added DCM (13 mL), MnO$_2$ (0.452 g, 5.2 mmol, 4.0 equiv.) and a solution of t-BuOOH (5.5 M in decane, 2.4 mL, 13 mmol, 10 equiv.). The resulting mixture was heated at 40° C. overnight and other 4.0 equiv. of MnO$_2$ and 10 equiv. of t-BuOOH solution were added to the reaction mixture. After another overnight reaction, the reaction mixture was filtered through Celite, concentrated, and purified by flash chromatography (SiO$_2$, 10 to 20% EtOAc/Hex) to furnish the desired product (0.272 g, 0.629 mmol, 48% yield over 2 steps). $^1$H NMR (400 MHZ, Chloroform-d) δ 8.11 (dd, J=8.2, 2.7 Hz, 1H), 7.62 (d, J=8.3 Hz, 1H), 7.58 (dd, J=7.2, 2.9 Hz, 1H), 6.87 (d, J=8.4 Hz, 1H), 5.23-5.13 (m, 3H), 4.87 (s, 2H), 3.51 (s, 3H), 2.75-2.64 (m, 2H), 2.63-2.55 (m, 1H), 2.49-2.41 (m, 1H).

Step i: To a 40-mL vial was charged with the product from step h (78.1 mg, 0.18 mmol, 1.0 equiv.), RuCl(p-cymene)[(R,R)-TsDPEN] (11.5 mg, 18 μmol, 10 mol %), HCO$_2$H (41.4 mg, 0.90 mmol, 5.0 equiv.), Et$_3$N (54.6 mg, 0.54 mmol, 3.0 equiv.) and DCM (5 mL). The reaction mixture was stirred at room temperature for 1 h and then concentrated. The crude was purified by flash chromatography (SiO$_2$, 30 to 50% EtOAc/Hex) to furnish the desired product (27.2 mg, 62.6 μmol, 35% yield). $^1$H NMR (400 MHZ, Chloroform-d) δ 7.70 (dd, J=9.2, 2.7 Hz, 1H), 7.60 (d, J=8.3 Hz, 1H), 7.31-7.23 (m, 1H), 6.92 (d, J=8.3 Hz, 1H), 5.20-5.06 (m, 2H), 4.92-4.81 (m, 4H), 3.50 (s, 3H), 2.40-2.26 (m, 2H), 2.18-1.99 (m, 2H), 1.84-1.70 (m, 1H).

Step j: To a solution of Deoxo-Fluor (2.7 M in toluene, 0.219 mmol, 80 μL, 3.5 equiv.) in DCM (2 mL) was added TMS-morpholine (0.222 mmol, 35.4 mg, 3.55 equiv.) dropwise over 1 min at −78° C. The resulting solution was stirred at this temperature for 5 min then warmed to room temperature for 2 h before being cooled back to −78° C. A solution of the product from step i (27.2 mg, 62.6 μmol, 1.0 equiv.) in DCM (1 mL) was then added to the reaction mixture. The resulting mixture was then stirred at room temperature for another 15 min when the TLC showed the reaction was completed. The reaction mixture was then diluted with DCM (10 mL), washed with saturated NaHCO$_3$ aqueous solution (5 mL), dried over Na$_2$SO$_4$, and concentrated. The residue was then purified by flash chromatography (SiO$_2$, 25% EtOAc/Hex) which furnished the fluorinated product (25.1 mg, 57.5 μmol, 92% yield). $^1$H NMR (400 MHZ, Chloroform-d) δ 7.62-7.51 (m, 2H), 7.40 (ddd, J=7.5, 2.7, 1.6 Hz, 1H), 6.68 (d, J=8.2 Hz, 1H), 5.61 (dt, J=49.9, 3.8 Hz, 1H), 5.21-5.07 (m, 2H), 4.99-4.92 (m, 1H), 4.89-4.83 (m, 2H), 3.51 (s, 3H), 2.65-2.51 (m, 1H), 2.23-2.08 (m, 1H), 2.04-1.90 (m, 2H).

Step k: A solution of the product from step j (23.0 mg, 52.7 μmol, 1.0 equiv.) in MeOH (0.5 mL) and 6 M HCl (aq., 0.5 mL) was heated at 60° C. for 1 h and then concentrated. The residue was purified by flash chromatography (SiO$_2$, 30% EtOAc/Hex) which furnished the title compound as a white solid (17.3 mg, 44.0 μmol, 84% yield). $^1$H NMR (400 MHZ, Chloroform-d) δ 7.66 (d, J=7.9 Hz, 1H), 7.59-7.55 (m, 1H), 7.43 (ddd, J=7.4, 2.7, 1.8 Hz, 1H), 6.78 (d, J=7.8 Hz, 1H), 5.73-5.55 (m, 2H), 5.37 (d, J=15.6 Hz, 1H), 4.61-4.51 (m, 1H), 2.58 (tdd, J=13.7, 6.3, 3.1 Hz, 1H), 2.29-2.19 (m, 1H), 2.13-1.90 (m, 1H), 1.84 (ddt, J=14.0, 5.8, 3.2 Hz, 1H). ESI MS [M+H]$^+$ for C$_{20}$H$_{12}$F$_5$NO$_2$, calcd. 394.1, found 394.0.

Example 143: (5S,8R)-8-[(1S)-2,2-difluoro-1-hydroxy-7-(2-methylpyrazol-3-yl)-1,3-dihydroinden-4-yl]3,5-difluoro-5,6,7,8-tetrahydronaphthalene-1-carbonitrile ent) to yield the (5S)-8-[(1S)-1-[tert-butyl(dimethyl)silyl]oxy-7-chloro-2,2-difluoro-1,3-dihydroinden-4-yl]-3,5-difluoro-5,6,7,8-tetrahydronaphthalene-1-carbonitrile (12 mg, 0.024 mmol, 67%). ESI MS [M+H]+ for $C_{26}H_{28}ClF_4NOSi$, calcd 511.0, found 527.0.

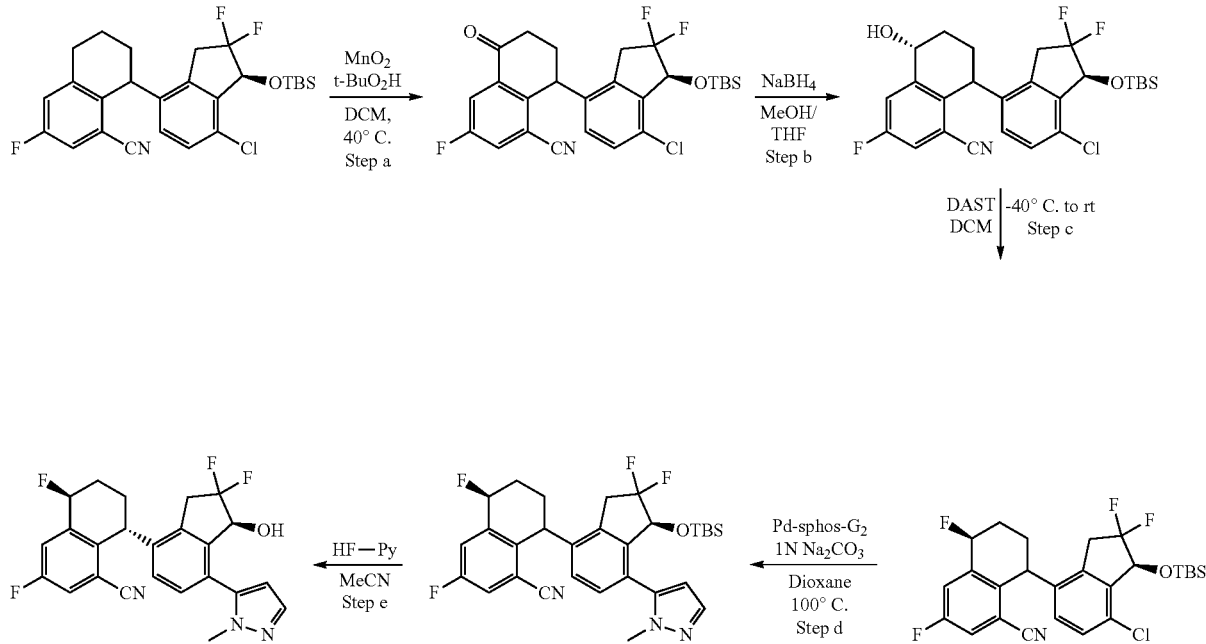

Step a: From 8-[(1S)-1-[tert-butyl(dimethyl)silyl]oxy-7-chloro-2,2-difluoro-1,3-dihydroinden-4-yl]-3-fluoro-5,6,7,8-tetrahydronaphthalene-1-carbonitrile, followed the same procedure described in Example 134 to prepare compound 8-[(1S)-1-[tert-butyl(dimethyl)silyl]oxy-7-chloro-2,2-difluoro-1,3-dihydroinden-4-yl]-3-fluoro-5-oxo-7,8-dihydro-6H-naphthalene-1-carbonitrile. $^1$H NMR (400 MHZ, Chloroform-d) δ 8.04 (dddd, J=8.4, 2.9, 1.6, 0.5 Hz, 1H), 7.53 (dt, J=7.3, 2.9 Hz, 1H), 7.09 (d, J=8.3 Hz, 1H), 6.35 (dd, J=13.2, 8.3 Hz, 1H), 5.29-5.01 (m, 1H), 4.62 (m, 1H), 3.80-3.33 (m, 2H), 2.80-2.30 (m, 2H), 2.20-2.10 (m, 1H), 1.60-1.50 (m, 1H), 1.00-0.72 (m, 9H), 0.36-0.11 (m, 6H).

Step b: A vial was charged with 8-[(1S)-1-[tert-butyl(dimethyl)silyl]oxy-7-chloro-2,2-difluoro-1,3-dihydroinden-4-yl]-3-fluoro-5-oxo-7,8-dihydro-6H-naphthalene-1-carbonitrile from step a (30 mg, 0.06 mmol, 1.0 equiv.) and mixture solvent (MeOH 0.2 ml, THF 0.3 ml). The reaction mixture was cooled to 0° C. and NaBH4 (2.2 mg, 0.06 mmol, 1.0 equiv.) was added. The reaction mixture was stirred at 0° ° C. for 30 min. Once complete, purification by flash chromatography (SiO$_2$, hexane to 30% EtOAc) furnished the (5R)-8-[(1S)-1-[tert-butyl(dimethyl)silyl]oxy-7-chloro-2,2-difluoro-1,3-dihydroinden-4-yl]-3-fluoro-5-hydroxy-5,6,7,8-tetrahydronaphthalene-1-carbonitrile. (18 mg, 0.035 mmol, 59%). ESI MS [M+H]+ for $C_{26}H_{29}ClF_3NO_2Si$, calcd 509.1, found 525.1.

Step c: To a vial containing the product from step b (18 mg, 0.035 mmol, 1.0 equiv.) was added 0.4 ml DCM. The reaction was cooled at −40° C. and DAST (11 mg, 0.071 mmol, 2.0 equiv.) was added. The reaction mixture was stirred at −40° C. for 30 min. Once complete, purification by flash chromatography (SiO$_2$, hexane to 10% EtOAc gradient) to yield the (5S)-8-[(1S)-1-[tert-butyl(dimethyl)silyl]oxy-7-chloro-2,2-difluoro-1,3-dihydroinden-4-yl]-3,5-difluoro-5,6,7,8-tetrahydronaphthalene-1-carbonitrile (12 mg, 0.024 mmol, 67%). ESI MS [M+H]+ for $C_{26}H_{28}ClF_4NOSi$, calcd 511.0, found 527.0.

Step d: To a vial containing the product from step c (12 mg, 0.024 mmol, 1.0 equiv.) was added 1-Methyl-1H-pyrazole-5-boronic acid pinacol ester (6.4 mg, 0.031 mmol, 1.3 equiv.), Pd-Sphos-G2 (1.7 mg, 0.0024 mmol, 0.1 equiv.) The vial was evacuated and back-filled with N$_2$ (×3). 1M aq. Na$_2$CO$_3$ solution (0.1 ml, 0.096 mmol, 4.0 equiv.) and Dioxane (0.25 mL) were added. The reaction was heated at 100° C. and stirred for overnight. Once complete, purification by flash chromatography (SiO$_2$, hexane to 30% EtOAc gradient) to yield (5S)-8-[(1S)-1-[tert-butyl(dimethyl)silyl]oxy-2,2-difluoro-7-(2-methylpyrazol-3-yl)-1,3-dihydroinden-4-yl]-3,5-difluoro-5,6,7,8-tetrahydronaphthalene-1-carbonitrile (13 mg, 0.023 mmol, 97%). ESI MS [M+H]+ for $C_{30}H_{33}F_4N_3OSi$, calcd 556.7, found 556.2.

Step e: A solution of the product from step d (13 mg, 0.023 mmol) in CH$_3$CN (0.4 mL) was placed in a 3 mL vial equipped with a magnetic stirrer, then HF·Py complex (hydrogen fluoride ~70%, pyridine ~30%, 0.2 mL) was added. The resulting colorless solution was stirred for 1 hr at ambient temperature. Once complete, purification by HPLC to yield (5S,8R)-8-[(1S)-2,2-difluoro-1-hydroxy-7-(2-methylpyrazol-3-yl)-1,3-dihydroinden-4-yl]-3,5-difluoro-5,6,7,8-tetrahydronaphthalene-1-carbonitrile (2.2 mg, 0.005 mmol, 22%). $^1$H NMR (400 MHZ, Methanol-d$_4$) δ 7.69-7.57 (m, 2H), 7.54 (d, J=2.0 Hz, 1H), 7.16 (d, J=8.0 Hz, 1H), 6.55-6.46 (m, 2H), 5.73-5.60 (m, 2H), 4.84-4.80 (m, 1H), 4.68-4.61 (m, 1H), 3.84-3.67 (m, 1H), 3.47 (td, J=16.6, 4.7 Hz, 1H), 2.52-2.40 (m, 1H), 2.16-1.95 (m, 2H), 1.84-1.73 (m, 1H). ESI MS [M+H]+ for $C_{30}H_{33}F_4N_3OSi$, calcd 442.4, found 442.0.

Example 144: (5S,8R)-8-[(1S)-2,2-difluoro-1-hydroxy-7-(2-methylphenyl)-2,3-dihydro-1H-inden-4-yl]-3,5-difluoro-5,6,7,8-tetrahydronaphthalene-1-carbonitrile

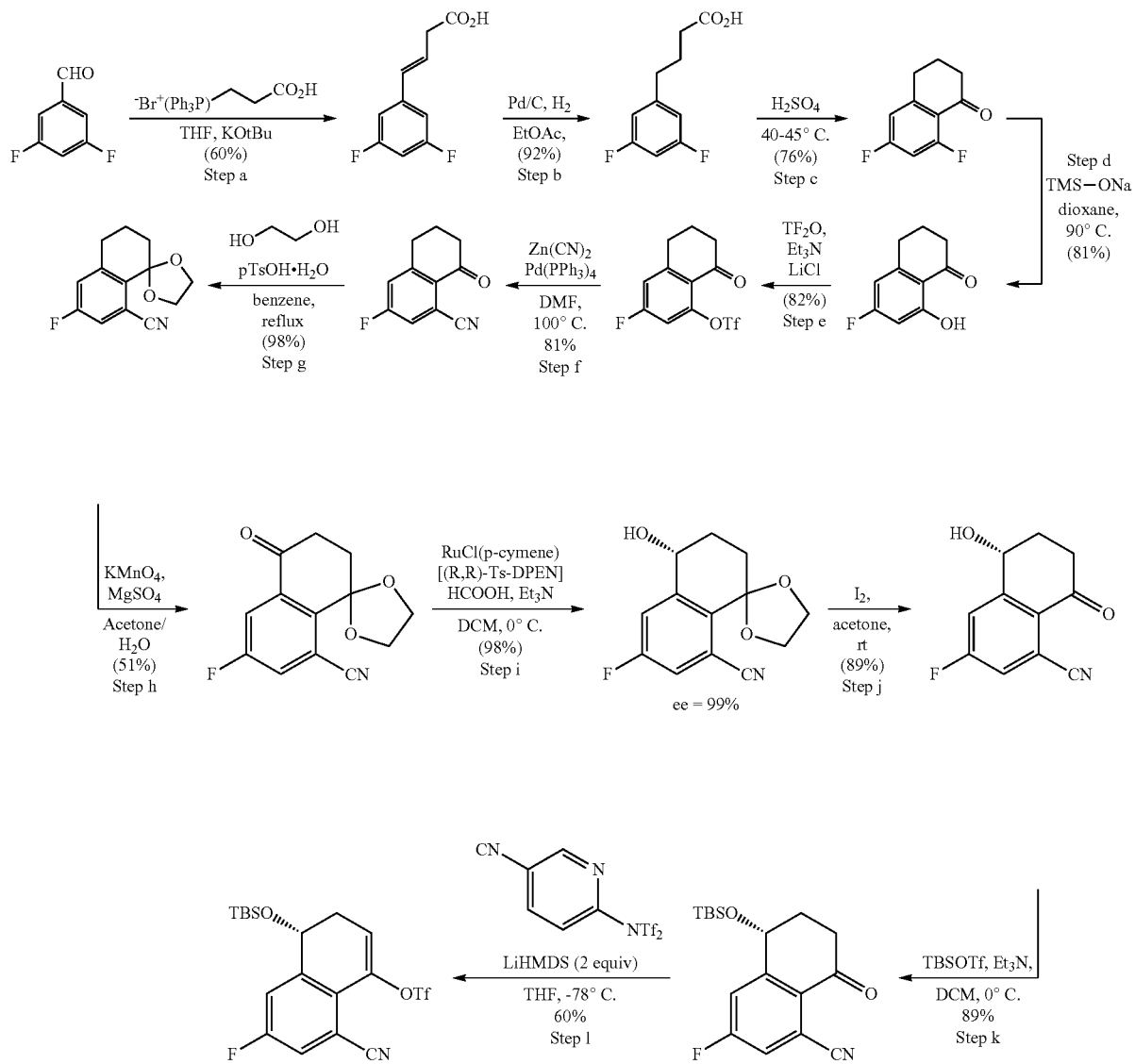

Step a: Into a 50-L reactor purged and maintained with an inert atmosphere of nitrogen, was placed 3,5-difluorobenzaldehyde (1500.00 g, 10555.57 mmol, 1.00 equiv), tetrahydrofuran (15 L), (2-carboxyethyl)triphenylphosphanium bromide (5260.06 g, 12666.69 mmol, 1.20 equiv). This was followed by the addition of a solution of tert-butoxypotassium (2961.18 g, 26388.93 mmol, 2.50 equiv) in THF (15 L) dropwise with stirring at 0° C. in 2 h. The resulting solution was stirred for 1 overnight at room temperature. The reaction was repeated 1 time. The reaction was then quenched by the addition of 20 L of water. The resulting mixture was concentrated under vacuum. The resulting solution was extracted with 2×8 L of ethyl acetate and the aqueous layers combined. HCl (3 mol/L) was employed to adjust the pH to 4-5. The resulting solution was extracted with 3×6 L of ethyl acetate and the organic layers combined and dried over anhydrous sodium sulfate and concentrated under vacuum. The residue was applied onto a silica gel column with ethyl acetate/petroleum ether (1:10-1:5). This resulted in 2500 g (59.76%) of (3E)-4-(3,5-difluorophenyl)but-3-enoic acid as a white solid.

Step b: Into a 20-L High-Pressure autoclave was placed (3E)-4-(3,5-difluorophenyl)but-3-enoic acid (2500.00 g, 12615.49 mmol, 1.00 equiv), EA (12.5 L), 10% Pd/C (125 g). The reaction was then purged with nitrogen and pressurized with hydrogen gas to 150 psi, The mixture was stirred 4 h at room temperature. The solids were filtered out. Rinsed with EA (2.5 L), The resulting mixture was concentrated under vacuum. This resulted in 2318 g (91.79%) of 4-(3,5-difluorophenyl)butanoic acid as colorless oil.

Step c: Into a 20-L 4-necked round-bottom flask purged and maintained with an inert atmosphere of nitrogen, was placed sulfuric acid (6.6 L), 4-(3,5-difluorophenyl)butanoic acid (2318.00 g, 11579.28 mmol, 1.00 equiv). The resulting solution was stirred for 4 h at 40-45° C. The reaction mixture was cooled to 0° C. with a water/ice bath. The reaction mixture was transferred onto 30 L of water/ice. The resulting solution was extracted with 3×8 L of MTBE and the organic layers combined. The resulting mixture was washed with 1×5 L of H$_2$O and 1×5 L of brine. The mixture was dried over anhydrous sodium sulfate and concentrated under vacuum. The crude product was re-crystallized from MTBE: hexane (5V) in the ratio of 1:3. This resulted in 1600 g (75.85%) of 6,8-difluoro-3,4-dihydro-2H-naphthalen-1-one as a off-white solid. 500.4000 g was submitted to QC and other was used to TG2. LCMS-PH-ACS-002-TG1-0: (ES, m/z): [M+H]$^+$=183. $^1$H-NMR-PH-ACS-002-TG1-0: (300 MHz, DMSO-d$_6$, ppm) δ 7.24-7.07 (m, 2H), 2.97 (t, J=6.1 Hz, 2H), 2.57 (dd, J=7.2, 5.8 Hz, 2H), 2.07-1.93 (m, 2H).

Step d: Into a 50-L reactor purged and maintained with an inert atmosphere of nitrogen, was placed dioxane (13.50 L), trimethyl(sodiooxy)silane (1661.00 g, 14806.69 mmol, 3.00 equiv). This was followed by the addition of a solution of 6,8-difluoro-3,4-dihydro-2H-naphthalen-1-one (900.00 g, 4940.440 mmol, 1.00 equiv) in dioxane (4.5 L) dropwise with stirring at 80-90° C. in 2 h. The resulting solution was stirred for 1 h at 80-90° C. The reaction mixture was cooled to 20° C. with a water/ice bath. The reaction was then quenched by the addition of 10 L of HCl (1 mol/L). The resulting solution was extracted with 1×6 L of ethyl acetate. The organic layer was washed with 1×8 L of H$_2$O and 1×8 L of brine. The mixture was dried over anhydrous sodium sulfate and concentrated under vacuum. The residue was applied onto a silica gel column with ethyl acetate/petroleum ether (1:20-1:10). This resulted in 720 g (80.88%) of 6-fluoro-8-hydroxy-3,4-dihydro-2H-naphthalen-1-one as a yellow solid.

Step e: Into a 20-L reactor purged and maintained with an inert atmosphere of nitrogen, was placed 6-fluoro-8-hydroxy-3,4-dihydro-2H-naphthalen-1-one (720.00 g, 3996.04 mmol, 1.00 equiv), DCM (10.00 L), TEA (1010.00 g, 9981.22 mmol, 2.50 equiv), LiCl (185.00 g, 4363.82 mmol, 1.09 equiv). The reactor was cooled to 0° C. This was followed by the addition of Tf$_2$O (1128.00 g, 3998.02 mmol, 1.00 equiv) dropwise with stirring at 0° C. in 1.5 hrs. The resulting solution was stirred for 3 h at room temperature. The reaction was then quenched by the addition of 10 L of water. The resulting solution was extracted with 2×5 L of dichloromethane and the organic layers combined. The resulting mixture was washed with 1×5 L of brine. The mixture was dried over anhydrous sodium sulfate and concentrated under vacuum. The residue was applied onto a silica gel column with ethyl acetate/petroleum ether (1:10). This resulted in 1025 g (82.15%) of 3-fluoro-8-oxo-6,7-dihydro-5H-naphthalen-1-yl trifluoromethanesulfonate as a brown solid.

Step f: Into a 20-L 4-necked round-bottom flask purged and maintained with an inert atmosphere of nitrogen, was placed 3-fluoro-8-oxo-6,7-dihydro-5H-naphthalen-1-yl trifluoromethanesulfonate (1025.00 g, 3282.83 mmol, 1.00 equiv), DMF (10.00 L), Zn(CN)$_2$ (304.00 g, 2588.46 mmol, 0.79 equiv), Pd(PPh$_3$)$_4$ (150.00 g, 129.80 mmol, 0.04 equiv). The resulting solution was stirred for 4 h at 100° C. The reaction mixture was cooled with a water/ice bath. The reaction was then quenched by the addition of 30 L of water/ice. The resulting solution was extracted with 3×8 L of ethyl acetate and the organic layers combined. The resulting mixture was washed with 2×8 L of H$_2$O and 1×8 L of brine. The mixture was dried over anhydrous sodium sulfate and concentrated under vacuum. The residue was applied onto a silica gel column with dichloromethane/petroleum ether (1:2-1:1). This resulted in 501.4000 g (80.83%) of 3-fluoro-8-oxo-6,7-dihydro-5H-naphthalene-1-carbonitrile as a yellow solid. LC-MS: (ES, m/z): [M+H]$^+$=190. $^1$H-NMR (300 MHz, CDCl$_3$) δ 7.40 (dd, J=8.0, 2.6 Hz, 1H), 7.23 (ddd, J=8.4, 2.2, 1.2 Hz, 1H), 3.04 (t, J=6.1 Hz, 2H), 2.74 (dd, J=7.3, 5.9 Hz, 2H), 2.19 (p, J=6.5 Hz, 2H).

Step g: To a mixture of the product from step f (25 g, 132 mmol) and ethylene glycol (5 eq.) and benzene (330 mL) was added pTsOH·H$_2$O (2.51 g, 13.2 mmol, 0.1 equiv). The reaction mixture was refluxed overnight with Dean Stark apparatus and quenched with saturated NaHCO$_3$. The mixture was extracted with EtOAc, dried over Na$_2$SO$_4$, and concentrated. The crude material was purified by column chromatography (hexanes/EtOAc), 5-15% gradient to afford the acetal as a yellow solid (31.9 g, 100%).

Step h: To a stirred solution of the product from step g (6.0 g, 25.7 mmol) in acetone (68 mL) and water (17 mL), MgSO$_4$ (6.50 g, 54.0 mmol, 2.1 equiv) was added in one portion. A reflux condenser was fitted to the reaction vessel and KMnO$_4$ (21.1 g, 133.6 mmol, 5.2 equiv) was added in portions over the course of 20 minutes (probably use ice bath for higher scale) and the resulting strongly purple reaction mixture was stirred at 45° C. for 20 h. The reaction mixture was quenched with saturated Na$_2$S$_2$O$_3$ and water. The mixture was extracted with EtOAc, dried over Na$_2$SO$_4$, and concentrated. The crude material was purified by column chromatography (hexanes/EtOAc), 10-40% gradient to afford the ketone as a yellow solid (3.24 g, 51%).

Step i: To a mixture of the product from step h (3.80 g, 15.4 mmol) and DCM (77 mL) was added formic acid (1.7 mL, 46.2 mmol, 3 equiv) and Et$_3$N (4.2 mL, 30.8 mmol, 2 equiv). The reaction mixture was cooled to 0° C. and catalyst (293 mg, 0.46 mmol, 0.03 equiv) was added. After stirring overnight at 4° C. (fridge) the reaction was quenched with saturated NaHCO$_3$. The mixture was extracted with DCM, dried over Na$_2$SO$_4$, and concentrated. The crude material was purified by column chromatography (hexanes/EtOAc), 20-50% gradient to afford the alcohol as a yellow solid (3.74 g, 98%).

Step j: To a mixture of the product from step i (3.72 g, 14.9 mmol) and acetone (149 mL) was added I$_2$ (379 mg, 1.49 mmol, 0.1 equiv). The reaction mixture was stirred at rt for 30 minutes and quenched with Na$_2$S$_2$O$_3$ in water. The mixture was extracted with EtOAc, dried over Na$_2$SO$_4$, and concentrated. The crude material was purified by column chromatography (hexanes/EtOAc), 20-50% gradient to afford the ketone as a yellow solid (2.72 g, 89%).

Step k: To a mixture of the product from step j (2.72 g, 13.3 mmol) and DCM (89 mL) was added Et$_3$N (2.7 mL, 20.0 mmol, 1.5 equiv) at 0° C. followed by TBSOTf (3.7 mL, 15.9 mmol, 1.2 equiv) and the mixture was stirred at 0° C. for 1 h. The reaction mixture was washed with NaHCO$_3$sat., extracted with DCM, dried over Na$_2$SO$_4$, and concentrated. The crude material was purified by column chromatography (hexanes/EtOAc), 0-20% gradient to afford the protected alcohol as a yellow solid (3.79 g, 89%).

Step l: To a mixture of product from step k (2.51 g, 7.86 mmol) and THF (52 mL) was added ArNTf$_2$ (9.2 g, 23.6 mmol, 3 equiv). The reaction mixture was cooled to −78° C. and LiHMDS (1M in THF, 11.8 mL, 11.8 mmol, 1.5 equiv) was added and the mixture was stirred 20 minutes at −78° C. As the conversion was incomplete LiHMDS (3.9 mL, 3.9 mmol, 0.5 equiv) was added and the reaction was stirred for another 20 minutes. The mixture was quenched with NaHCO$_3$sat., extracted with THF, dried over Na$_2$SO$_4$, and concentrated. The crude material was purified by column chromatography (hexanes/EtOAc), 0-10% gradient to afford the triflate as a white solid (2.14 g, 60%).

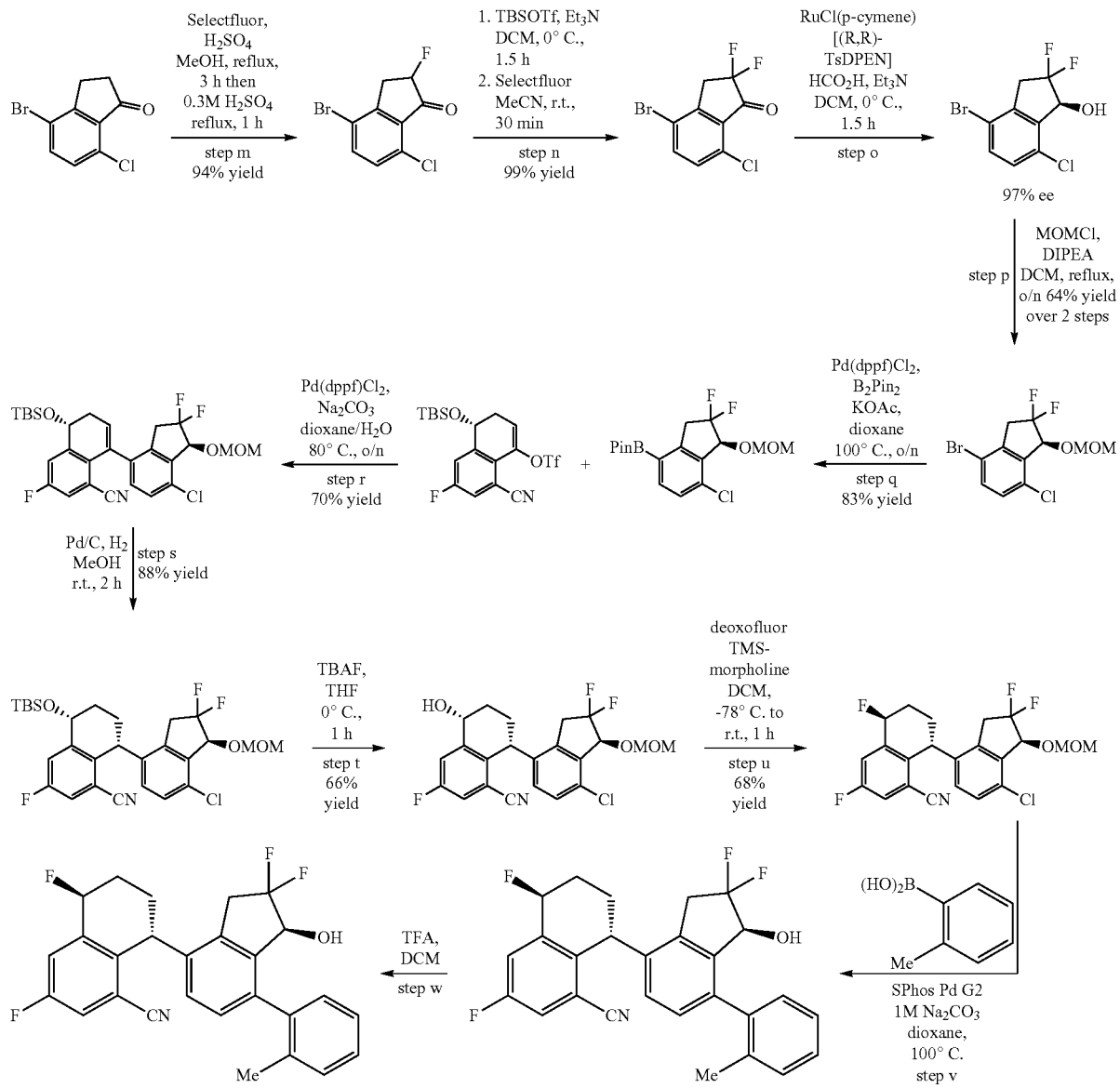

Step m: To a solution of 4-bromo-7-chloro-1-indanone (40.0 g, 163 mmol, 1.0 equiv.) in MeOH (800 mL) was added Selectfluor (63.5 g, 179 mmol, 1.1 equiv.) and concentrated $H_2SO_4$ (1.0 mL). The resulting mixture was heated at reflux for 3 h. After cooling to room temperature, 0.3 M $H_2SO_4$ (aq., 200 mL) was added to the reaction mixture. The resulting mixture was heated at reflux for another 1 h. After cooling to room temperature, large amount of the product was precipitated out and collected via filtration. The filtrate was concentrated and diluted with DCM (500 mL) and washed with $H_2O$ and brine. The organic phase was dried over $Na_2SO_4$ and concentrated. Combining the previous filtering cake, 40.4 g (153 mmol, 94% yield) of the desired product was obtained as pale brown solid.

Step n: To a solution of the product from step m (40.4 g, 153 mmol, 1.0 equiv.) and $Et_3N$ (92.9 g, 128 mL, 918 mmol, 6.0 equiv.) in DCM (380 mL) was added TBSOTf (80.9 g, 70.3 mL, 306 mmol, 2.0 equiv.) dropwise at 0° C. The resulting solution was stirred at 0° C. for 1.5 h, and then quenched with saturated $NaHCO_3$ (aq.) and kept stirring for 1 h. The resulting mixture was then separated, and the aqueous phase was extracted with DCM (3×150 mL). The combined organic phase was then washed with brine, dried over $Na_2SO_4$ and concentrated to afford the crude silyl enol ether. The crude product was then dissolved in MeCN (750 mL). Selectfluor (81.3 g, 230 mmol, 1.5 equiv.) was added portion-wise at room temperature. The resulting mixture was stirred at room temperature for 30 min and then filtered to remove the precipitated salts. The filtrate was concentrated and diluted with DCM (500 mL) and $H_2O$ (500 mL). The aqueous phase was extracted with DCM (2×200 mL). The combined organic phase was then washed with brine, dried over $Na_2SO_4$ and concentrated to afford crude solid. Trituration with hexanes (3×150 mL) and drying under vacuum afforded 42.4 g (151 mmol, 99% yield) of desired product that was obtained as light yellow powdery solid.

Step o: $HCO_2H$ (34.8 g, 28 mL, 755 mmol, 5.0 equiv.) was added to a solution of $Et_3N$ (45.8 g, 63 mL, 453 mmol, 3.0 equiv.) in DCM (100 mL) dropwise. The resulting solution was stirred at room temperature for 30 min, and then added to a solution of the product from step n (42.4 g, 151 mmol, 1.0 equiv.) and RuCl(p-cymene)[(R,R)-TsDPEN] (1.92 g, 3.02 mmol, 2.0 mol %) in DCM (400 mL) at 0° C. The resulting mixture was kept stirring at this temperature for 1.5 h and then concentrated. The crude product was directly used in the next step.

Step p: Chloromethyl methyl ether (32.6 g, 34 mL, 454 mmol, 3.0 equiv.) was added dropwise to a solution of the crude product from step o (151 mmol) and diisopropylethylamine (58.7 g, 79 mL, 454 mmol, 3.0 equiv.) in DCM (300 mL). The resulting solution was then heated at reflux overnight, cooled to room temperature and then directly concentrated on Celite and purified by flash chromatography (SiO$_2$, 10 to 20% EtOAc/Hex) to afford the protected indanol product (31.4 g, 95.9 mmol, 64% yield over 2 steps) and recovered free indanol (97% ee, 6.2 g, 21.9 mmol, 14% yield).

Step q: A 250-mL flask was charged with the product from step p (15.0 g, 45.8 mmol, 1.0 equiv.), B$_2$Pin$_2$ (12.2 g, 48.1 mmol, 1.05 equiv.), Pd(dppf)Cl$_2$ (3.35 g, 4.58 mmol, 10 mol %), KOAc (8.99 g, 91.6 mmol, 2.0 equiv.) and 1,4-dioxane (120 mL). The reaction mixture was degassed with N$_2$ bubbling for 10 min before being heated. After stirring at 100° C. overnight, the reaction mixture was cooled, concentrated on Celite and purified by flash chromatography (SiO$_2$, 0 to 15% EtOAc/Hex) to afford the product (14.2 g, 37.9 mmol, 83% yield) as pale-yellow liquid.

Step r: A 500-mL flask was charged with the product from i (22.8 g, 50.4 mmol, 1.0 equiv.), the product from step q (20.8 g, 55.4 mmol, 1.1 equiv.), Pd(dppf)Cl$_2$ (3.66 g, 5.04 mmol, 10 mol %), Na$_2$CO$_3$ (10.6 g, 100 mmol, 2.0 equiv.), 1,4-dioxane (200 mL) and H$_2$O (50 mL). The reaction mixture was degassed with N$_2$ bubbling for 10 min before being heated to 80° C. and stirred overnight. The reaction mixture was cooled, concentrated onto Celite and purified by flash chromatography (SiO$_2$, 0 to 15% EtOAc/Hex) to afford the desired product (19.3 g, 35.1 mmol, 70% yield).

Step s: A mixture of the product from step r (8.20 g, 14.9 mmol, 1.0 equiv.), Pd/C (10 wt % Pd, 1.58 g, 10 mol %) in MeOH (75 mL) was shaken in parr hydrogenator under H$_2$ (50 psi) for 2 h. After this time LCMS showed no remaining starting material. The reaction mixture was then filtered through Celite and concentrated to afford the product (7.25 g, 13.1 mmol, 88% yield).

Step t: To a solution of the product from step s (7.25 g, 13.1 mmol, 1.0 equiv.) in THF (65 mL) was added TBAF (1M in THF, 14 mL, 1.1 equiv.) at 0° C. The resulting solution was stirred at 0° C. for 15 min, and then quenched by saturated NH$_4$Cl (aq.). The aqueous phase was extracted with EtOAc×2. The combined organic layer was then washed with brine, dried over Na$_2$SO$_4$, concentrated and purified by flash chromatography (SiO$_2$, 10 to 15% EtOAc/Hex) to afford the product (3.78 g, 8.6 mmol, 66% yield).

Step u: To a solution of 4-(trimethylsilyl)morpholine (6.28 g, 39.4 mmol, 3.55 equiv.) in DCM (70 mL) was added deoxofluor (2.7M in toluene, 14 mL, 3.5 equiv.) dropwise at −78° C. The resulting solution was then stirred at this temperature for 5 min and warmed to room temperature for 1 h. The reaction mixture was then cooled back to −78° C. and a solution of the product from step t (4.88 g, 11.1 mmol, 1.0 equiv.) in DCM (15 mL) was added dropwise. The resulting solution was then stirred at this temperature for 5 min, after which the reaction vessel was warmed to room temperature and stirred for an additional 1 h. The reaction was quenched with saturated NaHCO$_3$ (aq.). The aqueous layer was extracted with DCM×2. The combined organic layer was then washed with brine, dried over Na$_2$SO$_4$, concentrated and purified by flash chromatography (SiO$_2$, 0 to 20% EtOAc/Hex) to afford the product (3.33 g, 7.6 mmol, 68% yield).

Step v: A flask containing the product from step u (50 mg, 0.114 mmol), o-Tolylboronic acid (0.14 mmol), and Pd-SPhos-G2 (9 mg, 0.011 mmol) was evacuated and backfilled with nitrogen. Degassed dioxane (1.1 mL) and 1.0M Na$_2$CO$_3$ (0.46 mL) were added and mixture heated to 100° C. for two hours. After cooling to room temperature, the reaction was partition between EtOAc and water. The organics were dried over MgSO$_4$ and concentrated.

Step w: The crude product from step v was dissolved in CH$_2$Cl$_2$ (1 mL) and TFA (0.2 mL) was added. After stirring at room temperature for 4 hours, the reaction was diluted with toluene and evaporate under reduced pressure. The product was reconstituted in DMSO and purified by reverse phase HPLC (gradient MeCN/H$_2$O) to afford the desired product (39 mg, 71% yield) as a white solid after lyophilization. $^1$H NMR (400 MHZ, Chloroform-d) δ 7.51 (d, J=8.6 Hz, 1H), 7.40 (dd, J=7.7, 2.2 Hz, 1H), 7.32-7.17 (m, 4H), 6.96 (d, J=7.9 Hz, 1H), 6.36 (d, J=7.9 Hz, 1H), 5.62 (dt, J=50.1, 3.7 Hz, 1H), 4.81 (d, J=85.0 Hz, 1H), 4.53 (s, 1H), 3.83 (ddd, J=21.6, 16.7, 10.0 Hz, 1H), 3.41 (t, J=16.7 Hz, 1H), 2.61-2.40 (m, 1H), 2.26-2.11 (m, 2H), 2.10 (s, 3H), 1.97-1.81 (m, 1H). ESI MS [M+H]$^+$ for C$_{27}$H$_{21}$F$_4$NO, calcd 452.2, found 452.3.

Example 145: 5-[(3S)-7-[(1R,4S)-8-cyano-4,6-difluoro-1,2,3,4-tetrahydronaphthalen-1-yl]-2,2-difluoro-3-hydroxy-1,3-dihydroinden-4-yl]-1-methylpyrazole-4-carbonitrile

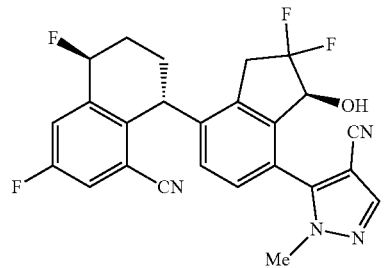 [SMILES: Cn1ncc(C#N)c1-c1ccc([C@H]2CC[C@H](F)c3cc(F)cc(C#N)c32)c2c1[C@H](O)C(F)(F)C2]

The title compound was prepared in a similar fashion to Example 144. $^1$H NMR (400 MHz, CDCl$_3$) δ 7.85 (s, 1H), 7.53 (d, J=8.9 Hz, 1H), 7.41 (dt, J=7.6, 2.2 Hz, 1H), 7.06 (d, J=7.8 Hz, 1H), 6.44 (d, J=8.0 Hz, 1H), 5.62 (dt, J=50.0, 3.7 Hz, 1H), 5.28-5.12 (m, 1H), 4.54 (app. s, 1H), 3.98-3.76 (m, 1H), 3.71 (s, 3H), 3.60-3.40 (m, 1H), 2.59-2.41 (m, 1H), 2.34-1.93 (m, 2H), 1.86 (d, J=14.2 Hz, 1H). ESI MS [M+H]$^+$ for C$_{25}$H$_{18}$F$_4$NO, calcd 467.1, found 467.3.

Example 146: (5S,8R)-8-[(1S)-2,2-difluoro-1-hydroxy-7-(1-methyl-1H-1,2,3-triazol-4-yl)-2,3-dihydro-1H-inden-4-yl]-3,5-difluoro-5,6,7,8-tetrahydronaphthalene-1-carbonitrile

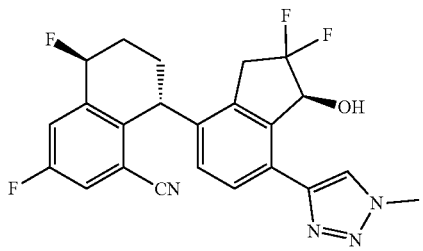 [SMILES: Cn1cc(-c2ccc([C@H]3CC[C@H](F)c4cc(F)cc(C#N)c43)c3c2[C@H](O)C(F)(F)C3)nn1]

The title compound was prepared in a similar fashion to Example 144. $^1$H NMR (400 MHz, CDCl$_3$): δ 7.83 (s, 1H), 7.53-7.48 (m, 1H), 7.41-7.36 (m, 1H), 7.06 (d, J=7.9 Hz, 1H), 6.46 (d, J=7.9 Hz, 1H), 5.60 (dt, J=50.0, 3.7 Hz, 1H), 4.83 (dd, J=11.9, 5.0 Hz, 1H), 4.56-4.49 (m, 1H), 3.93 (s, 3H), 3.91-3.78 (m, 1H), 3.42 (td, J=16.9, 2.6 Hz, 1H), 2.96 (dd, J=5.2, 1.9 Hz, 1H), 2.56-2.44 (m, 1H), 2.23-2.04 (m, 2H), 1.87-1.76 (m, 1H). ESI MS [M+H]$^+$ for C$_{23}$H$_{18}$F$_4$N$_4$O, calcd 442.1, found 442.1.

Example 147: (5S,8R)-8-[(1S)-2,2-difluoro-1-hydroxy-7-(3-methyltriazol-4-yl)-1,3-dihydroinden-4-yl]-3,5-difluoro-5,6,7,8-tetrahydronaphthalene-1-carbonitrile

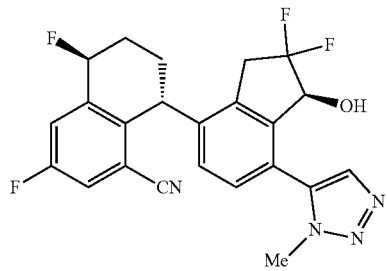 [SMILES: Cn1nncc1-c1ccc([C@H]2CC[C@H](F)c3cc(F)cc(C#N)c32)c2c1[C@H](O)C(F)(F)C2]

The title compound was prepared in a similar fashion to Example 144. $^1$H NMR (400 MHz, CDCl$_3$) δ 7.87 (s, 1H), 7.53 (d, J=7.6 Hz, 1H), 7.42-7.38 (m, 1H), 7.08 (d, J=8.0 Hz, 1H), 6.48 (d, J=7.9 Hz, 1H), 5.62 (dt, J=49.9, 3.7 Hz, 1H), 4.83 (d, J=11.7 Hz, 1H), 4.55 (s, 1H), 3.96 (s, 3H), 3.94-3.81 (m, 1H), 3.52-3.38 (m, 1H), 2.59-2.44 (m, 1H), 2.27-1.97 (m, 2H), 1.90-1.79 (m, 1H). ESI MS [M+H]$^+$ for C$_{23}$H$_{18}$F$_4$N$_4$O, calcd 443.1, found 443.3.

Example 148: (5S,8R)-8-[(1S)-2,2-difluoro-1-hydroxy-7-(2-methyl-1,3-oxazol-5-yl)-1,3-dihydroinden-4-yl]-3,5-difluoro-5,6,7,8-tetrahydronaphthalene-1-carbonitrile

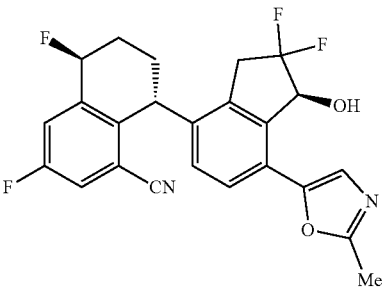 [SMILES: Cc1ncc(-c2ccc([C@H]3CC[C@H](F)c4cc(F)cc(C#N)c43)c3c2[C@H](O)C(F)(F)C3)o1]

The title compound was prepared in a similar fashion to Example 144. $^1$H NMR (400 MHz, CDCl$_3$) δ 7.51 (d, J=6.7 Hz, 1H), 7.46 (s, 1H), 7.42 (d, J=8.2 Hz, 1H), 7.38 (dt, J=7.7, 2.3 Hz, 1H), 6.39 (d, J=8.1 Hz, 1H), 5.61 (dt, J=50.1, 3.7 Hz, 1H), 5.14 (d, J=12.8 Hz, 1H), 4.54-4.40 (m, 1H), 3.95-3.77 (m, 1H), 3.43 (t, J=17.3 Hz, 1H), 2.53 (s, 3H), 2.52-2.41 (m, 1H), 2.26-1.95 (m, 2H), 1.86-1.73 (m, 1H). ESI MS [M+H]$^+$ for C$_{24}$H$_{18}$F$_4$N$_2$O$_2$, calcd 443.1, found 443.2.

Example 149: 2-amino-5-[(3S)-7-[(1R,4S)-8-cyano-4,6-difluoro-1,2,3,4-tetrahydronaphthalen-1-yl]-2,2-difluoro-3-hydroxy-1,3-dihydroinden-4-yl]pyridine-4-carbonitrile

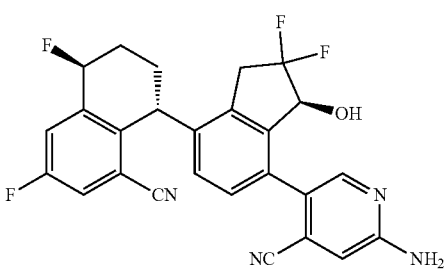

The title compound was prepared in a similar fashion to Example 144. $^1$H NMR (400 MHz, Chloroform-d) δ 8.38 (s, 1H), 7.51 (d, J=7.7 Hz, 1H), 7.44-7.36 (m, 1H), 7.12 (d, J=8.0 Hz, 1H), 6.78 (s, 1H), 6.38 (d, J=8.0 Hz, 1H), 5.61 (dt, J=49.9, 3.3 Hz, 1H), 5.10 (dd, J=11.0, 3.5 Hz, 1H), 4.80 (s, 2H), 4.58-4.50 (m, 1H), 3.96-3.79 (m, 1H), 3.54-3.39 (m, 1H), 2.55-2.43 (m, 1H), 2.23-1.98 (m, 2H), 1.84 (d, J=13.1 Hz, 1H). ESI MS [M+H]$^+$ for C$_{26}$H$_{18}$F$_4$N$_4$O, calcd 479.1, found 479.3.

Example 150: (5S,8R)-8-[(1S)-2,2-difluoro-1-hydroxy-7-(1-methylpyrazol-4-yl)-1,3-dihydroinden-4-yl]-3,5-difluoro-5,6,7,8-tetrahydronaphthalene-1-carbonitrile

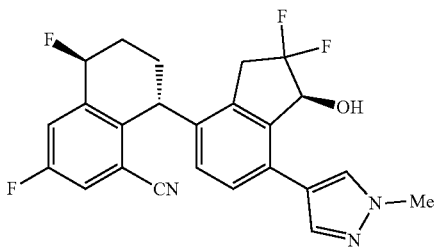 [SMILES: Cn1cc(-c2ccc([C@H]3CC[C@H](F)c4cc(F)cc(C#N)c43)c3c2[C@H](O)C(F)(F)C3)cn1]

The title compound was prepared in a similar fashion to Example 144. $^1$H NMR (400 MHz, Chloroform-d) δ 7.89 (s, 1H), 7.77 (d, J=0.8 Hz, 1H), 7.50 (d, J=8.8 Hz, 1H), 7.37 (dt, J=7.4, 2.4 Hz, 1H), 7.23 (d, J=8.1 Hz, 1H), 6.33 (d, J=8.0 Hz, 1H), 5.61 (dt, J=50.2, 3.7 Hz, 1H), 4.93 (d, J=12.3 Hz, 1H), 4.50-4.45 (m, 1H), 3.96 (s, 3H), 3.93-3.78 (m, 1H), 3.43 (t, J=17.3 Hz, 1H), 2.53-2.41 (m, 1H), 2.20-1.99 (m, 2H), 1.81 (dd, J=13.9, 4.1 Hz, 1H). ESI MS [M+H]$^+$ for $C_{24}H_{19}F_4N_3O$, calcd 442.2, found 442.3.

Example 151: (5S,8R)-8-[(1S)-2,2-difluoro-1-hydroxy-7-(4-methyl-1,3-oxazol-5-yl)-1,3-dihydroinden-4-yl]-3,5-difluoro-5,6,7,8-tetrahydronaphthalene-1-carbonitrile

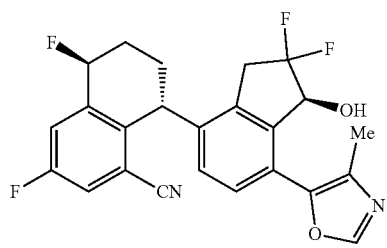 [SMILES: Cc1ncoc1-c1ccc([C@H]2CC[C@H](F)c3cc(F)cc(C#N)c32)c2c1[C@H](O)C(F)(F)C2]

The title compound was prepared in a similar fashion to Example 144. $^1$H NMR (400 MHz, Chloroform-d) δ 7.91 (s, 1H), 7.51 (d, J=7.7 Hz, 1H), 7.39 (dt, J=7.7, 2.2 Hz, 1H), 7.23 (d, J=8.1 Hz, 1H), 6.39 (d, J=8.0 Hz, 1H), 5.60 (dt, J=50.0, 3.5 Hz, 1H), 5.33 (d, J=12.4 Hz, 1H), 4.56-4.48 (m, 1H), 3.95-3.76 (m, 1H), 3.42 (td, J=16.6, 4.1 Hz, 1H), 2.57-2.38 (m, 1H), 2.24-1.96 (m, 2H), 1.87-1.76 (m, 1H). ESI MS [M+H]$^+$ for $C_{24}H_{18}F_{64}N_2O_2$, calcd 443.4, found 443.2.

Example 152: (5S,8R)-8-[(1S,2R)-7-chloro-2-fluoro-1-(methoxymethoxy)-2,3-dihydro-1H-inden-4-yl]-3,5-difluoro-5,6,7,8-tetrahydronaphthalene-1-carbonitrile The title compound was prepared in a similar fashion to Example 144. $^1$H NMR (400 MHz, Chloroform-d) δ 7.51-7.48 (m, 1H), 7.40-7.39 (m, 1H), 7.35-7.34 (m, 1H), 6.96-6.92 (m, 1H), 6.40-6.36 (m, 1H), 5.59 (ddd, J=50.1, 3.7, 3.7 Hz, 1H), 5.39-5.22 (m, 1H), 5.08-4.97 (m, 1H), 4.62-4.60 (m, 1H), 3.61-3.60 (m, 3H), 3.59-3.46 (m, 1H), 3.24-3.04 (m, 1H), 2.51-2.42 (m, 1H), 2.19-1.99 (m, 3H), 1.89-1.78 (m, 5H). ESI MS [M+H]$^+$ for $C_{25}H_{22}F_3N_3O$, calcd 438.2, found 438.1.

Example 153: (5S,8R)-8-[(1S)-7-(2-aminopyridin-3-yl)-2,2-difluoro-1-hydroxy-1,3-dihydroinden-4-yl]-3,5-difluoro-5,6,7,8-tetrahydronaphthalene-1-carbonitrile

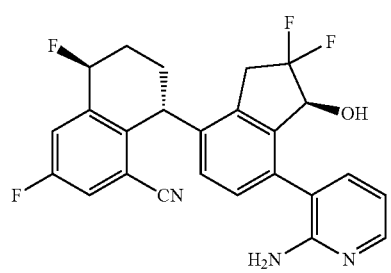

The title compound was prepared in a similar fashion to Example 144. $^1$H NMR (400 MHz, Chloroform-d) δ 8.01 (s, 1H), 7.51 (dt, J=8.2, 2.0 Hz, 1H), 7.46-7.29 (m, 2H), 7.03 (d, J=7.9 Hz, 1H), 6.76 (s, 1H), 6.42 (d, J=7.9 Hz, 1H), 5.61 (dt, J=50.0, 3.7 Hz, 1H), 4.91 (s, 1H), 4.49 (d, J=35.4 Hz, 2H), 3.85 (ddd, J=21.8, 16.6, 9.5 Hz, 1H), 3.48-3.29 (m, 1H), 2.49 (td, J=12.7, 5.6 Hz, 1H), 2.28-2.07 (m, 2H), 1.85 (dq, J=13.8, 3.9 Hz, 1H). ESI MS [M+H]$^+$ for $C_{25}H_{19}F_4N_3O$ calcd. 454.1, found 454.1.

Example 154: (5S,8R)-8-[(1S)-2,2-difluoro-1-hydroxy-7-(4-methyl-1H-pyrazol-5-yl)-1,3-dihydroinden-4-yl]-3,5-difluoro-5,6,7,8-tetrahydronaphthalene-1-carbonitrile

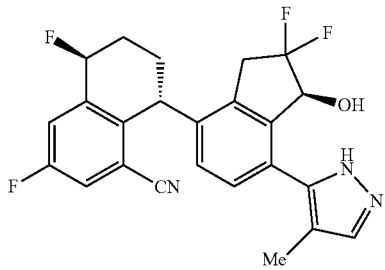 [SMILES: Cc1cn[nH]c1-c1ccc([C@H]2CC[C@H](F)c3cc(F)cc(C#N)c32)c2c1[C@H](O)C(F)(F)C2]

The title compound was prepared in a similar fashion to Example 144. $^1$H NMR (400 MHz, Chloroform-d) δ 7.53-7.48 (m, 1H), 7.47 (s, 1H), 7.38 (dt, J=7.8, 2.3 Hz, 1H), 7.29 (d, J=8.0 Hz, 1H), 6.38 (d, J=8.0 Hz, 1H), 5.77-5.45 (m, 1H), 4.93 (d, J=15.8 Hz, 1H), 4.60-4.45 (m, 1H), 3.93 (ddd, J=25.9, 16.6, 9.2 Hz, 1H), 3.47 (t, J=17.5 Hz, 1H), 2.50 (ddt, J=17.7, 11.7, 5.2 Hz, 1H), 2.22 (s, 3H), 2.19-2.04 (m, 1H), 1.94-1.80 (m, 1H). ESI MS [M+H]$^+$ for $C_{24}H_{19}F_4N_3O$ calcd. 442.1, found 442.1.

Example 155: (5S,8R)-8-[(1S)-7-(3-cyano-2-methylphenyl)-2,2-difluoro-1-hydroxy-1,3-dihydroinden-4-yl]-3,5-difluoro-5,6,7,8-tetrahydronaphthalene-1-carbonitrile

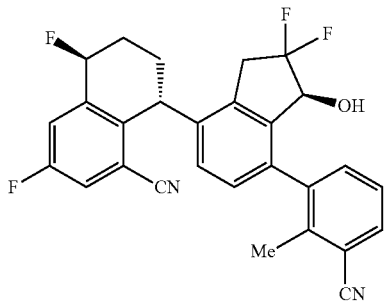 [SMILES: Cc1c(C#N)cccc1-c1ccc([C@H]2CC[C@H](F)c3cc(F)cc(C#N)c32)c2c1[C@H](O)C(F)(F)C2]

The title compound was prepared in a similar fashion to Example 144. $^1$H NMR (400 MHz, Chloroform-d) δ 7.69-7.60 (m, 1H), 7.61-7.47 (m, 2H), 7.47-7.28 (m, 2H), 6.92 (t, J=7.1 Hz, 1H), 6.40 (d, J=7.9 Hz, 1H), 5.72-5.52 (m, 1H), 4.73 (ddd, J=68.1, 11.7, 6.0 Hz, 1H), 4.52 (s, 1H), 3.83 (td, J=19.2, 17.8, 9.7 Hz, 1H), 3.42 (t, J=17.1 Hz, 1H), 2.59-2.43 (m, 1H), 2.30 (s, 3H), 2.28-2.04 (m, 3H), 1.93-1.79 (m, 1H). ESI MS [M+NH+]$^+$ for $C_{28}H_{20}F_4N_2O$ calcd. 494.2, found 494.2.

Example 156: (5S,8R)-8-[(1S)-2,2-difluoro-1-hydroxy-7-pyridin-4-yl-1,3-dihydroinden-4-yl]-3,5-difluoro-5,6,7,8-tetrahydronaphthalene-1-carbonitrile

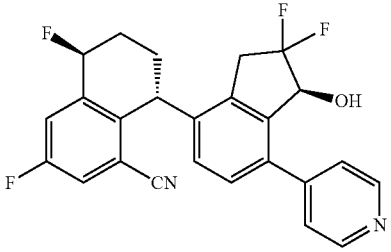 [SMILES: N#Cc1cc(F)cc2c1[C@@H](c1ccc(-c3ccncc3)c3c1CC(F)(F)[C@H]3O)CC[C@@H]2F]

The title compound was prepared in a similar fashion to Example 144. $^1$H NMR (400 MHz, Chloroform-d) δ 8.67-8.62 (m, 2H), 7.66-7.49 (m, 2H), 7.24-7.14 (m, 3H), 6.61 (d, J=8.0 Hz, 1H), 4.95 (d, J=11.0 Hz, 1H), 4.47 (dd, J=6.1, 3.2 Hz, 1H), 3.89 (ddd, J=24.5, 16.6, 8.9 Hz, 1H), 3.40 (t, J=16.9 Hz, 1H), 3.11-2.81 (m, 2H), 2.16 (dddd, J=13.4, 10.7, 6.1, 4.0 Hz, 1H), 1.97-1.73 (m, 2H). ESI MS [M+OH]$^+$ for $C_{25}H_{18}F_4N_2O$ calcd. 420.1, found 420.1.

Example 157: (5S,8R)-3,5-difluoro-8-[(1S,2R)-2-fluoro-1-hydroxy-7-(2-methylpyrazol-3-yl)-2,3-dihydro-1H-inden-4-yl]-5,6,7,8-tetrahydronaphthalene-1-carbonitrile

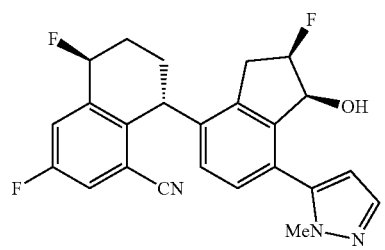 [SMILES: Cn1nccc1-c1ccc([C@H]2CC[C@H](F)c3cc(F)cc(C#N)c32)c2c1[C@H](O)[C@H](F)C2]

The title compound was prepared in a similar fashion to Example 144. $^1$H NMR (400 MHz, Chloroform-d) δ 7.56-7.47 (m, 2H), 7.40 (ddd, J=7.6, 2.7, 1.7 Hz, 1H), 7.04 (d, J=7.9 Hz, 1H), 6.43-6.35 (m, 2H), 5.61 (dt, J=50.1, 3.7 Hz, 1H), 5.38 (dt, J=5.8, 4.6 Hz, OH), 5.24 (dt, J=5.8, 4.5 Hz, OH), 5.11 (dd, J=10.0, 4.7 Hz, 1H), 4.66-4.59 (m, 1H), 3.76 (s, 3H), 3.65-3.49 (m, 1H), 3.20 (ddd, J=18.8, 16.4, 6.0 Hz, 1H), 2.48 (tdd, J=12.5, 5.8, 3.3 Hz, 1H), 2.26 (s, 1H), 2.20-1.98 (m, 2H), 1.87-1.76 (m, 1H). ESI MS [M+H]$^+$ for $C_{24}H_{20}F_3N_3O$ calcd. 424.2, found 424.1.

Example 158: (5S,8R)-8-[(1S)-2,2-difluoro-1-hydroxy-7-(1,3-thiazol-5-yl)-1,3-dihydroinden-4-yl]-3,5-difluoro-5,6,7,8-tetrahydronaphthalene-1-carbonitrile

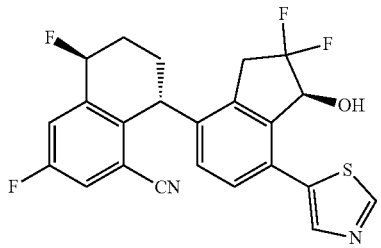 [SMILES: N#Cc1cc(F)cc2c1[C@@H](c1ccc(-c3cncs3)c3c1CC(F)(F)[C@H]3O)CC[C@@H]2F]

The title compound was prepared in a similar fashion to Example 144. $^1$H NMR (400 MHz, Chloroform-d) δ 8.85 (s, 1H), 8.33 (s, 1H), 7.57-7.48 (m, 1H), 7.43-7.35 (m, 1H), 7.28 (s, 1H), 6.39 (d, J=8.0 Hz, 1H), 5.61 (dt, J=50.0, 3.6 Hz, 1H), 5.01 (dd, J=11.7, 4.4 Hz, 1H), 4.58-4.47 (m, 1H), 3.91 (ddd, J=25.2, 16.7, 8.6 Hz, 1H), 3.44 (t, J=17.1 Hz, 1H), 3.31 (s, 1H), 2.50 (ddd, J=18.7, 13.3, 4.4 Hz, 1H), 2.25-1.96 (m, 2H), 1.87-1.74 (m, 1H), 0.96-0.77 (m, 1H). ESI MS [M+H]$^+$ for $C_{23}H_{16}F_4N_2OS$ calcd. 445.1, found 445.1.

Example 159: (5S,8R)-8-[(1S)-2,2-difluoro-1-hydroxy-7-(2-methylpyridin-3-yl)-1,3-dihydroinden-4-yl]-3,5-difluoro-5,6,7,8-tetrahydronaphthalene-1-carbonitrile

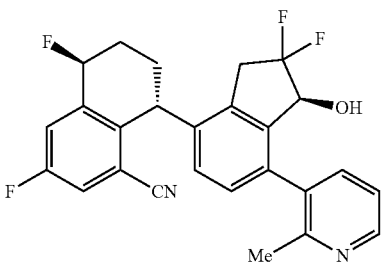

The title compound was prepared in a similar fashion to Example 144. $^1$H NMR (400 MHz, Chloroform-d) δ 8.39 (dd, J=4.9, 1.8 Hz, 1H), 7.57 (br s, 1H) 7.51 (ddd, J=8.4, 2.8, 1.3 Hz, 1H), 7.40 (dt, J=7.7, 2.3 Hz, 1H), 7.15 (ddd, J=7.7, 4.9, 0.7 Hz, 1H), 6.95 (d, J=7.8 Hz, 1H), 6.38 (d, J=7.9 Hz, 1H), 5.62 (dt, J=50.1, 3.7 Hz, 1H), 4.80 (s, 1H), 4.62-4.43 (m, 1H), 3.84 (ddd, J=20.8, 16.8, 10.1 Hz, 1H), 3.41 (td, J=16.6, 4.0 Hz, 1H), 2.63-2.39 (m, 1H), 2.25 (s, 3H), 2.22-2.01 (m, 1H), 1.96-1.62 (m, 2H). ESI MS [M+H]$^+$ for $C_{26}H_{20}F_4N_2O$ calcd. 452.2, found 452.2.

Example 160: (5S,8R)-8-[(1S)-2,2-difluoro-1-hydroxy-7-pyridin-3-yl-1,3-dihydroinden-4-yl]-3,5-difluoro-5,6,7,8-tetrahydronaphthalene-1-carbonitrile

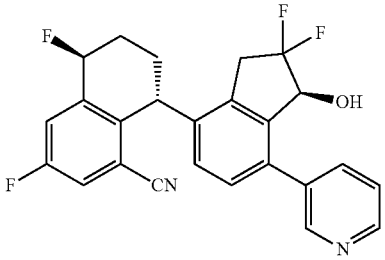

The title compound was prepared in a similar fashion to Example 144. $^1$H NMR (400 MHz, Chloroform-d) δ 8.89 (s, 1H), 8.61 (s, 1H) 7.99 (d, J=8.0 Hz, 1H), 7.58-7.47 (m, 1H), 7.39 (dt, J=7.2, 2.2 Hz, 2H), 7.16 (d, J=8.0 Hz, 1H), 6.43 (d, J=8.0 Hz, 1H), 5.63 (dt, J=50.2, 3.6 Hz, 1H), 4.93 (d, J=10.9 Hz, 1H), 4.56 (s, 1H), 3.93 (ddd, J=24.4, 16.5, 8.7 Hz, 1H), 3.57 (s, 1H), 3.43 (t, J=16.7 Hz, 1H), 2.58-2.43 (m, 1H), 2.28-2.02 (m, 1H), 1.92-1.76 (m, 1H). ESI MS [M+H]$^+$ for $C_{25}H_{18}F_4N_2O$ calcd. 439.1, found 439.1.

Example 161: (5S,8R)-8-[(1S)-2,2-difluoro-1-hydroxy-7-(2-methyl-6-oxo-1H-pyridin-3-yl)-1,3-dihydroinden-4-yl]-3,5-difluoro-5,6,7,8-tetrahydronaphthalene-1-carbonitrile

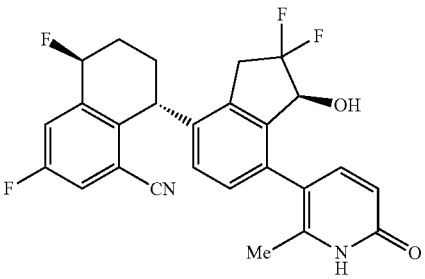 [SMILES: Cc1[nH]c(=O)ccc1-c1ccc([C@H]2CC[C@H](F)c3cc(F)cc(C#N)c32)c2c1[C@H](O)C(F)(F)C2]

The title compound was prepared in a similar fashion to Example 144. $^1$H NMR (400 MHz, DMSO-$d_6$): δ 11.76 (bs, 1H), 7.95 (dd, J=8.2, 2.3 Hz, 1H), 7.84 (d, J=8.7 Hz, 1H), 7.35 (d, J=9.3 Hz, 1H), 6.94 (d, J=7.9 Hz, 1H), 6.33 (d, J=7.9 Hz, 1H), 6.17 (d, J=9.3 Hz, 1H), 5.77 (d, J=49.7 Hz, 1H), 4.82 (d, J=12.0 Hz, 1H), 4.59 (s, 1H), 3.73-3.32 (m, 2H), 2.31 (d, J=11.3 Hz, 1H), 2.16-1.77 (m, 5H), 1.68 (d, J=13.8 Hz, 1H).

Example 162: (5S,8R)-8-[(1S)-7-(2-cyanophenyl)-2,2-difluoro-1-hydroxy-1,3-dihydroinden-4-yl]-3,5-difluoro-5,6,7,8-tetrahydronaphthalene-1-carbonitrile

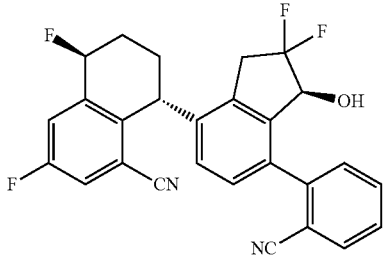

The title compound was prepared in a similar fashion to Example 144. $^1$H NMR (400 MHz, DMSO-$d_6$): δ 7.97 (dt, J=8.3, 2.3 Hz, 1H), 7.93-7.84 (m, 2H), 7.73 (td, J=7.7, 1.3 Hz, 1H), 7.67-7.62 (m, 1H), 7.55 (td, J=7.6, 1.2 Hz, 1H), 7.15 (d, J=7.9 Hz, 1H), 6.43 (d, J=7.9 Hz, 1H), 6.00 (d, J=6.9 Hz, 1H), 5.79 (d, J=49.7 Hz, 1H), 5.16 (dt, J=12.4, 6.5 Hz, 1H), 4.65 (s, 1H), 3.64 (tq, J=29.8, 15.5, 14.6 Hz, 2H), 2.32 (dd, J=16.9, 6.1 Hz, 1H), 2.15-1.79 (m, 2H), 1.74 (d, J=13.8 Hz, 1H).

Example 163: (5S,8R)-8-[(1S)-2,2-difluoro-7-(4-fluoropyridin-3-yl)-1-hydroxy-2,3-dihydro-1H-inden-4-yl]-3,5-difluoro-5,6,7,8-tetrahydronaphthalene-1-carbonitrile

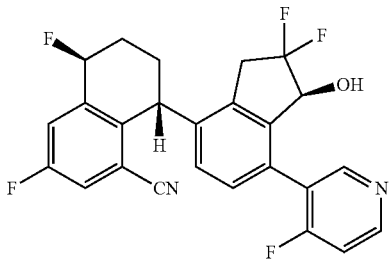 [SMILES: N#Cc1cc(F)cc2c1[C@@H](c1ccc(-c3cnccc3F)c3c1CC(F)(F)[C@H]3O)CC[C@@H]2F]

The title compound was prepared in a similar fashion to Example 144. $^1$H NMR (400 MHz, Chloroform-d) δ 8.95 (d, J=7.9 Hz, 1H), 8.74 (t, J=6.0 Hz, 1H), 7.56-7.38 (m, 3H), 7.15 (d, J=8.0 Hz, 1H), 6.82 (s, br., 1H), 6.44 (d, J=8.0 Hz, 1H), 5.61 (dt, J=50.0, 3.5 Hz, 1H), 5.18 (dd, J=10.8, 6.1 Hz, 1H), 4.59-4.52 (m, 1H), 3.82 (ddd, J=16.9, 14.0, 11.1 Hz, 1H), 3.43 (m, 1H), 2.51 (tdd, J=13.4, 6.2, 3.1 Hz, 1H), 2.21-1.95 (m, 2H), 1.86-1.77 (m, 1H). ESI MS [M+H]$^+$ for $C_{25}H_{18}F_5N_2O$, calcd 457.1, found 457.0.

Example 164: (5S,8R)-8-[(1S)-2,2-difluoro-1-hydroxy-7-(2-oxo-2,3-dihydro-1H-indol-4-yl)-2,3-dihydro-1H-inden-4-yl]-3,5-difluoro-5,6,7,8-tetrahydronaphthalene-1-carbonitrile

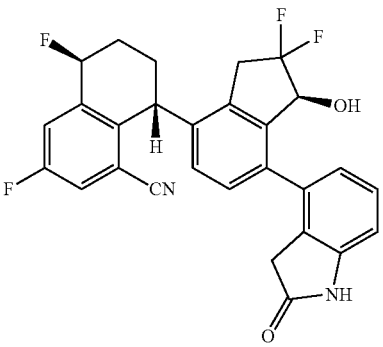

The title compound was prepared in a similar fashion to Example 144. $^1$H NMR (400 MHz, Chloroform-d) δ 8.40 (s, 1H), 7.55-7.47 (m, 1H), 7.39 (dt, J=7.6, 2.1 Hz, 1H), 7.22 (t, J=7.8 Hz, 1H), 7.06 (d, J=8.0 Hz, 1H), 7.01 (d, J=7.6 Hz, 1H), 6.79 (d, J=7.7 Hz, 1H), 6.36 (d, J=7.9 Hz, 1H), 5.62 (dt, J=50.0, 3.7 Hz, 1H), 4.91 (dd, J=11.5, 6.4 Hz, 1H), 4.55-4.48 (m, 1H), 3.83 (ddd, J=21.3, 16.7, 10.0 Hz, 1H), 3.48-3.34 (m, 2H), 3.26 (d, J=22.8 Hz, 1H), 3.11 (d, J=6.5 Hz, 1H), 2.56-2.42 (m, 1H), 2.21-2.04 (m, 2H), 1.90-1.81 (m, 1H). ESI MS [M+H]$^+$ for $C_{28}H_{21}F_4N_2O_2$, calcd 493.2, found 493.0.

Example 165: (5S,8R)-8-[(1S)-7-[2-(aminomethyl)phenyl]-2,2-difluoro-1-hydroxy-2,3-dihydro-1H-inden-4-yl]-3,5-difluoro-5,6,7,8-tetrahydronaphthalene-1-carbonitrile

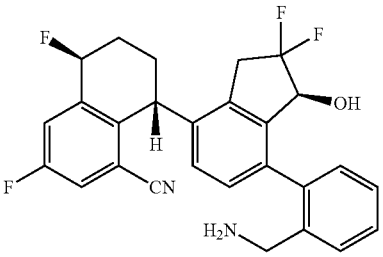

The title compound was prepared in a similar fashion to Example 144. $^1$H NMR (400 MHz, Chloroform-d) δ 7.55-7.47 (m, 1H), 7.32-7.42 (m, 3H), 7.30-7.18 (m, 2H), 6.88 (d, J=7.8 Hz, 1H), 6.33 (d, J=7.8 Hz, 1H), 5.62 (dt, J=50.0, 4.0 Hz, 1H), 4.75 (dd, J=11.9, 1.8 Hz, 1H), 4.51 (m, 1H), 3.83 (ddd, J=22.8, 16.4, 9.1 Hz, 1H), 3.62 (d, J=12.2 Hz, 1H), 3.49 (d, J=12.2 Hz, 1H), 3.38 (td, J=16.3, 3.1 Hz, 1H), 2.51 (td, J=14.4, 13.8, 7.5 Hz, 1H), 2.26-2.04 (m, 2H), 2.01 (s, 2H), 1.90 (dq, J=13.1, 4.0 Hz, 1H). ESI MS [M+H]$^+$ for $C_{27}H_{23}F_4N_2O$, calcd 467.2, found 467.0.

Example 166: (5S,8R)-8-[(1S)-7-(1,5-dimethyl-1H-pyrazol-4-yl)-2,2-difluoro-1-hydroxy-2,3-dihydro-1H-inden-4-yl]-3,5-difluoro-5,6,7,8-tetrahydronaphthalene-1-carbonitrile

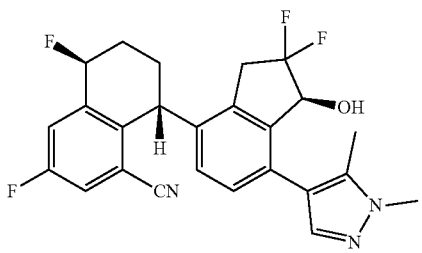

The title compound was prepared in a similar fashion to Example 144. $^1$H NMR (400 MHz, Chloroform-d, appearing as ~2:1 rotamers) δ 8.14-7.27 (m, 3H), 6.99 (d, J=8.0 Hz, 1H), 6.40 (d, J=8.0 Hz, 1H), 5.61 (dt, J=50.0, 3.7 Hz, 1H), 4.95-4.85 (m, 1H), 4.82 (d, J=11.6 Hz, 1H), 4.51 (m, 1H), 4.05-3.14 (m, 5H), 2.98-1.68 (m, 7H). ESI MS [M+H]$^+$ for $C_{25}H_{22}F_4N_3O$, calcd 456.2, found 456.1.

Example 167: (5S,8R)-8-[(1S)-2,2-difluoro-1-hydroxy-7-(4-methyl-1,3-thiazol-5-yl)-2,3-dihydro-1H-inden-4-yl]-3,5-difluoro-5,6,7,8-tetrahydronaphthalene-1-carbonitrile

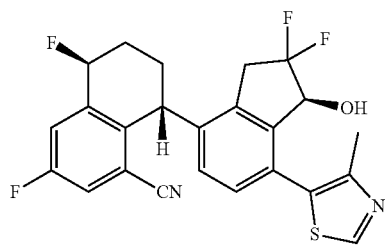

The title compound was prepared in a similar fashion to Example 144. $^1$H NMR (400 MHz, Chloroform-d) δ 8.71 (s, 1H), 7.51 (dt, J=8.5, 2.0 Hz, 1H), 7.40 (dt, J=7.6, 2.2 Hz, 1H), 7.09 (d, J=7.9 Hz, 1H), 6.37 (d, J=7.9 Hz, 1H), 5.62 (dt, J=50.0, 3.6 Hz, 1H), 5.02-4.92 (m, 1H), 4.56-4.49 (m, 1H), 3.84 (ddd, J=21.0, 16.8, 10.2 Hz, 1H), 3.42 (td, J=16.7, 3.8 Hz, 1H), 2.87 (dd, J=6.4, 1.6 Hz, 1H), 2.50 (tq, J=13.2, 5.4, 4.5 Hz, 1H), 2.33 (s, 3H), 2.25-2.02 (m, 2H), 2.00 (s, 3H), 1.89-1.80 (m, 1H). ESI MS [M+H]$^+$ for $C_{24}H_{19}F_4N_2OS$, calcd 459.1, found 459.0.

Example 168: (5S,8R)-8-[(1S)-7-(2-amino-4-methylpyrimidin-5-yl)-2,2-difluoro-1-hydroxy-1,3-dihydroinden-4-yl]-3,5-difluoro-5,6,7,8-tetrahydronaphthalene-1-carbonitrile

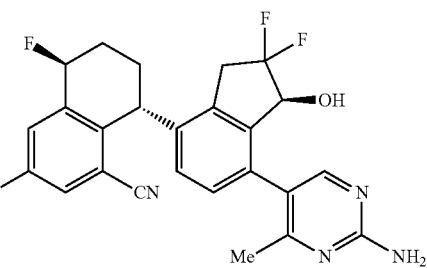

The title compound was prepared in a similar fashion to Example 144. $^1$H NMR (400 MHz, DMSO-d$_6$) δ 8.02 (s, 1H), 7.95 (d, J=7.7 Hz, 1H), 7.85 (d, J=9.0 Hz, 1H), 6.96 (d, J=7.9 Hz, 1H), 6.54 (s, 2H), 6.36 (d, J=7.9 Hz, 1H), 5.98 (d, J=6.5 Hz, 1H), 5.87-5.63 (m, 1H), 4.85-4.75 (m, 1H), 4.63-4.57 (m, 1H), 3.62 (td, J=17.3, 11.7 Hz, 1H), 3.47 (td, J=16.6, 8.3 Hz, 1H), 2.34-2.25 (m, 1H), 2.10-1.80 (m, 5H), 1.75-1.66 (m, 1H). ESI MS [M+H]$^+$ for $C_{25}H_{21}F_4N_4O$, calcd 469.2, found 469.3.

Example 169: (5S,8R)-8-[(1S)-7-(2,5-dimethylpyrazol-3-yl)-2,2-difluoro-1-hydroxy-1,3-dihydroinden-4-yl]-3,5-difluoro-5,6,7,8-tetrahydronaphthalene-1-carbonitrile

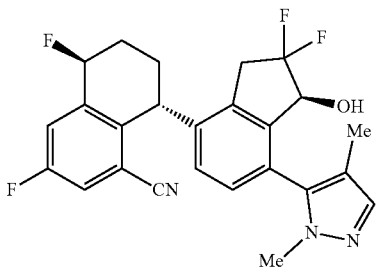 [SMILES: Cc1cnn(C)c1-c1ccc([C@H]2CC[C@H](F)c3cc(F)cc(C#N)c32)c2c1[C@H](O)C(F)(F)C2]

The title compound was prepared in a similar fashion to Example 144. $^1$H NMR (400 MHz, Chloroform-d) δ 7.55-7.48 (m, 1H), 7.39 (dt, J=7.8, 2.2 Hz, 1H), 7.07 (d, J=8.0 Hz, 1H), 6.41 (d, J=8.0 Hz, 1H), 6.25 (s, 1H), 5.73-5.51 (m, 1H), 4.93 (d, J=11.6 Hz, 1H), 4.58-4.48 (m, 2H), 3.86 (ddd, J=22.8, 16.9, 9.8 Hz, 1H), 3.67 (s, 3H), 3.49-3.35 (m, 1H), 2.57-2.43 (m, 1H), 2.30 (s, 3H), 2.23-2.03 (m, 2H), 1.90-1.78 (m, 1H). ESI MS [M+H]$^+$ for $C_{25}H_{22}F_4N_3O_3$, calcd 456.2, found 456.3.

Example 170: (5S,8R)-8-[(1S)-7-(2,4-dimethylpyrazol-3-yl)-2,2-difluoro-1-hydroxy-1,3-dihydroinden-4-yl]-3,5-difluoro-5,6,7,8-tetrahydronaphthalene-1-carbonitrile

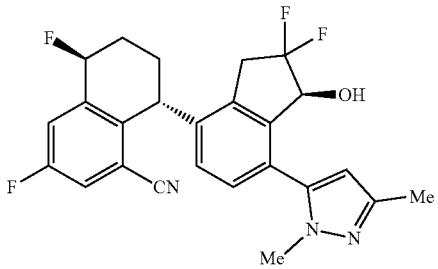 [SMILES: Cc1cc(-c2ccc([C@H]3CC[C@H](F)c4cc(F)cc(C#N)c43)c3c2[C@H](O)C(F)(F)C3)n(C)n1]

The title compound was prepared in a similar fashion to Example 144 and isolated as a 2:1 mixture of rotational isomers. $^1$H NMR (400 MHZ, Chloroform-d) δ 7.56-7.49 (m, 1H), 7.44-7.39 (m, 1H), 7.37 (s, 1H), 7.04-6.96 (m, 1H), 6.50-6.40 (m, 1H), 5.63 (dt, J=49.9, 3.5 Hz, 1H), 4.85-4.76 (m, 1H), 4.56-4.50 (m, 1H), 3.93-3.74 (m, 1H), 3.60 (s, 3H), 3.51-3.32 (m, 1H), 2.59-2.44 (m, 1H), 2.26-2.02 (m, 2H), 1.96-1.83 (m, 4H). ESI MS [M+H]$^+$ for $C_{25}H_{22}F_4N_3O_3$, calcd 456.2, found 456.3.

Example 171: (5S,8R)-8-[(1S)-2,2-difluoro-1-hydroxy-7-(1-methyl-6-oxopyridin-2-yl)-1,3-dihydroinden-4-yl]-3,5-difluoro-5,6,7,8-tetrahydronaphthalene-1-carbonitrile

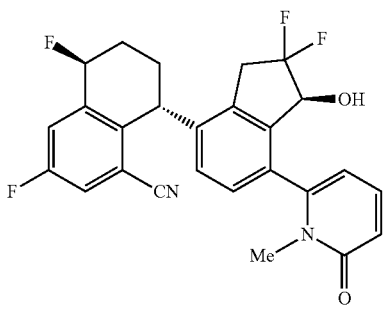

The title compound was prepared in a similar fashion to Example 144 and isolated as a 3:2 mixture of rotational isomers. $^1$H NMR (400 MHZ, Chloroform-d) δ 7.57-7.48 (m, 1H), 7.44-7.37 (m, 1H), 7.38-7.30 (m, 1H), 7.05 (d, J=7.9 Hz, 0.4H), 7.01 (d, J=8.0 Hz, 0.6H), 6.61 (d, J=9.1 Hz, 1H), 6.49-6.39 (m, 1H), 6.26 (dd, J=6.9, 1.2 Hz, 0.4H), 6.05 (dd, J=6.7, 1.2 Hz, 0.6H), 5.71-5.53 (m, 1H), 5.05 (d, J=12.9 Hz, 0.6H), 4.93-4.83 (m, 0.4H), 4.58-4.48 (m, 1H), 3.94-3.74 (m, 1H), 3.54-3.33 (m, 1H), 3.27 (s, 1H), 3.23 (s, 2H), 2.61-2.44 (m, 1.5H), 2.27-1.96 (m, 1.5H), 1.92-1.78 (m, 1H). ESI MS [M+H]$^+$ for $C_{26}H_{21}F_4N_2O_2$, calcd 469.2, found 469.3.

Example 172: (5S,8R)-3,5-difluoro-8-[(1S,2R)-2-fluoro-1-hydroxy-7-(1H-pyrazol-5-yl)-2,3-dihydro-1H-inden-4-yl]-5,6,7,8-tetrahydronaphthalene-1-carbonitrile

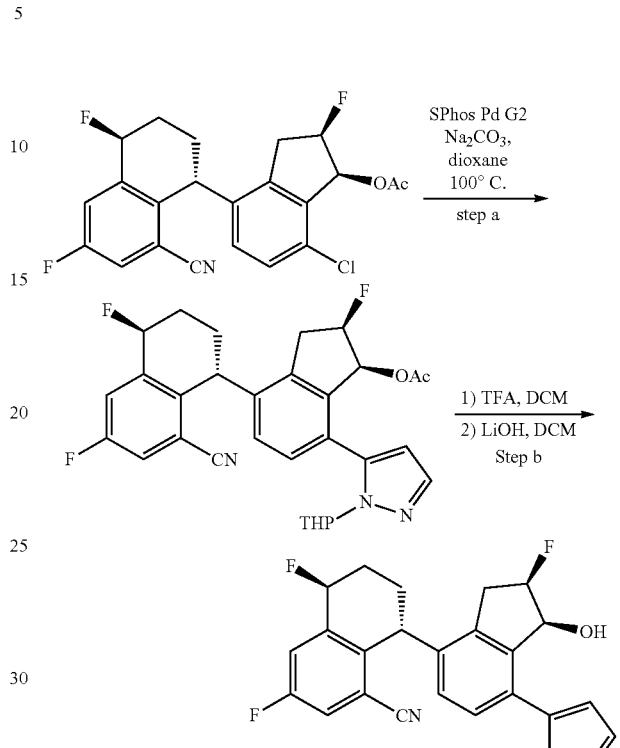

Step a: A solution of [(1S,2R)-7-chloro-4-[(1R,4S)-8-cyano-4,6-difluoro-1,2,3,4-tetrahydronaphthalen-1-yl]-2-fluoro-2,3-dihydro-1H-inden-1-yl] acetate (40 mg, 0.1 mmol), 1-(oxan-2-yl)-5-(4,4,5,5-tetramethyl-1,3,2-dioxaborolan-2-yl)pyrazole (34 mg, 0.12 mmol, 1.2 equiv.), SPhos Pd G2 (7.2 mg, 0.01 mmol, 10 mol %) and Na$_2$CO$_3$ (150 µl, 3 equiv.) in dioxane (1 ml) was heated to reflux for three hours. Upon completion, the reaction was cooled, filtered over celite, and concentrated. The crude material was taken on without further purification.

Step b: The crude material was taken up in methylene chloride (1 ml) and TFA (500 µl) was added slowly at 0° C. Upon completion, toluene was added to the solution, and the resulting mixture was concentrated. The crude material was purified by prep HPLC to yield [(1S,2R)-4-[(1R,4S)-8-cyano-4,6-difluoro-1,2,3,4-tetrahydronaphthalen-1-yl]-2-fluoro-7-(1H-pyrazol-5-yl)-2,3-dihydro-1H-inden-1-yl] acetate. The resulting material was dissolved in methylene chloride (1 ml) and 300 µl of 0.5N LiOH was added to the solution at 0° C. Upon completion the reaction was concentrated and purified by preparative HPLC to yield (5S,8R)-3,5-difluoro-8-[(1S,2R)-2-fluoro-1-hydroxy-7-(1H-pyrazol-5-yl)-2,3-dihydro-1H-inden-4-yl]-5,6,7,8-tetrahydronaphthalene-1-carbonitrile. $^1$H NMR (400 MHZ, Chloroform-d) δ 7.59 (s, 1H), 7.48 (d, 7.8 Hz, 1H), 7.38-7.35 (m, 2H), 6.56 (d, J=2.2 Hz, 1H), 6.34 (d, J=8.0 Hz, 1H), 5.64-5.32 (m, 3H), 4.60 (s, 1H), 3.58 (ddd, J=21.1, 16.5, 4.3, Hz, 1H), 3.20 (ddd, J=21.4, 16.5, 6.1 Hz, 1H), 2.40-2.38 (m, 1H), 2.12-1.96 (3H), 1.79-1.74 (m, 1H). ESI MS [M+H]$^+$ for $C_{23}H_{18}F_3N_3O$, calcd 410.1, found 410.1.

Example 173: (5S,8R)-3,5-difluoro-8-[(1S,2R)-2-fluoro-7-[2-(fluoromethyl)pyridin-3-yl]-1-hydroxy-2,3-dihydro-1H-inden-4-yl]-5,6,7,8-tetrahydronaphthalene-1-carbonitrile

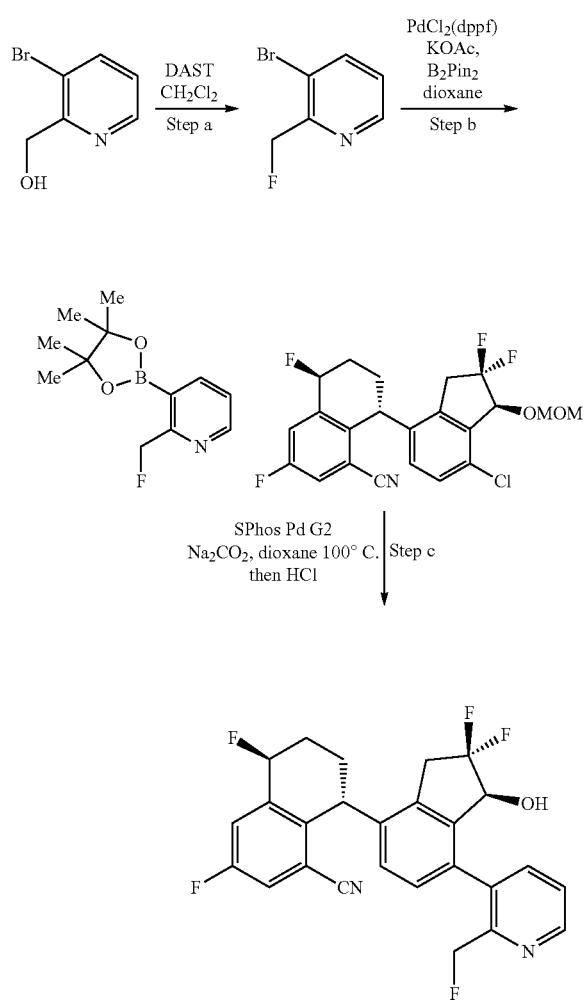

Step a: (3-bromopyridin-2-yl)methanol (500 mg, 2.66 mmol) was dissolved in $CH_2Cl_2$ (13.3 ml). The solution was cooled to 0° C., and (Diethylamino)sulfur trifluoride (414 ul, 472 mg, 1.1 equiv.) was added dropwise. The solution was allowed to warm to room temperature. Upon completion, the reaction was quenched with saturated $NaHCO_3$, extracted with methylene chloride, dried over $Na_2SO_4$, and concentrated. The crude residue was purified by flash column chromatography ($SiO_2$, 0% to 20% ethyl acetate in hexanes) to provide 3-bromo-2-(fluoromethyl)pyridine as a clear oil (196 mg, 39% yield).

Step b: 3-bromo-2-(fluoromethyl)pyridine (196 mg, 1 mmol) was combined with Pd(dppf)$Cl_2$ (73.2 mg, 0.1 mmol), KOAc (216 mg, 2.2 mmol) and $B_2Pin_2$ (330 mg, 1.3 mmol) in dioxane (5 ml). The resulting solution was heated to 100° C. Upon completion, the reaction was cooled, filtered over celite, and concentrated to a crude residue which was taken on without further purification.

Step c: The title compound was prepared in a similar fashion to Example 144. $^1H$ NMR (400 MHZ, Chloroform-d) δ 8.68 (dd, J=4.7, 1.6 Hz, 1H), 7.90-7.50 (br. m, 1H), 7.52-7.48 (m, 1H), 7.40-7.36 (m, 2H), 7.84 (d, J=7.9 Hz, 1H), 5.68-5.54 (m, 1H), 5.29 (br s, 1H), 5.16 (br s, 1H) 4.76 (br s, 1H), 4.53-4.51 (m, 1H), 3.90-3.78 (m, 1H), 3.46-3.36 (m, 1H), 2.55-2.45 (m, 1H), 2.23-2.05 (m, 3H), 1.88-1.81 (m, 1H), ESI MS [M+H]$^+$ for $C_{26}H_{19}F_5N_2O$, calcd 471.1, found 471.1.

Example 174: (5S,8R)-8-[(1S)-2,2-difluoro-1-hydroxy-7-(2-methyl-1,2,4-triazol-3-yl)-1,3-dihydroinden-4-yl]-3,5-difluoro-5,6,7,8-tetrahydronaphthalene-1-carbonitrile

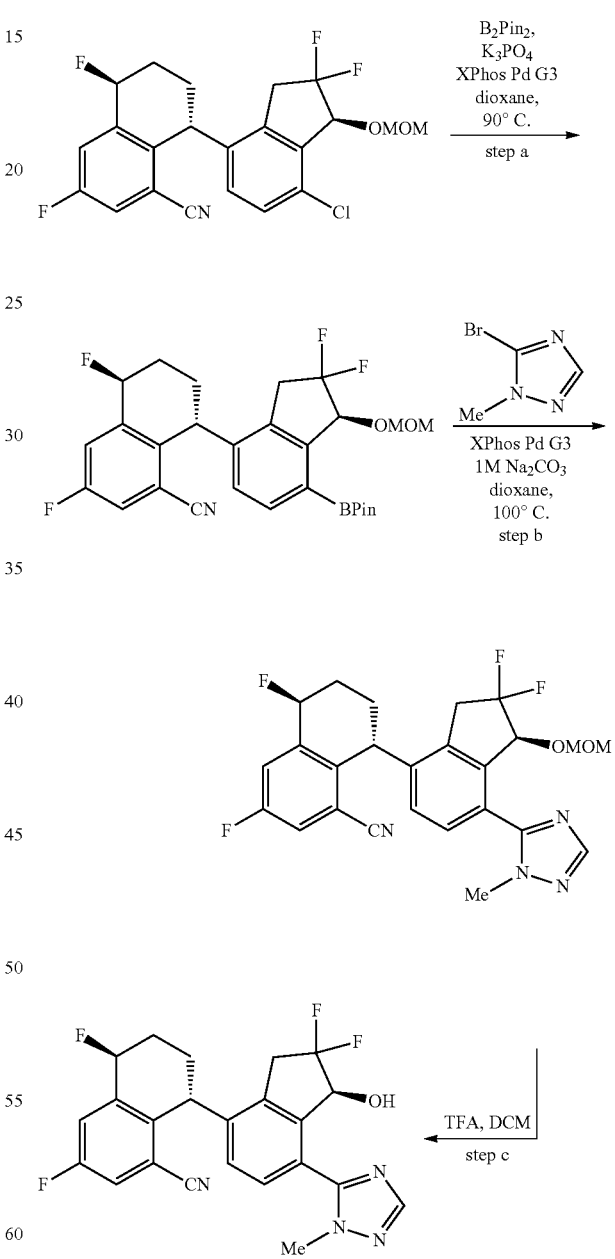

Step a: A flask was charged with (5S,8R)-8-[(1S)-7-chloro-2,2-difluoro-1-(methoxymethoxy)-1,3-dihydroinden-4-yl]-3,5-difluoro-5,6,7,8-tetrahydronaphthalene-1-carbonitrile (489 mg, 1.11 mmol, 1.0 equiv.), $B_2Pin_2$ (846 mg, 3.33 mmol, 3.0 equiv.), $K_3PO_4$ (707 mg, 3.33 mmol, 3.0 equiv.), XPhos Pd G3 (51 mg, 0.06 mmol, 0.05 equiv.), and 1,4-dioxane (11 mL, 0.1 M). The reaction mixture was sparged with $N_2$ for 10 minutes, heated to 90° C., and stirred under $N_2$ overnight. The reaction was quenched with water and extracted with EtOAc (2×50 mL). The combined organics were washed with brine (50 mL), dried over $MgSO_4$, filtered, and concentrated in vacuo. The residue was purified by column chromatography (silica gel, 0→40% EtOAc in hexanes) to afford the product (374 mg, 63% yield).

Step b: A flask was charged with (5S,8R)-8-[(1S)-2,2-difluoro-1-(methoxymethoxy)-7-(4,4,5,5-tetramethyl-1,3,2-dioxaborolan-2-yl)-1,3-dihydroinden-4-yl]-3,5-difluoro-5,6,7,8-tetrahydronaphthalene-1-carbonitrile (45 mg, 0.08 mmol, 1.0 equiv.), 5-bromo-1-methyl-1,2,4-triazole (17 mg, 0.10 mmol, 1.2 equiv.), and XPhos Pd G3 (7 mg, 0.008 mmol, 0.1 equiv.). The reagents were dissolved in 1,4-dioxane (0.8 mL, 0.1 M) and 1M $Na_2CO_3$ in $H_2O$ (0.32 mL, 0.32 mmol, 4.0 equiv) was added. The reaction mixture was sparged with $N_2$ for 10 minutes, heated to 100° C., and stirred under $N_2$ for 1 hour. The reaction was quenched into saturated aqueous NaCl and extracted with EtOAc (3×10 mL). The combined organics were dried over $MgSO_4$, filtered, and concentrated in vacuo. The crude residue was moved directly into step c without further purification.

Step c: The crude residue from step b (0.08 mmol) was dissolved in DCM (1.0 mL). TFA (0.2 mL) was added and the reaction mixture was stirred for 16 hours at 20° C. The reaction mixture was azeotroped with PhMe and the crude residue was dissolved in DCM, filtered over celite, and concentrated in vacuo. The crude residue was purified by prep-HPLC (40→100% MeCN in water) to afford the product was a white solid (8 mg, 23% yield over 2 steps). $^1$H NMR (400 MHZ, Chloroform-d) δ 7.97 (s, 1H), 7.52 (d, J=7.4 Hz, 1H), 7.40 (dt, J=7.6, 2.2 Hz, 1H), 7.28 (d, J=8.4 Hz, 1H), 6.49 (d, J=8.0 Hz, 1H), 5.60 (dt, J=50.0, 3.6 Hz, 1H), 4.94 (d, J=16.4 Hz, 1H), 4.62-4.54 (m, 1H), 4.03 (s, 3H), 3.98-3.80 (m, 1H), 3.42 (t, J=17.3 Hz, 1H), 2.58-2.45 (m, 1H), 2.28-1.92 (m, 2H), 1.90-1.81 (m, 1H). ESI MS [M+H]$^+$ for $C_{23}H_{18}F_4NO$, calcd 443.1, found 443.3.

Example 175: (5S,8R)-3,5-difluoro-8-[(1S,2R)-2-fluoro-1-hydroxy-7-(3-methyltriazol-4-yl)-2,3-dihydro-1H-inden-4-yl]-5,6,7,8-tetrahydronaphthalene-1-carbonitrile

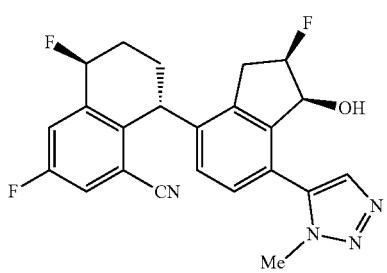

The title compound was prepared in a similar fashion to Example 174. $^1$H NMR (400 MHz, Chloroform-d) δ 7.75 (s, 1H), 7.52-7.48 (m, 1H), 7.40-7.37 (m, 1H), 7.01 (d, J=7.9 Hz, 1H), 6.41 (d, J=7/9 Hz, 1H), 5.59 (ddd, J=50.0, 3.7, 3.7 Hz, 1H), 5.30 (ddd, J=52.6, 8.8, 4.5 Hz, 1H), 5.05 (ddd, J=10.3, 7.2, 4.7 Hz, 1H), 4.62-4.60 (m, 1H), 3.94 (s, 3H), 3.57 (ddd, J=20.4, 16.5, 4.3 Hz, 1H), 3.20 (ddd, J=19.7, 16.5, 5.8 Hz, 1H), 2.53-2.40 (m, 2H), 2.20-1.95 (m, 2H), 1.82-1.75 (m, 1H). ESI MS [M+H]$^+$ for $C_{25}H_{19}F_3N_4O$, calcd 425.2, found 425.1.

Example 176: (5S,8R)-8-[(1S)-2,2-difluoro-1-hydroxy-7-(3-methylpyrazin-2-yl)-1,3-dihydroinden-4-yl]-3,5-difluoro-5,6,7,8-tetrahydronaphthalene-1-carbonitrile

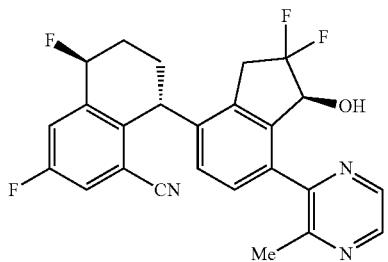

The title compound was prepared in a similar fashion to Example 174. $^1$H NMR (400 MHz, Chloroform-d) δ 8.53 (d, J=2.5 Hz, 1H), 8.44 (d, J=2.2 Hz, 1H), 7.51 (d, J=7.9 Hz, 1H), 7.39 (dt, J=7.6, 2.2 Hz, 1H), 7.24 (d, J=8.2 Hz, 1H), 6.40 (d, J=8.0 Hz, 1H), 5.62 (dt, J=50.1, 3.5 Hz, 1H), 4.81 (d, J=14.3 Hz, 1H), 4.63-4.53 (m, 1H), 4.05-3.83 (m, 1H), 3.45 (t, J=17.1 Hz, 1H), 2.66 (s, 3H), 2.59-2.46 (m, 1H), 2.30-1.99 (m, 2H), 1.94-1.83 (m, 1H). ESI MS [M+H]$^+$ for $C_{25}H_{19}F_4N_3O$, calcd 454.2, found 454.3.

Example 177: (5S,8R)-8-[(1S)-7-(4-aminopyrimidin-5-yl)-2,2-difluoro-1-hydroxy-1,3-dihydroinden-4-yl]-3,5-difluoro-5,6,7,8-tetrahydronaphthalene-1-carbonitrile

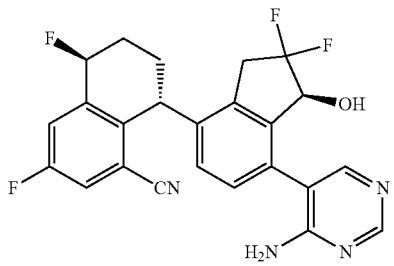

The title compound was prepared in a similar fashion to Example 174. $^1$H NMR (400 MHz, Chloroform-d) δ 8.57 (s, 1H), 8.18 (s, 1H), 7.53 (d, J=6.1 Hz, 1H), 7.40 (dt, J=7.3, 2.2 Hz, 1H), 7.07 (d, J=7.8 Hz, 1H), 6.48 (d, J=7.9 Hz, 1H), 5.74-5.51 (m, 1H), 5.04-4.85 (m, 3H), 4.53 (s, 1H), 3.96-3.78 (m, 1H), 3.43 (t, J=17.4 Hz, 1H), 2.56-2.45 (m, 1H), 2.32-2.00 (m, 2H), 1.91-1.79 (m, 1H). ESI MS [M+H]$^+$ for $C_{24}H_{18}F_4NO$, calcd 455.1, found 455.2.

Example 178: (5S,8R)-8-[(1S)-7-(5-aminopyridazin-4-yl)-2,2-difluoro-1-hydroxy-1,3-dihydroinden-4-yl]-3,5-difluoro-5,6,7,8-tetrahydronaphthalene-1-carbonitrile

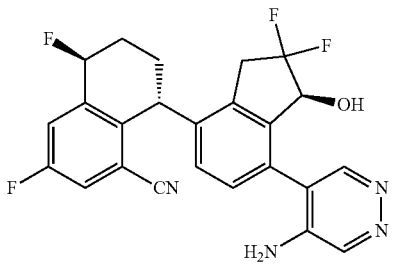

The title compound was prepared in a similar fashion to Example 174. $^1$H NMR (400 MHz, DMSO-d$_6$) δ 8.62 (s, 1H), 8.47 (s, 1H), 8.01 (d, J=8.2 Hz, 1H), 7.91 (d, J=8.5 Hz, 1H), 7.09 (d, J=7.9 Hz, 1H), 6.40 (d, J=7.9 Hz, 1H), 6.13 (s, 2H), 5.97 (d, J=7.1 Hz, 1H), 5.81 (d, J=49.5 Hz, 1H), 5.18-5.03 (m, 1H), 4.68 (s, 1H), 3.79-3.48 (m, 2H), 2.40-2.28 (m, 1H), 2.17-1.85 (m, 2H), 1.73 (d, J=13.7 Hz, 1H). ESI MS [M+H]$^+$ for C$_{24}$H$_{18}$F$_4$N$_4$O, calcd 455.1, found 455.3.

Example 179: (5S,8R)-8-[(1S)-7-(5-amino-3-methylpyrazin-2-yl)-2,2-difluoro-1-hydroxy-1,3-dihydroinden-4-yl]-3,5-difluoro-5,6,7,8-tetrahydronaphthalene-1-carbonitrile

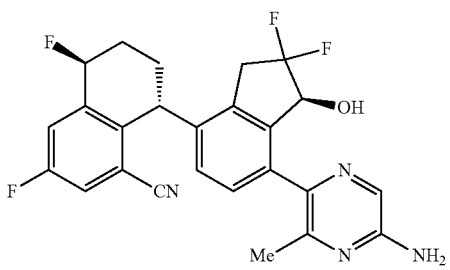

The title compound was prepared in a similar fashion to Example 174. $^1$H NMR (400 MHz, Chloroform-d) δ 7.83 (s, 1H), 7.50 (d, J=8.6 Hz, 1H), 7.38 (dt, J=7.6, 2.3 Hz, 1H), 7.14 (d, J=8.1 Hz, 1H), 6.32 (d, J=8.0 Hz, 1H), 4.79 (d, J=14.8 Hz, 1H), 4.68 (s, 2H), 4.60-4.52 (m, 1H), 4.00-3.84 (m, 1H), 3.43 (t, J=17.3 Hz, 1H), 2.54-2.43 (m, 1H), 2.47 (s, 3H), 2.24-2.00 (m, 2H), 1.87 (d, J=13.7 Hz, 1H). ESI MS [M+H]$^+$ for C$_{25}$H$_{20}$F$_4$N$_4$O, calcd 469.2, found 469.3.

Example 180: 5-[(3S)-7-[(1R,4S)-8-cyano-4,6-difluoro-1,2,3,4-tetrahydronaphthalen-1-yl]-2,2-difluoro-3-hydroxy-1,3-dihydroinden-4-yl]-1,3-thiazole-2-carboxamide

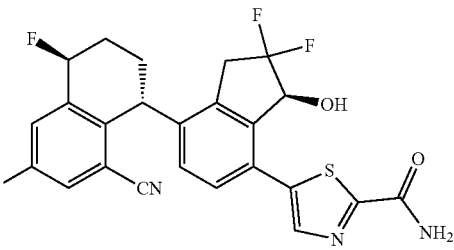

The title compound was prepared in a similar fashion to Example 174. $^1$H NMR (400 MHz, Chloroform-d) δ 8.25 (s, 1H), 7.52 (d, J=7.6 Hz, 1H), 7.39 (dt, J=7.6, 2.2 Hz, 1H), 7.29 (d, J=8.1 Hz, 1H), 7.13 (s, 1H), 6.42 (d, J=8.0 Hz, 1H), 5.72-5.49 (m, 2H), 5.04 (d, J=11.8 Hz, 1H), 4.56-4.47 (m, 1H), 3.91 (ddd, J=24.9, 16.8, 8.8 Hz, 1H), 3.47 (t, J=17.1 Hz, 1H), 2.51 (td, J=15.0, 13.1, 4.3 Hz, 1H), 2.25-1.98 (m, 2H), 1.88-1.74 (m, 1H). ESI MS [M+H]$^+$ for C$_{24}$H$_{17}$F$_4$N$_3$O$_2$S, calcd 488.1, found 488.2.

Example 181: (5S,8R)-8-[(1S)-7-(5-aminopyrimidin-4-yl)-2,2-difluoro-1-hydroxy-1,3-dihydroinden-4-yl]-3,5-difluoro-5,6,7,8-tetrahydronaphthalene-1-carbonitrile

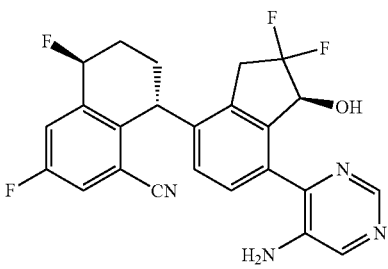

The title compound was prepared in a similar fashion to Example 174. $^1$H NMR (400 MHz, Chloroform-d) δ 8.72 (s, 1H), 8.46 (s, 1H), 7.56-7.47 (m, 2H), 7.40 (d, J=7.4 Hz, 1H), 6.50 (d, J=8.0 Hz, 1H), 5.61 (dt, J=50.0, 3.0 Hz, 1H), 4.98 (d, J=13.9 Hz, 1H), 4.62-4.53 (m, 1H), 3.98-3.81 (m, 1H), 3.41 (t, J=17.0 Hz, 1H), 2.58-2.46 (m, 1H), 2.25-1.96 (m, 2H), 1.84 (d, J=15.5 Hz, 1H). ESI MS [M+H]$^+$ for C$_{24}$H$_{18}$F$_4$N$_4$O, calcd 455.1, found 455.3.

Example 182: (5S,8R)-8-[(1S)-2,2-difluoro-1-hydroxy-7-(1-methyl-1,2,4-triazol-3-yl)-1,3-dihydroinden-4-yl]-3,5-difluoro-5,6,7,8-tetrahydronaphthalene-1-carbonitrile

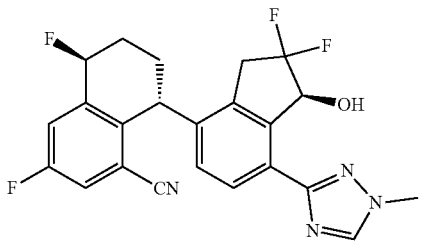 [SMILES: Cn1cnc(-c2ccc([C@H]3CC[C@H](F)c4cc(F)cc(C#N)c43)c3c2[C@H](O)C(F)(F)C3)n1]

The title compound was prepared in a similar fashion to Example 174. $^1$H NMR (400 MHz, Chloroform-d) δ 8.11 (s, 1H), 7.81 (d, J=8.1 Hz, 1H), 7.51 (d, J=9.0 Hz, 1H), 7.38 (dt, J=7.6, 2.3 Hz, 1H), 6.36 (d, J=8.1 Hz, 1H), 5.60 (dt, J=50.0, 3.5 Hz, 1H), 5.31 (d, J=17.4 Hz, 1H), 4.60-4.49 (m, 1H), 4.00 (s, 3H), 3.94-3.80 (m, 1H), 3.45 (td, J=17.1, 4.1 Hz, 1H), 2.54-2.41 (m, 1H), 2.23-1.91 (m, 2H), 1.87-1.76 (m, 1H). ESI MS [M+H]$^+$ for $C_{23}H_{18}F_4NO$, calcd 443.1, found 443.3.

Example 183: (5S,8R)-8-[(1S)-7-(1,5-dimethyltriazol-4-yl)-2,2-difluoro-1-hydroxy-1,3-dihydroinden-4-yl]-3,5-difluoro-5,6,7,8-tetrahydronaphthalene-1-carbonitrile

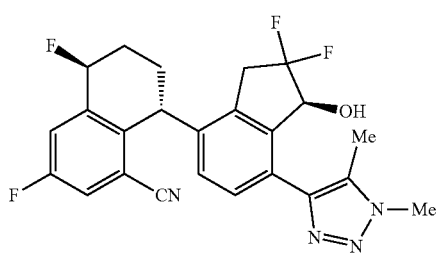 [SMILES: Cc1c(-c2ccc([C@H]3CC[C@H](F)c4cc(F)cc(C#N)c43)c3c2[C@H](O)C(F)(F)C3)nnn1C]

The title compound was prepared in a similar fashion to Example 174. $^1$H NMR (400 MHz, Chloroform-d) δ 7.50 (d, J=8.2, 2.2 Hz, 1H), 7.38 (dt, J=7.5, 2.6 Hz, 1H), 7.11 (d, J=8.0 Hz, 1H), 6.39 (d, J=8.0 Hz, 1H), 5.59 (dt, J=50.1, 3.7 Hz, 1H), 4.96 (d, J=16.6 Hz, 1H), 4.62-4.53 (m, 1H), 4.04 (s, 3H), 3.97-3.80 (m, 1H), 3.39 (d, J=17.0 Hz, 1H), 2.54-2.42 (m, OH), 2.45 (s, 3H), 2.22-1.98 (m, 2H), 1.89-1.81 (m, 1H). ESI MS [M+H]$^+$ for $C_{24}H_{20}F_4NO$, calcd 457.2, found 457.3.

Example 184: 3-[(3S)-7-[(1R,4S)-8-cyano-4,6-difluoro-1,2,3,4-tetrahydronaphthalen-1-yl]-2,2-difluoro-3-hydroxy-1,3-dihydroinden-4-yl]pyridine-2-carbonitrile The title compound was prepared in a similar fashion to Example 174. $^1$H NMR (400 MHz, Chloroform-d) δ 8.72 (dd, J=4.7, 1.6 Hz, 1H), 8.07 (dd, J=8.0, 1.6 Hz, 1H), 7.58 (dd, J=8.0, 4.7 Hz, 1H), 7.55-7.50 (m, 1H), 7.40 (ddd, J=7.5, 2.7, 1.7 Hz, 1H), 7.20 (d, J=7.8 Hz, 1H), 6.44 (d, J=8.0 Hz, 1H), 5.62 (dt, J=50.0, 3.5 Hz, 1H), 5.06 (d, J=10.9 Hz, 1H), 4.55 (t, J=3.9 Hz, 1H), 3.99-3.76 (m, 1H), 3.49 (td, J=16.1, 7.7 Hz, 1H), 2.59-2.42 (m, 2H), 2.25-2.11 (m, 2H), 1.94-1.76 (m, 1H). ESI MS [M+H]$^+$ for $C_{26}H_{17}F_4N_3O$ calcd. 464.1, found 464.1.

Example 185: (5S,8R)-8-[(1S)-7-(2-amino-6-methylpyridin-3-yl)-2,2-difluoro-1-hydroxy-1,3-dihydroinden-4-yl]-3,5-difluoro-5,6,7,8-tetrahydronaphthalene-1-carbonitrile

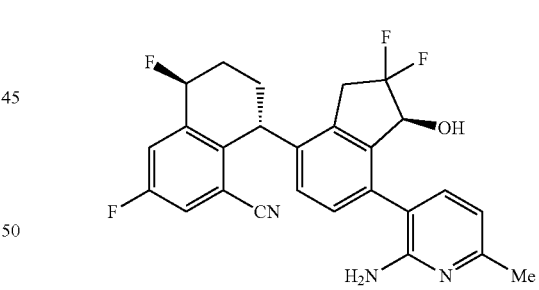

The title compound was prepared in a similar fashion to Example 174. $^1$H NMR (400 MHz, DMSO-d$_6$) δ 8.01-7.91 (m, 1H), 7.85 (d, J=9.1 Hz, 1H), 7.26 (d, J=7.4 Hz, 1H), 6.98 (d, J=7.9 Hz, 1H), 6.47 (d, J=7.5 Hz, 1H), 6.35 (d, J=7.9 Hz, 1H), 5.93 (d, J=6.3 Hz, 1H), 5.78 (d, J=49.7 Hz, 1H), 5.25 (s, 2H), 4.89 (s, 1H), 4.60 (s, 1H), 3.72-3.53 (m, 1H), 3.52-3.38 (m, 1H), 2.32 (q, J=1.9 Hz, 1H), 2.27 (s, 3H), 2.06 (d, J=15.3 Hz, 1H), 1.70 (d, J=13.7 Hz, 1H). ESI MS [M+H]$^+$ for $C_{26}H_{21}F_4N_3O$ calcd. 468.2, found 468.2.

Example 186: (5S,8R)-8-[(1S)-7-(3-aminopyrazin-2-yl)-2,2-difluoro-1-hydroxy-1,3-dihydroinden-4-yl]-3,5-difluoro-5,6,7,8-tetrahydronaphthalene-1-carbonitrile

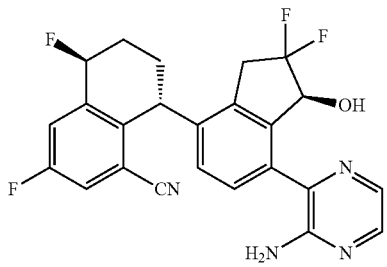

The title compound was prepared in a similar fashion to Example 174. $^1$H NMR (400 MHz, Chloroform-d) δ 8.04 (d, J=2.7 Hz, 1H), 7.98 (d, J=2.7 Hz, 1H), 7.56-7.49 (m, 2H), 7.39 (ddd, J=7.5, 2.8, 1.7 Hz, 1H), 6.43 (d, J=8.0 Hz, 1H), 5.61 (dt, J=50.1, 3.6 Hz, 1H), 5.24 (s, 1H), 4.93-4.80 (m, 3H), 4.61-4.53 (m, 1H), 4.00-3.79 (m, 1H), 3.40 (t, J=17.2 Hz, 1H), 2.51 (ddq, J=16.5, 9.4, 3.5 Hz, 1H), 2.26-2.06 (m, 2H), 1.91-1.79 (m, 1H), 1.63 (s, 1H). ESI MS [M+H]$^+$ for $C_{24}H_{18}F_4N_4O$ calcd. 455.1, found 455.1.

Example 187: (5S,8R)-8-[(1S)-2,2-difluoro-1-hydroxy-7-(1H-indazol-7-yl)-1,3-dihydroinden-4-yl]-3,5-difluoro-5,6,7,8-tetrahydronaphthalene-1-carbonitrile

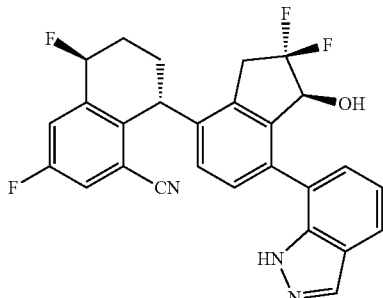

The title compound was prepared in a similar fashion to Example 174. $^1$H NMR (400 MHz, CDCl$_3$) δ 8.07 (d, J=0.9 Hz, 1H), 7.76 (dd, J=8.0, 1.0 Hz, 1H), 7.52 (ddd, J=8.4, 2.9, 1.2 Hz, 1H), 7.39 (ddd, J=7.6, 2.8, 1.7 Hz, 1H), 7.34 (dd, J=7.1, 1.0 Hz, 1H), 7.22 (dt, J=8.0, 3.6 Hz, 2H), 6.48 (d, J=8.0 Hz, 1H), 5.64 (dt, J=50.1, 3.5 Hz, 1H), 4.89 (d, J=9.3 Hz, 1H), 4.71-4.44 (m, 1H), 4.08-3.94 (m, 1H), 3.41 (t, J=16.6 Hz, 1H), 2.52 (td, J=14.7, 14.1, 6.2 Hz, 1H), 2.28-2.08 (m, 2H), 1.95-1.75 (m, 1H). ESI MS [M+H]$^+$ for $C_{27}H_{20}F_4N_3O$, calcd 478.2, found 478.0.

Example 188: (5S,8R)-8-[(1S)-7-(2-amino-4-methyl-1,3-thiazol-5-yl)-2,2-difluoro-1-hydroxy-1,3-dihydroinden-4-yl]-3,5-difluoro-5,6,7,8-tetrahydronaphthalene-1-carbonitrile

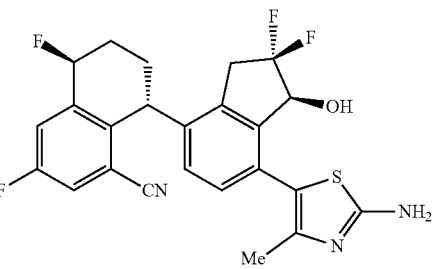

The title compound was prepared in a similar fashion to Example 174. $^1$H NMR (400 MHz, CDCl$_3$) δ 8.70 (s, 1H), 7.51 (d, J=7.2 Hz, 1H), 7.38 (d, J=7.2 Hz, 1H), 7.05 (d, J=8.0 Hz, 1H), 6.38 (d, J=8.0 Hz, 1H), 5.59 (d, J=49.9 Hz, 1H), 4.98 (d, J=11.7 Hz, 1H), 4.48 (s, 1H), 3.89-3.69 (m, 1H), 3.48-3.32 (m, 1H), 2.46 (m, 1H), 2.18 (s, 3H), 2.12-1.90 (m, 2H), 1.77 (s, 1H). ESI MS [M+H]$^+$ for $C_{24}H_{20}F_4N_3OS$, calcd 474.1, found 474.0.

Example 189: (5S,8R)-8-[(1S)-7-(1,3-benzothiazol-7-yl)-2,2-difluoro-1-hydroxy-1,3-dihydroinden-4-yl]-3,5-difluoro-5,6,7,8-tetrahydronaphthalene-1-carbonitrile

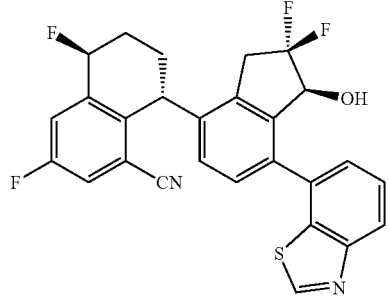

The title compound was prepared in a similar fashion to Example 174. $^1$H NMR (400 MHz, CDCl$_3$) δ 8.92 (d, J=0.4 Hz, 1H), 8.08 (dd, J=8.1, 1.2 Hz, 1H), 7.64 (ddd, J=7.4, 1.2, 0.5 Hz, 1H), 7.57 (dd, J=8.0, 7.4 Hz, 1H), 7.52 (ddd, J=8.4, 2.8, 1.3 Hz, 1H), 7.41 (ddd, J=7.6, 2.7, 1.7 Hz, 1H), 7.31 (d, J=8.0 Hz, 1H), 6.43 (d, J=7.9 Hz, 1H), 5.63 (dt, J=50.1, 3.6 Hz, 1H), 4.98 (dd, J=11.1, 1.4 Hz, 1H), 4.68-4.29 (m, 1H), 4.00-3.74 (m, 1H), 3.40 (td, J=16.4, 3.0 Hz, 1H), 2.56-2.39 (m, 1H), 2.28-2.00 (m, 2H), 1.95-1.77 (m, 1H). ESI MS [M+H]$^+$ for $C_{27}H_{19}F_4N_2OS$, calcd 495.1, found 495.0.

Example 190: (5S,8R)-8-[(1S)-7-(1,3-benzothiazol-4-yl)-2,2-difluoro-1-hydroxy-1,3-dihydroinden-4-yl]-3,5-difluoro-5,6,7,8-tetrahydronaphthalene-1-carbonitrile

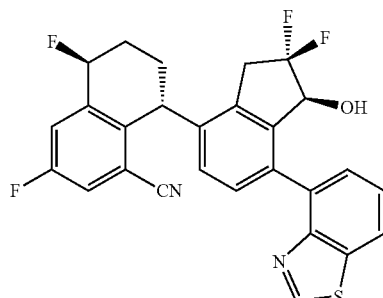

The title compound was prepared in a similar fashion to example 174. $^1$H NMR (400 MHz, CDCl$_3$) δ 9.19 (s, 1H), 8.02 (dd, J=8.0, 1.2 Hz, 1H), 7.57 (t, J=7.7 Hz, 1H), 7.54-7.47 (m, 2H), 7.39 (ddd, J=7.6, 2.7, 1.7 Hz, 1H), 7.14 (d, J=8.0 Hz, 1H), 6.44 (d, J=7.9 Hz, 1H), 5.62 (dt, J=49.6, 3.5 Hz, 1H), 5.13-4.69 (m, 1H), 4.59 (dd, J=6.0, 2.9 Hz, 1H), 4.01-3.78 (m, 1H), 3.41 (td, J=16.4, 3.0 Hz, 1H), 2.57-2.36 (m, 1H), 2.21-2.04 (m, 2H), 1.93-1.75 (m, 1H). ESI MS [M+H]$^+$ for C$_{27}$H$_{19}$F$_4$N$_2$OS, calcd 495.1, found 495.0.

Example 191: (5S,8R)-8-[(1S)-2,2-difluoro-1-hydroxy-7-[4-(hydroxymethyl)-1,3-thiazol-5-yl]-1,3-dihydroinden-4-yl]-3,5-difluoro-5,6,7,8-tetrahydronaphthalene-1-carbonitrile

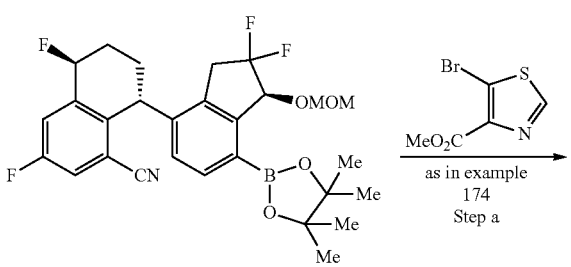

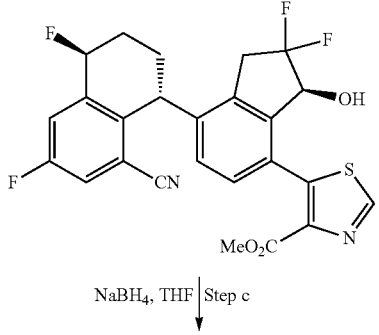

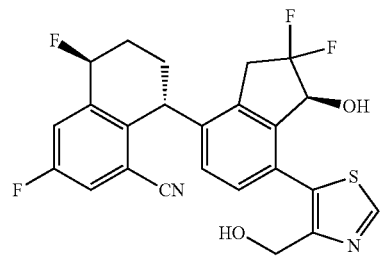

Step a: The reaction was performed in a similar fashion to step b of Example 174. The crude product was purified by flash column chromatography (SiO$_2$, 0 to 100% EtOAc/hexanes) to yield the product as a yellow solid (28 mg, 0.051 mmol, 51%).

Step b: The reaction was performed in a similar fashion to step c of Example 174. The crude product was carried forward without further purification (20 mg).

Step c: To a 40-mL scintillation vial containing the product from step b (20 mg, 0.40 mmol, 1.0 equiv.) dissolved in THF (1 mL) was added sodium borohydride (15.1 mg, 0.40 mmol, 10.0 equiv.) in one portion. The resulting mixture was kept stirring at 23° C. for 2 h when TLC showed the reaction was complete. The reaction mixture was then quenched with sat. aq. brine solution (4 mL), and then extracted with EtOAc (5 mL×3). The organic layers were combined and dried over Na$_2$SO$_4$. Concentration under reduced pressure and purification by HPLC afforded a white solid (5 mg, 0.009 mmol, 23%). $^1$H NMR (400 MHZ, CDCl$_3$) δ 9.09 (s, 1H), 7.56-7.49 (m, 1H), 7.43-7.37 (m, 1H), 7.18 (d, J=8.1, 1H), 6.45 (d, J=8.0 Hz, 1H), 5.83-5.42 (m, 1H), 5.00-4.86 (m, 1H), 4.69 (d, J=13.2 Hz, 1H), 4.58 (d, J=13.3 Hz, 1H), 4.53 (dd, J=5.7, 2.6 Hz, 1H), 3.94-3.78 (m, 1H), 3.40 (td, J=16.4, 4.9 Hz, 1H), 2.56-2.41 (m, 1H), 2.26-1.97 (m, 2H), 1.87-1.74 (m, 1H). ESI MS [M+H]$^+$ for C$_{24}$H$_{19}$F$_4$N$_2$O$_2$S, calcd 475.1, found 475.0.

Example 192: (5S,8R)-8-[(1S)-2,2-difluoro-1-hydroxy-7-(5-methyl-1,3-thiazol-4-yl)-1,3-dihydroinden-4-yl]-3,5-difluoro-5,6,7,8-tetrahydronaphthalene-1-carbonitrile

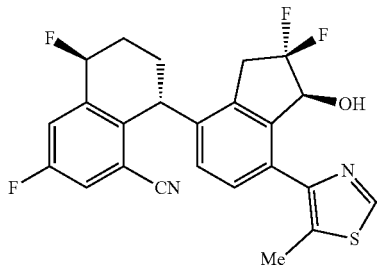

The title compound was prepared in a similar fashion to Example 174. $^1$H NMR (400 MHz, CDCl$_3$) δ 8.68 (s, 1H), 7.50 (dt, J=8.4, 2.2 Hz, 1H), 7.42-7.32 (m, 1H), 7.17 (d, J=7.9 Hz, 1H), 6.36 (d, J=8.0 Hz, 1H), 5.60 (dt, J=50.1, 3.5 Hz, 1H), 4.84 (d, J=16.0 Hz, 1H), 4.60-4.41 (m, 1H), 3.90 (ddd, J=26.1, 16.6, 8.7 Hz, 1H), 3.42 (t, J=17.4 Hz, 1H), 2.58 (s, 3H), 2.54-2.36 (m, 1H), 2.17-1.97 (m, 2H), 1.93-1.78 (m, 1H). ESI MS [M+H]$^+$ for C$_{24}$H$_{19}$F$_4$N$_2$OS, calcd 459.1, found 459.0.

Example 193: (5S,8R)-8-[(1S)-7-(2,4-dimethyl-1,3-thiazol-5-yl)-2,2-difluoro-1-hydroxy-1,3-dihydroinden-4-yl]-3,5-difluoro-5,6,7,8-tetrahydronaphthalene-1-carbonitrile

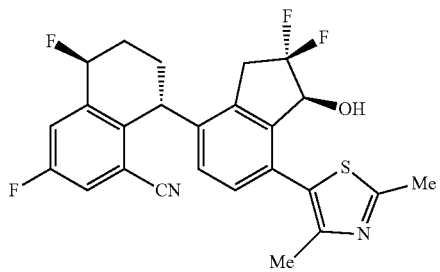

The title compound was prepared in a similar fashion to Example 174. $^1$H NMR (400 MHz, CDCl$_3$) δ 7.51 (dt, J=8.4, 2.0 Hz, 1H), 7.39 (ddd, J=7.6, 2.7, 1.7 Hz, 1H), 7.06 (d, J=8.0 Hz, 1H), 6.35 (d, J=8.0 Hz, 1H), 5.60 (dt, J=50.1, 3.6 Hz, 1H), 5.04-4.98 (m, 1H), 4.57-4.44 (m, 1H), 3.93-3.73 (m, 1H), 3.41 (td, J=16.7, 4.0 Hz, 1H), 2.66 (s, 3H), 2.49 (ddd, J=18.5, 11.3, 4.2 Hz, 1H), 2.23 (s, 3H), 2.20-2.06 (m, 2H), 1.89-1.75 (m, 1H). ESI MS [M+H]$^+$ for C$_{25}$H$_{20}$F$_4$N$_2$OS, calcd 473.1, found 473.0.

Example 194: (5S,8R)-8-[(1S)-7-(2-amino-4-fluorophenyl)-2,2-difluoro-1-hydroxy-1,3-dihydroinden-4-yl]-3,5-difluoro-5,6,7,8-tetrahydronaphthalene-1-carbonitrile

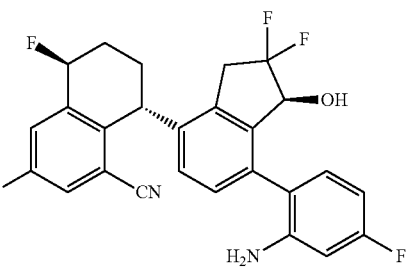

The title compound was prepared in a similar fashion to Example 174. $^1$H NMR (400 MHz, Chloroform-d) δ 7.55-7.48 (m, 1H), 7.38 (dt, J=7.6, 2.1 Hz, 1H), 7.18-6.91 (m, 2H), 6.63 (t, J=7.4 Hz, 1H), 6.56 (d, J=9.1 Hz, 1H), 6.41 (d, J=7.7 Hz, 1H), 5.62 (dt, J=50.0, 3.7 Hz, 1H), 4.72 (d, J=12.4 Hz, 1H), 4.56-4.50 (m, 1H), 4.06-3.75 (m, 1H), 3.39 (t, J=16.8 Hz, 1H), 2.57-2.43 (m, 1H), 2.25-2.07 (m, 2H), 1.93-1.81 (m, 1H). ESI MS [M+H]$^+$ for C$_{26}$H$_{20}$F$_5$N$_2$O, calcd 471.1, found 471.3.

Example 195: (5S,8R)-8-[(1S)-7-(2-amino-4-methylphenyl)-2,2-difluoro-1-hydroxy-1,3-dihydroinden-4-yl]-3,5-difluoro-5,6,7,8-tetrahydronaphthalene-1-carbonitrile

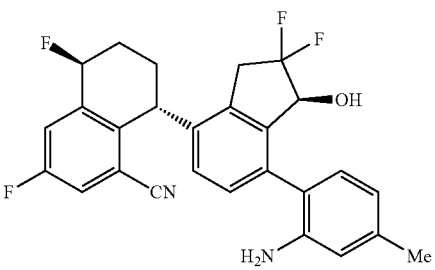 [SMILES: Cc1ccc(-c2ccc([C@H]3CC[C@H](F)c4cc(F)cc(C#N)c43)c3c2[C@H](O)C(F)(F)C3)c(N)c1]

The title compound was prepared in a similar fashion to Example 174. $^1$H NMR (400 MHz, Chloroform-d) δ 7.54-7.47 (m, 1H), 7.38 (dt, J=7.6, 2.2 Hz, 1H), 6.96 (d, J=7.8 Hz, 2H), 6.78 (d, J=7.5 Hz, 1H), 6.69 (s, 1H), 6.38 (d, J=7.8 Hz, 1H), 5.61 (dt, J=50.0, 3.7 Hz, 1H), 4.69 (d, J=12.7 Hz, 1H), 4.56-4.51 (m, 1H), 3.88 (ddd, J=25.1, 16.1, 7.8 Hz, 1H), 3.38 (t, J=16.6 Hz, 1H), 2.56-2.42 (m, 1H), 2.33 (s, 3H), 2.22-2.01 (m, 2H), 1.91-1.81 (m, 1H). ESI MS [M+H]$^+$ for C$_{27}$H$_{23}$F$_4$N$_2$O, calcd 467.2, found 467.3.

Example 196: (5S,8R)-8-[(1S)-7-(2-amino-6-fluorophenyl)-2,2-difluoro-1-hydroxy-1,3-dihydroinden-4-yl]-3,5-difluoro-5,6,7,8-tetrahydronaphthalene-1-carbonitrile

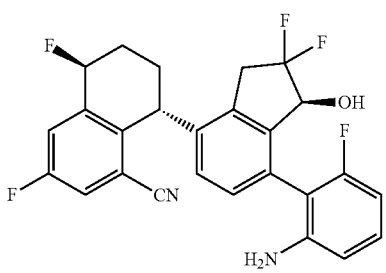 [SMILES: N#Cc1cc(F)cc2c1[C@@H](c1ccc(-c3c(N)cccc3F)c3c1CC(F)(F)[C@H]3O)CC[C@@H]2F]

The title compound was prepared in a similar fashion to Example 174. ¹H NMR (400 MHz, Chloroform-d) δ 7.55-7.48 (m, 1H), 7.42-7.34 (m, 1H), 7.23-7.14 (m, 1H), 7.03 (d, J=7.9 Hz, 1H), 6.71-6.59 (m, 2H), 6.41 (d, J=7.9 Hz, 1H), 5.62 (dt, J=50.2, 3.7 Hz, 1H), 4.84-4.76 (m, 1H), 4.55-4.50 (m, 1H), 3.88 (ddd, J=22.4, 16.5, 9.0 Hz, 1H), 3.61 (bs, 2H), 3.44 (td, J=16.4, 3.1 Hz, 1H), 2.58-2.43 (m, 1H), 2.24-2.11 (m, 2H), 1.95-1.83 (m, 1H). ESI MS [M+H]⁺ for $C_{26}H_{20}F_5N_2O$, calcd 471.1, found 471.3.

Example 197: (5S,8R)-8-[(1S)-7-(2-amino-4-cyanophenyl)-2,2-difluoro-1-hydroxy-1,3-dihydroinden-4-yl]-3,5-difluoro-5,6,7,8-tetrahydronaphthalene-1-carbonitrile

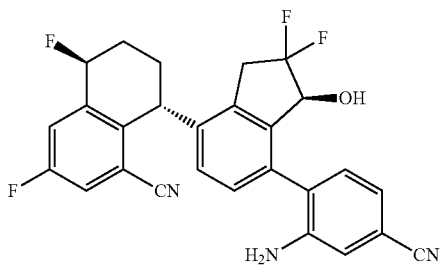

The title compound was prepared in a similar fashion to Example 174. ¹H NMR (400 MHz, Chloroform-d) δ 7.56-7.49 (m, 1H), 7.39 (dt, J=7.3, 2.2 Hz, 1H), 7.24-7.12 (m, 2H), 7.10-7.02 (m, 1H), 6.98 (d, J=7.8 Hz, 1H), 6.46 (d, J=7.9 Hz, 1H), 5.62 (dt, J=50.1, 3.9 Hz, 1H), 4.76 (d, J=12.0 Hz, 1H), 4.56-4.50 (m, 1H), 3.97-3.62 (m, 3H), 3.42 (t, J=16.7 Hz, 1H), 2.58-2.44 (m, 1H), 2.30-2.00 (m, 2H), 1.90-1.80 (m, 1H), 0.08 (d, J=4.5 Hz, 1H). ESI MS [M+H]⁺ for $C_{27}H_{20}F_3N_3O$, calcd 478.2, found 478.3.

Example 198: (5S,8R)-8-[(1S)-2,2-difluoro-1-hydroxy-7-(2-methyl-6-methylsulfonylpyridin-3-yl)-1,3-dihydroinden-4-yl]-3,5-difluoro-5,6,7,8-tetrahydronaphthalene-1-carbonitrile

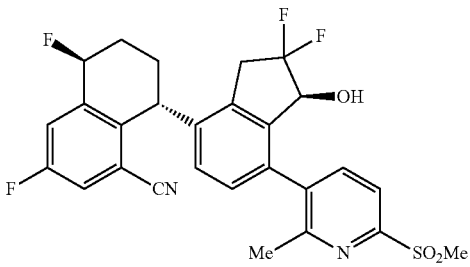 [SMILES: Cc1nc(S(C)(=O)=O)ccc1-c1ccc([C@H]2CC[C@H](F)c3cc(F)cc(C#N)c32)c2c1[C@H](O)C(F)(F)C2]

The title compound was prepared in a similar fashion to Example 174. ¹H NMR (400 MHz, Chloroform-d) δ 7.97 (d, J=7.6 Hz, 1H), 7.75-7.67 (m, 1H), 7.57-7.49 (m, 1H), 7.44-7.37 (m, 1H), 6.96 (d, J=7.9 Hz, 1H), 6.44 (d, J=7.9 Hz, 1H), 5.63 (dt, J=49.6, 3.3 Hz, 1H), 4.56-4.51 (m, 1H), 4.28-4.16 (m, 2H), 3.86 (ddd, J=20.8, 16.9, 10.3 Hz, 1H), 3.45 (t, J=16.7 Hz, 1H), 3.28 (s, 3H), 2.59-2.47 (m, 1H), 2.43 (s, 3H), 2.17-1.98 (m, 2H), 1.91-1.83 (m, 1H). ESI MS [M+H]⁺ for $C_{27}H_{23}F_4N_2O_3S$, calcd 531.1, found 531.2.

Example 199: (5S,8R)-8-[(1S)-2,2-difluoro-1-hydroxy-7-imidazol-1-yl-1,3-dihydroinden-4-yl]-3,5-difluoro-5,6,7,8-tetrahydronaphthalene-1-carbonitrile

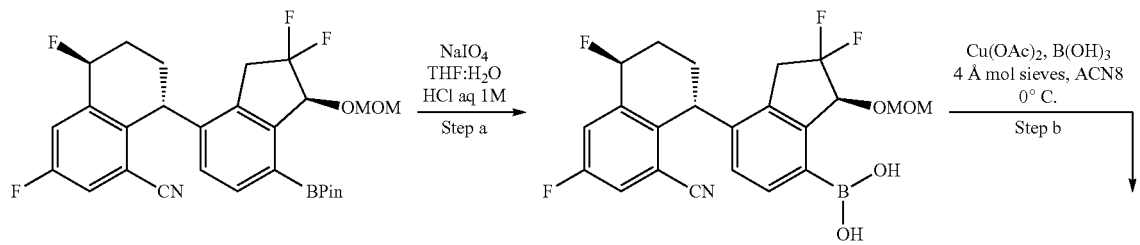

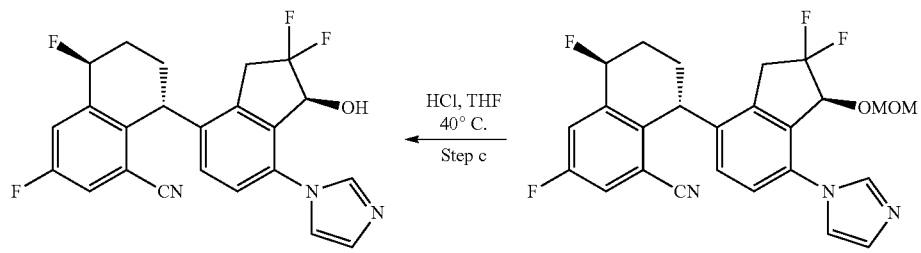

Step a: To a 40-mL scintillation vial containing (5S,8R)-8-[(1S)-2,2-difluoro-1-(methoxymethoxy)-7-(4,4,5,5-tetramethyl-1,3,2-dioxaborolan-2-yl)-1,3-dihydroinden-4-yl]-3,5-difluoro-5,6,7,8-tetrahydronaphthalene-1-carbonitrile (159.4 mg, 0.30 mmol, 1.0 equiv.) dissolved in THF (2.4 mL) and H₂O (0.6 mL) was added NaIO₄ (256.7 mg, 1.20 mmol, 4.0 equiv.) in one portion. After stirring for 15 min, HCl (1.0 M in H₂O mL, 0.60 mL, 0.60 mmol, 2.0 equiv.) was added in one portion and the resulting mixture was kept stirring for another 1.5 h when TLC showed the reaction was complete. The reaction mixture was then quenched with sat. aq. brine solution (4 mL), and then extracted with EtOAc (10 mL×3). The organic layers were combined and dried over Na₂SO₄. Concentration under reduced pressure afforded the desired crude boronic acid, which was taken directly onto the next step without purification (122 mg).

Step b: To a 4 mL scintillation vial containing the crude product from step a (17 mg, 0.038 mmol, 1.0 equiv.) was added cupric acetate (7 mg, 0.038 mmol, 1.0 equiv.), imidazole (13 mg, 0.19 mmol, 5.00 equiv.), boric acid (5 mg, 0.076 mmol, 2.00 equiv.), and 20 mg of activated 4 angstrom mol sieves. The resulting mixture was then dissolved in MeCN (0.2 mL), sealed, and heated overnight at 80° ° C. After reacting overnight, the reaction mixture was cooled to room temperature and then directly filtered over celite. The mixture was then concentrated under reduced pressure which was taken directly onto the next step without purification (10 mg).

Step c: To a 40-mL vial containing the product from step b was added THF (1 mL), H₂O (0.5 mL), and HCl (0.5 mL). The resulting solution was heated at 40° ° C. and vigorously stirred. Upon completion of the reaction as indicated by TLC, the reaction mixture was cooled, diluted with EtOAc (5 mL) and NaOH (1M aq, 5 mL), the organic layers were combined rinsed with brine (5 mL), dried over Na₂SO₄. Concentration under reduced pressure and purification by HLPC afforded the product as a white powder (7 mg, 0.016 mmol, 43% yield). ¹H NMR (400 MHz, CDCl₃) 9.07 (s, 1H), 7.56 (dt, J=7.2, 2.2 Hz, 1H), 7.54 (s, 1H), 7.49 (d, J=1.7 Hz, 1H), 7.41 (dt, J=7.2, 2.2 Hz, 1H), 7.27 (d, J=8.2 Hz, 1H), 6.57 (d, J=8.2 Hz, 1H), 5.62 (d, J=49.7 Hz, 1H), 5.05 (d, J=11.4 Hz, 1H), 4.55 (s, 1H), 3.99-3.67 (m, 1H), 3.42 (td, J=16.4, 4.5 Hz, 1H), 2.59-2.49 (m, 1H), 2.28-1.96 (m, 2H), 1.80 (d, J=14.1 Hz, 1H). ESI MS [M+H]⁺ for C₂₃H₁₈F₄N₃O, calcd 428.1, found 428.1.

Example 200: (5S,8R)-8-[(1S)-2,2-difluoro-1-hydroxy-7-(pyridin-2-ylamino)-1,3-dihydroinden-4-yl]-3,5-difluoro-5,6,7,8-tetrahydronaphthalene-1-carbonitrile

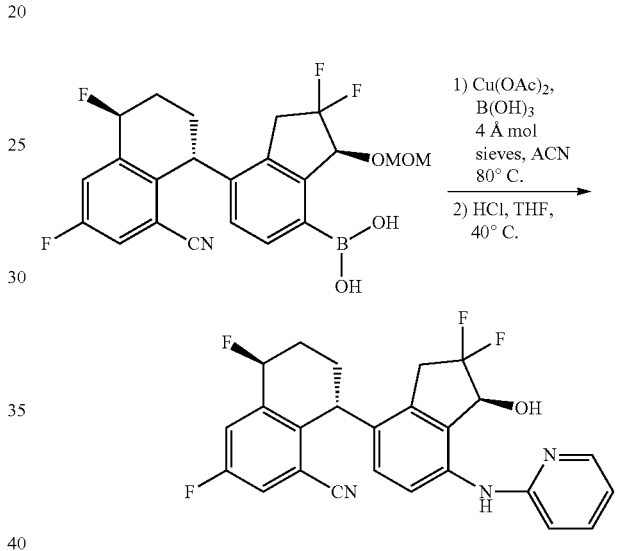

The title compound was prepared in a similar fashion to Example 174. ¹H NMR (400 MHz, CDCl₃) δ 11.89 (s, 1H), 7.88 (ddd, J=6.2, 1.8, 0.8 Hz, 1H), 7.84-7.75 (m, 1H), 7.51 (ddd, J=8.9, 2.8, 1.2 Hz, 1H), 7.45-7.35 (m, 1H), 7.16-7.06 (m, 2H), 6.90 (ddd, J=7.2, 6.2, 1.0 Hz, 1H), 6.43 (d, J=8.2 Hz, 1H), 5.71-5.44 (m, 1H), 5.28-5.22 (m, 1H), 4.52 (d, J=4.1 Hz, 1H), 3.88-3.64 (m, 1H), 3.38-3.12 (m, 1H), 2.56-2.39 (m, 1H), 2.24-2.05 (m, 1H), 2.05-1.91 (m, 2H), 1.82-1.64 (m, 1H). ESI MS [M+H]⁺ for C₂₅H₂₀F₄N₃O, calcd 454.2, found 454.2.

Example 201: (5S,8R)-8-[(1S)-7-cyano-2,2-difluoro-1-hydroxy-1,3-dihydroinden-4-yl]-3,5-difluoro-5,6,7,8-tetrahydronaphthalene-1-carbonitrile

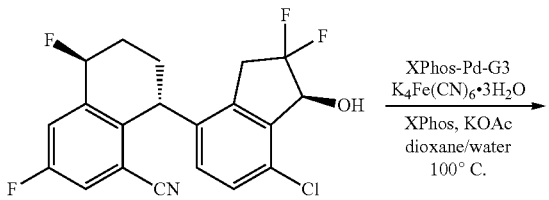

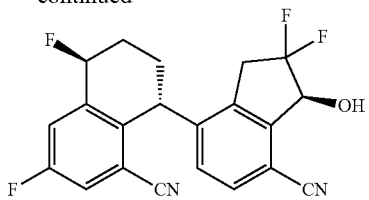

(5S,8R)-8-[(1S)-7-Chloro-2,2-difluoro-1-hydroxy-1,3-dihydroinden-4-yl]-3,5-difluoro-5,6,7,8-tetrahydronaphthalene-1-carbonitrile (100 mg, 0.20 mmol, 1 equiv.), $K_4Fe(CN)_6 \cdot 3H_2O$ (59 mg, 0.14 mmol, 0.7 equiv.), XPhos Pd G3 (17 mg, 0.02 mmol, 0.1 equiv.), XPhos (10 mg, 0.02 mmol, 0.1 equiv.), and KOAc (4 mg, 0.04 mmol, 0.2 equiv.) were dissolved in 1:1 water/dioxane (2 mL, 0.1 M). The reaction mixture was sparged with nitrogen for 10 minutes and then heated to 100° C. After 2 hours, the reaction was judged complete by LCMS. The reaction mixture was let to cool to room temperature and then partitioned between EtOAc and water. The layers were separated and the aqueous was extracted three times with EtOAc. The combined organics were dried over $Na_2SO_4$ and concentrated. The crude product was purified by flash column chromatography ($SiO_2$, 0 to 50% EtOAc/hexanes) to afford the desired product. $^1$H NMR (400 MHZ, Chloroform-d) δ 7.56-7.49 (m, 1H), 7.46 (d, J=8.0 Hz, 1H), 7.40 (ddd, J=7.4, 2.7, 1.7 Hz, 1H), 6.45 (d, J=8.0 Hz, 1H), 5.59 (dt, J=49.9, 3.6 Hz, 1H), 5.32 (dd, J=11.8, 3.6 Hz, 1H), 4.66-4.38 (m, 1H), 3.82 (td, J=16.2, 12.4 Hz, 1H), 3.41 (td, J=16.3, 15.8, 8.7 Hz, 1H), 2.83 (s, 1H), 2.51 (tdd, J=13.6, 6.3, 3.0 Hz, 1H), 2.29-2.09 (m, 1H), 2.09-1.86 (m, 1H), 1.75 (ddt, J=14.0, 6.0, 3.3 Hz, 1H). ESI MS [M+NH$_4$]$^+$ for $C_{21}H_{14}F_4N_2O$ calcd. 410.1, found 404.0.

Example 202: (5S,8R)-3,5-Difluoro-8-[(1S)-2,2,6-trifluoro-1-hydroxy-7-(1-methyltriazol-4-yl)-1,3-dihydroinden-4-yl]-5,6,7,8-tetrahydronaphthalene-1-carbonitrile

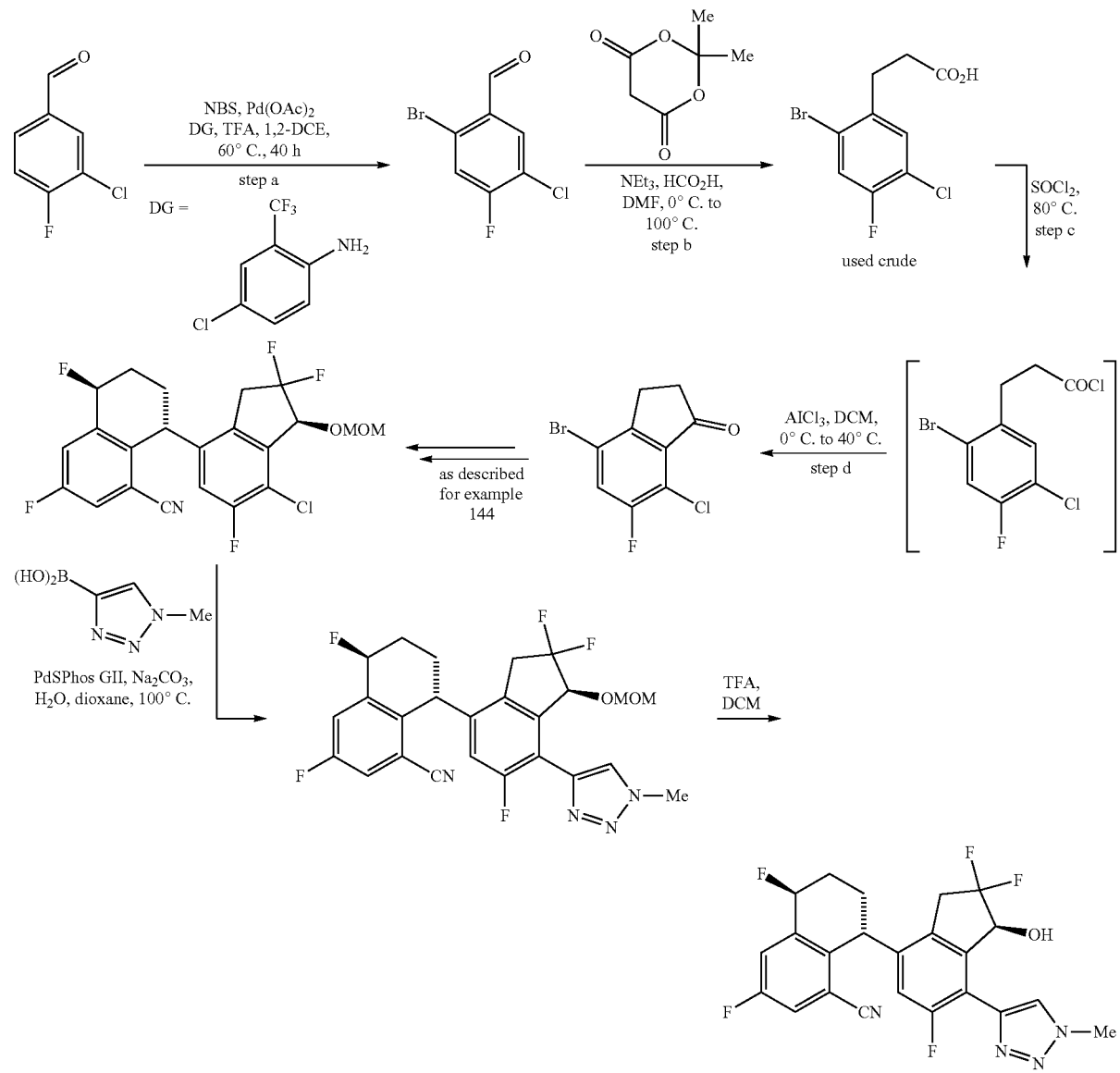

Step a: To a mixture of 3-chloro-4-fluorobenzylaldehyde (20.0 g, 126 mmol, 1.0 equiv.) in 1,2-DCE/TFA (5:1 v/v, 420 mL) was added NBS (26.9 g, 151 mmol, 1.2 equiv.), 2-amino-5-chlorobenzotrifluoride (4.93 g, 25.2 mmol, 20 mol %) and Pd(OAc)$_2$ (2.83 g, 12.6 mmol, 10 mol %), under N$_2$. The resulting mixture was heated at 60° C. for 40 h, after which the substrate was fully consumed, confirmed by NMR monitoring. After cooling to room temperature, the reaction mixture was concentrated under vacuum and then diluted with EtOAc. The resulting mixture was washed with water then brine, dried over MgSO$_4$, and purified by flash chromatography (SiO$_2$, 10 to 20% EtOAc/Hex) to afford the product 2-bromo-5-chloro-4-fluorobenzylaldehyde (19.5 g, 82.1 mmol, 65%).

Step b: NEt$_3$ (16.2 mL, 115 mmol, 2.5 mol. equiv.) was added to HCO$_2$H (10.6 mL, 278 mmol, 6.0 mol. equiv.) at 0° C. A separate flask was charged with 2-bromo-5-chloro-4-fluorobenzylaldehyde (11 g, 46.3 mmol, 1.0 mol. equiv.), DMF (50 mL) and Meldrum's acid (6.68 g, 46.3 mmol, 1.0 mol. equiv.), and the mixture was cooled to 0° C. The cooled NEt$_3$-HCO$_2$H mixture was added slowly to the DMF mixture at 0° C. The reaction was allowed to warm to room temperature, followed by heating to reflux at 100° C. and was stirred for 12 h. The reaction was cooled and decanted onto ice. The mixture was diluted with EtOAc and acidified with 2M aq. HCl. The aqueous layer was separated and back extracted with EtOAc. The organic layers were combined, washed with 2M aq. HCl, H$_2$O and brine, and dried over MgSO$_4$. Concentration under reduced pressure and azeotropic removal of residual DMF with toluene afforded 3-(2-bromo-5-chloro-4-fluorophenyl)propanoic acid (12.2 g) that was of sufficient purity to use in the next step.

Step c: The crude material from step b was placed in an ice-bath and thionyl chloride (20 mL) was added, and the reaction was heated to 80° C. for 1 h. The reaction was cooled, and residual thionyl chloride was removed upon concentration under reduced pressure in a fume-hood. This furnished 3-(2-bromo-5-chloro-4-fluorophenyl)propanoyl chloride that was used directly in the next step.

Step d: Crude 3-(2-bromo-5-chloro-4-fluorophenyl)propanoyl chloride from the previous step was dissolved in DCM (100 mL) and cooled to 0° C. AlCl$_3$ (14.5 g, 108 mmol, 2.5 mol. equiv.) was added and the resulting mixture was heated to 40° C. and stirred for 15 h. The reaction mixture was cooled and decanted carefully onto ice. The mixture was acidified with 2M aq. HCl and diluted with additional DCM. The aqueous layer was separated and extracted with DCM. The organic layers were combined and washed with additional 2M aq. HCl, water, brine, and dried over MgSO$_4$. Concentration under reduced pressure and purification by flash chromatography (SiO$_2$, 20 to 60% hexanes/DCM) furnished 4-bromo-7-chloro-6-fluoro-2,3-dihydroinden-1-one (5.22 g, 19.8 mmol, 43% over 3 steps) as a yellow solid.

The title compound was prepared from 4-bromo-7-chloro-6-fluoro-2,3-dihydroinden-1-one in a similar fashion to the sequence described for Example 144. $^1$H NMR (400 MHZ, CDCl$_3$) δ 7.88 (s, 1H), 7.58-7.52 (m, 1H), 7.43 (ddd, J=7.5, 2.8, 1.7 Hz, 1H), 6.22 (d, J=10.5 Hz, 1H), 5.63 (dt, J=49.8, 3.6 Hz, 1H), 4.81 (dd, J=11.8, 4.7 Hz, 1H), 4.57-4.50 (m, 1H), 3.94 (d, J=1.4 Hz, 3H), 3.90-3.75 (m, 1H), 3.41 (t, J=16.8 Hz, 1H), 2.70 (d, J=4.7 Hz, 1H), 2.54 (tdd, J=13.4, 6.2, 3.2 Hz, 1H), 2.29-1.98 (m, 2H), 1.85 (ddd, J=12.2, 6.3, 3.4 Hz, 1H). ESI MS [M+H]$^+$ for C$_{23}$H$_{17}$F$_5$N$_4$O, calcd 461.1, found 461.0.

Example 203: (5S,8R)-8-[(1S)-7-(6-amino-2-methylpyridin-3-yl)-2,2,6-trifluoro-1-hydroxy-1,3-dihydroinden-4-yl]-3,5-difluoro-5,6,7,8-tetrahydronaphthalene-1-carbonitrile

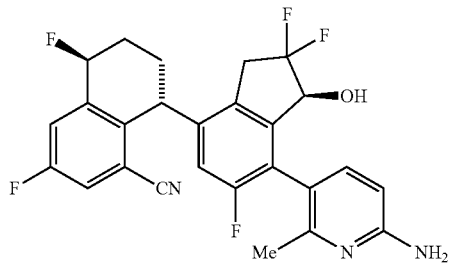 [SMILES: Cc1nc(N)ccc1-c1c(F)cc([C@H]2CC[C@H](F)c3cc(F)cc(C#N)c32)c2c1[C@H](O)C(F)(F)C2]

The title compound was prepared in a similar fashion to Example 202. $^1$H NMR (400 MHz, CDCl$_3$, appears as a 1.2:1 mixture of rotamers with mostly overlapping peaks) δ 7.56-7.48 (m, 1H), 7.46-7.38 (m, 1.4H), 7.22 (d, J=8.3 Hz, 0.5H), 6.41 (d, J=8.3 Hz, 0.5H), 6.36-6.33 (m, 0.4H), 6.08 (d, J=10.3 Hz, 1H), 5.61 (dt, J=50.0, 3.6 Hz, 1H), 4.97 (dd, J=11.9, 2.5 Hz, 0.5H), 4.79 (d, J=11.7 Hz, 0.4H), 4.59-4.39 (m, 3H), 3.88-3.71 (m, 1H), 3.45-3.30 (m, 1H), 2.57-2.42 (m, 1H), 2.27-2.11 (m, 2H), 2.08 (s, 1.2H), 2.04 (s, 1.5H), 1.93-1.80 (m, 1H). ESI MS [M+H]$^+$ for C$_{26}$H$_{20}$F$_5$N$_3$O, calcd 486.2, found 486.0.

Example 204: (5S,8R)-8-[(1S)-7-(2-amino-4-cyanophenyl)-2,2,6-trifluoro-1-hydroxy-2,3-dihydro-1H-inden-4-yl]-3,5-difluoro-5,6,7,8-tetrahydronaphtalene-1-carbonitrile

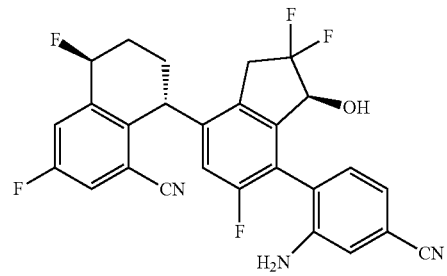 [SMILES: N#Cc1ccc(-c2c(F)cc([C@H]3CC[C@H](F)c4cc(F)cc(C#N)c43)c3c2[C@H](O)C(F)(F)C3)c(N)c1]

The title compound was prepared in a similar fashion to Example 202. $^1$H NMR (400 MHz, DMSO-d$_6$, appears as a 3.5:1 rotamers) δ 8.00-7.93 (m, 1H), 7.88-7.81 (m, 1H), 7.17 (d, J=7.8 Hz, 0.2H), 7.14 (d, J=7.7 Hz, 0.8H), 7.09 (d, J=1.5 Hz, 0.8H), 7.04 (d, J=1.5 Hz, 0.2H), 7.00 (dd, J=7.7, 1.7 Hz, 0.8H), 6.93 (dd, J=7.8, 1.7 Hz, 0.2H), 6.33 (d, J=10.7 Hz, 0.8H), 6.24 (d, J=10.8 Hz, 0.2H), 6.05 (d, J=6.4 Hz, 0.8H), 5.96 (d, J=6.6 Hz, 0.2H), 5.79 (dt, J=49.4, 3.1 Hz, 1H), 5.23 (s, 0.4H), 4.99 (s, 1.6H), 4.92-4.76 (m, 1H), 4.67-4.57 (m, 1H), 3.70-3.38 (m, 2H), 2.41-2.23 (m, 1H), 2.15-1.88 (m, 2H), 1.83-1.65 (m, 1H). ESI MS [M+H]$^+$ for C$_{27}$H$_{18}$F$_5$N$_3$O, calcd 496.1, found 496.0.

Example 205: (5S,8R)-8-[(1S)-7-(4-amino-2-methylpyrimidin-5-yl)-2,2,6-trifluoro-1-hydroxy-2,3-dihydro-1H-inden-4-yl]-3,5-difluoro-5,6,7,8-tetrahydronaphthalene-1-carbonitrile

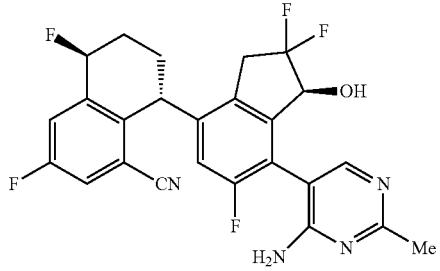 [SMILES: Cc1ncc(-c2c(F)cc([C@H]3CC[C@H](F)c4cc(F)cc(C#N)c43)c3c2[C@H](O)C(F)(F)C3)c(N)n1]

The title compound was prepared in a similar fashion to Example 202. $^1$H NMR (400 MHz, CDCl$_3$, appears as a 1.5:1 mixture of rotamers) § 8.27 (s, 0.4H), 8.01 (s, 0.6H), 7.62-7.50 (m, 1H), 7.48-7.36 (m, 1H), 6.26 (d, J=10.3 Hz, 0.4H), 6.16 (d, J=10.1 Hz, 0.6 zH), 5.63 (dt, J=50.2, 2.5 Hz, 1H), 5.04-4.75 (m, 3H), 4.55-4.47 (m, 4H), 3.91-3.69 (m, 1H), 3.66-3.52 (m, 1H), 3.50-3.21 (m, 1H), 2.67-2.44 (m, 4H), 2.31-1.98 (m, 2H), 1.94-1.79 (m, 1H). ESI MS [M+H]$^+$ for C$_{25}$H$_{19}$F$_5$N$_4$O, calcd 487.2, found 487.0.

Example 206: 5-[(3S)-7-[(1R,4S)-8-cyano-4,6-difluoro-1,2,3,4-tetrahydronaphthalen-1-yl]-2,2,5-trifluoro-3-hydroxy-2,3-dihydro-1H-inden-4-yl]-4-methylpyrimidine-2-carbonitrile

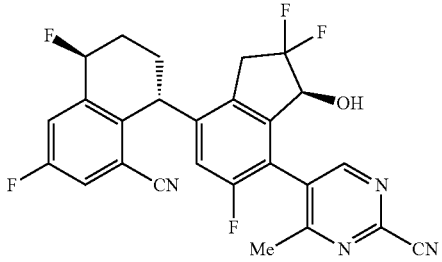 [SMILES: Cc1nc(C#N)ncc1-c1c(F)cc([C@H]2CC[C@H](F)c3cc(F)cc(C#N)c32)c2c1[C@H](O)C(F)(F)C2]

The title compound was prepared in a similar fashion to Example 202. $^1$H NMR (400 MHz, CDCl$_3$, appears as a 1:1 mixture of rotamers) δ 8.84 (s, 0.5H), 8.55 (s, 0.5H), 7.58-7.48 (m, 1H), 7.49-7.37 (m, 1H), 6.22 (t, J=9.8 Hz, 0.5H), 6.12 (d, J=9.9 Hz, 0.5H), 5.72-5.51 (m, 1H), 5.24-5.14 (m, 0.5H), 4.98-4.60 (m, 0.5H), 4.58-4.49 (m, 1H), 4.47-4.40 (m, 1H), 3.89-3.72 (m, 1H), 3.51-3.29 (m, 1H), 2.68-2.34 (m, 4H), 2.30-1.94 (m, 2H), 1.92-1.72 (m, 1H). ESI MS [M+H]$^+$ for C$_{26}$H$_{17}$F$_5$N$_4$O, calcd 497.1, found 497.0.

Example 207: (5S,8R)-8-[(1S)-7-chloro-2,2,6-trifluoro-1-hydroxy-1,3-dihydroinden-4-yl]-3,5-difluoro-5,6,7,8-tetrahydronaphthalene-1-carbonitrile

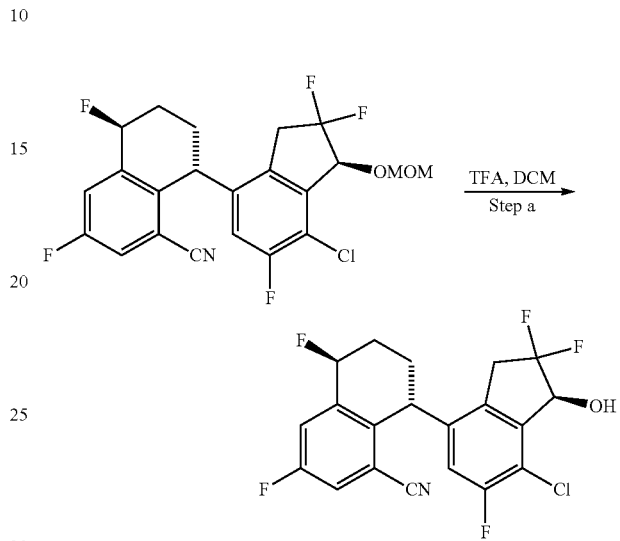

Step a: A solution (5S,8R)-8-[(1S)-7-chloro-2,2,6-trifluoro-1-(methoxymethoxy)-1,3-dihydroinden-4-yl]-3,5-difluoro-5,6,7,8-tetrahydronaphthalene-1-carbonitrile in TFA/DCM (1:10, 2.0 mL) was heated at 40° ° C. for 1 h, after which LCMS full consumption of starting material. The reaction mixture was concentrated under reduced pressure, and the residue was purified by HPLC to yield (5S,8R)-8-[(1S)-7-chloro-2,2,6-trifluoro-1-hydroxy-2,3-dihydro-1H-inden-4-yl]-3,5-difluoro-5,6,7,8-tetrahydronaphthalene-1-carbonitrile as a white solid (20 mg, 63%). $^1$H NMR (400 MHZ, DMSO-d$_6$) δ 7.95 (ddd, J=8.3, 2.8, 1.6 Hz, 1H), 7.84 (ddd, J=9.2, 2.6, 1.1 Hz, 1H), 6.47 (d, J=10.5 Hz, 1H), 5.76 (dt, J=50.0, 3.1 Hz, 1H), 5.07 (d, J=12.6 Hz, 1H), 4.64-4.50 (m, 1H), 3.69-3.38 (m, 2H), 2.28 (td, J=14.2, 13.0, 7.1 Hz, 1H), 2.08-1.82 (m, 2H), 1.70-1.60 (m, 1H). ESI MS [M+Na]$^+$ for C$_{20}$H$_{13}$ClF$_5$NO, calcd 436.1, found 436.0.

Example 208: (5R,6S)-3,5,6-trifluoro-8-[(1S)-2,2,6-trifluoro-1-hydroxy-7-(1-methyl-1H-imidazol-5-yl)-2,3-dihydro-1H-inden-4-yl]-5,6,7,8-tetrahydronaphthalene-1-carbonitrile

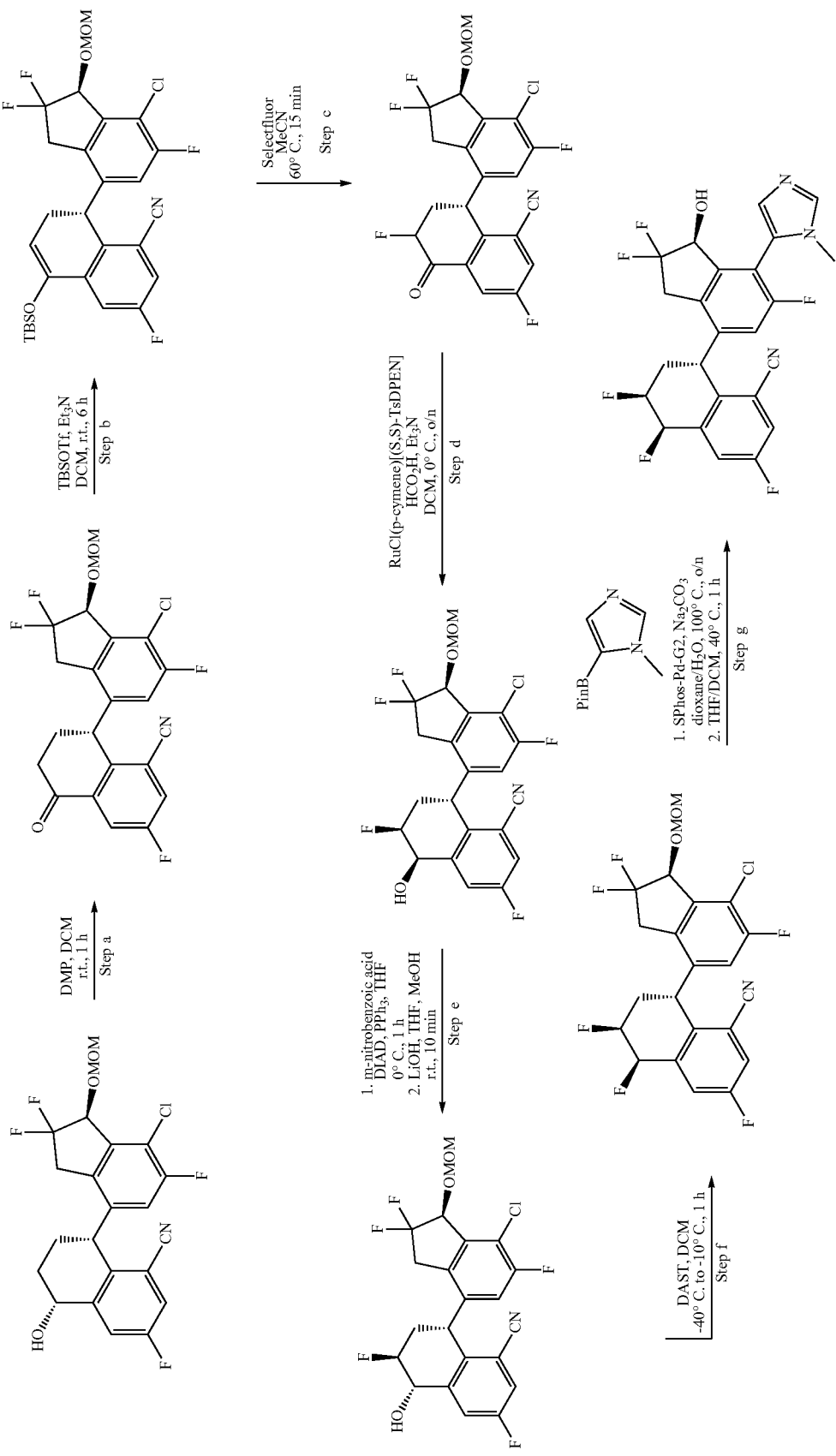

Step a: To a solution of (5R,8R)-8-[(1S)-7-chloro-2,2,6-trifluoro-1-(methoxymethoxy)-1,3-dihydroinden-4-yl]-3-fluoro-5-hydroxy-5,6,7,8-tetrahydronaphthalene-1-carbonitrile (accessed during the preparation of example 202, 1.17 g, 2.57 mmol, 1.0 equiv.) in DCM (26 mL) was added DMP (1.64 g, 3.86 mmol, 1.5 mol. equiv.) at 0° C. The resulting mixture was then stirred at room temperature for 1 h, and then quenched with saturated NaHCO$_3$ (aq.) and saturated Na$_2$S$_2$O$_3$ (aq.). The aqueous layer was extracted with DCM× 2. The combined organic layer was then washed with brine, dried over Na$_2$SO$_4$, concentrated and purified by flash chromatography (SiO$_2$, 10 to 40% EtOAc/hexanes) to afford the product (1.16 g, 2.56 mmol, 100%) as a white solid.

Step b: To a solution of the crude product from step a (1.16 g, 2.56 mmol, 1.0 equiv.) in DCM (10 mL) was added Et$_3$N (1.55 g, 2.1 mL, 15.3 mmol, 6.0 equiv.) then TBSOTf (2.03 g, 1.8 mL, 7.68 mmol, 2.0 equiv.) dropwise at 0° C. The resulting solution was stirred at room temperature for 6 h, and then quenched with saturated NaHCO$_3$ (aq.). The resulting mixture was then separated, and the aqueous phase was extracted with DCM. The combined organic phase was then washed with brine, dried over Na$_2$SO$_4$ and concentrated to afford the crude product which was used directly in the next step.

Step c: The crude product from step b (~2.56 mmol) was then dissolved in MeCN (15 mL). Selectfluor (2.00 g, 5.63 mmol, 2.2 equiv.) was added at room temperature. The resulting mixture was stirred at 60° C. for 15 min upon which TLC analysis showed the full consumption of starting material. The reaction was concentrated under reduced pressure to remove MeOH. The residue was treated with DCM and washed with water. The aqueous phase was extracted with DCM. The combined organic phase was then washed with brine, dried over Na$_2$SO$_4$, concentrated and purified by flash column chromatography (SiO$_2$, 0 to 30% EtOAc/hexanes) to afford the product as an off-white foam (dr 6:1, 0.945 g, 2.06 mmol, 78% yield over 2 steps).

Step d: A solution of the product from step c (0.945 g, 2.06 mmol, 1.0 equiv.), RuCl(p-cymene)[(S,S)-TsDPEN] (63.6 mg, 0.10 mmol, 5 mol %), HCO$_2$H (0.184 g, 0.15 mL, 4.0 mmol, 2.0 equiv.) and Et$_3$N (0.607 g, 0.84 mL, 6.0 mmol, 3.0 equiv.) in DCM (20 mL) was stirred at 0° C. overnight. The reaction mixture was then quenched with saturated NaHCO$_3$ (aq.). The resulting mixture was then separated, and the aqueous phase was extracted with DCM. The combined organic phase was then washed with brine, dried over Na$_2$SO$_4$, concentrated and purified by flash column chromatography (SiO$_2$, 0 to 30% EtOAc/hexanes) to afford the product as an off-white foam (dr 6:1, 0.888 g, 1.87 mmol, 94% yield).

Step e: To a solution of the product from step d (0.888 g, 1.87 mmol, 1.0 equiv.) in THF (18 mL) was added m-nitrobenzoic acid (0.938 g, 5.61 mmol, 3.0 equiv.), DIAD (0.908 g, 0.88 mL, 4.49 mmol, 2.4 equiv.) and PPh$_3$ (1.18 g, 4.49 mmol, 2.4 equiv.) at 0° C. The resulting mixture was stirred at this temperature for 1 h, and then quenched by the addition of water. The aqueous phase was extracted with EtOAc. The combined organic phase was then washed with brine, dried over Na$_2$SO$_4$, concentrated and purified by flash column chromatography (SiO$_2$, 0 to 30% EtOAc/hexanes) to afford the ester intermediate. The ester was then dissolved in THF/MeOH (2:1, 15 mL). A solution of LiOH.H$_2$O (0.118 g, 2.80 mmol, 1.5 equiv.) in H$_2$O (3 mL) was added at room temperature. The resulting mixture was stirred at room temperature for 10 min and then concentrated under vacuum. The residue was treated with EtOAc and H$_2$O. The aqueous phase was extracted with EtOAc. The combined organic phase was then washed with brine, dried over Na$_2$SO$_4$ and concentrated to afford the product which was directly used in the next step.

Step f: To a solution of the product from step e (~1.87 mmol) in DCM (18 mL) was added DAST (1.51 g, 1.2 mL, 9.35 mmol, 5.0 equiv.) dropwise at −40° ° C. The reaction temperature was gradually raised to −10° C. in 1 h, upon which TLC analysis showed full conversion of the substrate. The reaction mixture was then quenched with saturated NaHCO$_3$ (aq.). The resulting mixture was then separated, and the aqueous phase was extracted with DCM. The combined organic phase was then washed with brine, dried over Na$_2$SO$_4$, concentrated and purified by flash column chromatography (SiO$_2$, 0 to 20% EtOAc/hexanes) to afford the single diastereomer product as an off-white foam (0.418 g, 0.878 mmol, 47% yield over 2 steps).

Step g: A 40-mL vial was charged with the product from step f (60.0 mg, 0.126 mmol, 1.0 equiv.), 1-methyl-5-(4,4,5,5-tetramethyl-1,3,2-dioxaborolan-2-yl)-1H-imidazole (28.9 mg, 0.139 mmol, 1.1 equiv.), SPhos-Pd-G2 (9.4 mg, 13 μmol, 10 mol %), 1M Na$_2$CO$_3$ aqueous solution (0.25 mL, 0.25 mmol, 2.0 equiv.) and 1,4-dioxane (1.3 mL). The resulting mixture was heated at 100° C. and stirred overnight. After cooling to room temperature, the reaction mixture was diluted with EtOAc and washed with H$_2$O. The aqueous layer was separated and extracted with EtOAc. The combined organic phase was then washed with brine, dried over Na$_2$SO$_4$ and concentrated. The residue was treated with TFA/DCM (1:10, 2.0 mL) and heated to 40° C. for 1 h. The mixture was then concentrated and purified by HPLC to afford the title compound as a white solid (5.5 mg, 11.5 μmol, 9% yield). $^1$H NMR (400 MHZ, CDCl$_3$) δ 7.61-7.57 (m, 2H), 7.44 (ddd, J=7.7, 2.8 Hz, 1H), 7.39 (s, 1H), 6.38 (d, J=10.6 Hz, 1H), 5.70 (dd, J=50.3, 15.8 Hz, 1H), 5.35-5.13 (m, 1H), 4.73 (d, J=11.5 Hz, 1H), 4.66 (t, J=6.8 Hz, 1H), 3.75 (ddd, J=24.3, 16.2, 8.1 Hz, 1H), 3.54 (d, J=1.7 Hz, 3H), 3.13 (t, J=16.6 Hz, 1H), 2.93-2.80 (m, 1H), 2.05 (ddd, J=26.0, 14.7, 6.7 Hz, 1H). ESI MS [M+H]$^+$ for C$_{24}$H$_{17}$F$_6$N$_3$O, calcd 478.1, found 478.0.

Example 209: (5R,6S)-8-[(1S)-7-(1,5-dimethyl-1H-pyrazol-4-yl)-2,2,6-trifluoro-1-hydroxy-2,3-dihydro-1H-inden-4-yl]-3,5,6-trifluoro-5,6,7,8-tetrahydronaphthalene-1-carbonitrile

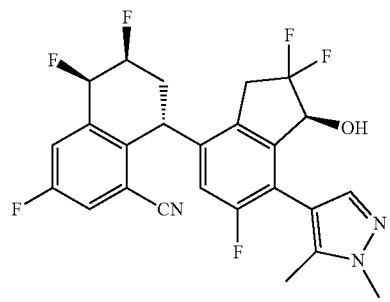 [SMILES: Cc1c(-c2c(F)cc([C@H]3C[C@H](F)[C@H](F)c4cc(F)cc(C#N)c43)c3c2[C@H](O)C(F)(F)C3)cnn1C]

The title compound was prepared in a similar fashion to Example 208. $^1$H NMR (400 MHz, DMSO-d$_6$) δ 7.97 (ddd, J=8.3, 2.9, 1.1 Hz, 1H), 7.87 (dd, J=9.0, 2.8 Hz, 1H), 6.57 (d, J=11.2 Hz, 1H), 6.25 (d, J=5.9 Hz, 1H), 6.03 (ddd, J=51.0, 15.9, 2.1 Hz, 1H), 5.46-5.18 (m, 1H), 4.71 (t, J=6.3 Hz, 1H), 4.64 (dd, J=12.0, 5.9 Hz, 1H), 3.78 (s, 3H), 3.57 (ddd, J=24.7, 16.6, 9.4 Hz, 1H), 3.25 (t, J=17.0 Hz, 1H), 2.85-2.64 (m, 1H), 2.11 (d, J=2.1 Hz, 3H), 2.06-1.88 (m, 1H). ESI MS [M+H]$^+$ for $C_{25}H_{19}F_6N_3O$, calcd 492.2, found 492.0.

Example 210: (5S,8R)-8-[(1S,2R)-2,6-difluoro-1-hydroxy-7-(2-methylpyrazol-3-yl)-2,3-dihydro-1H-inden-4-yl]-3,5-difluoro-5,6,7,8-tetrahydronaphthalene-1-carbonitrile tional EtOAc. The organic layers were combined, washed with H$_2$O (3×100 mL), brine, and dried over MgSO$_4$. Concentration under reduced pressure and purification by column chromatography (SiO$_2$, hexanes to 30% EtOAc) furnished the alcohol product as a single diastereomer (2.94 g, 64%, 75% ee as determined via analytical chiral HPLC using an AD-H column).

Step c: To a solution of indanol product from step b (2.94 g, 10.37 mmol, 1.0 mol. equiv.) in DCM (35 mL) was added

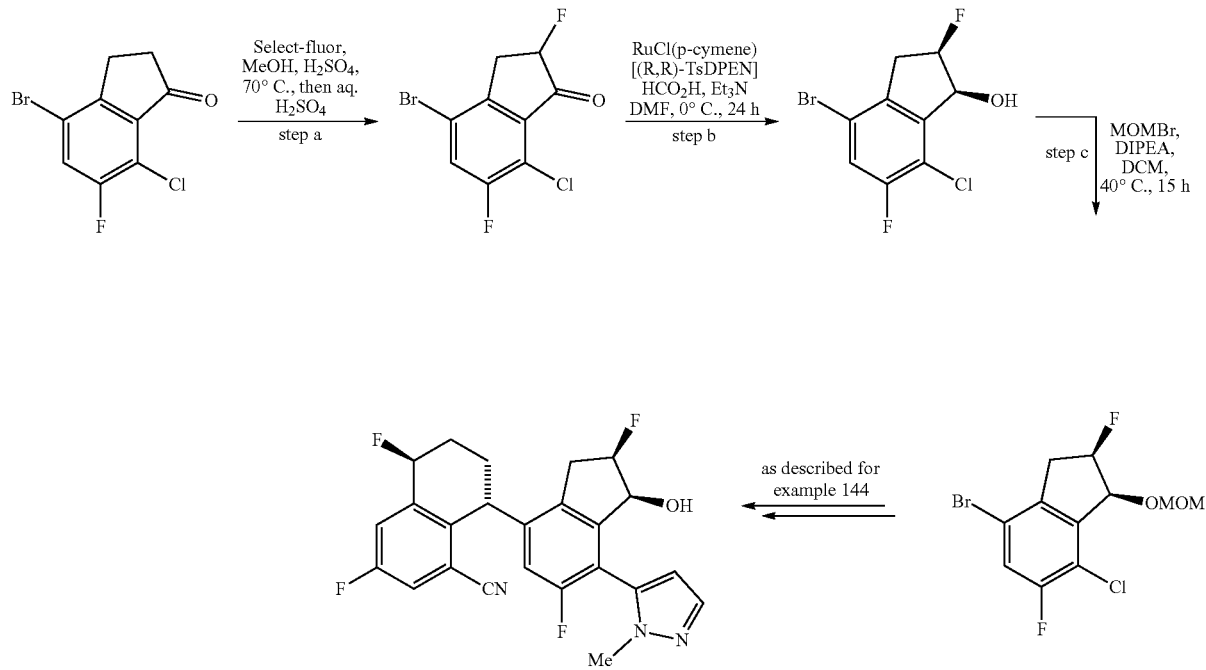

Step a: To a solution 4-bromo-7-chloro-6-fluoro-2,3-dihydroinden-1-one (5.20 g, 21.9 mmol, 1.0 equiv.) in MeOH (100 mL) was added SelectFluor (9.31 g, 26.3 mmol, 1.2 equiv.) and concentrated H$_2$SO$_4$ (5 drops). The resulting mixture was heated at reflux for 2 h. After cooling to room temperature, 0.3 M H$_2$SO$_4$ (aq., 220 mL) was added to the reaction mixture. The resulting mixture was heated at reflux for another 1 h. After cooling to room temperature, the reaction was partitioned between EtOAc (200 mL) and H$_2$O (200 mL). The aqueous layer was separated and back extracted with additional EtOAc (200 mL). The organic layers were combined, washed with water, then brine and dried over MgSO$_4$. Concentration under reduced pressure gave mono-fluoro indanone that was taken crude onto the next step without purification (4.60 g, 75%).

Step b: To a solution of 4-bromo-7-chloro-2,6-difluoro-2,3-dihydroinden-1-one (4.6 g, 21.9 mmol, 1.0 mol. equiv.) in DMF (60 mL) was added HCO$_2$H (1.9 mL, 48.9 mmol, 3.0 mol. equiv.) and NEt$_3$ (4.6 mL, 32.6 mmol, 2.0 mol. equiv.) at 0° C. RuCl(p-cymene)[(R,R)-TsDPEN] (418 mg, 0.652 mmol, 4.0 mol %) was added and the reaction was stirred in the fridge for 48 h. The reaction was poured onto sat. aq. NaHCO$_3$ solution and diluted with EtOAc. The aqueous layer was separated and back extracted with addi- DIPEA (3.7 mL, 20.7 mmol, 2.0 mol. equiv.) and MOMBr (1.3 mL, 15.6 mmol, 1.5 mol. equiv.) at 0° C. The reaction was allowed to warm to room temperature and was then heated at 40° C. overnight. The reaction was poured onto sat. aq. NaHCO$_3$ solution and diluted with DCM. The aqueous layer was separated and back extracted with additional DCM. The organic layers were combined, washed with H$_2$O, brine, and dried over MgSO$_4$. Concentration under reduced pressure and purification by column chromatography (SiO$_2$, hexanes to 70% DCM) furnished the MOM protected indanol (2.3 g, 68%).

The title compound was prepared from (1S,2R)-4-bromo-7-chloro-2,6-difluoro-1-(methoxymethoxy)-2,3-dihydro-1H-indene in analogous fashion to the sequence described for Example 144. $^1$H NMR (400 MHZ, CDCl$_3$) δ 7.57 (d, J=1.9 Hz, 1H), 7.55-7.50 (m, 1H), 7.43 (dt, J=7.6, 2.3 Hz, 1H), 6.40 (s, 1H), 6.13 (d, J=10.4 Hz, 1H), 5.61 (dt, J=50.0, 3.6 Hz, 1H), 5.32 (d, J=52.4 Hz, 1H), 5.07 (s, 1H), 4.60 (s, 1H), 3.73 (d, J=1.3 Hz, 3H), 3.61-3.44 (m, 1H), 3.24-3.10 (m, 1H), 2.49 (tdd, J=13.4, 6.0, 3.1 Hz, 1H), 2.34-2.01 (m, 3H), 1.88-1.77 (m, 1H). ESI MS [M+H]$^+$ for $C_{24}H_{19}F_4N_3O$, calcd 442.1, found 442.0.

Example 211: (5S,8R)-8-[(1S,2R)-2,6-Difluoro-1-hydroxy-7-methylsulfonyl-2,3-dihydro-1H-inden-4-yl]-3,5-difluoro-5,6,7,8-tetrahydronaphthalene-1-carbonitrile

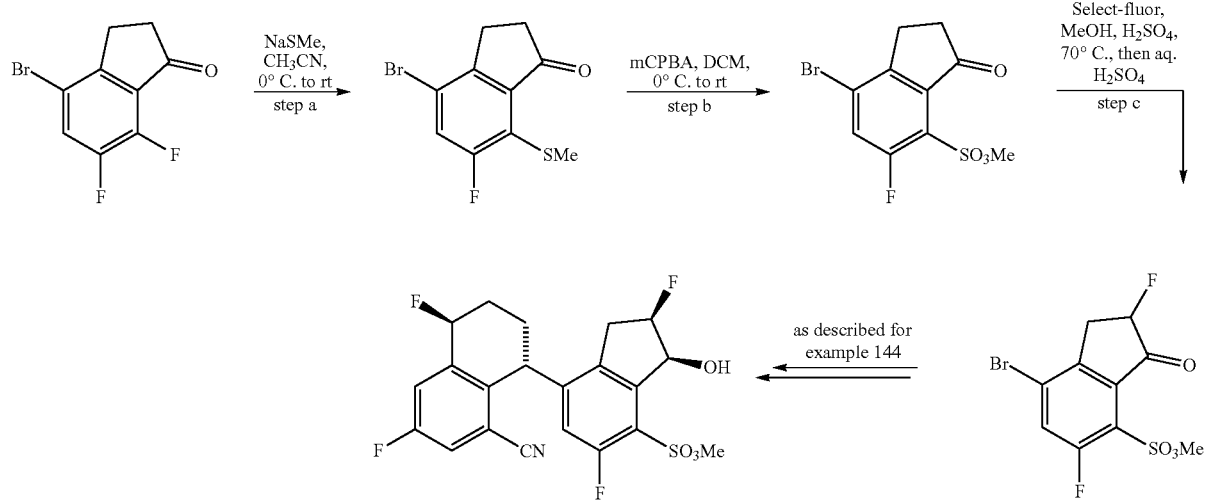

Step a: To a mixture of 4-bromo-6,7-difluoro-2,3-dihydroinden-1-one (5.0 g, 20.2 mmol, 1.0 mol. equiv.) in CH₃CN (60 mL) was added NaSMe (1.84 g, 26.3 mmol, 1.3 mol. equiv.) at 0° C. The reaction was allowed to warm to room temperature and stirred for 1 h. The reaction was quenched with sat. aq. NH₄Cl solution and diluted with EtOAc. The aqueous layer was separated and back extracted with additional EtOAc. The organic layers were combined, washed with water, brine and dried over MgSO₄. Concentration under reduced pressure furnished crude thioether that was taken directly onto the next step without additional purification.

Step b: The crude thioether product of step a was dissolved in DCM (100 mL) and cooled to 0° C. mCPBA (9.50 g, 42.4 mmol, 2.1 mol. equiv.) was added portion-wise and the reaction was allowed to warm to room temperature and stirred for 2 h. The reaction was cooled in an ice-bath and carefully quenched by the addition of sat. aq. Na₂S₂O₃ solution and sat. aq. NaHCO₃ solution. After vigorous stirring, the aqueous layer was separated and extracted with additional DCM. The organic layers were combined, washed with brine and dried over MgSO₄. Concentration under reduced pressure furnished crude sulfone that was taken onto the next step without additional purification.

Step c: To a solution of crude 4-bromo-6-fluoro-7-methylsulfonyl-2,3-dihydroinden-1-one from the previous step (~20.2 mmol, 1.0 equiv.) in MeOH (120 mL) was added SelectFluor (8.58 g, 24.2 mmol, 1.2 equiv.) and concentrated H₂SO₄ (5 drops). The resulting mixture was heated at reflux for 2 h. After cooling to room temperature, 0.3 M H₂SO₄ (aq., 200 mL) was added to the reaction mixture. The resulting mixture was heated at reflux for another 1 h. After cooling to room temperature, the reaction was partitioned between EtOAc (200 mL) and H₂O (200 mL). The aqueous layer was separated and back extracted with additional EtOAc (200 mL). The organic layers were combined, washed with water, then brine and dried over MgSO₄. Concentration under reduced pressure furnished the monofluoroindanone as a white solid (5.98 g, 91% over 3 steps).

The title compound was prepared in a similar fashion to the sequence described for the preparation of Example 144 from the product of step c. ¹H NMR (400 MHZ, DMSO-d₆) δ 7.97 (ddd, J=8.3, 2.8, 1.6 Hz, 1H), 7.91-7.84 (m, 1H), 6.40 (d, J=11.8 Hz, 1H), 5.85-5.67 (m, 2H), 5.62 (q, J=5.4 Hz, 1H), 5.37-5.18 (m, 1H), 4.74-4.63 (m, 1H), 3.35 (s, 3H), 3.31-3.16 (m, 2H), 2.30 (qd, J=11.2, 10.0, 5.4 Hz, 1H), 2.08-1.66 (m, 3H). ESI MS [M+Na]⁺ for C₂₁H₁₇F₄NO₃S, calcd 462.1, found 462.0.

Example 212: (5S,8R)-8-[(1S,2R)-6-amino-2-fluoro-1-hydroxy-7-methylsulfonyl-2,3-dihydro-1H-inden-4-yl]-3,5-difluoro-5,6,7,8-tetrahydronaphthalene-1-carbonitrile

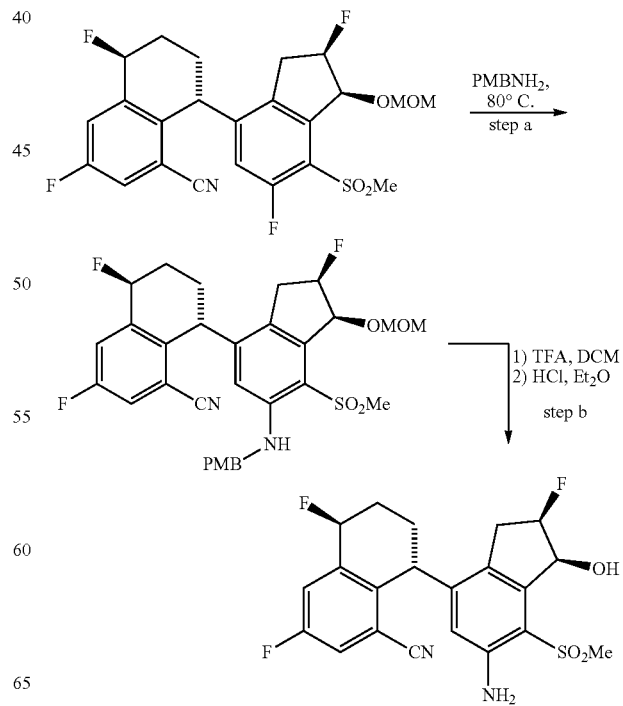

Step a: (5S,8R)-8-[(1S,2R)-2,6-Difluoro-1-(methoxymethoxy)-7-methylsulfonyl-2,3-dihydro-1H-inden-4-yl]-3,5-difluoro-5,6,7,8-tetrahydronaphthalene-1-carbonitrile (80 mg, 0.166 mmol, 1.0 mol. equiv.) was stirred in neat PMBNH$_2$ (1 mL) and heated at 80° C. After 1 h, the reaction was partitioned between 10% aq. citric acid solution and EtOAc. The aqueous layer was separated and extracted with additional EtOAc. The organic layers were combined, washed with water, brine and dried over MgSO$_4$. Concentration under reduced pressure and purification by column chromatography (SiO$_2$, hexanes to 50% EtOAc) furnished the PMB protect aniline contaminated with unreacted starting material. This mixture was taken directly onto the next step without purification.

Step b: The material from step a was dissolved in DCM (1 mL). TFA (1 mL) was added and the solution was heated at 40° C. for 1 h. Concentration under reduced pressure and purification by HPLC, followed by precipitation as the HCl salt from Et$_2$O gave the title compound as a white solid. $^1$H NMR (400 Mz, CDCl$_3$) δ 7.50 (d, J=8.4 Hz, 1H), 7.42 (dd, J=7.6, 2.1 Hz, 1H), 5.68 (dd, J=9.7, 5.1 Hz, 1H), 5.65-5.48 (m, 3H), 5.33 (dq, J=52.2, 5.3 Hz, 1H), 4.54-4.47 (m, 1H), 3.43-3.29 (m, 1H), 3.24 (s, 3H), 3.05 (ddd, J=18.1, 15.8, 6.1 Hz, 1H), 2.50-2.36 (m, 1H), 2.21-1.88 (m, 3H), 1.81-1.69 (m, 1H). ESI MS [M+Na]$^+$ for C$_{21}$H$_{19}$F$_3$N$_2$O$_3$S, calcd 459.1, found 459.0.

Example 213: (5S,8R)-8-[(1S,2R)-6-Chloro-2-fluoro-1-hydroxy-7-methylsulfonyl-2,3-dihydro-1H-inden-4-yl]-3,5-difluoro-5,6,7,8-tetrahydronaphthalene-1-carbonitrile Step b: To a solution of 4-bromo-6-chloro-7-hydroxy-2,3-dihydroinden-1-one (11.5 g, 43.9 mmol, 1.0 mol. equiv.) in DCM (300 mL) was added NEt$_3$ (13 mL, 87.8 mmol, 2.0 mol. equiv.) and triflic anhydride (8.1 mL, 48.3 mmol, 1.1 mol. equiv.) at 0° C. Upon completion, the reaction was carefully poured onto sat. aq. NaHCO$_3$ solution at 0° C. The aqueous layer was separated and back extracted with additional DCM. The organic layer was combined, washed with sat. aq. NaHCO$_3$ solution, brine, and dried over MgSO$_4$. Concentration under reduced and purification by column chromatography (SiO$_2$, hexane to 20% EtOAc) furnished the triflate product (11.2 g, 65%).

Step c: To a solution of (7-bromo-5-chloro-3-oxo-1,2-dihydroinden-4-yl) trifluoromethanesulfonate (11.2 g, 28.4 mmol, 1.0 mol equiv.) in CH$_3$CN (120 mL) at 0° C. was added NaSMe (2.98 g, 42.6 mmol, 1.5 mol. equiv.) at 0° C. The reaction was allowed to warm to room temperature and stirred for 1 h. The reaction was quenched with sat. aq. NH$_4$Cl solution and diluted with EtOAc. The aqueous layer was separated and back extracted with additional EtOAc. The organic layers were combined, washed with water, brine and dried over MgSO$_4$. Concentration under reduced pressure furnished crude thioether that was taken directly onto the next step without additional purification.

Step d: The crude thioether product of step c was dissolved in DCM (140 mL) and cooled to 0° C. mCPBA (13.7 g, 59.6 mmol, 2.1 mol. equiv.) was added portion-wise and the reaction warmed to room temperature and stirred for 2 h. The reaction was cooled in an ice-bath and carefully quenched by the addition of sat. aq. Na$_2$S$_2$O$_3$ solution and sat. aq. NaHCO$_3$ solution. After vigorous stirring, the aque-

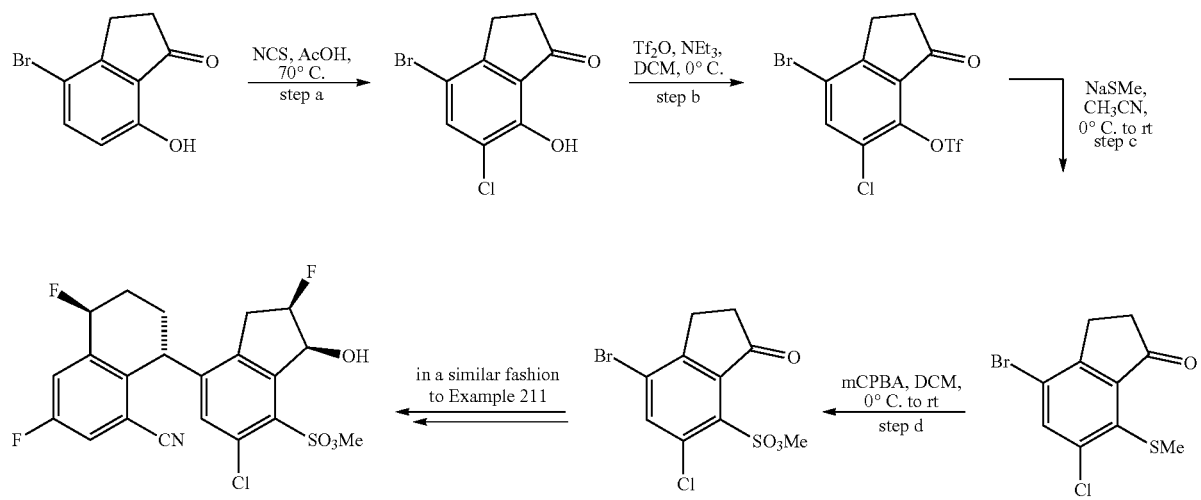

Step a: To a solution of 4-bromo-7-hydroxy-2,3-dihydroinden-1-one (12.0 g, 52.8 mmol, 1.0 mol. equiv.) in AcOH (120 mL) was added N-chlorosuccinimide (7.41 g, 55.4 mmol, 1.05 mol. equiv.). The reaction was warmed to 70° C. and stirred for 18 h. After this time, the reaction was poured onto ice and diluted with EtOAc. The aqueous layer was separated and back extracted with EtOAc. The organic layer was combined, washed with sat. aq. NaHCO$_3$ solution, water, brine, and dried over MgSO$_4$. Concentration under reduced pressure furnished the chloroindanone product (13.0 g, 94%) which was used in the next step without purification.

ous layer was separated and extracted with additional DCM. The organic layers were combined, washed with brine and dried over MgSO$_4$. Concentration under reduced and purification by column chromatography (SiO$_2$, hexane to 50% EtOAc) furnished the sulfone product (5.16 g, 56% over 2 steps).

The title compound was prepared from the product of step d in a similar fashion to Example 211. $^1$H NMR (400 MHz, DMSO-d$_6$) δ 8.01-7.95 (m, 1H), 7.91-7.85 (m, 1H), 6.54 (s, 1H), 5.92-5.67 (m, 3H), 5.27 (dq, J=52.2, 6.2 Hz, 1H), 4.72-4.66 (m, 1H), 3.36 (s, 3H), 3.32-3.17 (m, 2H), 2.38-2.24 (m, 1H), 2.07-1.66 (m, 3H). ESI MS [M+Na]$^+$ for C$_{21}$H$_{17}$ClF$_3$NO$_3$S, calcd 478.0, found 477.9.

Example 214: (5S,8R)-8-[(1S,2R)-6-Cyano-2-fluoro-1-hydroxy-7-methylsulfonyl-2,3-dihydro-1H-inden-4-yl]-3,5-difluoro-5,6,7,8-tetrahydronaphthalene-1-carbonitrile

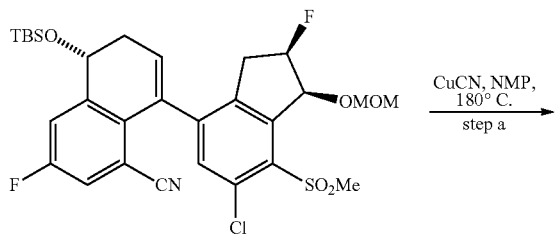

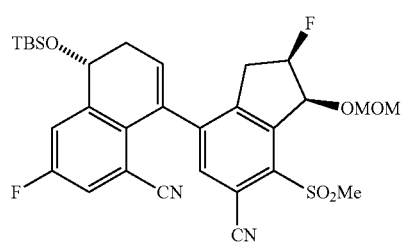

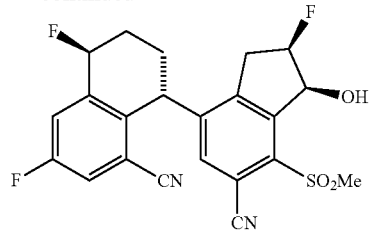

Step a: To a mixture of (5R)-5-[tert-butyl(dimethyl)silyl]oxy-8-[(1S,2R)-6-chloro-2-fluoro-1-(methoxymethoxy)-7-methylsulfonyl-2,3-dihydro-1H-inden-4-yl]-3-fluoro-5,6-dihydronaphthalene-1-carbonitrile (190 mg, 0.310 mmol, 1.0 mol. equiv.) in NMP (1.8 mL) was added CuCN (110 mg, 1.24 mmol, 4.0 mol. equiv.). The reaction was heated to 180° C. and stirred for 1.5 h. The reaction was poured onto sat. aq. NaHCO$_3$ solution and diluted with EtOAc. The aqueous layer was separated and back extracted with additional EtOAc. The organic layers were combined, washed with H$_2$O, brine and dried over MgSO$_4$. Concentration under reduced pressure and purification by column chromatography (SiO$_2$, hexane to 40% EtOAc) furnished the benzonitrile adduct (71 mg, 38%).

The title compound was accessed from the product of step a in a similar fashion to that described for Example 144. $^1$H NMR (400 MHZ, DMSO-d$_6$) δ 8.00-7.95 (m, 1H), 7.92-7.87 (m, 1H), 7.01 (s, 1H), 6.07 (d, J=6.7, 1.0 Hz, 1H), 5.78 (d, J=49.9 Hz, 1H), 5.62 (ddd, J=11.4, 6.7, 4.9 Hz, 1H), 5.33 (dq, J=52.7, 5.0 Hz, 1H), 4.81-4.75 (m, 1H), 3.48 (s, 3H), 3.44-3.30 (m, 2H), 2.37-2.23 (m, 1H), 2.06-1.65 (m, 3H). ESI MS [M+Na]$^+$ for C$_{22}$H$_{17}$F$_3$N$_2$O$_3$S, calcd 469.1, found 469.0.

Example 215: (5R,6S,8R)-3,5,6-trifluoro-8-[(1S,2R)-2-fluoro-1-hydroxy-7-methanesulfonyl-2,3-dihydro-1H-inden-4-yl]-5,6,7,8-tetrahydronaphthalene-1-carbonitrile

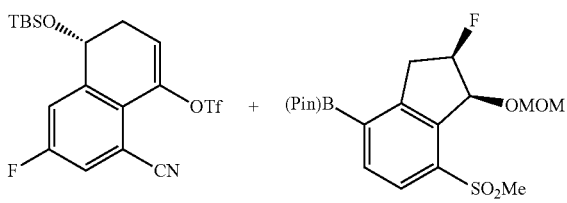

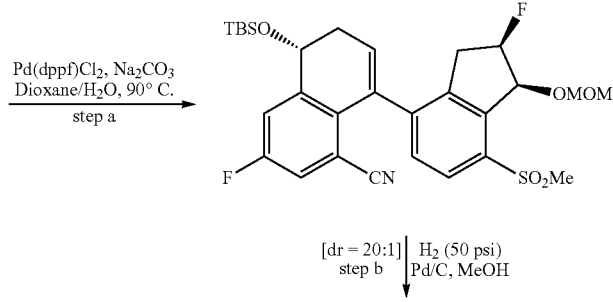

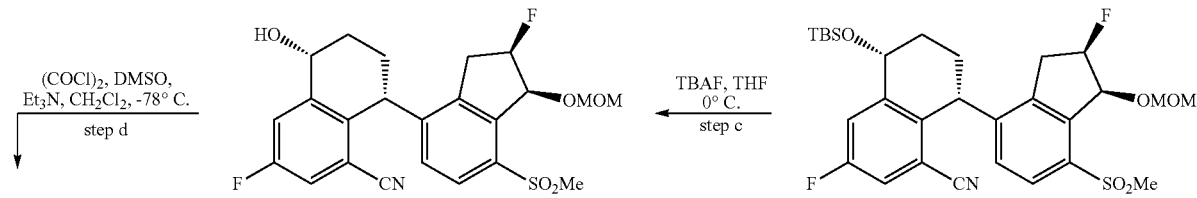

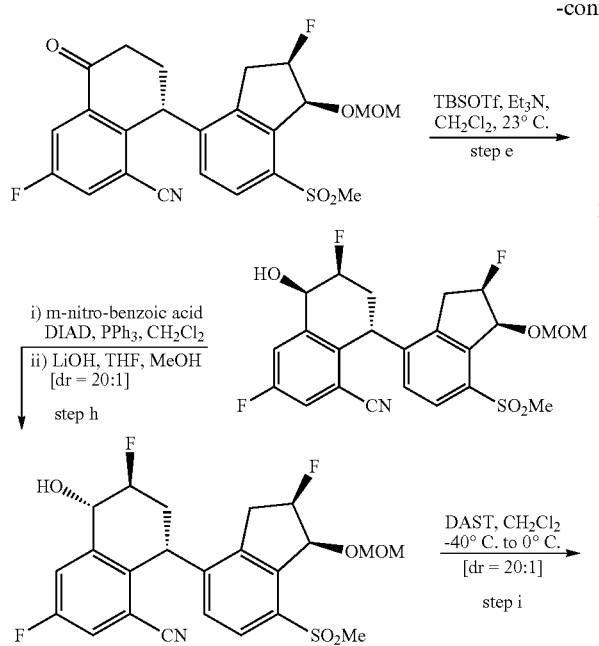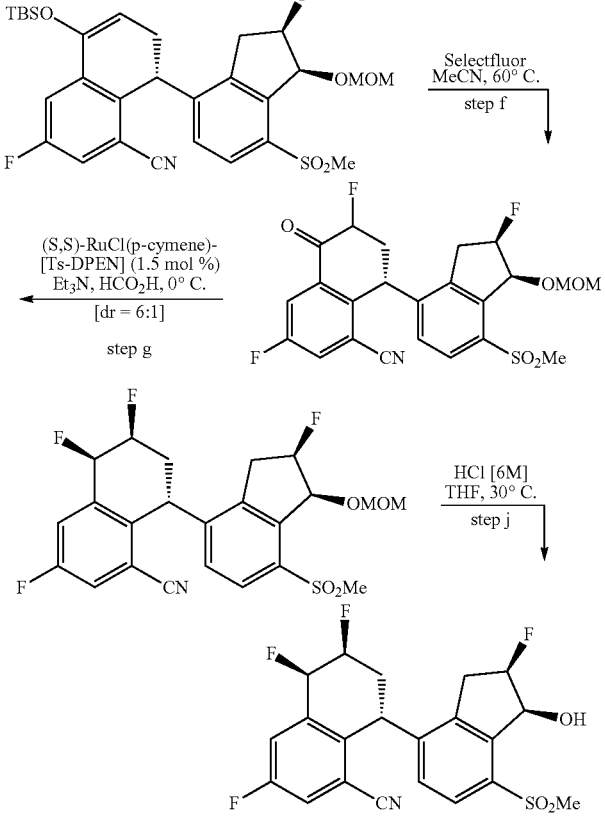

Step a. A round-bottomed flask was charged with triflate (10.0 g, 22.15 mmol, 1.0 equiv.), and boronate (9.75 g, 24.37 mmol, 1.1 equiv.), Pd(dppf)Cl$_2$ (1.62 g, 2.21 mmol, 0.1 equiv.), Na$_2$CO$_3$ (4.67 g, 44.30 mmol, 2.0 equiv.), 1,4-dioxane (80 mL) and H$_2$O (20 mL). The reaction mixture was degassed with N$_2$ bubbling for 10 min before it was stirred at 80° C. for 16 h. The reaction mixture was then quenched with saturated NaCl (aq) and extracted with EtOAc. The combined organic extract was washed with sat. sol. NaCl and the solvent was evaporated. The residue was purified using column chromatography on silica gel (Hexane/EtOAc—0%→32%) to afford the product (10.0 g, 78%) as an off-white foam.

Step b: Product of step a (10.0 g, 17.37 mmol, 1.0 equiv.) was dissolved in degassed MeOH (110 mL) and Pd/C (20 wt % Pd, 2.00 g, 10 mol %) was added. The reaction was then shaken in parr hydrogenator under H$_2$ (50 psi) for 2 h or until LCMS showed no starting material remaining. The reaction mixture was then filtered through Celite, concentrated and the residue was purified using column chromatography on silica gel (Hexane/EtOAc—0%→35%) to afford to afford the product (8.0 g, 80%) as an off-white foam.

Step c. TBAF (25.0 mL, 1M in THF, 1.8 equiv.) was added to a solution of product of step b (8.00 g, 13.85 mmol, 1.0 equiv.) in THF (100 mL) at 0° C. The reaction was slowly warmed to 23° ° C., stirred for 30 min and quenched with H$_2$O. The solution was extracted with EtOAc and the combined organic extract was washed with sat. sol. NaCl. The solvent was evaporated, and the residue was used in the next step without further purification.

Step d. Oxalyl chloride (1.31 mL, 15.24 mmol, 1.1 equiv.) was dissolved in dry CH$_2$Cl$_2$ (30 mL) and cooled to −78° C. DMSO (2.36 mL, 33.24 mmol, 2.4 equiv.) was added dropwise to the reaction mixture and the reaction was stirred for 15 minutes at −78° C. Next, product of step e was dissolved in dry CH$_2$Cl$_2$ (20 mL) and was added dropwise. The reaction was stirred for 30 minutes. Et$_3$N (9.60 mL, 69.25 mmol, 5.0 equiv.) was then added and the reaction was stirred at −78° C. for 1 h. The dry-ice bath was removed, and the reaction mixture was allowed to warm to room temperature and quenched with sat. sol. NaCl. The solution was extracted with EtOAc and the solvent was evaporated. The residue was purified using column chromatography on silica gel (Hexane/EtOAc—0%→60%) to afford to afford the product (6.14 g, 96%) as an off-white foam.

Step e. Product of step d (6.40 g, 13.9 mmol, 1.0 equiv.) was dissolved in CH$_2$Cl$_2$ (100 mL) and Et$_3$N (15.5 mL, 110 mmol, 8.0 equiv.) and TBSOTf (10.7 mL, 55.5 mmol, 4.0 equiv.) were added sequentially. The mixture was stirred for 2 h at 23° C. The reaction mixture was then quenched with sat. sol. NaHCO$_3$ and extracted with CH$_2$Cl$_2$. The combined organic extract was washed with sat. sol. NaCl and the solvent was evaporated. The residue was purified using column chromatography on silica gel (Hexane/EtOAc—0%→14%) to afford the product (7.11 g, 89%) as an off-white foam.

Step f. Product of step e (7.11 g, 12.4 mmol, 1.0 equiv.) was dissolved in MeCN (100 mL) and SelectFluor (9.63 g, 27.2 mmol, 2.2 equiv.) was added. The mixture was stirred for 15 min at 60° C. The reaction mixture was then quenched with sat. sol. NaHCO$_3$ and extracted with EtOAc. The combined organic extract was washed with sat. sol. NaCl and the solvent was evaporated. The residue was purified using column chromatography on silica gel (Hexane/EtOAc—0%→30%) to afford the product (5.21 g, 88%) as an off-white foam.

Step g. Product of step f (5.21 g, 10.87 mmol, 1.0 equiv.) was dissolved in CH$_2$Cl$_2$ (55 mL) and cooled to 0° C. Et$_3$N (3.03 mL, 21.74 mmol, 3.0 equiv.) and HCO$_2$H (1.23 mL, 32.61 mmol, 2.0 equiv.) were then added and the solution was degassed for 10 min before RuCl(p-cymene)[(S,S)-Ts-DPEN] (104 mg, 0.163 mmol, 0.015 equiv.) was added. The reaction flask was sealed with a septum and the reaction was stirred at 4° C. for 16 h. The reaction mixture was poured into a sat. sol. NaHCO$_3$ and extracted with CH$_2$Cl$_2$. The organic layer was washed with brine, dried over Na$_2$SO$_4$, filtered, and concentrated. The combined organic extract was washed with sat. sol. NaCl and the solvent was evaporated. The residue was purified using column chromatography on silica gel (Hexane/EtOAc—0%→55%) to afford the product as a separable mixture of diastereosiomer (6:1 dr, 4.31 g, 83%) with the cis-isomer (0.61 g, 12%) and trans-isomer (3.70 g, 71%) obtained as off-white foams.

Step h. Product of step g (3.60 g, 7.48 mmol, 1.0 equiv.) was dissolved in THF (80 mL) at 0° C. and 3-nitrobenzoic acid (3.37 g, 22.43 mmol, 3.0 equiv.), triphenylphosphine (4.71 g, 17.94 mmol, 2.4 equiv.) and DIAD (3.53 mL, 17.94 mmol, 2.4 equiv.) were added sequentially. The reaction mixture was stirred at 23° C. for 2 h and then quenched with H$_2$O. The mixture was extracted with EtOAc, the combined organic extract was washed with sat. sol. NaHCO$_3$ and the solvent was evaporated. The residue was purified using column chromatography on silica gel (Hexane/EtOAc—0%→65%) to afford the desired product (4.70 g, 99%) as an off-white foam. The residue was dissolved in THF/MeOH (2:1, 60 mL) and LiOH·H$_2$O (471 mg, 11.22 mmol, 1.5 equiv.) in H$_2$O (20 mL) was added dropwise. The reaction was stirred at 23° C. for 45 minutes. The solution was extracted with EtOAc, the combined organic extract was washed with sat. sol. NaCl and the solvent was evaporated. The residue was purified using column chromatography on silica gel (Hexane/EtOAc—0%→55%) to afford the product (2.80 g, 78%) as an off-white foam.

Step i. Product of step h (1.20 g, 2.49 mmol, 1.0 equiv.) was dissolved in CH$_2$Cl$_2$ (25 mL) and the solution was cooled to −40° ° C. under an atmosphere of nitrogen. DAST (1.65 mL, 12.46 mmol, 5.0 equiv.) was then added dropwise at −40° C. The reaction mixture was slowly warmed from −40° ° C. to −10° C. over a period of 2 h. When the reaction reached completion, the solution was poured in a cold sat. sol. NaHCO$_3$ and extracted with EtOAc. The combined organic extract was washed with sat. sol. NaCl and the solvent was evaporated. The residue was purified using column chromatography on silica gel (Hexane/EtOAc—0%→50%) to afford the product (0.98 g, 82%) as an off-white foam.

Step j. Product of step i (0.98 g, 2.03 mmol, 1.0 equiv.) was dissolved in THF (12 mL) at 23° C. A solution of hydrochloric acid (12 mL, 6M) was added dropwise, and the mixture was stirred at 30° ° C. for 2 h. When the reaction reached completion, the solution was poured in an ice-cold sat. sol. NaHCO$_3$ and extracted with EtOAc. The combined organic extract was washed with sat. sol. NaCl and the solvent was evaporated. The residue was purified using column chromatography on silica gel (Hexane/EtOAc—0%→50%) to afford the desired product (0.845 g, 95%) as an off-white foam. The material was dissolved in CH$_2$Cl$_2$ at 50° ° C., cooled to 0° C. and hexanes was added. The precipitate was collected by filtration to afford a white solid (0.714 g, 80%, >96% purity according to $^1$H and $^{19}$F NMR). $^1$H NMR (400 MHZ, DMSO-d$_6$) δ 7.96 (ddd, J=8.3, 2.7, 1.3 Hz, 1H), 7.89 (dd, J=8.9, 2.7 Hz, 1H), 7.57 (d, J=8.1 Hz, 1H), 6.66 (d, J=8.1 Hz, 1H), 5.95 (ddd, J=51.2, 13.5, 2.2 Hz, 1H), 5.89 (d, J=5.6 Hz, 1H), 5.47 (ddd, J=10.0, 6.2, 4.9 Hz, 1H), 5.26 (qd, J=52.5, 5.4 Hz, 1H), 5.12 (tddd, J=47.4, 18.7, 10.3, 2.7 Hz, 1H), 4.83 (t, J=5.4 Hz, 1H), 3.30 (s, 3H), 3.28-3.13 (m, 2H), 2.71-2.60 (m, 1H), 2.02-1.85 (m, 1H). $^{19}$F NMR (376 MHZ, DMSO-d$_6$) δ −112.3, −179.6, −196.7, −199.4. ESI MS [M+Na]$^+$ for C$_{21}$H$_{17}$F$_4$NO$_3$SNa, calcd 462.0, found 461.9.

Example 216: (5R,6S,8R)-8-[(1S)-7-(6-amino-2-methylpyridin-3-yl)-2,2-difluoro-1-hydroxy-2,3-dihydro-1H-inden-4-yl]-3,5,6-trifluoro-5,6,7,8-tetrahydronaphthalene-1-carbonitrile

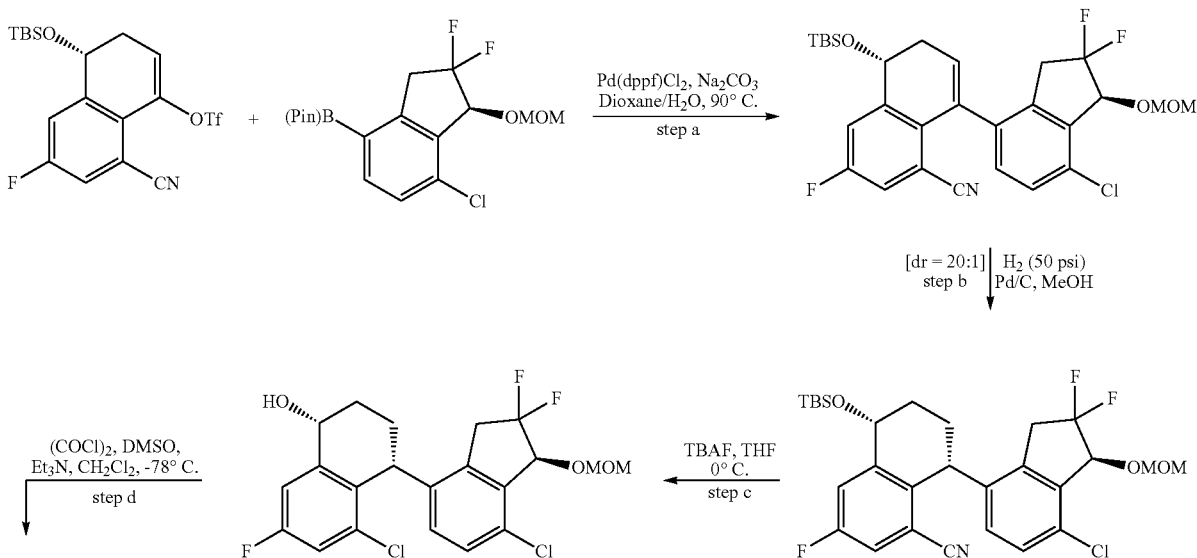

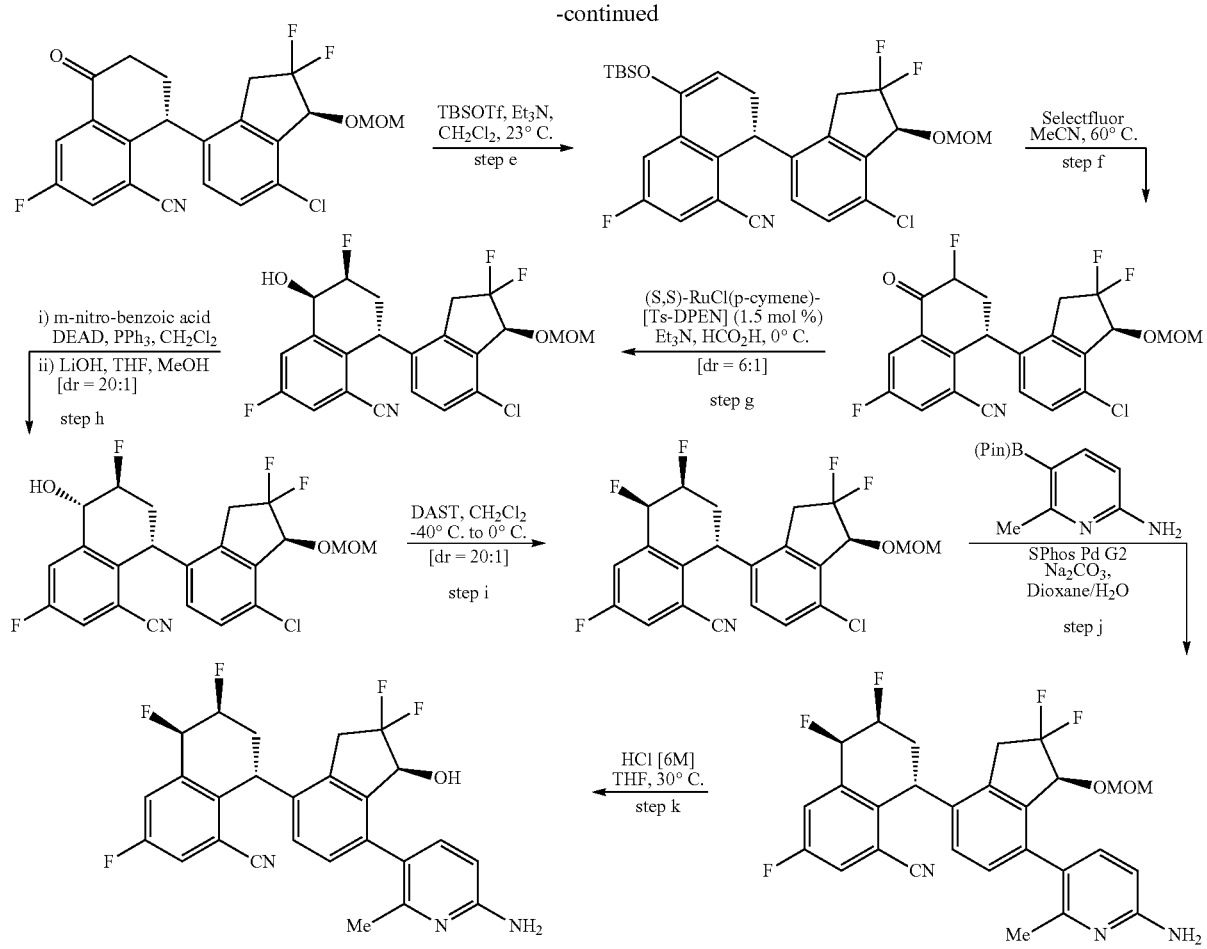

Steps a and b were performed under similar conditions as previously described using starting material previously prepared according to Example 215.

Step c. Tetrabutylammonium fluoride [4.5 mL, 1M in THF] was added to a solution of product of step b (1.2 g, 2.17 mmol, 1.0 equiv.) in THF [0.15M] at 0° C. The reaction was slowly warmed to 23° C., stirred for 30 min and quenched with H$_2$O. The solution was extracted with EtOAc and the combined organic extract was washed with sat. sol. NaCl. The solvent was evaporated, and the residue was used in the next step without further purification.

Step d. Oxalyl chloride (0.205 mL, 2.39 mmol, 1.1 equiv.) was dissolved in dry CH$_2$Cl$_2$ (5 mL) and cooled to −78° C. DMSO (0.37 mL, 5.22 mmol, 2.4 equiv.) was added dropwise to the reaction mixture and the reaction was stirred for 15 minutes at −78° C. Next, product of step c was dissolved in dry CH$_2$Cl$_2$ (4 mL) and was added dropwise, and the reaction was stirred for 15 minutes. Et$_3$N (1.51 mL, 10.87 mmol, 5.0 equiv.) was then added and the reaction was stirred at −78° C. for 1 h. The dry-ice bath was removed, and the reaction mixture was allowed to warm to room temperature and quenched with sat. sol. NaCl. The solution was extracted with EtOAc and the solvent was evaporated. The residue was purified using column chromatography on silica gel (Hexane/EtOAc—0%→30%) to afford to afford the product (852 mg, 90%) as an off-white foam.

Step e. Product of step d (650 mg, 1.49 mmol, 1.0 equiv.) was dissolved in CH$_2$Cl$_2$ (6.0 mL) and Et$_3$N (1.25 mL, 8.94 mmol, 6.0 equiv.) and TBSOTf (1.03 mL, 4.47 mmol, 3.0 equiv.) were added sequentially. The mixture was stirred for 2 h at 23° C. The reaction mixture was then quenched with sat. sol. NaHCO$_3$ and extracted with CH$_2$Cl$_2$. The combined organic extract was washed with sat. sol. NaCl and the solvent was evaporated. The residue was purified using column chromatography on silica gel (Hexane/EtOAc—0%→14%) to afford the product (720 mg, 88%) as an off-white foam.

Step f. Product of step e (720 mg, 1.31 mmol, 1.0 equiv.) was dissolved in MeCN (8.0 mL) and SelectFluor (1.02 g, 2.88 mmol, 2.2 equiv.) was added. The mixture was stirred for 45 min at 60° C. The reaction mixture was then quenched with sat. sol. NaHCO$_3$ and extracted with EtOAc. The combined organic extract was washed with sat. sol. NaCl and the solvent was evaporated. The residue was purified using column chromatography on silica gel (Hexane/EtOAc—0%→30%) to afford the product (403 mg, 68%) as an off-white foam.

Step g. Product of step f (402 mg, 0.89 mmol, 1.0 equiv.) was dissolved in CH$_2$Cl$_2$ (4.5 mL) and cooled to 0° C. Et$_3$N (0.25 mL, 1.77 mmol, 3.0 equiv.) and HCO$_2$H (0.1 mL, 2.66 mmol, 2.0 equiv.) were then added and the solution was degassed for 10 min before RuCl(p-cymene)[(S,S)-Ts-DPEN] (8.5 mg, 0.013 mmol, 0.015 equiv.) was added. The reaction flask was sealed with a septum and the reaction was stirred at 4° C. for 16 h. The reaction mixture was poured into saturated NaHCO$_3$ and extracted with CH$_2$Cl$_2$. The organic layer was washed with brine, dried over Na₂SO₄, filtered, and concentrated. The combined organic extract was washed with sat. sol. NaCl and the solvent was evaporated. The residue was purified using column chromatography on silica gel (Hexane/EtOAc—0%→30%) to afford the product as a separable mixture of diastereosiomer (6:1 dr, 368 mg, 92%) with the cis-isomer (56 mg, 14%) and trans-isomer (312 mg, 78%) obtained as off-white foams.

Step h. Product of step g (312 mg, 0.68 mmol, 1.0 equiv.) was dissolved in THF (6.5 mL) at 0° C. and 3-nitrobenzoic acid (0.34 g, 2.05 mmol, 3.0 equiv.), triphenylphosphine (0.43 g, 1.64 mmol, 2.4 equiv.) and DIAD (0.32 mL, 1.64 mmol, 2.4 equiv.) were added sequentially. The reaction mixture was stirred at 0° C. for 2 h and then quenched with H₂O. The solution was extracted with EtOAc, the combined organic extract was washed with sat. sol. NaCl and the solvent was evaporated. The residue was purified using column chromatography on silica gel (Hexane/EtOAc—0%→35%) to afford product (414 mg, 97%) as an off-white foam. The residue was dissolved in THF/MeOH (2:1, 5.0 mL) and LiOH (43 mg, 1.03 mmol, 1.5 equiv.) in H₂O (1.5 mL) was added dropwise. The reaction was stirred at 23° C. for 1 h. The solution was extracted with EtOAc, the combined organic extract was washed with sat. sol. NaCl and the solvent was evaporated. The residue was purified using column chromatography on silica gel (Hexane/EtOAc—0%→25%) to afford the product (250 mg, 80%) as an off-white foam.

Step i. Product of step h (305 mg, 0.67 mmol, 1.0 equiv.) was dissolved in CH₂Cl₂ (6.5 mL) and the solution was cooled to −40° C. under an atmosphere of nitrogen. DAST (0.44 mL, 3.35 mmol, 5.0 equiv.) was then added dropwise at −40° C. The reaction mixture was stirred and slowly warmed from −40° C. to −10° C. over a period of 2 h. When the reaction reached completion, the solution was poured in a cold sat. sol. NaHCO₃ and extracted with EtOAc. The combined organic extract was washed with sat. sol. NaCl and the solvent was evaporated. The residue was purified using column chromatography on silica gel (Hexane/EtOAc—0%→20%) to afford the product (250 mg, 82%) as an off-white foam.

Step j. A vial was charged with product of step i (50 mg, 0.11 mmol, 1.0 equiv.), 6-amino-2-methylpyridin-3-ylboronic acid pinacol ester (38 mg, 0.163 mmol, 1.5 equiv.), SPhos Pd G2 (16 mg, 0.022 mmol, 0.2 equiv.), aq. Na₂CO₃ (46 mg, 0.44 mmol, 4.0 equiv., 1M), and dioxane (1.2 mL). The reaction mixture was then sparged with N₂ for 10 minutes before being heated to 100° C. for 2 h. The solution was extracted with EtOAc, the combined organic extract was washed with sat. sol. NaCl and the solvent was evaporated. The residue was purified using column chromatography on silica gel (Hexane/EtOAc—0%→80%) to afford the product (45 mg, 78%) as an off-white foam.

Step k. Hydrochloric acid [2.0 mL, 6M] was added to previous product (1.0 equiv.) dissolved in THF [2.0 mL, 0.02M], and the mixture was stirred at 30° C. for 2 h. When the reaction reached completion, the solution was poured in a cold sat. sol. NaHCO₃ and extracted with EtOAc. The combined organic extract was washed with sat. sol. NaCl and the solvent was evaporated. The residue was purified using column chromatography on silica gel (Hexane/EtOAc—0%→90%) to afford the product (25 mg, 50%) as an off-white foam. ¹H NMR (400 MHZ, DMSO-d₆) δ 7.93 (dd, J=8.2, 1.9 Hz, 1H), 7.83 (dd, J=9.0, 2.7 Hz, 1H), 7.20 (d, J=8.2 Hz, 1H), 6.91 (d, J=7.9 Hz, 1H), 6.54 (d, J=7.9 Hz, 1H), 6.25 (d, J=8.3 Hz, 1H), 6.11-5.90 (m, 1H), 5.87-5.79 (m, 3H), 5.23 (ddd, J=48.3, 17.2, 9.6 Hz, 1H), 4.70-4.57 (m, 2H), 3.55 (ddd, J=22.0, 16.8, 10.3 Hz, 1H), 3.28-3.18 (m, 1H), 2.75-2.63 (m, 1H), 1.99 (s, 3H), 1.96-1.86 (m, 1H). ¹⁹F NMR (376 MHz, DMSO-d₆) δ −102.59, −112.72, −113.45, −180.54, −200.09. ESI MS [M+H]⁺ for C₂₆H₂₁F₅N₃O₁, calcd 486.1, found 486.0.

Example 217: (5R,6S,8R)-8-[(1S)-2,2-difluoro-1-hydroxy-7-(1-methyl-1H-pyrazol-5-yl)-2,3-dihydro-1H-inden-4-yl]-3,5,6-trifluoro-5,6,7,8-tetrahydronaphthalene-1-carbonitrile

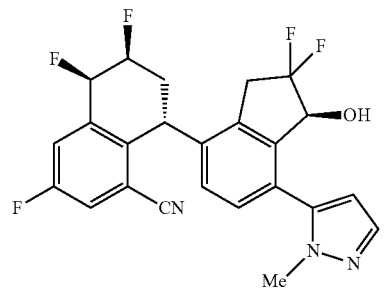 [SMILES: Cn1nccc1-c1ccc([C@H]2C[C@H](F)[C@H](F)c3cc(F)cc(C#N)c32)c2c1[C@H](O)C(F)(F)C2]

The title compound was prepared in a similar fashion to Example 216. ¹H NMR (400 MHz, DMSO-d₆) δ 7.94 (dd, J=8.2, 1.7 Hz, 1H), 7.85 (dd, J=9.0, 2.7 Hz, 1H), 7.44 (d, J=1.9 Hz, 1H), 7.18 (d, J=8.0 Hz, 1H), 6.64 (d, J=8.0 Hz, 1H), 6.44 (d, J=1.9 Hz, 1H), 6.10 (d, J=6.0 Hz, 1H), 6.09-5.91 (m, 1H), 5.40-5.00 (m, 1H), 4.82-4.74 (m, 1H), 4.72 (t, J=5.7 Hz, 1H), 3.64 (s, 3H), 3.63-3.53 (m, 1H), 3.40-3.31 (m, 1H), 2.76-2.65 (m, 1H), 2.02-1.84 (m, 1H). ¹⁹F NMR (376 MHz, DMSO-d₆) δ −102.6, −112.5, −113.3, −180.3, −200.0. ESI MS [M+H]⁺ for C₂₄H₁₉F₅N₃O₁, calcd 460.1, found 460.0.

Example 218: (5R,6S,8R)-8-[(1S)-2,2-difluoro-1-hydroxy-7-(1-methyl-1H-1,2,3-triazol-5-yl)-2,3-dihydro-1H-inden-4-yl]-3,5,6-trifluoro-5,6,7,8-tetrahydronaphthalene-1-carbonitrile

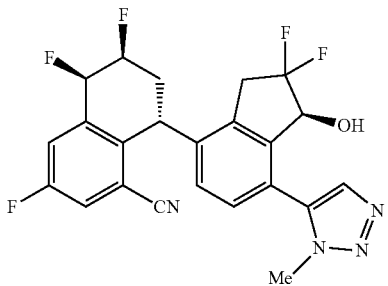 [SMILES: Cn1nncc1-c1ccc([C@H]2C[C@H](F)[C@H](F)c3cc(F)cc(C#N)c32)c2c1[C@H](O)C(F)(F)C2]

The title compound was prepared in a similar fashion to Example 216. ¹H NMR (400 MHz, DMSO-d₆) δ 7.97-7.93 (m, 1H), 7.87 (d, J=2.8 Hz, 1H), 7.85 (s, 1H), 7.25 (d, J=8.0 Hz, 1H), 6.65 (d, J=8.0 Hz, 1H), 6.15 (d, J=6.5 Hz, 1H), 6.00 (dd, J=51.1, 14.7 Hz, 1H), 5.35-5.09 (m, 1H), 4.89 (dt, J=11.5, 5.4 Hz, 1H), 4.74 (s, 1H), 3.86 (s, 3H), 3.62 (td, J=17.0, 12.5 Hz, 1H), 3.47-3.33 (m, 1H), 2.75-2.62 (m, 1H), 2.00-1.82 (m, 1H). ¹⁹F NMR (376 MHZ, DMSO-d₆) δ −102.9, −112.5, −112.6, −180.2, −200.0. ESI MS [M+H]⁺ for C₂₃H₁₈F₅N₄O₁, calcd 461.1, found 461.0.

Example 219: (5R,6S,8R)-8-[(1S)-7-chloro-2,2-difluoro-1-hydroxy-2,3-dihydro-1H-inden-4-yl]-3,5,6-trifluoro-5,6,7,8-tetrahydronaphthalene-1-carbonitrile

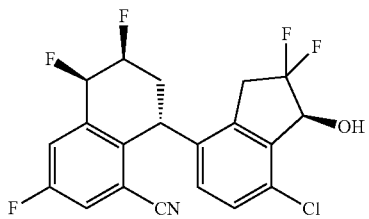 [SMILES: N#Cc1cc(F)cc2c1[C@@H](c1ccc(Cl)c3c1CC(F)(F)[C@H]3O)C[C@H](F)[C@@H]2F]

The title compound was prepared in a similar fashion to Example 216. $^1$H NMR (400 MHz, CDCl$_3$) δ 7.54 (dd, J=8.3, 2.8 Hz, 1H), 7.40-7.35 (m, 1H), 7.17 (d, J=8.3 Hz, 1H), 6.42 (d, J=8.3 Hz, 1H), 5.66 (ddd, J=50.3, 16.8, 2.7 Hz, 1H), 5.31-5.08 (m, 2H), 4.54 (t, J=6.8 Hz, 1H), 3.84-3.69 (m, 1H), 3.30 (td, J=16.9, 2.6 Hz, 1H), 2.88-2.73 (m, 1H), 2.50 (d, J=5.9 Hz, 1H), 2.00-1.83 (m, 1H). $^{19}$F NMR (376 MHz, CDCl$_3$) δ −101.8, −110.5, −114.8, −182.4, −202.9. ESI MS [M+Na]$^+$ for C$_{20}$H$_{13}$Cl$_1$F$_5$N$_1$O$_1$Na, calcd 436.0, found 436.0.

Example 220: 5-[(3S)-7-[(1R,3S,4R)-8-cyano-3,4,6-trifluoro-1,2,3,4-tetrahydronaphthalen-1-yl]-2,2-difluoro-3-hydroxy-2,3-dihydro-1H-inden-4-yl]-4-methylpyrimidine-2-carbonitrile

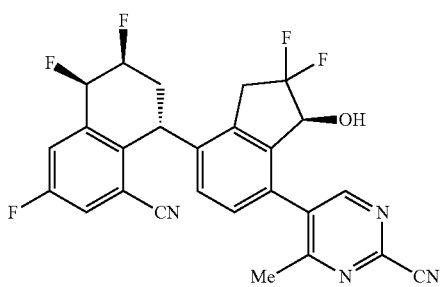 [SMILES: Cc1nc(C#N)ncc1-c1ccc([C@H]2C[C@H](F)[C@H](F)c3cc(F)cc(C#N)c32)c2c1[C@H](O)C(F)(F)C2]

The title compound was prepared in a similar fashion to Example 216. $^1$H NMR (400 MHz, CD$_3$OD) δ 8.69 (s, 1H), 7.70 (dd, J=8.7, 2.8 Hz, 1H), 7.68-7.60 (m, 1H), 7.13 (d, J=8.0 Hz, 1H), 6.70 (d, J=8.0 Hz, 1H), 5.94-5.75 (m, 1H), 5.29-5.08 (m, 1H), 5.00-4.91 (m, 1H), 4.82-4.76 (m, 1H), 3.70 (dt, J=17.0, 13.5 Hz, 1H), 3.50-3.31 (m, 1H), 2.87-2.76 (m, 1H), 2.39 (s, 3H), 2.08-1.94 (m, 1H). $^{19}$F NMR (376 MHz, CD$_3$OD) δ −102.6, −111.3, −113.9, −183.6, −203.6. ESI MS [M+H]$^+$ for C$_{26}$H$_{18}$F$_5$N$_4$O$_1$, calcd 497.1, found 497.1.

Example 221: (5R,6S,8R)-8-[(1S)-7-(4-amino-2-methylpyrimidin-5-yl)-2,2-difluoro-1-hydroxy-2,3-dihydro-1H-inden-4-yl]-3,5,6-trifluoro-5,6,7,8-tetrahydronaphthalene-1-carbonitrile

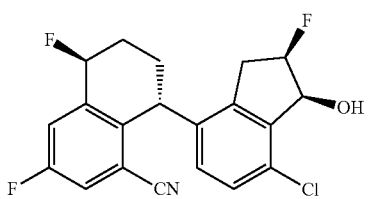 [SMILES: N#Cc1cc(F)cc2c1[C@@H](c1ccc(Cl)c3c1C[C@@H](F)[C@H]3O)CC[C@@H]2F]

The title compound was prepared in a similar fashion to Example 216. $^1$H NMR (400 MHz, DMSO-d$_6$) δ 7.97 (ddd, J=8.3, 2.9, 1.5 Hz, 1H), 7.90-7.86 (m, 2H), 6.97 (d, J=7.9 Hz, 1H), 6.43 (d, J=7.9 Hz, 1H), 6.27 (s, 1H), 6.05-5.86 (m, 2H), 5.29-5.04 (m, 1H), 4.92 (dt, J=12.3, 6.1 Hz, 1H), 4.75 (s, 1H), 3.65-3.52 (m, 1H), 3.47-3.32 (m, 1H), 2.70-2.58 (m, 1H), 2.31 (s, 3H), 2.00-1.87 (m, 1H). $^{19}$F NMR (376 MHz, DMSO-d$_6$) δ −103.1, −111.6, −112.6, −177.8, −198.8. ESI MS [M+H]$^+$ for C$_{25}$H$_{20}$F$_5$N$_4$O$_1$, calcd 487.1, found 487.0.

Example 222: (5S,8R)-8-[(1S,2R)-7-chloro-2-fluoro-1-hydroxy-2,3-dihydro-1H-inden-4-yl]-3,5-difluoro-5,6,7,8-tetrahydronaphthalene-1-carbonitrile The title compound was prepared in a similar fashion to Example 144. $^1$H NMR (400 MHz, Chloroform-d) δ 7.47 (ddd, J=8.3, 2.7, 1.4 Hz, 1H), 7.36 (ddd, J=7.6, 2.8, 1.8 Hz, 1H), 7.05 (d, J=8.1 Hz, 1H), 6.22 (d, J=8.1 Hz, 1H), 5.55 (ddd, J=50.0, 3.6, 3.6 Hz, 1H), 5.41-5.24 (m, 2H), 4.53-4.51 (m, 1H), 3.56-3.46 (m, 1H), 3.12 (ddd, J=21.6, 16.7, 5.7 Hz, 1H), 2.53-2.50 (m, 1H), 2.46-2.36 (m, 1H), 2.15-1.89 (m, 2H), 1.72-1.66 (m, 1H). ESI MS [M+Na]$^+$ for C$_{20}$H$_{15}$ClF$_3$NO, calcd 400.1, found 400.0.

Example 223: (3S)-7-[(1R,4S)-8-cyano-4,6-difluoro-1,2,3,4-tetrahydronaphthalen-1-yl]-2,2-difluoro-3-hydroxy-1,3-dihydroindene-4-carboxylic Acid

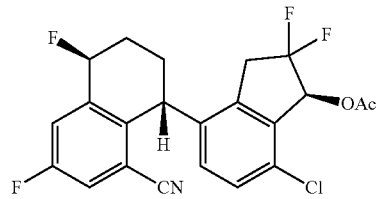
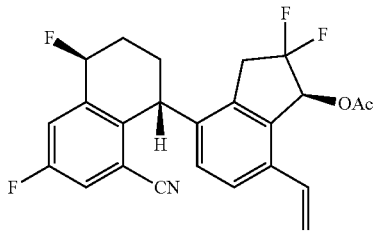
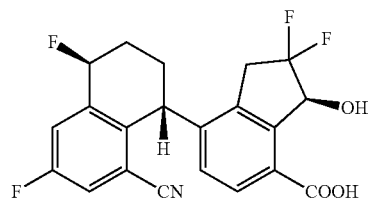
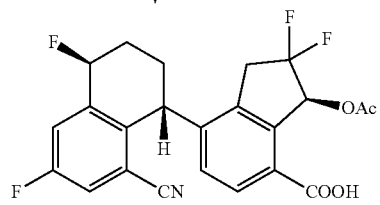

Step a: The starting material [(1S)-7-chloro-4-[(1R,4S)-8-cyano-4,6-difluoro-1,2,3,4-tetrahydronaphthalen-1-yl]-2,2-difluoro-1,3-dihydroinden-1-yl] acetate (42.0 mg, 0.106 mmol, 1.0 mol. equiv.) was dissolved in 1 mL dioxane. Vinylboronic acid pinacol ester (19.6 mg, 0.127 mmol, 1.2 mol. equiv.), SPhos-Pd gen. II (7.9 mg, 0.011 mmol, 0.1 mol. equiv.), and 0.42 mL 1 M $Na_2CO_3$ aqueous solution (0.42 mmol, 4.0 mol. equiv.) were added. The mixture was sparged with $N_2$ for 10 min and then heated at 100° C. for 70 min. The reaction mixture was partitioned between ethyl acetate and water. The organic phase was separated and dried using $Na_2SO_4$. The drying agent was filtered off and the organic solution was evaporated and chromatographed ($SiO_2$, hexanes to 30% EtOAc/hexanes). The desired product (20.2 mg, 0.047 mmol, 44% yield) was obtained.

Step b: The product from step a (20.2 mg, 0.047 mmol, 1.0 mol. equiv.) was dissolved in 0.2 mL $CCl_4$ and 0.2 mL acetonitrile, then 0.2 mL water was added. $RuCl_3 \cdot 3H_2O$ (6.7 mg, 0.026 mmol, 0.55 mol. equiv.) and $NaIO_4$ (53 mg, 0.25 mmol, 5.3 mol. equiv.) were added. The reaction mixture was stirred for 1 h. The reaction was quenched by acetic acid and water. The organic phase was separated and dried over $Na_2SO_4$. Prep-TLC ($SiO_2$, hexanes/EtOAc=1:1, with a few drops of acetic acid) gave the desired product (14 mg, 0.031 mmol, 66% yield).

Step c: The product from step b (14 mg, 0.031 mmol) was dissolved in the mixture of 1 mL THF, 1 mL dioxane and 1 mL water. LiOH. $H_2O$ (20 mg, excess) was added. The reaction mixture was stirred for 2 h before being quenched by acetic acid. All the volatiles were evaporated, then DCM was added. The DCM solution was dried over $Na_2SO_4$. HPLC (acetonitrile/water=10/90 to 90/10, with 0.1% TFA, 20 mL/min for 36 min) gave the desired product (3S)-7-[(1R,4S)-8-cyano-4,6-difluoro-1,2,3,4-tetrahydronaphthalen-1-yl]-2,2-difluoro-3-hydroxy-1,3-dihydroindene-4-carboxylic acid (6.2 mg, 0.015 mmol, 49%).

$^1$H NMR (400 MHZ, Chloroform-d) δ 9.99 (s, br, 2H), 7.63 (d, J=8.0 Hz, 1H), 7.48 (dt, J=8.8, 1.7 Hz, 1H), 7.35 (dt, J=7.7, 2.0 Hz, 1H), 6.28 (d, J=8.0 Hz, 1H), 5.56 (d, J=49.8 Hz, 1H), 5.34-5.26 (m, 1H), 4.45 (s, 1H), 3.81-3.64 (m, 1H), 3.31 (td, J=16.7, 4.7 Hz, 1H), 2.40 (d, J=14.7 Hz, 1H), 2.13-1.89 (m, 2H), 1.72 (d, J=13.4 Hz, 1H). ESI MS $[M+H]^+$ for $C_{21}H_{16}F_4NO_3$, calcd 406.1, found 406.0.

Example 224: (3S)-7-[(1R,4S)-8-cyano-4,6-difluoro-1,2,3,4-tetrahydronaphthalen-1-yl]-2,2-difluoro-3-hydroxy-N,N-dimethyl-1,3-dihydroindene-4-carboxamide

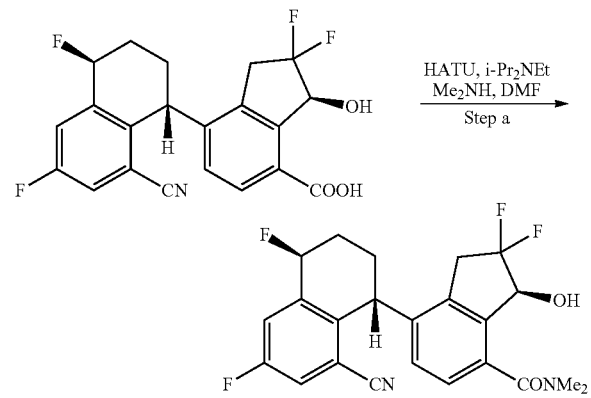

Step a: The starting material (3S)-7-[(1R,4S)-8-cyano-4,6-difluoro-1,2,3,4-tetrahydronaphthalen-1-yl]-2,2-difluoro-3-hydroxy-1,3-dihydroindene-4-carboxylic acid (12.6 mg, 0.031 mmol, 1.0 mol. equiv.), prepared according to example 223, was dissolved in 0.5 mL DMF. HATU (95 mg, 0.25 mmol, 8 mol. equiv.), i-$Pr_2$NEt (74 mg, 0.10 mL, 0.57 mmol, 19 mol. equiv.), and dimethylamine (2.0 M in THF solution, 0.09 mL, 0.18 mmol, 6 mol. equiv.) were added. The reaction mixture was stirred for 18 h. The reaction mixture was quenched by aqueous HCl (1 M) and extracted with EtOAc. The organic phase was separated and dried over Na$_2$SO$_4$. After filtration and evaporation, the residue was purified by HPLC (acetonitrile/water=20/80 to 80/20, with 0.1% TFA, 20 mL/min for 25 min). The desired product (3S)-7-[(1R,4S)-8-cyano-4,6-difluoro-1,2,3,4-tetrahydronaphthalen-1-yl]-2,2-difluoro-3-hydroxy-N,N-dimethyl-1,3-dihydroindene-4-carboxamide was obtained (7.1 mg, 0.016 mmol, 53% yield).

$^1$H NMR (400 MHZ, Chloroform-d) δ 7.50 (dt, J=8.4, 2.0 Hz, 1H), 7.38 (dt, J=7.6, 2.2 Hz, 1H), 7.06 (d, J=7.9 Hz, 1H), 6.34 (d, J=7.9 Hz, 1H), 5.58 (dt, J=50.0, 3.7 Hz, 1H), 5.14 (dd, J=13.7, 2.6 Hz, 1H), 4.55-4.48 (m, 1H), 3.77 (td, J=15.6, 7.6 Hz, 1H), 3.33 (td, J=16.4, 6.3 Hz, 1H), 3.12 (s, 3H), 3.01 (s, 3H), 2.65 (s, br, 1H), 2.46 (tdd, J=13.3, 6.1, 3.2 Hz, 1H), 2.29-2.12 (m, 1H), 2.12-1.90 (m, 1H), 1.78 (ddt, J=13.9, 5.8, 3.3 Hz, 1H). ESI MS [M+H]$^+$ for C$_{23}$H$_{21}$F$_4$N$_2$O$_2$, calcd 433.2, found 433.0.

Example 225: (5S,8R)-8-[(1S)-2,2-difluoro-1-hydroxy-7-methyl-1,3-dihydroinden-4-yl]-3,5-difluoro-5,6,7,8-tetrahydronaphthalene-1-carbonitrile

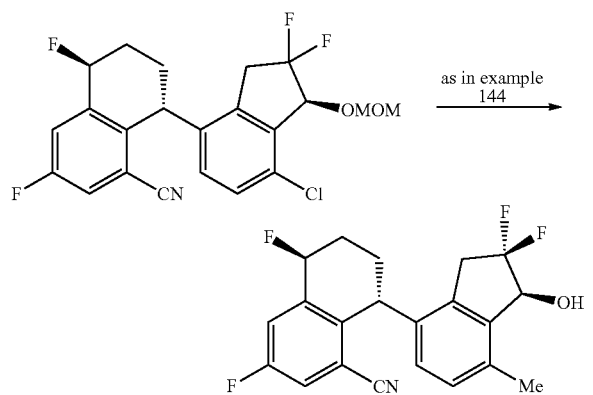

Synthesis of the title compound was performed in a similar fashion to Example 144 using methyl boronic acid. The crude product was purified by flash column chromatography (SiO$_2$, 0 to 100% EtOAc/hexanes) to afford a white solid (11 mg, 0.029 mmol, 35%). $^1$H NMR (400 MHZ, CDCl$_3$) δ 7.53-7.42 (m, 1H), 7.36 (dt, J=7.7, 2.2 Hz, 1H), 6.92 (d, J=7.8 Hz, 1H), 6.19 (d, J=7.8 Hz, 1H), 5.58 (dt, J=50.1, 3.6 Hz, 1H), 5.14-4.99 (m, 1H), 4.48-4.38 (m, 1H), 3.76 (td, J=18.0, 11.8 Hz, 1H), 3.36 (td, J=16.9, 5.7 Hz, 1H), 2.47-2.40 (m, 1H), 2.39 (s, 3H), 2.19-1.93 (m, 2H), 1.75 (dq, J=13.5, 3.5 Hz, 1H). ESI MS [M+H]$^+$ for C$_{21}$H$_{18}$F$_4$NO, calcd 376.1, found 376.0.

Example 226: (5S,8R)-8-[(1S)-2,2-difluoro-1-hydroxy-7-(2-hydroxypropan-2-yl)-1,3-dihydroinden-4-yl]-3,5-difluoro-5,6,7,8-tetrahydronaphthalene-1-carbonitrile

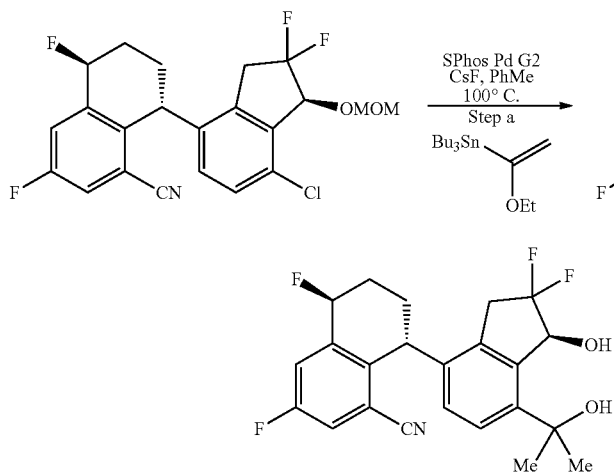

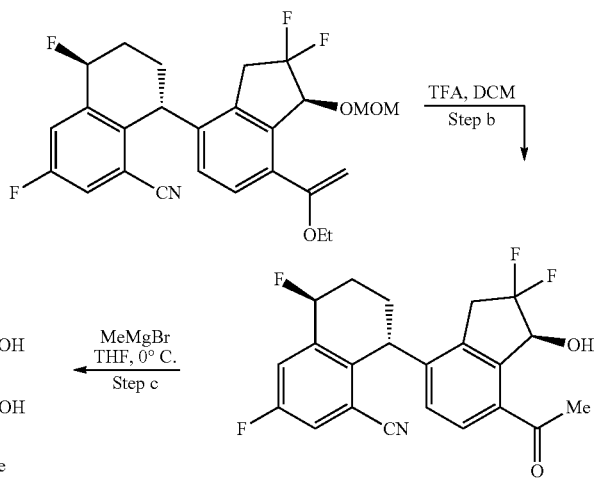

Step a: To a 40 mL scintillation vial containing (5S,8R)-8-[(1S)-7-chloro-2,2-difluoro-1-(methoxymethoxy)-1,3-dihydroinden-4-yl]-3,5-difluoro-5,6,7,8-tetrahydronaphthalene-1-carbonitrile (50 mg, 0.114 mmol, 1.0 equiv.) was added SPhos Pd G2 (5 mg, 0.006 mmol, 0.05 equiv.) and CsF (35 mg, 0.228 mmol, 2.00 equiv.). The vial was then sealed evacuated of air and backfilled with nitrogen (3×). Tributyl(1-ethoxyvinyl)stannane (78 μL 0.228 mmol, 2.00 equiv.) and PhMe (1 mL) were charged to the reaction mixture and the resulting solution was heated overnight at 100° C. After reacting overnight, the reaction mixture was cooled, diluted with EtOAc (5 mL). The mixture was extracted with NH$_4$Cl (5 mL), the organic layers were combined, rinsed with brine (5 mL), and dried over Na$_2$SO$_4$. Concentration under reduced pressure and purified by flash column chromatography (SiO$_2$, 0 to 25% EtOAc/hexanes) to afford a white solid (49 mg, 0.103 mmol, 90%).

Step b: To a 40-mL vial containing the product from step a (49 mg, 0.103 mmol, 1.00 equiv.) was added DCM (1 mL), and TFA (30 μL 0.351 mmol, 6.00 equiv). The resulting solution was stirred at room temperature. Upon completion of the reaction as indicated by TLC, the reaction mixture was cooled, diluted with DCM (5 mL) and NH$_4$Cl (5 mL), the organic layers were combined rinsed with brine (5 mL), dried over Na$_2$SO$_4$. Concentration under reduced pressure and purified by flash column chromatography (SiO$_2$, 0 to 40% EtOAc/hexanes) to afford a white film (36 mg, 0.089 mmol, 90%).

Step c: To a THF (1 mL) solution of the product from step b (36 mg, 0.089 mmol, 1.00 equiv.) in a round bottom flask at 0° C. was added MeMgBr (3M solution in diethyl ether, 149 μL 0.45 mmol, 5.00 equiv) dropwise down the side of the flask. Upon completion of the reaction as indicated by TLC the reaction mixture was poured into water, diluted with EtOAc (5 mL) and NH$_4$Cl (5 mL), the organic layers were combined rinsed with brine (5 mL), dried over Na$_2$SO$_4$. Concentration under reduced pressure and purified by flash column chromatography (SiO$_2$, 0 to 45% EtOAc/hexanes) to afford a white solid (17 mg, 0.041 mmol, 45%). $^1$H NMR (400 MHZ, CDCl$_3$) δ 7.49 (dt, J=8.3, 2.1 Hz, 1H), 7.40-7.28 (m, 1H), 6.98 (d, J=8.2 Hz, 1H), 6.21 (d, J=8.2 Hz, 1H), 5.57 (dt, J=50.1, 3.5 Hz, 1H), 5.47 (d, J=13.9 Hz, 1H), 4.56-4.40 (m, 1H), 3.88 (bs, 1H), 3.86-3.66 (m, 1H), 3.36 (td, J=16.8, 4.9 Hz, 1H), 3.09 (bs, 1H), 2.43 (tdd, J=13.3, 6.0, 3.4 Hz, 1H), 2.19-1.92 (m, 2H), 1.78 (dq, J=13.6, 3.6 Hz, 1H), 1.64 (s, 3H), 1.59 (s, 3H). ESI MS [M+H]$^+$ for C$_{23}$H$_{22}$F$_4$NO$_2$, calcd 420.2, found 420.1.

Example 227: (5S,8S)-3,5-difluoro-8-[(6R,7S)-6-fluoro-7-hydroxy-1-(2-methylpyridin-3-yl)-5H,6H,7H-cyclopenta[c]pyridin-4-yl]-5,6,7,8-tetrahydronaphthalene-1-carbonitrile

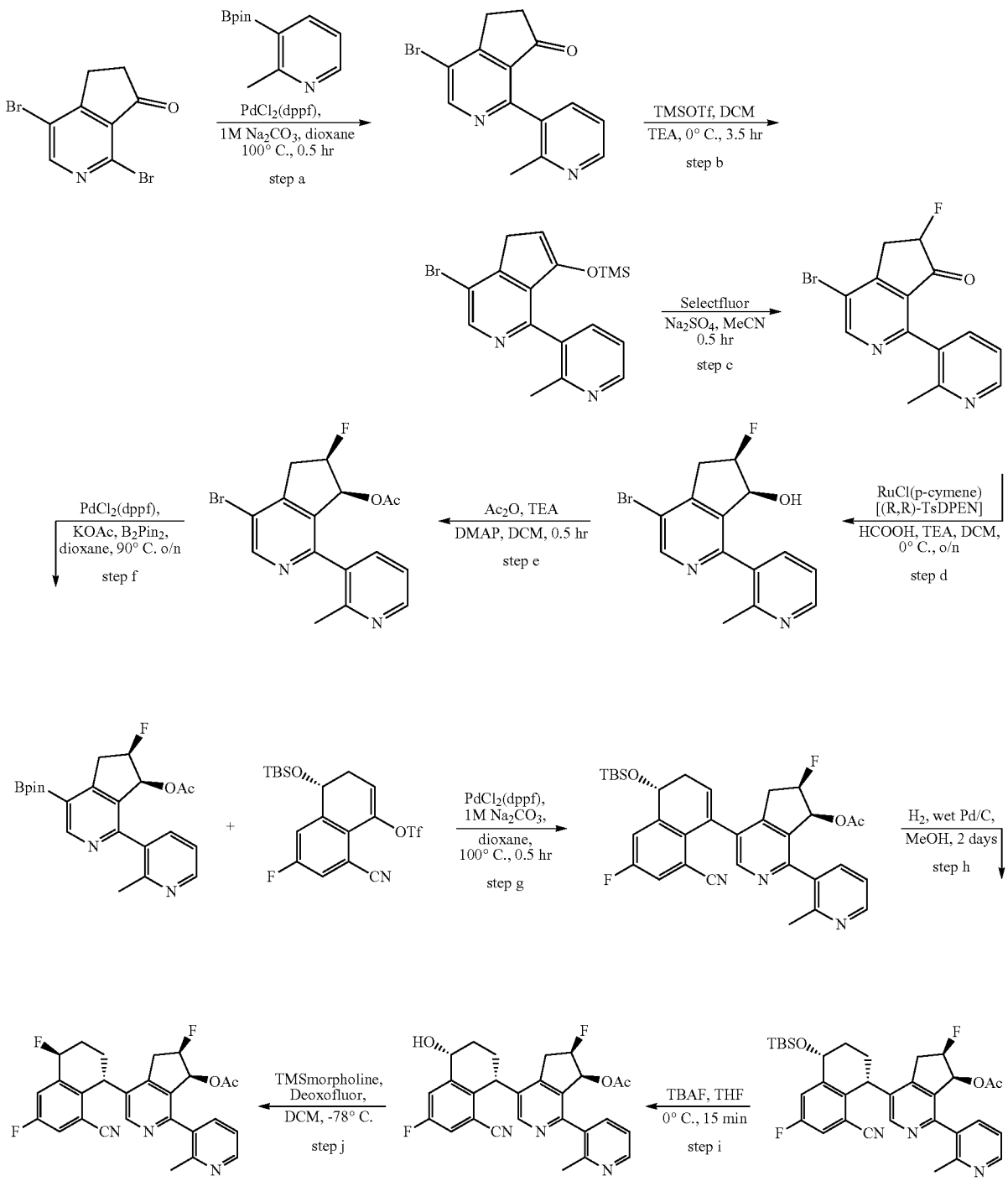

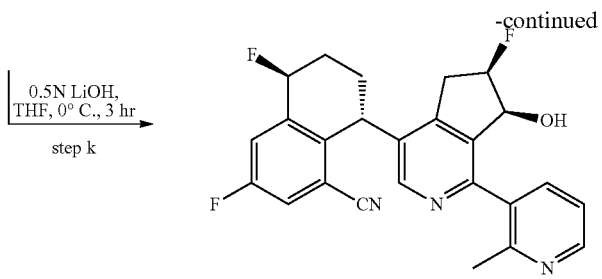

Step a: A 250-mL round bottom flask was charged with 1,4-dibromo-5,6-dihydro-7H-cyclopenta[c]pyridine-7-one (3.14 g, 10.87 mmol, 1.0 equiv.), 2-methylpyridine-3-boronic acid pinacol ester (2.38 g, 10.87 mmol, 1.0 equiv.), Pd(dppf)Cl$_2$ (795 mg, 1.087 mmol, 10 mol %), 1M Na$_2$CO$_3$ aq. soln (32.61 ml, 32.61 mmol, 3.0 equiv.) and 1,4-dioxane (50 mL). The reaction mixture was degassed with N$_2$ bubbling for 10 min before being heated. After stirring at 100° C. for 0.5 h, the reaction mixture was cooled, then diluted with water. The aqueous layer was extracted with EtOAc×3. The combined organic layer was then washed with brine, dried over Na$_2$SO$_4$, concentrated and purified by flash chromatography (SiO$_2$, 0 to 100% EtOAc/Hex) to afford the product (1.81 g, 5.98 mmol, 55% yield).

Step b: To a solution of the product from step a (1 g, 3.31 mmol, 1.0 equiv.), Et$_3$N (1.4 ml, 9.93 mmol, 3.0 equiv.) in DCM (16.5 mL) was added TMSOTf (1.2 mL, 6.62 mmol, 2.0 equiv.) dropwise at 0° C. The resulting solution was stirred at 0° C. for 2.5 h, and more added Et$_3$N (1.4 ml, 9.93 mmol, 3.0 equiv.) and TMSOTf (1.2 mL, 6.62 mmol, 2.0 equiv.). The resulting solution was stirred at room temperature for another 1 h, then quenched with saturated NaHCO$_3$ (aq.) in ice bath and kept stirring for 1 h. The resulting mixture was then separated, and the aqueous phase was extracted with DCM×3. The combined organic phase was then washed with brine, dried over Na$_2$SO$_4$ and concentrated to afford the silyl enol ether crude.

Step c: The crude of step b and Na$_2$SO$_4$ (2.35 g, 16.55 mmol, 5.0 equiv.) was dissolved in MeCN (33 mL) under N$_2$. The reaction mixture was stirred at RT for 10 min, and selectfluor (1.3 g, 3.64 mmol, 1.1 equiv.) was added. The resulting mixture was stirred at room temperature for 30 min and then filtered to remove the precipitated salts. The filtrate got concentrated and diluted with EtOAc and water. The aqueous phase was extracted with EtOAc×3. The combined organic layer was then washed with brine, dried over Na$_2$SO$_4$, concentrated and purified by flash chromatography (SiO$_2$, 0 to 100% EtOAc/Hex) to afford the monofluorinated product with the inseparable product of step a (ratio 3.3:1).

Step d: HCO$_2$H (0.37 mL, 9.93 mmol, 3.0 equiv.) was added to the solution of Et$_3$N (0.93 mL, 6.62 mmol, 2.0 equiv.) in DCM (15 mL) dropwise. The resulting solution was stirred at 0° C. for 30 min, and then added to a solution of the product from step c (3.31 mmol, 1.0 equiv.) and RuCl(p-cymene)[(R,R)-TsDPEN] (63.2 mg, 0.099 mmol, 3.0 mol %) in DCM (15 mL) at this temperature. The resulting mixture was kept stirring overnight in fridge and then quenched with saturated NaHCO$_3$ (aq.). The aqueous phase was extracted with DCM×3. The combined organic phase was then washed with brine, dried over Na$_2$SO$_4$, concentrated and purified by flash chromatography (SiO$_2$, 0 to 100% EtOAc/Hex) to afford the alcohol product (319.7 mg, 0.99 mmol, 30% yield; three steps, 99.6% ee) and recovered the product of step a.

Step e: Acetic anhydride (0.28 mL, 3.0 mmol, 3.0 equiv.) was added to a solution of the product from step d (319.7 mg, 0.99 mmol, 1.0 equiv.), TEA (0.2 mL, 1.49 mmol, 1.5 equiv.) and DMAP (36.3 mg, 0.3 mmol, 0.3 equiv.) in DCM (10 mL) under N$_2$. After stirring at room temperature for 0.5 h, the reaction mixture was diluted with water. The aqueous layer was extracted with DCM×3. The combined organic layer was then washed with brine, dried over Na$_2$SO$_4$, concentrated and purified by flash chromatography (SiO$_2$, 0 to 100% EtOAc/Hex) to afford the acetylated product (356.8 mg, 0.98 mmol, 99% yield).

Step f: A 40-mL vial was charged with the product of step e (356.8 mg, 0.98 mmol, 1.0 equiv.), B$_2$Pin$_2$ (257.7 mg, 1.2 mmol, 1.2 equiv.), Pd(dppf)Cl$_2$ (73.7 mg, 0.1 mmol, 10 mol %), KOAc (192 mg, 1.96 mmol, 2.0 equiv.) and 1,4-dioxane (10 mL). The reaction mixture was degassed with N$_2$ bubbling for 10 min before being heated. After stirring at 90° C. overnight, the reaction mixture was cooled, then diluted with water. The aqueous layer was extracted with EtOAc×3. The combined organic layer was then washed with brine, dried over Na$_2$SO$_4$, and then concentrated. The crude product was directly used in the next step.

Step g: A 40-mL vial was charged with the triflate (442.1 mg, 0.98 mmol, 1.0 equiv.), the product of step f (0.98 mmol, 1.0 equiv.), Pd(dppf)Cl$_2$ (71.1 mg, 0.1 mmol, 10 mol %), 1M aq. Na$_2$CO$_3$ soln(2.9 ml, 2.9 mmol, 3.0 equiv.) and 1,4-dioxane (10 mL). The reaction mixture was degassed with N$_2$ bubbling for 10 min before being heated. After stirring at 100° C. for 0.5 h, the reaction mixture was cooled, then diluted with water. The aqueous layer was extracted with EtOAc×3. The combined organic layer was then washed with brine, dried over Na$_2$SO$_4$, concentrated and purified by flash chromatography (SiO$_2$, 0 to 100% EtOAc/Hex) to afford the coupled product (282 mg, 0.48 mmol, 49% yield; two steps).

Step h: A mixture of the product of step g (282 mg, 0.48 mmol, 1.0 equiv.), Pd/C (10 wt % Pd, 282 mg, 100 wt %) in MeOH (30 mL) was shaken in parr hydrogenator under H$_2$ (50 psi) for 1 day. The reaction mixture was filtered through Celite, dried over Na$_2$SO$_4$, concentrated and then reloaded with Pd/C (10 wt % Pd, 282 mg, 100 wt %) in MeOH (30 mL). The mixture was shaken in parr hydrogenator under H$_2$ (50 psi) for another 1 day when LCMS showed no substrate remaining. Filtration through Celite, drying over Na$_2$SO$_4$, concentration and then purification by flash chromatography (SiO$_2$, 0 to 100% EtOAc/Hex) afforded the product (56.6 mg, 0.096 mmol, 20% yield).

Step i: To a solution of the product of step h (56.6 mg, 0.096 mmol, 1.0 equiv.) in THF (1 mL) was added TBAF (1M in THF, 0.1 mL, 1.1 equiv.) at 0° C. The resulting solution was stirred at 0° C. for 15 min, and then quenched by water. The aqueous phase was extracted with EtOAc×2. The combined organic layer was then washed with brine, dried over Na$_2$SO$_4$, concentrated and purified by flash chromatography (SiO₂, 0 to 100% EtOAc/Hex then 0 to 30% MeOH/EtOAc) to afford the product (29.2 mg, 0.06 mmol, 64% yield).

Step j: To a solution of 4-(trimethylsilyl)morpholine (0.076 ml, 0.43 mmol, 7.1 equiv.) in DCM (1 mL) was added deoxofluor (2.7M in toluene, 0.16 mL, 7.0 equiv.) dropwise at −78° C. The resulting solution was then stirred at this temperature for 5 min and then raised to room temperature for 1 h. The reaction mixture was then cooled back to −78° C. and a solution of the product step i (29.2 mg, 0.06 mmol, 1.0 equiv.) in DCM (0.5 ml) was added dropwise. The resulting solution was then stirred at this temperature for 5 min and again raised to room temperature for 1 h, and then quenched by saturated NaHCO₃ (aq.). The aqueous layer was extracted with DCM×2. The combined organic layer was then washed with brine, dried over Na₂SO₄, concentrated and purified by flash chromatography (SiO₂, 0 to 100% EtOAc/Hex then 0 to 30% MeOH/EtOAc) to afford the product (12.3 mg, 0.026 mmol, 43% yield).

Step k: A solution of the product from step j (12.3 mg, 0.026 mmol, 1.0 equiv.) in MeOH (0.5 mL) was placed in a 3 mL vial equipped with a magnetic stirrer, then 0.5N LiOH (0.08 ml, 1.5 equiv.) was added. The resulting solution was stirred for 3 hr at 0° C. Once complete, purification by HPLC to yield (5S,8S)-3,5-difluoro-8-[(6R,7S)-6-fluoro-7-hydroxy-1-(2-methylpyridin-3-yl)-5H,6H,7H-cyclopenta[c]pyridin-4-yl]-5,6,7,8-tetrahydronaphthalene-1-carbonitrile (6.8 mg, 0.016 mmol, 60% yield). ¹H NMR (400 MHZ, MeOD) δ 8.73 (dd, J=5.8, 1.6 Hz, 1H), 8.54 (dd, J=8.0, 1.6 Hz, 1H), 7.93 (dd, J=7.9, 5.9 Hz, 1H), 7.77 (s, 1H), 7.71-7.63 (m, 2H), 5.70 (dt, J=49.8, 3.9 Hz, 1H), 5.36 (d, J=1.9 Hz, 1H), 5.31 (d, J=4.2 Hz, 0.5H), 5.23 (m, 0.5H), 4.83-4.78 (m, 1H), 3.53-3.40 (m, 1H), 3.24-3.12 (m, 1H), 2.62 (s, 3H), 2.58-2.46 (m, 1H), 2.20-1.94 (m, 2H), 1.91-1.82 (m, 1H). ESI MS [M+H]⁺ for C₂₅H₂₁F₃N₃O, calcd 436.16, found 436.1.

Example 228: (5S,8R)-8-[(1S)-7-(1,3-benzoxazol-7-yl)-2,2-difluoro-1-hydroxy-1,3-dihydroinden-4-yl]-3,5-difluoro-5,6,7,8-tetrahydronaphthalene-1-carbonitrile

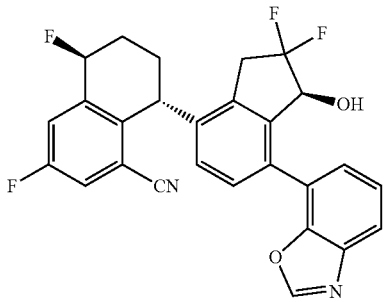

The title compound was prepared in a similar fashion to Example 174. ¹H NMR (400 MHz, Chloroform-d) (4:1 mixture of rotamers) δ 8.30 (d, J=2.2 Hz, 1H), 8.13 (s, 1H), 7.92 (s, 1H), 7.53-7.48 (m, 1H), 7.42-7.37 (m, 1H), 7.04-6.989 (m, 3H), 6.45-6.37 (m, 1H), 5.70-5.51 (m, 1H), 4.95-4.85 (m, 1H), 4.55-4.48 (m, 1H), 3.97-3.76 (m, 1H), 3.43 (t, J=16.9 Hz, 1H), 2.56-2.42 (m, 1H), 2.22-2.05 (m, 2H), 1.88-1.79 (m, 1H). ESI MS [M+H]⁺ for C₂₇H₁₈F₄N₂O₂, calcd 479.1, found 479.0.

Example 229: (5S,8R)-8-[(1S)-7-(2-amino-3-fluorophenyl)-2,2-difluoro-1-hydroxy-1,3-dihydroinden-4-yl]-3,5-difluoro-5,6,7,8-tetrahydronaphthalene-1-carbonitrile

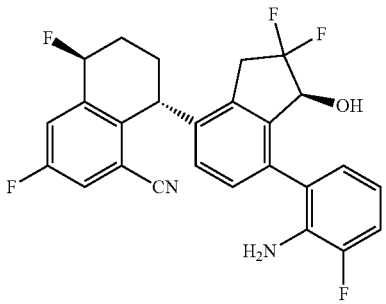 [SMILES: N#Cc1cc(F)cc2c1[C@@H](c1ccc(-c3cccc(F)c3N)c3c1CC(F)(F)[C@H]3O)CC[C@@H]2F]

The title compound was prepared in a similar fashion to Example 174. ¹H NMR (400 MHz, Chloroform-d) δ 7.53-7.47 (m, 1H), 7.39-7.35 (m, 1H), 7.09-6.93 (m, 2H), 6.90-6.77 (m, 2H), 6.40 (d, J=7.9 Hz, 1H), 5.69-5.51 (m, 1H), 5.15 (s, 1H), 4.70 (d, J=12.4 Hz, 1H), 4.55-4.49 (m, 1H), 3.95-3.75 (m, 1H), 3.66-3.56 (m, 2H), 3.37 (t, J=16.5 Hz, 1H), 2.54-2.43 (m, 1H), 2.19-1.98 (m, 2H), 1.88-1.80 (m, 1H). ESI MS [M+H]⁺ for C₂₆H₁₉F₅N₂O, calcd 471.1, found 471.0.

Example 230: (5S,8R)-8-[(1S)-7-(8-aminoimidazo[1,2-a]pyridin-3-yl)-2,2-difluoro-1-hydroxy-1,3-dihydroinden-4-yl]-3,5-difluoro-5,6,7,8-tetrahydronaphthalene-1-carbonitrile

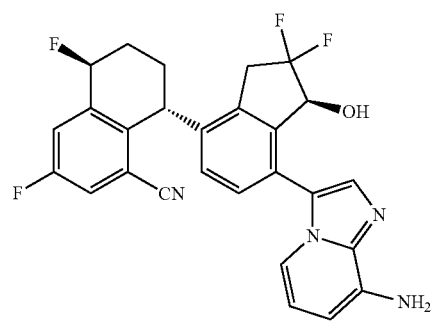 [SMILES: N#Cc1cc(F)cc2c1[C@@H](c1ccc(-c3cnc4c(N)cccn34)c3c1CC(F)(F)[C@H]3O)CC[C@@H]2F]

The title compound was prepared in a similar fashion to Example 174. ¹H NMR (400 MHz, Chloroform-d) δ 7.87 (s, 1H), 7.58 (dd, J=6.8, 1.0 Hz, 1H), 7.54-7.47 (m, 1H), 7.41-7.37 (m, 1H), 7.29 (dd, J=7.1, 6.8 Hz, 1H), 6.59 (t, J=7.1 Hz, 1H), 6.45 (d, J=8.0 Hz, 1H), 6.32 (d, J=7.3 Hz, 1H), 5.69-5.52 (m, 1H), 4.99 (d, J=11.8 Hz, 1H), 4.62 (s, 2H), 4.59 (m, 1H), 4.01-3.86 (m, 1H), 3.39 (t, J=16.9 Hz, 1H), 2.56-2.44 (m, 1H), 2.24-2.03 (m, 2H), 1.91-1.79 (m, 1H). ESI MS [M+H]⁺ for C₂₇H₂₀F₄NO, calcd 493.2, found 493.0.

Example 231: (5S,8R)-8-[(1S)-2,2-difluoro-1-hydroxy-7-(2-methylimidazo[1,2-a]pyridin-3-yl)-1,3-dihydroinden-4-yl]-3,5-difluoro-5,6,7,8-tetrahydronaphthalene-1-carbonitrile

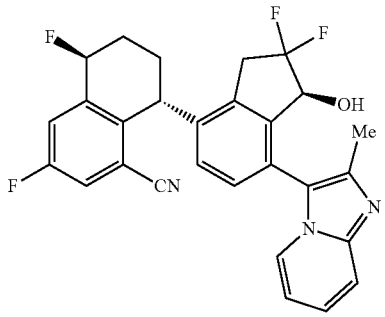 [SMILES: Cc1nc2ccccn2c1-c1ccc([C@H]2CC[C@H](F)c3cc(F)cc(C#N)c32)c2c1[C@H](O)C(F)(F)C2]

The title compound was prepared in a similar fashion to Example 174. ¹H NMR (400 MHz, Chloroform-d) (2:1 mixture of rotamers) δ 7.74-7.61 (m, 1H), 7.55-7.38 (m, 2H), 7.19-7.09 (m, 1H), 7.06-7.01 (m, 1H), 6.99-6.91 (m, 1H), 6.80-6.57 (m, 1H), 6.47-6.40 (m, 1H), 5.70-5.49 (m, 1H), 5.05-4.87 (m, 1H), 4.59 (s, 1H), 3.97-3.76 (m, 1H), 3.53-3.36 (m, 1H), 2.57-2.43 (m, 1H), 2.25-2.02 (m, 2H), 2.21-1.91 (s, 3H), 1.96-1.85 (m, 1H). ESI MS [M+H]⁺ for $C_{28}H_{21}F_4N_3O$, calcd 492.2, found 492.0.

Example 232: (5S,8R)-8-[(1S)-7-(3,5-dimethylimidazol-4-yl)-2,2-difluoro-1-hydroxy-1,3-dihydroinden-4-yl]-3,5-difluoro-5,6,7,8-tetrahydronaphthalene-1-carbonitrile

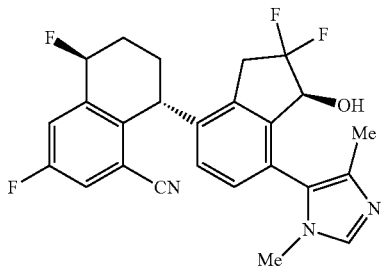 [SMILES: Cc1ncn(C)c1-c1ccc([C@H]2CC[C@H](F)c3cc(F)cc(C#N)c32)c2c1[C@H](O)C(F)(F)C2]

The title compound was prepared in a similar fashion to Example 174. ¹H NMR (400 MHz, Chloroform-d) (3:1 mixture of rotamers) δ 7.52-7.47 (m, 1H), 7.40-7.35 (m, 1H), 7.24 (s, 1H), 6.99-6.90 (m, 1H), 6.46-6.34 (m, 1H), 5.68-5.52 (m, 1H), 4.91-4.75 (m, 1H), 4.56-5.49 (m, 1H), 3.89-3.73 (m, 1H), 3.48-3.24 (m, 1H), 3.34 (s, 3H), 2.55-2.42 (m, 1H), 2.19-2.03 (m, 2H), 1.98 (s, 3H), 1.91-1.83 (m, 1H). ESI MS [M+H]⁺ for $C_{25}H_{21}F_4N_3O$, calcd 456.2, found 456.0.

Example 233: (5S,8R)-8-[(1S)-2,2-difluoro-1-hydroxy-7-imidazo[1,2-a]pyrimidin-3-yl-1,3-dihydroinden-4-yl]-3,5-difluoro-5,6,7,8-tetrahydronaphthalene-1-carbonitrile

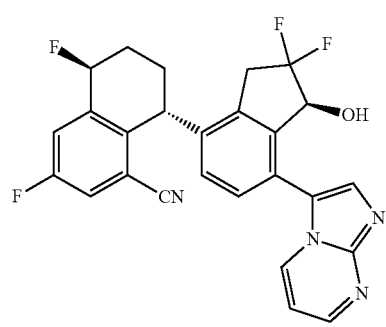 [SMILES: N#Cc1cc(F)cc2c1[C@@H](c1ccc(-c3cnc4ncccn34)c3c1CC(F)(F)[C@H]3O)CC[C@@H]2F]

The title compound was prepared in a similar fashion to Example 174. ¹H NMR (400 MHz, DMSO-d₆) δ 8.90-8.86 (m, 1H), 8.84 (dd, J=6.9, 1.8 Hz, 1H), 8.26 (s, 1H), 7.98-7.93 (m, 1H), 7.88-7.82 (m, 1H), 7.41 (dd, J=6.9, 4.3 Hz, 1H), 7.36 (d, J=8.0 Hz, 1H), 6.50 (d, J=8.0 Hz, 1H), 5.86-5.68 (s, 1H), 5.09 (dd, J=11.8, 6.0 Hz, 1H), 4.70-4.62 (m, 1H), 3.76-3.47 (m, 3H), 2.39-2.27 (m, 1H), 2.08-1.82 (m, 2H), 1.72-1.65 (m, 1H). ESI MS [M+H]⁺ for $C_{26}H_{18}F_4N_4O$, calcd 479.1, found 479.0.

Example 234: (5S,8R)-8-[(1S)-2,2-difluoro-1-hydroxy-7-imidazo[1,2-a]pyrazin-3-yl-1,3-dihydroinden-4-yl]-3,5-difluoro-5,6,7,8-tetrahydronaphthalene-1-carbonitrile

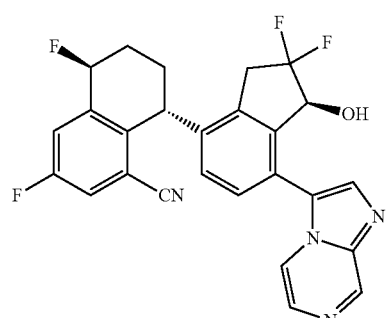

The title compound was prepared in a similar fashion to Example 174. ¹H NMR (400 MHz, DMSO-d₆) δ 9.19 (d, J=1.4 Hz, 1H), 8.32 (dd, J=4.7, 1.5 Hz, 1H), 8.11 (s, 1H), 7.97-7.91 (m, 2H), 7.87-7.81 (m, 1H), 7.37 (d, J=8.0 Hz, 1H), 6.47 (d, J=8.0 Hz, 1H), 5.84-5.68 (m, 1H), 5.05 (dd, J=11.7, 5.2 Hz, 1H), 4.68-4.63 (m, 1H), 3.76-3.47 (m, 3H), 2.37-2.26 (m, 1H), 2.08-1.83 (m, 2H), 1.73-1.66 (m, 1H). ESI MS [M+H]⁺ for $C_{26}H_{18}F_4N_4O$, calcd 479.1, found 479.0.

Example 235: (5S,8R)-8-[(1S)-7-(2-amino-5-fluorophenyl)-2,2-difluoro-1-hydroxy-1,3-dihydroinden-4-yl]-3,5-difluoro-5,6,7,8-tetrahydronaphthalene-1-carbonitrile

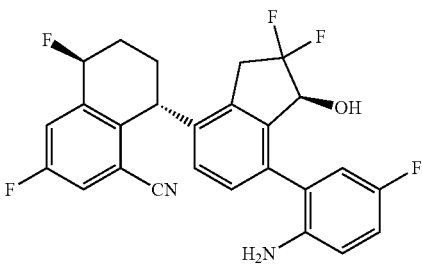 [SMILES: N#Cc1cc(F)cc2c1[C@@H](c1ccc(-c3cc(F)ccc3N)c3c1CC(F)(F)[C@H]3O)CC[C@@H]2F]

The title compound was prepared in a similar fashion to Example 174. $^1$H NMR (400 MHz, DMSO-d$_6$) δ 7.95-7.91 (m, 1H), 7.85-7.80 (m, 1H), 7.08-6.83 (m, 4H), 6.37 (d, J=7.9 Hz, 1H), 5.84-5.67 (m, 1H), 4.85 (d, J=11.9 Hz, 1H), 4.60 (s, 1H), 3.70-3.55 (m, 1H), 3.53-3.40 (m, 1H), 2.34-2.23 (m, 1H), 2.05-1.87 (m, 2H), 1.70-1.61 (m, 1H). ESI MS [M+H]$^+$ for C$_{26}$H$_{19}$F$_5$N$_2$O, calcd 471.1, found 471.0.

Example 236: (5S,8R)-8-[(1S)-7-(2,3-dimethylimidazol-4-yl)-2,2-difluoro-1-hydroxy-1,3-dihydroinden-4-yl]-3,5-difluoro-5,6,7,8-tetrahydronaphthalene-1-carbonitrile

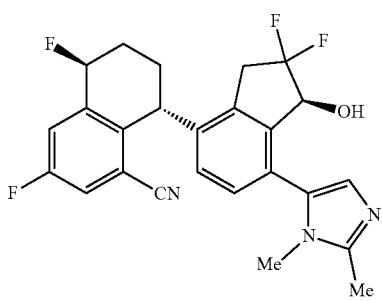 [SMILES: Cc1ncc(-c2ccc([C@H]3CC[C@H](F)c4cc(F)cc(C#N)c43)c3c2[C@H](O)C(F)(F)C3)n1C]

The title compound was prepared in a similar fashion to Example 174. $^1$H NMR (400 MHz, DMSO-d$_6$) δ 7.96-7.91 (m, 1H), 7.87-7.82 (m, 1H), 7.61 (s, 1H), 7.16 (d, J=7.9 Hz, 1H), 6.47 (d, J=7.9 Hz, 1H), 6.19 (s, 1H), 5.82-5.67 (m, 1H), 5.08-4.97 (m, 1H), 4.65-4.61 (m, 1H), 3.72-3.47 (m, 2H), 3.45 (s, 3H), 2.60 (s, 3H), 2.36-2.24 (m, 1H), 2.06-1.80 (m, 2H), 1.71-1.61 (m, 1H). ESI MS [M+H]$^+$ for C$_{25}$H$_{21}$F$_4$N$_3$O, calcd 456.2, found 456.0.

Example 237: (5S,8R)-8-[(1S)-2,2-difluoro-1-hydroxy-7-imidazo[1,2-b]pyridazin-3-yl-1,3-dihydroinden-4-yl]-3,5-difluoro-5,6,7,8-tetrahydronaphthalene-1-carbonitrile

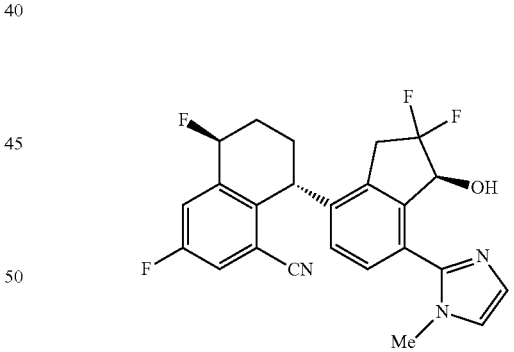

The title compound was prepared in a similar fashion to Example 174. $^1$H NMR (400 MHz, DMSO-d$_6$) δ 8.51 (dd, J=4.4, 1.6 Hz, 1H), 8.17 (dd, J=9.2, 1.6 Hz, 1H), 7.96-7.91 (m, 1H), 7.86-7.80 (m, 1H), 7.57 (d, J=8.1 Hz, 1H), 7.25 (dd, J=9.2, 4.4 Hz, 1H), 6.43 (d, J=8.1 Hz, 1H), 6.04 (d, J=6.6 Hz, 1H), 5.84-5.68 (m, 1H), 5.14-5.06 (m, 1H), 4.65-4.59 (m, 1H), 3.73-3.47 (m, 2H), 2.36-2.24 (m, 1H), 2.05-1.80 (m, 2H), 1.74-1.65 (m, 1H). ESI MS [M+H]$^+$ for C$_{26}$H$_{18}$F$_4$NO, calcd 479.1, found 479.0.

Example 238: (5S,8R)-8-[(1S)-2,2-difluoro-1-hydroxy-7-(1-methylimidazol-2-yl)-1,3-dihydroinden-4-yl]-3,5-difluoro-5,6,7,8-tetrahydronaphthalene-1-carbonitrile The title compound was prepared in a similar fashion to Example 174. $^1$H NMR (400 MHz, Chloroform-d) δ 7.51-7.46 (m, 1H), 7.39-7.34 (m, 1H), 7.17 (d, J=8.0 Hz, 1H), 7.10 (d, J=1.3 Hz, 1H), 6.96 (d, J=1.3 Hz, 1H), 6.40 (d, J=8.0 Hz, 1H), 5.66-5.50 (m, 1H), 4.89 (d, J=17.4 Hz, 1H), 4.57-4.52 (m, 1H), 3.93-3.79 (m, 1H), 3.78 (s, 3H), 3.42-3.31 (m, 1H), 2.52-2.42 (m, 1H), 2.20-2.00 (m, 2H), 1.87-1.79 (m, 1H). ESI MS [M+H]$^+$ for C$_{24}$H$_{19}$F$_4$N$_3$O, calcd 442.1, found 442.0.

Example 239: (5S,8R)-8-[(1S)-2,2-difluoro-1-hydroxy-7-imidazo[1,2-a]pyridin-3-yl-1,3-dihydroinden-4-yl]-3,5-difluoro-5,6,7,8-tetrahydronaphthalene-1-carbonitrile

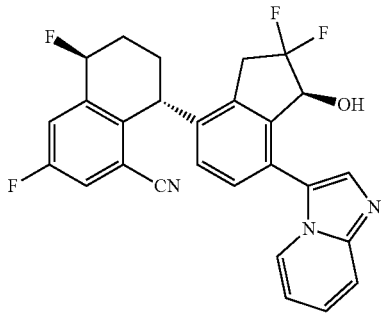

The title compound was prepared in a similar fashion to Example 174. $^1$H NMR (400 MHz, Chloroform-d) δ 8.25 (s, 1H), 8.20 (d, J=7.0 Hz, 1H), 7.96 (s, 1H), 7.71 (d, J=9.1 Hz, 1H), 7.53-7.47 (m, 1H), 7.41-7.36 (m, 1H), 7.31 (d, J=8.0 Hz, 1H), 7.21 (ddd, J=9.1, 6.7, 1.2 Hz, 1H), 6.77 (td, J=6.8, 1.2 Hz, 1H), 6.50 (d, J=8.0 Hz, 1H), 5.70-5.53 (m, 1H), 4.81 (d, J=11.9 Hz, 1H), 4.65-4.58 (m, 1H), 4.07-3.91 (m, 1H), 3.35 (t, J=16.8 Hz, 1H), 2.56-2.43 (m, 1H), 2.24-2.03 (m, 2H), 1.93-1.83 (m, 1H). ESI MS [M+H]$^+$ for $C_{27}H_{19}F_4N_3O$, calcd 478.1, found 478.0.

Example 240: (5S,8R)-8-[(1S)-2,2-difluoro-1-hydroxy-7-(3-methylimidazol-4-yl)-1,3-dihydroinden-4-yl]-3,5-difluoro-5,6,7,8-tetrahydronaphthalene-1-carbonitrile

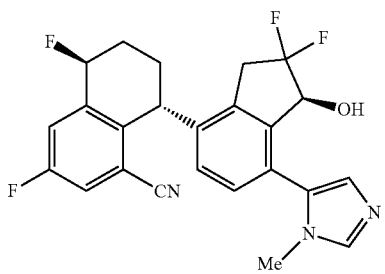 [SMILES: Cn1cncc1-c1ccc([C@H]2CC[C@H](F)c3cc(F)cc(C#N)c32)c2c1[C@H](O)C(F)(F)C2]

The title compound was prepared in a similar fashion to Example 144. $^1$H NMR (400 MHz, Chloroform-d) δ 7.55 (s, 1H), 7.52-7.47 (m, 1H), 7.39-7.35 (m, 1H), 7.33 (s, 1H), 7.04 (d, J=7.9 Hz, 1H), 6.41 (d, J=8.0 Hz, 1H), 5.68-5.51 (m, 1H), 4.83 (d, J=11.8 Hz, 1H), 4.53 (s, 1H), 3.85 (ddd, J=24.5, 16.6, 9.0 Hz, 1H), 3.54 (s, 3H), 3.33 (t, J=16.7 Hz, 1H), 2.52-2.40 (m, 1H), 2.18-1.99 (m, 2H), 1.86-1.77 (m, 1H). ESI MS [M+H]$^+$ for $C_{24}H_{19}F_4N_3O$, calcd 442.1, found 442.1.

Example 241: (5S,8R)-8-[(1S)-2,2-difluoro-1-hydroxy-7-(4-methylpyridin-3-yl)-2,3-dihydro-1H-inden-4-yl]-3,5-difluoro-5,6,7,8-tetrahydronaphthalene-1-carbonitrile

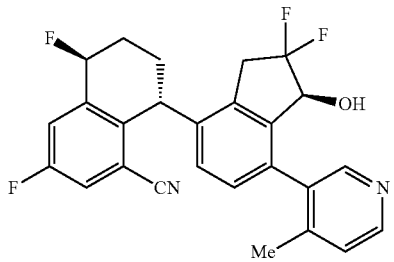

The title compound was prepared in a similar fashion to Example 144. $^1$H NMR (400 MHz, CDCl$_3$) δ 8.74 (s, 1H), 8.61 (d, J=5.8 Hz, 1H), 7.67 (d, J=5.8 Hz, 1H), 7.52 (m, 1H), 7.40 (dt, J=7.5, 2.2 Hz, 1H), 6.96 (d, J=7.9 Hz, 1H), 6.46 (d, J=8.0 Hz, 1H), 5.71-5.49 (m, 1H), 4.92-4.78 (m, 1H), 4.55-4.51 (m, 1H), 3.89-3.76 (m, 1H), 3.51-3.36 (m, 1H), 2.55-2.46 (m, 2H), 2.39 (s, 3H), 2.21-2.14 (m, 1H), 2.10-2.02 (m, 1H), 1.87-1.80 (m, 1H). ESI MS [M+H]$^+$ for $C_{26}H_{21}F_4N_2O$, calcd 453.16, found 453.1.

Example 242: (5S,8R)-8-[(1S)-2,2-difluoro-1-hydroxy-7-(3-methylpyridin-4-yl)-2,3-dihydro-1H-inden-4-yl]-3,5-difluoro-5,6,7,8-tetrahydronaphthalene-1-carbonitrile

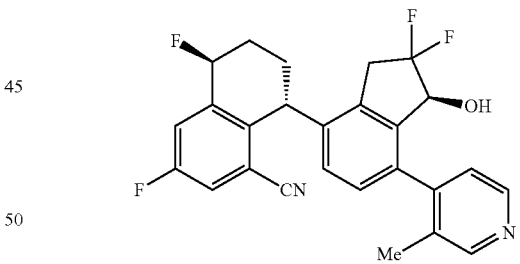

The title compound was prepared in a similar fashion to Example 144. $^1$H NMR (400 MHz, CDCl$_3$) δ 8.60 (s, 1H), 8.52 (d, J=5.6 Hz, 1H), 7.62-7.52 (m, 1H), 7.52 (d, J=2.8 Hz, 1H), 7.39 (dt, J=7.5, 2.3 Hz, 1H), 6.93 (d, J=7.9 Hz, 1H), 6.45 (d, J=7.9 Hz, 1H), 5.6 (dt, J=50.0, 3.7 Hz, 1H), 4.91-4.78 (m, 1H), 4.55-4.50 (m, 1H), 3.81 (td, J=17.3, 11.5 Hz, 1H), 3.41 (td, J=16.2, 6.7 Hz, 1H), 2.56-2.45 (m, 1H), 2.22 (s, 3H), 2.21-1.98 (m, 2H), 1.88-1.80 (m, 1H). ESI MS [M+H]$^+$ for $C_{26}H_{21}F_4N_2O$, calcd 453.16, found 453.1.

Example 243: (5S,8R)-8-[(1S)-2,2-difluoro-1-hydroxy-7-{1H-pyrrolo[2,3-b]pyridin-3-yl}-2,3-dihydro-1H-inden-4-yl]-3,5-difluoro-5,6,7,8-tetrahydronaphthalene-1-carbonitrile

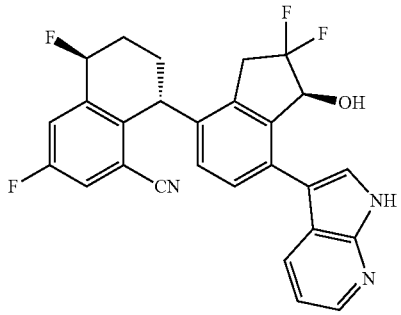 [SMILES: N#Cc1cc(F)cc2c1[C@@H](c1ccc(-c3c[nH]c4ncccc34)c3c1CC(F)(F)[C@H]3O)CC[C@@H]2F]

The title compound was prepared in a similar fashion to Example 144. $^1$H NMR (400 MHz, CDCl$_3$) δ 13.83 (s, 1H), 8.50 (dd, J=7.9, 1.1 Hz, 1H), 8.19 (dd, J=5.8, 1.2 Hz, 1H), 7.99 (d, J=1.9 Hz, 1H), 7.52 (ddd, J=8.2, 2.8, 1.1 Hz, 1H), 7.42-7.36 (m, 2H), 7.30 (d, J=8.0 Hz, 1H), 6.50 (d, J=8.0 Hz, 1H), 5.62 (dt, J=50.1, 3.6 Hz, 1H), 4.79 (d, J=11.7 Hz, 1H), 4.56-4.51 (m, 1H), 3.90 (ddd, J=25.1, 16.7, 8.5 Hz, 1H), 3.43 (t, J=17.1 Hz, 1H), 2.57-2.45 (m, 1H), 2.23-2.03 (m, 2H), 1.89-1.79 (m, 1H). ESI MS [M+H]$^+$ for C$_{28}$H$_{21}$F$_4$N$_2$O, calcd 477.16, found 478.1.

Example 244: (5S,8R)-8-[(1S)-2,2-difluoro-1-hydroxy-7-(3-methylpyridin-2-yl)-2,3-dihydro-1H-inden-4-yl]-3,5-difluoro-5,6,7,8-tetrahydronaphthalene-1-carbonitrile

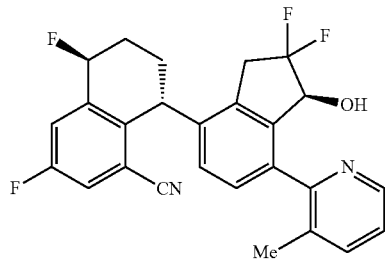

The title compound was prepared in a similar fashion to Example 174. $^1$H NMR (400 MHz, CDCl$_3$) δ 8.51 (d, J=5.0 Hz, 1H), 8.02 (d, J=8.0 Hz, 1H), 7.57 (dd, J=7.9, 5.3 Hz, 1H), 7.51 (d, J=8.5 Hz, 1H), 7.37 (ddd, J=7.5, 2.8, 1.5 Hz, 1H), 7.12 (d, J=7.9 Hz, 1H), 6.58 (d, J=7.9 Hz, 1H), 5.59 (dt, J=52.0, 4.0 Hz, 1H), 4.92 (d, J=12.7 Hz, 1H), 4.54 (m, 1H), 3.77-3.62 (m, 1H), 3.27-3.13 (m, 1H), 2.62-2.34 (m, 2H), 2.35 (s, 3H), 2.21-2.03 (m, 2H), 1.90-1.79 (m, 1H). ESI MS [M+H]$^+$ for C$_{26}$H$_{20}$F$_4$N$_2$O, calcd 453.16, found 453.1.

Example 245: (5S,8R)-8-[(1S)-2,2-difluoro-1-hydroxy-7-{imidazo[1,2-a]pyridin-8-yl}-2,3-dihydro-1H-inden-4-yl]-3,5-difluoro-5,6,7,8-tetrahydronaphthalene-1-carbonitrile

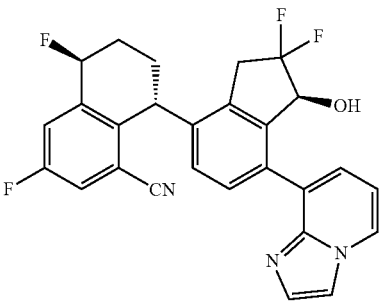

The title compound was prepared in a similar fashion to Example 174. $^1$H NMR (400 MHz, CDCl$_3$) δ 8.31 (dd, J=6.8, 1.1 Hz, 1H), 7.84 (s, 1H), 7.74 (d, J=1.6 Hz, 1H), 7.66 (d, J=7.0 Hz, 1H), 7.56-7.46 (m, 1H), 7.37 (dt, J=7.4, 2.3 Hz, 1H), 7.29 (t, J=7.0 Hz, 1H), 7.20 (d, J=7.9 Hz, 1H), 6.67-6.60 (m, 1H), 5.59 (dt, J=50.1, 4.0 Hz, 1H), 4.98-4.87 (m, 1H), 4.57-4.52 (m, 1H), 3.77-3.62 (m, 1H), 3.21-3.08 (m, 1H), 2.57-2.23 (m, 3H), 2.23-2.06 (m, 2H), 1.91-1.81 (m, 1H). ESI MS [M+H]$^+$ for C$_{27}$H$_{20}$F$_4$N$_3$O, calcd 478.15, found 478.1.

Example 246: (5S,8S)-3,5-difluoro-8-[(6R,7S)-6-fluoro-7-hydroxy-1-(2-methylpyridin-3-yl)-5H,6H,7H-cyclopenta[c]pyridin-4-yl]-5,6,7,8-tetrahydronaphthalene-1-carbonitrile

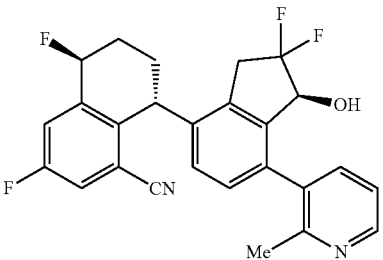

The title compound was prepared in a similar fashion to Example 174. $^1$H NMR (400 MHz, MeOD) δ 8.73 (dd, J=5.8, 1.6 Hz, 1H), 8.54 (dd, J=8.0, 1.6 Hz, 1H), 7.93 (dd, J=7.9, 5.9 Hz, 1H), 7.77 (s, 1H), 7.71-7.63 (m, 2H), 5.70 (dt, J=49.8, 3.9 Hz, 1H), 5.36 (d, J=1.9 Hz, 1H), 5.31 (d, J=4.2 Hz, 0.5H), 5.23 (m, 0.5H), 4.83-4.78 (m, 1H), 3.53-3.40 (m, 1H), 3.24-3.12 (m, 1H), 2.62 (s, 3H), 2.58-2.46 (m, 1H), 2.20-1.94 (m, 2H), 1.91-1.82 (m, 1H). ESI MS [M+H]$^+$ for C$_{25}$H$_{21}$F$_3$N$_3$O, calcd 436.16, found 436.1.

Example 247: (5S,8R)-8-[(1S,2S)-2-cyano-2-fluoro-1-hydroxy-7-methylsulfonyl-1,3-dihydroinden-4-yl]-3,5-difluoro-5,6,7,8-tetrahydronaphthalene-1-carbonitrile
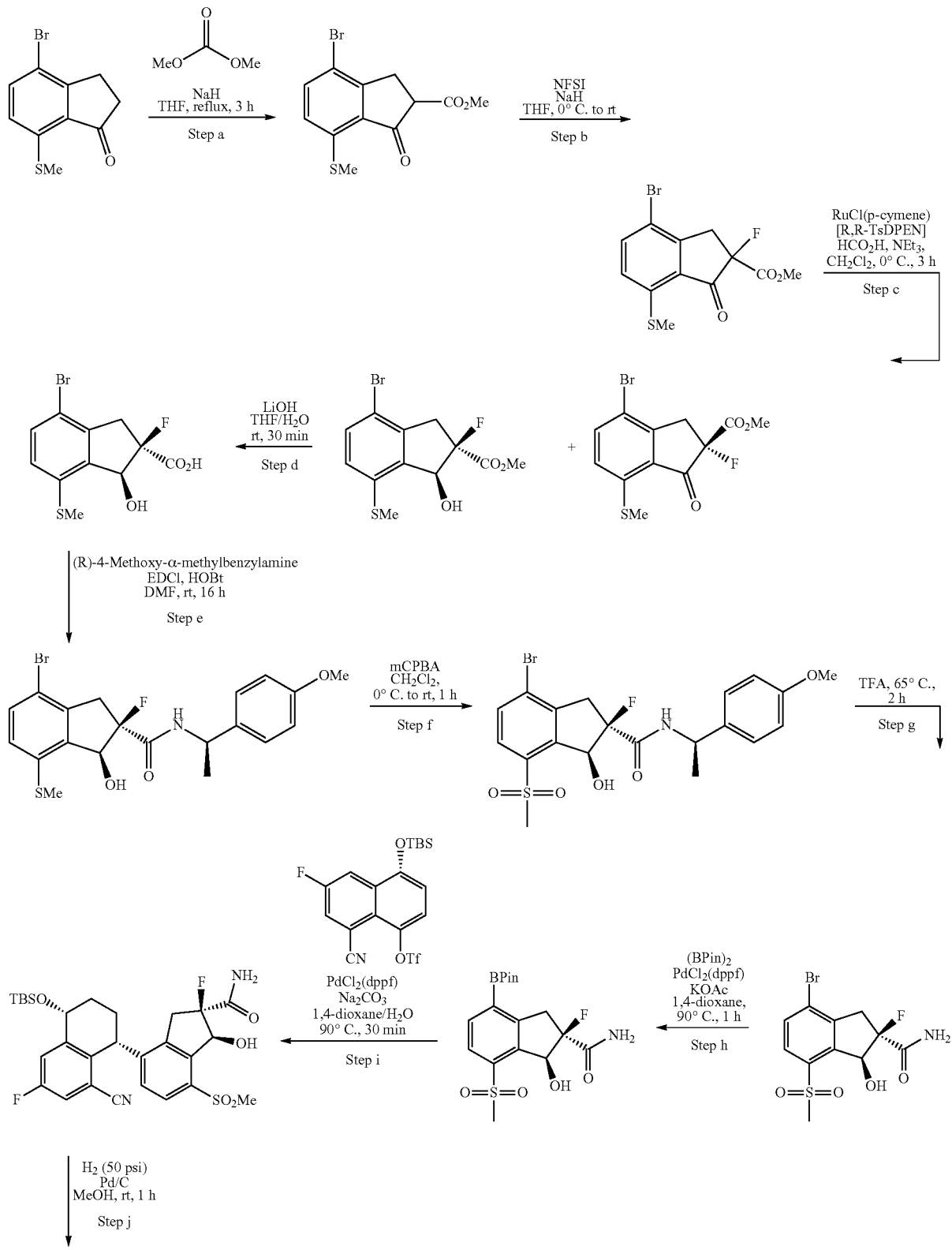

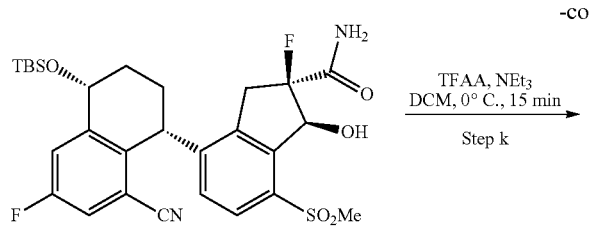

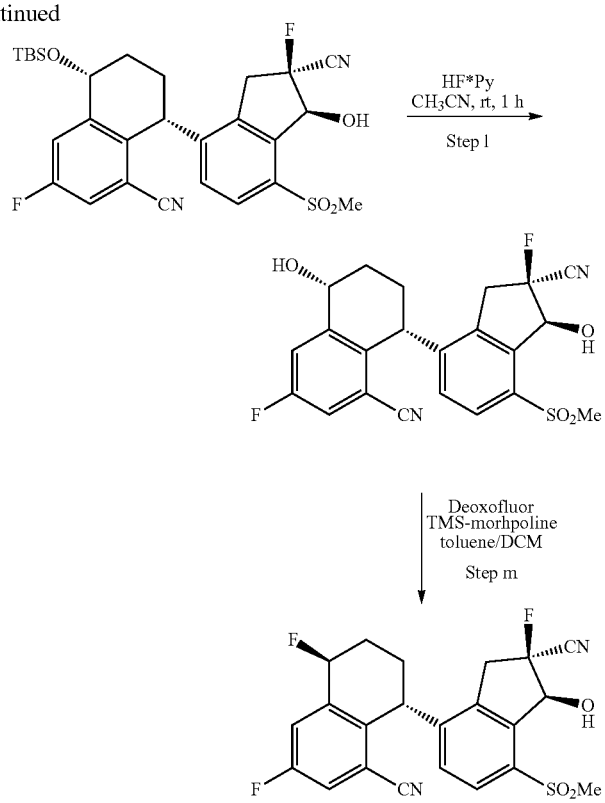

Step a: A suspension of NaH (1.4 g, 35.1 mmol, 60% in mineral oil) in THF (120 mL) was loaded in 250 ml single-neck round-bottom flask equipped with a stirring bar and a reflux condenser with a drying tube. Dimethyl carbonate (2.0 mL, 23.3 mmol) was added in one portion and the mixture was cooled to 0° C. Then solid 4-bromo-7-methylsulfanyl-2,3-dihydroinden-1-one (3.0 g, 11.7 mmol) was added in one portion. The reaction was allowed to warm to ambient temperature and stirred for 10 min. The resulting suspension was reflux for 3 h. Once TLC analysis indicated complete consumption of the starting material the reaction was cooled to room temperature and poured in 1M aqueous HCl solution (200 mL). The mixture was diluted with EtOAc (200 mL), the organic phase was separated, and the aqueous solution was extracted with EtOAc (2×70 mL). Combined organic extract was washed with brine (500 mL), dried over $Na_2SO_4$ and concentrated to dryness. The crude product was purified by column chromatography ($SiO_2$, dichloromethane/EtOAc gradient) to produce the desired product (3.4 g, 10.8 mmol, 93% yield) as a yellow solid.

Step b: The solution of indanone from step a (2.6 g, 8.3 mmol) in THF (82 mL) was loaded in 250 ml single-neck round-bottom flask equipped with a stirring bar and a drying tube. The reaction mixture was cooled to 0° C., and NaH (0.35 g, 8.7 mmol, 60% in mineral oil) was added in one portion. The cooling bath was removed, and the mixture was stirred at ambient temperature for 30 min. Upon complete dissolution of NaH the reaction was cooled back to 0° C. and NFSI (3.1 g, 9.9 mmol) was added. The cooling bath was removed, and the reaction was stirred at room temperature for 30 min. Upon complete disappearance of the starting material by TLC analysis the mixture was quenched with saturated aqueous $NH_4Cl$ (70 mL) and diluted with EtOAc (150 ml) and water (100 mL). The organic phase was separated, and the aqueous solution was extracted with EtOAc (2×50 mL). Combined organic extract was dried over $Na_2SO_4$ and concentrated to dryness. The crude product was purified by column chromatography ($SiO_2$, hexanes/EtOAc gradient) to produce the desired product (2.5 g, 7.5 mmol, 92% yield) as a yellowish solid.

Step c: The α-fluoroindanone from step b (5.1 g, 15.4 mmol) in dichloromethane (80 mL) was placed in 250 ml single-neck round-bottom flask equipped with a stirring bar and a drying tube. The solution was cooled to 0° C., then formic acid (1.75 mL, 46.2 mmol), triethylamine (4.1 mL, 30.8 mmol) and RuCl(p-cymene)[R,R-TsDPEN] (0.5 g, 0.77 mmol) were sequentially added. The reaction was stirred at 0° C. and monitored by $^1$H NMR every 30 min until it reached 52% conversion. Then the resulting brown solution was diluted with dichloromethane (100 mL) and washed with aqueous saturated $NaHCO_3$ solution (100 mL). The organic phase was separated, and the aqueous solution was extracted with dichloromethane (2×30 mL). Combined organic extract was dried over $Na_2SO_4$ and concentrated to dryness. The crude residue was fractionated by column chromatography ($SiO_2$, hexanes/EtOAc gradient) to produce enantioenriched α-fluoroindane-1-ol (2.7 g, 8.1 mmol, 53% yield) as a colorless oil and recovered α-fluoroindanone (2.1 g, 6.3 mmol, 41% yield) as a yellowish solid. The enantiopurity of indane-1-ol product was determined (88% ee) using $^1$H NMR after hydrolysis and amide coupling with enantiopure (R)-4-methoxy-α-methylbenzylamine.

Step d: To a solution of α-fluoroindane-1-ol from step c (1.0 g, 3.0 mmol) in tetrahydrofuran (20 mL) a solution of LiOH·$H_2O$ (1.25 g, 30 mmol) in water (20 mL) was added at ambient temperature. The resulting biphasic mixture was vigorously stirred for 20 min. Once TLC analysis indicated complete consumption of the starting material, the mixture was slowly acidified with 1M aqueous HCl to pH=3. The resulting mixture was diluted with EtOAc (40 mL), and the organic layer was separated. The aqueous phase was additionally extracted with EtOAc (20 mL). Combined organic extract was washed with brine, dried over $Na_2SO_4$ and concentrated to dryness. The crude product was used for the step e without additional purification.

Step e: β-Hydroxy acid step d (3.0 mmol) was dissolved in DMF (15 mL) and (R)-4-methoxy-α-methylbenzylamine (0.68 mL, 4.5 mmol), 1-hydroxybenzotriazole hydrate (0.86 g, 4.5 mmol, contains 20 wt. % of water) and N-(3-dimethylaminopropyl)-N'-ethylcarbodiimide hydrochloride (0.86 g, 4.5 mmol) were added sequentially. After 24 h of stirring at room temperature the mixture was diluted with water (100 mL), and the crude product was extracted with EtOAc (3×40 mL). Combined organic extract was thoroughly washed with water (3×70 mL), dried over $Na_2SO_4$ and concentrated to dryness. The crude residue was fractionated by column chromatography ($SiO_2$, hexanes/EtOAc gradient) to produce corresponding amide (1.1 g, 2.4 mmol, 81% yield) as a single diastereomer in a form of white foam.

Step f: Amide from step e (1.7 g, 3.7 mmol) was dissolved in dichloromethane (37 mL) and m-CPBA (2.2 g, 9.4 mmol, contained 25 wt. % of water) was added in one portion. The resulting solution was stirred at ambient temperature for 1 h. The resulting mixture was diluted with dichloromethane (50 mL) and sequentially washed with 2M aqueous NaOH (2×30 mL) and brine (90 mL). The organic extract was dried over $Na_2SO_4$ and concentrated to dryness. The crude sulfone-containing product was used for step g without purification.

Step g: The crude material from step f was dissolved in 35 ml of trifluoroacetic acid. The obtained solution was stirred at 65° C. for 2 h. The bright red solution was diluted with water (300 mL). The formed precipitate was removed by filtration, washed with MTBE and dried on filter for 2 h to produce the desired primary amide as a white solid (1.08 g, 3.1 mmol, 84% yield over two steps).

Step h: The primary amide product from the previous step (0.4 g, 1.1 mmol) was combined with $B_2Pin_2$ (0.35 g, 1.4 mmol), Pd(dppf)Cl$_2$ (83.0 g, 0.11 mmol) and potassium acetate (0.2 g, 2.2 mmol) in dioxane (6 ml) in 40 mL screw cap vial equipped with a magnetic stirring bar. The mixture was degassed under vacuum, backfilled with nitrogen and heated to 100° C. for 1.5 h. After $^1$H NMR analysis of an aliquot indicated complete consumption of the starting material the reaction mixture was allowed to cool to ambient temperature and concentrated to dryness under reduced pressure. The residue was partitioned between EtOAc (70 mL) and water (40 mL). Organic layer was separated, and the aqueous phase was additionally extracted with EtOAc (2×20 mL). The combined organic extract was dried over $Na_2SO_4$ and the solvent was evaporated under reduced pressure to yield crude boronic pinacol ester that was used for the next step without further purification.

Step i: A solution of crude boronic pinacol ester (1.1 mmol) from the previous step and (4R)-4-[tert-butyl(dimethyl)silyl]oxy-8-cyano-6-fluoro-3,4-dihydronaphthalen-1-yl] trifluoromethanesulfonate (0.51 g, 1.1 mmol) in dioxane (6 mL) was placed in 40 mL screw cap vial equipped with a magnetic stirring bar. Then Pd(dppf)Cl$_2$ (83 mg, 0.11 mmol) and aqueous sodium carbonate (2M solution, 1.2 ml, 2.3 mmol) were sequentially added. The mixture was degassed under vacuum, backfilled with nitrogen and heated to 100° C. for 0.5 h. Upon reaction completion, dioxane was removed under reduced pressure. The residue was partitioned between EtOAc (70 mL) and water (50 mL). Organic layer was separated, and the aqueous phase was additionally extracted with EtOAc (2×15 mL). The combined organic extract was washed with brine (50 mL), dried over $Na_2SO_4$ and concentrated to dryness. The crude product was purified by column chromatography ($SiO_2$, hexanes/EtOAc gradient) to yield the desired alkene (0.65 g, 1.1 mmol, 100% yield over two steps) as a brownish foam.

Step j: The alkene of step i (0.65 g, 1.1 mmol) was dissolved in dry methanol (15 mL) and added to palladium on carbon (0.25 g, 10% Pd by weight) under an atmosphere of nitrogen. The reaction mixture was placed under an atmosphere of hydrogen at 50 psi and agitated in a Parr shaker for 1 h. The excess hydrogen was vented out and the mixture was sparged with nitrogen to remove residual hydrogen gas. TLC analysis indicated incomplete reaction. Additional 0.25 g of palladium on carbon was added and the reaction was agitated under an atmosphere of hydrogen at 50 psi for additional hour. The resulting suspension was filtered through a celite pad, and the filtrate was concentrated to dryness under reduced pressure. The crude residue was subjected to column chromatography ($SiO_2$, hexanes/EtOAc gradient) to produce the desired tetralin derivative (0.5 g, 0.9 mmol, 77% yield) as a colorless oil.

Step k: A mixture of tetralin from previous step (0.5 g, 0.9 mmol) and triethylamine (0.6 mL, 4.4 mmol) in dichloromethane (9 mL) was place in 100 mL single-neck round-bottom flask equipped with a stirring bar and a drying tube. The mixture was cooled to 0° C. and trifluoroacetic anhydride (0.4 mL, 2.6 mmol) was added dropwise over 5 min. The resulting yellow solution was stirred at 0° C. for 10 min, diluted with dichloromethane (40 mL) and sequentially washed with water (50 mL) and saturated aqueous $NaHCO_3$ (50 mL). The organic phase was separated, dried over $Na_2SO_4$ and concentrated to dryness. The crude product was purified by column chromatography ($SiO_2$, hexanes/EtOAc gradient) to produce the desired α-fluoronitrile derivative (0.27 g, 0.5 mmol, 55% yield) as a colorless oil.

Step l: The α-fluoronitrile from step k (100.0 mg, 0.18 mmol) was dissolved in acetonitrile (2 mL) and HF·Py (0.2 mL, HF −70%, pyridine −30%) was added in one portion at ambient temperature. The reaction mixture was stirred for 1 h, diluted with EtOAc (30 mL) and carefully washed with aqueous saturated $NaHCO_3$ (20 mL). The organic extract was washed with brine (30 mL), dried over $Na_2SO_4$ and concentrated to dryness. The crude product was purified by column chromatography ($SiO_2$, hexanes/EtOAc gradient) to produce the desired hydroxytetralin derivative (73.0 mg, 0.16 mmol, 92% yield) as a white powder.

Step m: A solution of Deoxo-Fluor (106 μl, 0.57 mmol) in toluene (3.3 mL) was placed in 40 ml screw cap vial equipped with a magnetic stirring bar and nitrogen balloon. The solution was cooled to 0° C., then TMS-morpholine (103 μl, 0.58 mmol) was added dropwise. The reaction was stirred at 0° C. for 5 min, then the mixture was allowed to warm to room temperature and stirred for 2 h. The resulting cloudy solution was cooled to 0° C. and a solution of 1,2,3,4-tetrahydro-1-naphthol from step 1 (73.0 mg, 0.16 mmol) in dichloromethane (1 mL) was added dropwise over 1 min. The resulting mixture was stirred for 5 min and immediately diluted with dichloromethane (20 mL) and quenched with aqueous saturated NaHCO$_3$ (20 mL). The organic phase was separated, dried over Na$_2$SO$_4$ and concentrated to dryness. The dry residue was fractionated by column chromatography (SiO$_2$, dichloromethane/EtOAc gradient) to produce the product that was further purified by reversed phase HPLC (C18 column, water with 1% TFA/CH$_3$CN gradient, 20 mL/min) to yield the title compound (26 mg, 0.06 mmol, 36% yield, single epimer) as a colorless oil. $^1$H NMR (400 MHZ, CDCl$_3$) δ 7.72 (d, J=8.0 Hz, 1H), 7.53 (ddd, J=8.2, 2.7, 1.3 Hz, 1H), 7.39 (ddd, J=7.5, 2.8, 1.7 Hz, 1H), 6.56 (d, J=8.1 Hz, 1H), 5.80 (dd, J=15.3, 5.0 Hz, 1H), 5.60 (dt, J=49.8, 3.6 Hz, 1H), 4.60-4.48 (m, 1H), 4.08 (ddd, J=31.8, 17.4, 1.0 Hz, 1H), 3.94 (d, J=5.2 Hz, 1H), 3.61 (dd, J=21.2, 17.4 Hz, 1H), 3.16 (s, 3H), 2.60-2.42 (m, 1H), 2.29-2.08 (m, 1H), 2.07-1.87 (m, 1H), 1.82-1.70 (m, 1H). $^{19}$F NMR (376 MHz, CDCl$_3$) δ −110.39 (t, J=7.8 Hz), −151.11 (ddd, J=31.8, 21.3, 15.5 Hz), −157.85. ESI MS [M+Na]$^+$ for C$_{22}$H$_{17}$F$_3$N$_2$SO$_3$Na, calcd 469.1, found 469.1).

Example 248: (5S,8R)-8-[(1S,2R)-2-cyano-2-fluoro-1-hydroxy-7-methylsulfonyl-1,3-dihydroinden-4-yl]-3,5-difluoro-5,6,7,8-tetrahydronaphthalene-1-carbonitrile

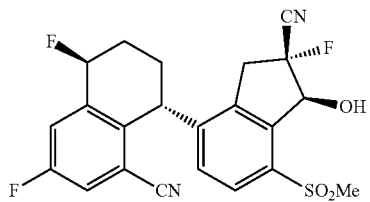 [SMILES: CS(=O)(=O)c1ccc([C@H]2CC[C@H](F)c3cc(F)cc(C#N)c32)c2c1[C@H](O)[C@](F)(C#N)C2]

The title compound was prepared in a similar fashion to Example 247. $^1$H NMR (400 MHz, CDCl$_3$) δ 7.73 (d, J=8.1 Hz, 1H), 7.53 (ddd, J=8.3, 2.8, 1.4 Hz, 1H), 7.39 (ddd, J=7.5, 2.7, 1.7 Hz, 1H), 6.51 (d, J=8.1 Hz, 1H), 5.93 (ddd, J=11.9, 6.1, 0.6 Hz, 1H), 5.58 (dt, J=49.8, 3.5 Hz, 1H), 4.69-4.51 (m, 1H), 4.07 (d, J=6.1 Hz, 1H), 3.96 (dd, J=18.4, 17.3 Hz, 1H), 3.58 (dd, J=21.7, 16.9 Hz, 1H), 3.24 (s, 3H), 2.65-2.40 (m, 1H), 2.24-2.08 (m, 1H), 1.98-1.79 (m, 1H), 1.74-1.62 (m, 1H). $^{19}$F NMR (376 MHz, CDCl$_3$) δ −110.4 (t, J=8.7 Hz), −157.3 (m), −170.6 (m). ESI MS [M+Na]$^+$ for C$_{22}$H$_{17}$F$_3$N$_2$SO$_3$Na, calcd 469.1, found 469.1.

Analytical Methods:
LC: Agilent 1100 series; Mass spectrometer: Agilent G6120BA, single quad
LC-MS method: Agilent Zorbax Eclipse Plus C18, 4.6×100 mm, 3.5 μM, 35° C., 1.5 mL/min flow rate, a 2.5 min gradient of 0% to 100% B with 0.5 min wash at 100% B; A=0.1% of formic acid/5% acetonitrile/94.9% water; B=0.1% of formic acid/5% water/94.9% acetonitrile
Flash column: ISCO Rf+
Reverse phase HPLC: ISCO-EZ or Agilent 1260; Column: Kinetex 5 μm EVO C18 100 A; 250×21.2 mm (Phenomenex)

BIOLOGICAL EXAMPLES

Generation of HIF-2α Luciferase 786-0 Cell Line:

Stable cell lines were generated by transducing 786-O cells (ATCC, CRL-1932) with Cignal Lenti HIF Luc Reporter lentivirus (CLS-007L, Qiagen) according to the manufacturer's guidelines. In brief, 0.3×106 786-0 cells were transduced with lentivirus at a Multiplicity of Infection (MOI) of 25 for 24 hours. After transduction, cells were replenished with fresh RPMI 1640 Medium (Cat. No. 11875085, Thermo Fisher,) supplemented with 10% FBS (Cat. No. A3160502, Gibco), 2 mM GlutaMax (Cat. No. 35050-061, Invitrogen) and 100 units of penicillin and 100 μg of streptomycin/mL (Cat. No 15070063, Thermo Fisher) for another 24 hours. Antibiotic selection was performed in cell media containing 4 μg/mL of Puromycin. After 7 days of antibiotic selection, stable pools of surviving cells were expanded and used in a luciferase reporter assay.

HIF-2α Luciferase Reporter Assay:

On day one, 20 μL of HIF-Luc-786-0 cells in OptiMem (Cat. No. 31985088, Thermo Fisher) were seeded into each well of a 384 well white opaque plate (Corning 3570) and incubated at 37° C. and 5% CO2. Twenty microliters of 2× test compounds in OptiMem were added to cells after 4 hours of incubation. Final assay conditions comprised 20,000 cells per well in 1% DMSO with test compound concentrations ranging from 50 uM to 0 uM. After 20 hours incubation at 37° C. and 5% CO2, luciferase activity was determined using ONE-Glo Luciferase Assay Reagent (E6110, Promega) following the manufacture's recommended procedure. Briefly, 40 uL of ONE-Glo luciferase reagents were added to each well and luciferase signals were measured using an Envision 2102 Multilabel Reader. Percentage maximum activity in each test well was calculated based on DMSO (maximum activity) and no cell control wells (baseline activity). The IC50 values of the test compounds were determined from compound dose response curves fitted using a standard four parameter fit equation.

HIF-2α Scintillation Proximity Assay (SPA) Binding Assay:

Tritium labeled compound N-(3-chlorophenyl)-4-nitro-2,1,3-benzoxadiazol-5-amine was obtained from American Radiolabeled Chemicals Inc. and copper chelate PVT SPA beads were from PerkinElmer (Cat #RPNQ0095). Histidine tagged HIF-2α protein containing PAS-B domain (240-350) was prepared and purified in house.

Compounds solubilized in DMSO were dispensed into a white 384-well polystyrene non-binding flat clear bottom plate (Greiner Bio-One, Cat #781903) using an HP D300 dispenser. Ten microliters of HIS-tagged HIF-2α protein in buffer (25 mM Tris-HCl, pH 7.4, 150 mM NaCl, 0.15% BSA and 0.001% Tween 20) was added to the compound wells and allowed to incubate for 1 hour at room temperature. Ten microliters of SPA bead mix were added to the wells and incubated for an additional 45 minutes, followed by 10 ul of $^3$H-tracer solution. Final assay conditions comprised 50 nM HIF-2α protein, 25 nM radiolabeled tracer and 3 ug beads per well with compounds in 2% DMSO. The plate was read using a MicroBeta Microplate Counter (PerkinElmer) for luminescence detection. The IC$_{50}$ values of the test compounds were determined from compound dose response curves fitted using a standard four parameter fit equation and are reported in Table 1, Table 2, and Table 3.

TABLE 1

Potency of select compounds
Less than 100 nM (+++), 100 nM to 1 µM (++), greater than 1 µM (+)

| Example # | Structure | HIF-2α Scintillation Proximity Assay | HIF-2α Luciferase Assay |
|---|---|---|---|
| 1 | 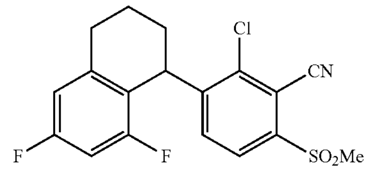 [SMILES: CS(=O)(=O)c1ccc(C2CCCc3cc(F)cc(F)c32)c(Cl)c1C#N] | ++ | + |
| 2a | 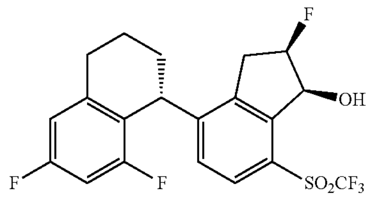 | +++ | +++ |
| 2b | 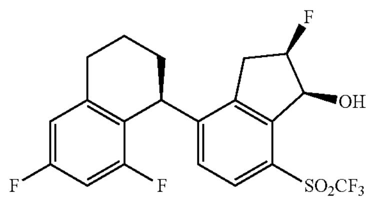 | ++ | ++ |
| 3 | 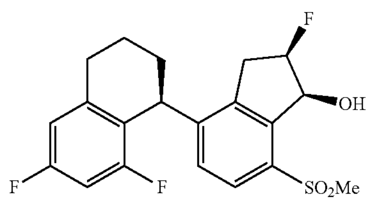 [SMILES: CS(=O)(=O)c1ccc([C@@H]2CCCc3cc(F)cc(F)c32)c2c1[C@H](O)[C@H](F)C2] | + | + |
| 4 | 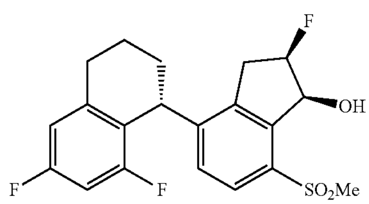 [SMILES: CS(=O)(=O)c1ccc([C@H]2CCCc3cc(F)cc(F)c32)c2c1[C@H](O)[C@H](F)C2] | +++ | ++ |
| 5 | 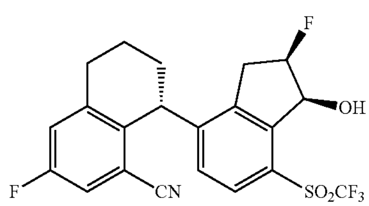 | +++ | +++ |
| 6 | 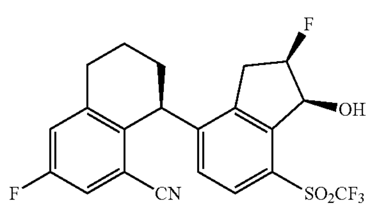 | + | + |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 7 | 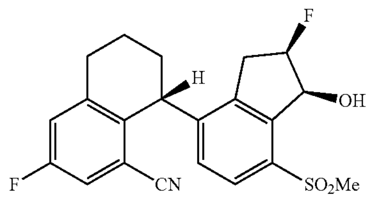 [SMILES: CS(=O)(=O)c1ccc([C@H]2CCCc3cc(F)cc(C#N)c32)c2c1[C@H](O)[C@H](F)C2] | +++ | +++ |
| 8 | 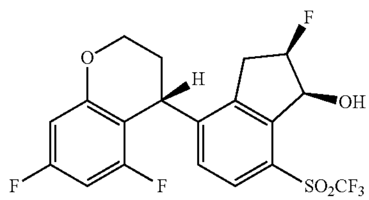 | ++ | ++ |
| 9 | 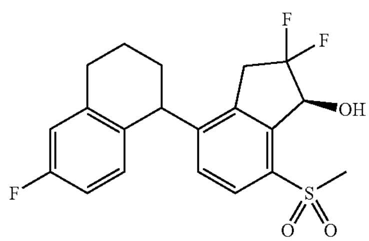 [SMILES: CS(=O)(=O)c1ccc(C2CCCc3cc(F)ccc32)c2c1[C@H](O)C(F)(F)C2] | ++ | ++ |
| 10 | 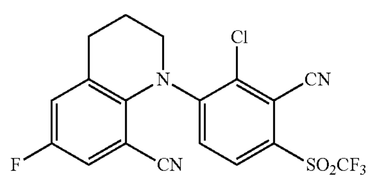 | +++ | +++ |
| 11 | 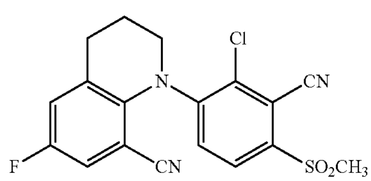 [SMILES: CS(=O)(=O)c1ccc(N2CCCc3cc(F)cc(C#N)c32)c(Cl)c1C#N] | ++ | ++ |
| 12 | 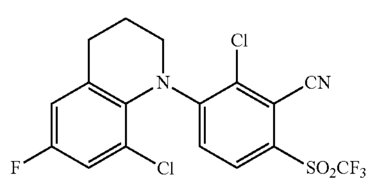 | ++ | + |
| 13 | 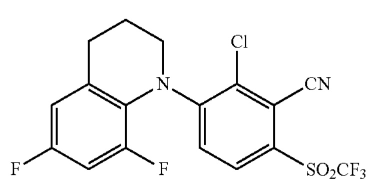 | ++ | + |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 14 | 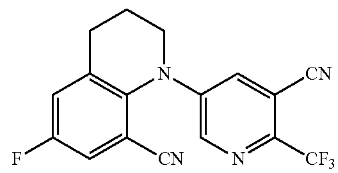 [SMILES: N#Cc1cc(N2CCCc3cc(F)cc(C#N)c32)cnc1C(F)(F)F] | ++ | ++ |
| 15 | 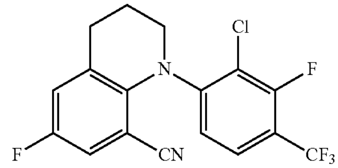 [SMILES: N#Cc1cc(F)cc2c1N(c1ccc(C(F)(F)F)c(F)c1Cl)CCC2] | ++ | ++ |
| 16 | 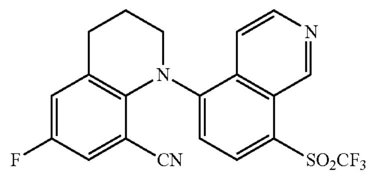 | ++ | ++ |
| 17 | 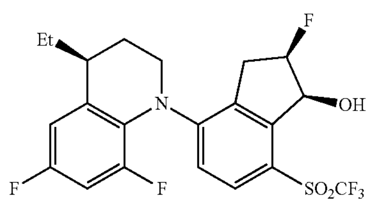 | ++ | ++ |
| 18 | 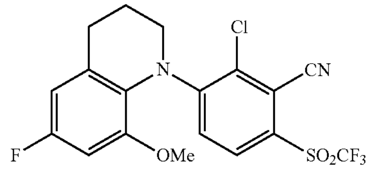 | + | + |
| 19 | 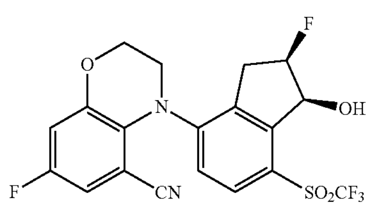 [SMILES: CS(=O)(=O)c1ccc(N2CCOc3cc(F)cc(C#N)c32)c2c1[C@H](O)[C@H](F)C2] | ++ | ++ |
| 20 | 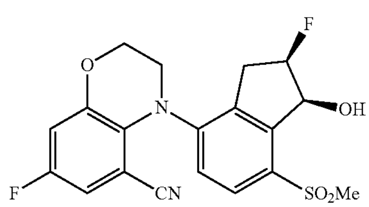 | + | + |
| 21 | 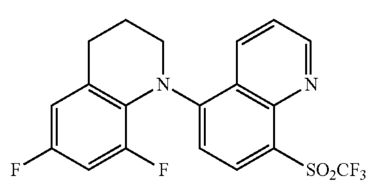 | + | + |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 22 | 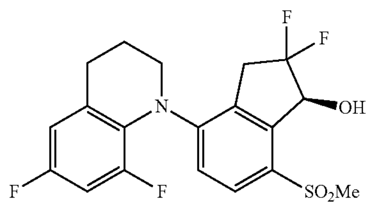 | ++ | + |
| 23 | 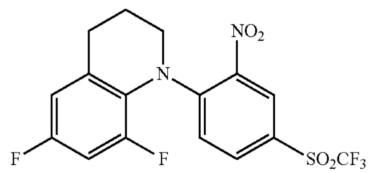 | + | + |
| 24 | 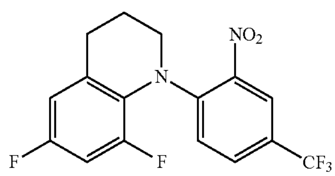 [SMILES: O=[N+]([O-])c1cc(C(F)(F)F)ccc1N1CCCc2cc(F)cc(F)c21] | + | + |
| 25 | 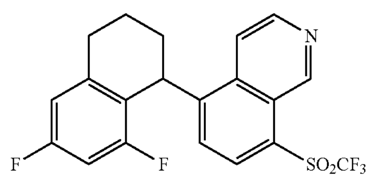 | + | + |
| 26 | 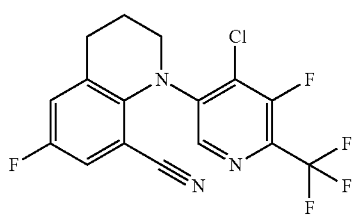 | ++ | ++ |
| 27 | 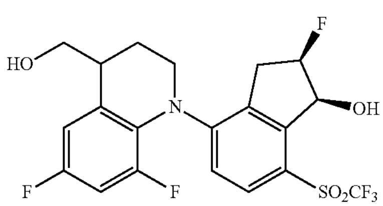 | ++ | ++ |
| 28 | 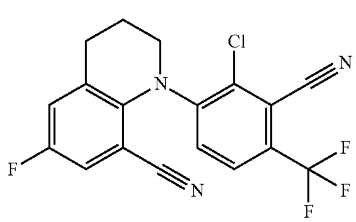 | ++ | ++ |

TABLE 1-continued

Potency of select compounds
Less than 100 nM (+++), 100 nM to 1 µM (++), greater than 1 µM (+)

| Example # | Structure | HIF-2α Scintillation Proximity Assay | HIF-2α Luciferase Assay |
|---|---|---|---|
| 29 | 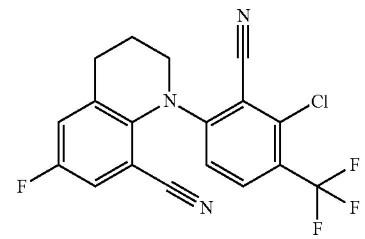 [SMILES: N#Cc1cc(F)cc2c1N(c1ccc(C(F)(F)F)c(Cl)c1C#N)CCC2] | ++ | ++ |
| 30 | 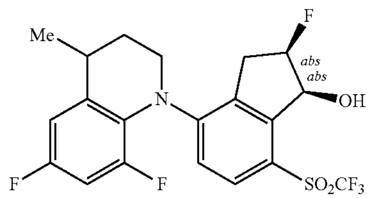 | ++ | ++ |
| 31 | 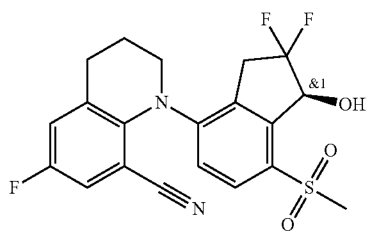 [SMILES: CS(=O)(=O)c1ccc(N2CCCc3cc(F)cc(C#N)c32)c2c1[C@H](O)C(F)(F)C2] | ++ | ++ |
| 32 | 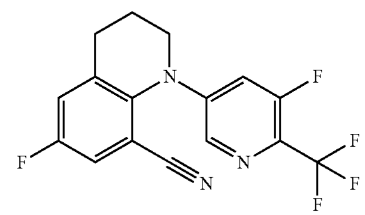 [SMILES: N#Cc1cc(F)cc2c1N(c1cnc(C(F)(F)F)c(F)c1)CCC2] | ++ | ++ |
| 33 | 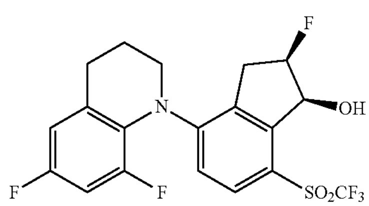 | ++ | ++ |
| 34 | 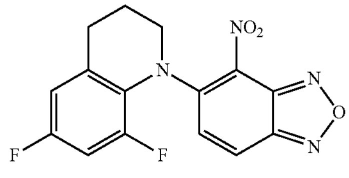 [SMILES: O=[N+]([O-])c1c(N2CCCc3cc(F)cc(F)c32)ccc2nonc12] | + | ++ |
| 35 | 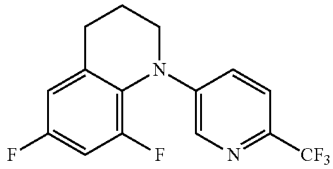 [SMILES: Fc1cc(F)c2c(c1)CCCN2c1ccc(C(F)(F)F)nc1] | + | ++ |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 36 | 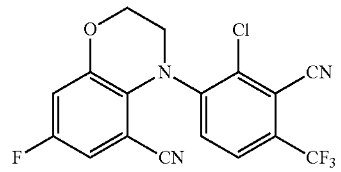 [SMILES: N#Cc1cc(F)cc2c1N(c1ccc(C(F)(F)F)c(C#N)c1Cl)CCO2] | ++ | ++ |
| 37 | 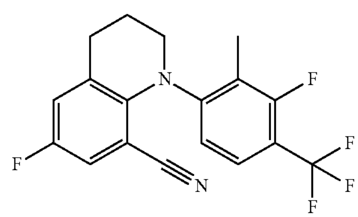 [SMILES: Cc1c(N2CCCc3cc(F)cc(C#N)c32)ccc(C(F)(F)F)c1F] | ++ | ++ |
| 38 | 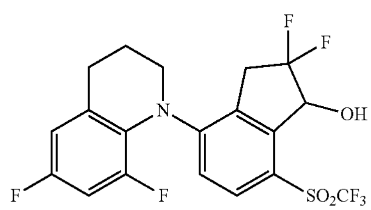 | ++ | ++ |
| 39 | 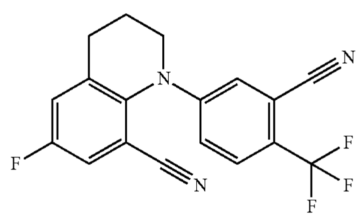 [SMILES: N#Cc1cc(N2CCCc3cc(F)cc(C#N)c32)ccc1C(F)(F)F] | +++ | + |
| 40 | 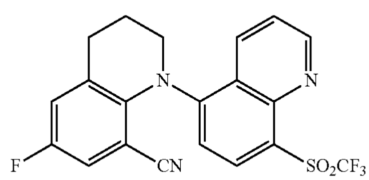 | ++ | + |
| 41 | 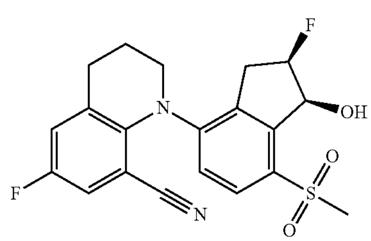 [SMILES: CS(=O)(=O)c1ccc(N2CCCc3cc(F)cc(C#N)c32)c2c1[C@H](O)[C@H](F)C2] | ++ | + |
| 42 | 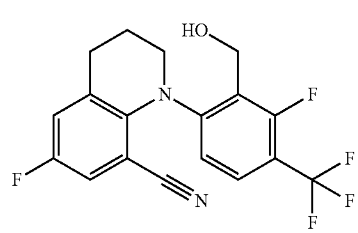 [SMILES: N#Cc1cc(F)cc2c1N(c1ccc(C(F)(F)F)c(F)c1CO)CCC2] | ++ | + |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 43 | 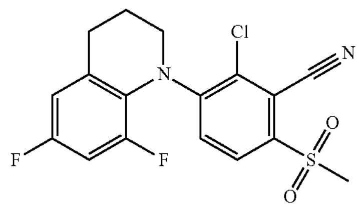 [SMILES: CS(=O)(=O)c1ccc(N2CCCc3cc(F)cc(F)c32)c(Cl)c1C#N] | ++ | + |
| 44 | 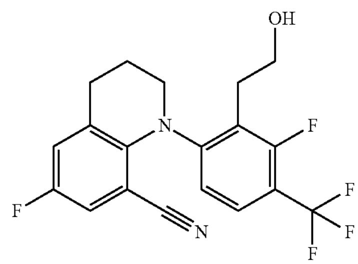 [SMILES: N#Cc1cc(F)cc2c1N(c1ccc(C(F)(F)F)c(F)c1CCO)CCC2] | + | + |
| 45 | 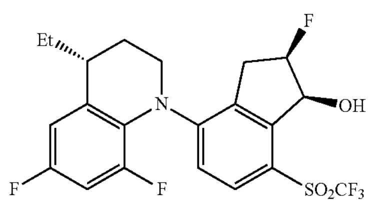 | ++ | + |
| 46 | 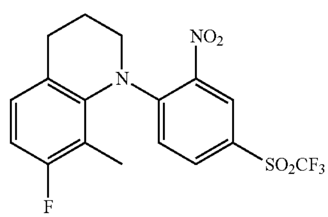 | + | + |
| 47 | 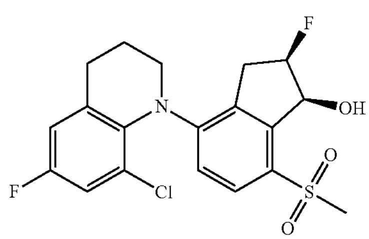 [SMILES: CS(=O)(=O)c1ccc(N2CCCc3cc(F)cc(Cl)c32)c2c1[C@H](O)[C@H](F)C2] | ++ | + |
| 48 | 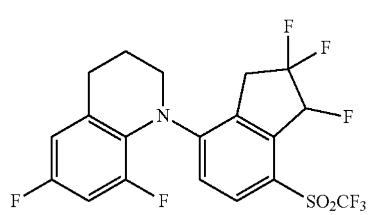 | ++ | + |
| 49 | 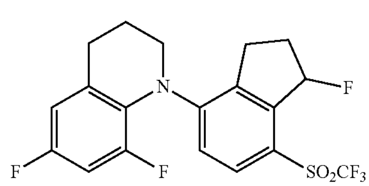 | ++ | + |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 50 | 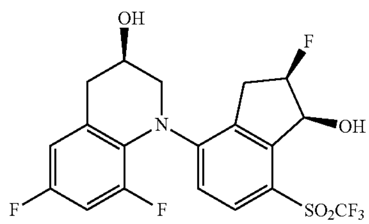 | + | + |
| 51 | 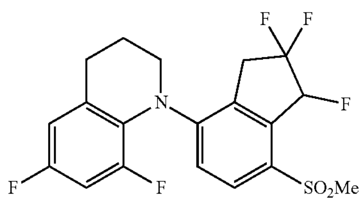 [SMILES: CS(=O)(=O)c1ccc(N2CCCc3cc(F)cc(F)c32)c2c1C(F)C(F)(F)C2] | + | + |
| 52 | 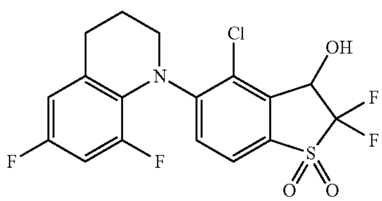 [SMILES: O=S1(=O)c2ccc(N3CCCc4cc(F)cc(F)c43)c(Cl)c2C(O)C1(F)F] | ++ | + |
| 53 | 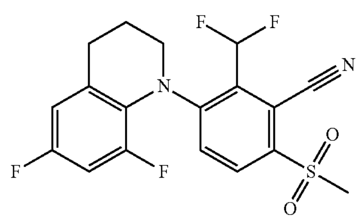 [SMILES: CS(=O)(=O)c1ccc(N2CCCc3cc(F)cc(F)c32)c(C(F)F)c1C#N] | + | + |
| 54 | 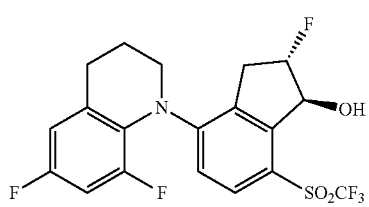 | + | + |
| 55 | 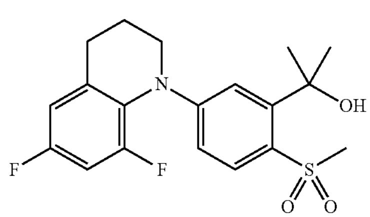 [SMILES: CC(C)(O)c1cc(N2CCCc3cc(F)cc(F)c32)ccc1S(C)(=O)=O] | + | + |
| 56 | 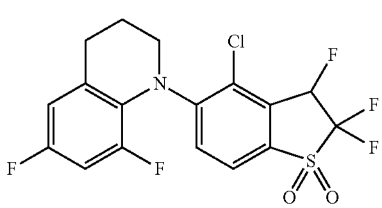 [SMILES: O=S1(=O)c2ccc(N3CCCc4cc(F)cc(F)c43)c(Cl)c2C(F)C1(F)F] | ++ | + |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 57 | 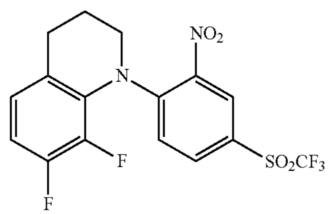 | + | + |
| 58 | 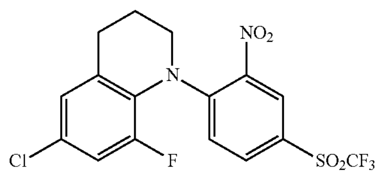 | + | + |
| 59 | 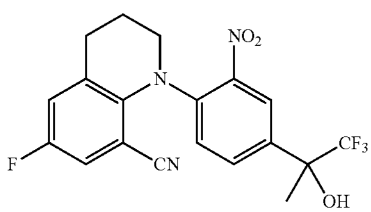 [SMILES: CC(O)(c1ccc(N2CCCc3cc(F)cc(C#N)c32)c([N+](=O)[O-])c1)C(F)(F)F] | + | + |
| 60 | 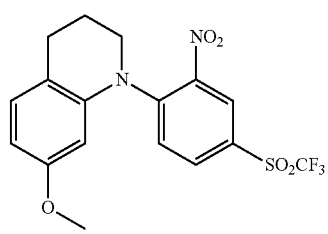 | + | + |
| 61 | 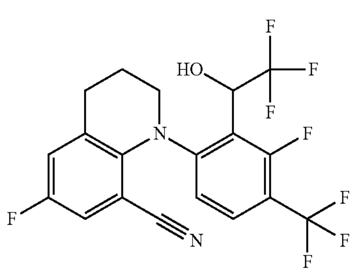 [SMILES: N#Cc1cc(F)cc2c1N(c1ccc(C(F)(F)F)c(F)c1C(O)C(F)(F)F)CCC2] | + | + |
| 62 | 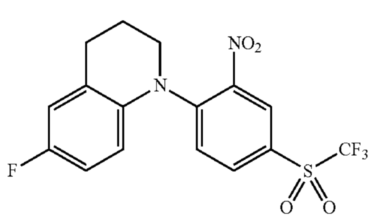 [SMILES: O=[N+]([O-])c1cc(S(=O)(=O)C(F)(F)F)ccc1N1CCCc2cc(F)ccc21] | + | + |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 63 | 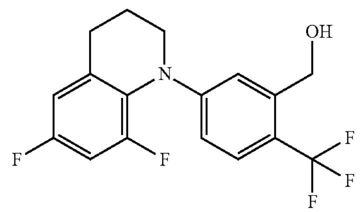 [SMILES: OCc1cc(N2CCCc3cc(F)cc(F)c32)ccc1C(F)(F)F] | + | + |
| 64 | 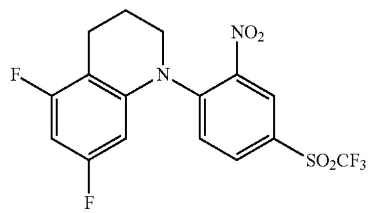 | + | + |
| 65 | 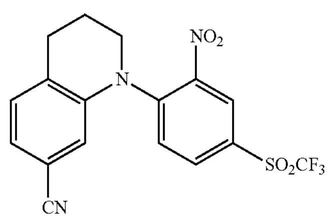 | + | + |
| 66 | 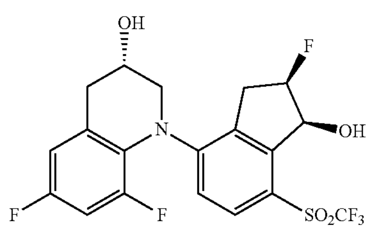 | + | + |
| 67 | 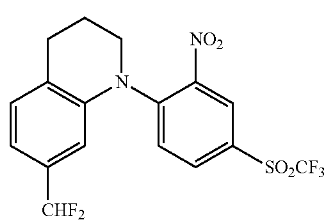 | n.d. | + |
| 68 | 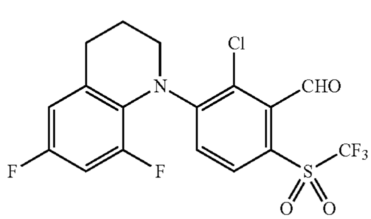 [SMILES: O=Cc1c(S(=O)(=O)C(F)(F)F)ccc(N2CCCc3cc(F)cc(F)c32)c1Cl] | + | + |
| 69 | 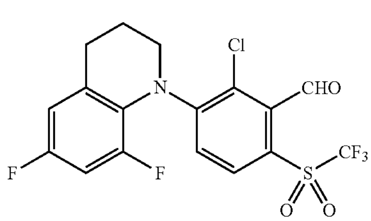 [SMILES: O=Cc1c(S(=O)(=O)C(F)(F)F)ccc(N2CCCc3cc(F)cc(F)c32)c1Cl] | ++ | + |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 70 | 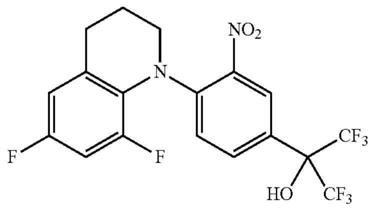 [SMILES: O=[N+]([O-])c1cc(C(O)(C(F)(F)F)C(F)(F)F)ccc1N1CCCc2cc(F)cc(F)c21] | + | + |
| 71 | 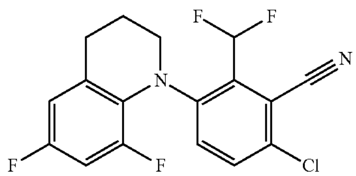 [SMILES: N#Cc1c(Cl)ccc(N2CCCc3cc(F)cc(F)c32)c1C(F)F] | + | + |
| 72 | 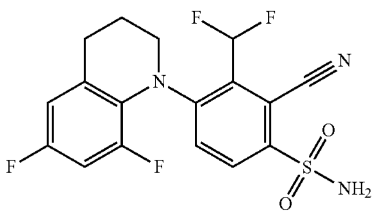 [SMILES: N#Cc1c(S(N)(=O)=O)ccc(N2CCCc3cc(F)cc(F)c32)c1C(F)F] | + | + |
| 73 | 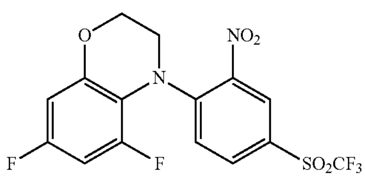 | + | + |
| 74 | 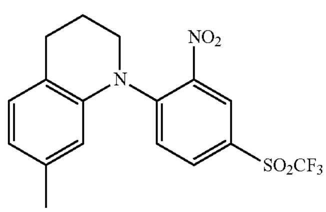 | + | + |
| 75 | 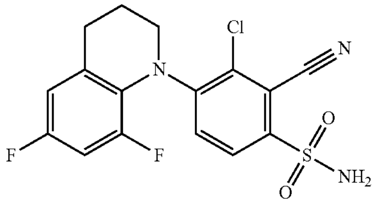 [SMILES: N#Cc1c(S(N)(=O)=O)ccc(N2CCCc3cc(F)cc(F)c32)c1Cl] | + | + |
| 76 | 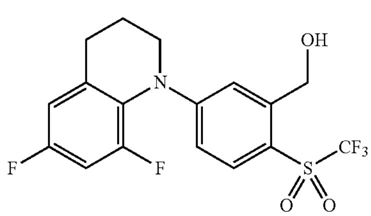 [SMILES: O=S(=O)(c1ccc(N2CCCc3cc(F)cc(F)c32)cc1CO)C(F)(F)F] | + | + |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 77 | 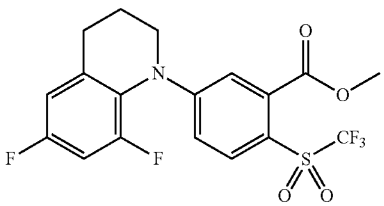 [SMILES: COC(=O)c1cc(N2CCCc3cc(F)cc(F)c32)ccc1S(=O)(=O)C(F)(F)F] | + | + |
| 78 | 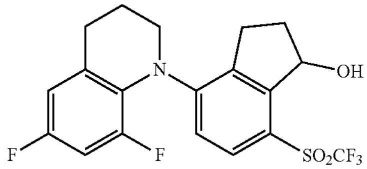 | + | + |
| 79 | 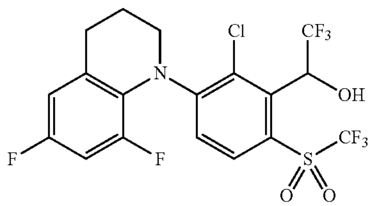 [SMILES: O=S(=O)(c1ccc(N2CCCc3cc(F)cc(F)c32)c(Cl)c1C(O)C(F)(F)F)C(F)(F)F] | + | + |
| 80 | 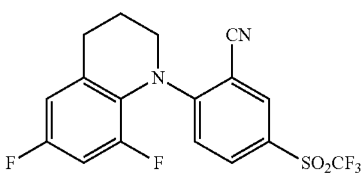 | + | + |
| 81 | 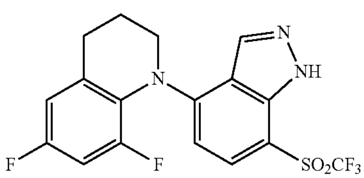 | + | + |
| 82 | 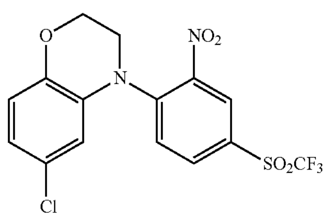 | n.d. | + |
| 83 | 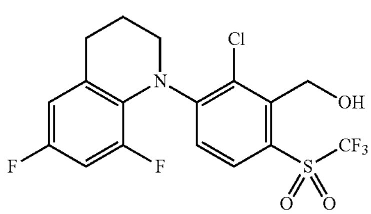 [SMILES: O=S(=O)(c1ccc(N2CCCc3cc(F)cc(F)c32)c(Cl)c1CO)C(F)(F)F] | + | + |

TABLE 1-continued
Potency of select compounds
Less than 100 nM (+++), 100 nM to 1 μM (++), greater than 1 μM (+)
| Example # | Structure | HIF-2α Scintillation Proximity Assay | HIF-2α Luciferase Assay |
|---|---|---|---|
| 84 | 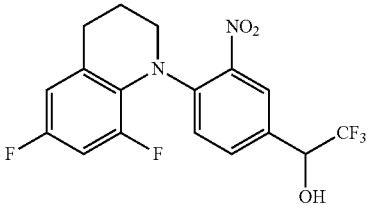 | + | + |
| 85 | 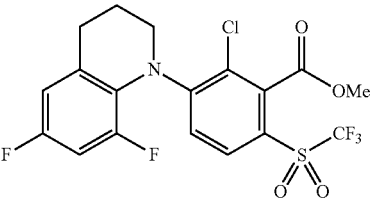 [SMILES: COC(=O)c1c(S(=O)(=O)C(F)(F)F)ccc(N2CCCc3cc(F)cc(F)c32)c1Cl] | + | + |
| 86 | 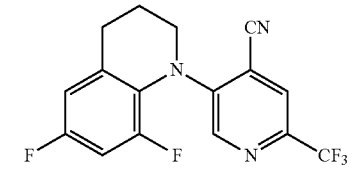 | + | + |
| 87 | 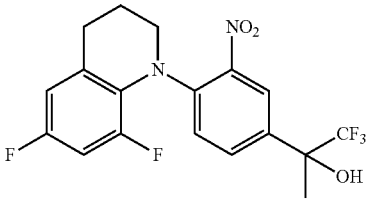 [SMILES: CC(O)(c1ccc(N2CCCc3cc(F)cc(F)c32)c([N+](=O)[O-])c1)C(F)(F)F] | + | + |
| 88 | 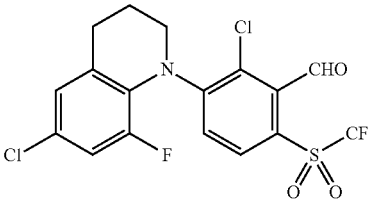 | + | + |
| 89 | 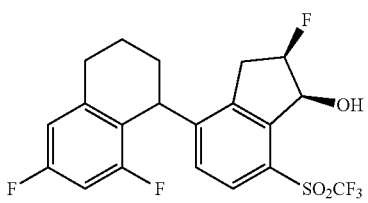 | +++ | +++ |
| 90 | 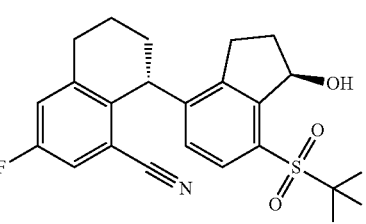 | +++ | +++ |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 91 | 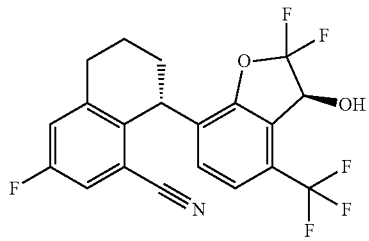 [SMILES: N#Cc1cc(F)cc2c1[C@@H](c1ccc(C(F)(F)F)c3c1OC(F)(F)[C@H]3O)CCC2] | +++ | +++ |
| 92 | 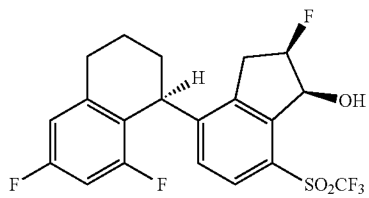 | ++ | ++ |
| 93 | 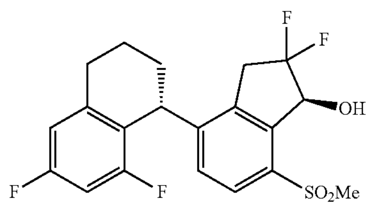 [SMILES: CS(=O)(=O)c1ccc([C@H]2CCCc3cc(F)cc(F)c32)c2c1[C@H](O)C(F)(F)C2] | +++ | ++ |
| 94 | 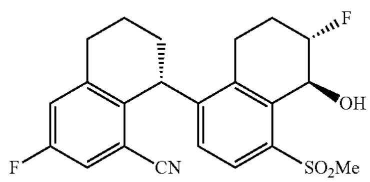 [SMILES: CS(=O)(=O)c1ccc([C@H]2CCCc3cc(F)cc(C#N)c32)c2c1[C@H](O)[C@@H](F)CC2] | ++ | ++ |
| 95 | 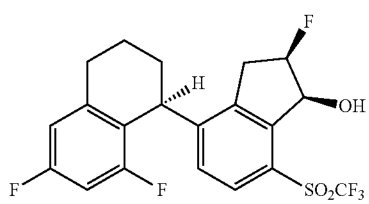 | ++ | ++ |
| 96 | 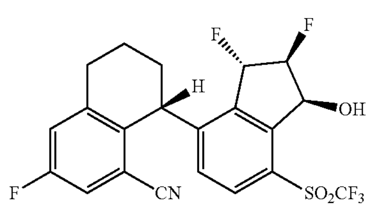 | ++ | ++ |
| 97 | 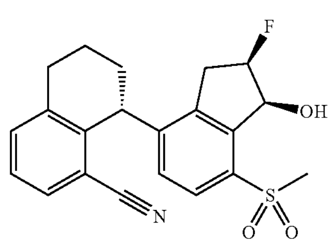 [SMILES: CS(=O)(=O)c1ccc([C@H]2CCCc3cccc(C#N)c32)c2c1[C@H](O)[C@H](F)C2] | ++ | ++ |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 98 | 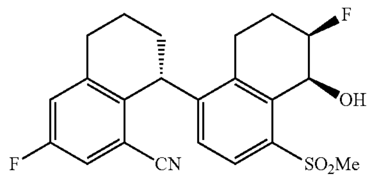 [SMILES: CS(=O)(=O)c1ccc([C@H]2CCCc3cc(F)cc(C#N)c32)c2c1[C@H](O)[C@H](F)CC2] | ++ | ++ |
| 99 | 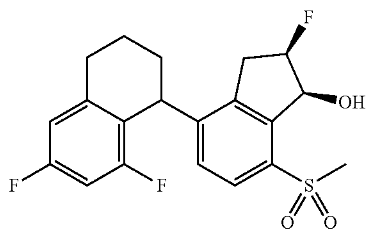 | ++ | ++ |
| 100 | 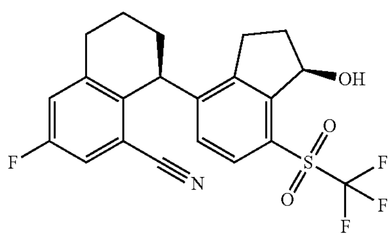 [SMILES: N#Cc1cc(F)cc2c1[C@H](c1ccc(S(=O)(=O)C(F)(F)F)c3c1CC[C@H]3O)CCC2] | ++ | ++ |
| 101 | 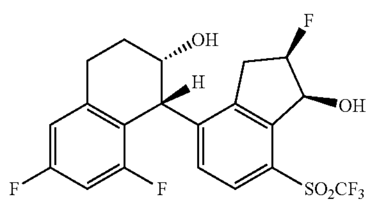 | ++ | + |
| 102 | 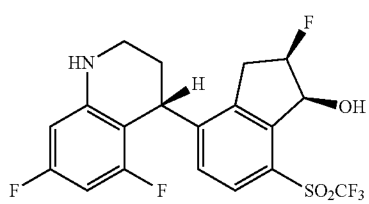 | + | + |
| 103 | 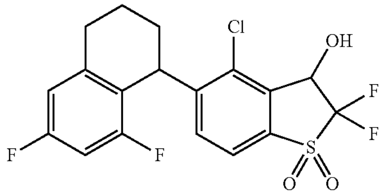 [SMILES: O=S1(=O)c2ccc(C3CCCc4cc(F)cc(F)c43)c(Cl)c2C(O)C1(F)F] | + | + |
| 104 | 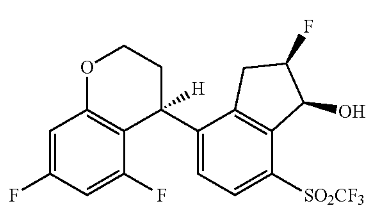 | + | + |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 105 | 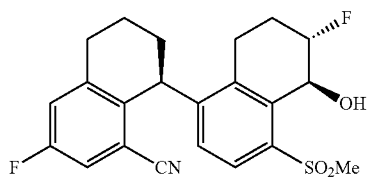 [SMILES: CS(=O)(=O)c1ccc([C@@H]2CCCc3cc(F)cc(C#N)c32)c2c1[C@H](O)[C@@H](F)CC2] | + | + |
| 106 | 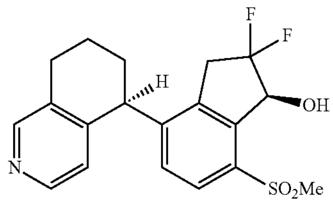 [SMILES: CS(=O)(=O)c1ccc([C@@H]2CCCc3cnccc32)c2c1[C@H](O)C(F)(F)C2] | + | + |
| 107 | 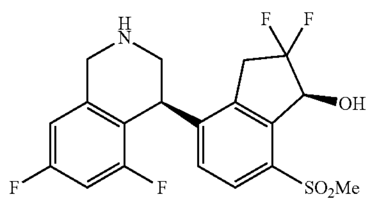 [SMILES: CS(=O)(=O)c1ccc([C@@H]2CNCc3cc(F)cc(F)c32)c2c1[C@H](O)C(F)(F)C2] | + | + |
| 108 | 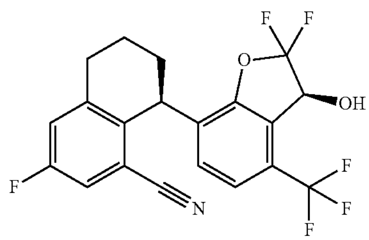 [SMILES: N#Cc1cc(F)cc2c1[C@H](c1ccc(C(F)(F)F)c3c1OC(F)(F)[C@H]3O)CCC2] | + | + |
| 109 | 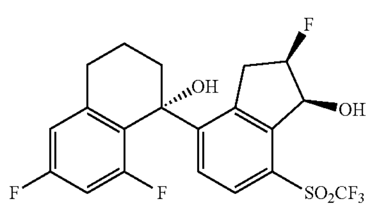 | + | + |
| 110 | 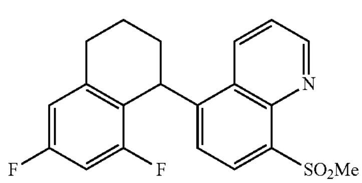 [SMILES: CS(=O)(=O)c1ccc(C2CCCc3cc(F)cc(F)c32)c2cccnc12] | + | + |
| 111 | 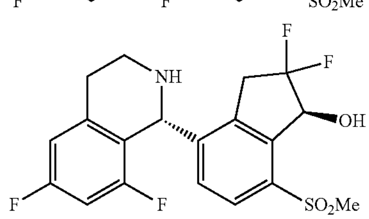 | + | + |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 112 | 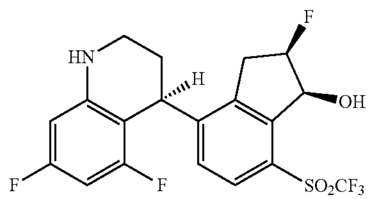 | + | + |
| 113 | 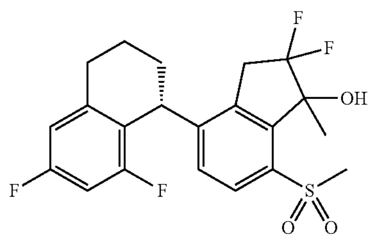 [SMILES: CC1(O)c2c(S(C)(=O)=O)ccc([C@H]3CCCc4cc(F)cc(F)c43)c2CC1(F)F] | + | + |
| 114 | 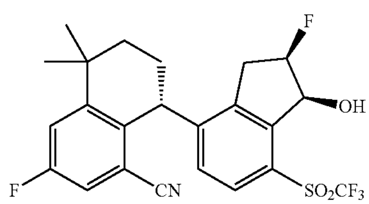 | +++ | +++ |
| 115 | 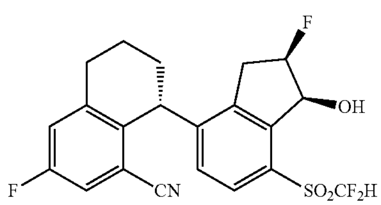 | +++ | +++ |
| 116 | 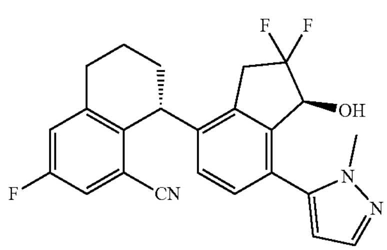 [SMILES: Cn1nccc1-c1ccc([C@H]2CCCc3cc(F)cc(C#N)c32)c2c1[C@H](O)C(F)(F)C2] | +++ | +++ |
| 117 | 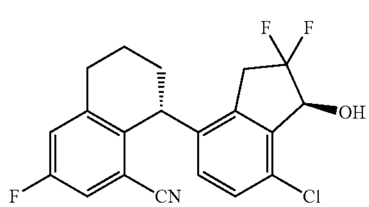 [SMILES: N#Cc1cc(F)cc2c1[C@@H](c1ccc(Cl)c3c1CC(F)(F)[C@H]3O)CCC2] | ++ | ++ |

TABLE 1-continued

Potency of select compounds
Less than 100 nM (+++), 100 nM to 1 μM (++), greater than 1 μM (+)

| Example # | Structure | HIF-2α Scintillation Proximity Assay | HIF-2α Luciferase Assay |
|---|---|---|---|
| 118 | 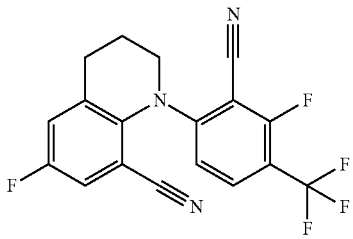 | ++ | ++ |
| 119 | 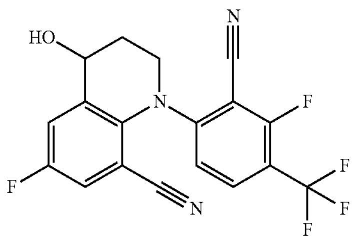 [SMILES: N#Cc1cc(F)cc2c1N(c1ccc(C(F)(F)F)c(F)c1C#N)CCC2O] | + | ++ |
| 120 | 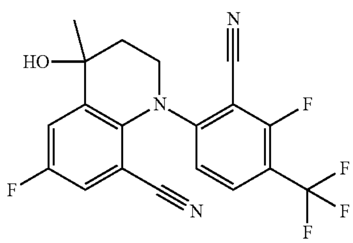 [SMILES: CC1(O)CCN(c2ccc(C(F)(F)F)c(F)c2C#N)c2c(C#N)cc(F)cc21] | ++ | ++ |

TABLE 2

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 121 | 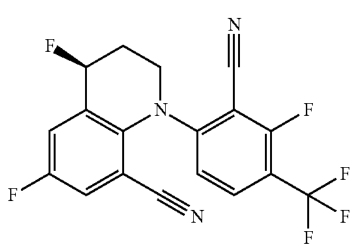 [SMILES: N#Cc1cc(F)cc2c1N(c1ccc(C(F)(F)F)c(F)c1C#N)CC[C@@H]2F] | +++ | +++ |
| 122 | 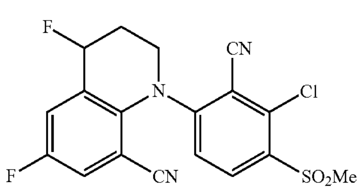 [SMILES: CS(=O)(=O)c1ccc(N2CCC(F)c3cc(F)cc(C#N)c32)c(C#N)c1Cl] | +++ | +++ |

TABLE 2-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 123 | 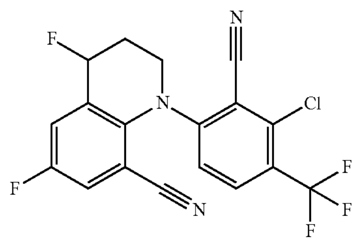 [SMILES: N#Cc1cc(F)cc2c1N(c1ccc(C(F)(F)F)c(Cl)c1C#N)CCC2F] | +++ | +++ |
| 124 | 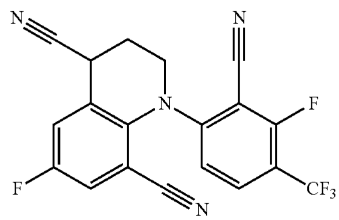 [SMILES: N#Cc1cc(F)cc2c1N(c1ccc(C(F)(F)F)c(F)c1C#N)CCC2C#N] | +++ | +++ |
| 125 | 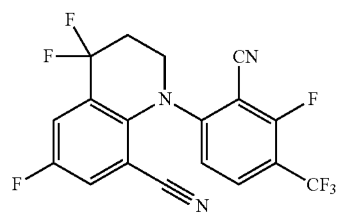 [SMILES: N#Cc1cc(F)cc2c1N(c1ccc(C(F)(F)F)c(F)c1C#N)CCC2(F)F] | +++ | +++ |
| 126 | 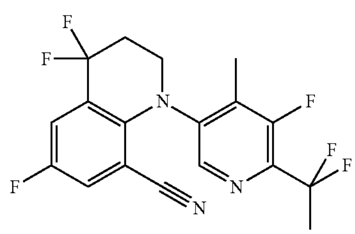 [SMILES: Cc1c(N2CCC(F)(F)c3cc(F)cc(C#N)c32)cnc(C(C)(F)F)c1F] | +++ | +++ |
| 127 | 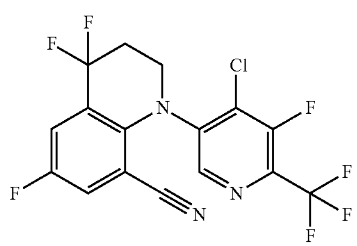 [SMILES: N#Cc1cc(F)cc2c1N(c1cnc(C(F)(F)F)c(F)c1Cl)CCC2(F)F] | +++ | +++ |
| 128 | 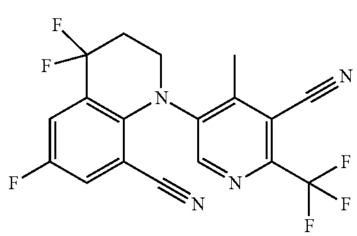 [SMILES: Cc1c(N2CCC(F)(F)c3cc(F)cc(C#N)c32)cnc(C(F)(F)F)c1C#N] | +++ | +++ |

TABLE 2-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 129 | 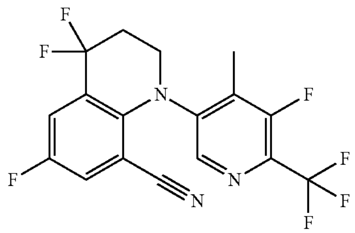 [SMILES: Cc1c(N2CCC(F)(F)c3cc(F)cc(C#N)c32)cnc(C(F)(F)F)c1F] | +++ | +++ |
| 130 | 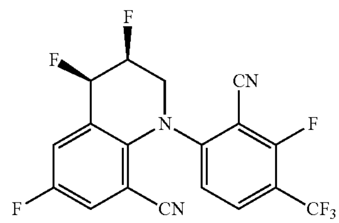 [SMILES: N#Cc1cc(F)cc2c1N(c1ccc(C(F)(F)F)c(F)c1C#N)C[C@H](F)[C@@H]2F] | +++ | +++ |
| 131 | 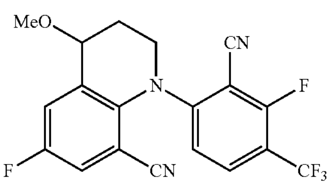 [SMILES: COC1CCN(c2ccc(C(F)(F)F)c(F)c2C#N)c2c(C#N)cc(F)cc21] | +++ | +++ |
| 132 | 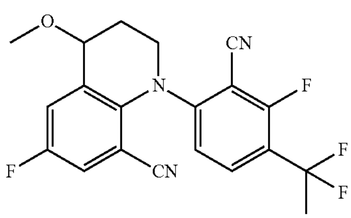 [SMILES: COC1CCN(c2ccc(C(C)(F)F)c(F)c2C#N)c2c(C#N)cc(F)cc21] | +++ | +++ |
| 133 | 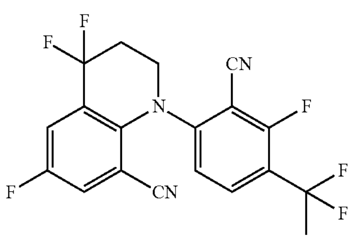 [SMILES: CC(F)(F)c1ccc(N2CCC(F)(F)c3cc(F)cc(C#N)c32)c(C#N)c1F] | +++ | +++ |
| 134 | 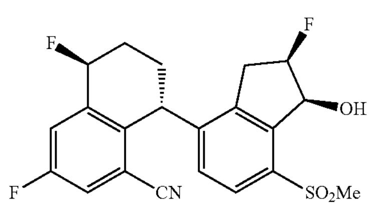 [SMILES: CS(=O)(=O)c1ccc([C@H]2CC[C@H](F)c3cc(F)cc(C#N)c32)c2c1[C@H](O)[C@H](F)C2] | +++ | +++ |
| 135 | 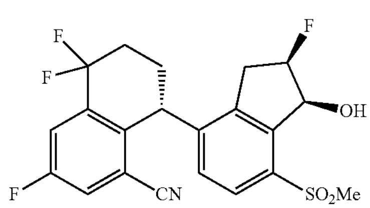 [SMILES: CS(=O)(=O)c1ccc([C@H]2CCC(F)(F)c3cc(F)cc(C#N)c32)c2c1[C@H](O)[C@H](F)C2] | +++ | +++ |

TABLE 2-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 136 | 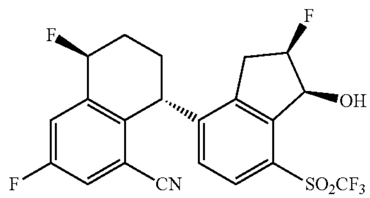 | +++ | +++ |
| 137 | 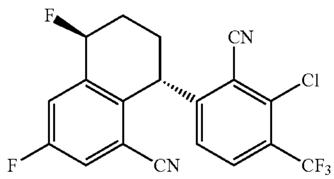 [SMILES: N#Cc1cc(F)cc2c1[C@@H](c1ccc(C(F)(F)F)c(Cl)c1C#N)CC[C@@H]2F] | +++ | +++ |
| 138 | 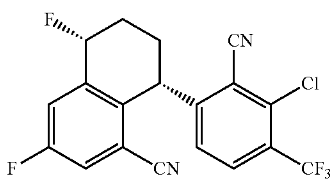 [SMILES: N#Cc1cc(F)cc2c1[C@@H](c1ccc(C(F)(F)F)c(Cl)c1C#N)CC[C@H]2F] | ++ | + |
| 139 | 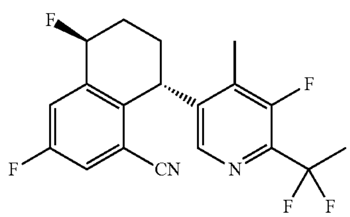 [SMILES: Cc1c([C@H]2CC[C@H](F)c3cc(F)cc(C#N)c32)cnc(C(C)(F)F)c1F] | +++ | +++ |
| 140 | 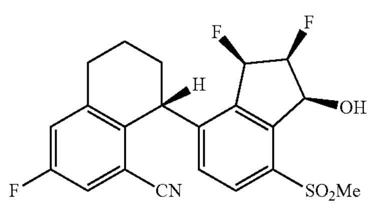 [SMILES: CS(=O)(=O)c1ccc([C@H]2CCCc3cc(F)cc(C#N)c32)c2c1[C@H](O)[C@H](F)[C@@H]2F] | +++ | +++ |
| 141 | 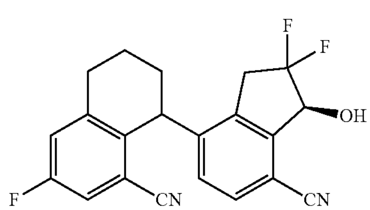 [SMILES: N#Cc1cc(F)cc2c1C(c1ccc(C#N)c3c1CC(F)(F)[C@H]3O)CCC2] | +++ | +++ |
| 142 | 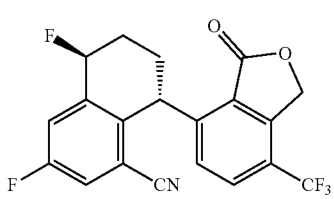 [SMILES: N#Cc1cc(F)cc2c1[C@@H](c1ccc(C(F)(F)F)c3c1C(=O)OC3)CC[C@@H]2F] | +++ | +++ |

TABLE 2-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 143 | 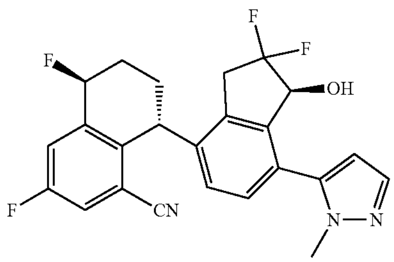 [SMILES: Cn1nccc1-c1ccc([C@H]2CC[C@H](F)c3cc(F)cc(C#N)c32)c2c1[C@H](O)C(F)(F)C2] | +++ | +++ |

TABLE 3

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 144 | 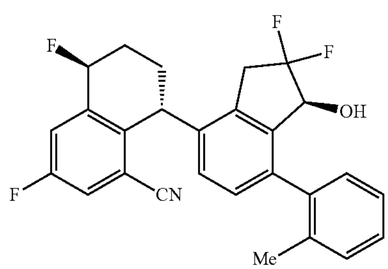 [SMILES: Cc1ccccc1-c1ccc([C@H]2CC[C@H](F)c3cc(F)cc(C#N)c32)c2c1[C@H](O)C(F)(F)C2] | +++ | − |
| 145 | 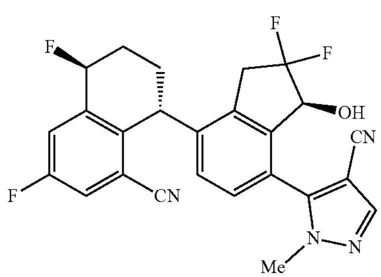 [SMILES: Cn1ncc(C#N)c1-c1ccc([C@H]2CC[C@H](F)c3cc(F)cc(C#N)c32)c2c1[C@H](O)C(F)(F)C2] | +++ | +++ |
| 146 | 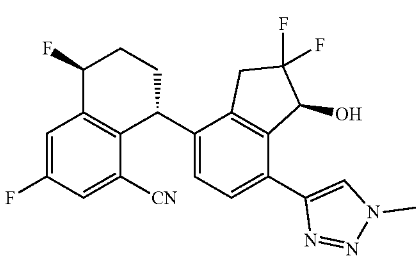 [SMILES: Cn1cc(-c2ccc([C@H]3CC[C@H](F)c4cc(F)cc(C#N)c43)c3c2[C@H](O)C(F)(F)C3)nn1] | +++ | − |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 147 | 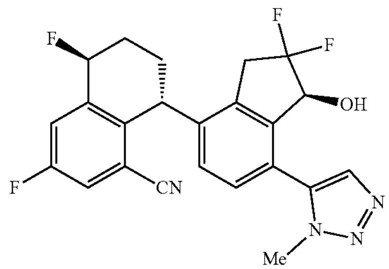 [SMILES: Cn1nncc1-c1ccc([C@H]2CC[C@H](F)c3cc(F)cc(C#N)c32)c2c1[C@H](O)C(F)(F)C2] | +++ | +++ |
| 148 | 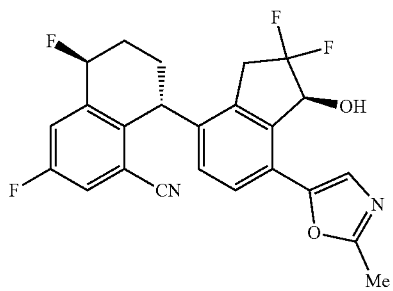 [SMILES: Cc1ncc(-c2ccc([C@H]3CC[C@H](F)c4cc(F)cc(C#N)c43)c3c2[C@H](O)C(F)(F)C3)o1] | ++ | − |
| 149 | 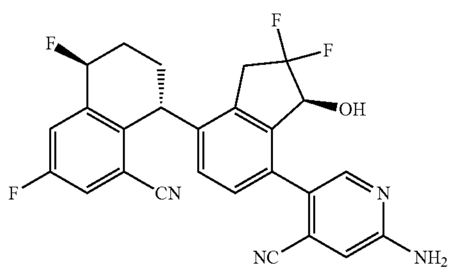 [SMILES: N#Cc1cc(N)ncc1-c1ccc([C@H]2CC[C@H](F)c3cc(F)cc(C#N)c32)c2c1[C@H](O)C(F)(F)C2] | +++ | − |
| 150 | 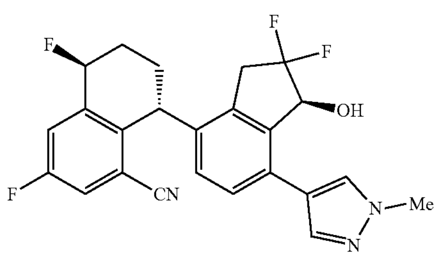 [SMILES: Cn1cc(-c2ccc([C@H]3CC[C@H](F)c4cc(F)cc(C#N)c43)c3c2[C@H](O)C(F)(F)C3)cn1] | ++ | − |
| 151 | 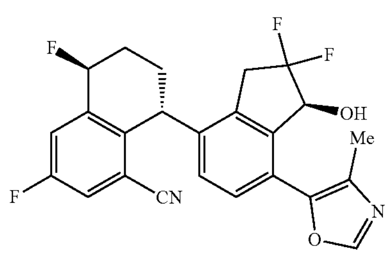 [SMILES: Cc1ncoc1-c1ccc([C@H]2CC[C@H](F)c3cc(F)cc(C#N)c32)c2c1[C@H](O)C(F)(F)C2] | +++ | − |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 152 | 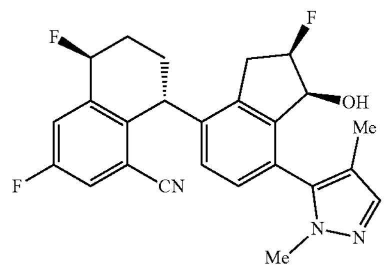 [SMILES: Cc1cnn(C)c1-c1ccc([C@H]2CC[C@H](F)c3cc(F)cc(C#N)c32)c2c1[C@H](O)[C@H](F)C2] | +++ | +++ |
| 153 | 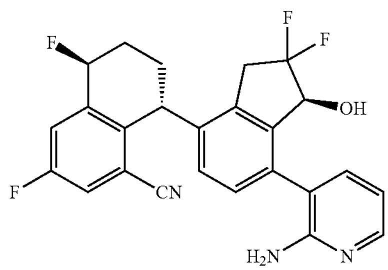 [SMILES: N#Cc1cc(F)cc2c1[C@@H](c1ccc(-c3cccnc3N)c3c1CC(F)(F)[C@H]3O)CC[C@@H]2F] | +++ | +++ |
| 154 | 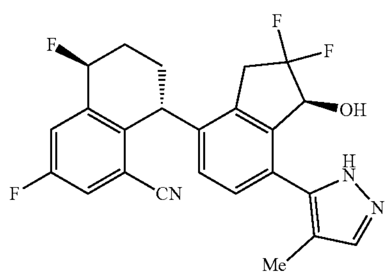 [SMILES: Cc1cn[nH]c1-c1ccc([C@H]2CC[C@H](F)c3cc(F)cc(C#N)c32)c2c1[C@H](O)C(F)(F)C2] | +++ | +++ |
| 155 | 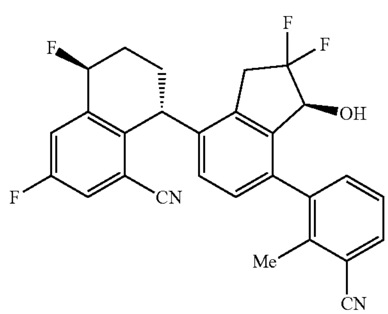 [SMILES: Cc1c(C#N)cccc1-c1ccc([C@H]2CC[C@H](F)c3cc(F)cc(C#N)c32)c2c1[C@H](O)C(F)(F)C2] | +++ | − |
| 156 | 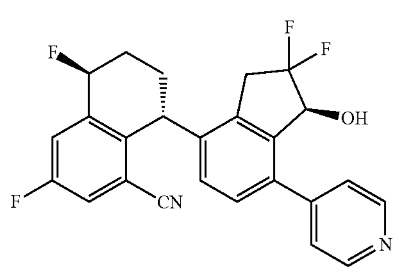 [SMILES: N#Cc1cc(F)cc2c1[C@@H](c1ccc(-c3ccncc3)c3c1CC(F)(F)[C@H]3O)CC[C@@H]2F] | ++ | − |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 157 | 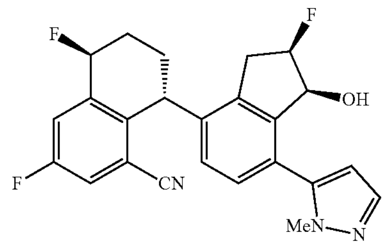 [SMILES: Cn1nccc1-c1ccc([C@H]2CC[C@H](F)c3cc(F)cc(C#N)c32)c2c1[C@H](O)[C@H](F)C2] | +++ | +++- |
| 158 | 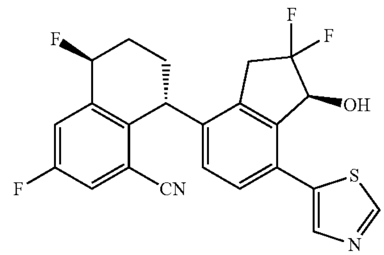 [SMILES: N#Cc1cc(F)cc2c1[C@@H](c1ccc(-c3cncs3)c3c1CC(F)(F)[C@H]3O)CC[C@@H]2F] | +++ | – |
| 159 | 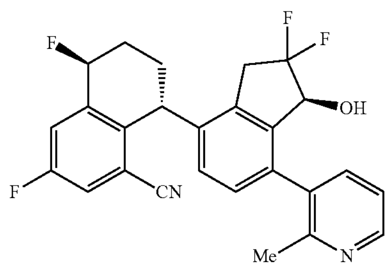 | +++ | +++ |
| 160 | 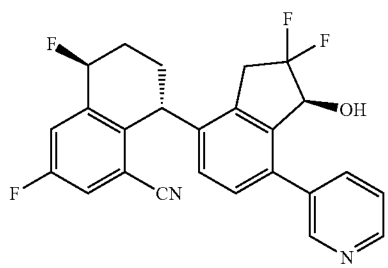 [SMILES: N#Cc1cc(F)cc2c1[C@@H](c1ccc(-c3cccnc3)c3c1CC(F)(F)[C@H]3O)CC[C@@H]2F] | +++ | – |
| 161 | 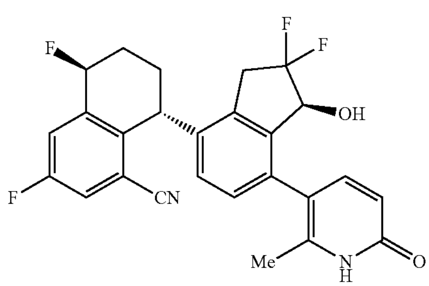 [SMILES: Cc1[nH]c(=O)ccc1-c1ccc([C@H]2CC[C@H](F)c3cc(F)cc(C#N)c32)c2c1[C@H](O)C(F)(F)C2] | ++ | – |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 162 | 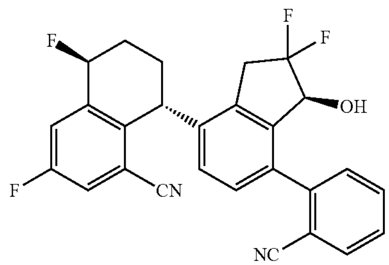 [SMILES: N#Cc1ccccc1-c1ccc([C@H]2CC[C@H](F)c3cc(F)cc(C#N)c32)c2c1[C@H](O)C(F)(F)C2] | +++ | +++ |
| 163 | 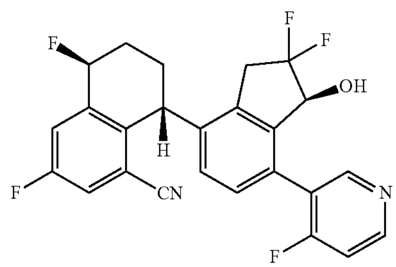 [SMILES: N#Cc1cc(F)cc2c1[C@@H](c1ccc(-c3cnccc3F)c3c1CC(F)(F)[C@H]3O)CC[C@@H]2F] | +++ | − |
| 164 | 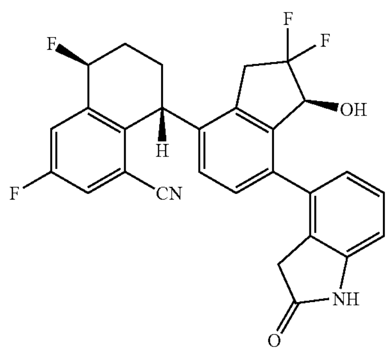 [SMILES: N#Cc1cc(F)cc2c1[C@@H](c1ccc(-c3cccc4c3CC(=O)N4)c3c1CC(F)(F)[C@H]3O)CC[C@@H]2F] | ++ | − |
| 165 | 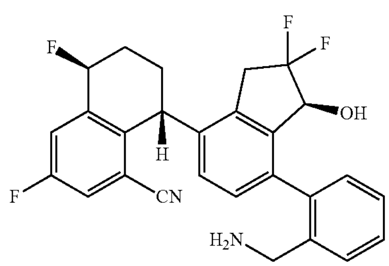 [SMILES: N#Cc1cc(F)cc2c1[C@@H](c1ccc(-c3ccccc3CN)c3c1CC(F)(F)[C@H]3O)CC[C@@H]2F] | ++ | − |
| 166 | 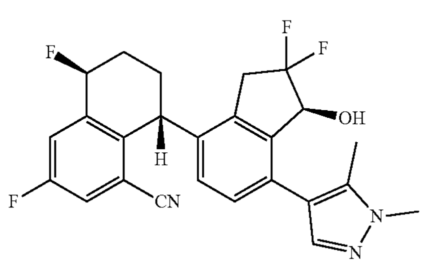 [SMILES: Cc1c(-c2ccc([C@H]3CC[C@H](F)c4cc(F)cc(C#N)c43)c3c2[C@H](O)C(F)(F)C3)cnn1C] | +++ | +++ |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
| --- | --- | --- | --- |
| 167 | 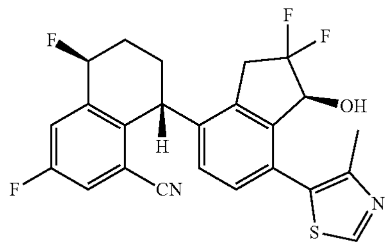 [SMILES: Cc1ncsc1-c1ccc([C@H]2CC[C@H](F)c3cc(F)cc(C#N)c32)c2c1[C@H](O)C(F)(F)C2] | +++ | +++ |
| 168 | 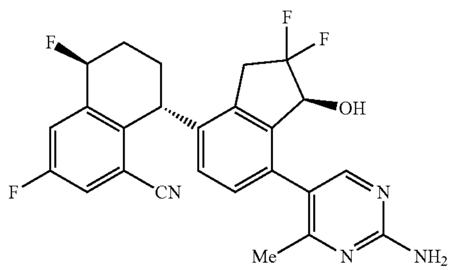 [SMILES: Cc1nc(N)ncc1-c1ccc([C@H]2CC[C@H](F)c3cc(F)cc(C#N)c32)c2c1[C@H](O)C(F)(F)C2] | +++ | – |
| 169 | 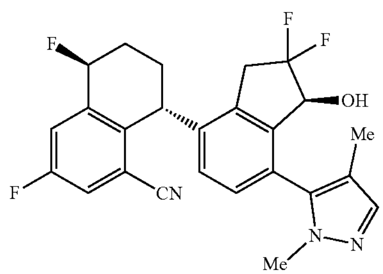 [SMILES: Cc1cnn(C)c1-c1ccc([C@H]2CC[C@H](F)c3cc(F)cc(C#N)c32)c2c1[C@H](O)C(F)(F)C2] | +++ | – |
| 170 | 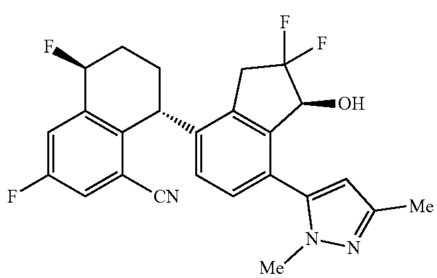 [SMILES: Cc1cc(-c2ccc([C@H]3CC[C@H](F)c4cc(F)cc(C#N)c43)c3c2[C@H](O)C(F)(F)C3)n(C)n1] | +++ | – |
| 171 | 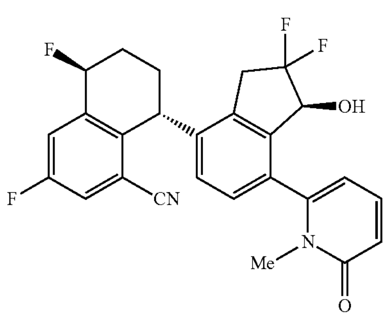 [SMILES: Cn1c(-c2ccc([C@H]3CC[C@H](F)c4cc(F)cc(C#N)c43)c3c2[C@H](O)C(F)(F)C3)cccc1=O] | +++ | – |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 172 | 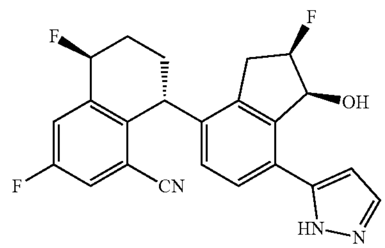 [SMILES: N#Cc1cc(F)cc2c1[C@@H](c1ccc(-c3ccn[nH]3)c3c1C[C@@H](F)[C@H]3O)CC[C@@H]2F] | + | – |
| 173 | 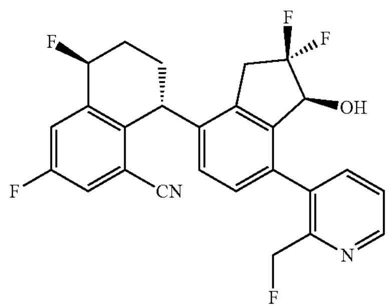 | +++ | +++ |
| 174 | 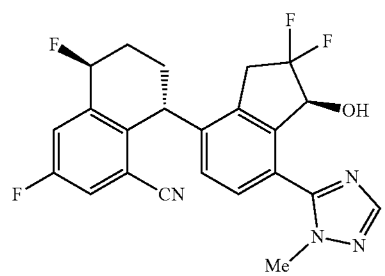 [SMILES: Cn1ncnc1-c1ccc([C@H]2CC[C@H](F)c3cc(F)cc(C#N)c32)c2c1[C@H](O)C(F)(F)C2] | +++ | +++ |
| 175 | 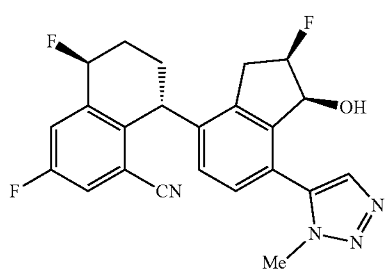 [SMILES: Cn1nncc1-c1ccc([C@H]2CC[C@H](F)c3cc(F)cc(C#N)c32)c2c1[C@H](O)[C@H](F)C2] | +++ | – |
| 176 | 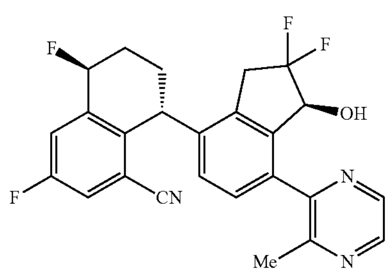 | +++ | – |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 177 | 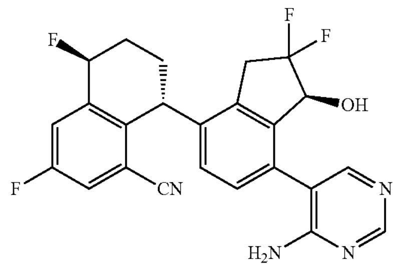 [SMILES: N#Cc1cc(F)cc2c1[C@@H](c1ccc(-c3cncnc3N)c3c1CC(F)(F)[C@H]3O)CC[C@@H]2F] | +++ | – |
| 178 | 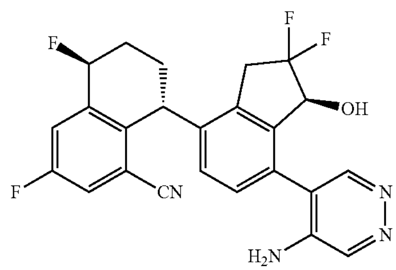 | ++ | – |
| 179 | 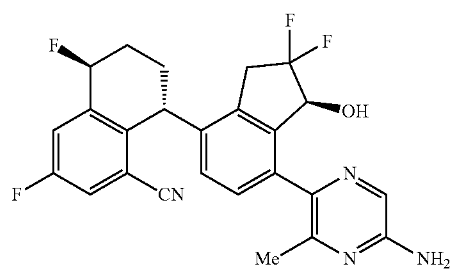 [SMILES: Cc1nc(N)cnc1-c1ccc([C@H]2CC[C@H](F)c3cc(F)cc(C#N)c32)c2c1[C@H](O)C(F)(F)C2] | +++ | – |
| 180 | 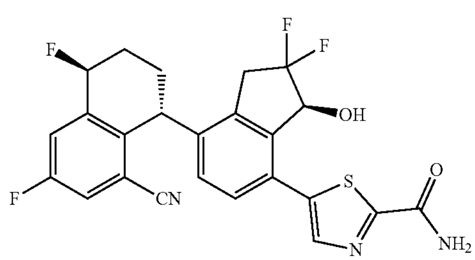 [SMILES: N#Cc1cc(F)cc2c1[C@@H](c1ccc(-c3cnc(C(N)=O)s3)c3c1CC(F)(F)[C@H]3O)CC[C@@H]2F] | +++ | – |
| 181 | 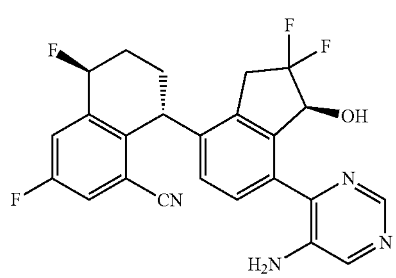 [SMILES: N#Cc1cc(F)cc2c1[C@@H](c1ccc(-c3ncncc3N)c3c1CC(F)(F)[C@H]3O)CC[C@@H]2F] | ++ | – |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 182 | 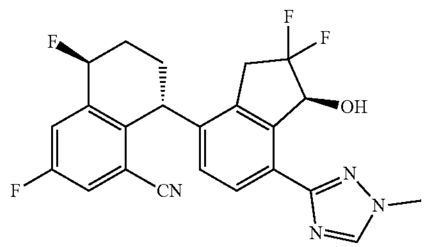 [SMILES: Cn1cnc(-c2ccc([C@H]3CC[C@H](F)c4cc(F)cc(C#N)c43)c3c2[C@H](O)C(F)(F)C3)n1] | ++ | − |
| 183 | 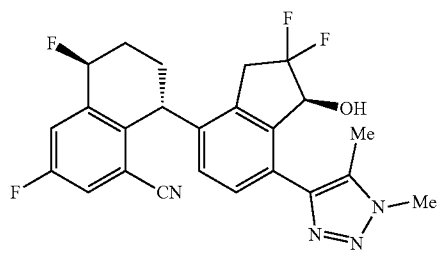 [SMILES: Cc1c(-c2ccc([C@H]3CC[C@H](F)c4cc(F)cc(C#N)c43)c3c2[C@H](O)C(F)(F)C3)nnn1C] | ++ | − |
| 184 | 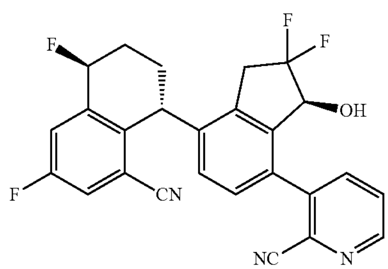 | +++ | − |
| 185 | 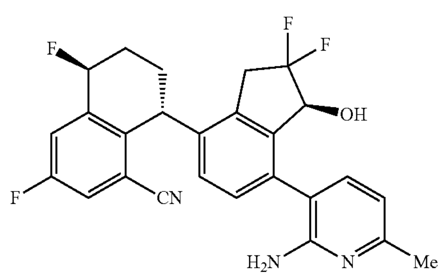 [SMILES: Cc1ccc(-c2ccc([C@H]3CC[C@H](F)c4cc(F)cc(C#N)c43)c3c2[C@H](O)C(F)(F)C3)c(N)n1] | +++ | − |
| 186 | 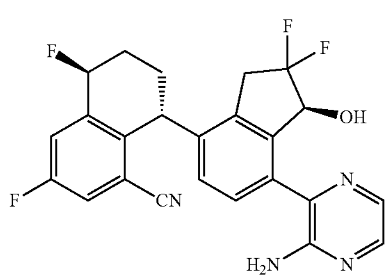 | +++ | − |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 187 | 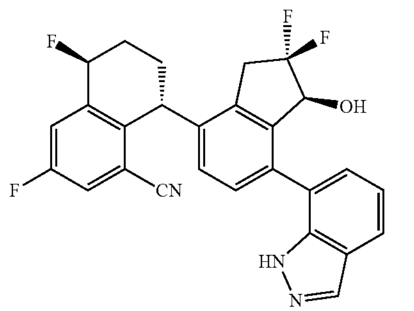 | +++ | − |
| 188 | 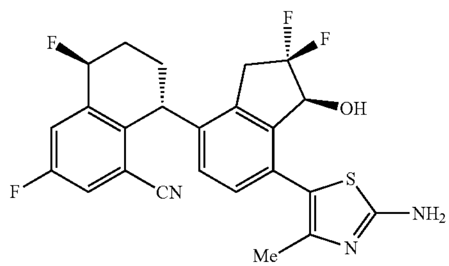 | ++ | − |
| 189 | 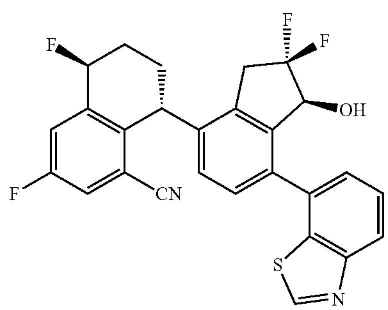 | +++ | − |
| 190 | 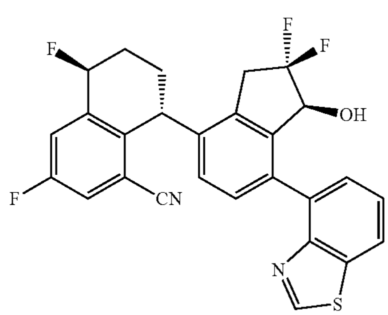 | ++ | − |
| 191 | 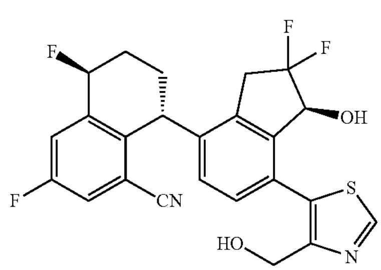 [SMILES: N#Cc1cc(F)cc2c1[C@@H](c1ccc(-c3scnc3CO)c3c1CC(F)(F)[C@H]3O)CC[C@@H]2F] | +++ | − |

TABLE 3-continued
Potency of select compounds
Less than 100 nM (+++), 100 nM to 1 μM (++), greater than 1 μM (+)
| Example # | Structure | HIF-2α Luciferase Assay | HIF-2α Scintillation Proximity Assay |
|---|---|---|---|
| 192 | 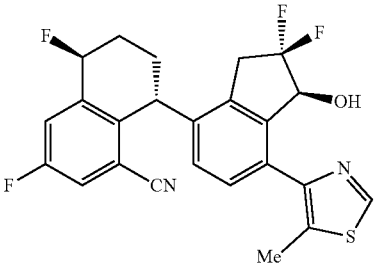 | +++ | – |
| 193 | 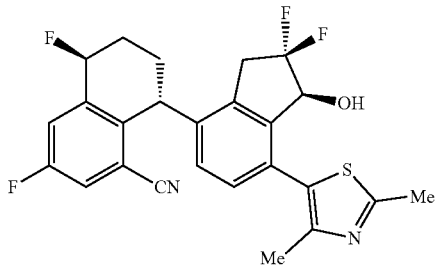 | +++ | – |
| 194 | 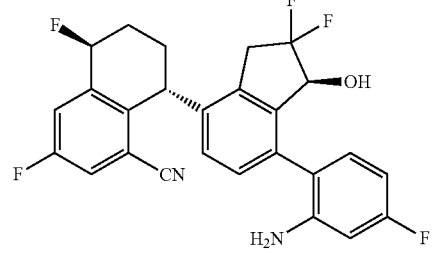 | +++ | – |
| 195 | 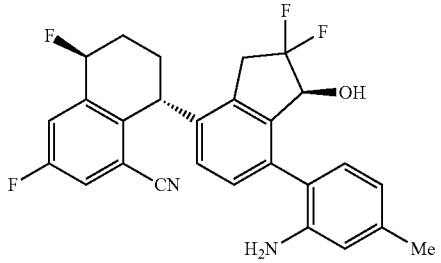 [SMILES: Cc1ccc(-c2ccc([C@H]3CC[C@H](F)c4cc(F)cc(C#N)c43)c3c2[C@H](O)C(F)(F)C3)c(N)c1] | +++ | – |
| 196 | 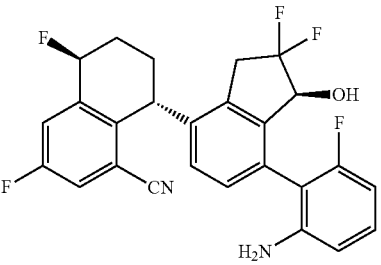 [SMILES: N#Cc1cc(F)cc2c1[C@@H](c1ccc(-c3c(N)cccc3F)c3c1CC(F)(F)[C@H]3O)CC[C@@H]2F] | +++ | – |

TABLE 3-continued

Potency of select compounds
Less than 100 nM (+++), 100 nM to 1 µM (++), greater than 1 µM (+)

| Example # | Structure | HIF-2α Luciferase Assay | HIF-2α Scintillation Proximity Assay |
|---|---|---|---|
| 197 | 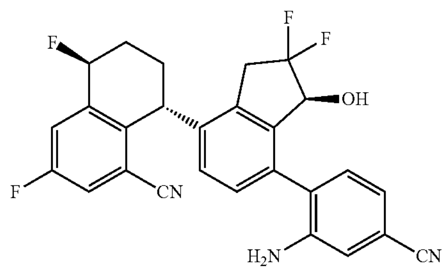 [SMILES: N#Cc1ccc(-c2ccc([C@H]3CC[C@H](F)c4cc(F)cc(C#N)c43)c3c2[C@H](O)C(F)(F)C3)c(N)c1] | +++ | − |
| 198 | 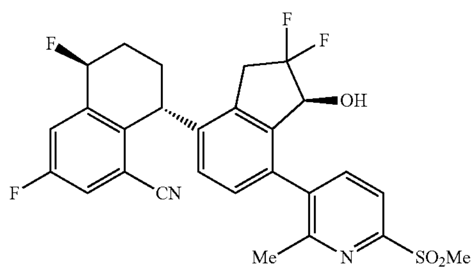 [SMILES: Cc1nc(S(C)(=O)=O)ccc1-c1ccc([C@H]2CC[C@H](F)c3cc(F)cc(C#N)c32)c2c1[C@H](O)C(F)(F)C2] | ++ | − |
| 199 | 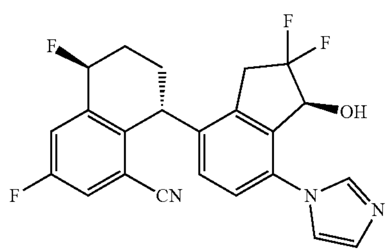 [SMILES: N#Cc1cc(F)cc2c1[C@@H](c1ccc(-n3ccnc3)c3c1CC(F)(F)[C@H]3O)CC[C@@H]2F] | +++ | − |
| 200 | 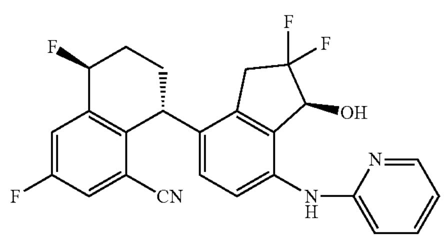 [SMILES: N#Cc1cc(F)cc2c1[C@@H](c1ccc(Nc3ccccn3)c3c1CC(F)(F)[C@H]3O)CC[C@@H]2F] | ++ | − |
| 201 | 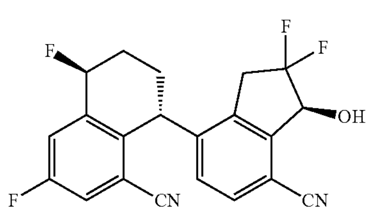 [SMILES: N#Cc1cc(F)cc2c1[C@@H](c1ccc(C#N)c3c1CC(F)(F)[C@H]3O)CC[C@@H]2F] | +++ | − |
| 202 | 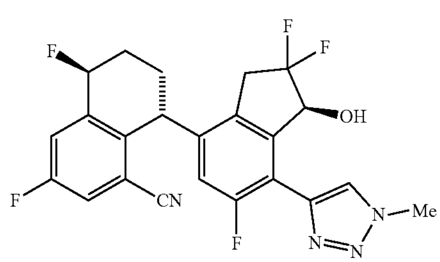 [SMILES: Cn1cc(-c2c(F)cc([C@H]3CC[C@H](F)c4cc(F)cc(C#N)c43)c3c2[C@H](O)C(F)(F)C3)nn1] | +++ | − |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 203 | 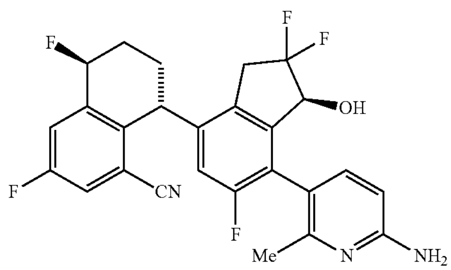 [SMILES: Cc1nc(N)ccc1-c1c(F)cc([C@H]2CC[C@H](F)c3cc(F)cc(C#N)c32)c2c1[C@H](O)C(F)(F)C2] | +++ | − |
| 204 | 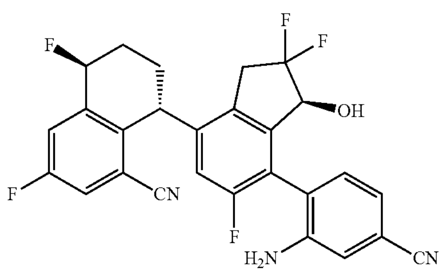 [SMILES: N#Cc1ccc(-c2c(F)cc([C@H]3CC[C@H](F)c4cc(F)cc(C#N)c43)c3c2[C@H](O)C(F)(F)C3)c(N)c1] | +++ | − |
| 205 | 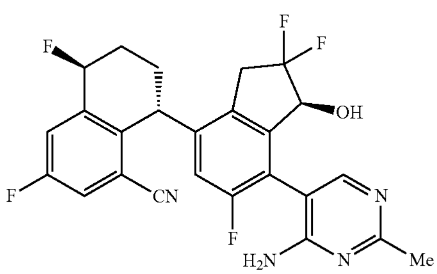 | +++ | − |
| 206 | 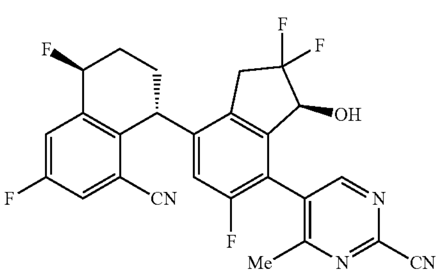 [SMILES: Cc1nc(C#N)ncc1-c1c(F)cc([C@H]2CC[C@H](F)c3cc(F)cc(C#N)c32)c2c1[C@H](O)C(F)(F)C2] | +++ | − |
| 207 | 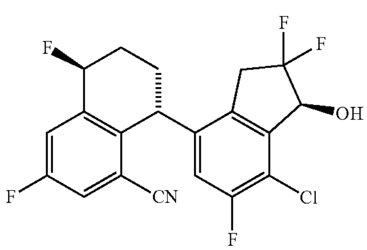 [SMILES: N#Cc1cc(F)cc2c1[C@@H](c1cc(F)c(Cl)c3c1CC(F)(F)[C@H]3O)CC[C@@H]2F] | +++ | − |

TABLE 3-continued
Potency of select compounds
Less than 100 nM (+++), 100 nM to 1 μM (++), greater than 1 μM (+)
| Example # | Structure | HIF-2α Luciferase Assay | HIF-2α Scintillation Proximity Assay |
|---|---|---|---|
| 208 | 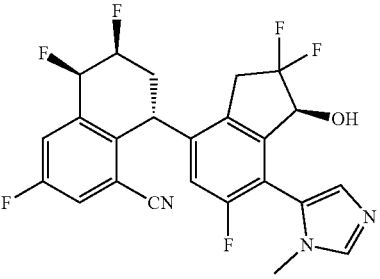 [SMILES: Cn1cncc1-c1c(F)cc([C@H]2C[C@H](F)[C@H](F)c3cc(F)cc(C#N)c32)c2c1[C@H](O)C(F)(F)C2] | +++ | − |
| 209 | 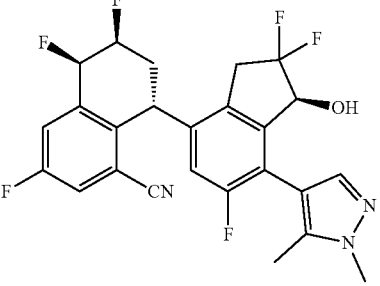 | +++ | − |
| 210 | 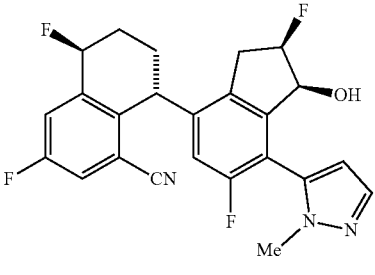 [SMILES: Cn1nccc1-c1c(F)cc([C@H]2CC[C@H](F)c3cc(F)cc(C#N)c32)c2c1[C@H](O)[C@H](F)C2] | +++ | − |
| 211 | 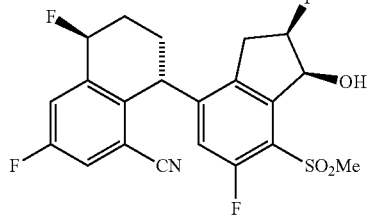 | +++ | − |
| 212 | 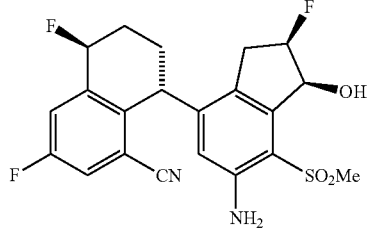 [SMILES: CS(=O)(=O)c1c(N)cc([C@H]2CC[C@H](F)c3cc(F)cc(C#N)c32)c2c1[C@H](O)[C@H](F)C2] | +++ | − |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 213 | 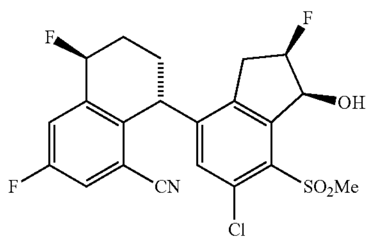 [SMILES: CS(=O)(=O)c1c(Cl)cc([C@H]2CC[C@H](F)c3cc(F)cc(C#N)c32)c2c1[C@H](O)[C@H](F)C2] | +++ | +++ |
| 214 | 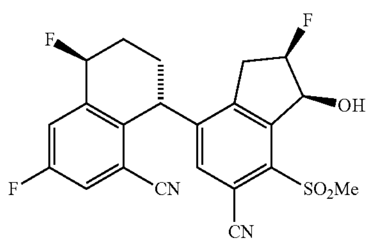 [SMILES: CS(=O)(=O)c1c(C#N)cc([C@H]2CC[C@H](F)c3cc(F)cc(C#N)c32)c2c1[C@H](O)[C@H](F)C2] | ++ | − |
| 215 | 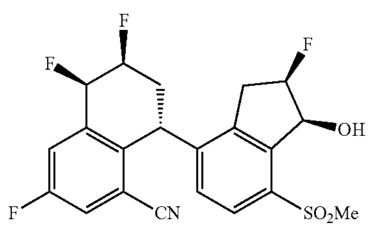 [SMILES: CS(=O)(=O)c1ccc([C@H]2C[C@H](F)[C@H](F)c3cc(F)cc(C#N)c32)c2c1[C@H](O)[C@H](F)C2] | +++ | +++ |
| 216 | 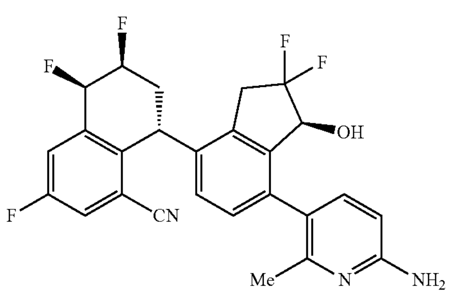 [SMILES: Cc1nc(N)ccc1-c1ccc([C@H]2C[C@H](F)[C@H](F)c3cc(F)cc(C#N)c32)c2c1[C@H](O)C(F)(F)C2] | +++ | − |
| 217 | 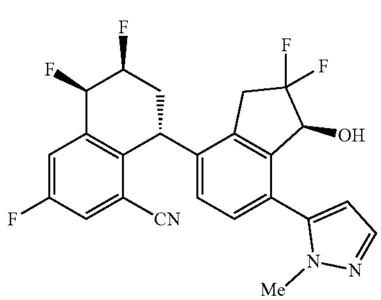 [SMILES: Cn1nccc1-c1ccc([C@H]2C[C@H](F)[C@H](F)c3cc(F)cc(C#N)c32)c2c1[C@H](O)C(F)(F)C2] | +++ | − |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 218 | 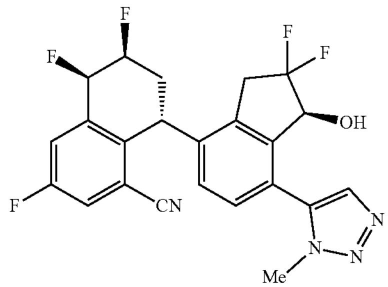 [SMILES: Cn1nncc1-c1ccc([C@H]2C[C@H](F)[C@H](F)c3cc(F)cc(C#N)c32)c2c1[C@H](O)C(F)(F)C2] | +++ | – |
| 219 | 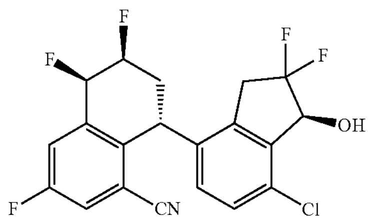 [SMILES: N#Cc1cc(F)cc2c1[C@@H](c1ccc(Cl)c3c1CC(F)(F)[C@H]3O)C[C@H](F)[C@@H]2F] | +++ | – |
| 220 | 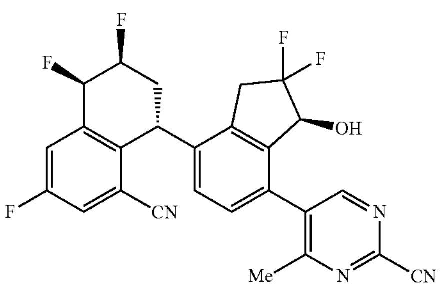 [SMILES: Cc1nc(C#N)ncc1-c1ccc([C@H]2C[C@H](F)[C@H](F)c3cc(F)cc(C#N)c32)c2c1[C@H](O)C(F)(F)C2] | +++ | – |
| 221 | 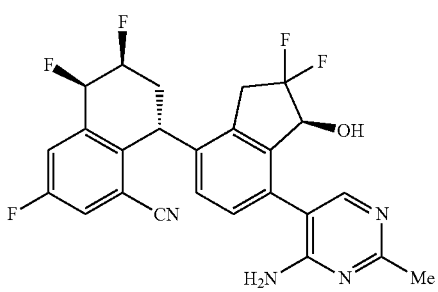 [SMILES: Cc1ncc(-c2ccc([C@H]3C[C@H](F)[C@H](F)c4cc(F)cc(C#N)c43)c3c2[C@H](O)C(F)(F)C3)c(N)n1] | +++ | – |
| 222 | 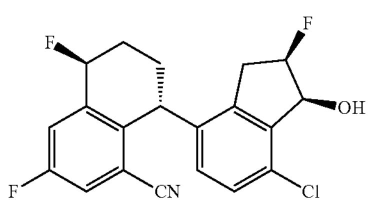 [SMILES: N#Cc1cc(F)cc2c1[C@@H](c1ccc(Cl)c3c1C[C@@H](F)[C@H]3O)CC[C@@H]2F] | +++ | – |
| 223 | 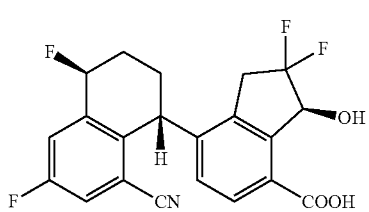 [SMILES: N#Cc1cc(F)cc2c1[C@@H](c1ccc(C(=O)O)c3c1CC(F)(F)[C@H]3O)CC[C@@H]2F] | ++ | |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 224 | 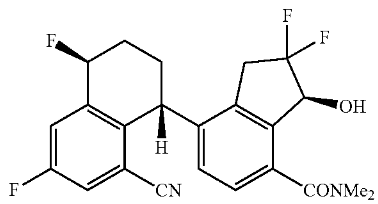 | | ++ |
| 225 | 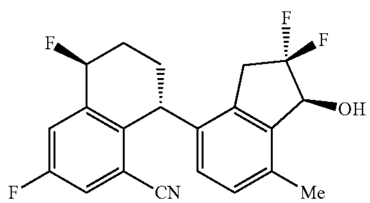 | | +++ |
| 226 | 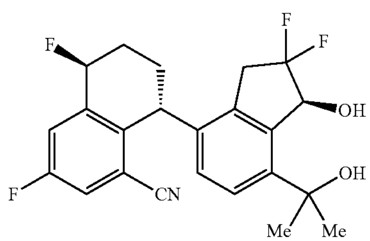 [SMILES: CC(C)(O)c1ccc([C@H]2CC[C@H](F)c3cc(F)cc(C#N)c32)c2c1[C@H](O)C(F)(F)C2] | | +++ |
| 227 | 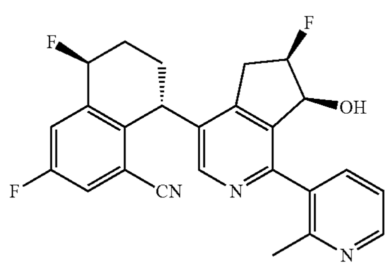 [SMILES: Cc1ncccc1-c1ncc([C@H]2CC[C@H](F)c3cc(F)cc(C#N)c32)c2c1[C@H](O)[C@H](F)C2] | | ++ |
| 228 | 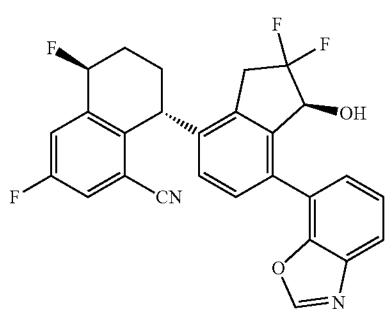 [SMILES: N#Cc1cc(F)cc2c1[C@@H](c1ccc(-c3cccc4ncoc34)c3c1CC(F)(F)[C@H]3O)CC[C@@H]2F] | | +++ |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 229 | 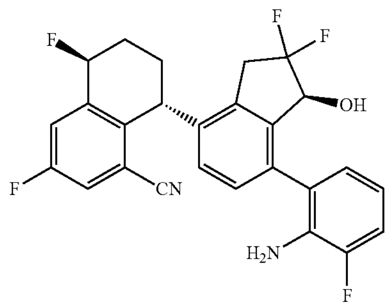 [SMILES: N#Cc1cc(F)cc2c1[C@@H](c1ccc(-c3cccc(F)c3N)c3c1CC(F)(F)[C@H]3O)CC[C@@H]2F] | | +++ |
| 230 | 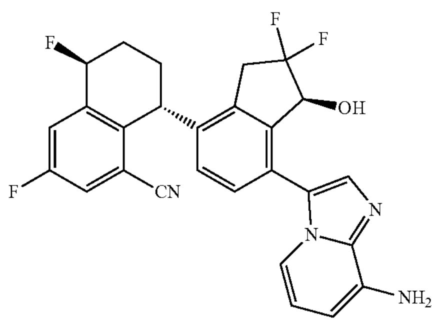 [SMILES: N#Cc1cc(F)cc2c1[C@@H](c1ccc(-c3cnc4c(N)cccn34)c3c1CC(F)(F)[C@H]3O)CC[C@@H]2F] | | +++ |
| 231 | 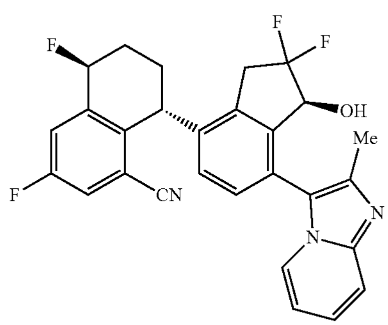 [SMILES: Cc1nc2ccccn2c1-c1ccc([C@H]2CC[C@H](F)c3cc(F)cc(C#N)c32)c2c1[C@H](O)C(F)(F)C2] | | ++ |
| 232 | 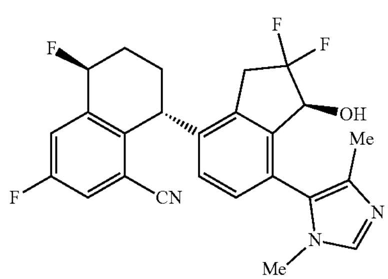 [SMILES: Cc1ncn(C)c1-c1ccc([C@H]2CC[C@H](F)c3cc(F)cc(C#N)c32)c2c1[C@H](O)C(F)(F)C2] | | +++ |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 233 | 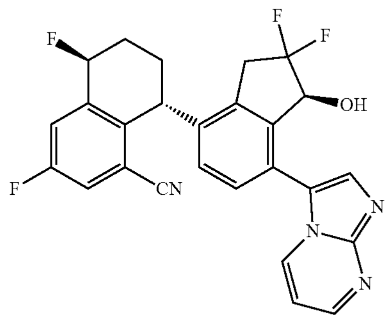 [SMILES: N#Cc1cc(F)cc2c1[C@@H](c1ccc(-c3cnc4ncccn34)c3c1CC(F)(F)[C@H]3O)CC[C@@H]2F] | | ++ |
| 234 | 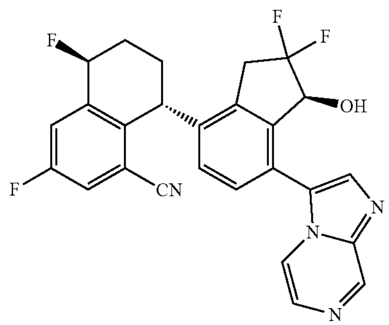 [SMILES: N#Cc1cc(F)cc2c1[C@@H](c1ccc(-c3cnc4cnccn34)c3c1CC(F)(F)[C@H]3O)CC[C@@H]2F] | | +++ |
| 235 | 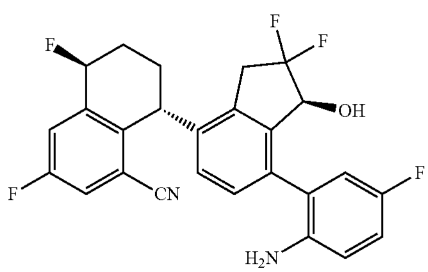 [SMILES: N#Cc1cc(F)cc2c1[C@@H](c1ccc(-c3cc(F)ccc3N)c3c1CC(F)(F)[C@H]3O)CC[C@@H]2F] | | +++ |
| 236 | 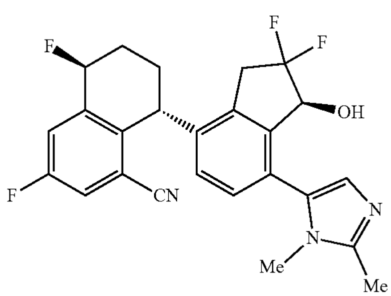 [SMILES: Cc1ncc(-c2ccc([C@H]3CC[C@H](F)c4cc(F)cc(C#N)c43)c3c2[C@H](O)C(F)(F)C3)n1C] | | +++ |
| 237 | 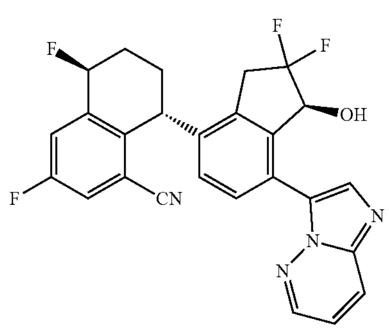 | | +++ |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 238 | 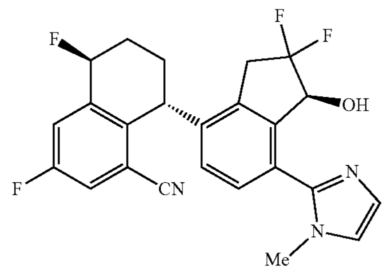 [SMILES: Cn1ccnc1-c1ccc([C@H]2CC[C@H](F)c3cc(F)cc(C#N)c32)c2c1[C@H](O)C(F)(F)C2] | ++ | |
| 239 | 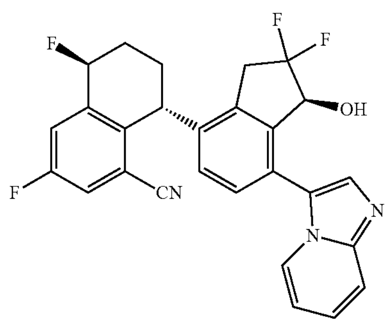 [SMILES: N#Cc1cc(F)cc2c1[C@@H](c1ccc(-c3cnc4ccccn34)c3c1CC(F)(F)[C@H]3O)CC[C@@H]2F] | +++ | |
| 240 | 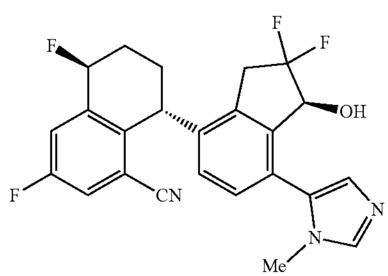 [SMILES: Cn1cncc1-c1ccc([C@H]2CC[C@H](F)c3cc(F)cc(C#N)c32)c2c1[C@H](O)C(F)(F)C2] | +++ | +++ |
| 241 | 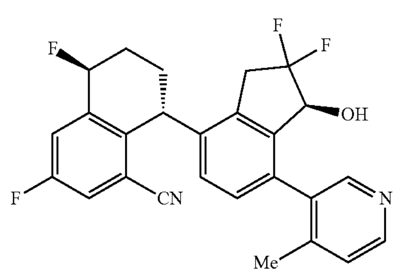 [SMILES: Cc1ccncc1-c1ccc([C@H]2CC[C@H](F)c3cc(F)cc(C#N)c32)c2c1[C@H](O)C(F)(F)C2] | +++ | +++ |
| 242 | 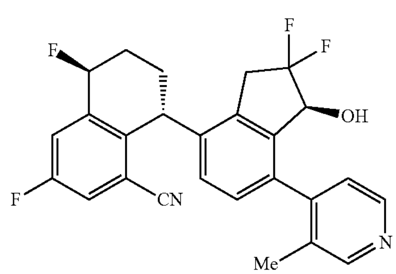 [SMILES: Cc1cnccc1-c1ccc([C@H]2CC[C@H](F)c3cc(F)cc(C#N)c32)c2c1[C@H](O)C(F)(F)C2] | +++ | +++ |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 243 | 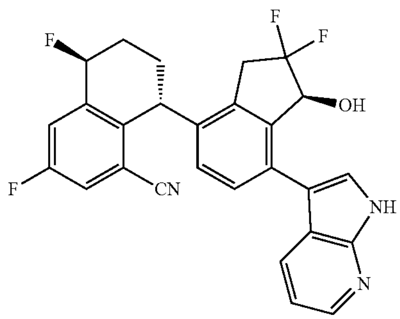 [SMILES: N#Cc1cc(F)cc2c1[C@@H](c1ccc(-c3c[nH]c4ncccc34)c3c1CC(F)(F)[C@H]3O)CC[C@@H]2F] | ++ | |
| 244 | 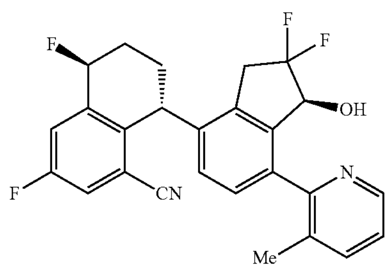 [SMILES: Cc1cccnc1-c1ccc([C@H]2CC[C@H](F)c3cc(F)cc(C#N)c32)c2c1[C@H](O)C(F)(F)C2] | +++ | |
| 245 | 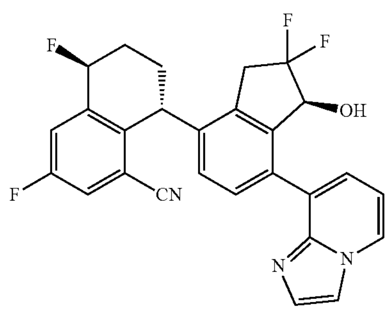 [SMILES: N#Cc1cc(F)cc2c1[C@@H](c1ccc(-c3cccn4ccnc34)c3c1CC(F)(F)[C@H]3O)CC[C@@H]2F] | ++ | |
| 246 | 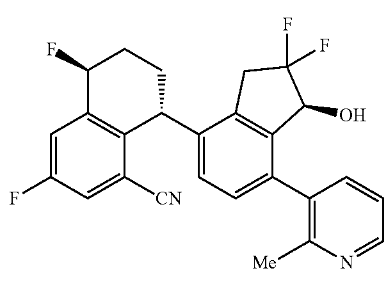 | ++ | |
| 247 | 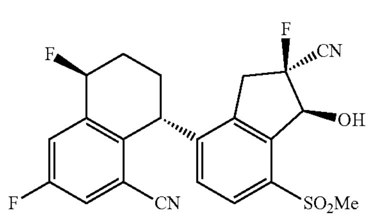 [SMILES: CS(=O)(=O)c1ccc([C@H]2CC[C@H](F)c3cc(F)cc(C#N)c32)c2c1[C@H](O)[C@@](F)(C#N)C2] | +++ | − |

TABLE 3-continued

Potency of select compounds
Less than 100 nM (+++), 100 nM to 1 μM (++), greater than 1 μM (+)

| Example # | Structure | HIF-2α Luciferase Assay | HIF-2α Scintillation Proximity Assay |
|---|---|---|---|
| 248 | ![structure] | ++ | − |

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound having the formula:

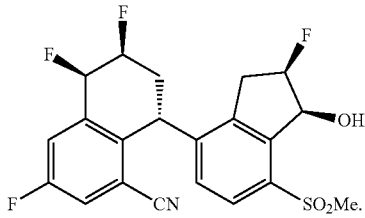 [SMILES: CS(=O)(=O)c1ccc([C@H]2C[C@H](F)[C@H](F)c3cc(F)cc(C#N)c32)c2c1[C@H](O)[C@H](F)C2]

* * * * *